(12) United States Patent
Patel et al.

(10) Patent No.: US 11,834,461 B2
(45) Date of Patent: Dec. 5, 2023

(54) BICYCLIC KETONE COMPOUNDS AND METHODS OF USE THEREOF

(71) Applicant: Genentech, Inc., South San Francisco, CA (US)

(72) Inventors: Snahel Patel, Foster City, CA (US); Gregory Hamilton, San Mateo, CA (US); Guiling Zhao, Palo Alto, CA (US); Huifen Chen, Burlingame, CA (US); Blake Daniels, South San Francisco, CA (US); Craig Stivala, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 218 days.

(21) Appl. No.: 17/147,449

(22) Filed: Jan. 12, 2021

(65) Prior Publication Data

US 2021/0139504 A1 May 13, 2021

Related U.S. Application Data

(62) Division of application No. 16/034,207, filed on Jul. 12, 2018, now Pat. No. 11,098,058.

(60) Provisional application No. 62/532,767, filed on Jul. 14, 2017.

(51) Int. Cl.
| | |
|---|---|
| C07D 498/04 | (2006.01) |
| C07D 487/04 | (2006.01) |
| A61P 25/16 | (2006.01) |
| A61P 25/28 | (2006.01) |
| A61P 17/06 | (2006.01) |
| A61P 21/00 | (2006.01) |
| A61P 19/02 | (2006.01) |
| A61P 1/00 | (2006.01) |
| C07D 235/12 | (2006.01) |
| C07D 471/04 | (2006.01) |

(52) U.S. Cl.
CPC ............ *C07D 498/04* (2013.01); *A61P 25/16* (2018.01); *A61P 25/28* (2018.01); *C07D 235/12* (2013.01); *C07D 471/04* (2013.01); *C07D 487/04* (2013.01); *A61P 1/00* (2018.01); *A61P 17/06* (2018.01); *A61P 19/02* (2018.01); *A61P 21/00* (2018.01)

(58) Field of Classification Search
CPC .. C07D 498/04; C07D 235/12; C07D 471/04; C07D 487/04; C07D 401/12; C07D 405/12; C07D 409/12; A61P 25/16; A61P 25/28; A61P 1/00; A61P 17/06; A61P 19/02; A61P 21/00; A61P 29/00; A61K 31/407; A61K 31/4196; A61K 31/5383
See application file for complete search history.

(56) References Cited

U.S. PATENT DOCUMENTS

| | | | |
|---|---|---|---|
| 3,773,919 A | | 11/1973 | Boswell et al. |
| 3,948,903 A | | 4/1976 | Doub et al. |
| 4,485,045 A | | 11/1984 | Regen |
| 4,544,545 A | | 10/1985 | Ryan et al. |
| 5,112,596 A | | 5/1992 | Malfroy-Camine |
| 2002/0038086 A1 | | 3/2002 | Hynynen et al. |
| 2018/0153831 A1 | | 6/2018 | Patel et al. |
| 2018/0170927 A1 | | 6/2018 | Patel |
| 2019/0127382 A1 | | 5/2019 | Patel et al. |
| 2020/0283446 A1 | | 9/2020 | Chen et al. |

FOREIGN PATENT DOCUMENTS

| | | |
|---|---|---|
| EP | 0102324 A2 | 3/1984 |
| EP | 0133988 A2 | 3/1985 |
| EP | 0244098 A2 | 11/1987 |
| FR | 94123 E | 7/1969 |
| WO | 98/27092 A1 | 6/1998 |
| WO | 98/56376 A1 | 12/1998 |
| WO | 01/58869 A2 | 8/2001 |
| WO | 2004/017908 A2 | 3/2004 |
| WO | 2004/098589 A1 | 11/2004 |
| WO | 2009/092565 A1 | 7/2009 |
| WO | 2010/099698 A1 | 9/2010 |
| WO | 2010/100070 A1 | 9/2010 |
| WO | 2011/006143 A2 | 1/2011 |
| WO | 2013/067260 | 5/2013 |
| WO | 2014/125444 A1 | 8/2014 |
| WO | 2015/006280 A1 | 1/2015 |
| WO | 2015/144609 A1 | 10/2015 |
| WO | 2016/027253 A1 | 2/2016 |
| WO | 2016/128908 A1 | 8/2016 |
| WO | 2018/128908 A1 | 8/2016 |
| WO | 2017/004500 A1 | 1/2017 |

(Continued)

OTHER PUBLICATIONS

U.S. Non-Final Rejection Issued in U.S. Appl. No. 16/175,206 dated Jun. 25, 2019.
Belikov, V.G. Pharmaceutical Chemistry—Tutorial "Part I: General Pharmaceutical Chemistry" (Extract—Eng. Translation), Fourth, Revised edition, Moscow-RU:MEDPress-Inform,:27-29 ( 2007).
Bertrand, M., et al., "cIAP1 and cIAP2 facilitate cancer cell survival by functioning as E3 ligases that promote RIP1 ubiquitination" Mol Cell 30(6):689-700 (Jun. 20, 2008).

(Continued)

*Primary Examiner* — John M Mauro
(74) *Attorney, Agent, or Firm* — Jelena Janjic Libby

(57) ABSTRACT

The invention provides novel compounds having the general formula I:

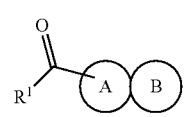

(I)

wherein $R^1$, the A ring and the B ring are as described herein, pharmaceutical compositions including the compounds, and methods of using the compounds.

11 Claims, No Drawings

(56) References Cited

FOREIGN PATENT DOCUMENTS

| WO | 2017/096301 A1 | 6/2017 |
| --- | --- | --- |
| WO | 2017/109724 A1 | 6/2017 |
| WO | 2017/136727 A2 | 8/2017 |
| WO | 2018/100070 A1 | 6/2018 |
| WO | 2019/012063 A1 | 1/2019 |
| WO | 2019/072942 A1 | 4/2019 |
| WO | 2019/086494 A1 | 5/2019 |

OTHER PUBLICATIONS

CAS Registry Compounds, RN:1554480-89-5, 1554480-83-9, 1542201-50-2, 1540456-83-4, 1539697-89-6, 1536914-91-6, 1529444-36-7, 1528724-76-6, 1526961-09-0,1515103-12-2; 1517186-33-2, 2092781-81-0, 1991193-96-4, 1989442-07-0, 1979877-21-8, 1979849-45-0, 1979849-27-8, 1554480-89-5, dated Aug. 25, 2016 through Apr. 20, 2017, pp. 1-7 (Oct. 3, 2019).

Chen, Z.,, "Ubiquitination in Signaling to and Activation of IKK" Immunol Rev 246(1):95-106 (Mar. 21, 2012).

Cho, Y.S. et al., "Phosphorylation-driven assembly of the RIP1-RIP3 complex regulates programmed necrosis and virus-induced inflammation" Cell 137(6):1112-1123 (Jun. 12, 2009).

Database Registry_RN1524863-46-4; RN 1524863-46-4, Database Registry [online], Retrieved from STN, Jan. 20, 2014, Ethanone, 1-(5,6,7,8-tetrahydro-8-methylimidazo[1,2-a]pyrimidin-2-yl)-(CA Index Name).

De Almagro, M., et al., "Necroptosis: Pathway diversity and characteristics" Semin Cell Dev Biol 39:56-62 (Mar. 1, 2015).

Degterev, A., et al., "Chemical inhibitor of nonapoptotic cell death with therapeutic potential for ischemic brain injury" Nat Chem Biol. 1(2):112-119 (Jul. 1, 2005).

Degterev, A., et al., "Identification of RIP1 kinase as a specific cellular target of necrostatins" Nat Chem Biol 4(5):313-321 (May 1, 2008).

Feoktistova, M., et al., "cIAPs block Ripoptosome formation, a RIP1/caspase-8 containing intracellular cell death complex differentially regulated by cFLIP isoforms" Mol Cell 43(3):449-463 (Aug. 5, 2011).

Harris, P., et al., "Discovery of a First-in-Class Receptor Interacting Protein 1 (RIP1) Kinase Specific Clinical Candidate (GSK2982772) for the Treatment of Inflammatory Diseases" J Med Chem 60(4):1247-1261 (Feb. 7, 2017).

Harris, P., et al., "Discovery of Small Molecule RIP1 Kinase Inhibitors for the Treatment of Pathologies Associated with Necroptosis" ACS Chem Lett 4(12):1238-1243 (Nov. 4, 2013).

He, S., et al., "Receptor Interacting Protein Kinase-3 Determines Cellular Cecrotic Response to TNF-α" Cell 137(6):1100-1111 (Jun. 12, 2009).

https://pubchem.ncbi.nlm.nih.gov/compound/11845422; compound name : 6,7-Dihydro-4H-pyrazolo[5,1-c][1,4]oxazine-2-carbaldehyde, created Nov. 6, 2006; 14 pages.

https://pubchem.ncbi.nlm.nih.gov/compound/20744102; compound name : 1-(5,6-Dihydro-4H-pyrrolo[1,2-b]pyrazol-2-yl)ethanone; created Dec. 5, 2007; 10 pages.

https://pubchem.ncbi.nlm.nih.gov/compound/82594726; compound name: 1-(6,7-Dihydro-5H-pyrrolo[1,2-a]imidazol-2-yl)ethanone; created Oct. 20, 2014; 10 pages.

https://pubchem.ncbi.nlm.nih.gov/compound/83875142; compound name : 1-(5-Methyl-5,6,7,8-tetrahydro-[1,2,4]triazolo[1,5-a]pyridin-2-yl) ethanone; created Oct. 20, 2014; 8 pages.

"International Search Report—PCT/EP2017/082851":pp. 1-7 (dated Feb. 20, 2018).

"International Search Report—PCT/EP2018/068998",:pp. 1-4 (dated Aug. 27, 2018).

Jensen et al., "Biochemical characterization and lysosomal localization of the mannose-6-phosphate protein p76 (hypothetical protein LOC196463)" Biochem J 402:449-463 ( 2007).

Joseph G. Cannon Chapter Nineteen in Burger's Medicinal Chemistry and Drug Discovery Fifth edition, vol. 1: Principles and Practice:783-802 ( 1995).

Kaiser, W., et al., "Toll-like receptor 3-mediated necrosis via TRIF, RIP3, and MLKL" J Biochem 288(43):31268-31279 (Oct. 25, 2013).

Kazuko Ohta et al., "Formation of pyridines by the reaction of isoxazoles with enamines" (with English Abstract), 9:1593-1600 (Jan. 1, 1989).

Linkermann, A., et al., "Necroptosis" New Engl J Med 370(5):455-465 (Jan. 30, 2014).

Lipson et al., "Reactions of 3-amino-1,2,4-triazoles with cinnamic aldehydes" Russ Chem Bull 58(7):1441-1444 (May 27, 2010).

Mashkovskiy, M.D. et al. Medicine [Meditisina] "Pharmaceuticals" (Russian with English translation attached), Moscow: vol. 1:8 (Jan. 1, 2002).

Najjar, M., et al., "Structure Guided Design of Potent and Selective Ponatinib-Based Hybrid Inhibitors for RIPKI" Cell Rep 10(11):1850-1860 (Mar. 24, 2015).

Newton, K. et al., "RIPK1 and RIPK3: critical regulators of inflammation and cell death" Trends Cell Biol 25(6):347-353 (Jun. 1, 2015).

Newton, K., et al., "Activity of protein kinase RIPK3 determines whether cells die by necroptosis or apoptosis" Science 343(6177):1357-1360 (Mar. 21, 2014).

O'Donnell, M., et al., "Ubiquitination of RIP1 regulates an NF-kappaB-independent cell-death switch in TNF signaling" Curr Biol 17(5):418-424 (Mar. 6, 2007).

PCT International Preliminary Report on Patentability (IPRP) for PCT/EP2017/076385, dated Apr. 23, 2019, 7 pages.

PCT International Preliminary Report on Patentability (IPRP) for PCT/EP2017/080996, dated Jun. 13, 2019, 10 pages.

PCT International Search Report and Written Opinion for PCT/EP2018/079772, dated Dec. 17, 2018, 25 pages.

PCT International Search Report and Written Opinion for PCT/EP2017/076385, dated Dec. 7, 2017, 7 pages.

PCT International Search Report for PCT/EP2017/080996, dated Feb. 2, 2018, 4 pages.

PCT Written Opinion of the International Searching Authority for PCT/EP2017/082851, dated Feb. 20, 2018, 8 pages.

Rojas-Rivera et al., "When PERK inhibitors turn out to be new potent RIPK1 inhibitors: critical issues on the specificity and use of GSK2606414 and GSK2656157" Cell Death and Differentiation 24:11001110 ( 2017).

Silverman, "The organic Chemistry of Drugs Design and Drug Action" Northwestern University. Second Edition. Evanstons Illinois. 2004. p. 29, table 2.2.

Sun, L., et al., "Mixed lineage kinase domain-like protein mediates necrosis signaling downstream of RIP3 kinase" Cell 148(1-2):213-227 (Jan. 20, 2012).

Surase, Y., et al., "Identification and synthesis of novel inhibitors of mycobacterium ATP synthase" Bioorg Med Chem Lett 27(15):3454-3459 (May 27, 2017).

Takahashi, N., et al., "Necrostatin-1 analogues: critical issues on the specificity, activity and in vivo use in experimental disease models" Cell Death Dis 3:e437 (Nov. 29, 2012).

"USPTO Non-Final Office Action, U.S. Appl. No. 15/828,271":1-13 (dated May 6, 2019).

"USPTO Notice of Allowance, U.S. Appl. No. 15/828,271":1-7 (dated Aug. 22, 2019).

USPTO Notice of Allowance, U.S. Appl. No. 16/175,206, dated Jan. 21, 2020, 10 pages.

Vanden Berghe, T. et al., "Regulated necrosis: the expanding network of non-apoptotic cell death pathways" Nat Rev Mol Cell Bio 15:135-147 (Feb. 1, 2014).

Waly, M. et al., "A novel Synthesis of Imidazo (4,5-d)azepine Ring System" Polish J Chem 70(3):296-301 ( 1996).

Wang, L., et al., "TNF-alpha induces two distinct caspase-8 activation pathways" Cell 133(4):693-703 (May 16, 2008).

Written Opinion of the International Searching Authority for PCT/EP2017/080996, dated Feb. 7, 2018, 8 pages.

Zhao, J., et al., "Mixed lineage kinase domain-like is a key receptor interacting protein 3 downstream component of TNF-induced necrosis" PNAS 109(14):5322-5327 (Apr. 3, 2012).

BICYCLIC KETONE COMPOUNDS AND METHODS OF USE THEREOF

CROSS-REFERENCE TO RELATED APPLICATIONS

This application is a divisional application of U.S. patent application Ser. No. 16/034,207, filed on Jul. 12, 2018, which claims benefit of priority to U.S. Provisional Patent Application No. 62/532,767, filed on Jul. 14, 2017. The entire content of each of the above patent applications is hereby incorporated by reference.

FIELD OF THE INVENTION

The present invention relates to organic compounds useful for therapy and/or prophylaxis in a mammal, and in particular to inhibitors of RIP1 kinase useful for treating diseases and disorders associated with inflammation, cell death and others.

BACKGROUND OF THE INVENTION

Receptor-interacting protein-1 ("RIP1") kinase is a serine/threonine protein kinase. RIP1 is a regulator of cell signaling that is involved, among other things, in the mediation of programmed cell death pathways, e.g., necroptosis. The best studied form of necroptotic cell death is initiated by TNFα (tumor necrosis factor), but necroptosis can also be induced by other members of the TNFα death ligand family (Fas and TRAIL/Apo2L), interferons, Toll-like receptors (TLRs) signaling and viral infection via the DNA sensor DAI (DNA-dependent activator of interferon regulatory factor) [1-3]. Binding of TNFα to the TNFR1 (TNF receptor 1) prompts TNFR1 trimerization and formation of an intracellular complex, Complex-I. TRADD (TNF receptor associated death domain protein) binds to the intracellular death domain of TNFR1 and recruits the protein kinase RIP1 (receptor-interacting protein 1) through the death domain present in both proteins [4]. Following initial recruitment into TNFR1-associated signaling complex, RIP1 translocates to a secondary cytoplasmatic complex, Complex-II [5-7]. Complex-II is formed by the death domain containing protein FADD (Fas-associated Protein), RIP1, caspase-8 and cFLIP. If caspase-8 is not fully activated or its activity is blocked, the protein kinase RIP3 gets recruited to the complex, forming a necrosome, which will lead to necroptotic cell death initiation [8-10]. Once the necrosome is formed, RIP1 and RIP3 engage in a series of auto and cross phosphorylation events that are essential for necroptotic cell death. Necroptosis can be completely blocked either by the kinase inactivating mutation in any of the two kinases, or chemically by RIP1 kinase inhibitors (necrostatins), or RIP3 kinase inhibitors [11-13]. Phosphorylation of RIP3 allows the binding and phosphorylation of pseudokinase MLKL (mixed lineage kinase domain-like), a key component of necroptotic cell death [14, 15].

Necroptosis has crucial pathophysiological relevance in myocardial infarction, stroke, atherosclerosis, ischemia-reperfusion injury, inflammatory bowel diseases, retinal degeneration and a number of other common clinical disorders [16]. Therefore, selective inhibitors of RIP1 kinase activity are therefore desired as a potential treatment of diseases mediated by this pathway and associated with inflammation and/or necroptotic cell death.

Inhibitors of RIP1 kinase have been previously described. The first published inhibitor of RIP1 kinase activity was necrostatin 1 (Nec-1) [17]. This initial discovery was followed by modified versions of Nec-1 with various abilities to block RIP1 kinase activity [11, 18]. Recently, additional RIP1 kinase inhibitors have been described that differ structurally from necrostatin class of compounds [19, 20, 21].

References cited above, each of which is hereby incorporated by reference in its entirety:
1) Vanden Berghe, T., Linkermann, A., Jouan-Lanhouet, S., Walczak, H. and Vandenabeele, P. (2014) Regulated necrosis: the expanding network of non-apoptotic cell death pathways. Nature reviews. Molecular cell biology. 15, 135-147.
2) Newton, K. (2015) RIPK1 and RIPK3: critical regulators of inflammation and cell death. Trends in cell biology. 25, 347-353.
3) de Almagro, M. C. and Vucic, D. (2015) Necroptosis: Pathway diversity and characteristics. Semin Cell Dev Biol. 39, 56-62.
4) Chen, Z. J. (2012) Ubiquitination in signaling to and activation of IKK. Immunological reviews. 246, 95-106.
5) O'Donnell, M. A., Legarda-Addison, D., Skountzos, P., Yeh, W. C. and Ting, A. T. (2007) Ubiquitination of RIP1 regulates an NF-kappaB-independent cell-death switch in TNF signaling. Curr Biol. 17, 418-424.
6) Feoktistova, M., Geserick, P., Kellert, B., Dimitrova, D. P., Langlais, C., Hupe, M., Cain, K., MacFarlane, M., Hacker, G. and Leverkus, M. (2011) cIAPs block Ripoptosome formation, a RIP1/caspase-8 containing intracellular cell death complex differentially regulated by cFLIP isoforms. Molecular cell. 43, 449-463.
7) Bertrand, M. J., Milutinovic, S., Dickson, K. M., Ho, W. C., Boudreault, A., Durkin, J., Gillard, J. W., Jaquith, J. B., Morris, S. J. and Barker, P. A. (2008) cIAP and cIAP2 facilitate cancer cell survival by functioning as E3 ligases that promote RIP1 ubiquitination. Mol Cell. 30, 689-700.
8) Wang, L., Du, F. and Wang, X. (2008) TNF-alpha induces two distinct caspase-8 activation pathways. Cell. 133, 693-703.
9) He, S., Wang, L., Miao, L., Wang, T., Du, F., Zhao, L. and Wang, X. (2009) Receptor interacting protein kinase-3 determines cellular necrotic response to TNF-alpha. Cell. 137, 1100-1111.
10) Cho, Y. S., Challa, S., Moquin, D., Genga, R., Ray, T. D., Guildford, M. and Chan, F. K. (2009) Phosphorylation-driven assembly of the RIP1-RIP3 complex regulates programmed necrosis and virus-induced inflammation. Cell. 137, 1112-1123.
11) Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem Biol. 4, 313-321.
12) Newton, K., Dugger, D. L., Wickliffe, K. E., Kapoor, N., de Almagro, M. C., Vucic, D., Komuves, L., Ferrando, R. E., French, D. M., Webster, J., Roose-Girma, M., Warming, S. and Dixit, V. M. (2014) Activity of protein kinase RIPK3 determines whether cells die by necroptosis or apoptosis. Science. 343, 1357-1360.
13) Kaiser, W. J., Sridharan, H., Huang, C., Mandal, P., Upton, J. W., Gough, P. J., Sehon, C. A., Marquis, R. W., Bertin, J. and Mocarski, E. S. (2013) Toll-like receptor 3-mediated necrosis via TRIF, RIP3, and MLKL. The Journal of biological chemistry. 288, 31268-31279.
14) Zhao, J., Jitkaew, S., Cai, Z., Choksi, S., Li, Q., Luo, J. and Liu, Z. G. (2012) Mixed lineage kinase domain-like is a key receptor interacting protein 3 downstream component of TNF-induced necrosis. Proceedings of the National Academy of Sciences of the United States of America. 109, 5322-5327.

15) Sun, L., Wang, H., Wang, Z., He, S., Chen, S., Liao, D., Wang, L., Yan, J., Liu, W., Lei, X. and Wang, X. (2012) Mixed Lineage Kinase Domain-like Protein Mediates Necrosis Signaling Downstream of RIP3 Kinase. Cell. 148, 213-227.

16) Linkermann, A. and Green, D. R. (2014) Necroptosis. The New England journal of medicine. 370, 455-465.

17) Degterev, A., Huang, Z., Boyce, M., Li, Y., Jagtap, P., Mizushima, N., Cuny, G. D., Mitchison, T. J., Moskowitz, M. A. and Yuan, J. (2005) Chemical inhibitor of nonapoptotic cell death with therapeutic potential for ischemic brain injury. Nat Chem Biol. 1, 112-119.

18) Takahashi, N., Duprez, L., Grootjans, S., Cauwels, A., Nerinckx, W., DuHadaway, J. B., Goossens, V., Roelandt, R., Van Hauwermeiren, F., Libert, C., Declercq, W., Callewaert, N., Prendergast, G. C., Degterev, A., Yuan, J. and Vandenabeele, P. (2012) Necrostatin-1 analogues: critical issues on the specificity, activity and in vivo use in experimental disease models. Cell Death Dis. 3, e437.

19) Harris, P. A., Bandyopadhyay, D., Berger, S. B., Campobasso, N., Capriotti, C. A., Cox, J. A., Dare, L., Finger, J. N., Hoffman, S. J., Kahler, K. M., Lehr, R., Lich, J. D., Nagilla, R., Nolte, R. T., Ouellette, M. T., Pao, C. S., Schaeffer, M. C., Smallwood, A., Sun, H. H., Swift, B. A., Totoritis, R. D., Ward, P., Marquis, R. W., Bertin, J. and Gough, P. J. (2013) Discovery of Small Molecule RIP1 Kinase Inhibitors for the Treatment of Pathologies Associated with Necroptosis. ACS medicinal chemistry letters. 4, 1238-1243.

20) Najjar, M., Suebsuwong, C., Ray, S. S., Thapa, R. J., Maki, J. L., Nogusa, S., Shah, S., Saleh, D., Gough, P. J., Bertin, J., Yuan, J., Balachandran, S., Cuny, G. D. and Degterev, A. (2015) Structure Guided Design of Potent and Selective Ponatinib-Based Hybrid Inhibitors for RIPK1. Cell Rep.

21) International Patent Publication No. WO 2014/125444.
22) International Patent Publication No. WO 2017/004500.

SUMMARY OF THE INVENTION

Provided herein are compounds of formula I:

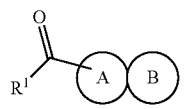

(I)

or pharmaceutically acceptable salts thereof, wherein
$R^1$ is selected from the group consisting of $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-$N(R^N)_2$, phenyl, benzyl, 4 to 8 membered heterocyclyl and 5 to 6 membered heteroaryl; wherein $R^1$ is bound to the adjacent carbonyl by a carbon atom, and wherein $R^1$ is optionally substituted by one or two substituents selected from the group consisting of F, Cl, Br, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-$N(R^N)_2$, hydroxyl, hydroxymethyl, cyano, cyanomethyl, cyanoethyl, $C(O)C_1$-$C_6$ alkyl, phenyl, benzyl, $CH_2$—($C_3$-$C_6$ cycloalkyl), 5 to 6 membered heteroaryl, and $CH_2$-(5 to 6 membered heteroaryl); each $R^N$ is independently selected from the group consisting of H, $C_1$-$C_6$ alkyl, $C_3$-$C_6$ cycloalkyl, $C_1$-$C_6$ alkoxy, and $C_1$-$C_6$ haloalkyl; or two $R^N$ may together with the adjacent N form a 4-6 membered ring;

the A ring is a 5 membered heteroaryl having as the only heteroatoms, either (i) two or three nitrogen atoms, (ii) one nitrogen atom and one oxygen atom, or (iii) one nitrogen atom and one sulfur atom; wherein the A ring is bound to the adjacent carbonyl by a carbon atom; and the B ring is a 4 to 8 membered cycloalkyl, or a 4 to 8 membered heterocyclyl having 1 to 3 heteroatoms selected from the group consisting of nitrogen, oxygen and sulfur; wherein the B ring is substituted according to (a), (b), or both (a) and (b):

(a) 1 to 2 substituents selected from the group consisting of halogen, deuterium, hydroxy, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, and cyano; wherein two $C_1$-$C_6$ alkyl substituents may together for a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

(b) 1 substituent selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring or 5 to 6 membered heteroaryl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, cyano, and cyclopropyl.

Also provided herein are pharmaceutical compositions comprising a compound of formula I, or a pharmaceutically acceptable salt thereof, and one or more pharmaceutically acceptable carriers or excipients. Specific embodiments include pharmaceutical compositions suitable for oral delivery.

Also provided herein are oral formulations of a compound of formula I, or a pharmaceutically acceptable salt thereof, and one or more pharmaceutically acceptable carriers or excipients suitable for oral delivery.

Also provided herein are methods of treatment of diseases and disorders associated with inflammation, cell death, and others related to RIP1 kinase, as described further below.

Also provided herein is a compound of formula I or a pharmaceutically acceptable salt thereof, for use as a therapeutically active substance.

Also provided herein is a compound of formula I or a pharmaceutically acceptable salt thereof, for the treatment of a disease or disorder selected from the group consisting of Parkinson's Disease, Lewy body dementia, multiple system atrophy, Parkinson-plus syndromes, taupathies, Alzheimer's Disease, frontotemporal dementia, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

Also provided herein is a compound of formula I or a pharmaceutically acceptable salt thereof, or composition thereof according to any one of the embodiments provided herein, for the treatment of a disease or disorder selected from the group consisting of Parkinson's Disease, Lewy body dementia, multiple system atrophy, Parkinson-plus syndromes, taupathies, Alzheimer's Disease, frontotemporal dementia, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

Also provided herein is a compound of formula I or a pharmaceutically acceptable salt thereof, for the preparation of a medicament for the treatment of a disease or disorder selected from the group consisting of Parkinson's Disease, Lewy body dementia, multiple system atrophy, Parkinson-plus syndromes, taupathies, Alzheimer's Disease, frontotemporal dementia, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

Also provided herein is a compound of formula I or a pharmaceutically acceptable salt thereof, for the treatment of a disease or disorder selected from the group consisting of inflammatory bowel disease, Crohn's disease, ulcerative colitis, glaucoma, psoriasis, psoriatic arthritis, rheumatoid arthritis, spondyloarthritis, juvenile idiopathic arthritis, and osteoarthritis.

DETAILED DESCRIPTION OF THE INVENTION

Definitions

As provided herein, all chemical formulae and generic chemical structures should be interpreted to provide proper valence and chemically stable bonds between atoms as understood by one of ordinary skill in the art. Where appropriate, substituents may be bonded to more than one adjacent atom (e.g., alkyl includes methylene where two bonds are present).

In the chemical formulae provided herein, "halogen" or "halo" refers to flurorine, chlorine, and bromine (i.e., F, Cl, Br).

Alkyl, unless otherwise specifically defined, refers to an optionally substituted, straight-chain or branched $C_1$-$C_{12}$ alkyl group. In some embodiments, alkyl refers to a $C_1$-$C_6$ alkyl group. Exemplary alkyl groups include methyl, ethyl, propyl, iso-propyl, n-butyl, iso-butyl, tert-butyl, sec-butyl, n-pentyl, n-hexyl, n-heptyl, and n-oxtyl. Substituted alkyl groups provided herein are substituted by one or more substituents selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, the substituted alkyl group has 1 or 2 substituents. In some embodiments, the alkyl group is unsubstituted.

Cycloalkyl, unless otherwise specifically defined, refers to an optionally substituted $C_3$-$C_{12}$ cycloalkyl group and includes fused, spirocyclic, and bridged bicyclic groups, wherein the substituents are selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, cycloalkyl refers to a $C_3$-$C_6$ cycloalkyl group. In some embodiments, the $C_3$-$C_6$ cycloalkyl group is optionally substituted with 1 to three halogen atoms. In some embodiments, the $C_3$-$C_6$ cycloalkyl group is optionally substituted with 1 to three fluorine atoms. Exemplary $C_3$-$C_6$ cycloalkyl groups include cyclopropyl, cyclobutyl, cyclopentyl and cyclohexyl. Exemplary $C_3$-$C_{12}$ cycloalkyl groups further include bicyclo[3.1.0]hexyl, bicyclo[2.1.1]hexyl, cycloheptyl, bicycle [4.1.0]heptyl, spiro[4.2]heptyl, cyclooctyl, spiro [4.3]octyl, spiro[5.2]octyl, bicyclo[2.2.1]heptanyl, bicycle [2.2.2]octanyl, adamantanyl, decalinyl, and spiro[5.4] decanyl. Where appropriate, cycloalkyl groups may be fused to other groups such that more than one chemical bond exists between the cycloalkyl group and another ring system (e.g., the C ring of formula I). In some embodiments, the cycloalkyl group is unsubstituted.

Haloalkyl, unless otherwise specifically defined, refers to a straight-chain or branched $C_1$-$C_{12}$ alkyl group, wherein one or more hydrogen atoms are replaced by a halogen. In some embodiments, haloalkyl refers to a $C_1$-$C_6$ haloalkyl group. In some embodiments, 1 to 3 hydrogen atoms of the haloalkyl group are replaced by a halogen. In some embodiments, every hydrogen atom of the haloalkyl group is replaced by a halogen (e.g, trifluoromethyl). In some embodiments, the haloalkyl is as defined herein wherein the halogen in each instance is fluorine. Exemplary haloalkyl groups include fluoromethyl, difluoromethyl, trifluromethyl, trifluoroethyl, and pentafluoroethyl.

Alkoxy, unless otherwise specifically defined, refers to a straight-chain or branched $C_1$-$C_{12}$ alkyl group, wherein one or more oxygen atoms are present, in each instance between two carbon atoms. In some embodiments, alkoxy refers to a $C_1$-$C_6$ alkoxy group. In some embodiments, $C_1$-$C_6$ alkoxy groups provided herein have one oxygen atom. Exemplary alkoxy groups include methoxy, ethoxy, $CH_2OCH_3$, $CH_2CH_2OCH_3$, $CH_2OCH_2CH_3$, $CH_2CH_2OCH_2CH_3$, $CH_2OCH_2CH_2CH_3$, $CH_2CH_2CH_2OCH_3$, $CH_2OCH(CH_3)_2$, $CH_2OC(CH_3)_3$, $CH(CH_3)OCH_3$, $CH_2CH(CH_3)OCH_3$, $CH(CH_3)OCH_2CH_3$, $CH_2OCH_2OCH_3$, $CH_2CH_2OCH_2CH_2OCH_3$, and $CH_2OCH_2OCH_2OCH_3$.

Cycloalkoxy, unless otherwise specifically defined, refers to a $C_4$-$C_{10}$ or a $C_4$-$C_6$ alkoxy group as defined above wherein the group is cyclic and contains one oxygen atom. Exemplary cycloalkoxy groups include oxetanyl, tetrahydrofuranyl, and tetrahydropyranyl.

Haloalkoxy, unless otherwise specifically defined, refers to a $C_1$-$C_6$ haloalkyl group as defined above, wherein one or two oxygen atoms are present, in each instance between two carbon atoms. In some embodiments, $C_1$-$C_6$ haloalkoxy groups provided herein have one oxygen atom. Exemplary haloalkoxy groups include $OCF_3$, $OCHF_2$ and $CH_2OCF_3$.

Thioalkyl, unless otherwise specifically defined, refers to a $C_1$-$C_{12}$ or a $C_1$-$C_6$ alkoxy group as defined above wherein the oxygen atom is replaced by a sulfur atom. In some embodiments, thioalkyl groups may include sulfur atoms substituted by one or two oxygen atoms (i.e., alkylsulfones and alkylsulfoxides). Exemplary thioalkyl groups are those exemplified in the definition of alkoxy above, wherein each oxygen atom is replaced by a sulfur atom in each instance.

Thiocycloalkyl, unless otherwise specifically defined, refers to a $C_4$-$C_{10}$ or a $C_4$-$C_6$ thioalkyl group as defined above wherein the group is cyclic and contains one sulfur atom. In some embodiments, the sulfur atom of the thiocycloalkyl group is substituted by one or two oxygen atoms (i.e., a cyclic sulfone or sulfoxide). Exemplary thiocycloalkyl groups include thietanyl, thiolanyl, thianyl, 1,1-dioxothiolanyl, and 1,1-dioxothianyl.

Heterocyclyl, unless otherwise specifically defined, referes to a single saturated or partially unsaturated 4 to 8 membered ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems have from 7 to 12 atoms and are further described below. Thus, the term includes single saturated or partially unsaturated rings (e.g., 3, 4, 5, 6, 7 or 8 membered rings) from about 1 to 7 carbon atoms and from about 1 to 4 heteroatoms selected from the group consisting of oxygen, nitrogen and sulfur in the ring. The ring may be C-branched (i.e., substituted by $C_1$-$C_4$ alkyl). The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system. It is also to be understood that the point of attachment for a heterocycle or heterocycle multiple condensed ring system can be at any suitable atom of the heterocyclyl group including a carbon atom and a nitrogen atom. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R, 4R)-2-oxa-5-azabicyclo[2.2.2]octane and pyrrolidin-2-one.

In some embodiments, the heterocyclyl is a $C_4$—C heterocyclyl having 1 to 3 heteroatoms selected from the group consisting of nitrogen, oxygen and sulfur. In some embodiments, the heterocyclyl group is neither bicyclic nor spirocyclic. In some embodiments, the heterocyclyl is a $C_5$-$C_6$ heterocylcyl having 1 to 3 heteroatoms, wherein at least 2 are nitrogen if 3 heteroatoms are present.

Aryl, unless otherwise specifically defined, refers to a single all carbon aromatic ring or a multiple condensed all carbon ring system wherein at least one of the rings is aromatic and wherein the aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromaticornotaromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Exemplary aryl groups include phenyl, indenyl, naphthyl, 1, 2, 3, 4-tetrahydronaphthyl, anthracenyl, and the like.

Heteroaryl, unless otherwise specifically defined, refers to a 5 to 6 membered aromatic ring that has at least one atom other than carbon in the ring, wherein the atom is selected from the group consisting of oxygen, nitrogen and sulfur; "heteroaryl" also includes multiple condensed ring systems having 8 to 16 atoms that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2 or 3 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1 to 15 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "⌇" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water. In some embodiments, a hydrate of a compound provided herein is a ketone hydrate.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, $(C_{1-6})$ alkoxycarbonyloxymethyl, N—$(C_{1-6})$alkoxycarbonylaminomethyl, succinoyl, $(C_{1-6})$alkanoyl, alpha-amino$(C_{1-4})$ alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})$alkyl$)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or 3H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Inhibitors of RIP1 Kinase

The present invention provides novel compounds having the general formula I:

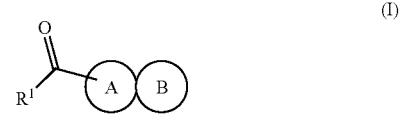

(I)

or pharmaceutically acceptable salts thereof, wherein $R^1$ is selected from the group consisting of $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-N($R^N$)$_2$, phenyl, benzyl, 4 to 8 membered heterocyclyl and 5 to 6 membered heteroaryl; wherein $R^1$ is bound to the adjacent carbonyl by a carbon atom, and wherein $R^1$ is optionally substituted by one or two substituents selected from the group consisting of F, Cl, Br, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-N($R^N$)$_2$, hydroxyl, hydroxymethyl, cyano, cyanomethyl, cyanoethyl, C(O)$C_1$-$C_6$ alkyl, phenyl, benzyl, CH$_2$—($C_3$-$C_6$ cycloalkyl), 5 to 6 membered heteroaryl, and CH$_2$-(5 to 6 membered heteroaryl); each $R^N$ is independently selected from the group consisting of H, $C_1$-$C_6$ alkyl, $C_3$-$C_6$ cycloalkyl, $C_1$-$C_6$ alkoxy, and $C_1$-$C_6$ haloalkyl; or two $R^N$ may together with the adjacent N form a 4-6 membered ring;

the A ring is a 5 membered heteroaryl having as the only heteroatoms, either (i) two or three nitrogen atoms, (ii) one nitrogen atom and one oxygen atom, or (iii) one nitrogen atom and one sulfur atom; wherein the A ring is bound to the adjacent carbonyl by a carbon atom; and the B ring is a 4 to 8 membered cycloalkyl, or a 4 to 8 membered heterocyclyl having 1 to 3 heteroatoms selected from the group consisting of nitrogen, oxygen and sulfur; wherein the B ring is substituted according to (a), (b), or both (a) and (b):

(a) 1 to 2 substituents selected from the group consisting of halogen, deuterium, hydroxy, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^N$)$_2$, and cyano; wherein two $C_1$-$C_6$ alkyl substituents may together for a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

(b) 1 substituent selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^N$)$_2$, phenyl, benzyl, CH$_2$—($C_3$-$C_6$ cycloalkyl), CH$_2$CH$_2$—($C_3$-$C_6$ cycloalkyl), CH$_2$-(4 to 6 membered heterocyclyl), CH$_2$CH$_2$-(4 to 6 membered heterocyclyl), 5 to 6 membered heteroaryl, and CH$_2$-(5 to 6 membered heteroaryl); wherein when a phenyl ring or 5 to 6 membered heteroaryl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In another embodiment, provided herein are compounds of formula I:

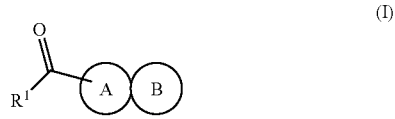

or pharmaceutically acceptable salts thereof, wherein
$R^1$ is selected from the group consisting of $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-$N(R^N)_2$, phenyl, benzyl, 4 to 6 membered heterocyclyl and 5 to 6 membered heteroaryl; wherein $R^1$ is bound to the adjacent carbonyl by a carbon atom, and wherein $R^1$ is optionally substituted by one or two substituents selected from the group consisting of F, Cl, methyl, ethyl, hydroxyl, hydroxymethyl, methoxymethyl, cyano, trifluoromethyl, difluoromethoxy and trifluoromethoxy.

each $R^N$ is independently selected from the group consisting of H, $C_1$-$C_6$ alkyl, $C_3$-$C_6$ cycloalkyl, $C_1$-$C_6$ alkoxy, and $C_1$-$C_6$ haloalkyl; or two $R^N$ may together with the adjacent N form a 4-6 membered ring;

the A ring is a 5 membered heteroaryl having as the only heteroatoms, either (i) two or three nitrogen atoms, (ii) one nitrogen atom and one oxygen atom, or (iii) one nitrogen atom and one sulfur atom; wherein the A ring is bound to the adjacent carbonyl by a carbon atom; and the B ring is a 4 to 8 membered cycloalkyl, or a 4 to 8 membered heterocyclyl having 1 to 3 heteroatoms selected from the group consisting of nitrogen, oxygen and sulfur; wherein the B ring is substituted according to (a), (b), or both (a) and (b):

(a) 1 to 2 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, and cyano; wherein two $C_1$-$C_6$ alkyl substituents may together for a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

(b) 1 substituent selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, cyano, and cyclopropyl.

In some embodiments, $R^1$ is selected from the group consisting of $C_1$-$C_6$ alkyl, $C_3$-$C_6$ cycloalkyl, $C_1$-$C_6$ haloalkyl, phenyl, benzyl, oxetanyl, oxabicyclo[3.1.0]hexan-6-yl, thienyl and pyrazolyl; wherein $R^1$ is optionally substituted by: (i) one substituent selected from the group consisting of F, Cl, methyl, hydroxyl, hydroxymethyl, cyano and trifluoromethyl, or (ii) two F substituents. In some of the above embodiments, $R^1$ is $C_1$-$C_6$ alkyl. In some embodiments, $R^1$ is $C_1$-$C_4$ alkyl. In some embodiments, $R^1$ is $C_3$-$C_5$ cycloalkyl. In some embodiments, $R^1$ is $C_3$-$C_4$ cycloalkyl. In some embodiments, $R^1$ is methyl. In some embodiments, $R^1$ is ethyl. In some embodiments, $R^1$ is $CF_3CH_2$. In some embodiments, $R^1$ is 2-propyl. In some embodiments, $R^1$ is tert-butyl. In some embodiments, $R^1$ is (2-hydroxy)-2-propyl. In some embodiments, $R^1$ is (2-cyano)-2-propyl. In some embodiments, $R^1$ is $C_1$-$C_6$ haloalkyl. In some embodiments, $R^1$ is $C_1$-$C_4$ haloalkyl. In some embodiments, $R^1$ is cyclopropyl. In some embodiments, $R^1$ is mono- or difluorocyclopropyl. In some embodiments, $R^1$ is 1-fluorocyclopropyl. In some embodiments, $R^1$ is 2-fluorocyclopropyl. In some embodiments, $R^1$ is 2,2-difluorocyclopropyl. In some embodiments, $R^1$ is 1-(trifluoromethyl)cyclopropyl. In some embodiments, $R^1$ is 1-methylcyclopropyl. In some embodiments, $R^1$ is 1-(hydroxymethyl)cyclopropyl. In some embodiments, $R^1$ is cyclobutyl. In some embodiments, $R^1$ is cyclopentyl. In some embodiments, $R^1$ is phenyl. In some embodiments, $R^1$ is benzyl. In some embodiments, $R^1$ is oxetan-3-yl. In some embodiments, $R^1$ is 3-methyloxetan-3-yl. In some embodiments, $R^1$ is oxabicyclo[3.1.0]hexan-6-yl. In some embodiments, $R^1$ is 2-pyridyl. In some embodiments, $R^1$ is 1-methylpyrazol-4-yl. In some embodiments, $R^1$ is 2-thienyl.

In some embodiments, each $R^N$ is independently selected from the group consisting of H and $C_1$-$C_6$ alkyl. In some embodiments, each $R^N$ is a $C_1$-$C_4$ alkyl. In some embodiments, each $R^N$ is methyl.

In some embodiments of formula (I), R is as defined above, and the A ring and the B ring together are selected from the group consisting of

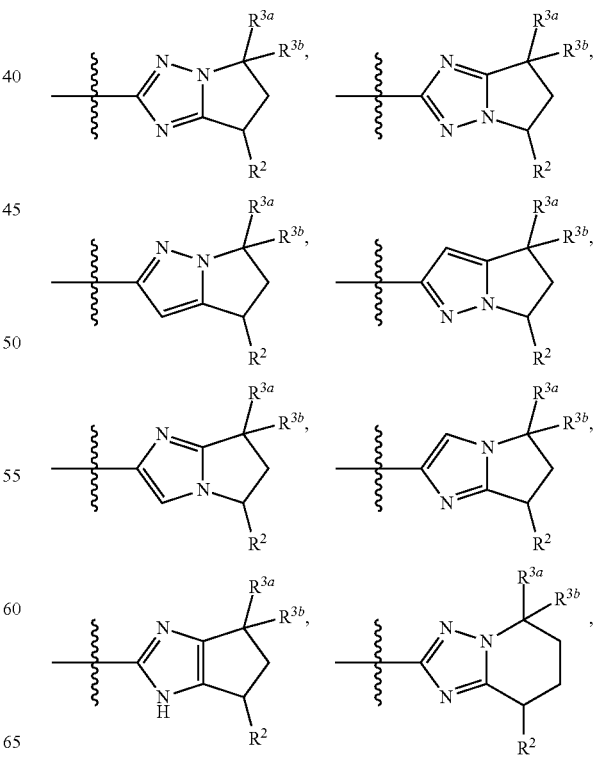

-continued

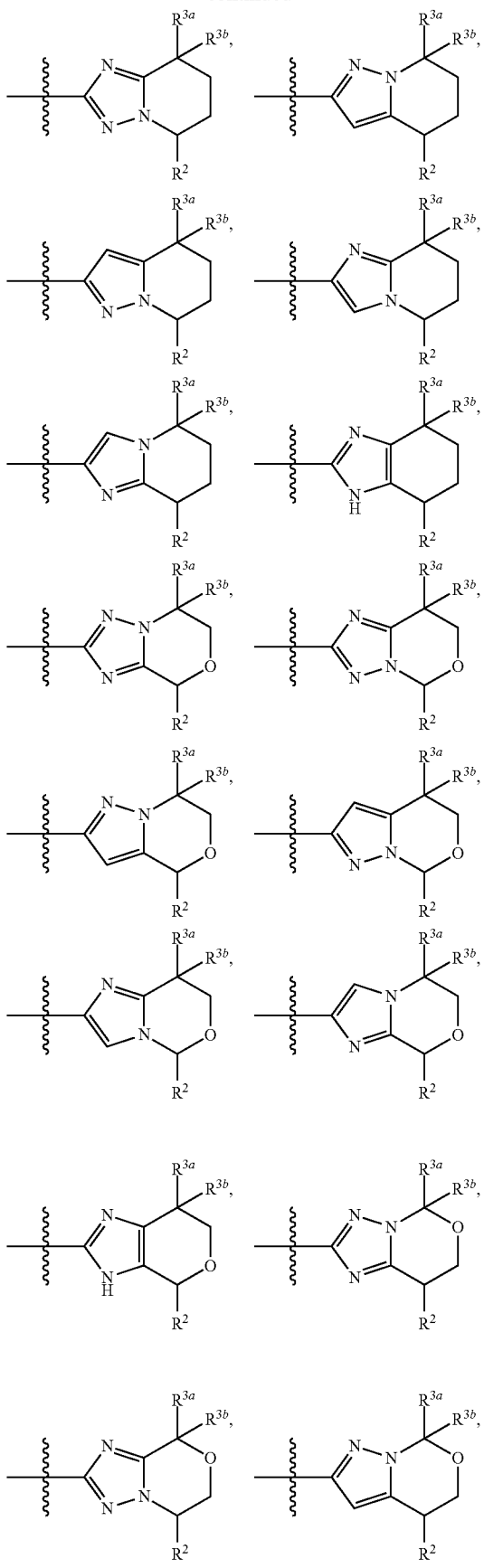
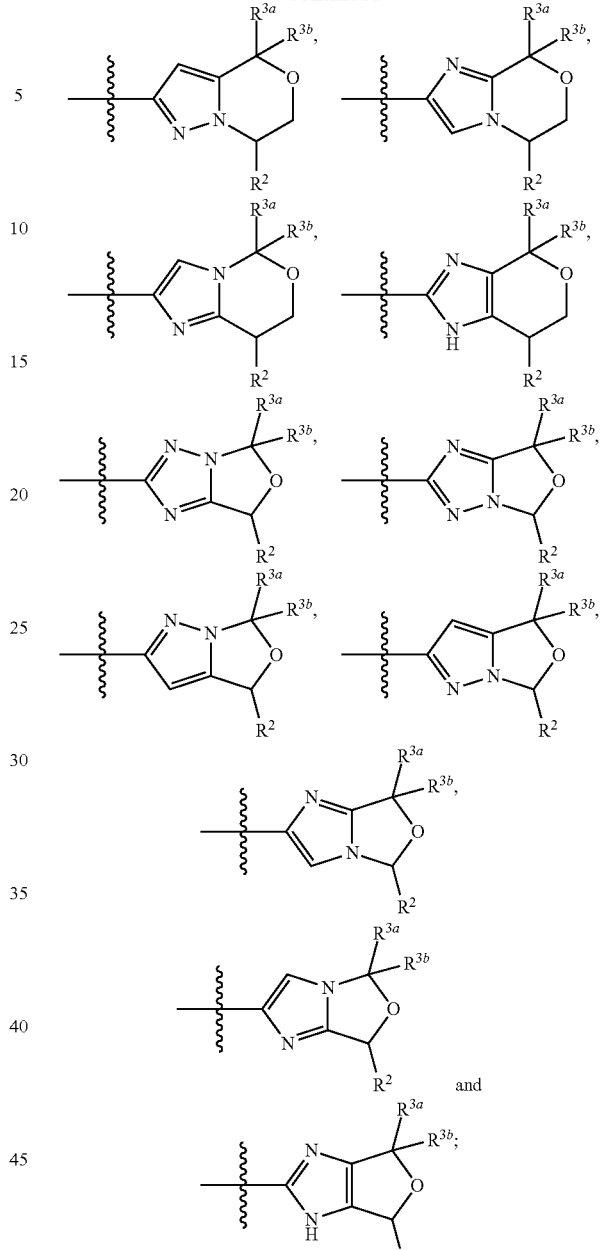

wherein
R² is selected from the group consisting of H, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano; and
$R^{3a}$ and $R^{3b}$ are selected as follows:
  (i) one of $R^{3a}$ and $R^{3b}$ is H, and the other is selected from the group consisting of D, F, Cl, OH, CN, $C_1$-$C_4$ alkyl, $C_1$-$C_4$ haloalkyl, cyclopropyl, $C_1$-$C_4$ alkoxy and $C_1$-$C_4$ haloalkoxy;

(ii) each of $R^{3a}$ and $R^{3b}$ is selected from the group consisting of D, F, Cl, OH, CN and methyl, provided that $R^{3a}$ and $R^{3b}$ cannot both be OH or CN; or (iii) $R^{3a}$ and $R^{3b}$ together form cyclopropyl.

In some embodiments of formula (I), $R^1$ is as defined above, and the A ring and the B ring together are selected from the group consisting of:

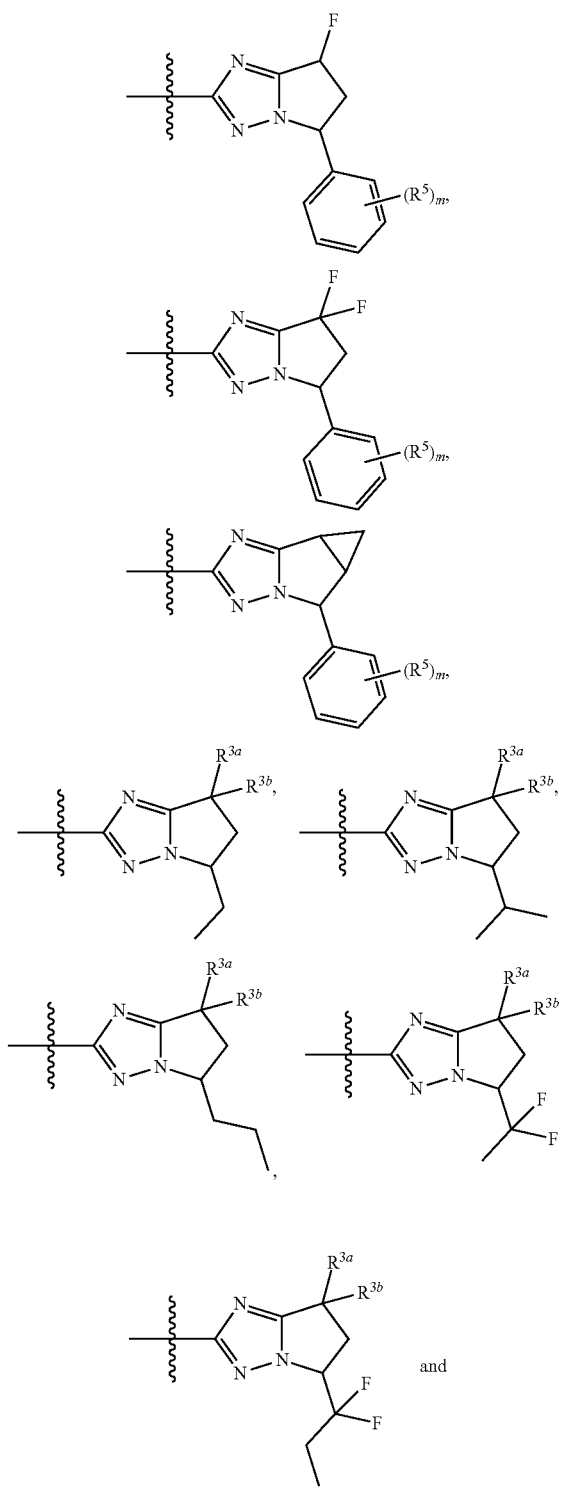

-continued

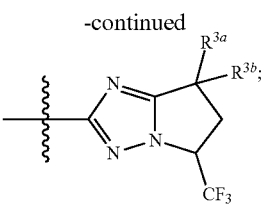

wherein $R^{3a}$ and $R^{3b}$ are selected as follows:

(i) one of $R^{3a}$ and $R^{3b}$ is H, and the other is selected from the group consisting of D, F, Cl, OH, CN, $C_1$-$C_4$ alkyl, $C_1$-$C_4$ haloalkyl, cyclopropyl, $C_1$-$C_4$ alkoxy and $C_1$-$C_4$ haloalkoxy;

(ii) each of $R^{3a}$ and $R^{3b}$ is selected from the group consisting of D, F, Cl, OH, CN and methyl, provided that $R^{3a}$ and $R^{3b}$ cannot both be OH or CN; or (iii) $R^{3a}$ and $R^{3b}$ together form cyclopropyl;

each $R^5$ is selected from the group consisting of H, F, Cl, $C_1$-$C_6$ alkyl, $C_1$-$C_6$ haloalkyl, $C_1$-$C_6$ alkoxy and $C_1$-$C_6$ haloalkoxy; and m is 1, 2 or 3.

In some embodiments of formula (I), R is as defined above, and the A ring and the B ring together are:

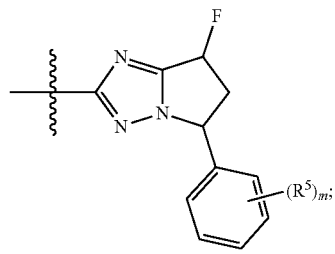

wherein each $R^5$ is selected from the group consisting of H, F, Cl, $C_1$-$C_6$ alkyl, $C_1$-$C_6$ haloalkyl, $C_1$-$C_6$ alkoxy and $C_1$-$C_6$ haloalkoxy; and m is 1, 2 or 3.

In some embodiments of formula (I), R is as defined above, and the A ring and the B ring together are selected from the group consisting of:

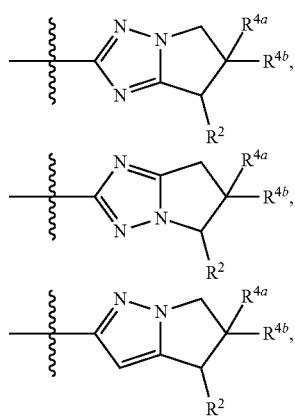

-continued
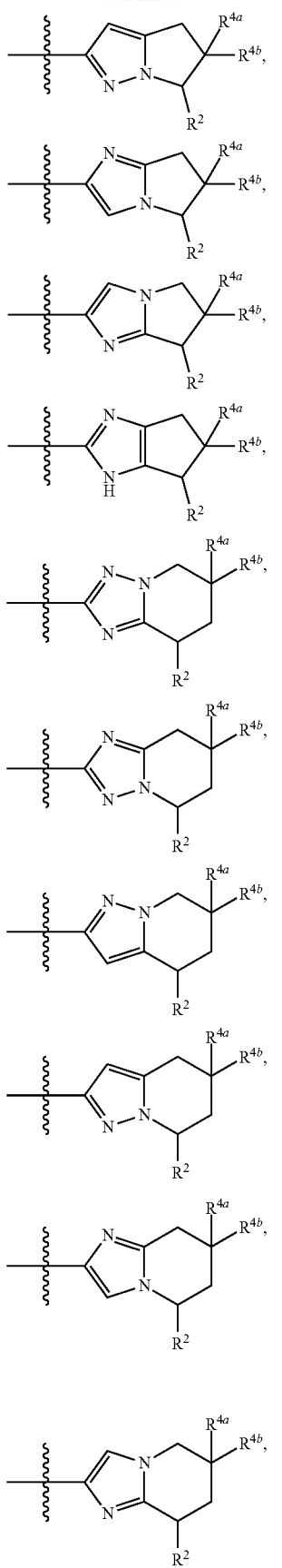
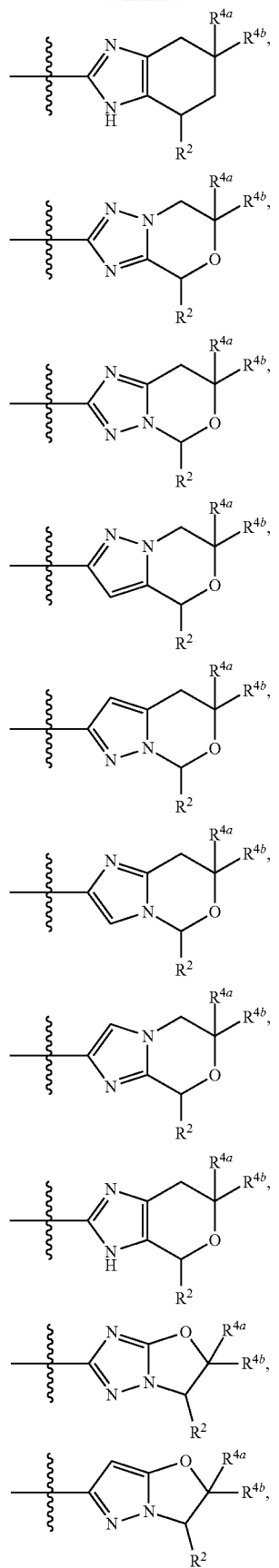

-continued

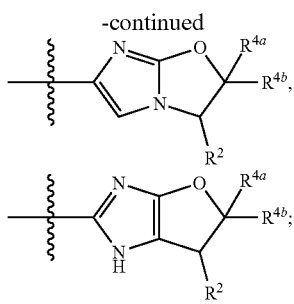

wherein
R² is selected from the group consisting of H, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;

$R^{4a}$ and $R^{4b}$ are selected as follows:
(i) one of $R^{4a}$ and $R^{4b}$ is H, and the other is selected from the group consisting of D, F, Cl, OH, CN, $C_1$-$C_4$ alkyl, $C_1$-$C_4$ haloalkyl, cyclopropyl, $C_1$-$C_4$ alkoxy and $C_1$-$C_4$ haloalkoxy; or
(ii) each of $R^{4a}$ and $R^{4b}$ is selected from the group consisting of D, F, Cl and methyl; and each $R^5$ is selected from the group consisting of H, F, Cl, $C_1$-$C_6$ alkyl, $C_1$-$C_6$ haloalkyl, $C_1$-$C_6$ alkoxy and $C_1$-$C_6$ haloalkoxy.

In some embodiments of formula (I), $R^1$ is as defined above, and the A ring and the B ring together are selected from the group consisting of:

wherein
$R^{4a}$ and $R^{4b}$ are selected as follows:
(i) one of $R^{4a}$ and $R^{4b}$ is H, and the other is selected from the group consisting of D, F, Cl, OH, CN, $C_1$-$C_4$ alkyl, $C_1$-$C_4$ haloalkyl, cyclopropyl, $C_1$-$C_4$ alkoxy and $C_1$-$C_4$ haloalkoxy; or
(ii) each of $R^{4a}$ and $R^{4b}$ is selected from the group consisting of D, F, Cl and methyl;
each $R^5$ is selected from the group consisting of H, F, Cl, $C_1$-$C_6$ alkyl, $C_1$-$C_4$ haloalkyl, $C_1$-$C_4$ alkoxy and $C_1$-$C_4$ haloalkoxy; and
m is 1,2 or 3.

In some of the above embodiments, $R^2$ is phenyl. In some embodiments, $R^2$ is mono- or difluorophenyl. In some embodiments, $R^2$ is mono- or dichlorophenyl. In some of the above embodiments, $R^2$ is pyridinyl. In some of the above embodiments, $R^2$ is chloro substituted pyridinyl. In some of the above embodiments, $R^2$ is fluoro substituted pyridinyl. In some of the above embodiments, $R^2$ is pyrazolyl. In some of the above embodiments, $R^2$ is 1-methyl-1H-pyrazol-4-yl. In some of the above embodiments, $R^2$ is 4-chloro-1-methyl-H-pyrazol-3-yl.

In some of the above embodiments, $R^{3a}$ and $R^{3b}$ are each H. In some of the above embodiments, $R^{3a}$ is H and $R^{3b}$ is F. In some of the above embodiments, $R^{3a}$ is H and $R^{3b}$ is Cl. In some of the above embodiments, $R^{3a}$ and $R^{3b}$ are each F. In some of the above embodiments, $R^{3a}$ and $R^{3b}$ are each Cl. In some of the above embodiments, $R^{3a}$ and $R^{3b}$ are each methyl. In some of the above embodiments, $R^{3a}$ is methyl and $R^{3b}$ is F. In some of the above embodiments, $R^{3a}$ is methyl and $R^{3b}$ is Cl. In some of the above embodiments, $R^{3a}$ is methyl and $R^{3b}$ is OH. In some of the above embodiments, $R^{3a}$ is methyl and $R^{3b}$ is CN. In some of the above embodiments, $R^{3a}$ and $R^{3b}$ are each D. In some of the above embodiments, $R^{3a}$ is H and $R^b$ is D. In some of the above embodiments, $R^{3a}$ is D and $R^{3b}$ is F. In some of the above embodiments, $R^{3a}$ is D and $R^{3b}$ is Cl. In some of the above embodiments, $R^{3a}$ is D and $R^{3b}$ is methyl.

In some of the above embodiments, $R^{4a}$ and $R^{4b}$ are each H. In some of the above embodiments one of $R^{4a}$ is H and $R^{4b}$ is F. In some of the above embodiments one of $R^{4a}$ is H and $R^{4b}$ is methyl. In some of the above embodiments one of $R^{4a}$ is H and $R^{4b}$ is Cl. In some of the above embodiments, $R^{4a}$ and R are each F. In some of the above embodiments, $R^{4a}$ and $R^{4b}$ are each D. In some of the above embodiments, $R^{4a}$ is H and $R^{4b}$ is D. In some of the above embodiments, $R^{4a}$ is D and $R^{4b}$ is F. In some of the above embodiments, $R^{4a}$ is D and $R^4$ is Cl.

In some of the above embodiments, $R^5$ is selected from the group consisting of H, F, Cl, $CH_3$, $CH_2CH_3$, $OCH_3$, $CF_3$, $OCF_3$, $CF_2H$, and $OCF_2H$.

In some of the above embodiments, m is 0. In some embodiments, m is 1. In some embodiments, m is 2.

In another embodiment, provided herein is a compound selected from the compounds of Table 1 below or a pharmaceutically acceptable salt thereof. In another embodiment, provided herein is a compound of Table 1 having a $K_i$ of less than 100 nM in a RIP1K biochemical or cell-based assay, including as herein described. In another embodiment, the compound of Table 1 has a $K_i$ of less than 50 nM in a RIP1K biochemical or cell-based assay, including as herein described. In yet another embodiment, the compound of Table 1 has a $K_i$ of less than 25 nM in a RIP1K biochemical or cell-based assay, including as herein described. In yet another embodiment, the compound of Table 1 has a $K_i$ of less than 10 nM in a RIP1K biochemical or cell-based assay, including as herein described.

In another embodiment, provided herein is a compound selected from the compounds of Table 2 below or a pharmaceutically acceptable salt thereof. In another embodiment, provided herein is a compound of Table 2 having a $K_i$ of less than 100 nM in a RIP1K biochemical or cell-based assay, including as herein described. In another embodiment, the compound of Table 2 has a $K_i$ of less than 50 nM in a RIP1K biochemical or cell-based assay, including as herein described. In yet another embodiment, the compound of Table 2 has a $K_i$ of less than 25 nM in a RIP1K biochemical or cell-based assay, including as herein described. In yet another embodiment, the compound of Table 2 has a $K_i$ of less than 10 nM in a RIP1K biochemical or cell-based assay, including as herein described.

In some embodiments, provided herein is a single stereoisomer of a compound of Table 1 or Table 2, as characterized by reference to its chiral separation and isolation (e.g., as described in the Examples by chiral SFC).

In some embodiments, provided herein are pharmaceutical compositions comprising a compound of formula I as described in any one of the above embodiments, or a pharmaceutically acceptable salt thereof, and one or more pharmaceutically acceptable carriers or excipients. Specific embodiments include pharmaceutical compositions suitable for oral delivery.

Also provided herein are oral formulations of a compound of formula I as described in any one of the above embodiments, or a pharmaceutically acceptable salt thereof, and one or more pharmaceutically acceptable carriers or excipients suitable for oral delivery.

In some embodiments, provided herein are uses of a compound of formula I as described in any one of the above embodiments, or a pharmaceutically acceptable salt thereof, for the treatment of neurodegenerative diseases and disorders. In some embodiments, the diseases and disorders to be treated are synucleopathies such as Parkinson's Disease, Lewy body dementia, multiple system atrophy, Parkinson-plus syndromes. In some embodiments, the diseases and disorders to be treated are taupathies such as Alzheimer's Disease and frontotemporal dementia. In some embodiments, the diseases and disorders to be treated are demyelination diseases such as multiple sclerosis.

In some embodiments, the diseases and disorders to be treated are other neurodegenerative diseases such as amyotrophic lateral sclerosis, spinal muscular atrophy, primary lateral sclerosis, Huntington's disease, ischemia, and stroke. Additional exemplary neurodegenerative diseases to be treated as provided herein include, but are not limited to, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

In some embodiments, the disease or disorder to be treated is Alzheimer's disease. In some embodiments, the disease or disorder to be treated is Parkinson's disease. In some embodiments, the disease or disorder to be treated is Huntington's disease. In some embodiments, the disease or disorder to be treated is multiple sclerosis. In some embodiments, the disease or disorder to be treated is amyotrophic lateral sclerosis (ALS). In some embodiments, the disease or disorder to be treated is spinal muscular atrophy (SMA).

In some embodiments, provided herein are uses of a compound of formula I as described in any one of the above embodiments, or a pharmaceutically acceptable salt thereof, for the treatment of inflammatory diseases and disorders. In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atrophy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the disease or disorder to be treated is an inflammatory bowel disease. In some embodiments, the disease or disorder to be treated is Crohn's disease. In some embodiments, the disease or disorder to be treated is ulcerative colitis. In some embodiments, the disease or disorder to be treated is glaucoma. In some embodiments, the disease or disorder to be treated is psoriasis. In some embodiments, the disease or disorder to be treated is rheumatoid arthritis. In some embodiments, the disease or disorder to be treated is spondyloarthritis. In some embodiments, the disease or disorder to be treated is juvenile idiopathic arthritis. In some embodiments, the disease or disorder to be treated is osteoarthritis.

In some embodiments, provided herein are methods for the treatment or prevention of a disease or disorder with a therapeutically effective amount of a compound of formula I, or a pharmaceutically acceptable salt thereof, wherein the disease or disorder is associated with inflammation and/or necroptosis. In some embodiments said disease or disorder is selected from the specific diseases and disorders recited herein.

In some embodiments, provided herein are methods of inhibiting RIP1 kinase activity by contacting a cell with a compound of formula I or a pharmaceutically acceptable salt thereof.

Pharmaceutical Compositions and Administration

Provided herein are pharmaceutical compositions or medicaments containing the compounds of the invention (or stereoisomers, geometric isomers, tautomers, solvates, metabolites, isotopes, pharmaceutically acceptable salts, or prodrugs thereof), and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In some embodiments, the "effective amount" of the compound to be administered will be governed by such considerations, and is the minimum amount necessary to inhibit RIP1 kinase activity in order to provide a therapeutic effect in the mammal being treated. In addition, such an effective amount may be below the amount that is toxic to normal cells, or the mammal as a whole.

In one example, the pharmaceutically effective amount of the compound of the invention administered intravenously or parenterally will be in the per dose range of about 0.1 to 100 mg/kg, alternatively about 0.1 to 20 mg/kg of patient body weight per day, or alternatively about 0.3 to 15 mg/kg/day.

In another embodiment, oral unit dosage forms, such as tablets and capsules, preferably contain from about 1 to about 1000 mg (e.g., 1 mg, 5 mg, 10 mg, 15 mg, 20 mg, 25 mg, 30 mg, 40 mg, 50 mg, 100 mg, 200 mg, 250 mg, 400 mg, 500 mg, 600 mg, 700 mg, 800 mg, 900 mg, or 1000 mg) of the compound of the invention. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

In some embodiments, a low dose of the compound of the invention is administered in order to provide therapeutic benefit while minimizing or preventing adverse effects.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In specific embodiments, the compound of formula I is administered orally. In other specific embodiments, the compound of formula I is administered intravenously.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, PA Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

An example of a suitable oral dosage form provided herein is a tablet containing about 1 to about 500 mg (e.g., about 1 mg, 5 mg, 10 mg, 25 mg, 30 mg, 50 mg, 80 mg, 100 mg, 150 mg, 250 mg, 300 mg and 500 mg) of the compound of the invention compounded with suitable amounts of anhydrous lactose, sodium croscarmellose, polyvinylpyrrolidone (PVP) K30, and magnesium stearate. The powdered ingredients are first mixed together and then mixed with a solution of the PVP. The resulting composition can be dried, granulated, mixed with the magnesium stearate and compressed to tablet form using conventional equipment.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 g of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

An embodiment, therefore, includes a pharmaceutical composition comprising a compound of formula I, or pharmaceutically acceptable salt thereof. In a further embodiment includes a pharmaceutical composition comprising a compound of formula I, or a pharmaceutically acceptable salt thereof, together with a pharmaceutically acceptable carrier or excipient.

When the binding target is located in the brain, certain embodiments of the invention provide for a compound of formula I (or an embodiment thereof) to traverse the blood-brain barrier. In these embodiments, the compounds provided herein exhibit sufficient brain penetration as potential therapeutics in neurological diseases. In some embodiments, brain penetration is assessed by evaluating free brain/plasma ratio (B/P) as measured in vivo pharmacokinetic studies in rodents or by other methods known to persons skilled in the art (see, e.g., Liu, X. et al., J. Pharmacol. Exp. Therap., 325:349-56, 2008).

Certain neurological diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods. Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™ Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Publication No. 2002/0025313), and coating a compound of formula I (or an embodiment thereof) in low-density lipoprotein particles (see, e.g., U.S. Patent Publication No. 2004/0204354) or apolipoprotein E (see, e.g., U.S. Patent Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Publication Nos. 2002/0065259, 2003/0162695, and 2005/0124533); activating potassium channels (see, e.g., U.S. Patent Publication No. 2005/0089473), inhibiting ABC drug transporters (see, e.g., U.S. Patent Publication No. 2003/0073713); coating a compound of formula I or I-I (or an embodiment thereof) with a transferrin and modulating activity of the one or more transferrin receptors (see, e.g., U.S. Patent Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

The compounds of the invention inhibit RIP1 kinase activity. Accordingly, the compounds of the invention are useful for the treatment of diseases and disorders mediated by this pathway and associated with inflammation and/or necroptotic cell death.

In some embodiments, the disease or disorder to be treated is a neurodegenerative disease or disorder. In some embodiments, the diseases and disorders to be treated are synucleopathies such as Parkinson's Disease, Lewy body dementia, multiple system atrophy, Parkinson-plus syndromes. In some embodiments, the diseases and disorders to be treated are taupathies such as Alzheimer's Disease and frontotemporal dementia. In some embodiments, the diseases and disorders to be treated are demyelination diseases such as multiple sclerosis.

In some embodiments, the diseases and disorders to be treated are other neurodegenerative diseases such as amyotrophic lateral sclerosis, spinal muscular atrophy, primary lateral sclerosis, Huntington's disease, ischemia, and stroke. Additional exemplary neurodegenerative diseases to be treated as provided herein include, but are not limited to, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

In some embodiments, the disease or disorder to be treated is Alzheimer's disease. In some embodiments, the disease or disorder to be treated is Parkinson's disease. In some embodiments, the disease or disorder to be treated is Huntington's disease. In some embodiments, the disease or disorder to be treated is multiple sclerosis. In some embodiments, the disease or disorder to be treated is amyotrophic lateral sclerosis (ALS). In some embodiments, the disease or disorder to be treated is spinal muscular atrophy (SMA).

In some embodiments, the disease or disorder to be treated is an inflammatory disease or disorder. In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atrophy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the disease or disorder to be treated is an inflammatory bowel disease. In some embodiments, the disease or disorder to be treated is Crohn's disease. In some embodiments, the disease or disorder to be treated is ulcerative colitis. In some embodiments, the disease or disorder to be treated is glaucoma. In some embodiments, the disease or disorder to be treated is psoriasis. In some embodiments, the disease or disorder to be treated is rheumatoid arthritis. In some embodiments, the disease or disorder to be treated is spondyloarthritis. In some embodiments, the disease or disorder to be treated is juvenile idiopathic arthritis. In some embodiments, the disease or disorder to be treated is osteoarthritis.

In some embodiments, the method of treatment provided herein is the treatment of one or more symptoms of a disease or disorder listed above.

Also provided herein is the use of a compound of the invention in therapy. In some embodiments, provided herein is the use of a compound of the invention for the treatment or prevention of the above diseases and disorders. Also provided herein is the use of a compound of the invention in the manufacture of a medicament for the treatment or prevention of the above diseases and disorders.

Also provided herein is a method of treating a disease or disorder as provided above in a mammal in need of such treatment, wherein the method comprises administering to said mammal a therapeutically effective amount of a compound of formula I, or a pharmaceutically acceptable salt thereof. In some embodiments, the mammal is a human.

Also provided herein is a method of treating a symptom of a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a disease or disorder in a human patient in need of such treatment, said disease or disorder being selected from those provided above, wherein the method comprises orally administering a therapeutically effective amount of a compound of formula I, or a pharmaceutically acceptable salt thereof, as an orally acceptable pharmaceutical composition.

Combination Therapy

Compounds of the invention may be combined with one or more other compounds of the invention or one or more other therapeutic agent as any combination thereof, in the treatment of the diseases and disorders provided herein. For example, a compound of the invention may be administered simultaneously, sequentially or separately in combination with other therapeutic agents known to be useful for the treatment of a disease or disorder selected from those recited above.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In some embodiments, a compound provided herein may be combined with another therapeutically active agent as recited in WO 2016/027253, the contents of which are hereby incorporated by reference in their entirety. In such embodiments, the compound that inhibits RIP1 kinase in the combinations recited in WO 2016/027253 is replaced by a compound of formula I of the present disclosure.

In some embodiments, a compound provided herein may be combined with a DLK inhibitor for the treatment of neurodegenerative diseases and disorders, such as those listed elsewhere herein, and including but not limited to the following: Parkinson's Disease, Lewy body dementia, multiple system atrophy, Parkinson-plus syndromes, Alzheimer's Disease, frontotemporal dementia, demyelination diseases such as multiple sclerosis, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, and corticobasal degeneration. DLK inhibitors are described, for example, in WO 2013/174780, WO 2014/177524, WO 2014/177060, WO 2014/111496, WO 2015/091889 and WO 2016/142310.

EXAMPLES

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated $CDCl_3$, $d_6$-DMSO, $CH_3OD$ or $d_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

All abbreviations used to describe reagents, reaction conditions or equipment are intended to be consistent with the definitions set forth in the following list of Abbreviations. The chemical names of discrete compounds of the invention were typically obtained using the structure naming feature of ChemDraw naming program.

ABBREVIATIONS

ACN Acetonitrile

Boc tert-Butoxycarbonyl

DAST Diethylaminosulfur trifluoride

DCE 1,2-dichloroethane

DCM Dichloromethane

DMF N,N-Dimethylformamide

DMSO Dimethyl sulfoxide

DPPH 2,2-Diphenyl-1-picrylhydrazyl

HPLC High Pressure Liquid Chromatography

LCMS Liquid Chromatography Mass Spectrometry

PCC Pyridinium chlorochromate

RP Reverse phase

RT or $R_T$ Retention time

SEM 2-(Trimethylsilyl)ethoxymethyl

SFC Supercritical Fluid Chromatography

TFA Trifluoroacetic acid

THF Tetrahydrofuran

Synthetic Schemes

In addition to the specific synthetic methods of the examples below, additional compounds of the present invention may be prepared, for example, according to the following synthetic schemes.

After following steps 1-5 of Method 9 below, Scheme 1 is followed to prepare gem-difluoro moieties:

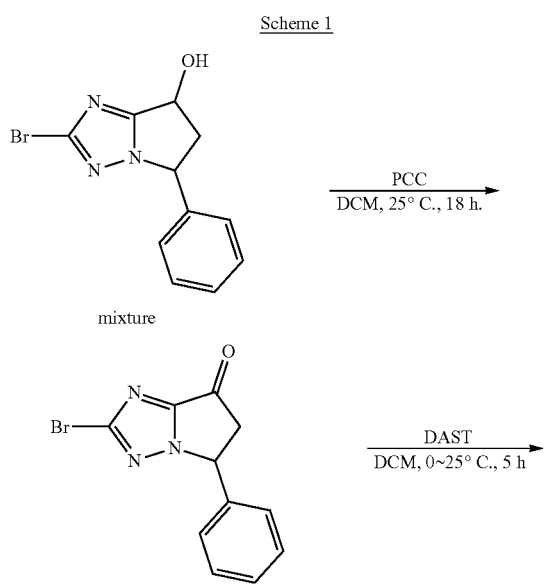

-continued
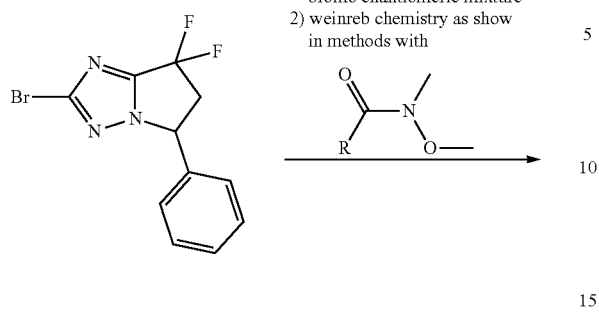
Scheme 2 is followed to prepare additional B ring diversity of compounds of formula I using a variety of nucleophiles including but not limited to halide and cyanide sources:
Scheme 3 is followed to prepare gem-dimethyl B ring substituted compounds of formula I:
Scheme 3
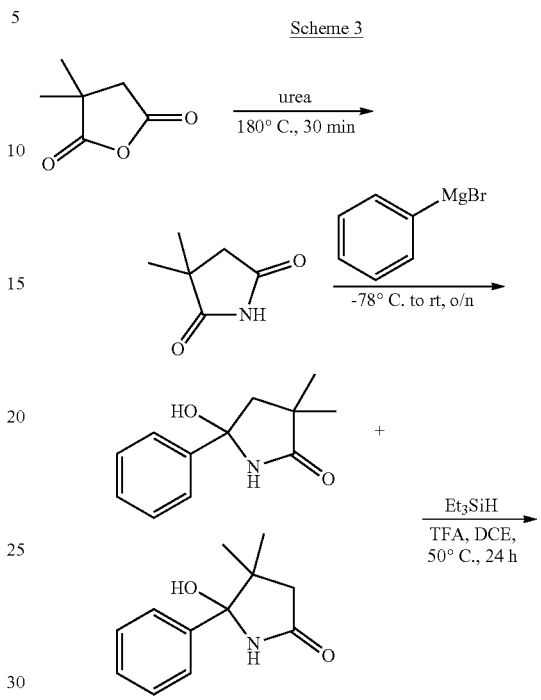
Scheme 2
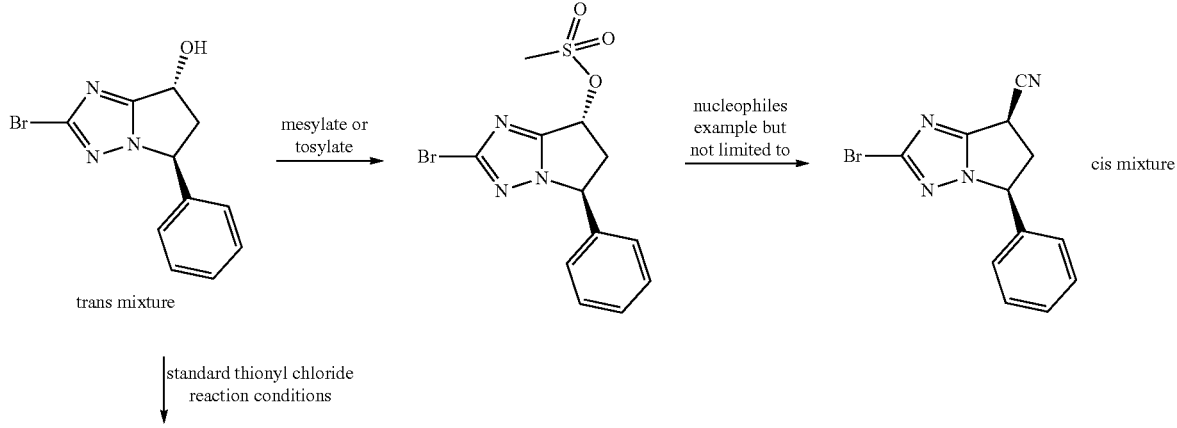
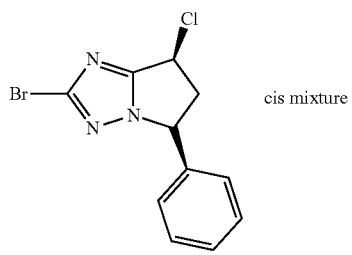

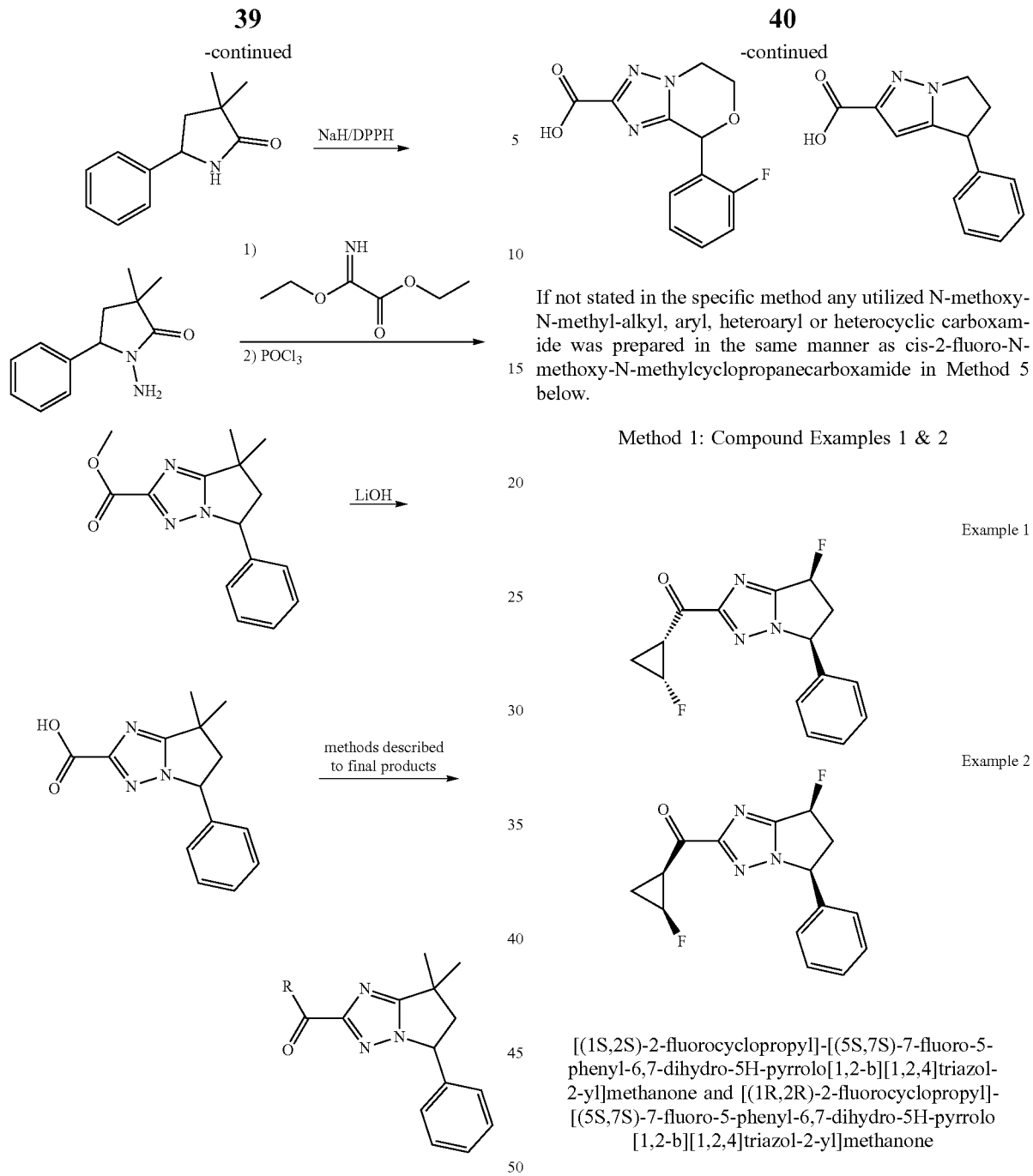

If not stated in the specific method any utilized N-methoxy-N-methyl-alkyl, aryl, heteroaryl or heterocyclic carboxamide was prepared in the same manner as cis-2-fluoro-N-methoxy-N-methylcyclopropanecarboxamide in Method 5 below.

Method 1: Compound Examples 1 & 2

Example 1

Example 2

[(1S,2S)-2-fluorocyclopropyl]-[(5S,7S)-7-fluoro-5-phenyl-6,7-dihydro-5H-pyrrolo[1,2-b][1,2,4]triazol-2-yl]methanone and [(1R,2R)-2-fluorocyclopropyl]-[(5S,7S)-7-fluoro-5-phenyl-6,7-dihydro-5H-pyrrolo[1,2-b][1,2,4]triazol-2-yl]methanone To a cooled (–70° C.) solution of (5S,7S)-2-bromo-7-fluoro-5-phenyl-6,7-dihydro-5H-pyrrolo[1,2-b][1,2,4]triazole (150 mg, 0.53 mmol) and cis-2-fluoro-N-methoxy-N-methyl-cyclopropanecarboxamide (157 mg, 1.06 mmol) in tetrahydrofuran (12 mL) was added n-butyllithium (2.5 M in hexanes, 0.64 mL, 1.60 mmol) dropwise under nitrogen atmosphere. After addition, the mixture was stirred at –70° C. for 1 h and then quenched by addition of saturated aqueous ammonium chloride (10 mL). The resulting mixture was extracted with ethyl acetate (3×15 mL). The combined organic layers were concentrated under reduce pressure and the residue was purified by RP-HPLC (acetonitrile 20-45%/0.225% HCl in water). The racemic material was further separated by chiral SFC to afford arbitrarily assigned:

[(1S,2S)-2-fluorocyclopropyl]-[(5S,7S)-7-fluoro-5-phenyl-6,7-dihydro-5H-pyrrolo[1,2-b][1,2,4]triazol-2-yl]methanone (Peak 1, retention time=3.635 min) (4.0 mg, The following intermediates used in the examples below were prepared according to the procedures described in WO 2017/004500 (the entirety of which is incorporated herein by reference):

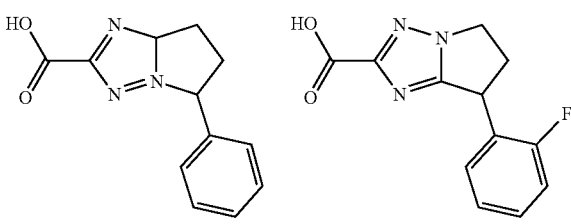

2.5%) as a white solid. $^1$H NMR (400 MHz, CD$_3$OD) δ 7.44-7.39 (m, 3H), 7.30-7.28 (m, 2H), 6.20-6.18 (m, 0.5H), 6.06-6.04 (m, 0.5H), 5.65-5.64 (m, 1H), 5.04-5.02 (m, 0.5H), 4.90-4.87 (m, 0.5H), 3.80-3.74 (m, 1H), 3.25-3.21 (m, 1H), 2.88-2.81 (m, 1H), 2.03-1.96 (m, 1H), 1.34-1.28 (m, 1H). LCMS $R_T$=1.662 min, m/z=290.1 [M+H]$^+$. LCMS (5 to 95% acetonitrile in water+0.03% trifluoacetic acid over 1.5 mins) retention time 1.662 min, ESI+ found [M+H]= 290.1.

[(1R,2R)-2-fluorocyclopropyl]-[(5S,7S)-7-fluoro-5-phenyl-6,7-dihydro-5H-pyrrolo[1,2-b][1,2,4]triazol-2-yl]methanone (Peak 2, retention time=3.995 min) (15.9 mg, 10%) as a white solid. $^1$H NMR (400 MHz, CD$_3$OD) δ 7.44-7.38 (m, 3H), 7.30-7.28 (m, 2H), 6.21-6.18 (m, 0.5H), 6.06-6.05 (m, 0.5H), 5.66-5.65 (m, 1H), 5.05-5.04 (m, 0.5H), 4.90-4.87 (m, 0.5H), 3.82-3.74 (m, 1H), 3.23-3.20 (m, 1H), 2.88-2.82 (m, 1H), 2.02-1.96 (m, 1H), 1.34-1.30 (m, 1H). LCMS $R_T$=1.654 min, m/z=290.1 [M+H]$^+$. LCMS (5 to 95% acetonitrile in water+0.03% trifluoacetic acid over 1.5 mins) retention time 1.654 min, ESI+ found [M+H]= 290.1.

SFC condition: Column: Chiralcel OD-3 150×4.6 mm I.D., 3 μm Mobile phase: A: CO$_2$ B:iso-propanol (0.05% DEA) Gradient: from 5% to 40% of B in 5 min and hold 40% for 2.5 min, then 5% of B for 2.5 min Flow rate: 2.5 mL/min Column temp. 35° C.

Method 2: Compound Examples 3 & 4

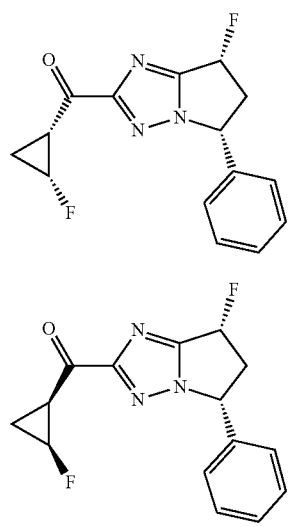

Example 3

Example 4

[(1S,2S)-2-fluorocyclopropyl]-[(5R,7R)-7-fluoro-5-phenyl-6,7-dihydro-5H-pyrrolo[1,2-b][1,2,4]triazol-2-yl]methanone and [(1R,2R)-2-fluorocyclopropyl]-[(5R,7R)-7-fluoro-5-phenyl-6,7-dihydro-5H-pyrrolo[1,2-b][1,2,4]triazol-2-yl]methanone To a cooled (−70° C.) solution of (5R,7R)-2-bromo-7-fluoro-5-phenyl-6,7-dihydro-5H-pyrrolo[1,2-b][1,2,4]triazole (150 mg, 0.53 mmol) and cis-2-fluoro-N-methoxy-N-methyl-cyclopropanecarboxamide (156.5 mg, 1.06 mmol) in tetrahydrofuran (10 mL) was added n-butyllithium (2.5 M in hexanes, 0.64 mL, 1.60 mmol) dropwise under nitrogen atmosphere. After addition, the mixture was stirred at −70° C. for 1 h and then quenched by addition of saturated aqueous ammonium chloride (30 mL). The resulting mixture was extracted with ethyl acetate (3×15 mL). The combined organic layers were concentrated under reduce pressure and the residue was purified by RP-HPLC (acetonitrile 35-65%/ 0.05% ammonia hydroxide in water) to afford [cis-2-fluorocyclopropyl]-[(5R,7R)-7-fluoro-5-phenyl-6,7-dihydro-5H-pyrrolo[1,2-b][1,2,4]triazol-2-yl]methanone (35 mg, 22.5%) as a pink solid. The racemic material was separated by chiral SFC to give arbitrarily assigned:

[(1S,2S)-2-fluorocyclopropyl]-[(5R,7R)-7-fluoro-5-phenyl-6,7-dihydro-5H-pyrrolo[1,2-b][1,2,4]triazol-2-yl]methanone (Peak 1, Retention time=4.787 min) (5.9 mg, 17%) as a white solid. $^1$H NMR (400 MHz, CDCl$_3$) δ 7.44-7.39 (m, 3H), 7.28-7.27 (m, 2H), 6.13-6.11 (m, 1H), 5.99-5.97 (m, 1H), 5.53-5.49 (m, 1H), 3.69-3.61 (m, 1H), 3.27-3.24 (m, 1H), 3.03-2.96 (m, 1H), 2.23-2.15 (m, 1H), 1.29-1.24 (m, 1H). LC-MS $R_T$=0.846 min, m/z=289.9 (M+H)+. LCMS (5 to 95% acetonitrile in water+0.03% trifluoacetic acid over 1.5 mins) retention time 0.846 min, ESI+ found [M+H]=289.9.

[(1R,2R)-2-fluorocyclopropyl]-[(5R,7R)-7-fluoro-5-phenyl-6,7-dihydro-5H-pyrrolo[1,2-b][1,2,4]triazol-2-yl]methanone (Peak 2, Retention time=5.711 min) (11.7 mg, 33%) as a white solid. $^1$H NMR (400 MHz, CDCl$_3$) δ 7.44-7.37 (m, 3H), 7.28-7.27 (m, 2H), 6.13-6.11 (m, 1H), 5.99-5.97 (m, 1H), 5.53-5.50 (m, 1H), 3.69-3.63 (m, 1H), 3.27-3.23 (m, 1H), 3.03-2.96 (m, 1H), 2.23-2.16 (m, 1H), 1.29-1.24 (m, 1H). LC-MS $R_T$=0.849 min, m/z=289.9 (M+H)+. LCMS (5 to 95% acetonitrile in water+0.03% trifluoacetic acid over 1.5 mins) retention time 0.849 min, ESI+ found [M+H]=289.9.

SFC condition: Column: Chiralcel OD-3 150×4.6 mm I.D., 3 μm Mobile phase: A: CO2 B:iso-propanol (0.05% DEA) Gradient: from 5% to 40% of B in 5 min and hold 40% for 2.5 min, then 5% of B for 2.5 min Flow rate: 2.5 mL/min Column temp: 35° C.

Chiral SFC Purification and Analytical Conditions:
In the methods provided in the following table, Solvent A is carbon dioxide and Solvent B is 0.1% NH$_4$(aq) in CH$_3$OH.

| Compound/ Method Peak/RT | Instrument | Initial % B | Final % B | Wavelength (nM) | column | column dimensions. | flow rate | column temp |
|---|---|---|---|---|---|---|---|---|
| Ex. 5/SP 5 Prep Peak 2 | PIC 100 Chiral | 15 | 15 | 211 | Chiralpak IG | 150 × 21.2 mm | 70 | 40 |
| Ex. 5/SP 5 Analytical Peak 2 R.T = 1.450 min | Waters UPC | 15 | 15 | 220 | Chiralpak IG | | | 40.0 |
| Ex. 6/SP 6 Prep | PIC 100 Chiral | 15 | 15 | 211 | Chiralpak IG | 150 × 21.2 mm | 70 | 40 |

-continued

| Compound/Method Peak/RT | Instrument | Initial % B | Final % B | Wavelength (nM) | column | column dimensions | flow rate | column temp |
|---|---|---|---|---|---|---|---|---|
| Peak 1 Ex. 6/SP 6 Analytical Peak 1 1.146 min | Waters UPC | 15 | 15 | 220 | Chiralpak IG | | | 40.0 |
| Ex. 37/ SP 37 Prep Peak 1 | PIC 100 Chiral | 20 | 20 | 220 | Chiralpak AD | 150 × 21.2 mm | 70 | 30 |
| Ex. 37/ SP 37 Analytical Peak 1 R.T = 0.427 min | Water UPC | 10 | 10 | 220 | Chiralpak AD | | | 40 |
| Ex. 38/ SP 38 Prep Peak 2 | PIC 100 Chiral | 20 | 20 | 220 | Chiralpak AD | 150 × 21.2 mm | 70 | 40 |
| Ex. 38/ SP 38 Analytical Peak 2 0.534 min | Water UPC | 10 | 10 | 220 | Chiralpak AD | | | 40 |
| Ex. 39/ SP 39 Prep Peak 2 | PIC 100 Chiral | 20 | 20 | 270 | Chiralpak AD | 150 × 21.2 mm | 70 | 40 |
| Ex. 39/ SP 39 Analytical Peak 2 R.T = 0.993 min | Waters UPC | 20 | 20 | 254 | Chiralpak AD | | | 40 |
| Ex. 40/ SP 40 Prep Peak 1 | PIC 100 Chiral | 20 | 20 | 270 | Chiralpak AD | 150 × 21.2 mm | 70 | 40 |
| Ex. 40/ SP 40 Analytical Peak 1 R.T = 0.861 min | Waters UPC | 20 | 20 | 254 | Chiralpak AD | | | 40 |

Method SP 5

Example 5

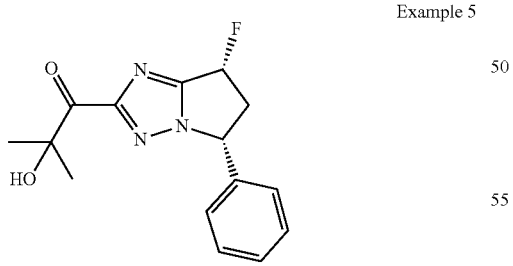

2-hydroxy-2-methyl-1-[rac-(5R,7R)-7-fluoro-5-phenyl-6,7-dihydro-5H-pyrrolo[1,2-b][1,2,4]triazol-2-yl]propan-1-one Arbitrarily assigned 2-hydroxy-2-methyl-1-[rac-(5R,7R)-7-fluoro-5-phenyl-6,7-dihydro-5H-pyrrolo[1,2-b][1,2,4]triazol-2-yl]propan-1-one (10.94 mg, 43% yield). $^1$H NMR (400 MHz, DMSO-$d_6$) δ 7.50-7.33 (m, 2H), 7.29-7.14 (m, 2H), 6.40-6.05 (m, 1H), 5.81-5.63 (m, 1H), 5.23 (s, 1H), 2.98-2.56 (m, 1H), 1.51 (s, 3H), 1.48 (s, 3H). LC-MS $R_T$=4.029 min, m z=290.1 (M+H).

Method SP 6

Example 6

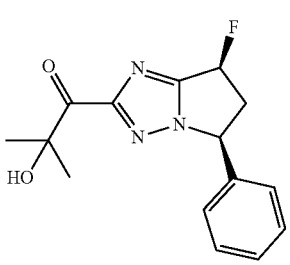

2-hydroxy-2-methyl-1-[rac-(5S,7S)-7-fluoro-5-phenyl-6,7-dihydro-5H-pyrrolo[1,2-b][1,2,4]triazol-2-yl]propan-1-one Arbitrarily assigned 2-hydroxy-2-methyl-1-[rac-(5S,7S)-7-fluoro-5-phenyl-6,7-dihydro-5H-pyrrolo[1,2-b][1,2,4]triazol-2-yl]propan-1-one (11.1 mg, 43% yield). $^1$H NMR (400 MHz, DMSO-$d_6$) δ 7.47-7.31 (m, 3H), 7.30-7.12 (m, 2H), 6.37-6.01 (m, 1H), 5.82-5.53 (m, 1H), 5.23 (s, 1H), 2.85-2.59 (m, 1H), 1.52-1.47 (m, 6H). LC-MS $R_T$=4.029 min, m/z=290.1 (M+H).

Method SP 37

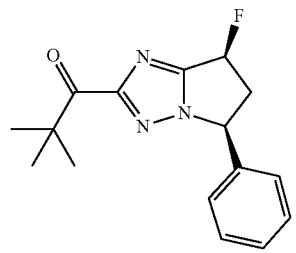

Example 37

2,2-dimethyl-1-[rac-(5S,7S)-7-fluoro-5-phenyl-6,7-dihydro-5H-pyrrolo[1,2-b][1,2,4]triazol-2-yl]propan-1-one Arbitrarily assigned 2,2-dimethyl-1-[rac-(5S,7S)-7-fluoro-5-phenyl-6,7-dihydro-5H-pyrrolo[1,2-b][1,2,4]triazol-2-yl]propan-1-one (2.84 mg, 48% yield). LC-MS $R_T$=5.26 min, m/z=288.1 (M+H).

Method SP 38

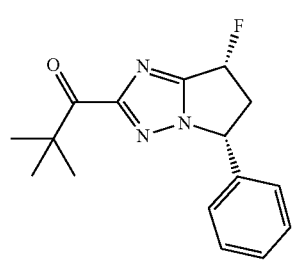

Example 38

2,2-dimethyl-1-[rac-(5R,7R)-7-fluoro-5-phenyl-6,7-dihydro-5H-pyrrolo[1,2-b][1,2,4]triazol-2-yl]propan-1-one Arbitrarily assigned 2,2-dimethyl-1-[rac-(5R,7R)-7-fluoro-5-phenyl-6,7-dihydro-5H-pyrrolo[1,2-b][1,2,4]triazol-2-yl]propan-1-one (4.2 mg, 77% yield). LC-MS $R_T$=5.26 min, m/z=288.1 (M+H).

Method SP 39

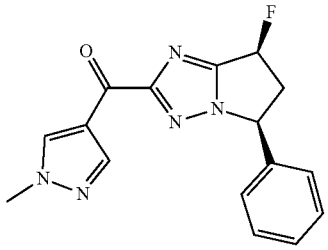

Example 39

(1-methylpyrazol-4-yl)-[rac-(5R,7R)-7-fluoro-5-phenyl-6,7-dihydro-5H-pyrrolo[1,2-b][1,2,4]triazol-2-yl]methanone Arbitrarily assigned (1-methylpyrazol-4-yl)-[rac-(5R,7R)-7-fluoro-5-phenyl-6,7-dihydro-5H-pyrrolo[1,2-b][1,2,4]triazol-2-yl]methanone (19.23 mg, 77% yield). $^1$H NMR (400 MHz, DMSO-$d_6$) δ 8.69 (s, 1H), 8.18 (d, J=0.7 Hz, 1H), 7.48-7.34 (m, 3H), 7.30-7.22 (m, 2H), 6.43-6.09 (m, 1H), 5.88-5.62 (m, 1H), 3.93 (s, 3H), 3.87-3.58 (m, 1H). LC-MS $R_T$=3.99 min, m/z=312.1 (M+H).

Method SP 40

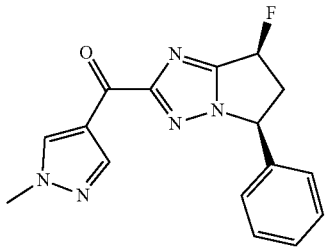

Example 40

(1-methylpyrazol-4-yl)-[rac-(5S,7S)-7-fluoro-5-phenyl-6,7-dihydro-5H-pyrrolo[1,2-b][1,2,4]triazol-2-yl]methanone Arbitrarily assigned (1-methylpyrazol-4-yl)-[rac-(5S,7S)-7-fluoro-5-phenyl-6,7-dihydro-5H-pyrrolo[1,2-b][1,2,4]triazol-2-yl]methanone (20.4 mg, 82% yield). $^1$H NMR (400 MHz, DMSO-$d_6$) δ 8.68 (s, 1H), 8.18 (s, 1H), 7.48-7.33 (m, 3H), 7.32-7.06 (m, 2H), 6.43-6.08 (m, 1H), 5.92-5.62 (m, 1H), 3.93 (s, 3H), 2.96-2.57 (m, 1H). LC-MS $R_T$=3.99 min, m/z=312.1 (M+H).

Method 3

Example 7

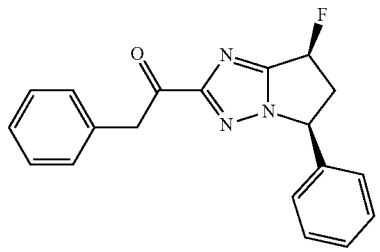

2-phenyl-1-[rac-(5S,7S)-7-fluoro-5-phenyl-6,7-di-hydro-5H-pyrrolo[1,2-b][1,2,4]triazol-2-yl]ethanone To a solution of ethyl [rac-(5S,7S)-7-fluoro-5-phenyl-6,7-dihydro-5H-pyrrolo[1,2-b][1,2,4]triazole-2-carboxylate (100 mg, 0.363 mmol) in tetrahydrofuran (2 mL) was added benzylmagnesium chloride (2 M in tetrahydrofuran, 0.20 mL, 0.400 mmol) at −78° C. under nitrogen. After addition, the reaction mixture was stirred at −78° C. for 1 h and then quenched by addition of saturated aqueous ammonium chloride (1 mL). The mixture was extracted with isopropyl acetate (3×10 mL). The combined organic layers were dried over anhydrous sodium sulfate and concentrated to dryness under reduced pressure. The residue was purified by column chromatography (silica gel, 100-200 mesh, 0 to 100% isopropyl acetate in heptane) to afford 2-phenyl-1-[rac-(5S,7S)-7-fluoro-5-phenyl-6,7-dihydro-5H-pyrrolo[1,2-b][1,2,4]triazol-2-yl]ethanone as a white solid (80 mg, 69% yield). LCMS $R_T$=5.24 min, m/z=322.1 [M+H]$^+$. LCMS (5 to 95% acetonitrile in water+0.1% formic acid over 10 mins) retention time 5.24 min, ESI+ found [M+H]=322.1

Method 4

Example 8

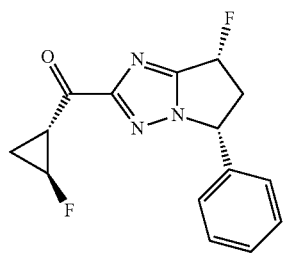

Example 9

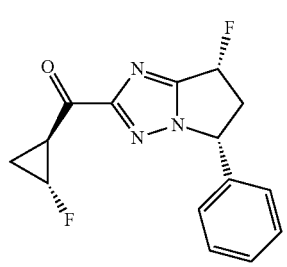

[(1S,2R)-2-fluorocyclopropyl]-[(5R,7R)-7-fluoro-5-phenyl-6,7-dihydro-5H-pyrrolo[1,2-b][1,2,4]triazol-2-yl]methanone and [(1R,2S)-2-fluorocyclopropyl]-[(5R,7R)-7-fluoro-5-phenyl-6,7-dihydro-5H-pyrrolo[1,2-b][1,2,4]triazol-2-yl]methanone To a cooled (−70° C.) solution of (5R,7R)-2-bromo-7-fluoro-5-phenyl-6,7-dihydro-5H-pyrrolo[1,2-b][1,2,4]triazole (150 mg, 0.53 mmol) and trans-fluoro-N-methoxy-N-methyl-cyclopropanecarboxamide (156 mg, 1.06 mmol) in tetrahydrofuran (10 mL) was added n-butyllithium (2.5 M in hexanes, 0.64 mL, 1.60 mmol) dropwise under nitrogen atmosphere. After addition, the mixture was stirred at −70° C. for 1 h and then quenched by addition of saturated aqueous ammonium chloride (30 mL). The resulting mixture was extracted with ethyl acetate (3×15 mL). The combined organic layers were concentrated under reduce pressure and the residue was purified by RP-HPLC (acetonitrile 35-65%/0.05% ammonia hydroxide in water) to afford [trans-2-fluorocyclopropyl]-[(5R,7R)-7-fluoro-5-phenyl-6,7-dihydro-5H-pyrrolo[1,2-b][1,2,4]triazol-2-yl]methanone (35 mg, 23%) as a pink solid. This racemic material was further separated by chiral SFC to give arbitrarily assigned:

[(1S,2R)-2-fluorocyclopropyl]-[(5R,7R)-7-fluoro-5-phenyl-6,7-dihydro-5H-pyrrolo[1,2-b][1,2,4]triazol-2-yl]methanone (Peak 1, Retention time=2.836 min) (14.3 mg, 40%) as a white solid. $^1$H NMR (400 MHz, CDCl$_3$) δ 7.43-7.39 (m, 3H), 7.28-7.27 (m, 2H), 6.13-5.97 (m, 1H), 5.54-5.51 (m, 1H), 5.02-4.84 (m, 1H), 3.69-3.53 (m, 2H), 3.03-2.97 (m, 1H), 1.70-1.63 (m, 2H). LC-MS $R_T$=0.866 min, m/z=289.9 (M+H)$^+$. LCMS (5 to 95% acetonitrile in water+0.03% trifluoacetic acid over 1.5 mins) retention time 0.866 min, ESI+ found [M+H]=289.9.

[(1R,2S)-2-fluorocyclopropyl]-[(5R,7R)-7-fluoro-5-phenyl-6,7-dihydro-5H-pyrrolo[1,2-b][1,2,4]triazol-2-yl]methanone (Peak 2, Retention time=3.725 min) (11.3 mg, 32%) as a white solid. $^1$H NMR (400 MHz, CDCl$_3$) δ 7.43-7.39 (m, 3H), 7.28-7.27 (m, 2H), 6.12-5.97 (m, 1H), 5.54-5.50 (m, 1H), 5.03-4.87 (m, 1H), 3.69-3.51 (m, 2H), 3.04-2.97 (m, 1H), 1.70-1.62 (m, 2H). LC-MS $R_T$=0.865 min, m/z=289.9 (M+H)$^+$. LCMS (5 to 95% acetonitrile in water+0.03% trifluoacetic acid over 1.5 mins) retention time 0.865 min, ESI+ found [M+H]=289.9.

SFC condition: Column: Chiralpak AD-3 150×4.6 mm I.D., 3 μm Mobile phase: A: CO2 B:methanol (0.05% DEA) Gradient: from 5% to 40% of B in 5 min and hold 40% for 2.5 min, then 5% of B for 2.5 min, Flow rate: 2.5 mL/min.

Method 5

Example 10

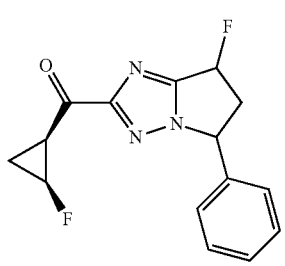

(rac-(5S,7S)-7-fluoro-5-phenyl-6,7-dihydro-5H-pyrrolo[1,2-b][1,2,4]triazol-2-yl)-[rac-(1S,2S)-2-fluorocyclopropyl]methanone

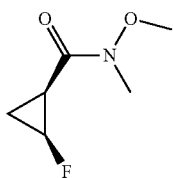

Step 1: cis-2-fluoro-N-methoxy-N-methylcyclopropanecarboxamide

A mixture of cis-2-fluorocyclopropanecarboxylic acid (500 mg, 4.80 mmol), N,O-dimethylhydroxylamine hydrochloride (610 mg, 6.25 mmol), 1-[bis(dimethylamino)methylene]-1H-1,2,3-triazolo[4,5-b]pyridinium 3-oxide hexafluorophosphate (2375 mg, 6.25 mmol) and N,N-diisopropylethylamine (1552 mg, 12.0 mmol) in N,N-dimethylformamide (15 mL) was stirred at 25° C. for 12 h. The mixture was poured into water (10 mL) and extracted with ethyl acetate (3×10 mL). The combined organic layers were washed with water (2×10 mL), brine (20 mL) and concentrated under reduced pressure. The residue was purified by column chromatography (silica gel, 100-200 mesh, 0 to 30% ethyl acetate in petroleum ether) to give cis-2-fluoro-N-methoxy-N-methyl-cyclopropanecarboxamide (420 mg, 59%) as a colorless oil. $^1$H NMR (400 MHz, CDCl$_3$) δ 4.87-4.67 (m, 1H), 3.78 (s, 3H), 3.26 (s, 3H), 2.35-2.33 (m, 1H), 1.94-1.86 (m, 1H), 1.11-1.05 (m, 1H).

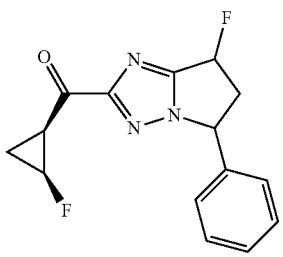

cis LHS
cis RHS

Step 2: (rac-(5S,7S)-7-fluoro-5-phenyl-6,7-dihydro-5H-pyrrolo[1,2-b][1,2,4]triazol-2-yl)-[rac-(1S,2S)-2-fluorocyclopropyl]methanone To a cooled (−78° C.) solution of cis-2-bromo-7-fluoro-5-phenyl-6,7-dihydro-5H-pyrrolo[1,2-b][1,2,4]triazole (50 mg, 0.18 mmol) and cis-2-fluoro-N-methoxy-N-methylcyclopropanecarboxamide (52 mg, 0.35 mmol) in tetrahydrofuran (5 mL) was added n-butyllithium (2.5 M in hexanes, 0.21 mL, 0.53 mmol) dropwise under a nitrogen atmosphere. After addition, the mixture was stirred at −78° C. for 1 h and then quenched by addition of saturated aqueous ammonium chloride (10 mL). The mixture was extracted with ethyl acetate (3×20 mL). The combined organic layers were concentrated under reduce pressure. The residue was purified by RP-HPLC (acetonitrile 30-60%/0.05% ammonia hydroxide in water) to afford (rac-(5S,7S)-7-fluoro-5-phenyl-6,7-dihydro-5H-pyrrolo[1,2-b][1,2,4]triazol-2-yl)-[rac-(1S,2S)-2-fluorocyclopropyl]methanone (2.0 mg, 4%) as a light yellow oil. $^1$H NMR (400 MHz, CD$_3$OD) δ 7.44-7.37 (m, 3H), 7.29-7.27 (m, 2H), 6.19-6.18 (m, 0.5H), 6.04-6.03 (m, 0.5H), 5.67-5.61 (m, 1H), 5.08-4.89 (m, 1H), 3.81-3.70 (m, 1H), 3.26-3.16 (m, 1H), 2.91-2.75 (m, 1H), 2.07-1.90 (m, 1H), 1.36-1.29 (m, 1H). LCMS R$_T$=1.038 min, m/z=290.1 [M+H]$^+$. LCMS (10 to 80% acetonitrile in water+0.03% trifluoacetic acid over 1.5 mins) retention time 1.038 min, ESI+ found [M+H]=290.1.

Method 6

Example 11

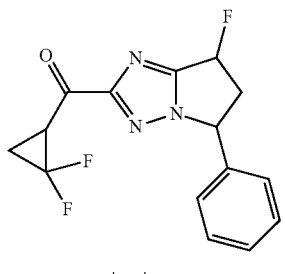

cis mixture

(2,2-difluorocyclopropyl)-(rac-(5S,7S)-7-fluoro-5-phenyl-6,7-dihydro-5H-pyrrolo[1,2-b][1,2,4]triazol-2-yl)methanone

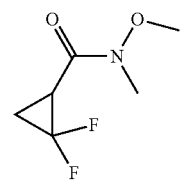

Step 1: 2,2-difluoro-N-methoxy-N-methyl-cyclopropanecarboxamide

A mixture of 2,2-difluorocyclopropanecarboxylic acid (300 mg, 2.46 mmol), N,O-dimethylhydroxylamine hydrochloride (312 mg, 3.19 mmol), 1-[bis(dimethylamino)methylene]-1H-1,2,3-triazolo[4,5-b]pyridinium 3-oxide hexafluorophosphate (1214 mg, 3.19 mmol) and N,N-diisopropylethylamine (794 mg, 6.14 mmol) in N,N-dimethylformamide (15 mL) was stirred at 25° C. for 12 h. The mixture was poured into water (10 mL) and extracted with ethyl acetate (3×10 mL). The combined organic layers were washed with water (2×10 mL), brine (20 mL) and concentrated under reduced pressure. The residue was purified by column chromatography (silica gel, 100-200 mesh, 0 to 20% ethyl acetate in petroleum ether) to give 2,2-difluoro-N-methoxy-N-methyl-cyclopropanecarboxamide (200 mg, 49%) as colorless oil. LCMS R$_T$=0.427 min, m/z=166.1 [M+H]$^+$. LCMS (5 to 95% acetonitrile in water+0.03% trifluoacetic acid over 1.5 mins) retention time 0.427 min, ESI+ found [M+H]=166.1.

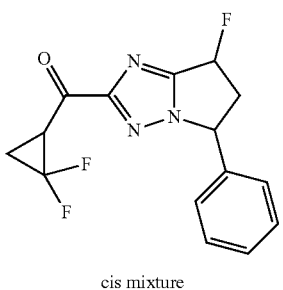 [SMILES: O=C(c1nc2n(n1)C(c1ccccc1)CC2F)C1CC1(F)F]

cis mixture

Step 2: (2,2-difluorocyclopropyl)-(rac-(5S,7S)-7-fluoro-5-phenyl-6,7-dihydro-5H-pyrrolo[1,2-b][1,2,4]triazol-2-yl)methanone To a cooled (−70° C.) solution of cis-2-bromo-7-fluoro-5-phenyl-6,7-dihydro-5H-pyrrolo[1,2-b][1,2,4]triazole (50 mg, 0.18 mmol) and 2,2-difluoro-N-methoxy-N-methyl-cyclopropanecarboxamide (59 mg, 0.35 mmol) in tetrahydrofuran (3 mL) was added n-butyllithium (2.5 M in hexanes, 0.25 mL, 0.62 mmol) under nitrogen atmosphere. After addition, the mixture was stirred at −70° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 35-65%/0.05% ammonia hydroxide in water) to afford (2,2-difluorocyclopropyl)-(rac-(5S,7S)-7-fluoro-5-phenyl-6,7-dihydro-5H-pyrrolo[1,2-b][1,2,4]triazol-2-yl)methanone (10.6 mg, 19%) as colorless oil. $^1$H NMR (400 MHz, CD$_3$OD) δ 7.44-7.39 (m, 3H), 7.30-7.29 (m, 2H), 6.21-6.05 (m, 1H), 5.69-5.64 (m, 1H), 3.84-3.74 (m, 2H), 2.90-2.82 (m, 1H), 2.32-2.27 (m, 1H), 1.97-1.90 (m, 1H). LCMS R$_T$=0.875 min, m/z=307.9 [M+H]$^+$. LCMS (5 to 95% acetonitrile in water+0.03% trifluoacetic acid over 1.5 mins) retention time 0.875 min, ESI+ found [M+H]=307.9.

Method 7

Example 12

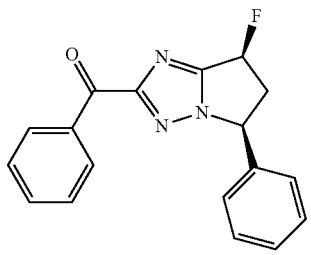

phenyl-[rac-(5S,7S)-7-fluoro-5-phenyl-6,7-dihydro-5H-pyrrolo[1,2-b][1,2,4]triazol-2-yl]methanone Phenyl-[rac-(5S,7S)-7-fluoro-5-phenyl-6,7-dihydro-5H-pyrrolo[1,2-b][1,2,4]triazol-2-yl]methanone was prepared from ethyl [rac-(5S,7S)-7-fluoro-5-phenyl-6,7-dihydro-5H-pyrrolo[1,2-b][1,2,4]triazole-2-carboxylate and phenylmagnesium according to Method 3. The crude residue was purified by column chromatography (silica gel, 100-200 mesh, 0 to 100% isopropyl acetate in heptane) to afford final product (17 mg, 30%) as a white solid. 1H NMR (400 MHz, DMSO-d6) δ 8.20-8.12 (m, 2H), 7.74-7.65 (m, 1H), 7.61-7.52 (m, 2H), 7.48-7.33 (m, 3H), 7.32-7.24 (m, 2H), 6.28 (ddd, J=56.4, 7.2, 1.9 Hz, 1H), 5.78 (ddd, J=8.5, 6.5, 3.1 Hz, 1H), 3.78 (dddd, J=25.8, 15.4, 8.5, 7.1 Hz, 1H), 2.74 (dddd, J=26.7, 15.2, 3.2, 2.0 Hz, 1H). LC-MS R$_T$=5.04 min, m/z=308.1 (M+H)+. LCMS (5 to 95% acetonitrile in water+0.1% formic acid over 10 mins) retention time 5.04 min, ESI+ found [M+H]=308.1.1

Method 8

Example 13

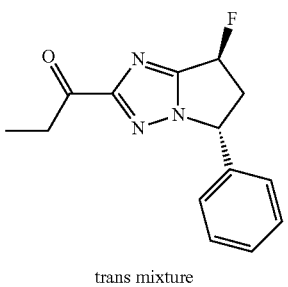

trans mixture

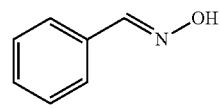

Step 1: (E)—benzaldehyde Oxime

To a solution of benzaldehyde (45.0 g, 424.1 mmol) in ethanol (100 mL) was added sodium carbonate (112.3 g, 1060.1 mmol) and hydroxylamine hydrochloride (35.3 g, 508.9 mmol). The reaction mixture was stirred at 25° C. for 3 h and filtered. The filtrate was concentrated under reduced pressure and the residue was diluted with water (50 mL). The resulting mixture was extracted with ethyl acetate (3×150 mL). The combined organic layers were washed with brine (60 mL), dried over anhydrous sodium sulfate and concentrated under reduced pressure to afford crude (E)-benzaldehyde oxime as colorless oil (51.0 g, 99%), used in the next step without further purification.

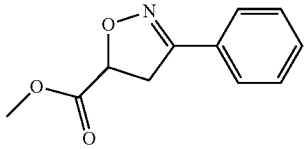

Step 2: methyl 3-phenyl-4,5-dihydroisoxazole-5-carboxylate

To a solution of (E)-benzaldehyde oxime (20.0 g, 165.1 mmol) in 1,4-dioxane (500 mL) was added methyl acrylate (14.2 g, 165.1 mmol), sodium iodide (24.7 g, 165.1 mmol), 2,6-lutidine (17.6 g, 165.1 mmol) and hypochlorous acid tert-butyl ester (17.9 g, 165.1 mmol). The reaction mixture was stirred at 25° C. for 24 h and subsequently concentrated under reduced pressure. The residue was purified by column chromatography (silica gel, 100-200 mesh, 0 to 20% ethyl acetate in petroleum ether) to afford methyl 3-phenyl-4,5-dihydroisoxazole-5-carboxylate as a yellow solid (25.0 g, 74%). LCMS $R_T$=0.871 min, m/z=206.2 [M+H]$^+$. LCMS (10 to 80% acetonitrile in water+0.03% trifluoacetic acid over 2.0 mins) retention time 0.871 min, ESI+ found [M+H]=206.2.

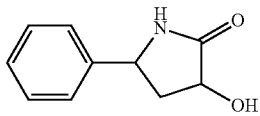 [SMILES: O=C1NC(c2ccccc2)CC1O]

Step 3: 3-hydroxy-5-phenyl-pyrrolidin-2-one

A mixture of methyl 3-phenyl-4, 5-dihydroisoxazole-5-carboxylate (25.0 g, 121.8 mmol) and palladium (10% on carbon, 2.5 g) in ethanol (800 mL) was hydrogenated (50 psi) at 25° C. for 2 h and then filtered and the filtrate was concentrated under reduced pressure to afford crude 3-hydroxy-5-phenyl-pyrrolidin-2-one as a yellow solid (18.0 g, 83%), used in the next step without further purification. LCMS $R_T$=0.270 min, m/z=177.8 [M+H]$^+$. LCMS (5 to 95% acetonitrile in water+0.03% trifluoacetic acid over 1.5 mins) retention time 0.270 min, ESI+ found [M+H]=177.8.

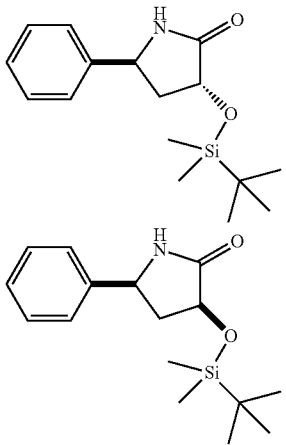

Step 4: cis-3-[tert-butyl(dimethyl)silyl]oxy-5-phenyl-pyrrolidin-2-one & trans-3-[tert-butyl(dimethyl)silyl]oxy-5-phenyl-pyrrolidin-2-one To a solution of 3-hydroxy-5-phenyl-pyrrolidin-2-one (15.0 g, 84.6 mmol) in dichloromethane (300 mL) was added tert-butyldimethylchlorosilane (19.1 g, 126.9 mmol) and imidazole (11.5 g, 169.3 mmol). The reaction mixture was stirred at 25° C. for 16 h and subsequently concentrated under reduced pressure. The residue was purified by column chromatography (silica gel, 100-200 mesh, 0 to 30% ethyl acetate in petroleum ether) to afford cis-3-[tert-butyl(dimethyl)silyl]oxy-5-phenyl-pyrrolidin-2-one as a colorless oil (12.4 g, 51%). $^1$H NMR (400 MHz, CDCl$_3$) δ 7.37-7.25 (m, 5H), 4.88-4.53 (m, 1H), 4.54-4.46 (m, 1H), 2.89-2.79 (m, 1H), 1.80-1.71 (m, 1H), 0.93-0.90 (m, 9H), 0.19-0.12 (in, 6H) and trans-3-[tert-butyl(dimethyl)silyl]oxy-5-phenyl-pyrrolidin-2-one as a colorless oil (9.3 g, 38%). $^1$H NMR (400 MHz, CDCl$_3$) δ 7.44-7.34 (m, 2H), 7.29-7.24 (m, 3H), 4.87-4.80 (m, 1H), 4.44-4.41 (m, 1H), 2.45-2.37 (m, 1H), 2.27-2.22 (m, 1H), 0.93-0.90 (m, 9H), 0.16-0.13 (m, 6H).

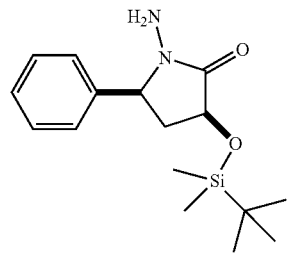

Step 5: cis-1-amino-3-[tert-butyl(dimethyl)silyl]oxy-5-phenyl-pyrrolidin-2-one

To a solution of cis-3-[tert-butyl(dimethyl)silyl]oxy-5-phenyl-pyrrolidin-2-one (12.4 g, 42.8 mmol) in N,N-dimethylformamide (400 mL) was slowly added sodium hydride (60%, 2.6 g, 64.1 mmol) at 0° C. After addition, the mixture was stirred at 0° C. for 20 min and subsequently 0-(diphenylphosphoryl)hydroxylamine (14.9 g, 64.1 mmol) was added. The reaction mixture was stirred at 25° C. for 16 h and then filtered. The filtrate was concentrated under reduced pressure to afford the crude cis-1-amino-3-[tert-butyl(dimethyl)silyl]oxy-5-phenyl-pyrrolidin-2-one as a yellow oil (9.5 g, 73%), used in the next step without further purification. LCMS $R_T$=0.877 min, m/z=307.0 [M+H]$^+$. LCMS (5 to 95% acetonitrile in water+0.03% trifluoacetic acid over 1.5 mins) retention time 0.877 min, ESI+ found [M+H]=307.0.

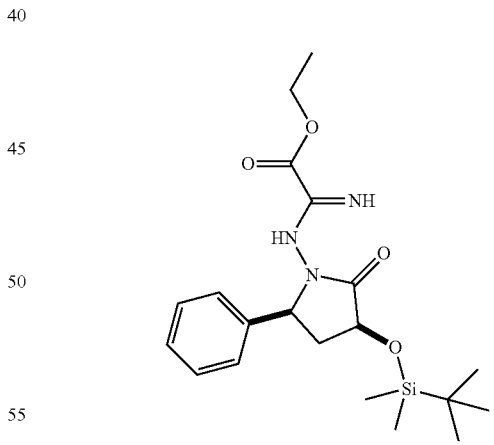

Step 6: Ethyl 2-[[cis-3-[tert-butyl(dimethyl)silyl]oxy-2-oxo-5-phenyl-pyrrolidin-1-yl]amino]-2-iminoacetate To a solution of cis-1-amino-3-[tert-butyl(dimethyl)silyl]oxy-5-phenyl-pyrrolidin-2-one (9.5 g, 31.0 mmol) in ethanol (250 mL) was added ethyl 2-ethoxy-2-imino-acetate (6.7 g, 46.5 mmol). The reaction mixture was stirred at 60° C. for 6 h and subsequently concentrated under reduced pressure to afford crude ethyl 2-[[cis-3-[tert-butyl(dimethyl)silyl]oxy-2-oxo-5-phenyl-pyrrolidin-1-yl]amino]-2-imino-acetate as a yellow oil (10.6 g, 84%), used in the next step without further purification. LCMS $R_T$=2.106 min, m/z=406.2 [M+H]$^+$. LCMS (10 to 80% acetonitrile in water+0.1% ammonia water over 3.0 mins) retention time 2.106 min, ESI+ found [M+H]=406.2.

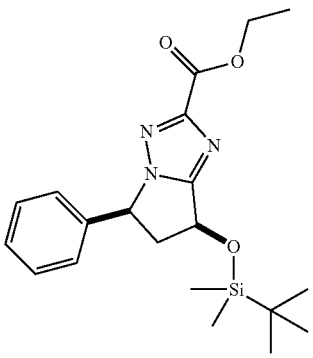 [SMILES: CCOC(=O)c1nc2n(n1)[C@H](c1ccccc1)C[C@@H]2O[Si](C)(C)C(C)(C)C]

Step 7: ethyl cis-7-[tert-butyl(dimethyl)silyl]oxy-5-phenyl-6,7-dihydro-5H-pyrrolo[1,2-b][1,2,4]triazole-2-carboxylate To a solution of ethyl 2-[[cis-3-[tert-butyl(dimethyl)silyl]oxy-2-oxo-5-phenyl-pyrrolidin-1-yl]amino]-2-imino-acetate (10.6 g, 26.1 mmol) in toluene (200 mL) was added p-toluenesulfonic acid (4.5 g, 26.1 mmol). The reaction mixture was heated at 120° C. for 24 h and subsequently concentrated under reduced pressure. The residue was purified by column chromatography (silica gel, 100-200 mesh, 0 to 80% ethyl acetate in petroleum ether) to afford ethyl cis-7-[tert-butyl(dimethyl)silyl]oxy-5-phenyl-6,7-dihydro-5H-pyrrolo[1,2-b][1,2,4]triazole-2-carboxylate as a white solid (6.5 g, 64%), used as is in the next step.

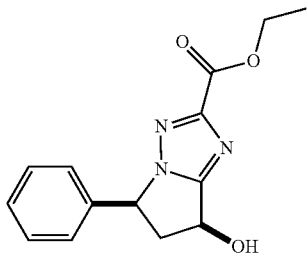

Step 8: Ethyl Cis-7-hydroxy-5-phenyl-6,7-dihydro-5H-pyrrolo[1,2-b][1,2,4]triazole-2-carboxylate A mixture of ethyl 2-[[cis-3-[tert-butyl(dimethyl)silyl]oxy-2-oxo-5-phenyl-pyrrolidin-1-yl]amino]-2-imino-acetate (3.1 g, 7.6 mmol) and tert-butylammonium fluoride (1.0 M in THF, 7.6 mL, 7.6 mmol) in tetrahydrofuran (60 mL) was heated at 60° C. for 18 h and subsequently concentrated under reduced pressure. The residue was purified by column chromatography (silica gel, 100-200 mesh, 0 to 100% ethyl acetate in petroleum ether) to give ethyl cis-7-hydroxy-5-phenyl-6,7-dihydro-5H-pyrrolo[1,2-b][1,2,4]triazole-2-carboxylate as white solid (1.4 g, 69%). $^1$H NMR (400 MHz, CDCl$_3$) δ7.39-7.32 (m, 5H), 5.73 (d, J=3.5 Hz, 1H), 5.50 (m, 1H), 4.41 (q, J=7.1 Hz, 2H), 3.73-3.65 (m, 1H), 2.76 (td, J=4.5 Hz, 13.9 Hz, 1H), 1.35 (t, J=7.1 Hz, 3H).

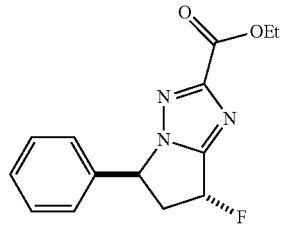

Step 1: Trans-Ethyl 7-fluoro-5-phenyl-6,7-dihydro-5H-pyrrolo[1,2-b][1,2,4]triazole-2-carboxylate To a solution of cis-ethyl-7-hydroxy-5-phenyl-6,7-dihydro-5H-pyrrolo[1,2-b][1,2,4]triazole-2-carboxylate (100 mg, 0.37 mmol) in dichloromethane (8 mL) was added diethylaminosulfur trifluoride (176.9 mg, 1.10 mmol) at 0° C. The reaction mixture was stirred at 0° C. for 2 h and then quenched by addition of water (20 mL). The mixture was extracted with dichloromethane (3×20 mL). The combined organic layers were washed with water (20 mL), brine (20 mL), dried over sodium sulfate and concentrated under reduced pressure. The residue was purified by preparative TLC (50% ethyl acetate in petroleum ether, $R_f$=0.5) to afford trans-ethyl-7-fluoro-5-phenyl-6,7-dihydro-5H-pyrrolo[1,2-b][1,2,4]triazole-2-carboxylate (30 mg, 30%) as light yellow oil. $^1$H NMR (400 MHz, CDCl$_3$) δ 7.40-7.37 (m, 3H), 7.14-7.12 (m, 2H), 6.14 (d, J=5.2 Hz, 0.5H), 6.00 (d, J=5.2 Hz, 0.5H), 5.74-5.71 (m, 1H), 4.51-4.45 (m, 2H), 3.42-3.35 (m, 1H), 3.07-2.96 (m, 1H), 1.42 (t, J=7.2 Hz, 3H).

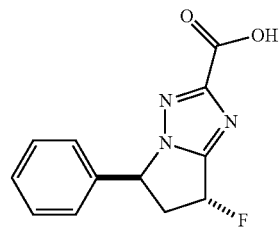

Step 2: trans-7-fluoro-5-phenyl-6,7-dihydro-5H-pyrrolo[1,2-b][1,2,4]triazole-2-carboxylicacid To a solution of trans-ethyl-7-fluoro-5-phenyl-6,7-dihydro-5H-pyrrolo[1,2-b][1,2,4]triazole-2-carboxylate (30 mg, 0.11 mol) in tetrahydrofuran (4 mL) and water (1 mL) was added lithium hydroxide monohydrate (14 mg, 0.33 mmol). The reaction mixture was stirred at 25° C. for 2 h and then concentrated under reduced pressure. The residue was adjusted to pH=5 by addition of hydrochloric acid (2 N). The mixture was extracted with ethyl acetate (3×20 mL). The combined organic layers were washed with water (20 mL), brine (20 mL), dried over anhydrous sodium sulfate and concentrated under reduced pressure to afford crude trans-7-fluoro-5-phenyl-6,7-dihydro-5H-pyrrolo[1,2-b][1,2,4]triazole-2-carboxylic acid as white solid (13 mg, 48%), used in the next step without further purification.

1-[rac-(5R,7S)-7-fluoro-5-phenyl-6,7-dihydro-5H-pyrrolo[1,2-b][1,2,4]triazol-2-yl]propan-1-one To a cooled (−78° C.) solution of trans-7-fluoro-N-methoxy-N-methyl-5-phenyl-6,7-dihydro-5H-pyrrolo[1,2-b][1,2,4]triazole-2-carboxamide (15 mg, 0.05 mmol) in tetrahydrofuran (10 mL) was added ethylmagnesium bromide (3 Min THF, 0.03 mL, 0.10 mmol) under nitrogen atmosphere. After addition, the mixture was stirred at −78° C. for 1 h and quenched by addition of saturated aqueous ammonium chloride (10 mL). The mixture was extracted with ethyl acetate (3×10 mL). The combined organic layers were dried over sodium sulfate and concentrated under reduce pressure. The residue was purified by RP-HPLC (acetonitrile 34-64%/0.05% hydrochloride in water) to afford 1-[rac-(5R,7S)-7-fluoro-5-phenyl-6,7-dihydro-5H-pyrrolo[1,2-b][1,2,4]triazol-2-yl]propan-1-one (7.4 mg, 50%) as a white solid. $^1$H NMR (400 MHz, CD$_3$OD) δ 7.44-7.38 (m, 3H), 7.30-7.26 (m, 2H), 6.27-6.26 (m, 0.5H), 6.14-6.12 (m, 0.5H), 5.87-5.84 (m, 1H), 3.44-3.41 (m, 1H), 3.12-3.02 (m, 3H), 1.16 (t, J=7.2 Hz, 3H). LCMS $R_T$=0.840 min, m/z=260.1 [M+H]$^+$. LCMS (5 to 95% acetonitrile in water+0.03% trifluoacetic acid over 1.5 mins) retention time 0.840 min, ESI+ found [M+H]=260.1.

Method 9

Example 14

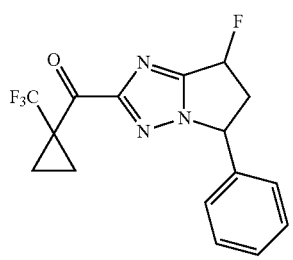

cis mixture (rac-(5S,7S)-7-fluoro-5-phenyl-6,7-dihydro-5H-pyrrolo[1,2-b][1,2,4]triazol-2-yl)-[1-(trifluoromethyl)cyclopropyl]methanone

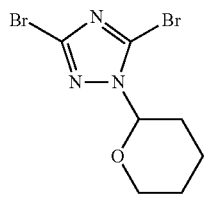 [SMILES: Brc1nc(Br)n(C2CCCCO2)n1]

Step 1: 3,5-dibromo-1-(tetrahydro-2H-pyran-2-yl)-1H-1,2,4-triazole

To a solution of 3,5-dibromo-1h-1,2,4-triazole (150.0 g, 661.2 mmol) in tetrahydrofuran (1500 mL) was slowly added p-toluenesulfonic acid (17.1 g, 99.2 mmol), followed by 3,4-dihydro-2h-pyran (166.9 g, 1983.6 mmol) at 0° C. After addition, the reaction mixture was heated at 70° C. for 3 h and concentrated under reduced pressure. The residue was poured into water (500 mL) and adjusted to pH=9 by addition of saturated aqueous sodium bicarbonate. The resulting mixture was extracted with ethyl acetate (3×400 mL). The combined organic layers were dried over sodium sulfate and concentrated under reduce pressure. The resulting crude product was washed with methanol (2×50 mL), dried under reduced pressure to give crude 3,5-dibromo-1-tetrahydropyran-2-yl-1,2,4-triazole (155 g, 75%) as a white solid. $^1$H NMR (400 MHz, CDCl$_3$) δ 5.49-5.46 (m, 1H), 4.12-3.99 (m, 1H), 3.72-3.61 (m, 1H), 2.38-2.26 (m, 1H), 2.18-2.07 (m, 1H), 1.98-1.90 (m, 1H), 1.78-1.60 (m, 3H).

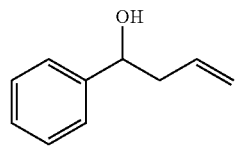

Step 2: 1-phenylbut-3-en-1-ol

To a cooled (0° C.) solution of benzaldehyde (130 g, 1.23 mol) in tetrahydrofuran (1000 mL) was added allylmagnesium chloride (2 M in THF, 858 mL, 1.72 mol) over 30 min. After addition, the reaction mixture was allowed to warm to room temperature and stirred for 2 h. The mixture was then quenched by addition of saturated aqueous ammonium chloride (1000 mL) and extracted with ethyl acetate (3×500 mL). The combined organic layers were dried over sodium sulfate and concentrated under reduce pressure. The residue was purified by column chromatography (silica gel, 100-200 mesh, 0 to 5% ethyl acetate in petroleum ether) to give 1-phenylbut-3-en-1-ol (140 g, 77%) as a light yellow oil. $^1$H NMR (400 MHz, CDCl$_3$) δ 7.37-7.34 (m, 4H), 7.29-7.26 (m, 1H), 5.83-5.75 (m, 1H), 5.21-5.08 (m, 2H), 4.76-4.69 (m, 1H), 2.55-2.45 (m, 2H), 2.12 (d, J=2.8 Hz, 1H).

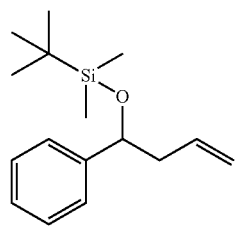 [SMILES: C=CCC(O[Si](C)(C)C(C)(C)C)c1ccccc1]

Step 3: tert-butyldimethyl((1-phenylbut-3-en-1-yl)oxy)silane

To a stirred solution of 1-phenyl-3-buten-1-ol (29.0 g, 195.7 mmol) in dichloromethane (400 mL) was added imidazole (27.0 g, 391.6 mmol) and tert-butyldimethylchlorosilane (39.0 g, 254.4 mmol). After addition, the reaction mixture was stirred at 25° C. for 16 h and then quenched by addition of water (200 mL). The mixture was extracted with dichloromethane (2×200 mL). The combined organic layers were washed with brine (100 mL), dried over sodium sulfate and concentrated under reduced pressure. The residue was purified by column chromatography (silica gel, 100-200 mesh, 100% petroleum ether) to afford tert-butyl-dimethyl-(1-phenylbut-3-enoxy)silane (43.0 g, 84%) as colorless oil, used as is in the next step.

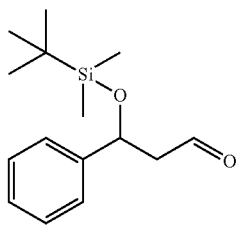 [SMILES: CC(C)(C)[Si](C)(C)OC(CC=O)c1ccccc1]

Step 4: 3-((tert-butyldimethylsilyl)oxy)-3-phenylpropanal

To a solution of tert-butyl-dimethyl-(1-phenylbut-3-enoxy)silane (50.0 g, 190.5 mmol) in tetrahydrofuran/water (600 mL, 1:1) was added osmium tetraoxide (968 mg, 3.8 mmol). After stirring for 30 min at 15° C., sodium periodate (163 g, 762.0 mmol) was added in small portions over 2 h. The resulting mixture was stirred for another 2 h at 30° C. and then quenched by addition of cold saturated aqueous sodium thiosulfate (500 mL). The mixture was stirred for 30 min and then extracted with ethyl acetate (3×400 mL). The combined organic layers were washed with water (200 mL), brine (200 mL), dried over sodium sulfate and concentrated under reduced pressure. The residue was purified by column chromatography (silica gel, 100-200 mesh, 0 to 10% ethyl acetate in petroleum ether) to afford 3-[tert-butyl(dimethyl)silyl]oxy-3-phenyl-propanal (33.0 g, 65%) as yellow oil. $^1$H NMR (400 MHz, CDCl$_3$) δ 9.94 (t, J=2.4 Hz, 1H), 7.48 (d, J=4.2 Hz, 4H), 7.44-7.39 (m, 1H), 5.37-5.34 (m, 1H), 2.99-2.97 (m, 1H), 2.80-2.75 (m, 1H), 1.01 (s, 9H), 0.19 (s, 3H), 0.00 (s, 3H).

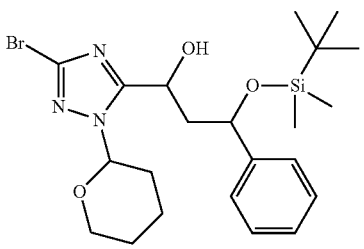 [SMILES: CC(C)(C)[Si](C)(C)OC(CC(O)c1nc(Br)nn1C1CCCCO1)c1ccccc1]

Step 5: 1-(3-bromo-1-(tetrahydro-2H-pyran-2-yl)-1H-1,2,4-triazol-5-yl)-3-((tert-butyldimethylsilyl)oxy)-3-phenylpropan-1-ol To a cooled (−78° C.) solution of 3,5-dibromo-1-tetrahydropyran-2-yl-1,2,4-triazole (39.0 g, 125.4 mmol) in tetrahydrofuran (400 mL) was added n-butyllithium (2.5 M in hexanes, 55.0 mL, 137.5 mmol) dropwise under N$_2$ atmosphere. The mixture was stirred at −78° C. for 30 min, then a solution of 3-[tert-butyl(dimethyl)silyl]oxy-3-phenyl-propanal (33.0 g, 124.2 mmol) in tetrahydrofuran (50 mL) was added dropwise. After addition, the mixture was stirred at −78° C. for 1.5 h and then quenched by addition of saturated aqueous ammonium chloride (500 mL). The resulting mixture was extracted with ethyl acetate (3×300 mL). The combined organic layers were dried over sodium sulfate and concentrated under reduce pressure. The residue was purified by column chromatography (silica gel, 100-200 mesh, 0 to 5% ethyl acetate in petroleum ether) to afford 1-(3-bromo-1-(tetrahydro-2H-pyran-2-yl)-1H-1,2,4-triazol-5-yl)-3-((tert-butyldimethylsilyl)oxy)-3-phenylpropan-1-ol (50.0 g, 80%) as light yellow oil.

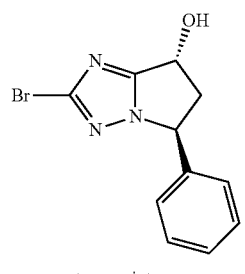

trans mixture

Step 6: trans-2-bromo-5-phenyl-6,7-dihydro-5H-pyrrolo[1,2-b][1,2,4]triazol-7-ol To a stirred solution of 1-(3-bromo-1-(tetrahydro-2H-pyran-2-yl)-1H-1,2,4-triazol-5-yl)-3-((tert-butyldimethylsilyl)oxy)-3-phenylpropan-1-ol (50.0 g, 100.7 mmol) in dichloromethane (150 mL) was slowly added trifluoroacetic acid (150 mL). The resulting mixture was heated at 50° C. for 2 h and then concentrated under reduced pressure. The residue was adjusted to pH=9 with saturated aqueous sodium bicarbonate and extracted with dichloromethane (3×200 mL). The combined organic layers were washed with water (100 mL), brine (100 mL), dried over sodium sulfate and concentrated under reduced pressure. The residue was purified by column chromatography (silica gel, 100-200 mesh, 0 to 32% ethyl acetate in petroleum ether) to afford trans-2-bromo-5-phenyl-6,7-dihydro-5H-pyrrolo[1,2-b][1,2,4]triazol-7-ol (5.5 g, 20%) as a yellow solid (A second fraction (8.5 g, 30%) was also obtained as a 4:3 mixture of trans/cis products). $^1$H NMR (400 MHz, CDCl$_3$) δ 7.46-7.32 (m, 3H), 7.15 (d, J=7.6 Hz, 2H), 5.65 (t, J=6.6 Hz, 1H), 5.50 (br s, 1H), 5.45 (d, J=6.4 Hz, 1H), 3.19-3.11 (m, 1H), 3.01-2.92 (m, 1H). LCMS RT=0.682 min, m/z=279.8 [M+H]$^+$. LCMS (5 to 95% acetonitrile in water+ 0.03% trifluoroacetic acid over 1.5 mins) retention time 0.682 min, ESI+ found [M+H]=279.8.

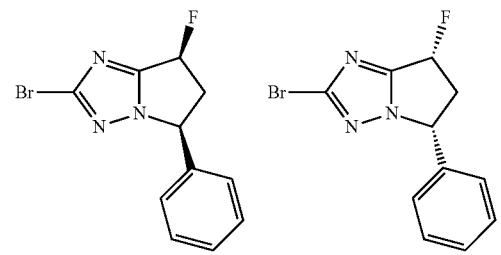 [SMILES: F[C@H]1C[C@@H](c2ccccc2)n2nc(Br)nc21 ; F[C@@H]1C[C@H](c2ccccc2)n2nc(Br)nc21]

Step 7: (5S,7S)-2-bromo-7-fluoro-5-phenyl-6,7-dihydro-5H-pyrrolo[1,2-b][1,2,4]triazole and (5R,7R)-2-bromo-7-fluoro-5-phenyl-6,7-dihydro-5H-pyrrolo[1,2-b][1,2,4]triazole To a stirred solution of trans-2-bromo-5-phenyl-6,7-dihydro-5H-pyrrolo[1,2-b][1,2,4]triazol-7-ol (3.0 g, 10.71 mmol) in dichloromethane (60 mL) was slowly added diethylaminosulfur trifluoride (7.8 g, 48.19 mmol) at 0° C.

The reaction mixture was stirred at 0° C. for 2.5 h and then slowly added into stirred aqueous saturated sodium bicarbonate (100 mL) at 0° C. The mixture was extracted with dichloromethane (3×100 mL). The combined organic layers were washed with water (100 mL), brine (100 mL), dried over sodium sulfate and concentrated under reduced pressure. The residue was purified by column chromatography (silica gel, 100-200 mesh, 0 to 20% ethyl acetate in petroleum ether) to afford racemic cis-2-bromo-7-fluoro-5-phenyl-6,7-dihydro-5H-pyrrolo[1,2-b][1,2,4]triazole (1.5 g, 49%) as a light yellow solid and racemic trans-2-bromo-7-fluoro-5-phenyl-6,7-dihydro-5H-pyrrolo[1,2-b][1,2,4]triazole (650 mg, 21%) as a white solid.

cis-2-bromo-7-fluoro-5-phenyl-6,7-dihydro-5H-pyrrolo[1,2-b][1,2,4]triazole: $^1$H NMR (400 MHz, CDCl$_3$) δ 7.31-7.24 (m, 3H), 7.17-7.07 (m, 2H), 5.97-5.77 (m, 1H), 5.37-5.27 (m, 1H), 3.52-3.37 (m, 1H), 2.84-2.70 (m, 1H). LCMS R$_T$=0.632 min, m/z=281.9 [M+H]$^+$. LCMS (5 to 95% acetonitrile in water+0.03% trifluoroacetic acid over 1.5 mins) retention time 0.632 min, ESI+ found [M+H]=281.9.

trans-2-bromo-7-fluoro-5-phenyl-6,7-dihydro-5H-pyrrolo[1,2-b][1,2,4]triazole: $^1$H NMR (400 MHz, CDCl$_3$) δ 7.58-7.29 (m, 3H), 7.24-7.05 (m, 2H), 6.14-5.93 (m, 1H), 5.70-5.65 (m, 1H), 3.41-3.25 (m, 1H), 3.04-2.87 (m, 1H).

The racemic cis material was further separated by chiral SFC to give arbitrarily assigned:

(5R,7R)-2-bromo-7-fluoro-5-phenyl-6,7-dihydro-5H-pyrrolo[1,2-b][1,2,4]triazole (Peak 1, retention time=2.963 min) (350 mg, 44%) as a white solid.

(5S,7S)-2-bromo-7-fluoro-5-phenyl-6,7-dihydro-5H-pyrrolo[1,2-b][1,2,4]triazole (Peak 2, retention time=3.174 min) (350 mg, 44%) as a white solid.

SFC condition: Column: Chiralpak AD-3 150×4.6 mm I.D., 3 µm Mobile phase: A: CO2 B:ethanol (0.05% DEA) Gradient: from 5% to 40% of B in 5 min and hold 40% for 2.5 min, then 5% of B for 2.5 min Flow rate: 2.5 mL/min.

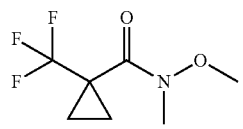

Step 8: N-methoxy-N-methyl-1-(trifluoromethyl)cyclopropanecarboxamide

A mixture of 1-(trifluoromethyl)cyclopropanecarboxylic acid (400 mg, 2.60 mmol), N,O-dimethylhydroxylamine hydrochloride (329 mg, 3.37 mmol), 1-[bis(dimethylamino)methylene]-1H-1,2,3-triazolo[4,5-b]pyridinium 3-oxide hexafluorophosphate (1283 mg, 3.37 mmol) and N,N-diisopropylethylamine (838 mg, 6.49 mmol) in N,N-dimethylformamide (15 mL) was stirred at 25° C. for 12 h. The mixture was diluted with water (20 mL) and extracted with ethyl acetate (3×30 mL). The combined organic layers were washed with brine (20 mL) and concentrated under reduced pressure. The residue was purified by column chromatography (silica gel, 100-200 mesh, 0 to 25% ethyl acetate in petroleum ether) to give N-methoxy-N-methyl-1-(trifluoromethyl)cyclopropanecarboxamide (330 mg, 64%) as a light oil. $^1$H NMR (400 MHz, CDCl$_3$) δ 3.74 (s, 3H), 3.29 (s, 3H), 1.37-1.17 (m, 4H).

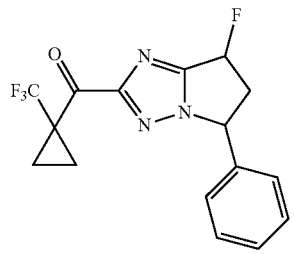 [SMILES: O=C(c1nc2n(n1)C(c1ccccc1)CC2F)C1(C(F)(F)F)CC1]

Step 9: (rac-(5S,7S)-7-fluoro-5-phenyl-6,7-dihydro-5H-pyrrolo[1,2-b][1,2,4]triazol-2-yl)-[1-(trifluoromethyl)cyclopropyl]methanone To a cooled (−70° C.) solution of cis-2-bromo-7-fluoro-5-phenyl-6,7-dihydro-5H-pyrrolo[1,2-b][1,2,4]triazole (50 mg, 0.18 mmol) and N-methoxy-N-methyl-1-(trifluoromethyl)cyclopropanecarboxamide (70 mg, 0.35 mmol) in tetrahydrofuran (4 mL) was added n-butyllithium (2.5 M in hexanes, 0.1 mL, 0.25 mmol) under nitrogen atmosphere. After addition, the mixture was stirred at −70° C. for 1 h and then quenched by addition of saturated aqueous ammonium chloride (5 mL). The resulting mixture was extracted with ethyl acetate (3×15 mL). The combined organic layers were concentrated under reduce pressure and the residue was purified by RP-HPLC ((acetonitrile 45-75/0.05% ammonia hydroxide in water)) to afford arbitrarily assigned (rac-(5S,7S)-7-fluoro-5-phenyl-6,7-dihydro-5H-pyrrolo[1,2-b][1,2,4]triazol-2-yl)-[1-(trifluoromethyl)cyclopropyl]methanone (14.1 mg, 23%) as a red solid. $^1$H NMR (400 MHz, CD$_3$OD) δ 7.43-7.35 (m, 3H), 7.24-7.22 (m, 2H), 6.15-5.99 (m, 1H), 5.61-5.60 (m, 1H), 3.77-3.68 (m, 1H), 2.84-2.77 (m, 1H), 2.27-2.17 (m, 2H), 1.60-1.55 (m, 2H). LC-MS R$_T$=0.933 min, m/z=339.9 [M+H]$^+$. LCMS (10 to 80% acetonitrile in water+0.03% ammonium bicarbonate over 3.0 mins) retention time 0.933 min, ESI+ found [M+H]=339.9.

Method 10

Example 15

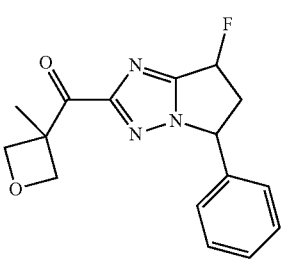

cis mixture

(rac-(5S,7S)-7-fluoro-5-phenyl-6,7-dihydro-5H-pyrrolo[1,2-b][1,2,4]triazol-2-yl)-(3-methyloxetan-3-yl)methanone

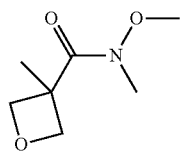

Step 1: N-methoxy-N,3-dimethyl-oxetane-3-carboxamide

A mixture of 3-methyloxetane-3-carboxylic acid (300 mg, 2.58 mmol), N,O-dimethylhydroxylamine hydrochloride (328 mg, 3.36 mmol), 1-[Bis(dimethylamino)methylene]-1H-1,2,3-triazolo[4,5-b]pyridinium 3-oxide hexafluorophosphate (1277 mg, 3.36 mmol) and N,N-diisopropylethylamine (835 mg, 6.46 mmol) in N,N-dimethylformamide (15 mL) was stirred at 25° C. for 12 h. The mixture was poured into water (10 mL) and extracted with ethyl acetate (3×10 mL). The combined organic layers were washed with water (2×10 mL), brine (20 mL) and concentrated under reduced pressure. The residue was purified by column chromatography (silica gel, 100-200 mesh, 0 to 50% ethyl acetate in petroleum ether) to give N-methoxy-N,3-dimethyl-oxetane-3-carboxamide (120 mg, 29.2%) as a colorless oil. $^1$H NMR (400 MHz, CDCl$_3$) δ 4.97 (d, J=6.4 Hz, 2H), 4.30 (d, J=6.4 Hz, 2H), 3.67 (s, 3H), 3.19 (s, 3H), 1.67 (s, 3H).

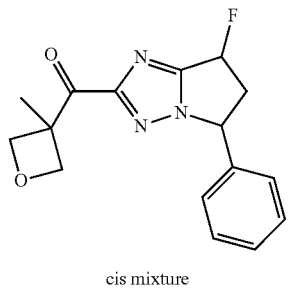 [SMILES: CC1(C(=O)c2nc3n(n2)C(c2ccccc2)CC3F)COC1]

cis mixture

Step 2: (rac-(5S,7S)-7-fluoro-5-phenyl-6,7-dihydro-5H-pyrrolo[1,2-b][1,2,4]triazol-2-yl)-(3-methyl-oxetan-3-yl)methanone To a cooled (−70° C.) solution of cis-2-bromo-7-fluoro-5-phenyl-6,7-dihydro-5H-pyrrolo[1,2-b][1,2,4]triazole (40 mg, 0.14 mmol) and N-methoxy-N,3-dimethyl-oxetane-3-carboxamide (45 mg, 0.28 mmol) in tetrahydrofuran (3 mL) was added n-butyllithium (2.5 M in hexanes, 0.17 mL, 0.43 mmol) under nitrogen atmosphere. After addition, the mixture was stirred at −70° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 30-60%/0.05% ammonia hydroxide in water) to afford (rac-(5S,7S)-7-fluoro-5-phenyl-6,7-dihydro-5H-pyrrolo[1,2-b][1,2,4]triazol-2-yl)-(3-methyloxetan-3-yl)methanone (11.5 mg, 27%) as a yellow oil. $^1$H NMR (400 MHz, CD$_3$OD) δ 7.43-7.37 (m, 3H), 7.26-7.23 (m, 2H), 6.17-6.01 (m, 1H), 5.65-5.63 (m, 1H), 5.08-5.03 (m, 2H), 4.52-4.48 (m, 2H), 3.78-3.70 (m, 1H), 2.86-2.76 (m, 1H), 1.75 (s, 3H). LCMS R$_T$=0.816 min, m/z=302.0 [M+H]$^+$. LCMS (5 to 95% acetonitrile in water+0.03% trifluoacetic acid over 1.5 mins) retention time 0.816 min, ESI+ found [M+H]=302.0.

Method 11

Example 16

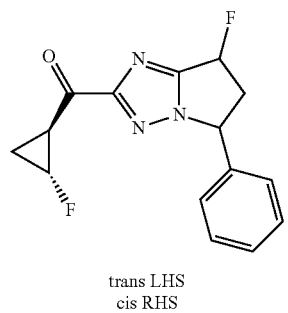

trans LHS
cis RHS

(rac-(5S,7S)-7-fluoro-5-phenyl-6,7-dihydro-5H-pyrrolo[1,2-b][1,2,4]triazol-2-yl)-[rac-(1S,2R)-2-fluorocyclopropyl]methanone

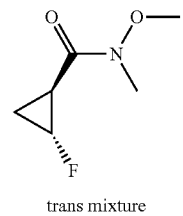

trans mixture

Step 1: trans-2-fluoro-N-methoxy-N-methyl-cyclopropanecarboxamide

A mixture of trans-2-fluorocyclopropane-1-carboxylic acid (100 mg, 0.96 mmol), N,O-dimethylhydroxylamine hydrochloride (122 mg, 1.25 mmol), 1-[bis(dimethylamino)methylene]-1H-1,2,3-triazolo[4,5-b]pyridinium 3-oxide hexafluorophosphate (475 mg, 1.25 mmol) and N,N-diisopropylethylamine (310 mg, 2.40 mmol) in N,N-dimethylformamide (5 mL) was stirred at 25° C. for 12 h. The mixture was poured into water (10 mL) and extracted with ethyl acetate (3×10 mL). The combined organic layers were washed with water (2×10 mL), brine (20 mL) and concentrated under reduced pressure. The residue was purified by column chromatography (silica gel, 100-200 mesh, 0 to 30% ethyl acetate in petroleum ether) to give trans-2-fluoro-N-methoxy-N-methyl-cyclopropanecarboxamide (70 mg, 50%) as colorless oil. $^1$H NMR (400 MHz, CDCl$_3$) δ 4.89-4.71 (m, 1H), 3.79 (s, 3H), 3.21 (s, 3H), 2.62-2.60 (m, 1H), 1.48-1.35 (m, 2H). LCMS R$_T$=0.292 min, m/z=148.1 [M+H]$^+$. LCMS (5 to 95% acetonitrile in water+0.03% trifluoacetic acid over 1.5 mins) retention time 0.292 min, ESI+ found [M+H]=148.1.

65

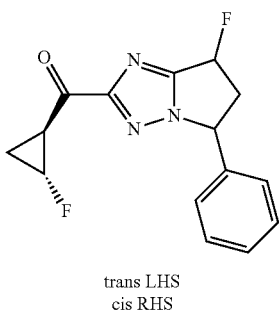 [SMILES: O=C(c1nc2n(n1)C(c1ccccc1)CC2F)[C@@H]1C[C@H]1F]

trans LHS
cis RHS

Step 2: (rac-(5S,7S)-7-fluoro-5-phenyl-6,7-dihydro-5H-pyrrolo[1,2-b][1,2,4]triazol-2-yl)-[rac-(1S,2R)-2-fluorocyclopropyl]methanone To a cooled (−70° C.) solution of cis-2-bromo-7-fluoro-5-phenyl-6,7-dihydro-5H-pyrrolo[1,2-b][1,2,4]triazole (40 mg, 0.14 mmol) and trans-2-fluoro-N-methoxy-N-methylcyclopropanecarboxamide (42 mg, 0.28 mmol) in tetrahydrofuran (3 mL) was added n-butyllithium (2.5 M in hexanes, 0.07 mL, 0.18 mmol) under nitrogen atmosphere. After addition, the mixture was stirred at −70° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 35-65%/0.05% ammonia hydroxide in water) to afford (rac-(5S,7S)-7-fluoro-5-phenyl-6,7-dihydro-5H-pyrrolo[1,2-b][1,2,4]triazol-2-yl)-[rac-(1S,2R)-2-fluorocyclopropyl]methanone (3.3 mg, 7.6%) as colorless oil. $^1$H NMR (400 MHz, CDCl$_3$) δ 7.42-7.37 (m, 3H), 7.28-7.27 (m, 2H), 6.13-5.97 (m, 1H), 5.54-5.52 (m, 1H), 5.03-4.85 (m, 1H), 3.71-3.51 (m, 2H), 3.04-2.94 (m, 1H), 1.70-1.62 (m, 2H). LCMS R$_T$=0.862 min, m/z=289.9 [M+H]$^+$. LCMS (5 to 95% acetonitrile in water+0.03% trifluoacetic acid over 1.5 mins) retention time 0.862 min, ESI+ found [M+H]=289.9.

Method 12

Example 17

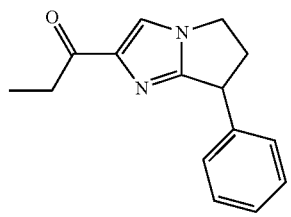

1-(7-phenyl-6,7-dihydro-5H-pyrrolo[1,2-a]imidazol-2-yl)propan-1-one

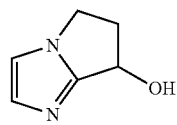

66

Step 1: 6,7-dihydro-5H-pyrrolo[1,2-a]imidazol-7-ol

To a solution of imidazole (40.0 g, 587.5 mmol), acetic acid (1.8 mL), and 1,4-dioxane (600 mL) was added acrolein (58.8 mL, 881.3 mmol). The resulting mixture was stirred at 110° C. for 24 h and cooled to 0° C. The resulting solid was collected by filtration, washed with petroleum ether (200 mL) to afford crude 6,7-dihydro-5H-pyrrolo[1,2-a]imidazol-7-ol (50.0 g, 69%) as a white solid. Used as is in the next step.

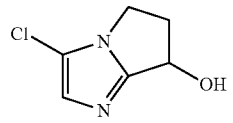

Step 2: 3-chloro-6,7-dihydro-5H-pyrrolo[1,2-a]imidazol-7-ol

To a solution of 6,7-dihydro-5H-pyrrolo[1,2-a]imidazol-7-ol (10.0 g, 80.6 mmol) in dichloromethane (300 mL) was added N-chlorosuccinimide (10.8 g, 80.6 mmol). The mixture was stirred at 50° C. for 2 h and subsequently concentrated under reduced pressure. The residue was purified by column chromatography (silica gel, 100-200 mesh, 0 to 10% methanol in dichloromethane) to afford 3-chloro-6,7-dihydro-5H-pyrrolo[1,2-a]imidazol-7-ol (8.0 g, 63%) as a white solid, used as is in the next step.

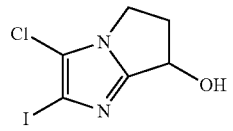

Step 3: 3-chloro-2-iodo-6,7-dihydro-5H-pyrrolo[1,2-a]imidazol-7-ol

To a solution of 3-chloro-6,7-dihydro-5H-pyrrolo[1,2-a]imidazol-7-ol (5.6 g, 35.3 mmol) in N,N-dimethylformamide (20 mL) was added N-iodosuccinimide (8.3 g, 37.1 mmol). The mixture was heated at 60° C. for 3 h and concentrated under reduced pressure. The residue was purified by column chromatography (silica gel, 100-200 mesh, 0 to 10% methanol in dichloromethane) to afford 3-chloro-2-iodo-6,7-dihydro-5H-pyrrolo[1,2-a]imidazol-7-ol (5.3 g, 53%) as light yellow solids, used as is in the next step.

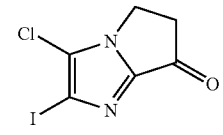 [SMILES: O=C1CCn2c1nc(I)c2Cl]

Step 4: 3-chloro-2-iodo-5H-pyrrolo[1,2-a]imidazol-7(6H)-one

To a solution of 3-chloro-2-iodo-6,7-dihydro-5H-pyrrolo[1,2-a]imidazol-7-ol (5.3 g, 18.6 mmol) in dichloromethane (20 mL) was added manganese dioxide (8.1 g, 93.2 mmol).

The mixture was heated at 40° C. for 5 h and filtered. The filtrate was concentrated to dryness under reduced pressure to afford crude 3-chloro-2-iodo-5,6-dihydropyrrolo[1,2-a]imidazol-7-one (3.2 g, 61%) as a brown solid, used as is in the next step.

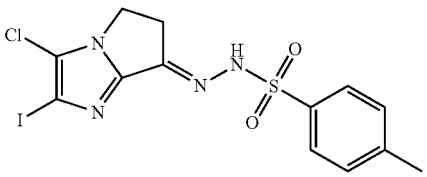 [SMILES: Cc1ccc(S(=O)(=O)N/N=C2\CCn3c2nc(I)c3Cl)cc1]

Step 5: N—[(Z)-(3-chloro-2-iodo-5,6-dihydropyrrolo[1,2-a]imidazol-7-ylidene)amino]-4-methylbenzenesulfonamide A mixture of 4-methylbenzenesulfonohydrazide (2.1 g, 11.3 mmol) and 3-chloro-2-iodo-5,6-dihydropyrrolo[1,2-a]imidazol-7-one (3.2 g, 11.3 mmol) in ethanol (70 mL) was heated at 90° C. for 7 h and cooled to 15° C. The resulting solid was collected by filtration and dried under reduced pressure to afford crude N—[(Z)-(3-chloro-2-iodo-5,6-dihydropyrrolo[1,2-a]imidazol-7-ylidene)amino]-4-methyl-benzenesulfonamide (2.8 g, 54%) as a pale green solid, used as is in the next step.

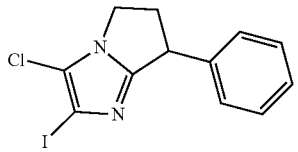 [SMILES: Clc1c(I)nc2n1CCC2c1ccccc1]

Step 6: 3-chloro-2-iodo-7-phenyl-6,7-dihydro-5H-pyrrolo[1,2-a]imidazole

A mixture of N—[(Z)-(3-chloro-2-iodo-5,6-dihydropyrrolo[1,2-a]imidazol-7-ylidene) amino]-4-methyl-benzenesulfonamide (1.8 g, 3.88 mmol), phenylboronic acid (710 mg, 5.82 mmol), potassium carbonate (1.6 g, 11.65 mmol) in 1,4-dioxane (40 mL) was heated at 110° C. for 18 h under $N_2$ atmosphere. The mixture was filtered and the filtrate was concentrated under reduced pressure. The residue was purified by column chromatography (silica gel, 100-200 mesh, 0 to 50% ethyl acetate in petroleum ether) to afford 3-chloro-2-iodo-7-phenyl-6,7-dihydro-5H-pyrrolo[1,2-a]imidazole (200 mg, 15%) as a light brown solid. LCMS $R_T$=0.879 min, m/z=334.9 [M+H]$^+$. LCMS (5 to 95% acetonitrile in water+0.03% trifluoacetic acid over 1.5 mins) retention time: 0.879 min, ESI+ found [M+H]=334.9.

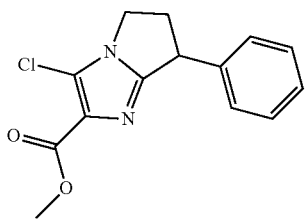 [SMILES: COC(=O)c1nc2n(c1Cl)CCC2c1ccccc1]

Step 7: Methyl 3-chloro-7-phenyl-6,7-dihydro-5H-pyrrolo[1,2-a]imidazole-2-carboxylate A mixture of 3-chloro-2-iodo-7-phenyl-6,7-dihydro-5H-pyrrolo[1,2-a]imidazole (200 mg, 0.58 mmol), 1,1'-bis(diphenylphosphino)ferrocene-palladium(II) dichloride dichloromethane complex (24 mg, 0.03 mmol) and triethylamine (0.4 mL, 2.9 mmol) in N,N-dimethylformamide (24 mL)/methanol (8 mL) was heated at 90° C. for 18 h under CO (50 Psi). The mixture was filtered through a short pad of Celite and the filtrate was concentrated under reduced pressure. The residue was purified by preparative TLC (50% ethyl acetate in petroleum ether, $R_f$=0.4) to afford methyl 3-chloro-7-phenyl-6,7-dihydro-5H-pyrrolo[1,2-a]imidazole-2-carboxylate (140 mg, 87%) as a light brown solid. LCMS $R_T$=0.676 min, m/z=277.0 [M+H]$^+$. LCMS (5 to 95% acetonitrile in water+0.03% trifluoacetic acid over 1.5 mins) retention time: 0.676 min, ESI+ found [M+H]=277.0

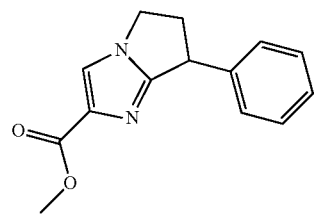 [SMILES: COC(=O)c1cn2c(n1)C(c1ccccc1)CC2]

Step 8: Methyl 7-phenyl-6,7-dihydro-5H-pyrrolo[1,2-a]imidazole-2-carboxylate

A mixture of methyl 3-chloro-7-phenyl-6,7-dihydro-5H-pyrrolo[1,2-a]imidazole-2-carboxylate (120 mg, 0.43 mmol) and palladium (10% on carbon, 103 mg, 0.10 mmol, 50% wet) in methanol (50 mL) was hydrogenated (40 psi) at 50° C. for 24 h and then filtered. The filtrate was concentrated under reduced pressure to afford crude methyl 7-phenyl-6,7-dihydro-5H-pyrrolo[1,2-a]imidazole-2-carboxylate (100 mg, 95%) as brown oil, used as is in the next step. $^1$H NMR (400 MHz, CDCl$_3$) δ 7.85-7.60 (m, 1H), 7.40-7.25 (m, 4H), 4.70-4.55 (m, 1H), 4.40-4.15 (m, 2H), 3.89 (s, 3H), 3.30-3.20 (m, 1H), 2.75-2.70 (m, 1H), 1.70-1.60 (m, 1H). LCMS $R_T$=0.513 min, m/z=243.1 [M+H]$^+$. LCMS (5 to 95% acetonitrile in water+0.03% trifluoacetic acid over 1.5 mins) retention time; 0.513 min, ESI+ found [M+H]=243.1.

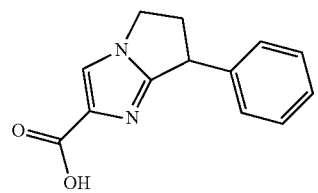 [SMILES: O=C(O)c1cn2c(n1)C(c1ccccc1)CC2]

Step 9: 7-phenyl-6,7-dihydro-5H-pyrrolo[1,2-a]imidazole-2-carboxylicacid

A mixture of methyl 7-phenyl-6,7-dihydro-5H-pyrrolo[1,2-a]imidazole-2-carboxylate (100 mg, 0.41 mmol) and lithium hydroxide monohydrate (118 mg, 2.89 mmol) in tetrahydrofuran (2 mL), water (1 mL) and methanol (2 mL) was heated at 25° C. for 18 h. Sodium hydroxide (100 mg)

was added and the mixture was heated at 40° C. for another 2 h. The resulting mixture was concentrated under reduced pressure. The residue was dissolved in water (5 mL) and adjusted to pH=3 by addition of 2 M HCl. The resulting mixture was lyophilized to dryness to afford the crude 7-phenyl-6,7-dihydro-5H-pyrrolo[1,2-a]imidazole-2-carboxylic acid (94 mg, 99%) as a white solid, used as is in the next step.

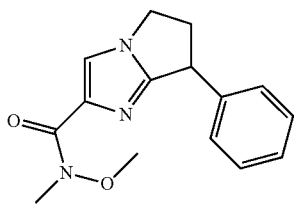 [SMILES: CON(C)C(=O)c1cn2c(n1)C(c1ccccc1)CC2]

Step 10: N-methoxy-N-methyl-7-phenyl-6,7-dihydro-5H-pyrrolo[1,2-a]imidazole-2-carboxamide A mixture of 7-phenyl-6,7-dihydro-5H-pyrrolo[1,2-a]imidazole-2-carboxylic acid (60 mg, 0.26 mmol), N,O-dimethylhydroxylamine hydrochloride (77 mg, 0.79 mmol), triethylamine (0.11 mL, 0.79 mmol), 1-[bis(dimethylamino)methylene]-1H-1,2,3-triazolo[4,5-b]pyridinium 3-oxide hexafluorophosphate (105 mg, 0.28 mmol) in N,N-dimethylformamide (4 mL) was stirred at 15° C. for 2 h. The mixture was concentrated under reduced pressure. The residue was purified by preparative TLC (50% ethyl acetate in petroleum ether, $R_f$=0.5) to afford N-methoxy-N-methyl-7-phenyl-6,7-dihydro-5H-pyrrolo[1,2-a]imidazole-2-carboxamide (70 mg, 98%) as a white solid. LCMS $R_T$=0.506 min, m/z=272.1 [M+H]$^+$. LCMS (5 to 95% acetonitrile in water+0.03% trifluoacetic acid over 1.5 mins) retention time: 0.506 min, ESI+ found [M+H]=272.1.

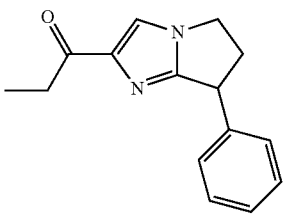 [SMILES: CCC(=O)c1cn2c(n1)C(c1ccccc1)CC2]

Step 11: 1-(7-phenyl-6,7-dihydro-5H-pyrrolo[1,2-a]imidazol-2-yl)propan-1-one

To a cooled (−70° C.) solution of N-methoxy-N-methyl-7-phenyl-6,7-dihydro-5H-pyrrolo[1,2-a]imidazole-2-carboxamide (50 mg, 0.18 mmol) in tetrahydrofuran (2 mL) was added ethylmagnesium bromide (3.0 M in THF, 0.61 mL, 1.83 mmol) under N$_2$ atmosphere. After addition, the mixture was stirred at −70° C. for 2 h and then quenched by addition of saturated aqueous ammonium chloride (3 mL). The mixture was concentrated under reduced pressure and the residue was purified by RP-HPLC (acetonitrile 25-55%/0.05% ammonium hydroxide in water) to afford 1-(7-phenyl-6,7-dihydro-5H-pyrrolo[1,2-a]imidazol-2-yl)propan-1-one (4.6 mg, 9%) as a light brown solid. $^1$H NMR (400 MHz, CD$_3$OD) δ 7.86 (s, 1H), 7.35-7.31 (m, 2H), 7.30-7.21 (m, 3H), 4.42-4.38 (m, 1H), 4.25-4.23 (m, 1H), 4.20-4.11 (m, 1H), 3.12-3.10 (m, 1H), 2.89-2.83 (m, 2H), 2.58-2.50 (m, 1H), 1.14-1.10 (m, 3H). LCMS $R_T$=0.634 min, m/z=241.1 [M+H]$^+$. LCMS (5 to 95% acetonitrile in water+0.03% trifluoacetic acid over 1.5 mins) retention time 0.634 min, ESI+ found [M+H]=241.1.

Method 13

Example 18

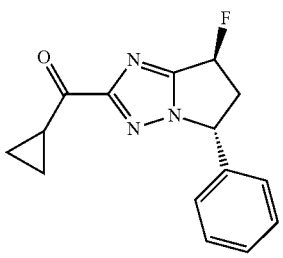

trans mixture

Cyclopropyl-[rac-(5R,7S)-7-fluoro-5-phenyl-6,7-dihydro-5H-pyrrolo[1,2-b][1,2,4]triazol-2-yl]methanone

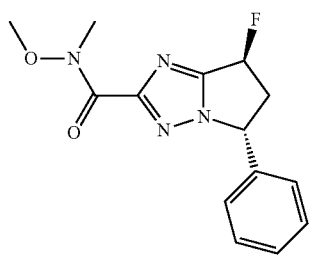

trans mixture

Step 1: trans-7-fluoro-N-methoxy-N-methyl-5-phenyl-6,7-dihydro-5H-pyrrolo[1,2-b][1,2,4]triazole-2-carboxamide A mixture of trans-7-fluoro-5-phenyl-6,7-dihydro-5H-pyrrolo[1,2-b][1,2,4]triazole-2-carboxylic acid (50 mg, 0.20 mmol), 1-(3-dimethylaminopropyl)-3-ethylcarbodiimide hydrochloride (46 mg, 0.24 mmol), 1-hydroxybenzotriazole (5 mg, 0.04 mmol), N,O-dimethylhydroxylamine hydrochloride (12 mg, 0.20 mmol) in N,N-dimethylformamide (5 mL) was stirred at 20° C. for 18 h. The mixture was concentrated under reduced pressure and the residue was purified by preparative TLC (50% ethyl acetate in petroleum ether, $R_f$=0.7) to afford trans-7-fluoro-N-methoxy-N-methyl-5-phenyl-6,7-dihydro-5H-pyrrolo[1,2-b][1,2,4]triazole-2-carboxamide (30 mg, 51%) as a white solid.

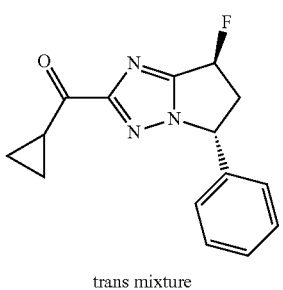 [SMILES: O=C(c1nc2n(n1)[C@@H](c1ccccc1)C[C@@H]2F)C1CC1]

trans mixture

Step 2: cyclopropyl-[rac-(5R,7S)-7-fluoro-5-phenyl-6,7-dihydro-5H-pyrrolo[1,2-b][1,2,4]triazol-2-yl]methanone To a cooled (−78° C.) solution of trans-7-fluoro-N-methoxy-N-methyl-5-phenyl-6,7-dihydro-5H-pyrrolo[1,2-b][1,2,4]triazole-2-carboxamide (15 mg, 0.05 mmol) in tetrahydrofuran (10 mL) was added cyclopropylmagnesium bromide (0.5 M in THF, 0.2 mL, 0.10 mmol) under nitrogen atmosphere. After addition, the mixture was stirred at −78° C. for 1 h and quenched by addition of saturated aqueous ammonium chloride (10 mL). The mixture was extracted with ethyl acetate (3×10 mL). The combined organic layers were dried over sodium sulfate and concentrated under reduce pressure. The residue was purified by RP-HPLC (acetonitrile 35-65%/0.05% hydrochloride in water) to afford cyclopropyl-[rac-(5R,7S)-7-fluoro-5-phenyl-6,7-dihydro-5H-pyrrolo[1,2-b][1,2,4]triazol-2-yl]methanone (7.6 mg, 50%) as a white solid. $^1$H NMR (400 MHz, CD$_3$OD) δ 7.44-7.40 (m, 3H), 7.30-7.26 (m, 2H), 6.29-6.26 (m, 0.5H), 6.14-6.12 (m, 0.5H), 5.92-5.87 (m, 1H), 3.44-3.41 (m, 1H), 3.01-3.02 (m, 2H), 1.19-1.16 (m, 2H), 1.12-1.09 (m, 2H). LCMS R$_T$=0.849 min, m/z=272.0 [M+H]$^+$. LCMS (5 to 95% acetonitrile in water+0.03% trifluoacetic acid over 1.5 mins) retention time 0.849 min, ESI+ found [M+H]=272.0.

Method 14

Example 19

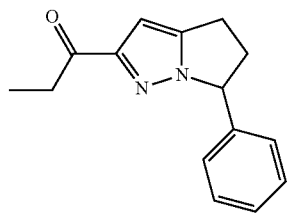

1-(6-phenyl-5,6-dihydro-4H-pyrrolo[1,2-b]pyrazol-2-yl)propan-1-one

Step 1: Ethyl 3-(hydroxymethyl)-1H-pyrazole-5-carboxylate and ethyl 4-(hydroxymethyl)-1H-pyrazole-5-carboxylate To a solution of prop-2-yn-1-ol (30.0 g, 535.14 mmol) in toluene (300 mL) was added ethyl 2-diazoacetate (67.2 g, 588.66 mmol). The reaction mixture was stirred at 110° C. for 5 h and cooled to room temperature. The crude product was collected by filtration and washed with 10% ethyl acetate in petroleum ether (50 mL) to afford a mixture of ethyl 4-(hydroxymethyl)-1H-pyrazole-5-carboxylate (15.8 g, 17%) and ethyl 3-(hydroxymethyl)-1H-pyrazole-5-carboxylate (not separable, 1:3, 63.1 g, 69%) as light yellow solids, used as mixture in the next step.

ethyl 3-(hydroxymethyl)-1H-pyrazole-5-carboxylate (major isomer): $^1$H NMR (DMSO-d6) 12.60 (1H, s, broad); 6.70 (1H, s); 4.70 (1H, s); 4.35 (2H, q, J=7.0 Hz); 4.45 (1H, s, broad); 1.25 (3H, t, J=7.0 Hz).

ethyl 4-(hydroxymethyl)-1H-pyrazole-5-carboxylate (minor isomer): $^1$H NMR (DMSO-d6) 12.60 (1H, s, broad); 7.65 (1H, s); 4.75 (1H, s); 4.35 (2H, q, J=7.0 Hz); 4.13 (1H, s, broad); 1.25 (3H, t, J=7.0 Hz).

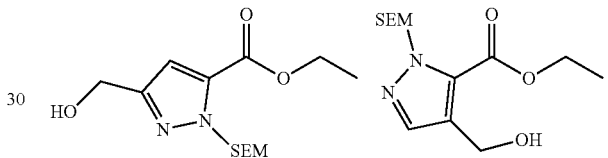

Step 2: Ethyl 3-(hydroxymethyl)-1-((2-(trimethylsilyl)ethoxy)methyl)-1H-pyrazole-5-carboxylate and Ethyl 4-(hydroxymethyl)-1-((2-(trimethylsilyl)ethoxy)methyl)-1H-pyrazole-5-carboxylate A mixture of ethyl 3-(hydroxymethyl)-1H-pyrazole-5-carboxylate and ethyl 4-(hydroxymethyl)-1H-pyrazole-5-carboxylate (3:1, 4.0 g, 23.5 mmol), (2-(chloromethoxy)ethyl)trimethylsilane (11.2 mL, 70.5 mmol) and cesium carbonate (45.9 g, 141.0 mmol) in acetone (100 mL) was stirred at 25° C. for 3 h and then filtered. The filtrate was concentrated under reduce pressure and the residue was purified by column chromatography (silica gel, 100-200 mesh, 0 to 40% ethyl acetate in petroleum ether) to afford ethyl 3-(hydroxymethyl)-1-((2-(trimethylsilyl) ethoxy)methyl)-1H-pyrazole-5-carboxylate and ethyl 4-(hydroxymethyl)-1-((2-(trimethylsilyl)ethoxy)methyl)-1H-pyrazole-5-carboxylate (not separable, 3.7 g, 52%), used as mixture in the next step. LC-MS R$_T$=0.855 min, m/z=322.9 (M+H)$^+$. LCMS (5 to 95% acetonitrile in water+0.03% trifluoacetic acid over 1.5 mins) retention time 0.855 min, ESI+ found [M+Na]=322.9.

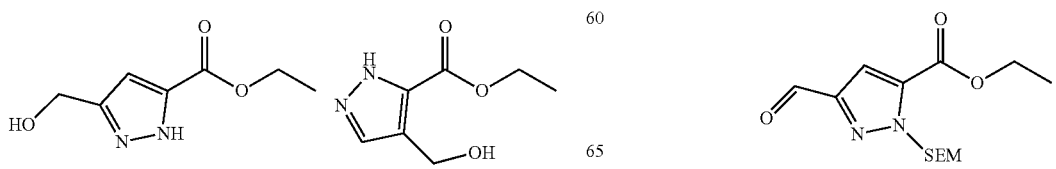

Step 3: Ethyl 3-formyl-1-((2-(trimethylsilyl)ethoxy)methyl)-1H-pyrazole-5-carboxylate To a solution of ethyl 3-(hydroxymethyl)-1-((2-(trimethylsilyl)ethoxy)methyl)-1H-pyrazole-5-carboxylate and ethyl 4-(hydroxymethyl)-1-((2-(trimethylsilyl)ethoxy) methyl)-1H-pyrazole-5-carboxylate (2.0 g, 6.66 mmol) in dichloromethane (100 mL) was added manganese dioxide (7.0 g, 80.52 mmol). The mixture was stirred at 25° C. for 15 h and filtered. The filtrate was concentrated under reduce pressure and the residue was purified by column chromatography (silica gel, 100-200 mesh, 0 to 20% ethyl acetate in petroleum ether) to afford ethyl 5-formyl-2-(2-trimethylsilyl ethoxymethyl)pyrazole-3-carboxylate (700 mg, 35%) as colorless oil. $^1$H NMR (400 MHz, CDCl$_3$) δ 10.02 (s, 1H), 7.38 (s, 1H), 5.94 (s, 2H), 4.40 (q, J=8.0 Hz, 2H), 3.69-3.60 (m, 2H), 1.40 (t, J=8.0 Hz, 3H), 0.98-0.89 (m, 2H), 0.02-0.07 (m, 9H).

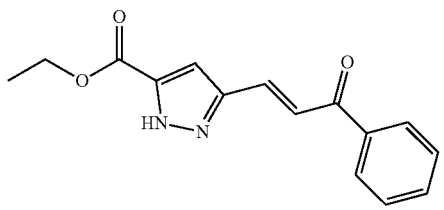 [SMILES: CCOC(=O)c1cc(/C=C/C(=O)c2ccccc2)n[nH]1]

Step 4: (E)-ethyl 3-(3-oxo-3-phenylprop-1-en-1-yl)-1H-pyrazole-5-carboxylate To a solution of ethyl 5-formyl-2-(2-trimethylsilylethoxymethyl) pyrazole-3-carboxylate (700 mg, 2.35 mmol) in dichloromethane (100 mL) was added trimethyl ((1-phenylvinyl)oxy)silane (499 mg, 2.59 mmol) and titanium tetrachloride (875 mg, 4.61 mmol). The mixture was stirred at 40° C. for 48 h and then quenched by addition of water (50 mL). The resulting mixture was extracted with dichloromethane (3×50 mL). The combined organic layers were concentrated under reduce pressure and the residue was purified by column chromatography (silica gel, 100-200 mesh, 0 to 30% ethyl acetate in petroleum ether) to afford (E)-ethyl 3-(3-oxo-3-phenylprop-1-en-1-yl)-1H-pyrazole-5-carboxylate (310 mg, 49%) as a yellow solid. LC-MS R$_T$=0.853 min, m/z=270.9 (M+H)$^+$. LCMS (5 to 95% acetonitrile in water+0.03% trifluoacetic acid over 1.5 mins) retention time 0.853 min, ESI+ found [M+H]=270.9.

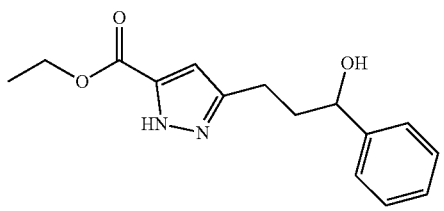 [SMILES: CCOC(=O)c1cc(CCC(O)c2ccccc2)n[nH]1]

Step 5: Ethyl 3-(3-hydroxy-3-phenylpropyl)-1H-pyrazole-5-carboxylate

A mixture of (E)-ethyl 3-(3-oxo-3-phenylprop-1-en-1-yl)-1H-pyrazole-5-carboxylate (310 mg, 1.15 mmol) and palladium (10% on carbon, 122 mg) in methanol (20 mL) was hydrogenated (15 psi) at 25° C. for 15 h and then filtered. The filtrate was concentrated under reduce pressure to afford crude ethyl 3-(3-hydroxy-3-phenylpropyl)-1H-pyrazole-5-carboxylate (314 mg, 99%) as light yellow oil. This crude was used directly in next step without further purification.

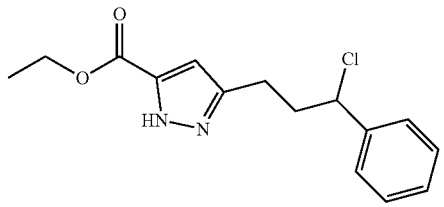 [SMILES: CCOC(=O)c1cc(CCC(Cl)c2ccccc2)n[nH]1]

Step 6: Ethyl 3-(3-chloro-3-phenylpropyl)-1H-pyrazole-5-carboxylate

To a solution of ethyl 3-(3-hydroxy-3-phenylpropyl)-1H-pyrazole-5-carboxylate (314 mg, 1.14 mmol) in acetonitrile (5 mL) was added sulfurous dichloride (681 mg, 5.72 mmol). The mixture was heated at 65° C. for 15 h and then concentrated under reduced pressure to afford crude ethyl 3-(3-chloro-3-phenyl-propyl)-1H-pyrazole-5-carboxylate (335 mg, 100%) as yellow oil. This crude was used directly in next step without further purification. LC-MS R$_T$=0.861 min, m/z=314.9 (M+H)$^+$.

LCMS (5 to 95% acetonitrile in water+0.03% trifluoacetic acid over 1.5 mins) retention time 0.861 min, ESI+ found [M+H]=314.9.

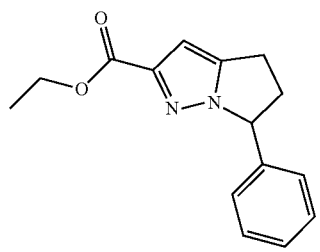 [SMILES: CCOC(=O)c1cc2n(n1)C(c1ccccc1)CC2]

Step 7: Ethyl 6-phenyl-5,6-dihydro-4H-pyrrolo[1,2-b]pyrazole-2-carboxylate

A mixture of ethyl 3-(3-chloro-3-phenyl-propyl)-1H-pyrazole-5-carboxylate (335 mg, 1.14 mmol) and cesium carbonate (3.0 g, 9.21 mmol) in acetonitrile (20 mL) was stirred at 15° C. for 15 h and then filtered. The filtrate was concentrated under reduce pressure and the residue was purified by column chromatography (silica gel, 100-200 mesh, 0 to 25% ethyl acetate in petroleum ether) to afford ethyl 6-phenyl-5,6-dihydro-4H-pyrrolo[1,2-b]pyrazole-2-carboxylate (120 mg, 41%) as light yellow oil. LC-MS R$_T$=0.824 min, m/z=279.0 (M+H)$^+$. LCMS (5 to 95% acetonitrile in water+0.03% trifluoacetic acid over 1.5 mins) retention time 0.824 min, ESI+ found [M+H]=279.0.

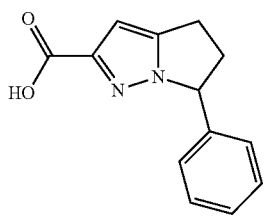 [SMILES: O=C(O)c1cc2n(n1)C(c1ccccc1)CC2]

Step 8: 6-phenyl-5,6-dihydro-4H-pyrrolo[1,2-b]pyrazole-2-carboxylic acid

A mixture of ethyl 6-phenyl-5,6-dihydro-4H-pyrrolo[1,2-b]pyrazole-2-carboxylate (60 mg, 0.23 mmol) and lithium hydroxide monohydrate (50 mg, 1.2 mmol) in tetrahydrofuran (5 mL), methanol (5 mL) and water (2 mL) was stirred at 25° C. for 3 h and then concentrated under reduced pressure. The residue was adjusted to pH=5 by additional of hydrochloric acid (2 N). The resulting mixture was extracted with ethyl acetate (3×20 mL). The combined organic layers were washed with water (20 mL), brine (20 mL), dried over anhydrous sodium sulfate and concentrated under reduced pressure to afford crude 6-phenyl-5,6-dihydro-4H-pyrrolo[1,2-b]pyrazole-2-carboxylic acid (30 mg, 56%) as a yellow solid, used as is in the next step.

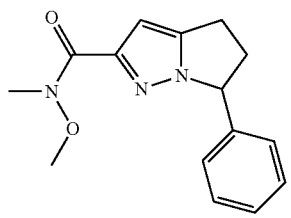 [SMILES: CON(C)C(=O)c1cc2n(n1)C(c1ccccc1)CC2]

Step 9: N-methoxy-N-methyl-6-phenyl-5,6-dihydro-4H-pyrrolo[1,2-b]pyrazole-2-carboxamide A mixture of 6-phenyl-5,6-dihydro-4H-pyrrolo[1,2-b]pyrazole-2-carboxylic acid (30 mg, 0.13 mmol), N,O-dimethylhydroxylamine hydrochloride (17 mg, 0.17 mmol), 1-[bis(dimethylamino)methylene]-1H-1,2,3-triazolo[4,5-b]pyridinium 3-oxide hexafluorophosphate (65 mg, 0.17 mmol), N,N-diisopropylethylamine (42 mg, 0.33 mmol) in tetrahydrofuran (5 mL) was stirred at 25° C. for 2 h. The mixture was diluted with water (20 mL) and extracted with ethyl acetate (3×15 mL). The combined organic layers were concentrated under reduce pressure. The residue was purified by column chromatography (silica gel, 100-200 mesh, 0 to 50% ethyl acetate in petroleum ether) to afford N-methoxy-N-methyl-6-phenyl-5,6-dihydro-4H-pyrrolo[1,2-b]pyrazole-2-carboxamide (25 mg, 70%) as a white solid. LC-MS $R_T$=0.952 min, m/z=272.1 (M+H)$^+$. LCMS (10 to 80% acetonitrile in water+0.03% trifluoacetic acid over 2.0 mins) retention time 0.952 min, ESI+ found [M+H]=272.1.

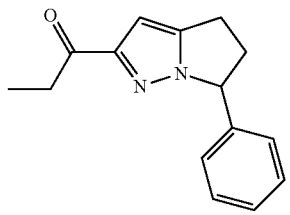 [SMILES: CCC(=O)c1cc2n(n1)C(c1ccccc1)CC2]

Step 10: 1-(6-phenyl-5,6-dihydro-4H-pyrrolo[1,2-b]pyrazol-2-yl)propan-1-one

To a cooled (−78° C.) solution of N-methoxy-N-methyl-6-phenyl-5,6-dihydro-4H-pyrrolo[1,2-b]pyrazole-2-carboxamide (24 mg, 0.09 mmol) in tetrahydrofuran (5 mL) was added ethylmagnesium chloride (3.0 M in THF, 0.07 mL, 0.21 mmol) dropwise under a nitrogen atmosphere. The mixture was stirred at −78° C. for 2 h and then quenched by addition of saturated aqueous ammonium chloride (10 mL). The mixture was extracted with ethyl acetate (3×10 mL). The combined organic layers were concentrated under reduce pressure and the residue was purified by column chromatography (silica gel, 100-200 mesh, 0 to 30% ethyl acetate in petroleum ether) to afford 1-(6-phenyl-5,6-dihydro-4H-pyrrolo[1,2-b]pyrazol-2-yl)propan-1-one (13.0 mg, 61%) as a white solid. $^1$H NMR (400 MHz, CD$_3$OD) δ 7.39-7.30 (m, 3H), 7.11-7.09 (m, 2H), 6.60 (s, 1H), 5.54-5.50 (m, 1H), 3.11-3.01 (m, 3H), 2.95-2.89 (m, 2H), 2.52-2.48 (m, 1H), 1.11 (t, J=7.2 Hz, 3H). LC-MS $R_T$=1.858 min, m/z=241.2 [M+H]$^+$. LCMS (10 to 80% acetonitrile in water+0.03% ammonium bicarbonate over 3.0 mins) retention time 1.858 min, ESI+ found [M+H]=214.2.

Method 15

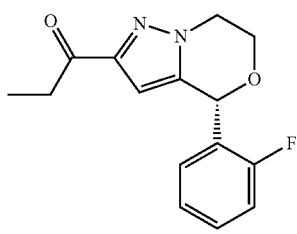

Example 20

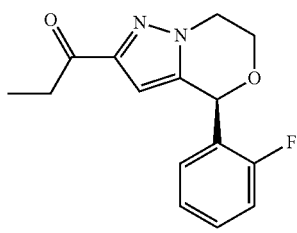

Example 21

1-[(4S)-4-(2-fluorophenyl)-6,7-dihydro-4H-pyrazolo[5,1-c][1,4]oxazin-2-yl]propan-1-one and 1-[(4R)-4-(2-fluorophenyl)-6,7-dihydro-4H-pyrazolo[5,1-c][1,4]oxazin-2-yl]propan-1-one To a cooled (−78° C.) solution of 4-(2-fluorophenyl)-6,7-dihydro-4H-pyrazolo[5,1-c][1,4]oxazine-2-carboxylate (200 mg, 0.63 mmol) in tetrahydrofuran (13 mL) was added ethylmagnesium chloride (2 M in THF, 0.63 mL, 1.26 mmol) dropwise under nitrogen atmosphere. After addition, the mixture was stirred at −78° C. for 2 h and then quenched by addition of saturated aqueous ammonium chloride (20 mL). The mixture was extracted with ethyl acetate (3×15 mL). The combined organic layers were concentrated under reduce pressure and the residue was purified by column chromatography (silica gel, 100-200 mesh, 0 to 30% ethyl acetate in petroleum ether) to give 1-[4-(2-fluorophenyl)-6,7-dihydro-4H-pyrazolo[5,1-c][1,4]oxazin-2-yl]propan-1-one (120 mg, 70%) as a white solid. This racemic material was further separated by chiral SFC to afford arbitrarily assigned:

1-[(4S)-4-(2-fluorophenyl)-6,7-dihydro-4H-pyrazolo[5,1-c][1,4]oxazin-2-yl]propan-1-one (Peak 1, retention time=2.979 min) (45.0 mg, 37%) as a white solid. $^1$H NMR (400 MHz, CD$_3$OD) δ 7.40-7.34 (m, 2H), 7.16-7.14 (m, 2H), 6.22 (s, 1H), 6.07 (s, 1H), 4.42-4.18 (m, 4H), 2.96-2.92 (m, 2H), 1.10 (t, J=7.2 Hz, 3H). LC-MS R$_T$=1.761 min, m/z=275.2 [M+H]$^+$. LCMS (10 to 80% acetonitrile in water+0.03% ammonium bicarbonate over 3.0 mins) retention time 1.761 min, ESI+ found [M+H]=275.2.

1-[(4R)-4-(2-fluorophenyl)-6,7-dihydro-4H-pyrazolo[5,1-c][1,4]oxazin-2-yl]propan-1-one (Peak 2, retention time=3.234 min) (52 mg, 43%) as a white solid. $^1$H NMR (400 MHz, CD$_3$OD) δ 7.40-7.34 (m, 2H), 7.16-7.14 (m, 2H), 6.22 (s, 1H), 6.08 (s, 1H), 4.41-4.15 (m, 4H), 3.00-2.92 (m, 2H), 1.10 (t, J=7.2 Hz, 3H). LC-MSR$_T$=1.755 min, m/z=275.2 [M+H]$^+$. LCMS (10 to 80% acetonitrile in water+0.03% ammonium bicarbonate over 3.0 mins) retention time 1.752 min, ESI+ found [M+H]=275.2.

SFC condition: Column: ChiralPak AD-3 150×4.6 mm I.D., 3 μm Mobile phase: A: CO$_2$ B:Ethanol (0.05% DEA) Gradient: from 5% to 40% of B in 5.5 min and hold 40% for 3 min, then 5% of B for 1.5 min Flow rate: 2.5 mL/min, Column temperature: 40° C.

Method 16

Example 22

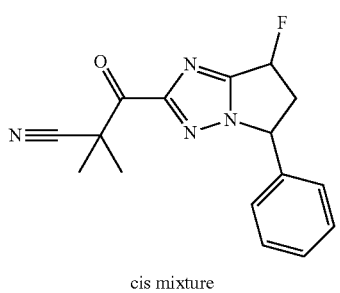

cis mixture

3-(rac-(5S,7S)-7-fluoro-5-phenyl-6,7-dihydro-5H-pyrrolo[1,2-b][1,2,4]triazol-2-yl)-2,2-dimethyl-3-oxo-propanenitrile

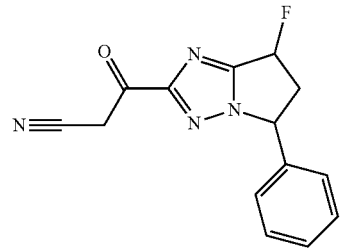 [SMILES: N#CCC(=O)c1nc2n(n1)C(c1ccccc1)CC2F]

Step 1: cis-3-(7-fluoro-5-phenyl-6,7-dihydro-5H-pyrrolo[1,2-b][1,2,4]triazol-2-yl)-3-oxopropanenitrile To a cooled (−78° C.) solution of acetonitrile (298 mg, 7.27 mmol) in tetrahydrofuran (15 mL) was added potassium t-butoxide (611.4 mg, 5.45 mmol). After stirring for 30 min, ethyl cis-7-fluoro-5-phenyl-6,7-dihydro-5H-pyrrolo[1,2-b][1,2,4]triazole-2-carboxylate (500 mg, 1.82 mmol) in tetrahydrofuran (5 mL) was added dropwise. After addition, the mixture was stirred at −78° C. for 2 h and then quenched by slow addition of cold saturated aqueous ammonium chloride (10 mL). The resulting mixture was extracted with ethyl acetate (3×15 mL). The combined organic layers were concentrated under reduce pressure to give crude cis-3-(7-fluoro-5-phenyl-6,7-dihydro-5H-pyrrolo[1,2-b][1,2,4]triazol-2-yl)-3-oxo-propanenitrile (150 mg, 31%) as a white solid, used as is in the next step.

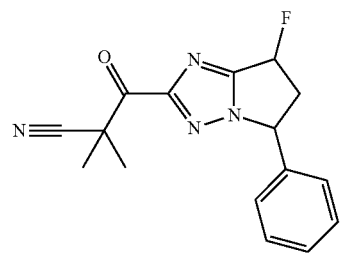

cis mixture

Step 2: 3-(rac-(5S,7S)-7-fluoro-5-phenyl-6,7-dihydro-5H-pyrrolo[1,2-b][1,2,4]triazol-2-yl)-2,2-dimethyl-3-oxo-propanenitrile To a cooled (0° C.) solution of cis-3-(7-fluoro-5-phenyl-6,7-dihydro-5H-pyrrolo[1,2-b][1,2,4]triazol-2-yl)-3-oxo-propanenitrile (140 mg, 0.52 mmol) in N,N-dimethylformamide (6 mL) was added cesium carbonate (422 mg, 1.30 mmol). After stirred for 30 min, iodomethane (2800 mg, 19.7 mmol) was added and the reaction mixture was stirred at 0° C. for 4 h. The mixture was then quenched by addition of cold saturated aqueous ammonium chloride (10 mL) and extracted with ethyl acetate (3×15 mL). The combined organic layers were concentrated under reduce pressure. The residue was purified by RP-HPLC (acetonitrile 30-60%/0.05% ammonia hyfroxide in water) to afford 3-(rac-(5S, 7S)-7-fluoro-5-phenyl-6,7-dihydro-5H-pyrrolo[1,2-b][1,2,4]triazol-2-yl)-2,2-dimethyl-3-oxo-propanenitrile (28.0 mg, 17%) as a white solid. ¹H NMR (400 MHz, CDCl₃) δ 7.44-7.38 (m, 3H), 7.27-7.25 (m, 2H), 6.15-6.13 (m, 0.5H), 6.01-5.99 (m, 0.5H), 5.57-5.56 (m, 1H), 3.74-3.63 (m, 1H), 3.06-2.95 (m, 1H), 1.81 (s, 3H), 1.78 (s, 3H). LC-MS R$_T$=1.734 min, m/z=299.2 [M+H]⁺. LCMS (10 to 80% acetonitrile in water+0.03% ammonium bicarbonate over 3.0 mins) retention time 1.734 min, ESI+ found [M+H]=299.2.

Method 17

Example 23

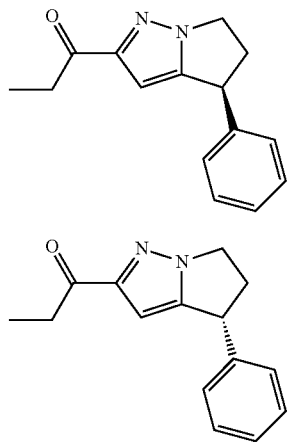

Example 24

1-[(4S)-4-phenyl-5,6-dihydro-4H-pyrrolo[1,2-b]pyrazol-2-yl]propan-1-one and 1-[(4R)-4-phenyl-5,6-dihydro-4H-pyrrolo[1,2-b]pyrazol-2-yl]propan-1-one

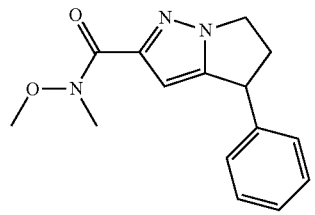 [SMILES: CON(C)C(=O)c1cc2n(n1)CCC2c1ccccc1]

Step 1: N-methoxy-N-methyl-4-phenyl-5,6-dihydro-4H-pyrrolo[1,2-b]pyrazole-2-carboxamide A mixture of 4-phenyl-5,6-dihydro-4H-pyrrolo[1,2-b]pyrazole-2-carboxylic acid (93 mg, 0.41 mmol), N,O-dimethylhydroxylamine hydrochloride (80 mg, 0.81 mmol), 1-[bis(dimethylamino)methylene]-1H-1,2,3-triazolo[4,5-b]pyridinium 3-oxide hexafluorophosphate (163 mg, 0.43 mmol) and triethylamine (124 mg, 1.22 mmol) in N,N-dimethylformamide (4 mL) was stirred at 25° C. for 2 h. The mixture was concentrated under reduced pressure and the residue was purified by preparative TLC (10% methanol in dichloromethane, R$_f$=0.7) to afford N-methoxy-N-methyl-4-phenyl-5,6-dihydro-4H-pyrrolo[1,2-b]pyrazole-2-carboxamide (100 mg, 91%) as a colorless oil. LCMS R$_T$=0.593 min, m/z=272.1 [M+H]⁺. LCMS (5 to 95% acetonitrile in water+0.03% trifluoacetic acid over 1.5 mins) retention time 0.593 min, ESI+ found [M+H]=272.1.

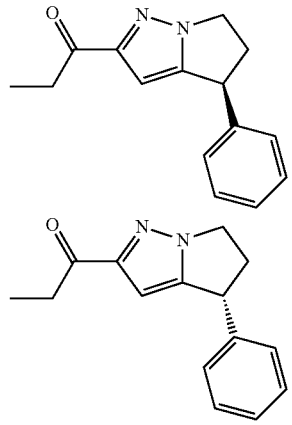

Step 2: 1-[(4S)-4-phenyl-5,6-dihydro-4H-pyrrolo[1,2-b]pyrazol-2-yl]propan-1-one and 1-[(4R)-4-phenyl-5,6-dihydro-4H-pyrrolo[1,2-b]pyrazol-2-yl]propan-1-one To a cooled (−78° C.) solution of N-methoxy-N-methyl-4-phenyl-5,6-dihydro-4H-pyrrolo[1,2-b]pyrazole-2-carboxamide (100 mg, 0.37 mmol) in tetrahydrofuran (5 mL) was added ethylmagnesium chloride (2.7 M in THF, 0.54 mL, 1.47 mmol) dropwise under nitrogen atmosphere. After addition, the mixture was stirred at −78° C. for 1 h and then quenched by addition of saturated aqueous ammonium chloride (10 mL). The mixture was extracted with ethyl acetate (2×15 mL). The combined organic layers were concentrated under reduce pressure to afford crude 1-(4-phenyl-5,6-dihydro-4H-pyrrolo[1,2-b]pyrazol-2-yl)propan-1-one (80 mg, 90%) as a light brown solid which was further separated by chiral SFC to afford arbitrarily assigned:

(R)-1-(4-phenyl-5,6-dihydro-4H-pyrrolo[1,2-b]pyrazol-2-yl)propan-1-one (Peak 1, retention time=2.581 min) (25.4 mg, 32%) as a white solid. ¹H NMR (400 MHz, CD₃OD) δ 7.32-7.21 (m, 5H), 6.43 (s, 1H), 4.50-4.37 (m, 1H), 4.36-4.33 (m, 1H), 4.24-4.22 (m, 1H), 3.13-3.10 (m, 1H), 2.99-2.95 (m, 2H), 2.57-2.53 (m, 1H), 1.15 (t, J=7.2 Hz, 3H). LCMS R$_T$=0.843 min, m/z=240.9 [M+H]⁺. LCMS (5 to 95% acetonitrile in water+0.03% trifluoacetic acid over 1.5 mins) retention time 0.843 min, ESI+ found [M+H]=240.9.

(S)-1-(4-phenyl-5,6-dihydro-4H-pyrrolo[1,2-b]pyrazol-2-yl)propan-1-one (Peak 2, retention time=2.968 min) (22.7 mg, 28%) as a white solid. ¹H NMR (400 MHz, CD₃OD) δ 7.35-7.22 (m, 5H), 6.43 (s, 1H), 4.51-4.38 (m, 1H), 4.37-4.33 (m, 1H), 4.25-4.22 (m, 1H), 3.14-3.12 (m, 1H), 3.02-2.96 (m, 2H), 2.58-2.54 (m, 1H), 1.16 (t, J=7.2 Hz, 3H). LCMS R$_T$=0.838 min, m/z=241.0 [M+H]⁺. LCMS (5 to 95% acetonitrile in water+0.03% trifluoacetic acid over 1.5 mins) retention time 0.838 min, ESI+ found [M+H]=241.0.

SFC condition: Column: Chiralpak AD (250 mm*30 mm, 5 μm); Condition: 0.1% NH₃H₂O iPrOH; Begin B 15% End B 15%; Flow Rate (60 mL/min), Column temperature 40° C.

Method 18

Example 25

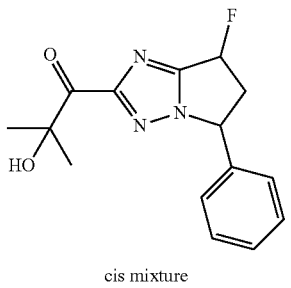

cis mixture 1-(rac-(5R,7R)-7-fluoro-5-phenyl-6,7-dihydro-5H-pyrrolo[1,2-b][1,2,4]triazol-2-yl)-2-hydroxy-2-methyl-propan-1-one To a solution of 1-[cis-(5R,7R)-7-fluoro-5-phenyl-6,7-dihydro-5H-pyrrolo[1,2-b][1,2,4]triazol-2-yl]-2-methyl-propan-1-one (50 mg, 0.18 mmol) in dimethyl sulfoxide (4 mL) was added 1-bromo-2,5-pyrrolidinedione (33 mg, 0.18 mmol). The mixture was heated at 100° C. for 15 h under air. The solvent was evaporated under reduced pressure and the residue was purified by RP-HPLC (acetonitrile 25-55%/0.05% ammonia hydroxide in water) and further by preparative TLC (ethyl acetate, $R_f$=0.6) to afford 1-(rac-(5R,7R)-7-fluoro-5-phenyl-6,7-dihydro-5H-pyrrolo[1,2-b][1,2,4]triazol-2-yl)-2-hydroxy-2-methyl-propan-1-one (48.6 mg, 91%) as a white solid. $^1$H NMR (400 MHz, CD$_3$OD) δ 7.43-7.37 (m, 3H), 7.27-7.25 (m, 2H), 6.20-6.03 (m, 1H), 5.66-5.57 (m, 1H), 3.79-3.71 (m, 1H), 2.87-2.77 (m, 1H), 1.60 (s, 3H), 1.56 (s, 3H). LC-MS $R_T$=0.771 min, m/z=290.1 (M+H)$^+$. LCMS (5 to 95% acetonitrile in water+0.03% trifluoacetic acid over 1.5 mins) retention time 0.771 min, ESI+ found [M+H]=290.1.

Method 19

Example 26

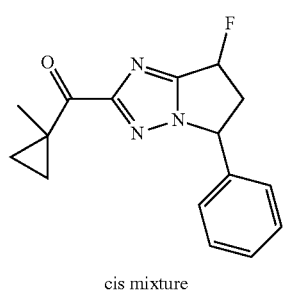

cis mixture (rac-(5S,7S)-7-fluoro-5-phenyl-6,7-dihydro-5H-pyrrolo[1,2-b][1,2,4]triazol-2-yl)-(1-methylcyclopropyl)methanone

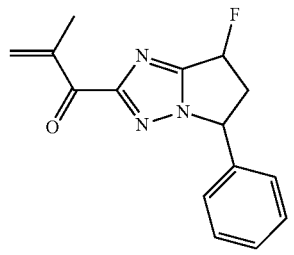 [SMILES: C=C(C)C(=O)c1nc2n(n1)C(c1ccccc1)CC2F]

Step 1: cis-1-(7-fluoro-5-phenyl-6,7-dihydro-5H-pyrrolo[1,2-b][1,2,4]triazol-2-yl)-2-methylprop-2-en-1-one A mixture of cis-1-(7-fluoro-5-phenyl-6,7-dihydro-5H-pyrrolo[1,2-b][1,2,4]triazol-2-yl)propan-1-one (120 mg, 0.46 mmol), dibromomethane (1931 mg, 11.11 mmol) and diethylamine (1625 mg, 22.22 mmol) in acetonitrile (10 mL) was heated at 100° C. for 30 min under microwave conditions. The solvent was evaporated under reduced pressure and the residue was purified by column chromatography (silica gel, 100-200 mesh, 0 to 40% ethyl acetate in petroleum ether) to give cis-1-(7-fluoro-5-phenyl-6,7-dihydro-5H-pyrrolo[1,2-b][1,2,4]triazol-2-yl)-2-methyl-prop-2-en-1-one (52 mg, 41%) as a white solid. LC-MS $R_T$=1.020 min, m/z=272.1 [M+H]$^+$. LCMS (0 to 60% acetonitrile in water+0.03% trifluoroacetic acid over 2 mins) retention time 1.020 min, ESI+ found [M+H]=272.1.

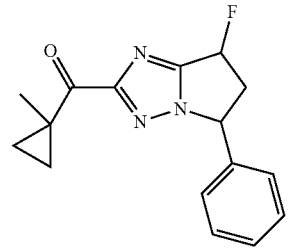 [SMILES: CC1(C(=O)c2nc3n(n2)C(c2ccccc2)CC3F)CC1]

Step 2: (rac-(5S,7S)-7-fluoro-5-phenyl-6,7-dihydro-5H-pyrrolo[1,2-b][1,2,4]triazol-2-yl)-(1-methylcyclopropyl)methanone To a mixture of diethylzinc (123 mg, 1.00 mmol) and nickel chloride (8 mg, 0.07 mmol) in dichloromethane (5 mL) was added diiodomethane (355 mg, 1.33 mmol) at 0° C. After stirred for 30 min, 1-(7-fluoro-5-phenyl-6,7-dihydro-5H-pyrrolo [1,2-b][1,2,4]triazol-2-yl)-2-methyl-prop-2-en-1-one (90 mg, 0.33 mmol) was added and the reaction mixture was stirred at 0° C. for 2 h. The mixture was quenched by addition of cold saturated aqueous ammonium chloride (10 mL) and extracted with ethyl acetate (3×15 mL). The combined organic layers were concentrated under reduce pressure. The residue was purified by RP-HPLC (acetonitrile 25-55%/0.05% HCl in acetonitrile) to afford (rac-(5S,7S)-7-fluoro-5-phenyl-6,7-dihydro-5H-pyrrolo[1, 2-b][1,2,4]triazol-2-yl)-(1-methylcyclopropyl)methanone (3.0 mg, 3%) as a white solid. $^1$H NMR (400 MHz, CD$_3$OD) δ 7.41-7.37 (m, 3H), 7.24-7.23 (m, 2H), 6.15-6.13 (m, 0.5H), 6.01-5.99 (m, 0.5H), 5.60-5.59 (m, 1H), 3.76-3.68 (m, 1H), 2.84-2.74 (m, 1H), 1.82-1.76 (m, 2H), 1.41 (s, 3H), 0.97-0.92 (m, 2H). LC-MS R$_T$=1.068 min, m/z=286.1 [M+H]$^+$. LCMS (10 to 80% acetonitrile in water+0.03% trifluoroacetic acid over 2 mins) retention time 1.068 min, ESI+ found [M+H]=286.1.

Method 20

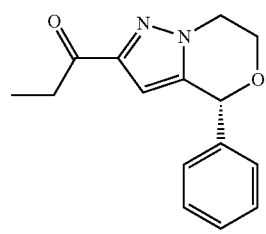

Example 27

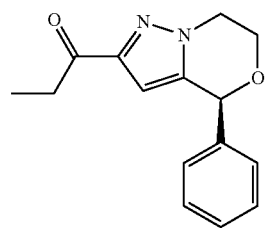

Example 28

1-[(4S)-4-phenyl-6,7-dihydro-4H-pyrazolo[5,1-c][1,4]oxazin-2-yl]propan-1-one & 1-[(4R)-4-phenyl-6,7-dihydro-4H-pyrazolo[5,1-c][1,4]oxazin-2-yl]propan-1-one

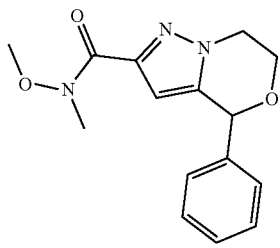 [SMILES: CON(C)C(=O)c1cc2n(n1)CCOC2c1ccccc1]

Step 1: N-methoxy-N-methyl-4-phenyl-6,7-dihydro-4H-pyrazolo[5,1-c][1,4]oxazine-2-carboxamide A mixture of 4-phenyl-6,7-dihydro-4H-pyrazolo[5,1-c][1,4]oxazine-2-carboxylic acid (156 mg, 0.64 mmol), N,O-dimethylhydroxylamine hydrochloride (125 mg, 1.28 mmol), 1-[bis(dimethylamino)methylene]-1H-1,2,3-triazolo[4,5-b]pyridinium 3-oxide hexafluorophosphate (291.42 mg, 0.77 mmol) and triethylamine (258 mg, 2.55 mmol) in N,N-dimethylformamide (5 mL) was stirred at 15° C. for 2 h and then concentrated under reduced pressure. The residue was purified by preparative TLC (10% methanol in dichloromethane, R$_f$=0.7) to afford N-methoxy-N-methyl-4-phenyl-6,7-dihydro-4H-pyrazolo[5,1-c][1,4]oxazine-2-carboxamide (80 mg, 43.6%) as colorless oil.

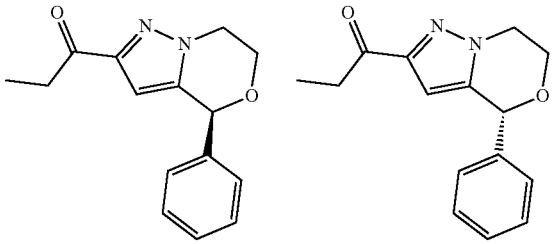

Step 2: 1-[(4S)-4-phenyl-6,7-dihydro-4H-pyrazolo[5,1-c][1,4]oxazin-2-yl]propan-1-one & 1-[(4R)-4-phenyl-6,7-dihydro-4H-pyrazolo[5,1-c][1,4]oxazin-2-yl]propan-1-one To a cooled (−78° C.) solution of N-methoxy-N-methyl-4-phenyl-6,7-dihydro-4H-pyrazolo[5,1-c][1,4]oxazine-2-carboxamide (60 mg, 0.21 mmol) in tetrahydrofuran (6 mL) was added dropwise with ethylmagnesiumchloride (2.7 M in THF, 0.39 mL, 1.04 mmol) dropwise under nitrogen atmosphere. After addition, the mixture was stirred at −78° C. for 1 h and then quenched by addition of saturated aqueous ammonium chloride (10 mL). The mixture was extracted with ethyl acetate (3×15 mL). The combined organic layers were concentrated under reduce pressure to afford crude racemic product, which was further separated by chiral SFC to afford arbitrarily assigned:

1-[(4S)-4-phenyl-6,7-dihydro-4H-pyrazolo[5,1-c][1,4]oxazin-2-yl]propan-1-one (Peak 1, retention time=3.254 min) (11.5 mg, 21%) as a white solid. $^1$H NMR (400 MHz, CD$_3$OD) δ 7.39-7.37 (m, 5H), 6.21 (s, 1H), 5.82 (s, 1H), 4.42-4.36 (m, 2H), 4.30-4.28 (m, 1H), 4.21-4.18 (m, 1H), 3.00-2.95 (m, 2H), 1.13 (t, J=7.2 Hz, 3H). LCMS R$_T$=1.026 min, m/z=257.1 [M+H]$^+$. LCMS (10 to 80% acetonitrile in water+0.03% trifluoacetic acid over 2 mins) retention time 1.026 min, ESI+ found [M+H]=257.1.

1-[(4R)-4-phenyl-6,7-dihydro-4H-pyrazolo[5,1-c][1,4]oxazin-2-yl]propan-1-one (Peak 2, retention time=4.381 min) (13.6 mg, 25%) as a white solid. $^1$H NMR (400 MHz, CD$_3$OD) δ 7.39-7.37 (m, 5H), 6.21 (s, 1H), 5.82 (s, 1H), 4.42-4.36 (m, 2H), 4.31-4.25 (m, 1H), 4.21-4.19 (m, 1H), 3.00-2.92 (m, 2H), 1.13 (t, J=7.2 Hz, 3H). LCMS R$_T$=1.023 min, m/z=257.1 [M+H]$^+$ LCMS (10 to 80% acetonitrile in water+0.03% trifluoacetic acid over 2 mins) retention time 1.023 min, ESI+ found [M+H]=257.1.

SFC condition: Column: OD (250 mm*30 mm, 5 μm); Condition: 0.1% NH$_3$H$_2$O EtOH; Begin B: 30%; End B: 30%; Flow Rate(60 mL/min), Column temperature 40° C.

Method 21

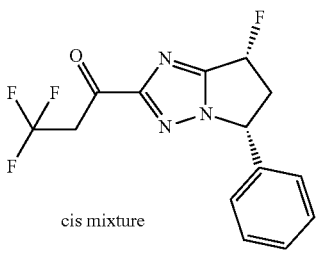

Example 29

3,3,3-trifluoro-1-(rac-(5R,7R)-7-fluoro-5-phenyl-6,7-dihydro-5H-pyrrolo[1,2-b][1,2,4]triazol-2-yl)propan-1-one

Step 1: 1-cis-7-fluoro-5-phenyl-2-(1-((trimethylsilyl)oxy)vinyl)-6,7-dihydro-5H-pyrrolo [1,2-b][1,2,4]triazole To a solution of 1-(cis-7-fluoro-5-phenyl-6,7-dihydro-5H-pyrrolo[1,2-b][1,2,4]triazol-2-yl)ethanone (200 mg, 0.82 mmol) in 1,4-dioxane (6 mL) was added triethylamine (165 mg, 1.63 mmol) and trimethylsilyl trifluoromethanesulfonate (254 mg, 1.14 mmol) at 0° C. The mixture was stirred at 0° C. for 2 h and quenched by addition of cold saturated aqueous ammonium chloride (10 mL). The resulting mixture was extracted with ethyl acetate (3×15 mL). The combined organic layers were concentrated under reduce pressure to give crude 1-(cis-7-fluoro-5-phenyl-6,7-dihydro-5H-pyrrolo[1,2-b][1,2,4]triazol-2-yl)vinyloxy-trimethyl-silane (245 mg, 95%) as light yellow oil. $^1$H NMR (400 MHz, CDCl$_3$) δ 7.17-7.10 (m, 3H), 6.98-6.96 (m, 2H), 5.79-5.78 (m, 0.5H), 5.65-5.64 (m, 0.5H), 5.21-5.17 (m, 2H), 4.40 (s, 1H), 4.49 (s, 1H), 3.37-3.27 (m, 1H), 2.66-2.56 (m, 1H), 0.03 (s, 9H).

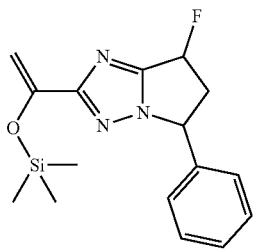 [SMILES: C=C(O[Si](C)(C)C)c1nc2n(n1)C(c1ccccc1)CC2F]

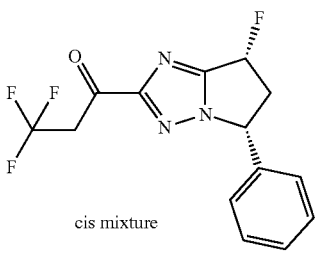 [SMILES: O=C(CC(F)(F)F)c1nc2n(n1)[C@@H](c1ccccc1)C[C@H]2F]

cis mixture

Step 2: 3,3,3-trifluoro-1-(rac-(5R,7R)-7-fluoro-5-phenyl-6,7-dihydro-5H-pyrrolo [1,2-b][1,2,4]triazol-2-yl)propan-1-one A mixture of 1-trifluoromethyl-1,2-benziodoxol-3(1H)-one (418 mg, 1.32 mmol), 1-(cis-7-fluoro-5-phenyl-6,7-dihydro-5H-pyrrolo[1,2-b][1,2,4]triazol-2-yl)vinyloxy-trimethyl-silane (210 mg, 0.66 mmol) and cuprous thiocyanate (16 mg, 0.13 mmol) in N,N-dimethylformamide (4 mL) was stirred at 15° C. for 15 h and then concentrated under reduced pressure. The residue was purified by RP-HPLC (acetonitrile 25-55%/0.05% HCl in acetonitrile) to afford 3,3,3-trifluoro-1-(rac-(5R,7R)-7-fluoro-5-phenyl-6,7-dihydro-5H-pyrrolo[1,2-b][1,2,4]triazol-2-yl)propan-1-one (31 mg, 15%) as a white solid. $^1$H NMR (400 MHz, CD$_3$OD) δ 7.40-7.37 (m, 3H), 7.28-7.26 (m, 2H), 6.19-6.17 (m, 0.5H), 6.05-6.03 (m, 0.5H), 5.65-5.63 (m, 1H), 4.09-4.01 (m, 2H), 3.78-3.29 (m, 1H), 2.89-2.77 (m, 1H). LC-MS R$_T$=1.072 min, m/z=314.1 [M+H]$^+$. LCMS (10 to 80% acetonitrile in water+0.03% ammonium bicarbonate over 2.0 mins) retention time 1.072 min, ESI+ found [M+H]=314.1.

Method 22

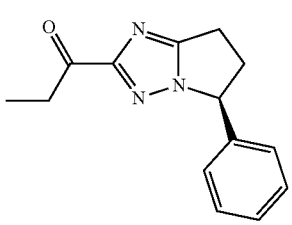

Example 30

1-[(5S)-5-phenyl-6,7-dihydro-5H-pyrrolo[1,2-b][1,2,4]triazol-2-yl]propan-1-one

To a cooled (−78° C.) solution of ethyl (S)-5-phenyl-6,7-dihydro-5H-pyrrolo [1,2-b][1,2,4]triazole-2-carboxylate (200 mg, 0.78 mmol) in tetrahydrofuran (20 mL) was added ethylmagnesium chloride (3.0 M in THF, 0.58 mL, 1.74 mmol) dropwise under a nitrogen atmosphere. After addition, the mixture was stirred at −78° C. for 2 h and then quenched by addition of saturated aqueous ammonium chloride (20 mL). The mixture was extracted with ethyl acetate (3×20 mL). The combined organic layers were concentrated under reduced pressure. The residue was purified by column chromatography (silica gel, 100-200 mesh, 0 to 50% ethyl acetate in petroleum ether) to afford 1-[(5S)-5-phenyl-6,7-dihydro-5H-pyrrolo[1,2-b][1,2,4]triazol-2-yl]propan-1-one (60 mg, 32%) as a white solid. $^1$H NMR (400 MHz, CDCl$_3$) δ 7.42-7.32 (m, 3H), 7.12-7.10 (m, 2H), 5.49 (dd, J=5.6, 8.4 Hz, 1H), 3.31-3.21 (m, 1H), 3.17-3.01 (m, 4H), 2.72-2.64 (m, 1H), 1.21 (t, J=7.2 Hz, 3H). LCMS R$_T$=1.523 min, m/z=242.2 [M+H]$^+$. LCMS (10 to 80% acetonitrile in water+0.1% ammonia water over 3.0 mins) retention time 1.523 min, ESI+ found [M+H]=242.2.

Method 23

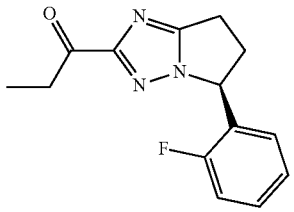

Example 31

1-[(5S)-5-(2-fluorophenyl)-6,7-dihydro-5H-pyrrolo[1,2-b][1,2,4]triazol-2-yl]propan-1-one To a cooled (−70° C.) solution of ethyl 5-(2-fluorophenyl)-6,7-dihydro-5H-pyrrolo[1,2-b][1,2,4]triazole-2-carboxylate (496 mg, 1.8 mmol) in tetrahydrofuran (10 mL) was added ethylmagnesium chloride (2.7 M in THF, 1.33 mL, 3.6 mmol) dropwise under a nitrogen atmosphere. After addition, the mixture was stirred at −70° C. for 1 h and then quenched by addition of saturated aqueous ammonium chloride (20 mL). The mixture was extracted with ethyl acetate (3×15 mL). The combined organic layers were dried over sodium sulfate and concentrated under reduce pressure to afford crude racemic product, which was further purified by chiral SFC and RP-HPLC (acetonitrile 25-55%/0.05% ammonia hydroxide in water) to afford arbitrarily assigned: 1-[(5S)-5-(2-fluorophenyl)-6,7-dihydro-5H-pyrrolo[1,2-b][1,2,4]triazol-2-yl]propan-1-one (Peak 2, retention time=3.038 min) (17 mg, 8%) as white solids. $^1$H NMR (400 MHz, CD$_3$OD) δ 7.45-7.35 (m, 1H), 7.20-7.12 (m, 3H), 5.80-5.75 (m, 1H), 3.30-3.28 (m, 1H), 3.15-3.05 (m, 2H), 3.01-2.97 (m, 2H), 2.72-2.66 (m, 1H), 1.12 (t, J=7.2 Hz, 3H). LCMS R$_T$=0.977 min, m/z=260.1 [M+H]$^+$. LCMS (5 to 95% acetonitrile in water+0.03% trifluoacetic acid over 1.5 mins) retention time 0.977 min, ESI+ found [M+H]=260.1.

SFC condition: Column: OJ(250 mm*30 mm, 5 μm); Condition: 0.1% NH$_3$H$_2$O EtOH; Begin B: 20%; End B: 20%; Flow Rate(60 mL/min), Column temperature 40° C.

Method 24

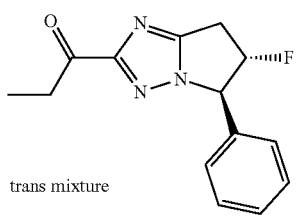

Example 32 trans mixture

1-[rac-(5R,6S)-6-fluoro-5-phenyl-6,7-dihydro-5H-pyrrolo[1,2-b][1,2,4]triazol-2-yl]propan-1-one

Step 1: (E)-methyl 4-phenylbut-3-enoate

To a solution of (E)-4-phenylbut-3-enoic acid (15.0 g, 92.48 mmol) in methanol (60 mL) was added sulfuric acid (2.3 g, 23.12 mmol). The mixture was heated at 90° C. for 18 h and cooled. The mixture was diluted with water (20 mL) and extracted with dichloromethane (3×50 mL). The combined organic layers were washed with water (30 mL), aqueous saturated sodium bicarbonate solution (30 mL), brine (30 mL), dried and concentrated under reduce pressure to afford crude methyl (E)-4-phenylbut-3-enoate (14.8 g, 91%) as light oil, used as is in the next step. $^1$H NMR (400 MHz, CDCl$_3$) δ 7.39-7.21 (m, 5H), 6.54-6.45 (m, 1H), 6.35-6.25 (m, 1H), 3.72 (s, 3H), 3.30-3.25 (m, 2H).

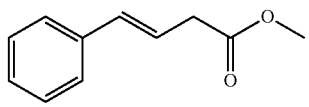

Step 2: Methyl 2-(3-phenyloxiran-2-yl)acetate

To a mixture of methyl (E)-4-phenylbut-3-enoate (14.8 g, 84.0 mmol) and sodium bicarbonate (34.4 g, 409.0 mmol) in acetone (300 mL) was added a solution of potassium monopersulfate triple salt (67.1 g, 109.2 mmol) in water (80 mL) dropwise at 0° C. After addition, the resulting mixture was allowed to warm to 25° C. and stirred for 4 h and filtered. The filtrate was concentrated under reduced pressure and the residue was purified by column chromatography (silica gel, 100-200 mesh, 0 to 5% ethyl acetate in petroleum ether) to afford methyl 2-(3-phenyloxiran-2-yl)acetate (15.0 g, 93%) as colorless oil. LC-MS R$_T$=0.799 min, m/z=233.9 [M+H]$^+$. LCMS (5 to 95% acetonitrile in water+0.03% trifluoacetic acid over 1.5 mins) retention time 0.799 min, ESI+ found [M+H]=233.9.

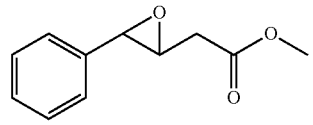

Step 3: Methyl (rac-3R,4S)-4-bromo-3-hydroxy-4-phenylbutanoate

To a solution of methyl 2-(3-phenyloxiran-2-yl)acetate (15.0 g, 78.0 mmol) in acetonitrile (400 mL) was added lithium bromide (6.8 g, 78.0 mmol) and magnesium perchlorate (1.7 g, 78.0 mmol) at 0° C. The mixture was stirred at 20° C. for 12 h and diluted with dichloromethane (100 mL). The resulting mixture was washed with hydrochloric acid (1N, 100 mL). The separated aqueous layer was washed with dichloromethane (3×100 mL). The combined organic layers were dried over sodium sulfate and concentrated under reduce pressure to give crude methyl (rac-3R,4S)-4-bromo-3-hydroxy-4-phenylbutanoate (20.0 g, 94%) as colorless oil. The crude was used in the next step without further purification. LC-MS R$_T$=0.610 min, m/z=256.9 [M+H]$^+$. LCMS (5 to 95% acetonitrile in water+0.03% trifluoacetic acid over 1.5 mins) retention time 0.610 min, ESI+ found [M+H]=256.9.

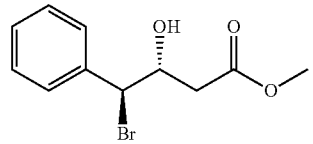

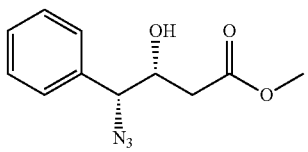 [SMILES: COC(=O)C[C@@H](O)[C@H](N=[N+]=[N-])c1ccccc1]

Step 4: Methyl (rac-3R,4R)-4-azido-3-hydroxy-4-phenylbutanoate

A mixture of methyl (rac-3R,4S)-4-bromo-3-hydroxy-4-phenylbutanoate (20.0 g, 73.2 mmol) and sodium azide (14.3 g, 219.7 mmol) in N,N-dimethylformamide (500 mL) was stirred at 20° C. for 16 h. The mixture was diluted with water (500 mL) and extracted with ethyl acetate (3×300 mL). The combined organic layers were washed with brine (150 mL), dried over anhydrous sodium sulfate and concentrated under reduced pressure to afford crude methyl (rac-3R,4R)-4-azido-3-hydroxy-4-phenylbutanoate (17.0 g, 99%) as yellow oil. LC-MS $R_T$=0.978 min, m/z=208.3 [M+H]$^+$. LCMS (10 to 80% acetonitrile in water+0.03% trifluoacetic acid over 2.0 mins) retention time 0.978 min, ESI+ found [M+H]=208.3.

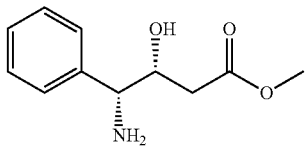

Step 5: Methyl (rac-3R,4R)-4-amino-3-hydroxy-4-phenylbutanoate

A mixture of methyl (rac-3R,4R)-4-azido-3-hydroxy-4-phenylbutanoate (17.0 g, 72.3 mmol) and palladium (10% on carbon, 7.7 g) in ethyl acetate (800 mL) was hydrogenated (15 psi) at 25° C. for 24 h and then filtered. The filtrate was concentrated under reduced pressure to give crude methyl (rac-3R,4R)-4-amino-3-hydroxy-4-phenylbutanoate (15.0 g, 99%) as colorless oil. The crude was used in the next step without further purification. LC-MS $R_T$=0.315 min, m/z=210.2 [M+H]$^+$. LCMS (10 to 80% acetonitrile in water+0.03% trifluoacetic acid over 2.0 mins) retention time 0.315 min, ESI+ found [M+H]=210.2.

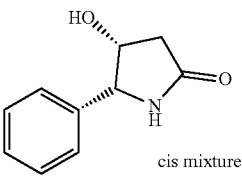

cis mixture

Step 6: cis-4-hydroxy-5-phenylpyrrolidin-2-one

A solution of methyl (rac-3R,4R)-4-amino-3-hydroxy-4-phenylbutanoate (15.0 g, 71.7 mmol) in methanol (200 mL) was heated at 50° C. for 16 h and concentrated under reduced pressure. The residue was purified by column chromatography (silica gel, 100-200 mesh, 0 to 5% methanol in dichloromethane) to afford cis-4-hydroxy-5-phenylpyrrolidin-2-one (9.6 g, 76%) as a white solid. $^1$H NMR (400 MHz, CDCl$_3$) δ 7.45-7.26 (m, 5H), 6.39 (br s, 1H), 4.89-4.87 (m, 1H), 4.66-4.48 (m, 1H), 2.80-2.62 (m, 1H), 2.53-2.30 (m, 1H). LC-MS $R_T$=0.678 min, m/z=178.2 [M+H]$^+$. LCMS (0 to 60% acetonitrile in water+0.03% trifluoacetic acid over 2.0 mins) retention time 0.678 min, ESI+ found [M+H]=178.2.

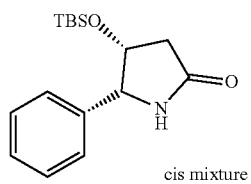

cis mixture

Step 7: cis-4-((tert-butyldimethylsilyl)oxy)-5-phenylpyrrolidin-2-one

To a solution of cis-4-hydroxy-5-phenylpyrrolidin-2-one (9.6 g, 54.2 mmol) in dichloromethane (300 mL) was added imidazole (11.1 g, 162.5 mmol) and tert-butyldimethylsilyl chloride (16.3 g, 108.4 mmol). The resulting mixture was stirred at 25° C. for 16 h and concentrated under reduced pressure. The residue was purified by column chromatography (silica gel, 100-200 mesh, 0 to 50% ethyl acetate in petroleum ether) to afford cis-4-((tert-butyldimethylsilyl)oxy)-5-phenyl pyrrolidin-2-one (10.0 g, 63%) as a white solid. LC-MS $R_T$=1.257 min, m/z=292.3 [M+H]$^+$. LCMS (10 to 80% acetonitrile in water+0.03% trifluoacetic acid over 2.0 mins) retention time 1.257 min, ESI+ found [M+H]= 292.3.

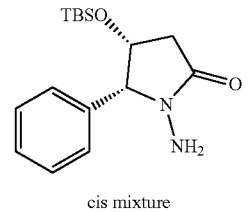 [SMILES: CC(C)(C)[Si](C)(C)O[C@@H]1CC(=O)N(N)[C@@H]1c1ccccc1]

cis mixture

Step 8: cis-1-amino-4-((tert-butyldimethylsilyl)oxy)-5-phenylpyrrolidin-2-one To a solution of cis-4-((tert-butyldimethylsilyl)oxy)-5-phenylpyrrolidin-2-one (10.0 g, 34.3 mmol) in N,N-dimethylformamide (50 mL) was added sodium hydride (60%, 2.1 g, 51.5 mmol) at 0° C. After stirring at 0° C. for 30 min, (aminooxy)diphenylphosphine oxide (12.0 g, 51.47 mmol) was added portion-wise. The resulting mixture was stirred at room temperature for 12 h and filtered. The filtrate was concentrated under reduced pressure to give crude cis--amino-4-((tert-butyldimethylsilyl)oxy)-5-phenylpyrrolidin-2-one (9.0 g, 86%) as a brown solid. This crude was used in the next step without further purification. LC-MS $R_T$=1.225 min, m/z=307.4 [M+H]$^+$. LCMS (10 to 80% acetonitrile in water+0.03% trifluoacetic acid over 2.0 mins) retention time 1.225 min, ESI+ found [M+H]=307.4.

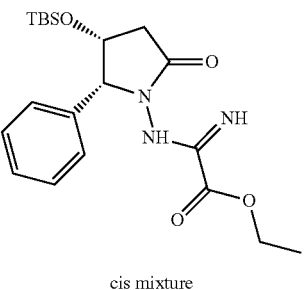 [SMILES: CCOC(=O)C(=N)NN1C(=O)C[C@@H](O[Si](C)(C)C(C)(C)C)[C@H]1c1ccccc1]

cis mixture

Step 9: Ethyl cis-2-((3-((tert-butyldimethylsilyl)oxy)-5-oxo-2-phenylpyrrolidin-1-yl)amino)-2-iminoacetate A mixture of cis-1-amino-4-((tert-butyldimethylsilyl)oxy)-5-phenylpyrrolidin-2-one (9.0 g, 29.4 mmol) and ethyl 2-ethoxy-2-imino-acetate (21.3 g, 146.8 mmol) in toluene (500 mL) was heated at 90° C. for 18 h and concentrated under reduced pressure. The residue was diluted with water (200 mL) and extracted with ethyl acetate (3×150 mL). The combined organic layers were concentrated under reduce pressure to afford crude ethyl cis-2-((3-((tert-butyldimethylsilyl)oxy)-5-oxo-2-phenylpyrrolidin-1-yl)amino)-2-iminoacetate (10.0 g, 84%) as a brown oil. LC-MS $R_T$=1.128 min, m/z=406.4 [M+H]$^+$. LCMS (10 to 80% acetonitrile in water+0.03% trifluoacetic acid over 2.0 mins) retention time 1.128 min, ESI+ found [M+H]=406.4.

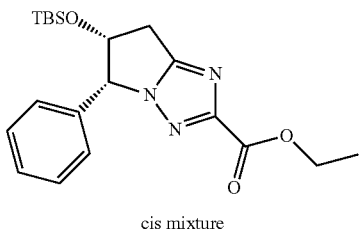 [SMILES: CCOC(=O)c1nc2n(n1)[C@H](c1ccccc1)[C@H](O[Si](C)(C)C(C)(C)C)C2]

cis mixture

Step 10: Ethyl cis-6-((tert-butyldimethylsilyl)oxy)-5-phenyl-6,7-dihydro-5H-pyrrolo[1,2-b][1,2,4]triazole-2-carboxylate A mixture of ethyl cis-2-((3-((tert-butyldimethylsilyl)oxy)-5-oxo-2-phenyl pyrrolidin-1-yl)amino)-2-iminoacetate (10.0 g, 24.7 mmol) and 4-methylbenzenesulfonic acid hydrate (4.7 g, 24.7 mmol) in toluene (300 mL) was heated at 120° C. for 16 h and then concentrated under reduced pressure. The residue was diluted with water (200 mL) and extracted with ethyl acetate (3×150 mL). The combined organic layers were concentrated under reduce pressure. The residue was purified by column chromatography (silica gel, 100-200 mesh, 0 to 20% ethyl acetate in petroleum ether) to afford ethyl cis-6-((tert-butyldimethylsilyl)oxy)-5-phenyl-6,7-dihydro-5H-pyrrolo[1,2-b][1,2,4]triazole-2-carboxylate (5.5 g, 58%) as brown oil. LC-MS $R_T$=1.345 min, m/z=388.4 [M+H]$^+$. LCMS (10 to 80% acetonitrile in water+0.03% trifluoacetic acid over 2.0 mins) retention time 1.345 min, ESI+ found [M+H]=388.4.

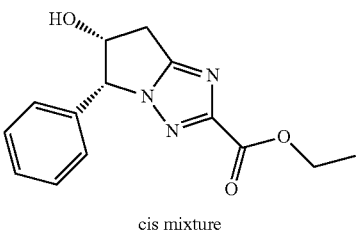 [SMILES: CCOC(=O)c1nc2n(n1)[C@H](c1ccccc1)[C@H](O)C2]

cis mixture

Step 11: Ethyl cis-6-hydroxy-5-phenyl-6,7-dihydro-5H-pyrrolo[1,2-b][1,2,4]triazole-2-carboxylate To a solution of tetrabutylammonium fluoride (18.5 g, 70.9 mmol) in tetrahydrofuran (200 mL) was added ethyl cis-6-((tert-butyldimethylsilyl)oxy)-5-phenyl-6,7-dihydro-5H-pyrrolo[1,2-b][1,2,4]triazole-2-carboxylate (5.5 g, 14.2 mmol). The resulting mixture was stirred at 25° C. for 16 h and diluted with ethyl acetate (300 mL). The mixture was washed with water (50 mL), brine (50 mL), dried over anhydrous sodium sulfate and concentrated under reduced pressure. The residue was purified by column chromatography (silica gel, 100-200 mesh, 0 to 50% ethyl acetate in petroleum ether) to afford ethyl cis-6-hydroxy-5-phenyl-6,7-dihydro-5H-pyrrolo[1,2-b][1,2,4]triazole-2-carboxylate (1.8 g, 46%) as a yellow solid. LC-MS $R_T$=1.036 min, m/z=274.3 [M+H]$^+$. LCMS (0 to 60% acetonitrile in water+0.03% trifluoacetic acid over 2.0 mins) retention time 1.036 min, ESI+ found [M+H]=274.3.

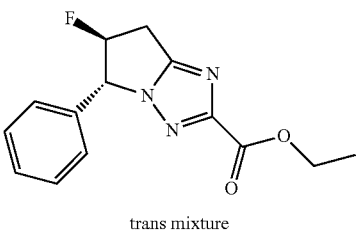 [SMILES: CCOC(=O)c1nc2n(n1)[C@H](c1ccccc1)[C@@H](F)C2]

trans mixture

Step 12: Ethyl trans-6-fluoro-5-phenyl-6,7-dihydro-5H-pyrrolo[1,2-b][1,2,4]triazole-2-carboxylate To a solution of ethyl cis-6-hydroxy-5-phenyl-6,7-dihydro-5H-pyrrolo[1,2-b][1,2,4]triazole-2-carboxylate (1.0 g, 3.66 mmol) in dichloromethane (50 mL) was added diethylaminosulfur trifluoride (10.0 g, 62.0 mmol) dropwise at 25° C. The resulting mixture was stirred at 25° C. for 1 h and then quenched by slow addition of saturated aqueous sodium bicarbonate (10 mL). The mixture was extracted with ethyl acetate (3×50 mL). The combined organic layers were washed with brine (50 mL), dried over anhydrous sodium sulfate and concentrated under reduced pressure. The residue was purified by column chromatography (silica gel, 100-200 mesh, 0 to 40% ethyl acetate in petroleum ether) to afford ethyl trans-6-fluoro-5-phenyl-6,7-dihydro-5H-pyrrolo[1,2-b][1,2,4]triazole-2-carboxylate (400 mg, 40%) as a white solid. $^1$H NMR (400 MHz, CDCl$_3$) δ 7.41-7.24 (m, 3H), 6.92-6.89 (m, 2H), 5.70-5.55 (m, 1H), 5.62-5.48 (m, 1H), 4.49-4.34 (m, 2H), 3.52-3.35 (m, 1H), 3.35-3.15 (m, 1H), 1.40-1.36 (m, 3H). LC-MS $R_T$=0.958 min, m/z=276.2 [M+H]$^+$ LCMS (10 to 80% acetonitrile in water+0.03% trifluoacetic acid over 2.0 mins) retention time 0.958 min, ESI+ found [M+H]=276.2.

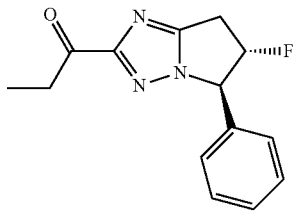 [SMILES: CCC(=O)c1nc2n(n1)[C@H](c1ccccc1)[C@@H](F)C2]

Step 13: 1-[rac-(5R,6S)-6-fluoro-5-phenyl-6,7-dihydro-5H-pyrrolo[1,2-b][1,2,4]triazol-2-yl]propan-1-one To a cooled (−78° C.) solution of ethyl trans-6-fluoro-5-phenyl-6,7-dihydro-5H-pyrrolo[1,2-b][1,2,4]triazole-2-carboxylate (30 mg, 0.11 mmol) in tetrahydrofuran (5 mL) was added ethylmagnesium chloride (3.0 M in THF, 0.25 mL, 0.75 mmol) dropwise under nitrogen atmosphere. After addition, the mixture was stirred at −78° C. for 2 h and then quenched by addition of saturated aqueous ammonium chloride (10 mL). The mixture was extracted with ethyl acetate (3×15 mL). The combined organic layers were concentrated under reduce pressure. The residue was purified by column chromatography (silica gel, 100-200 mesh, 0 to 50% ethyl acetate in petroleum ether) to afford arbitrarily assigned 1-[rac-(5R,6S)-6-fluoro-5-phenyl-6,7-dihydro-5H-pyrrolo[1,2-b][1,2,4]triazol-2-yl]propan-1-one (13.6 mg, 45%) as a yellow solid. $^1$H NMR (400 MHz, CDCl$_3$) δ 7.34-7.31 (m, 3H), 6.90-6.87 (m, 2H), 5.63-5.61 (m, 0.5H), 5.59-5.57 (m, 1H), 5.46-5.44 (m, 0.5H), 3.42-3.28 (m, 1H), 3.26-3.21 (m, 1H), 3.03-3.01 (m, 2H), 1.16 (t, J=7.2 Hz, 3H). LCMS R$_T$=0.977 min, m/z=260.1 [M+H]$^+$. LCMS (10 to 80% acetonitrile in water+0.03% trifluoacetic acid over 2.0 mins) retention time 0.977 min, ESI+ found [M+H]=260.1.

Method 25

Example 33

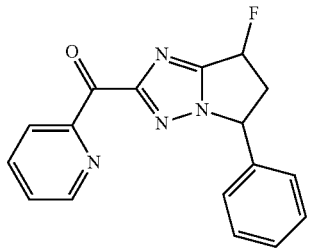

cis mixture (rac-(5S,7S)-7-fluoro-5-phenyl-6,7-dihydro-5H-pyrrolo[1,2-b][1,2,4]triazol-2-yl)-(2-pyridyl)methanone To a solution of 2-bromopyridine (435 mg, 2.76 mmol) in tetrahydrofuran (20 mL) was added n-butyllithium (2.5 M in hexanes, 1.10 mL, 2.76 mmol) at −78° C. After addition, the mixture was allowed to warm to 30° C. and stirred for 2 h. The mixture was cooled to −78° C. and cis-7-fluoro-N-methoxy-N-methyl-5-phenyl-6,7-dihydro-5H-pyrrolo[1,2-b][1,2,4]triazole-2-carboxamide (200 mg, 0.69 mmol) in tetrahydrofuran (5 mL) was added. The reaction mixture was stirred at −78° C. for 6 h and quenched by addition of saturated aqueous ammonium chloride (10 mL). The mixture was extracted with ethyl acetate (2×10 mL). The combined organic layers were concentrated under reduce pressure. The residue was purified by RP-HPLC (acetonitrile 25-55%/0.05% ammonia hydroxide in water) to afford (rac-(5S,7S)-7-fluoro-5-phenyl-6,7-dihydro-5H-pyrrolo[1,2-b][1,2,4]triazol-2-yl)-(2-pyridyl)methanone (32.0 mg, 15%) as a white solid. $^1$H NMR (400 MHz, DMSO-d$_6$) δ 8.69-8.65 (m, 1H), 8.00-7.90 (m, 2H), 7.62-7.59 (m, 1H), 7.42-7.30 (m, 3H), 7.25-7.20 (m, 2H), 6.30-6.22 (m, 0.5H), 6.18-6.14 (m, 0.5H), 5.75-5.55 (m, 1H), 3.77-3.67 (m, 1H), 2.74-2.45 (m, 1H). LCMS: R$_T$=1.510 min, m/z=309.1 [M+H]$^+$. LCMS (10 to 80% acetonitrile in water+0.1% ammonia water over 3.0 mins) retention time 1.510 min, ESI+ found [M+H]=309.1.

Method 26

Example 34

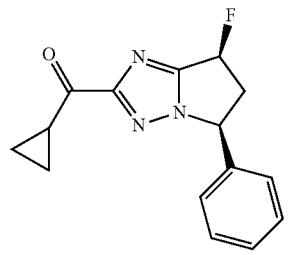

Example 35

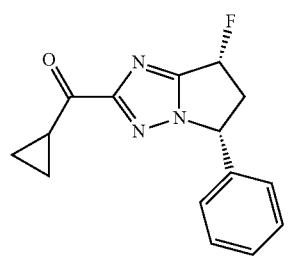

Cyclopropyl-[(5S,7S)-7-fluoro-5-phenyl-6,7-dihydro-5H-pyrrolo[1,2-b][1,2,4]triazol-2-yl]methanone and cyclopropyl-[(5R,7R)-7-fluoro-5-phenyl-6,7-dihydro-5H-pyrrolo[1,2-b][1,2,4]triazol-2-yl]methanone Example 42

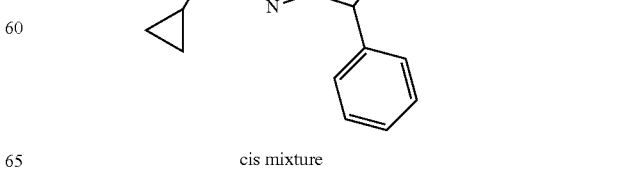

cis mixture

Step 1: Cyclopropyl-(rac-(5S,7S)-7-fluoro-5-phenyl-6,7-dihydro-5H-pyrrolo[1,2-b][1,2,4]triazol-2-yl)methanone To a cooled (−78° C.) solution of ethyl cis-7-fluoro-5-phenyl-6,7-dihydro-5H-pyrrolo [1,2-b][1,2,4]triazole-2-carboxylate (100 mg, 0.36 mmol) in tetrahydrofuran (4 mL) was added cyclopropylmagnesium bromide (0.5 M in THF, 1.45 mL, 0.73 mmol) dropwise under nitrogen atmosphere. After addition, the mixture was stirred at −78° C. for 2 h, and then quenched by addition of saturated aqueous ammonium chloride (20 mL). The mixture was extracted with ethyl acetate (2×10 mL). The combined organic layers were dried and concentrated under reduce pressure. The residue was purified by RP-HPLC (acetonitrile 30-60%/0.05% ammonia hydroxide in water) to afford cis racemic cyclopropyl-(rac-(5S,7S)-7-fluoro-5-phenyl-6,7-dihydro-5H-pyrrolo[1,2-b][1,2,4]triazol-2-yl)methanone (15 mg, 10%) as a white solid.
$^1$H NMR (400 MHz, CD$_3$OD) δ 7.45-7.35 (m, 3H), 7.27-7.25 (m, 2H), 6.18-6.15 (m, 0.5H), 6.05-6.00 (m, 0.5H), 5.65-5.60 (m, 1H), 3.77-3.65 (m, 1H), 3.05-2.95 (m, 1H), 2.90-2.70 (m, 1H), 1.17-1.13 (m, 2H), 1.10-1.05 (m, 2H). LCMS R$_T$=1.031 min, m/z=272.3 [M+H]$^+$. LCMS (10 to 80% acetonitrile in water+0.03% trifluoacetic acid over 2.0 mins) retention time 1.031 min, ESI+ found [M+H]=272.3.

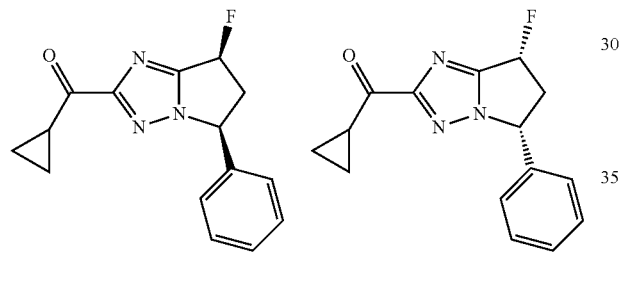

Step 2: Cyclopropyl-[(5S,7S)-7-fluoro-5-phenyl-6,7-dihydro-5H-pyrrolo[1,2-b][1,2,4]triazol-2-yl]methanone and cyclopropyl-[(5R,7R)-7-fluoro-5-phenyl-6,7-dihydro-5H-pyrrolo[1,2-b][1,2,4]triazol-2-yl]methanone The racemic cyclopropyl-(rac-(5S,7S)-7-fluoro-5-phenyl-6,7-dihydro-5H-pyrrolo [1,2-b][1,2,4]triazol-2-yl)methanone (100 mg, 0.37 mmol) was separated by chiral SFC to afford arbitrarily assigned: cyclopropyl-[(5R,7R)-7-fluoro-5-phenyl-6,7-dihydro-5H-pyrrolo[1,2-b][1,2,4]triazol-2-yl]methanone (Peak 1, retention time=3.575 min) (25.5 mg, 24%) as a white solid.
$^1$H NMR (400 MHz, CD$_3$OD) δ 7.44-7.38 (m, 3H), 7.29-7.27 (m, 2H), 6.19 (d, J=5.6 Hz, 0.5H), 6.05 (d, J=5.2 Hz, 0.5H), 5.66-5.62 (m, 1H), 3.79-3.71 (m, 1H), 3.05-3.02 (m, 1H), 3.01-2.81 (m, 1H), 1.29-1.09 (m, 4H). LCMS R$_T$=0.816 min, m/z=271.9 [M+H]$^+$. LCMS (5 to 95% acetonitrile in water+0.03% trifluoacetic acid over 1.5 mins) retention time 0.816 min, ESI+ found [M+H]=271.9.

cyclopropyl-[(5S,7S)-7-fluoro-5-phenyl-6,7-dihydro-5H-pyrrolo[1,2-b][1,2,4]triazol-2-yl]methanone (Peak 2, retention time=3.849 min) (18.5 mg, 17%) as a white solid. $^1$H NMR (400 MHz, CD$_3$OD) δ 7.44-7.27 (m, 5H), 6.20-6.17 (m, 0.5H), 6.06-6.03 (m, 0.5H), 5.66-5.64 (m, 1H), 3.79-3.71 (m, 1H), 3.05-3.02 (m, 1H), 3.01-2.81 (m, 1H), 1.19-1.09 (m, 4H). LCMS R$_T$=0.817 min, m/z=271.9 [M+H]$^+$.

LCMS (5 to 95% acetonitrile in water+0.03% trifluoacetic acid over 1.5 mins) retention time 0.817 min, ESI+ found [M+H]=271.9.

SFC condition: Column: Chiralpak AD (250 mm*30 mm, 10 μm); Condition: 0.1% NH$_3$H$_2$O iPrOH; Begin B 25% End B 25%; Flow Rate (60 mL/min), Column temperature 40° C.

Method 27

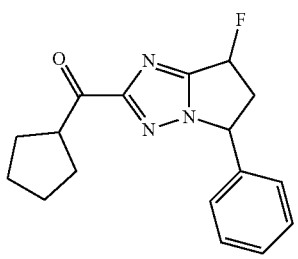

Example 36 cis mixture

Cyclopentyl-(rac-(5S,7S)-7-fluoro-5-phenyl-6,7-dihydro-5H-pyrrolo[1,2-b][1,2,4]triazol-2-yl)methanone

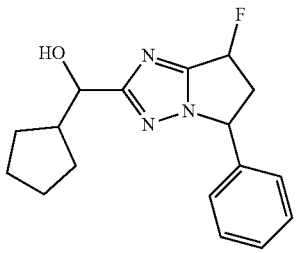 [SMILES: OC(c1nc2n(n1)C(c1ccccc1)CC2F)C1CCCC1]

Step 1: Cyclopentyl-(cis-7-fluoro-5-phenyl-6,7-dihydro-5H-pyrrolo[1,2-b][1,2,4]triazol-2-yl)methanol Cyclopentylmagnesium bromide (1 M in THF, 0.73 mL, 0.73 mmol) was added dropwise to a stirred and cooled (−78° C.) solution of cis-7-fluoro-5-phenyl-6,7-dihydro-5H-pyrrolo[1,2-b][1,2,4]triazole-2-carboxylate (100 mg, 0.36 mmol) in tetrahydrofuran (10 mL) under a nitrogen atmosphere. After addition, the mixture was stirred at 25° C. for 1 h and then quenched by addition of saturated aqueous ammonium chloride (20 mL). The mixture was extracted with ethyl acetate (2×10 mL). The combined organic layers were dried over sodium sulfate and concentrated under reduce pressure to afford crude cis-cyclopentyl(7-fluoro-5-phenyl-6,7-dihydro-5H-pyrrolo[1,2-b][1,2,4]triazol-2-yl)methanol (100 mg, 91%) as a white solid. LCMS R$_T$=0.611 min, m/z=302.1 [M+H]$^+$. LCMS (5 to 95% acetonitrile in water+0.03% trifluoacetic acid over 1.5 mins) retention time 0.611 min, ESI+ found [M+H]=302.1.

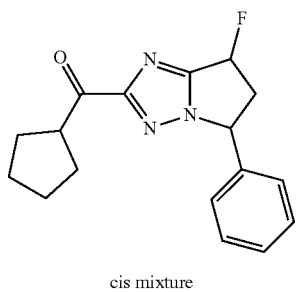 [SMILES: O=C(c1nc2n(n1)C(c1ccccc1)CC2F)C1CCCC1]

cis mixture

Step 2: Cyclopentyl-(rac-(5S,7S)-7-fluoro-5-phenyl-6,7-dihydro-5H-pyrrolo[1,2-b][1,2,4]triazol-2-yl)methanone To a solution of cis-cyclopentyl(7-fluoro-5-phenyl-6,7-dihydro-5H-pyrrolo [1,2-b][1,2,4]triazol-2-yl)methanol (100 mg, 0.33 mmol) in dichloromethane (15 mL) was added manganese dioxide (288 mg, 3.32 mmol). The reaction mixture was stirred at 35° C. for 2 h and then filtered through a short pad of Celite. The filtrate was concentrated under reduced pressure and the residue was purified by preparative TLC (40% ethyl acetate in petroleum ether) to afford cyclopentyl-(rac-(5S,7S)-7-fluoro-5-phenyl-6,7-dihydro-5H-pyrrolo[1,2-b][1,2,4]triazol-2-yl)methanone (18.2 mg, 18%) as a white solid. $^1$H NMR (400 MHz, CD$_3$OD) δ 7.44-7.40 (m, 3H), 7.28-7.26 (m, 2H), 6.19-6.17 (m, 0.5H), 6.05-6.03 (m, 0.5H), 5.64-5.63 (m, 1H), 3.89-3.68 (m, 2H), 2.88-2.75 (m, 1H), 2.02-1.60 (m, 8H). LCMS R$_T$=2.070 min, m/z=300.2 [M+H]$^+$. LCMS (0 to 60% acetonitrile in water+0.03% trifluoacetic acid over 3.0 mins) retention time 2.070 min, ESI+ found [M+H]=300.2.

Method 28

Example 41

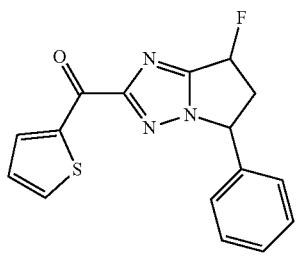

cis mixture (rac-(5S,7S)-7-fluoro-5-phenyl-6,7-dihydro-5H-pyrrolo[1,2-b][1,2,4]triazol-2-yl)-(2-thienyl)methanone To a cooled (−78° C.) solution of 2-iodothiophene (289 mg, 1.38 mmol) in tetrahydrofuran (10 mL) was added dropwise n-butyllithium (2.5 M in hexanes, 0.55 mL, 1.38 mmol) under N$_2$ atmosphere. The mixture was stirred at −78° C. for 1 h, then cis-7-fluoro-N-methoxy-N-methyl-5-phenyl-6,7-dihydro-5H-pyrrolo[1,2-b][1,2,4]triazole-2-carboxamide (100 mg, 0.34 mmol) in tetrahydrofuran (2 mL) was added. The mixture was stirred at −78° C. for another 2 h and then quenched by addition of saturated aqueous ammonium chloride (20 mL). The mixture was extracted with ethyl acetate (3×10 mL). The combined organic layers were dried over sodium sulfate and concentrated under reduce pressure. The residue was purified by RP-HPLC (acetonitrile 40-70%/0.05% hydrochloride in water) to afford (rac-(5S,7S)-7-fluoro-5-phenyl-6,7-dihydro-5H-pyrrolo[1,2-b][1,2,4]triazol-2-yl)-(2-thienyl)methanone (15.6 mg, 14%) as a white solid. $^1$H NMR (400 MHz, CD$_3$OD) δ 8.50-8.49 (m, 1H), 7.96-7.94 (m, 1H), 7.49-7.35 (m, 3H), 7.35-7.27 (m, 2H), 7.26-7.20 (m, 1H), 6.24-6.22 (m, 0.5H), 6.10-6.08 (m, 0.5H), 5.74-5.68 (m, 1H), 3.86-3.72 (m, 1H), 2.91-2.79 (m, 1H). LCMS R$_T$=0.891 min, m/z=314.1 [M+H]$^+$. LCMS (5 to 95% acetonitrile in water+0.03% trifluoacetic acid over 1.5 mins) retention time 0.891 min, ESI+ found [M+H]=314.1.

Method 29

Example 42

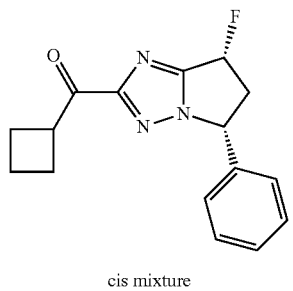

cis mixture

Cyclobutyl-[rac-(5R,7R)-7-fluoro-5-phenyl-6,7-dihydro-5H-pyrrolo[1,2-b][1,2,4]triazol-2-yl]methanone To a cooled (0° C.) mixture of magnesium (234 mg, 9.65 mmol), iodine (12 mg, 0.05 mmol), 1,2-dibromoethane (0.1 mL, 0.10 mmol) in tetrahydrofuran (15 mL) was added dropwise with bromocyclobutane (0.5 mL, 5.85 mmol) under N$_2$ atmosphere. The mixture was stirred at 35° C. for about 1 h. The above freshly prepared cyclobutylmagnesium bromide solution (1.0 mL, 0.39 mmol) was added dropwise to a stirred and cooled (−78° C.) solution of cis-7-fluoro-N-methoxy-N-methyl-5-phenyl-6,7-dihydro-5H-pyrrolo[1,2-b][1,2,4]triazole-2-carboxamide (28 mg, 0.10 mmol) in tetrahydrofuran (2 mL). After addition, the mixture was stirred at −78° C. for 1 h, and then quenched by addition of saturated aqueous ammonium chloride (10 mL). The mixture was extracted with ethyl acetate (2×5 mL). The combined organic layers were dried and concentrated under reduce pressure. The residue was purified by RP-HPLC (acetonitrile 42-62%/0.05% hydrochloride in water) to afford cyclobutyl-[rac-(5R,7R)-7-fluoro-5-phenyl-6,7-dihydro-5H-pyrrolo[1,2-b][1,2,4]triazol-2-yl]methanone (2 mg, 7%) as a white solid. $^1$H NMR (400 MHz, CD$_3$OD) δ 7.40-7.30 (m, 3H), 7.25-7.21 (m, 2H), 6.15-6.10 (m, 0.5H), 6.01-5.95 (m, 0.5H), 5.60-5.55 (m, 1H), 4.15-4.07 (m, 1H), 3.74-3.65 (m, 1H), 2.80-2.70 (m, 1H), 2.35-2.20 (m, 3H), 2.20-2.15 (m, 1H), 2.12-2.00 (m, 1H), 1.90-1.85 (m, 1H). LCMS R$_T$=0.883 min, m/z=286.0 [M+H]$^+$. LCMS (5 to 95% acetonitrile in water+0.03% trifluoacetic acid over 1.5 mins) retention time 0.883 min, ESI+ found [M+H]=286.0.

Method 30

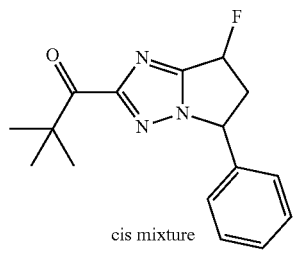

Example 44

1-(rac-(5S,7S)-7-fluoro-5-phenyl-6,7-dihydro-5H-pyrrolo[1,2-b][1,2,4]triazol-2-yl)-2,2-dimethyl-propan-1-one To a cooled (−78° C.) solution of ethyl cis-7-fluoro-5-phenyl-6,7-dihydro-5H-pyrrolo [1,2-b][1,2,4]triazole-2-carboxylate (30 mg, 0.11 mmol) in tetrahydrofuran (3 mL) was added tert-butyllithium (1.3 M in pentane, 0.17 mL, 0.22 mmol) dropwise under a nitrogen atmosphere. After addition, the mixture was stirred at −78° C. for 2 h, and then quenched by addition of saturated aqueous ammonium chloride (10 mL). The mixture was extracted with ethyl acetate (2×10 mL). The combined organic layers were dried and concentrated under reduce pressure. The residue was purified by RP-HPLC (acetonitrile 45-75%/0.05% hydrochloride in water) to afford 1-(rac-(5S,7S)-7-fluoro-5-phenyl-6,7-dihydro-5H-pyrrolo[1,2-b][1,2,4]triazol-2-yl)-2,2-dimethyl-propan-1-one (12.7 mg, 40%) as a white solid. $^1$H NMR (400 MHz, CD$_3$OD) δ 7.42-7.36 (m, 3H), 7.36-7.23 (m, 2H), 6.16-6.13 (m, 0.5H), 6.02-5.99 (m, 0.5H), 5.65-5.61 (m, 1H), 3.77-3.68 (m, 1H), 2.85-2.73 (m, 1H), 1.35 (s, 9H). LCMS $R_T$=0.907 min, m/z=288.0 [M+H]$^+$. LCMS (5 to 95% acetonitrile in water+0.03% trifluoacetic acid over 1.5 mins) retention time 0.907 min, ESI+ found [M+H]=288.0.

Method 31

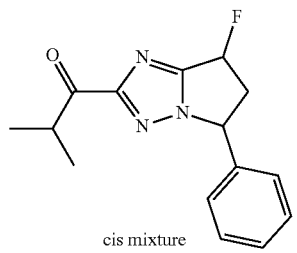

Example 45

1-(rac-(5S,7S)-7-fluoro-5-phenyl-6,7-dihydro-5H-pyrrolo[1,2-b][1,2,4]triazol-2-yl)-2-methyl-propan-1-one To a cooled (−78° C.) solution of ethyl cis-7-fluoro-5-phenyl-6,7-dihydro-5H-pyrrolo [1,2-b][1,2,4]triazole-2-carboxylate (200 mg, 0.73 mmol) in tetrahydrofuran (10 mL) was added isopropylmagnesium chloride (2.0 M in THF, 1.1 mL, 2.20 mmol) dropwise under nitrogen atmosphere. After addition, the mixture was stirred at −78° C. for 2 h, and then quenched by addition of saturated aqueous ammonium chloride (20 mL). The mixture was extracted with ethyl acetate (3×15 mL). The combined organic layers were dried and concentrated under reduce pressure. The residue was purified by RP-HPLC (acetonitrile 30-60%/0.05% ammonia hydroxide in water) to afford racemic 1-(rac-(5S,7S)-7-fluoro-5-phenyl-6,7-dihydro-5H-pyrrolo[1,2-b][1,2,4]triazol-2-yl)-2-methyl-propan-1-one (6.9 mg, 3.4%) as a white solid. $^1$H NMR (400 MHz, CD$_3$OD) δ 7.46-7.36 (m, 3H), 7.28-7.26 (m, 2H), 6.18-6.16 (m, 0.5H), 6.05-6.02 (m, 0.5H), 5.65-5.61 (m, 1H), 3.78-3.72 (m, 1H), 3.64-3.61 (m, 1H), 2.87-2.76 (m, 1H), 1.19 (d, J=7.2 Hz, 3H), 1.17 (d, J=6.8 Hz, 3H). LCMS $R_T$=1.971 min, m/z=274.2 [M+H]$^+$. LCMS (0 to 60% acetonitrile in water+0.03% trifluoacetic acid over 3.0 mins) retention time 1.971 min, ESI+ found [M+H]=274.2.

Method 32

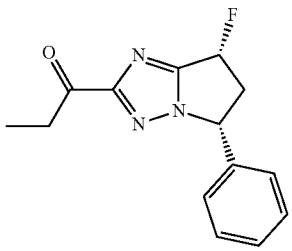

Example 46

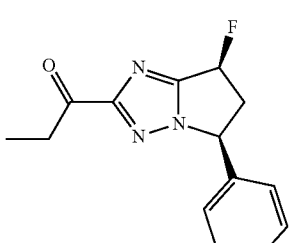

Example 47

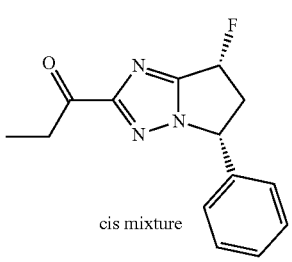

Example 49

1-[(5S,7S)-7-fluoro-5-phenyl-6,7-dihydro-5H-pyrrolo[1,2-b][1,2,4]triazol-2-yl]propan-1-one and 1-[(5R,7R)-7-fluoro-5-phenyl-6,7-dihydro-5H-pyrrolo[1,2-b][1,2,4]triazol-2-yl]propan-1-one

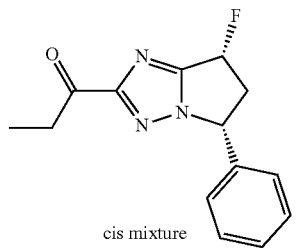 [SMILES: CCC(=O)c1nc2n(n1)[C@@H](c1ccccc1)C[C@H]2F]

cis mixture

Step 1: 1-[rac-(5R,7R)-7-fluoro-5-phenyl-6,7-dihydro-5H-pyrrolo[1,2-b][1,2,4]triazol-2-yl]propan-1-one To a cooled (−70° C.) solution of cis-7-fluoro-N-methoxy-N-methyl-5-phenyl-6,7-dihydro-5H-pyrrolo[1,2-b][1,2,4]triazole-2-carboxamide (30 mg, 0.10 mmol) in tetrahydrofuran (3 mL) was added ethylmagnesium bromide (3.0 M in THF, 0.1 mL, 0.30 mmol) dropwise under a nitrogen atmosphere. After addition, the mixture was stirred at 30° C. for about 3 h, and then quenched by addition of saturated aqueous ammonium chloride (20 mL). The mixture was extracted with ethyl acetate (3×15 mL). The combined organic layers were dried and concentrated under reduce pressure. The residue was purified by RP-HPLC (acetonitrile 25-55%/0.05% ammonia hydroxide in water) to afford 1-[rac-(5R,7R)-7-fluoro-5-phenyl-6,7-dihydro-5H-pyrrolo[1,2-b][1,2,4]triazol-2-yl]propan-1-one (6.3 mg, 23%) as a white solid. $^1$H NMR (400 MHz, CD$_3$OD) δ 7.38-7.35 (m, 3H), 7.25-7.23 (m, 2H), 6.15-6.13 (m, 0.5H), 6.01-5.99 (m, 0.5H), 5.59-5.53 (m, 1H), 3.77-3.67 (m, 1H), 3.05-2.99 (m, 2H), 2.84-2.73 (m, 1H), 1.13 (t, J=7.2 Hz, 3H). LCMS R$_T$=1.038 min, m/z=260.2 [M+H]$^+$. LCMS (10 to 80% acetonitrile in water+0.03% trifluoacetic acid over 2.0 mins) retention time 1.038 min, ESI+ found [M+H]=260.2.

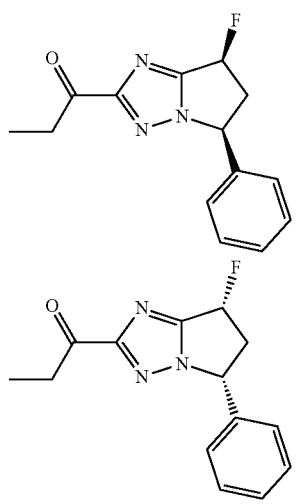

Step 2: 1-[(5S,7S)-7-fluoro-5-phenyl-6,7-dihydro-5H-pyrrolo[1,2-b][1,2,4]triazol-2-yl]propan-1-one and 1-[(5R,7R)-7-fluoro-5-phenyl-6,7-dihydro-5H-pyrrolo[1,2-b][1,2,4]triazol-2-yl]propan-1-one The racemic 1-[rac-(5R,7R)-7-fluoro-5-phenyl-6,7-dihydro-5H-pyrrolo[1,2-b][1,2,4]triazol-2-yl]propan-1-one (220 mg) was separated by chiral SFC to afford arbitrarily assigned:

1-[(5S,7S)-7-fluoro-5-phenyl-6,7-dihydro-5H-pyrrolo[1,2-b][1,2,4]triazol-2-yl]propan-1-one (peak 1, retention time=2.265 min) (78 mg, 35%, 88% ee) as light yellow oil. $^1$H NMR (400 MHz, CD$_3$OD) δ 7.43-7.32 (m, 3H), 7.27-7.23 (m, 2H), 6.17-6.14 (m, 0.5H), 6.02-6.00 (m, 0.5H), 5.65-5.58 (m, 1H), 3.84-3.64 (m, 1H), 3.06-3.00 (m, 2H), 2.88-2.69 (m, 1H), 1.13 (t, J=7.2 Hz, 3H). LCMS R$_T$=0.822 min, m/z=260.0 [M+H]$^+$. LCMS (5 to 95% acetonitrile in water+0.03% trifluoacetic acid over 1.5 mins) retention time 0.822 min, ESI+ found [M+H]=260.0.

1-[(5R,7R)-7-fluoro-5-phenyl-6,7-dihydro-5H-pyrrolo[1,2-b][1,2,4]triazol-2-yl]propan-1-one (peak 2, retention time=2.382 min) (80 mg, 35%, 91% ee) as light yellow oil. $^1$H NMR (400 MHz, CD$_3$OD) δ 7.43-7.32 (m, 3H), 7.27-7.23 (m, 2H), 6.17-6.14 (m, 0.5H), 6.02-6.00 (m, 0.5H), 5.65-5.58 (m, 1H), 3.84-3.64 (m, 1H), 3.06-3.00 (m, 2H), 2.88-2.69 (m, 1H), 1.13 (t, J=7.2 Hz, 3H). LCMS R$_T$=0.817 min, m/z=260.0 [M+H]$^+$. LCMS (5 to 95% acetonitrile in water+0.03% trifluoacetic acid over 1.5 mins) retention time 0.817 min, ESI+ found [M+H]=260.0.

SFC condition: Column: AS (250 mm*30 mm, 5 μm); Condition: 0.1% NH$_3$H$_2$O EtOH; Begin B 20% End B 20%; Flow Rate (60 mL/min), Column temperature 40° C.

Method 33

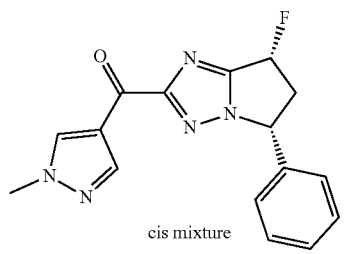 [SMILES: Cn1cc(C(=O)c2nc3n(n2)[C@@H](c2ccccc2)C[C@H]3F)cn1]

cis mixture

Example 48

(1-methylpyrazol-4-yl)-[rac-(5R,7R)-7-fluoro-5-phenyl-6,7-dihydro-5H-pyrrolo[1,2-b][1,2,4]triazol-2-yl]methanone To a cooled (−70° C.) solution of cis-7-fluoro-N-methoxy-N-methyl-5-phenyl-6,7-dihydro-5H-pyrrolo[1,2-b][1,2,4]triazole-2-carboxamide (137 mg, 0.47 mmol) and 1-methyl-4-iodo-1h-pyrazole (393 mg, 1.89 mmol) in tetrahydrofuran (10 mL) was added dropwise tert-butyllithium (1.3 M in hexane, 1.45 mL, 1.89 mmol) under a nitrogen atmosphere. The mixture was stirred at −70° C. for 1 h and then quenched by addition of saturated aqueous ammonium chloride (10 mL). The resulting mixture was extracted with ethyl acetate (2×10 mL). The combined organic layers were concentrated under reduce pressure and the residue was purified by RP-HPLC (acetonitrile 27-57%/0.05% hydrochloride in water) to afford cis racemic (1-methylpyrazol-4-yl)-[rac-(5R,7R)-7-fluoro-5-phenyl-6,7-dihydro-5H-pyrrolo[1,2-b][1,2,4]triazol-2-yl]methanone (53.4 mg, 36%) as a white solid. $^1$H NMR (400 MHz, CD$_3$OD) δ 8.61 (s, 1H), 8.24 (s, 1H), 7.46-7.34 (m, 3H), 7.32-7.25 (m, 2H), 6.22-6.19 (m, 0.5H), 6.08-6.05 (m, 0.5H), 5.72-5.65 (m, 1H), 3.93 (s, 3H), 3.85-3.70 (m, 1H), 2.90-2.75 (m, 1H). LCMS R$_T$=0.791 min, m/z=311.9 [M+H]$^+$. LCMS (5 to 95% acetonitrile in water+0.03% trifluoacetic acid over 1.5 mins) retention time 0.791 min, ESI+ found [M+H]=311.9.

Method 34

Example 50

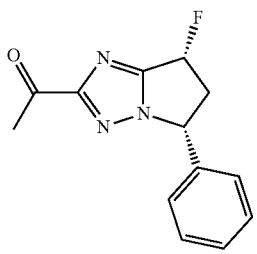

1-[rac-(5R,7R)-7-fluoro-5-phenyl-6,7-dihydro-5H-pyrrolo[1,2-b][1,2,4]triazol-2-yl]ethanone

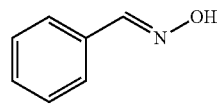

Step 1: (E)-benzaldehyde Oxime

To a solution of benzaldehyde (45.0 g, 424.1 mmol) in ethanol (100 mL) was added sodium carbonate (112.3 g, 1060.1 mmol) and hydroxylamine hydrochloride (35.3 g, 508.9 mmol). The reaction mixture was stirred at 25° C. for 3 h and filtered. The filtrate was concentrated under reduced pressure and the residue was diluted with water (50 mL). The resulting mixture was extracted with ethyl acetate (3×150 mL). The combined organic layers were washed with brine (60 mL), dried over anhydrous sodium sulfate and concentrated under reduced pressure to afford crude (E)-benzaldehyde oxime as colorless oil (51.0 g, 99%), used in the next step without further purification.

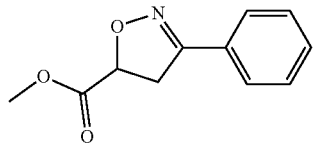

Step 2: Methyl 3-phenyl-4,5-dihydroisoxazole-5-carboxylate

To a solution of (E)-benzaldehyde oxime (20.0 g, 165.1 mmol) in 1,4-dioxane (500 mL) was added methyl acrylate (14.2 g, 165.1 mmol), sodium iodide (24.7 g, 165.1 mmol), 2,6-lutidine (17.6 g, 165.1 mmol) and hypochlorous acid tert-butyl ester (17.9 g, 165.1 mmol). The reaction mixture was stirred at 25° C. for 24 h and subsequently concentrated under reduced pressure. The residue was purified by column chromatography (silica gel, 100-200 mesh, 0 to 20% ethyl acetate in petroleum ether) to afford methyl 3-phenyl-4,5-dihydroisoxazole-5-carboxylate as a yellow solid (25.0 g, 74%). LCMS R$_T$=0.871 min, m/z=206.2 [M+H]$^+$. LCMS (10 to 80% acetonitrile in water+0.03% trifluoacetic acid over 2.0 mins) retention time 0.871 min, ESI+ found [M+H]= 206.2.

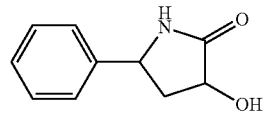 [SMILES: O=C1NC(c2ccccc2)CC1O]

Step 3: 3-hydroxy-5-phenyl-pyrrolidin-2-one

A mixture of methyl 3-phenyl-4, 5-dihydroisoxazole-5-carboxylate (25.0 g, 121.8 mmol) and palladium (10% on carbon, 2.5 g) in ethanol (800 mL) was hydrogenated (50 psi) at 25° C. for 2 h and then filtered and the filtrate was concentrated under reduced pressure to afford crude 3-hydroxy-5-phenyl-pyrrolidin-2-one as a yellow solid (18.0 g, 83%), used in the next step without further purification. LCMS R$_T$=0.270 min, m/z=177.8 [M+H]$^+$. LCMS (5 to 95% acetonitrile in water+0.03% trifluoacetic acid over 1.5 mins) retention time 0.270 min, ESI+ found [M+H]=177.8.

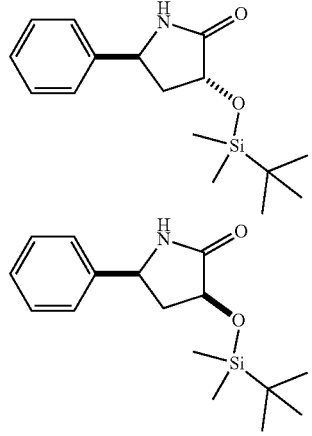

Step 4: cis-3-[tert-butyl(dimethyl)silyl]oxy-5-phenyl-pyrrolidin-2-one & trans-3-[tert-butyl(dimethyl)silyl]oxy-5-phenyl-pyrrolidin-2-one To a solution of 3-hydroxy-5-phenyl-pyrrolidin-2-one (15.0 g, 84.6 mmol) in dichloromethane (300 mL) was added tert-butyldimethylchlorosilane (19.1 g, 126.9 mmol) and imidazole (11.5 g, 169.3 mmol). The reaction mixture was stirred at 25° C. for 16 h and subsequently concentrated under reduced pressure. The residue was purified by column chromatography (silica gel, 100-200 mesh, 0 to 30% ethyl acetate in petroleum ether) to afford arbitrarily assigned:
cis-3-[tert-butyl(dimethyl)silyl]oxy-5-phenyl-pyrrolidin-2-one (12.4 g, 51%). $^1$H NMR (400 MHz, CDCl$_3$) δ 7.37-

7.25 (m, 5H), 4.88-4.53 (m, 1H), 4.54-4.46 (m, 1H), 2.89-2.79 (m, 1H), 1.80-1.71 (m, 1H), 0.93-0.90 (m, 9H), 0.19-0.12 (in, 6H) and trans-3-[tert-butyl(dimethyl)silyl]oxy-5-phenyl-pyrrolidin-2-one as a colorless oil (9.3 g, 38%). ¹H NMR (400 MHz, CDCl₃) δ 7.44-7.34 (m, 2H), 7.29-7.24 (m, 3H), 4.87-4.80 (m, 1H), 4.44-4.41 (m, 1H), 2.45-2.37 (m, 1H), 2.27-2.22 (m, 1H), 0.93-0.90 (m, 9H), 0.16-0.13 (m, 6H).

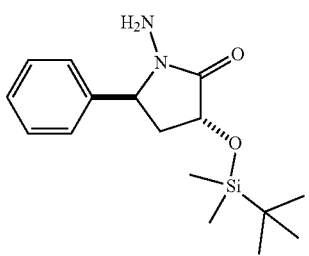 [SMILES: CC(C)(C)[Si](C)(C)O[C@@H]1C[C@@H](c2ccccc2)N(N)C1=O]

Step 5: Trans-1-amino-3-((tert-butyldimethylsilyl)oxy)-5-phenylpyrrolidin-2-one To a solution of tans-3-[tert-butyl(dimethyl)silyl]oxy-5-phenyl-pyrrolidin-2-one (7.0 g, 24.0 mmol) in N,N-dimethylformamide (200 mL) was added sodium hydride (1.44 g, 36.0 mmol) at 0° C. and the mixture was stirred at 0° C. for 20 min. Then o-(diphenylphosphoryl)hydroxylamine (8.40 g, 36.03 mmol) was added. The reaction mixture was stirred at 25° C. for 16 hours. The mixture was filtered and the filtrate was concentrated under reduced pressure to afford trans-1-amino-3-[tert-butyl(dimethyl)silyl]oxy-5-phenyl-pyrrolidin-2-one (7.0 g, 95.1%) as a yellow oil, use in the next step without further purification. LCMS $R_T$=0.775 min, m/z=307.0 [M+H]⁺. LCMS (5 to 95% acetonitrile in water+ 0.03% trifluoacetic acid over 1.5 mins) retention time 0.775 min, ESI+ found [M+H]=307.0.

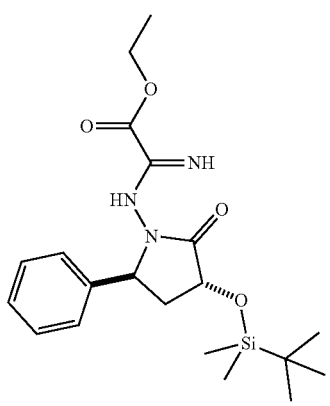 [SMILES: CCOC(=O)C(=N)NN1C(=O)[C@H](O[Si](C)(C)C(C)(C)C)C[C@H]1c1ccccc1]

Step 6: Trans-Ethyl 2-(3-((tert-butyldimethylsilyl)oxy)-2-oxo-5-phenylpyrrolidin-1-yl)amino)-2-iminoacetate To a solution of trans-1-amino-3-[tert-butyl(dimethyl)silyl]oxy-5-phenyl-pyrrolidin-2-one (7.0 g, 22.8 mmol) in ethanol (150 mL) was added ethyl 2-ethoxy-2-imino-acetate (6.63 g, 45.7 mmol). The reaction mixture was stirred at 60° C. for 16 h and subsequently concentrated under reduced pressure to afford crude trans-ethyl 2-(3-((tert-butyldimethylsilyl)oxy)-2-oxo-5-phenylpyrrolidin-1-yl)amino)-2-iminoacetate (8.50 g, 92%) as a yellow oil, used in the next step without further purification. LCMS $R_T$=2.154 min, m/z=406.3 [M+H]⁺. LCMS (0 to 60% acetonitrile in water+ 0.03% trifluoacetic acid over 3.0 mins) retention time 2.143 min, ESI+ found [M+H]=406.3.

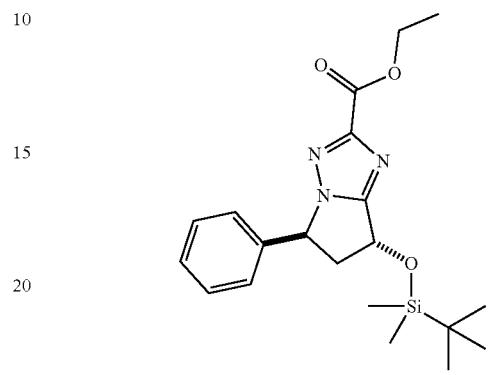

Step 7: Trans-Ethyl 7-((tert-butyldimethylsilyl)oxy)-5-phenyl-6,7-dihydro-5H-pyrrolo[1,2-b][1,2,4]triazole-2-carboxylate To a solution of ethyl 2-[[trans-3-[tert-butyl(dimethyl)silyl]oxy-2-oxo-5-phenyl-pyrrolidin-1-yl]amino]-2-iminoacetate (8.5 g, 21.0 mmol) in toluene (100 mL) was added p-toluenesulfonic acid (4.4 g, 25.2 mmol). The reaction mixture was stirred at 120° C. for 16 h and subsequently concentrated under reduced pressure to afford crude trans-ethyl 7-((tert-butyldimethylsilyl)oxy)-5-phenyl-6,7-dihydro-5H-pyrrolo[1,2-b][1,2,4]triazole-2-carboxylate (7.5 g, 92.3%) as a yellow oil, used in the next step without further purification. LCMS $R_T$=1.022 min, m/z=374.2 [M+H]⁺.

LCMS (10 to 80% acetonitrile in water+0.03% trifluoacetic acid over 2 mins) retention time 1.022 min, ESI+ found [M+H]=374.2.

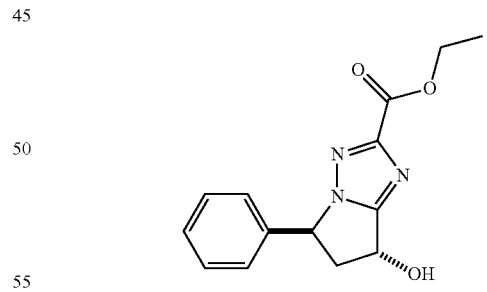

Step 8: Trans-Ethyl 7-hydroxy-5-phenyl-6,7-dihydro-5H-pyrrolo[1,2-b][1,2,4]triazole-2-carboxylate To a solution of ethyl trans-7-[tert-butyl(dimethyl)silyl]oxy-5-phenyl-6,7-dihydro-5H-pyrrolo[1,2-b][1,2,4]triazole-2-carboxylate (7.0 g, 18.06 mmol) in tetrahydrofuran (120 mL) was added tetrabutylammonium fluoride (1 N in THF, 18.06 mL, 18.06 mmol). The reaction mixture was stirred at 40° C. for 3 h and subsequently concentrated under reduced pressure to afford crude trans-ethyl 7-hydroxy-5-phenyl-6,7-dihydro-5H-pyrrolo[1,2-b][1,2,4]triazole-2-carboxylate (3.5 g, 57%) as a yellow oil, used in the next step without further purification. ¹H NMR (400 MHz, CDCl₃) δ 7.39-7.35 (m, 3H), 7.14-7.12 (m, 2H), 5.73-5.70 (m, 1H), 5.54-5.51 (m, 1H), 4.47-4.40 (m, 2H), 3.24-3.21 (m, 1H), 3.05-3.00 (m, 1H), 1.41-1.36 (m, 3H).

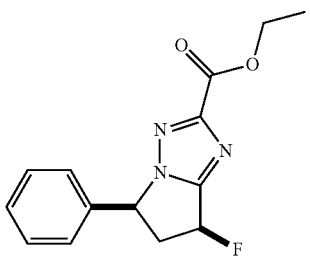 [SMILES: CCOC(=O)c1nc2n(n1)[C@H](c1ccccc1)C[C@@H]2F]

Step 9: cis-ethyl 7-fluoro-5-phenyl-6,7-dihydro-5H-pyrrolo[1,2-b][1,2,4]triazole-2-carboxylate To a solution of trans-ethyl-7-fluoro-5-phenyl-6,7-dihydro-5H-pyrrolo[1,2-b][1,2,4]triazole-2-carboxylate (100 mg, 0.37 mmol) in dichloromethane (8 mL) was added diethylaminosulfur trifluoride (176.9 mg, 1.10 mmol) at 0° C. The reaction mixture was stirred at 0° C. for 2 h and subsequently quenched by addition of water (20 mL). The resulting mixture was extracted with dichloromethane (3×20 mL). The combined organic layers were washed with water (20 mL), brine (20 mL), dried over sodium sulfate and concentrated under reduced pressure. The residue was purified by preparative TLC (50% ethyl acetate in petroleum ether, $R_f$=0.5) to afford cis-ethyl-7-fluoro-5-phenyl-6,7-dihydro-5H-pyrrolo[1,2-b][1,2,4]triazole-2-carboxylate (54 mg, 54%) as a light yellow oil. ¹H NMR (400 MHz, CDCl₃) δ 7.44-7.31 (m, 3H), 7.25-7.17 (m, 2H), 6.09 (dd, J=1.4 Hz, 7.2 Hz, 1H), 5.95 (dd, J=1.4 Hz, 7.2 Hz, 1H), 5.52-5.47 (m, 1H), 4.53-4.37 (m, 2H), 3.74-3.54 (m, 1H), 3.05-2.82 (m, 1H), 1.48-1.33 (m, 3H).

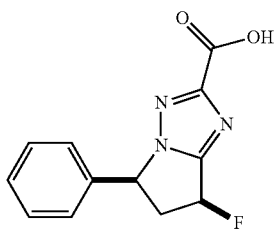 [SMILES: O=C(O)c1nc2n(n1)[C@H](c1ccccc1)C[C@@H]2F]

Step 10: cis-7-fluoro-5-phenyl-6,7-dihydro-5H-pyrrolo[1,2-b][1,2,4]triazole-2-carboxylic acid To a solution of cis-ethyl-7-fluoro-5-phenyl-6,7-dihydro-5H-pyrrolo[1,2-b][1,2,4]triazole-2-carboxylate (54 mg, 0.20 mol) in tetrahydrofuran (4 mL) and water (1 mL) was added lithium hydroxide monohydrate (25 mg, 0.59 mmol). The reaction mixture was stirred at 25° C. for 2 h and subsequently concentrated under reduced pressure. The residue was adjusted to pH=5 by addition of hydrochloric acid (2 N). The resulting mixture was extracted with ethyl acetate (3×10 mL). The combined organic layers were washed with water (10 mL), brine (10 mL), dried over anhydrous sodium sulfate and concentrated under reduced pressure to afford crude cis-7-fluoro-5-phenyl-6,7-dihydro-5H-pyrrolo[1,2-b][1,2,4]triazole-2-carboxylic acid (45 mg, 93%) as a white solid, used in the next step without further purification.

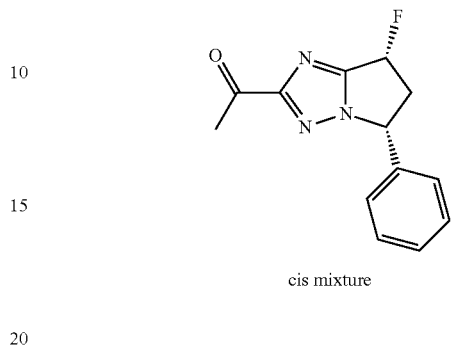

cis mixture

1-[rac-(5R,7R)-7-fluoro-5-phenyl-6,7-dihydro-5H-pyrrolo[1,2-b][1,2,4]triazol-2-yl]ethanone

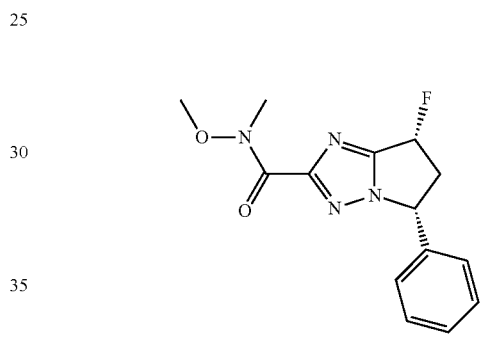

Step 11: cis-7-fluoro-N-methoxy-N-methyl-5-phenyl-6,7-dihydro-5H-pyrrolo[1,2-b][1,2,4]triazole-2-carboxamide A mixture of cis-7-fluoro-5-phenyl-6,7-dihydro-5H-pyrrolo[1,2-b][1,2,4]triazole-2-carboxylic acid (350 mg, 1.42 mmol), 1-hydroxybenzotriazole (201 mg, 1.49 mmol), 1-(3-dimethylaminopropyl)-3-ethylcarbodiimide hydrochloride (407 mg, 2.12 mmol), N,O-dimethylhydroxylamine hydrochloride (180 mg, 1.84 mmol) in N,N-dimethylformamide (10 mL) stirred at 20° C. for 18 h. The mixture was concentrated under reduced pressure and the residue was purified by preparative TLC (50% ethyl acetate in petroleum ether, $R_f$=0.7) to afford cis-7-fluoro-N-methoxy-N-methyl-5-phenyl-6,7-dihydro-5H-pyrrolo[1,2-b][1,2,4]triazole-2-carboxamide (225 mg, 54.7%) as a white solid. ¹H NMR (400 MHz, CDCl₃) δ 7.41-7.35 (m, 3H), 7.26-7.22 (m, 2H), 6.09-6.07 (m, 0.5H), 5.96-5.93 (m, 0.5H), 5.49-5.46 (m, 1H), 3.78 (s, 3H), 3.66-3.59 (m, 1H), 3.55-3.35 (brs, 3H), 2.99-2.88 (m, 1H). LCMS $R_T$=0.564 min, m/z=291.1 [M+H]⁺.

LCMS (5 to 95% acetonitrile in water+0.03% trifluoacetic acid over 1.5 mins) retention time 0.564 min, ESI+ found [M+H]=291.1.

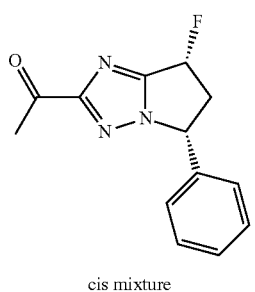 [SMILES: CC(=O)c1nc2n(n1)[C@@H](c1ccccc1)C[C@H]2F]

cis mixture

Step 12: 1-[rac-(5R,7R)-7-fluoro-5-phenyl-6,7-dihydro-5H-pyrrolo[1,2-b][1,2,4]triazol-2-yl]ethanone To a cooled (−70° C.) solution of cis-7-fluoro-N-methoxy-N-methyl-5-phenyl-6,7-dihydro-5H-pyrrolo[1,2-b][1,2,4]triazole-2-carboxamide (30 mg, 0.10 mmol) in tetrahydrofuran (3 mL) was added methylmagnesium bromide (3.0 M in THF, 0.1 mL, 0.30 mmol) dropwise under nitrogen atmosphere. After addition, the mixture was stirred at 30° C. for about 3 h, and then quenched by addition of saturated aqueous ammonium chloride (20 mL). The mixture was extracted with ethyl acetate (3×15 mL). The combined organic layers were dried and concentrated under reduce pressure. The residue was purified by RP-HPLC (acetonitrile 25-55%/0.05% ammonia hydroxide in water) to afford 1-[rac-(5R,7R)-7-fluoro-5-phenyl-6,7-dihydro-5H-pyrrolo[1,2-b][1,2,4]triazol-2-yl]ethanone (4 mg, 15%) as a white solid. $^1$H NMR (400 MHz, CD$_3$OD) δ 7.41-7.35 (m, 3H), 7.26-7.24 (m, 2H), 6.16-6.14 (m, 0.5H), 6.01-6.00 (m, 0.5H), 5.62-5.58 (m, 1H), 3.77-3.68 (m, 1H), 2.85-2.74 (m, 1H), 2.55 (s, 3H). LCMS R$_T$=0.954 min, m/z=246.2 [M+H]$^+$. LCMS (10 to 80% acetonitrile in water+0.03% trifluoacetic acid over 2.0 mins) retention time 0.954 min, ESI+ found [M+H]=246.2.

Method 35

Example 51

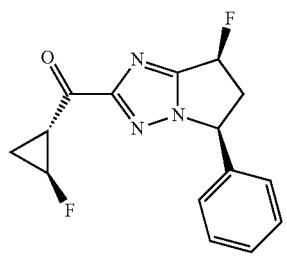

Example 52

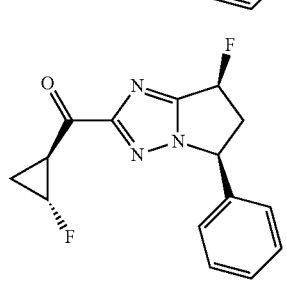

[(1S,2R)-2-fluorocyclopropyl]-[(5S,7S)-7-fluoro-5-phenyl-6,7-dihydro-5H-pyrrolo[1,2-b][1,2,4]triazol-2-yl]methanone and [(1R,2S)-2-fluorocyclopropyl]-[(5S,7S)-7-fluoro-5-phenyl-6,7-dihydro-5H-pyrrolo[1,2-b][1,2,4]triazol-2-yl]methanone To a cooled (−70° C.) solution of (5S,7S)-2-bromo-7-fluoro-5-phenyl-6,7-dihydro-5H-pyrrolo[1,2-b][1,2,4]triazole (150 mg, 0.53 mmol) and trans-2-fluoro-N-methoxy-N-methyl-cyclopropanecarboxamide (157 mg, 1.06 mmol) in tetrahydrofuran (10 mL) was added n-butyllithium (2.5 M in hexanes, 0.64 mL, 1.60 mmol) dropwise under nitrogen atmosphere. After addition, the mixture was stirred at −70° C. for 1 h then quenched by addition of saturated aqueous ammonium chloride (30 mL). The mixture was extracted with ethyl acetate (3×15 mL). The combined organic layers were concentrated under reduce pressure. The residue was purified by RP-HPLC (acetonitrile 37-67%/0.05% ammonia hydroxide in water) to give [trans-2-fluorocyclopropyl]-[(5S,7S)-7-fluoro-5-phenyl-6,7-dihydro-5H-pyrrolo[1,2-b][1,2,4]triazol-2-yl]methanone (25 mg, 16%) as a deep red solid. This material was further separated by chiral SFC to afford arbitrarily assigned:

[(1S,2R)-2-fluorocyclopropyl]-[(5S,7S)-7-fluoro-5-phenyl-6,7-dihydro-5H-pyrrolo[1,2-b][1,2,4]triazol-2-yl]methanone (Peak 1, Retention time=3.130 min) (11.2 mg, 44%) as a white solid. $^1$H NMR (400 MHz, CD$_3$OD) δ 7.51-7.33 (m, 3H), 7.30-7.28 (m, 2H), 6.21-6.03 (m, 1H), 5.68-5.64 (m, 1H), 5.02-4.94 (m, 1H), 4.84-4.80 (m, 1H), 3.84-3.70 (m, 1H), 3.47-3.44 (m, 1H), 2.90-2.78 (m, 1H), 1.73-1.62 (m, 1H), 1.60-1.52 (m, 1H). LCMS R$_T$=1.765 min, m/z=290.1 [M+H]$^+$. LCMS (10 to 80% acetonitrile in water+0.03% ammonium bicarbonate over 2.0 mins) retention time 1.765 min, ESI+ found [M+H]=290.1.

[(1R,2S)-2-fluorocyclopropyl]-[(5S,7S)-7-fluoro-5-phenyl-6,7-dihydro-5H-pyrrolo[1,2-b][1,2,4]triazol-2-yl]methanone (Peak 2, Retention time=3.464 min) (10.2 mg, 40%) as a white solid. $^1$H NMR (400 MHz, CD$_3$OD) δ 7.51-7.33 (m, 3H), 7.32-7.20 (m, 2H), 6.21-6.04 (m, 1H), 5.70-5.62 (m, 1H), 5.00-4.82 (m, 1H), 3.83-3.70 (m, 1H), 3.47-3.42 (m, 1H), 2.90-2.77 (m, 1H), 1.74-1.63 (m, 1H), 1.60-1.52 (m, 1H). LCMS R$_T$=1.756 min, m/z=290.1 [M+H]+. LCMS (10 to 80% acetonitrile in water+0.03% ammonium bicarbonate over 2.0 mins) retention time 1.756 min, ESI+ found [M+H]=290.1.

SFC condition: Column: Chiralcel OD-3 150×4.6 mm I.D., 3 μm Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min.

Method 36

Example 53

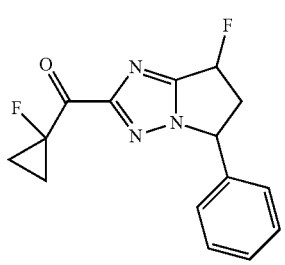

cix mixture (1-fluorocyclopropyl)(7-fluoro-5-phenyl-6,7-dihydro-5H-pyrrolo[1,2-b][1,2,4]triazol-2-yl)methanone

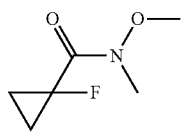

Step 1:
1-fluoro-N-methoxy-N-methylcyclopropanecarboxamide

A mixture of 1-fluorocyclopropanecarboxylic acid (150 mg, 1.44 mmol), N,N-diisopropylethylamine (465 mg, 3.60 mmol), 1-[bis(dimethylamino)methylene]-1H-1,2,3-triazolo[4,5-b]pyridinium 3-oxide hexafluorophosphate (712 mg, 1.87 mmol) and N,O-dimethylhydroxylamine hydrochloride (183 mg, 1.87 mmol) in N,N-dimethylformamide (5 mL) was stirred at 25° C. for 12 h. The reaction mixture was diluted with saturated aqueous ammonium chloride (15 mL) and extracted with ethyl acetate (3×20 mL). The combined organic layers were washed with water (2×20 mL), brine (20 mL) and concentrated under reduced pressure. The residue was purified by column chromatography (silica gel, 100-200 mesh, 0 to 20% ethyl acetate in petroleum ether) to give 1-fluoro-N-methoxy-N-methyl-cyclopropanecarboxamide (140 mg, 66%) as a colorless oil. $^1$H NMR (400 MHz, CDCl$_3$) δ 3.75 (s, 3H), 3.26 (s, 3H), 1.31-1.21 (m, 4H).

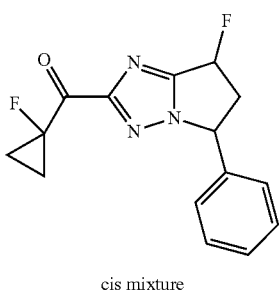 [SMILES: O=C(c1nc2n(n1)C(c1ccccc1)CC2F)C1(F)CC1]

cis mixture

Step 2: (1-fluorocyclopropyl)(rac-(5S,7S)-7-fluoro-5-phenyl-6,7-dihydro-5H-pyrrolo[1,2-b][1,2,4]triazol-2-yl)methanone To a cooled (−78° C.) solution of cis-2-bromo-7-fluoro-5-phenyl-6,7-dihydro-5H-pyrrolo[1,2-b][1,2,4]triazole (50 mg, 0.18 mmol) and 1-fluoro-N-methoxy-N-methyl-cyclopropanecarboxamide (52 mg, 0.35 mmol) in tetrahydrofuran (5 mL) was added n-butyllithium (2.5 M in hexanes, 0.21 mL, 0.53 mmol) dropwise under nitrogen atmosphere. After addition, the mixture was stirred at −78° C. for 1 h and then quenched by addition of saturated aqueous ammonium chloride (10 mL). The resulting mixture was extracted with ethyl acetate (2×15 mL). The combined organic layers were concentrated under reduce pressure and the residue was purified by RP-HPLC (acetonitrile 20-45%/0.05% HCl in water) to give the crude product (20 mg). This crude was further purified by preparative TLC (30% ethyl acetate in petroleum ether, R$_f$=0.3) to give (1-fluorocyclopropyl)(rac-(5S,7S)-7-fluoro-5-phenyl-6,7-dihydro-5H-pyrrolo[1,2-b][1,2,4]triazol-2-yl)methanone (10.2 mg, 19%) as a light yellow oil. $^1$H NMR (400 MHz, CDCl$_3$) δ 7.41-7.37 (m, 3H), 7.23-7.21 (m, 2H), 6.09-6.07 (m, 0.5H), 5.96-5.93 (m, 0.5H), 5.51-5.50 (m, 1H), 3.67-3.58 (m, 1H), 3.00-2.90 (m, 1H), 1.92-1.88 (m, 2H), 1.62-1.58 (m, 2H). LCMS R$_T$=1.726 min, m/z=290.1 [M+H]+. LCMS (10 to 80% acetonitrile in water+0.1% ammonia water over 3.0 mins) retention time: 1.726 min, ESI+ found [M+H]=290.1.

Method 37

Example 54

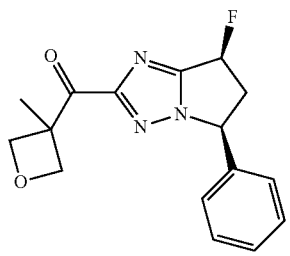

((5S,7S)-7-fluoro-5-phenyl-6,7-dihydro-5H-pyrrolo[1,2-b][1,2,4]triazol-2-yl)(3-methyloxetan-3-yl)methanone To a cooled (−78° C.) solution of (5S,7S)-2-bromo-7-fluoro-5-phenyl-6,7-dihydro-5H-pyrrolo[1,2-b][1,2,4]triazole (80 mg, 0.28 mmol) and N-methoxy-N,3-dimethyl-oxetane-3-carboxamide (90 mg, 0.57 mmol) in tetrahydrofuran (2 mL) was added n-butyllithium (2.5 M in hexanes, 0.34 mL, 0.85 mmol) dropwise under nitrogen atmosphere. After addition, the mixture was stirred at −78° C. for 1 h and then quenched by addition of saturated aqueous ammonium chloride (10 mL). The resulting mixture was extracted with ethyl acetate (2×15 mL). The combined organic layers were concentrated under reduce pressure and the residue was purified by RP-HPLC (acetonitrile 30-60%/0.05% ammonia hydroxide in water) to afford [(5S,7S)-7-fluoro-5-phenyl-6,7-dihydro-5H-pyrrolo[1,2-b][1,2,4]triazol-2-yl]-(3-methyloxetan-3-yl)methanone (16.3 mg, 19%) as a pink solid. $^1$H NMR (400 MHz, CD$_3$OD) δ 7.43-7.37 (m, 3H), 7.25-7.23 (m, 2H), 6.17-6.15 (m, 0.5H), 6.03-6.01 (m, 0.5H), 5.65-5.62 (m, 1H), 5.09-5.02 (m, 2H), 4.52-4.26 (m, 2H), 3.78-3.70 (m, 1H), 2.86-2.76 (m, 1H), 1.74 (s, 3H). LCMS R$_T$=0.675 min, m/z=302.1 [M+H]$^+$. LCMS (5 to 95% acetonitrile in water+0.03% trifluoacetic acid over 1.5 mins) retention time: 0.675 min, ESI+ found [M+H]=302.1.

Method 38

Example 55

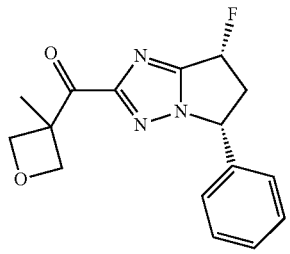

((5R,7R)-7-fluoro-5-phenyl-6,7-dihydro-5H-pyrrolo[1,2-b][1,2,4]triazol-2-yl)(3-methyloxetan-3-yl)methanone

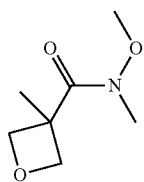

Step 1:
N-methoxy-N,3-dimethyloxetane-3-carboxamide

A mixture of N,O-dimethylhydroxylamine hydrochloride (252 mg, 2.58 mmol), 1-(3-dimethylaminopropyl)-3-ethyl-carbodiimide hydrochloride (396 mg, 2.07 mmol), 3-methyloxetane-3-carboxylic acid (200 mg, 1.72 mmol), 1-hydroxybenzotriazole (140 mg, 1.03 mmol) and N,N-diisopropylethylamine (556 mg, 4.31 mmol) in dichloromethane (10 mL) was stirred at 25° C. for 12 h. The reaction mixture was diluted with water (30 mL) and extracted with ethyl acetate (3×15 mL). The combined organic layers were washed with water (2×10 mL), brine (20 mL), dried and concentrated under reduced pressure to give crude N-methoxy-N,3-dimethyl-oxetane-3-carboxamide (270 mg, 98%) as a colorless oil. This crude was used in the next step without further purification. $^1$H NMR (400 MHz, CDCl$_3$) δ 4.96-4.93 (m, 2H), 4.29-4.27 (m, 2H), 3.66 (s, 3H), 3.18 (s, 3H), 1.66 (s, 3H).

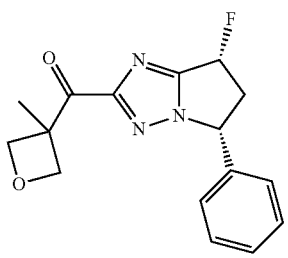 [SMILES: CC1(C(=O)c2nc3n(n2)[C@@H](c2ccccc2)C[C@H]3F)COC1]

Step 2: ((5R,7R)-7-fluoro-5-phenyl-6,7-dihydro-5H-pyrrolo[1,2-b][1,2,4]triazol-2-yl)(3-methyloxetan-3-yl)methanone To a cooled (−78° C.) solution of (5R,7R)-2-bromo-7-fluoro-5-phenyl-6,7-dihydro-5H-pyrrolo[1,2-b][1,2,4]triazole (100 mg, 0.35 mmol) and N-methoxy-N,3-dimethyl-oxetane-3-carboxamide (113 mg, 0.71 mmol) in tetrahydrofuran (2 mL) was added n-butyllithium (2.5 M in hexanes, 0.43 mL, 1.06 mmol) dropwise under nitrogen atmosphere. After addition, the mixture was stirred at −78° C. for 1 h and then quenched by addition of saturated aqueous ammonium chloride (10 mL). The resulting mixture was extracted with ethyl acetate (2×15 mL). The combined organic layers were concentrated under reduce pressure and the residue was purified by RP-HPLC (acetonitrile 30-60%/0.05% ammonia hydroxide in water) to afford [(5R,7R)-7-fluoro-5-phenyl-6,7-dihydro-5H-pyrrolo[1,2-b][1,2,4]triazol-2-yl]-(3-methyloxetan-3-yl)methanone (13.6 mg, 13%) as a pink solid. $^1$H NMR (400 MHz, CD$_3$OD) δ 7.43-7.37 (m, 3H), 7.25-7.23 (m, 2H), 6.17-6.15 (m, 0.5H), 6.03-6.01 (m, 0.5H), 5.65-5.62 (m, 1H), 5.09-5.02 (m, 2H), 4.52-4.26 (m, 2H), 3.78-3.70 (m, 1H), 2.86-2.76 (m, 1H), 1.74 (s, 3H). LCMS R$_T$=0.678 min, m/z=302.1 [M+H]$^+$. LCMS (5 to 95% acetonitrile in water+0.03% trifluoacetic acid over 1.5 mins) retention time: 0.678 min, ESI+ found [M+H]=302.1.

Method 39

Example 56

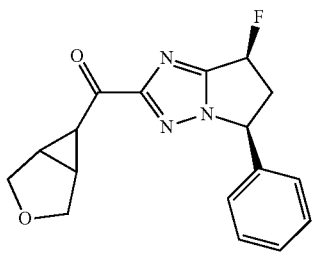

cis mixture RHS
trans LHS 3-oxabicyclo[3.1.0]hexan-6-yl-[rac-(5S,7S)-7-fluoro-5-phenyl-6,7-dihydro-5H-pyrrolo[1,2-b][1,2,4]triazol-2-yl]methanone

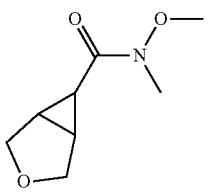

Step 1: N-methoxy-N-methyl-3-oxabicyclo[3.1.0]hexane-6-carboxamide

A mixture of 3-oxabicyclo[3.1.0]hexane-6-carboxylic acid (trans, 300 mg, 2.34 mmol), N,O-dimethylhydroxylamine hydrochloride (297 mg, 3.04 mmol), 1-[bis(dimethylamino)methylene]-1H-1,2,3-triazolo[4,5-b]pyridinium 3-oxide hexafluorophosphate (1157 mg, 3.04 mmol) and N,N-diisopropylethylamine (756 mg, 5.85 mmol) in N,N-dimethylformamide (15 mL) was stirred at 25° C. for 12 h. The reaction mixture was diluted with water (30 mL) and extracted with ethyl acetate (3×15 mL). The combined organic layers were washed with water (2×10 mL), brine (20 mL) and concentrated under reduced pressure. The residue was purified by column chromatography (silica gel, 100-200 mesh, 0 to 30% ethyl acetate in petroleum ether) to give N-methoxy-N-methyl-3-oxabicyclo[3.1.0]hexane-6-carboxamide (180 mg, 45%) as a colorless oil. $^1$H NMR (400 MHz, CDCl$_3$) δ 3.95-3.93 (m, 2H), 3.80-3.78 (m, 2H), 3.73 (s, 3H), 3.20 (s, 3H), 2.17-2.09 (m, 3H).

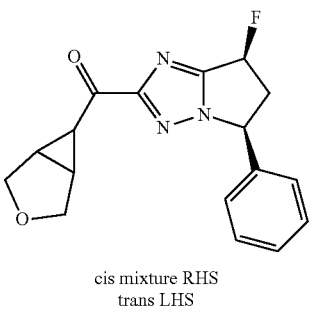 [SMILES: O=C(c1nc2n(n1)[C@H](c1ccccc1)C[C@@H]2F)C1C2COCC21]

cis mixture RHS
trans LHS

Step 2: 3-oxabicyclo[3.1.0]hexan-6-yl-[rac-(5S,7S)-7-fluoro-5-phenyl-6,7-dihydro-5H-pyrrolo[1,2-b][1,2,4]triazol-2-yl]methanone To a cooled (−70° C.) solution of cis-2-bromo-7-fluoro-5-phenyl-6,7-dihydro-5H-pyrrolo[1,2-b][1,2,4]triazole (50 mg, 0.18 mmol) and N-methoxy-N-methyl-3-oxabicyclo[3.1.0]hexane-6-carboxamide (61 mg, 0.35 mmol) in tetrahydrofuran (2 mL) was added n-butyllithium (2.5 M in hexanes, 0.21 mL, 0.53 mmol) dropwise under nitrogen atmosphere. After addition, the mixture was stirred at −70° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 30-60%/0.05% ammonia hydroxide in water) to afford 3-oxabicyclo[3.1.0]hexan-6-yl-[rac-(5S,7S)-7-fluoro-5-phenyl-6,7-dihydro-5H-pyrrolo[1,2-b][1,2,4]triazol-2-yl]methanone (2.2 mg, 3.9%) as a white solid. $^1$H NMR (400 MHz, CDCl$_3$) δ 7.43-7.39 (m, 3H), 7.27-7.26 (m, 2H), 6.12-5.96 (m, 1H), 5.53-5.49 (m, 1H), 4.02-3.99 (m, 2H), 3.82-3.80 (m, 2H), 3.70-3.61 (m, 1H), 3.07-3.05 (m, 1H), 3.02-2.95 (m, 1H), 2.45-2.43 (m, 2H). LCMS R$_T$=0.821 min, m/z=313.9 [M+H]$^+$. LCMS (5 to 95% acetonitrile in water+0.03% trifluoacetic acid over 1.5 mins) retention time 0.821 min, ESI+ found [M+H]=313.9.

Method 40

Example 57

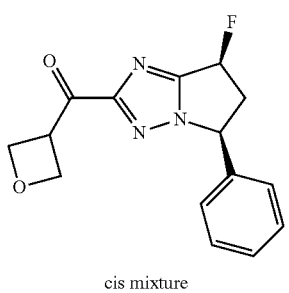

cis mixture

Oxetan-3-yl-[rac-(5S,7S)-7-fluoro-5-phenyl-6,7-dihydro-5H-pyrrolo[1,2-b][1,2,4]triazol-2-yl]methanone

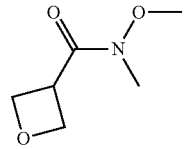

Step 1: N-methoxy-N-methyl-oxetane-3-carboxamide

A mixture of oxetane-3-carboxylic acid (300 mg, 2.94 mmol), 1,1'-carbonyldiimidazole (524 mg, 3.23 mmol) and N,O-dimethylhydroxylamine hydrochloride (286 mg, 2.94 mmol) in dichloromethane (8 mL) was stirred at 25° C. for 12 h. The reaction mixture was diluted with water (20 mL) and extracted with ethyl acetate (3×15 mL). The combined organic layers were washed with water (2×10 mL), brine (20 mL) and concentrated under reduced pressure. The residue was purified by preparative TLC (60% ethyl acetate in petroleum ether, R$_f$=0.3) to give N-methoxy-N-methyl-oxetane-3-carboxamide (60 mg, 14%) as a colorless oil. $^1$H NMR (400 MHz, CDCl$_3$) δ 4.92-4.89 (m, 2H), 4.80-4.76 (m, 2H), 4.19-4.13 (m, 1H), 3.63 (s, 3H), 3.21 (s, 3H).

cis mixture

Step 2: Oxetan-3-yl-[rac-(5S,7S)-7-fluoro-5-phenyl-6,7-dihydro-5H-pyrrolo[1,2-b][1,2,4]triazol-2-yl]methanone To a cooled (−70° C.) solution of cis-2-bromo-7-fluoro-5-phenyl-6,7-dihydro-5H-pyrrolo[1,2-b][1,2,4]triazole (38 mg, 0.13 mmol) and N-methoxy-N-methyl-oxetane-3-carboxamide (39 mg, 0.27 mmol) in tetrahydrofuran (2 mL) was added n-butyllithium (2.5 M in hexanes, 0.16 mL, 0.40 mmol) dropwise under nitrogen atmosphere. After addition, the mixture was stirred at −70° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 25-55%/0.05% ammonia hydroxide in water) to afford oxetan-3-yl-[rac-(5S,7S)-7-fluoro-5-phenyl-6,7-dihydro-5H-pyrrolo [1,2-b][1,2,4]triazol-2-yl] methanone (6.3 mg, 15.5%) as a white solid. $^1$H NMR (400 MHz, CDCl$_3$) δ 7.43-7.40 (m, 3H), 7.27-7.23 (m, 2H), 6.11-5.95 (m, 1H), 5.50-5.49 (m, 1H), 4.97-4.90 (m, 4H), 4.72-4.68 (m, 1H), 3.68-3.59 (m, 1H), 3.03-2.92 (m, 1H).

LCMS R$_T$=0.782 min, m/z=287.9 [M+H]$^+$. LCMS (5 to 95% acetonitrile in water+0.03% trifluoacetic acid over 1.5 mins) retention time 0.782 min, ESI+ found [M+H]=287.9.

Method 41

Example 58

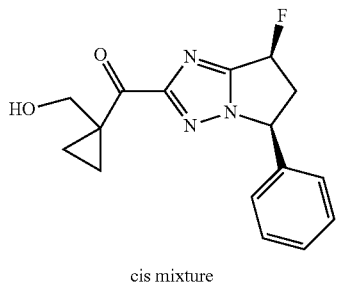

cis mixture

[1-(hydroxymethyl)cyclopropyl]-[rac-(5S,7S)-7-fluoro-5-phenyl-6,7-dihydro-5H-pyrrolo[1,2-b][1,2,4]triazol-2-yl]methanone

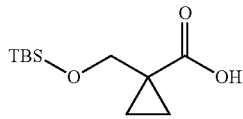

Step 1: 1-(((tert-butyldimethylsilyl)oxy)methyl)cyclopropanecarboxylic Acid

To a solution of 1-(hydroxymethyl)cyclopropanecarboxylic acid (200 mg, 1.72 mmol) in dichloromethane (5 mL) was added tert-butyldimethylchlorosilane (532 mg, 3.53 mmol) and imidazole (240 mg, 3.53 mmol). The mixture was stirred at 25° C. for 5 h and then quenched by addition of water (10 mL). The mixture was extracted with dichloromethane (2×10 mL). The combined organic layers were dried over anhydrous sodium sulfate and concentrated under reduced pressure. The residue was dissolved in acetonitrile (6 mL)/water (6 mL) and added sodium hydroxide (138 mg, 3.44 mmol). The resulting mixture was stirred at 25° C. for 10 h and then adjusted to pH=4 by addition of citric acid. The solution was extracted with ethyl acetate (2×20 mL). The combined organic layers were dried and concentrated under reduced pressure to afford crude 1-[[tert-butyl(dimethyl)silyl]oxymethyl]cyclopropanecarboxylic acid (400 mg, 100%) as a colorless oil.

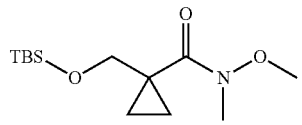

Step 2 1-(((tert-butyldimethylsilyl)oxy)methyl)-N-methoxy-N-methyl cyclopropane Carboxamide A mixture of 1-[[tert-butyl(dimethyl)silyl]oxymethyl]cyclopropanecarboxylic acid (400 mg, 1.74 mmol), N,O-dimethylhydroxylamine hydrochloride (423 mg, 4.34 mmol), 1-(3-dimethylaminopropyl)-3-ethylcarbodiimide hydrochloride (499 mg, 2.6 mmol), 1-hydroxybenzotriazole (235 mg, 1.74 mmol) and N,N-diisopropylethylamine (1.23 mL, 6.95 mmol) in dichloromethane (10 mL) was stirred at 25° C. for 18 h. The resulting mixture was partitioned between water (30 mL) and dichloromethane (30 mL). The separated organic layer was dried and concentrated under reduced pressure. The residue was purified by column chromatography (silica gel, 100-200 mesh, 0 to 30% ethyl acetate in petroleum ether) to afford 1-[[tert-butyl(dimethyl)silyl]oxymethyl]-N-methoxy-N-methyl-cyclopropanecarboxamide (200 mg, 42%) as a colorless oil. LCMS (5 to 95% acetonitrile in water+0.03% trifluoacetic acid over 1.5 mins) retention time: 0.848 min, ESI+ found [M+H]=274.1.

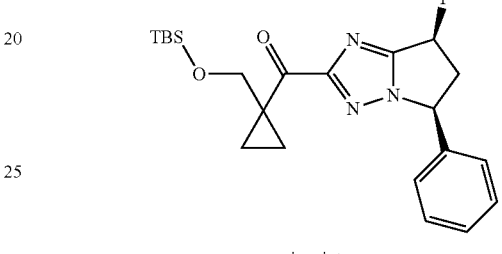

cis mixture

Step 3: (1-(((tert-butyldimethylsilyl)oxy)methyl)cyclopropyl)[rac-(5S,7S)-7-fluoro-5-phenyl-6,7-dihydro-5H-pyrrolo[1,2-b][1,2,4]triazol-2-yl]methanone To a cooled (−78° C.) solution of cis-2-bromo-7-fluoro-5-phenyl-6,7-dihydro-5H-pyrrolo[1,2-b][1,2,4]triazole (60 mg, 0.21 mmol) and 1-[[tert-butyl(dimethyl)silyl]oxymethyl]-N-methoxy-N-methyl-cyclopropanecarboxamide (116 mg, 0.43 mmol) in tetrahydrofuran (2 mL) was added n-butyllithium (2.5 M in hexanes, 0.26 mL, 0.64 mmol) dropwise under a nitrogen atmosphere. After addition, the mixture was stirred at −78° C. for 1 h and then quenched by addition of saturated aqueous ammonium chloride (10 mL). The resulting mixture was extracted with ethyl acetate (3×10 mL). The combined organic layers were concentrated under reduce pressure and the residue was purified by preparative TLC (50% ethyl acetate in petroleum ether, R$_f$=0.4) to afford [1-[[tert-butyl(dimethyl)silyl]oxymethyl]cyclopropyl]-[cis-7-fluoro-5-phenyl-6,7-dihydro-5H-pyrrolo[1,2-b][1,2,4]triazol-2-yl]methanone (34 mg, 38%) as a light brown oil.

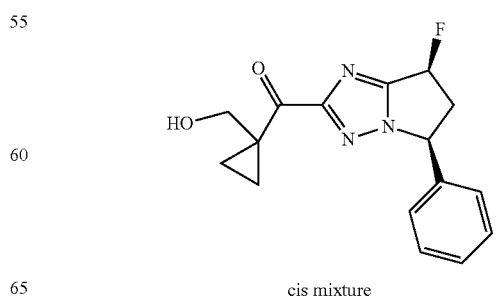

cis mixture

Step 4: [1-(hydroxymethyl)cyclopropyl]-[rac-(5S,7S)-7-fluoro-5-phenyl-6,7-dihydro-5H-pyrrolo[1,2-b][1,2,4]triazol-2-yl]methanone A mixture of [1-[[tert-butyl(dimethyl)silyl]oxymethyl]cyclopropyl]-[rac-(5S,7S)-7-fluoro-5-phenyl-6,7-dihydro-5H-pyrrolo[1,2-b][1,2,4]triazol-2-yl]methanone (34 mg, 0.08 mmol) and 2,2,2-trifluoroacetic acid (0.50 mL) in dichloromethane (3 mL) was stirred at 20° C. for 2 h and then concentrated under reduced pressure. The residue was purified by RP-HPLC (acetonitrile 30-60%/0.05% ammonia hydroxide in water) to afford [1-(hydroxymethyl)cyclopropyl]-[rac-(5S,7S)-7-fluoro-5-phenyl-6,7-dihydro-5H-pyrrolo[1,2-b][1,2,4]triazol-2-yl]methanone (4.1 mg, 16%) as a light brown oil. $^1$H NMR (400 MHz, CD$_3$OD) δ 7.43-7.37 (m, 3H), 7.27-7.25 (m, 2H), 6.17-6.15 (m, 0.5H), 6.03-6.01 (m, 0.5H), 5.63-5.61 (m, 1H), 3.96-3.85 (m, 2H), 3.77-3.71 (m, 1H), 2.86-2.75 (m, 1H), 1.71-1.67 (m, 2H), 1.10-1.07 (m, 2H). LCMS R$_T$=0.648 min, m/z=302.1 [M+H]+. LCMS (5 to 95% acetonitrile in water+0.03% trifluoacetic acid over 1.5 mins) retention time 0.648 min, ESI+ found [M+H]= 302.1.

Method 42

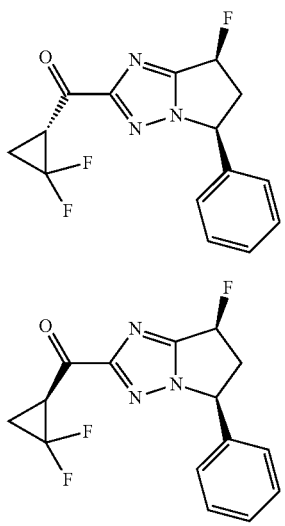

Example 59

Example 60

((1S)-2,2-difluorocyclopropyl)((5S,7S)-7-fluoro-5-phenyl-6,7-dihydro-5H-pyrrolo[1,2-b][1,2,4]triazol-2-yl)methanone and ((1R)-2,2-difluorocyclopropyl)((5S,7S)-7-fluoro-5-phenyl-6,7-dihydro-5H-pyrrolo[1,2-b][1,2,4]triazol-2-yl)methanone

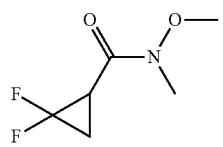

Step 1: 2,2-difluoro-N-methoxy-N-methylcyclopropanecarboxamide

A mixture of 2,2-difluorocyclopropanecarboxylic acid (1.00 g, 8.19 mmol), N,N-diisopropylethylamine (2646 mg, 20.5 mmol), 1-[bis(dimethylamino)methylene]-1H-1,2,3-triazolo[4,5-b]pyridinium 3-oxide hexafluorophosphate (4.05 g, 10.6 mmol), N,O-dimethylhydroxylamine hydrochloride (1.04 g, 10.7 mmol) in N,N-dimethylformamide (10 mL) was stirred at 25° C. for 12 h. The reaction mixture was diluted with saturated aqueous ammonium chloride (20 mL) and extracted with ethyl acetate (3×20 mL). The combined organic layers were washed with water (2×20 mL), brine (30 mL) and concentrated under reduced pressure. The residue was purified by column chromatography (silica gel, 100-200 mesh, 0 to 20% ethyl acetate in petroleum ether) to give 2,2-difluoro-N-methoxy-N-methylcyclopropanecarboxamide (700 mg, 52%) as a colorless oil. $^1$H NMR (400 MHz, CDCl$_3$) δ 3.77 (s, 3H), 3.26 (s, 3H), 2.96-2.91 (m, 1H), 2.16-2.12 (m, 1H), 1.69-1.65 (m, 1H).

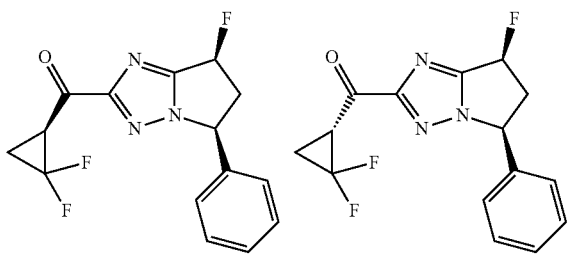

Step 2: ((1S)-2,2-difluorocyclopropyl)((5S,7S)-7-fluoro-5-phenyl-6,7-dihydro-5H-pyrrolo[1,2-b][1,2,4]triazol-2-yl)methanone and ((1R)-2,2-difluorocyclopropyl)((5S,7S)-7-fluoro-5-phenyl-6,7-dihydro-5H-pyrrolo[1,2-b][1,2,4]triazol-2-yl)methanone To a cooled (−78° C.) solution of (5S,7S)-2-bromo-7-fluoro-5-phenyl-6,7-dihydro-5H-pyrrolo[1,2-b][1,2,4]triazole (300 mg, 1.06 mmol) and 2,2-difluoro-N-methoxy-N-methyl-cyclopropanecarboxamide (351 mg, 2.13 mmol) in tetrahydrofuran (15 mL) was added n-butyllithium (2.5 M in hexanes, 1.28 mL, 3.19 mmol) dropwise under a nitrogen atmosphere. After addition, the mixture was stirred at −78° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 20-45%/0.225% HCl in water) to give (2,2-difluorocyclopropyl)-[(5S,7S)-7-fluoro-5-phenyl-6,7-dihydro-5H-pyrrolo[1,2-b][1,2,4]triazol-2-yl]methanone (120 mg, 37%) as a white solid. This material was further separated by chiral SFC to afford arbitrarily assigned:

((1S)-2,2-difluorocyclopropyl)((5S,7S)-7-fluoro-5-phenyl-6,7-dihydro-5H-pyrrolo[1,2-b][1,2,4]triazol-2-yl)methanone (peak 1, retention time=2.069 min) (35.0 mg, 29%) as a white solid. $^1$H NMR (400 MHz, CD$_3$OD) δ 7.42-7.38 (m, 3H), 7.31-7.29 (m, 2H), 6.21-6.19 (m, 0.5H), 6.07-6.05 (m, 0.5H), 5.68-5.66 (m, 1H), 3.85-3.76 (m, 2H), 2.86-2.83 (m, 1H), 2.32-2.28 (m, 1H), 1.96-1.93 (m, 1H). LCMS R$_T$=1.834 min, m/z=308.1 [M+H]$^+$. LCMS (10 to 80% acetonitrile in water+0.1% ammonia water over 3.0 mins) retention time: 1.834 min, ESI+ found [M+H]=308.1.

((1R)-2,2-difluorocyclopropyl)((5S,7S)-7-fluoro-5-phenyl-6,7-dihydro-5H-pyrrolo[1,2-b][1,2,4]triazol-2-yl) methanone (peak 2, retention time=3.055 min) (35.0 mg, 29%) as a white solid. ¹H NMR (400 MHz, CD₃OD) δ 7.45-7.41 (m, 3H), 7.30-7.28 (m, 2H), 6.21-6.19 (m, 0.5H), 6.07-6.05 (m, 0.5H), 5.66-5.65 (m, 1H), 3.87-3.74 (m, 2H), 2.89-2.79 (m, 1H), 2.33-2.28 (m, 1H), 1.98-1.97 (m, 1H). LCMS $R_T$=1.822 min, m/z=308.1 [M+H]⁺. LCMS (10 to 80% acetonitrile in water+0.1% ammonia water over 3.0 mins) retention time: 1.822 min, ESI+ found [M+H]=308.1.

SFC conditions: Column Chiralcel OD-3 150×4.6 mm I.D., 3 μm Mobile phase: A: CO₂ B:iso-propanol (0.05% DEA), Gradient: from 5% to 40% of B in 5 min and hold 40% for 2.5 min, then 5% of B for 2.5 min, Flow rate: 2.5 mL/min, Column temp.: 35° C.

Method 43

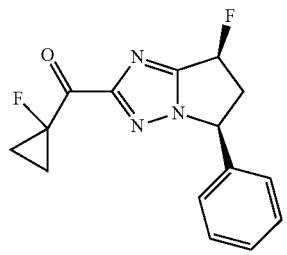

Example 61

(1-fluorocyclopropyl)((5S,7S)-7-fluoro-5-phenyl-6,7-dihydro-5H-pyrrolo[1,2-b][1,2,4]triazol-2-yl) methanone To a cooled (−78° C.) solution of 1-fluoro-N-methoxy-N-methyl-cyclopropane carboxamide (313 mg, 2.13 mmol) and (5S,7S)-2-bromo-7-fluoro-5-phenyl-6,7-dihydro-5H-pyrrolo[1,2-b][1,2,4]triazole (300 mg, 1.06 mmol) in tetrahydrofuran (30 mL) was added n-butyllithium (2.5 M in hexanes, 1.28 mL, 3.19 mmol) dropwise under a nitrogen atmosphere. After addition, the mixture was stirred at −78° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 20-45%/0.05% HCl in water), and then by preparative TLC (30% ethyl acetate in petroleum ether, $R_f$=0.3) to give (1-fluorocyclopropyl)((5S,7S)-7-fluoro-5-phenyl-6,7-dihydro-5H-pyrrolo[1,2-b][1,2,4]triazol-2-yl)methanone (80 mg, 25%) as alight yellow oil. ¹H NMR (400 MHz, CDCl₃) δ 7.40-7.37 (m, 3H), 7.23-7.21 (m, 2H), 6.09-6.07 (m, 0.5H), 5.96-5.94 (m, 0.5H), 5.51-5.49 (m, 1H), 3.67-3.58 (m, 1H), 3.00-2.90 (m, 1H), 1.92-1.88 (m, 2H), 1.62-1.60 (m, 2H). LCMS $R_T$=1.736 min, m/z=290.1 [M+H]⁺. LCMS (10 to 80% acetonitrile in water+0.1% ammonia water over 3.0 mins) retention time: 1.736 min, ESI+ found [M+H]=290.1.

Method 44

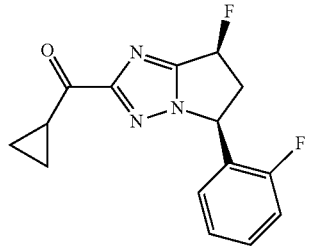

Example 62

Cyclopropyl-[(5S,7S)-7-fluoro-5-(2-fluorophenyl)-6,7-dihydro-5H-pyrrolo[1,2-b][1,2,4]triazol-2-yl] methanone

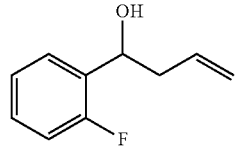

Step 1: 1-(2-fluorophenyl)but-3-en-1-ol

To a solution of 2-fluorobenzaldehyde (15.0 g, 120.86 mmol) in tetrahydrofuran (250 mL) was added allylmagnesium bromide (1.0 M in tetrahydrofuran, 150.0 mL, 150.0 mmol) at 0° C. under nitrogen atmosphere. After addition, the mixture was allowed to warm to 25° C. and stirred for 2 h before quenched by addition of saturated aqueous ammonium chloride (100 mL). The resulting mixture was extracted with ethyl acetate (2×100 mL). The combined organic layers were dried over sodium sulfate and concentrated under reduce pressure. The residue was purified by column chromatography (silica gel, 100-200 mesh, 0 to 5% ethyl acetate in petroleum ether) to afford 1-(2-fluorophenyl)but-3-en-1-ol (6.0 g, 24%) as a yellow oil. ¹H NMR (400 MHz, CDCl₃) δ 7.49-7.27 (m, 1H), 7.29-7.12 (m, 2H), 7.05-7.00 (m, 1H), 5.89-5.80 (m, 1H), 5.20-5.13 (m, 2H), 5.15-5.07 (m, 1H), 2.66-2.55 (m, 1H), 2.57-5.48 (m, 1H).

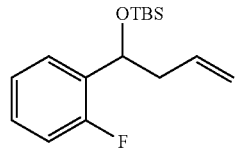 [SMILES: C=CCC(O[Si](C)(C)C(C)(C)C)c1ccccc1F]

Step 2: Tert-Butyl((1-(2-fluorophenyl)but-3-en-1-yl)oxy)dimethylsilane

To a solution of 1-(2-fluorophenyl)but-3-en-1-ol (6.0 g, 36.1 mmol) in dichloromethane (50 mL) was added imidazole (4.9 g, 72.2 mmol) and tert-butyldimethylchlorosilane (7.1 g, 146.9 mmol). The reaction mixture was stirred at 25° C. for 16 h and quenched by addition of water (100 mL). The mixture was extracted with dichloromethane (2×100 mL). The combined organic layers were washed with brine (100 mL), dried over sodium sulfate and concentrated under reduced pressure. The residue was purified by column chromatography (silica gel, 100-200 mesh, 100% petroleum ether) to afford tert-butyl-[1-(2-fluorophenyl)but-3-enoxy]-dimethyl-silane (8.5 g, 84%) as a light oil. ¹H NMR (400 MHz, CDCl₃) δ 7.60-7.36 (m, 1H), 7.34-7.18 (m, 2H), 7.13-7.02 (m, 1H), 5.97-5.85 (m, 1H), 5.21-5.07 (m, 3H), 2.60-2.48 (m, 2H), 0.99 (s, 9H), 0.15 (s, 3H), 0.00 (s, 3H).

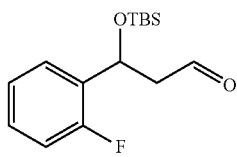 [SMILES: CC(C)(C)[Si](C)(C)OC(CC=O)c1ccccc1F]

Step 3: 3-((tert-butyldimethylsilyl)oxy)-3-(2-fluorophenyl)propanal

To a solution of tert-butyl-[1-(2-fluorophenyl)but-3-enoxy]-dimethyl-silane (8.50 g, 30.3 mmol) in water (100 mL) and tetrahydrofuran (100 mL) was added osmium tetroxide (0.15 g, 0.6 mmol). After stirred for 30 min at 25° C., sodium periodate (25.90 g, 121.2 mmol) was added in small portions over 2 h. The resulting mixture was stirred for 2 h at 25° C. and quenched by addition of cold saturated aqueous sodium thiosulfate (100 mL). The mixture was stirred for 30 min and then extracted with ethyl acetate (3×200 mL). The combined organic layers were washed with water (50 mL), brine (50 mL), dried over sodium sulfate and concentrated under reduced pressure. The residue was purified by column chromatography (silica gel, 100-200 mesh, 0 to 5% ethyl acetate in petroleum ether) to afford 3-[tert-butyl(dimethyl)silyl]oxy-3-(2-fluorophenyl) propanal (5.5 g, 64%) as a black oil. ¹H NMR (400 MHz, CDCl₃) δ 9.84-9.77 (m, 1H), 7.53-7.51 (m, 1H), 7.31-7.24 (m, 1H), 7.21-7.13 (m, 1H), 7.09-6.98 (m, 1H), 5.58-5.55 (m, 1H), 2.85-2.80 (m, 1H), 2.74-2.64 (m, 1H), 0.92-0.85 (m, 9H), 0.09 (s, 3H), −0.09 (s, 3H).

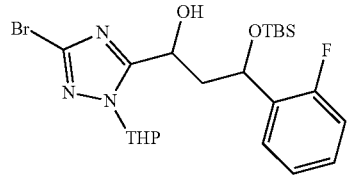

Step 4: 1-(3-bromo-1-(tetrahydro-2H-pyran-2-yl)-1H-1,2,4-triazol-5-yl)-3-((tert-butyldimethylsilyl)oxy)-3-(2-fluorophenyl)propan-1-ol To a cooled (−78° C.) solution of 3,5-dibromo-1-tetrahydropyran-2-yl-1,2,4-triazole (6.3 g, 20.1 mmol) in tetrahydrofuran (50 mL) was added n-butyllithium (2.5 M in hexanes, 8.6 mL, 21.4 mmol) under nitrogen atmosphere. The mixture was stirred at −78° C. for 30 min, then a solution of 3-[tert-butyl(dimethyl)silyl]oxy-3-(2-fluorophenyl)propanal (5.5 g, 19.5 mmol) in tetrahydrofuran (25 mL) was added dropwise. After addition, the mixture was stirred at −78° C. for 1.5 h and then quenched by addition of saturated aqueous ammonium chloride (50 mL). The resulting mixture was extracted with ethyl acetate (2×100 mL). The combined organic layers were dried over sodium sulfate and concentrated under reduce pressure. The residue was purified by column chromatography (silica gel, 100-200 mesh, 0 to 10% ethyl acetate in petroleum ether) to afford 1-(5-bromo-2-tetrahydropyran-2-yl-1,2,4-triazol-3-yl)-3-[tert-butyl(dimethyl)silyl]oxy-3-(2-fluorophenyl)propan-1-ol (8.0 g, 80%) as a yellow oil. Used as is in the next step.

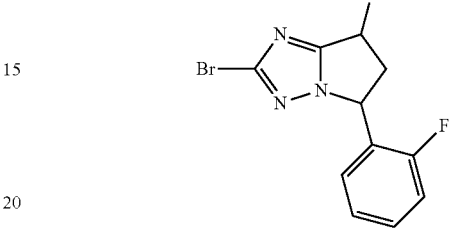

Step 5: 2-bromo-5-(2-fluorophenyl)-6,7-dihydro-5H-pyrrolo[1,2-b][1,2,4]triazol-7-ol A mixture of 1-(5-bromo-2-tetrahydropyran-2-yl-1,2,4-triazol-3-yl)-3-[tert-butyl(dimethyl)silyl]oxy-3-(2-fluorophenyl)propan-1-ol (8.0 g, 15.55 mmol) and trifluoroacetic acid (30.0 mL) in dichloromethane (3.0 mL) was stirred at 50° C. for 5 h and concentrated under reduced pressure. The residue was adjusted to pH=9 by addition of saturated aqueous sodium bicarbonate and extracted with dichloromethane (2×50 mL). The combined organic layers were washed with water (50 mL), brine (50 mL), dried over sodium sulfate and concentrated under reduced pressure. The residue was purified by column chromatography (silica gel, 100-200 mesh, 0 to 30% ethyl acetate in petroleum ether) to afford 2-bromo-5-(2-fluorophenyl)-6,7-dihydro-5H-pyrrolo[1,2-b][1,2,4]triazol-7-ol (2.0 g, 43%) as a light yellow solid. LCMS R$_T$=0.505 min, m/z=298.1 [M+H]⁺.

LCMS (10 to 80% acetonitrile in water+0.03% trifluoacetic acid over 2.0 mins) retention time 0.505 min, ESI+ found [M+H]=298.1.

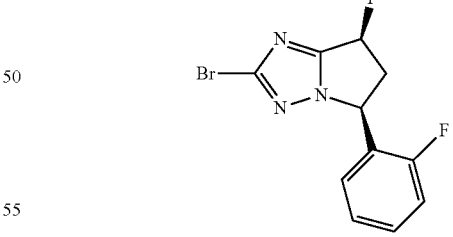

Step 6: (5S,7S)-2-bromo-7-fluoro-5-(2-fluorophenyl)-6,7-dihydro-5H-pyrrolo[1,2-b][1,2,4]triazole To a solution of 2-bromo-5-(2-fluorophenyl)-6,7-dihydro-5H-pyrrolo[1,2-b][1,2,4]triazol-7-ol (750 mg, 2.52 mmol) in toluene (20 mL) was added diethylaminosulfur trifluoride (1.62 g, 10.0 6 mmol) at 0° C. The reaction mixture was stirred at 0° C. for 1 h and then slowly added into ice water (20 mL) at 0° C. The mixture was extracted with dichloromethane (2×50 mL). The combined organic layers were washed with water (50 mL), brine (50 mL), dried over sodium sulfate and concentrated under reduced pressure. The residue was purified by column chromatography (silica gel, 100-200 mesh, 0 to 15% ethyl acetate in petroleum ether) to afford rac-(5S,7S)-2-bromo-7-fluoro-5-(2-fluorophenyl)-6,7-dihydro-5H-pyrrolo[1,2-b][1,2,4]triazole (250 mg, 33%) as a light yellow solid. $^1$H NMR (400 MHz, CDCl$_3$) δ 7.40-7.27 (q, J=6.6 Hz, 1H), 7.20-7.10 (m, 2H), 7.01-6.97 (m, 1H), 6.10-5.89 (m, 1H), 5.84-5.75 (m, 1H), 3.70-3.53 (m, 1H), 2.96-2.75 (m, 1H). LCMS R$_T$=1.112 min, m/z=300.0 [M+H]$^+$.

LCMS (10 to 80% acetonitrile in water+0.03% trifluoacetic acid over 2.0 mins) retention time 1.112 min, ESI+ found [M+H]=300.0.

This cis mixture was further separated by chiral SFC to afford arbitrarily assigned: (5S,7S)-2-bromo-7-fluoro-5-(2-fluorophenyl)-6,7-dihydro-5H-pyrrolo[1,2-b][1,2,4]triazole (Peak 2, retention time=3.408 min) (100 mg, 40%) as a white solid. (The 5R,7R-isomer was also collected (Peak 1, retention time=3.139 min) (100 mg, 40%)).

SFC condition: Column: ChiralPak AD-3 150×4.6 mm I.D., 3 μm mobile phase: A: CO2 B:ethanol (0.05% DEA) Gradient: from 5% to 40% of B in 5 min and hold 40% for 2.5 min, then 5% of B for 2.5 min Flow rate: 2.5 mL/min Column temp.: 35° C.

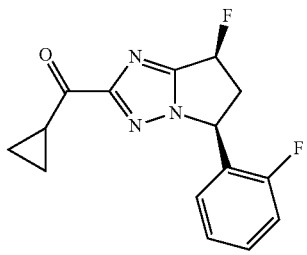 [SMILES: O=C(c1nc2n(n1)[C@H](c1ccccc1F)C[C@@H]2F)C1CC1]

Step 7: Cyclopropyl-[(5S,7S)-7-fluoro-5-(2-fluorophenyl)-6,7-dihydro-5H-pyrrolo[1,2-b][1,2,4]triazol-2-yl]methanone To a solution of (5S,7S)-2-bromo-7-fluoro-5-(2-fluorophenyl)-6,7-dihydro-5H-pyrrolo[1,2-b][1,2,4]triazole (100 mg, 0.33 mmol) and N-methoxy-N-methyl-cyclopropanecarboxamide (86 mg, 0.67 mmol) in tetrahydrofuran (10 mL) was added n-butyllithium (2.5 M in hexanes, 0.27 mL, 0.67 mmol) at −78° C. under nitrogen atmosphere. The mixture was stirred at −78° C. for 2 h and quenched by addition of saturated aqueous ammonium chloride (20 mL). The resulting mixture was extracted with ethyl acetate (3×15 mL). The combined organic layers were dried over sodium sulfate and concentrated under reduced pressure. The residue was purified by RP-HPLC (acetonitrile 35-65%/0.05% ammonium hydroxide in water) to afford arbitrarily assigned cyclopropyl-[(5S,7S)-7-fluoro-5-(2-fluorophenyl)-6,7-dihydro-5H-pyrrolo[1,2-b][1,2,4]triazol-2-yl]methanone (7.2 mg, 7%) as a yellow solid. $^1$H NMR (400 MHz, CD$_3$OD) δ 7.47-7.41 (m, 1H), 7.25-7.18 (m, 2H), 7.16-7.13 (m, 1H), 6.22-6.06 (m, 1H), 5.92-5.88 (m, 1H), 3.85-3.78 (m, 1H), 3.08-3.02 (m, 1H), 2.93-2.78 (m, 1H), 1.22-1.17 (m, 2H), 1.15-1.09 (m, 2H). LCMS R$_T$=1.043 min, m/z=290.2 [M+H]$^+$.

LCMS (10 to 80% acetonitrile in water+0.03% ammonium bicarbonate over 3.0 mins) retention time 1.043 min, ESI+ found [M+H]=290.2.

Method 45

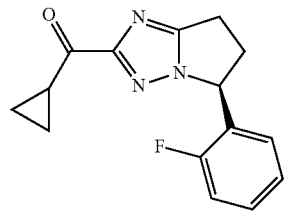

Example 63

(S)-cyclopropyl(5-(2-fluorophenyl)-6,7-dihydro-5H-pyrrolo[1,2-b][1,2,4]triazol-2-yl) methanone To a solution of ethyl (5S)-5-(2-fluorophenyl)-6,7-dihydro-5H-pyrrolo[1,2-b][1,2,4]triazole-2-carboxylate (100 mg, 0.36 mmol) in tetrahydrofuran (3 mL) was added cyclopropylmagnesium bromide (0.5 M in tetrahydrofuran, 0.72 mL, 0.36 mmol) dropwise under nitrogen atmosphere at −78° C. After addition, the mixture was stirred at −78° C. for 1 h and then quenched by addition of saturated aqueous ammonium chloride (10 mL). The resulting mixture was extracted with ethyl acetate (2×10 mL). The combined organic layers were dried over sodium sulfate and concentrated under reduced pressure. The residue was purified by RP-HPLC (acetonitrile 40-50%/0.05% ammonia hydroxide in water) to afford cyclopropyl-[(5S)-5-(2-fluorophenyl)-6,7-dihydro-5H-pyrrolo[1,2-b][1,2,4]triazol-2-yl]methanone (50 mg, 51%) as a white solid (80% ee). The product was further purified by chiral SFC to give arbitrarily assigned (S)-cyclopropyl(5-(2-fluorophenyl)-6,7-dihydro-5H-pyrrolo[1,2-b][1,2,4]triazol-2-yl)methanone (17.5 mg, 34%) as a brown oil. $^1$H NMR (400 MHz, CD$_3$OD) δ 7.44-7.35 (m, 1H), 7.23-7.16 (m, 3H), 5.81-5.77 (m, 1H), 3.37-3.29 (m, 1H), 3.21-3.03 (m, 2H), 2.99-2.93 (m, 1H), 2.77-2.65 (m, 1H), 1.16-1.09 (m, 2H), 1.09-1.00 (m, 2H). LC-MS R$_T$=0.699 min, m/z=272.1 [M+H]$^+$.

LCMS (5 to 95% acetonitrile in water+0.03% trifluoacetic acid over 1.5 mins) retention time 0.699 min, ESI+ found [M+H]=272.1.

SFC condition: Column: ChiralPak AD-3 150×4.6 mm I.D., 3 μm Mobile phase: A: CO$_2$ B: Ethanol (0.05% DEA) Gradient: from 5% to 40% of B in 5.5 min and hold 40% for 3 min, then 5% of B for 1.5 min Flow rate: 2.5 mL/min Column temp: 40° C.

Method 46

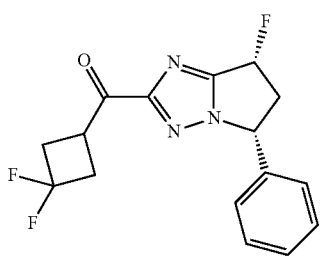

Example 64

(3,3-difluorocyclobutyl)((5R,7R)-7-fluoro-5-phenyl-6,7-dihydro-5H-pyrrolo[1,2-b][1,2,4]triazol-2-yl)methanone To a solution of 3,3-difluoro-N-methoxy-N-methyl-cyclobutanecarboxamide (76 mg, 0.43 mmol) and (5R,7R)-2-bromo-7-fluoro-5-phenyl-6,7-dihydro-5H-pyrrolo[1,2-b][1,2,4]triazole (60 mg, 0.21 mmol) in tetrahydrofuran (13 mL) was added n-butyllithium (2.5 M in hexanes, 0.26 mL, 0.64 mmol) dropwise at −78° C. After addition, the mixture was stirred at −78° C. for 2 h and quenched by addition of saturated aqueous ammonium chloride (25 mL). The mixture was extracted with ethyl acetate (3×25 mL). The combined organic layers were dried over sodium sulfate and concentrated under reduced pressure. The residue was purified by RP-HPLC (acetonitrile 20-45° o/0.225% hydrochloric acid in water) to give arbitrarily assigned (3,3-difluoro-cyclobutyl)-[(5R,7R)-7-fluoro-5-phenyl-6,7-dihydro-5H-pyrrolo[1,2-b][1,2,4]triazol-2-yl]methanone (11.0 mg, 16%) as a white solid. $^1$H NMR (400 MHz, CD$_3$OD) δ 7.43-7.38 (m, 3H), 7.29-7.27 (m, 2H), 6.19-6.17 (m, 0.5H), 6.05-6.03 (m, 0.5H), 5.64-5.63 (m, 1H), 3.94-3.93 (m, 1H), 3.79-3.75 (m, 1H), 2.90-2.82 (m, 5H). LCMS R$_T$=1.904 min, m/z=322.1 [M+H]$^+$.

LCMS (10 to 80% acetonitrile in water+0.1% ammonia water over 3.0 mins) retention time 1.904 min, ESI+ found [M+H]=322.1.

Method 47

Examples 66 and 67

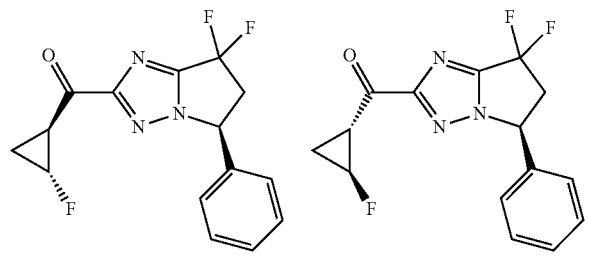

[(5S)-7,7-difluoro-5-phenyl-5,6-dihydropyrrolo[1,2-b][1,2,4]triazol-2-yl]-[(1S,2R)-2-fluorocyclopropyl]methanone & [(5S)-7,7-difluoro-5-phenyl-5,6-dihydropyrrolo [1,2-b][1,2,4]triazol-2-yl]-[(1R,2S)-2-fluorocyclopropyl]methanone

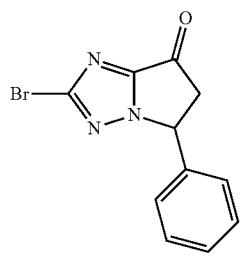 [SMILES: O=C1CC(c2ccccc2)n2nc(Br)nc21]

Step 1: 2-bromo-5-phenyl-5H-pyrrolo[1,2-b][1,2,4]triazol-7(6H)-one

To a solution of 2-bromo-5-phenyl-6,7-dihydro-5H-pyrrolo[1,2-b][1,2,4]triazol-7-ol (2.0 g, 7.14 mmol) in dichloromethane (100 mL) was added pyridinium chlorochromate (1.7 g, 7.85 mmol). The mixture was stirred at 20° C. for 18 h and then filtered. The filtrate was concentrated under reduced pressure and the residue was purified by column chromatography (silica gel, 100-200 mesh, 0 to 30% ethyl acetate in petroleum ether) to afford 2-bromo-5-phenyl-5,6-dihydropyrrolo[1,2-b][1,2,4]triazol-7-one (1.8 g, 88%) as a white solid. Used as is in the next step.

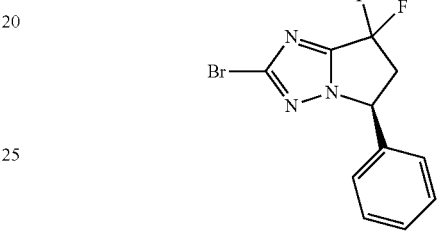

Step 2: (S)-2-bromo-7,7-difluoro-5-phenyl-6,7-dihydro-5H-pyrrolo[1,2-b][1,2,4]triazole To a cooled solution of 2-bromo-5-phenyl-5,6-dihydropyrrolo[1,2-b][1,2,4]triazol-7-one (1.7 g, 6.11 mmol) in dichloromethane (80 mL) was added diethylaminosulfur trifluoride (7.88 mL, 61.13 mmol) at 0° C. After stirred at 25° C. for 2 h, the mixture was poured into ice water (10 mL) and extracted with dichloromethane (2×100 mL). The combined organic layers were dried over sodium sulfate and concentrated under reduced pressure. The residue was purified by column chromatography (silica gel, 100-200 mesh, 0 to 30% ethyl acetate in petroleum ether) to afford racemic 2-bromo-7,7-difluoro-5-phenyl-5,6-dihydropyrrolo[1,2-b][1,2,4]triazole (1.5 g, 82%) as a pink solid. LC-MS R$_T$=0.774 min, m/z=303.1 [M+H]$^+$.

LCMS (5 to 95% acetonitrile in water+0.03% trifluoacetic acid over 1.5 mins) retention time 0.774 min, ESI+ found [M+H]=303.1.

The racemic material (950 mg, 3.17 mmol) was further separated by chiral SFC to give arbitrarily assigned:

(5R)-2-bromo-7,7-difluoro-5-phenyl-5,6-dihydropyrrolo [1,2-b][1,2,4]triazole (Peak 1, retention time=2.308 min) (410 mg, 43%) as a light brown solid.

(5S)-2-bromo-7,7-difluoro-5-phenyl-5,6-dihydropyrrolo [1,2-b][1,2,4]triazole (Peak 2, retention time=2.614 min) (440 mg, 46%) as a light brown solid.

SFC condition: Column: OJ (250 mm*50 mm, 10 um); Mobile phase: A: CO$_2$ B: 0.1% NH$_3$H$_2$O EtOH Gradient: from 20% to 20% of B; Flow rate: 180 mL/min, Column temperature:40° C.

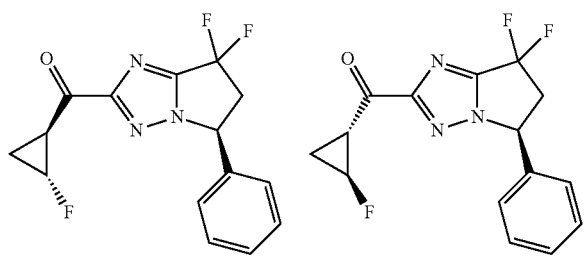

Step 3: [(5S)-7,7-difluoro-5-phenyl-5,6-dihydropyrrolo[1,2-b][1,2,4]triazol-2-yl]-[(1S,2R)-2-fluorocyclopropyl]methanone and [(5S)-7,7-difluoro-5-phenyl-5,6-dihydropyrrolo [1,2-b][1,2,4]triazol-2-yl]-[(1R,2S)-2-fluorocyclopropyl]methanone To a mixture of (5S)-2-bromo-7,7-difluoro-5-phenyl-5,6-dihydropyrrolo[1,2-b][1,2,4]triazole (200 mg, 0.67 mmol) and trans-2-fluoro-N-methoxy-N-methyl-cyclopropanecarboxamide (196 mg, 1.33 mmol) in tetrahydrofuran (10 mL) was added n-butyllithium (2.5 M in hexanes, 0.8 mL, 2.0 mmol) dropwise under nitrogen atmosphere at −78° C. After addition, the mixture was stirred at −78° C. for 1 h and then quenched by addition of saturated aqueous ammonium chloride (20 mL). The mixture was extracted with ethyl acetate (3×15 mL). The combined organic layers were concentrated to dryness under reduce pressure to give the crude product, which was purified by RP-HPLC (acetonitrile 45-75%/0.05% ammonia hydroxide in water) to afford the [(5S)-7,7-difluoro-5-phenyl-5,6-dihydropyrrolo[1,2-b][1,2,4]triazol-2-yl]-[trans-2-fluoro cyclopropyl]methanone (50 mg, 24%) as brown oil. This racemic material was separated by chiral SFC to give arbitrarily assigned:

[(5S)-7,7-difluoro-5-phenyl-5,6-dihydropyrrolo[1,2-b][1,2,4]triazol-2-yl]-[(1S,2R)-2-fluoro cyclopropyl]methanone (Peak 1, retention time=2.365 min) (15.1 mg, 30%) as a white solid. $^1$H NMR (400 MHz, CD$_3$OD) δ 7.49-7.44 (m, 3H), 7.33-7.30 (m, 2H), 5.99-5.92 (m, 1H), 5.02-5.00 (m, 0.5H), 4.86-4.82 (m, 0.5H), 3.89-3.86 (m, 1H), 3.51-3.47 (m, 1H), 3.34-3.33 (m, 0.5H), 3.32-3.22 (m, 0.5H), 1.78-1.70 (m, 1H), 1.63-1.57 (m, 1H). LC-MS R$_T$=0.822 min, m/z=308.0 [M+H]$^+$.

LCMS (5 to 95% acetonitrile in water+0.03% trifluoacetic acid over 1.5 mins) retention time 0.822 min, ESI+ found [M+H]=308.0.

[(5S)-7,7-difluoro-5-phenyl-5,6-dihydropyrrolo[1,2-b][1,2,4]triazol-2-yl]-[(1R,2S)-2-fluoro cyclopropyl]methanone (Peak 2, retention time=3.163 min) (13.6 mg, 27%) as a white solid. $^1$H NMR (400 MHz, CD$_3$OD) δ 7.47-7.43 (m, 3H), 7.31-7.29 (m, 2H), 5.98-5.94 (m, 1H), 5.05-4.99 (m, 0.5H), 4.86-4.83 (m, 0.5H), 3.91-3.86 (m, 1H), 3.47-3.45 (m, 1H), 3.34-3.26 (m, 1H), 1.74-1.68 (m, 1H), 1.62-1.56 (m, 1H). LC-MS R$_T$=0.818 min, m/z=308.1 [M+H]$^+$.

LCMS (5 to 95% acetonitrile in water+0.03% trifluoacetic acid over 1.5 mins) retention time 0.818 min, ESI+ found [M+H]=308.1.

SFC condition: Column: Column: AD (250 mm*30 mm, 5 μm); Mobile phase: A: CO$_2$ B:0.1% NH$_3$H$_2$O EtOH; Gradient: from 20% to 20% of B; Flow rate: 50 mL/min Column temperature:40° C.

Method 48

Example 68

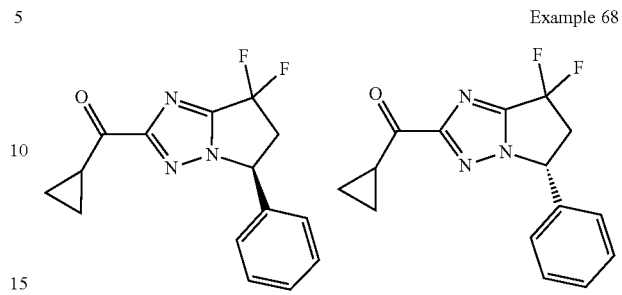

Cyclopropyl-[(5S)-7,7-difluoro-5-phenyl-5,6-dihydropyrrolo[1,2-b][1,2,4]triazol-2-yl]methanone and cyclopropyl-[(5R)-7,7-difluoro-5-phenyl-5,6-dihydropyrrolo[1,2-b][1,2,4]triazol-2-yl]methanone To a solution of 7,7-difluoro-N-methoxy-N-methyl-5-phenyl-5,6-dihydropyrrolo[1,2-b][1,2,4]triazole-2-carboxamide (100 mg, 0.32 mmol) in tetrahydrofuran (10 mL) was added cyclopropylmagnesium bromide (0.5 M in tetrahydrofuran, 2.6 mL, 1.3 mmol) at −78° C. under a nitrogen atmosphere. The mixture was stirred at −78° C. for 2 h and quenched by addition of saturated aqueous ammonium chloride (10 mL). The resulting mixture was extracted with ethyl acetate (3×10 mL). The combined organic layers were dried over sodium sulfate and concentrated under reduced pressure. The residue was purified by column chromatography (silica gel, 100-200 mesh, 0 to 30% ethyl acetate in petroleum ether) to afford cyclopropyl-(7,7-difluoro-5-phenyl-5,6-dihydropyrrolo[1,2-b][1,2,4]triazol-2-yl)methanone (60 mg, 64%) as a white solid. $^1$H NMR (400 MHz, CDCl$_3$) δ 7.38-7.31 (m, 3H), 7.16-7.11 (m, 2H), 5.66-5.60 (m, 1H), 3.73-3.61 (m, 1H), 3.23-3.11 (m, 1H), 3.00-2.96 (m, 1H), 1.31-1.19 (m, 2H), 1.11-0.96 (m, 2H).

This racemate was further separated by chiral SFC to give arbitrarily assigned:

cyclopropyl-[(5S)-7,7-difluoro-5-phenyl-5,6-dihydropyrrolo[1,2-b][1,2,4]triazol-2-yl]methanone (peak 2, retention time=2.971 min) (22.4 mg, 37%) as a white solid. $^1$H NMR (400 MHz, CDCl$_3$) δ 7.45-7.41 (m, 3H), 7.23-7.21 (m, 2H), 5.73-5.68 (m, 1H), 3.75-3.70 (m, 1H), 3.31-3.19 (m, 1H), 3.09-3.04 (m, 1H), 1.37-1.32 (m, 2H), 1.14-1.09 (m, 2H). LCMS R$_T$=1.238 min, m/z=290.2 [M+H]$^+$.

LCMS (10 to 80% acetonitrile in water+0.1% ammonia water over 3.0 mins) retention time 1.238 min, ESI+ found [M+H]=290.2.

cyclopropyl-[(5R)-7,7-difluoro-5-phenyl-5,6-dihydropyrrolo[1,2-b][1,2,4]triazol-2-yl]methanone (peak 1, retention time=2.677 min) (24.7 mg, 41%) as a white solid. $^1$H NMR (400 MHz, CDCl$_3$) δ 7.45-7.41 (m, 3H), 7.23-7.20 (m, 2H), 5.72-5.68 (m, 1H), 3.81-3.66 (m, 1H), 3.28-3.21 (m, 1H), 3.09-3.05 (m, 1H), 1.37-1.27 (m, 2H), 1.17-1.05 (m, 2H). LCMS R$_T$=1.239 min, m/z=290.2 [M+H]$^+$.

LCMS (10 to 80% acetonitrile in water+0.1% ammonia water over 3.0 mins) retention time 1.239 min, ESI+ found [M+H]=290.2.

SFC condition: Column: Chiralcel OJ(250 mm*30 mm, 5 μm) Mobile phase: A: CO$_2$ B:ethanol (0.1% NH$_3$H$_2$O) Gradient: from 25% to 25% of B in 5 min: 2.5 mL/min Column temp.: 35° C.

Method 49

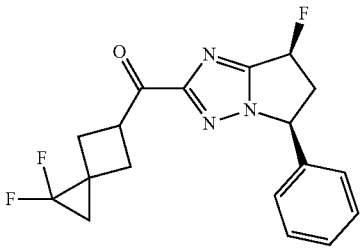

Example 70

(2,2-difluorospiro[2.3]hexan-5-yl)-[(5S,7S)-7-fluoro-5-phenyl-6,7-dihydro-5H-pyrrolo[1,2-b][1,2,4]triazol-2-yl]methanone

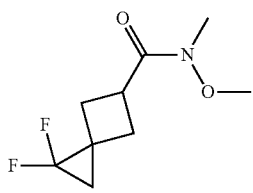

Step 1: 1,1-difluoro-N-methoxy-N-methylspiro[2.3]hexane-5-carboxamide

A mixture of 1-hydroxybenzotriazole (83 mg, 0.62 mmol), N,O-dimethylhydroxylamine hydrochloride (180 mg, 1.85 mmol), 2,2-difluorospiro[2.3]hexane-5-carboxylic acid (200 mg, 1.23 mmol), 1-(3-dimethylaminopropyl)-3-ethylcarbodiimidehydrochloride (284 mg, 1.48 mmol) and N,N-diisopropylethylamine (478 mg, 3.70 mmol) in dichloromethane (10 mL) was stirred at 25° C. for 12 h and diluted with water (30 mL). The mixture was extracted with ethyl acetate (3×15 mL). The combined organic layers were washed with brine (20 mL) and concentrated under reduced pressure. The residue was purified by column chromatography (silica gel, 100-200 mesh, 0 to 30% ethyl acetate in petroleum ether) to afford 2,2-difluoro-N-methoxy-N-methyl-spiro[2.3]hexane-5-carboxamide (130 mg, 51%) as a colorless oil. $^1$H NMR (400 MHz, CDCl$_3$) δ 3.67 (s, 3H), 3.65-3.51 (m, 1H), 3.21 (s, 3H), 2.78-2.68 (m, 1H), 2.57-2.47 (m, 1H), 2.48-2.37 (m, 1H), 2.28-2.17 (m, 1H), 1.32-1.13 (m, 2H).

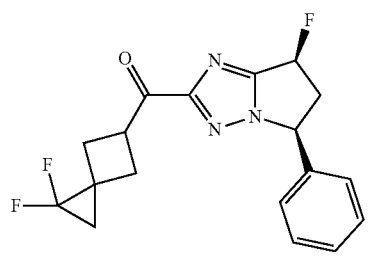 [SMILES: O=C(c1nc2n(n1)[C@H](c1ccccc1)C[C@@H]2F)C1CC2(C1)CC2(F)F]

Step 2: (2,2-difluorospiro[2.3]hexan-5-yl)-[(5S,7S)-7-fluoro-5-phenyl-6,7-dihydro-5H-pyrrolo[1,2-b][1,2,4]triazol-2-yl]methanone To a cooled (−78° C.) solution of (5S,7S)-2-bromo-7-fluoro-5-phenyl-6,7-dihydro-5H-pyrrolo[1,2-b][1,2,4]triazole (50 mg, 0.18 mmol) and 2,2-difluoro-N-methoxy-N-methyl-spiro[2.3]hexane-5-carboxamide (73 mg, 0.35 mmol) in tetrahydrofuran (10 mL) was added n-butyllithium (2.5 M in n-hexane, 0.28 mL, 0.71 mmol) under nitrogen atmosphere. The mixture was stirred at −78° C. for 2 h and quenched by addition of saturated aqueous ammonium chloride (10 mL). The resulting mixture was extracted with ethyl acetate (3×10 mL). The combined organic layers were dried over sodium sulfate and concentrated under reduced pressure. The residue was purified by RP-HPLC (acetonitrile 47-77%/0.2% formic acid in water) to afford (2,2-difluorospiro[2.3]hexan-5-yl)-[(5S,7S)-7-fluoro-5-phenyl-6,7-dihydro-5H-pyrrolo[1,2-b][1,2,4]triazol-2-yl]methanone (10.8 mg, 17%) as a white solid. $^1$H NMR (400 MHz, CD$_3$OD) δ 7.43-7.38 (m, 3H), 7.28-7.26 (m, 2H), 6.18-6.02 (m, 1H), 5.64-5.62 (m, 1H), 4.24-4.08 (m, 1H), 3.87-3.64 (m, 1H), 2.91-2.74 (m, 1H), 2.68-2.28 (m, 4H), 1.32-1.23 (m, 2H). LCMS R$_T$=1.281&1.298 min, m/z=348.1 [M+H]$^+$.

LCMS (5 to 95% acetonitrile in water+0.03% trifluoacetic acid over 1.5 mins) retention time 1.281&1.298 min, ESI+ found [M+H]=348.1

Method 50

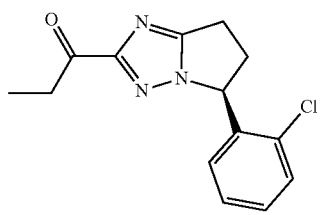

Example 71

1-[(5S)-5-(2-chlorophenyl)-6,7-dihydro-5H-pyrrolo[1,2-b][1,2,4]triazol-2-yl]propan-1-one

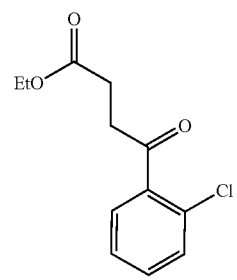 [SMILES: CCOC(=O)CCC(=O)c1ccccc1Cl]

Step 1: Ethyl 4-(2-chlorophenyl)-4-oxobutanoate

To a solution of 2-chloroacetophenone (100.0 g, 646.87 mmol), 1,3-dimethyl-3,4,5,6-tetrahydro-2(1h)-pyrimidinone (156.4 mL, 1293.70 mmol) in tetrahydrofuran (500 mL) was added [bis(trimethylsilyl)amino]lithium (1.0 M in tetrahydrofuran, 711.6 mL, 711.56 mmol) at −60° C. The mixture was stirred at −60° C. for 100 min and ethyl bromoacetate (143.5 mL, 1293.7 mmol) was added rapidly. The resulting mixture was allowed to warm to 25° C. and stirred for 15 h. The reaction was quenched by addition of water (400 mL) and extracted with ethyl acetate (3×1000 mL). The combined organic layers were washed with water (2×500 mL), brine (1500 mL), dried over sodium sulfate and concentrated under reduced pressure. The residue was purified by column chromatography (silica gel, 100-200 mesh, 0 to 10% ethyl acetate in petroleum ether) to give the ethyl 4-(2-chlorophenyl)-4-oxo-butanoate (50.0 g, 32%) as a colorless oil. Used as is in the next step.

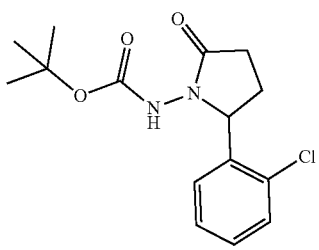 [SMILES: CC(C)(C)OC(=O)NN1C(=O)CCC1c1ccccc1Cl]

Step 2: Tert-Butyl (2-(2-chlorophenyl)-5-oxopyrrolidin-1-yl)carbamate

To a solution of ethyl 4-(2-chlorophenyl)-4-oxo-butanoate (10.0 g, 41.55 mmol) in acetic acid (33 mL) and tetrahydrofuran (100 mL) was added tert-butyl hydrazinecarboxylate (11.0 g, 83.10 mmol). The mixture was stirred 85° C. for 12 h and added sodium cyanoborohydride (7.8 g, 124.65 mmol). The resulting mixture was stirred at 85° C. for another 12 h and concentrated under reduced pressure. The residue was diluted with water (100 mL) and extracted with ethyl acetate (3×80 mL). The combined organic layers were washed with saturated sodium carbonate (80 mL), hydrochloric acid (2 M, 80 mL), dried over sodium sulfate and concentrated under reduced pressure. The residue was purified by column chromatography (silica gel, 100-200 mesh, 20 to 50% ethyl acetate in petroleum ether) to afford tert-butyl N-[2-(2-chlorophenyl)-5-oxo-pyrrolidin-1-yl]carbamate (5.0 g, 39%) as a light yellow oil. LCMS $R_T$=0.840 min, m/z=255.0 [M+H]$^+$.

LCMS (5 to 95% acetonitrile in water+0.03% trifluoacetic acid over 1.5 mins) retention time 0.840 min, ESI+ found [M-55]=255.0.

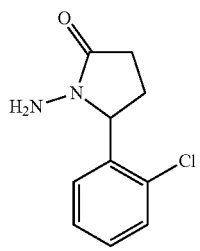 [SMILES: NN1C(=O)CCC1c1ccccc1Cl]

Step 3: 1-amino-5-(2-chlorophenyl)pyrrolidin-2-one

A solution of tert-butyl N-[2-(2-chlorophenyl)-5-oxo-pyrrolidin-1-yl]carbamate (5.0 g, 16.09 mmol) in hydrochloric acid (4.0 M in 1,4-dioxane, 40.2 mL, 160.89 mmol) was stirred at 25° C. for 12 h and filtered. The filtered cake was washed with ethyl acetate (20 mL) and dissolved in water (20 mL). The solution was adjusted to pH=9 by addition of saturated aqueous sodium bicarbonate and extracted with dichloromethane (4×50 mL). The combined organic layers were dried over sodium sulfate and concentrated under reduced pressure to afford crude 1-amino-5-(2-chlorophenyl)pyrrolidin-2-one (3.3 g, 97%) as a white solid. LCMS $R_T$=0.615 min, m/z=211.0 [M+H]$^+$.

LCMS (5 to 95% acetonitrile in water+0.03% trifluoacetic acid over 1.5 mins) retention time 0.615 min, ESI+ found [M+H]=211.0.

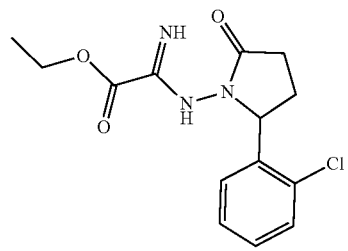 [SMILES: CCOC(=O)C(=N)NN1C(=O)CCC1c1ccccc1Cl]

Step 4: 1-amino-5-(2-chlorophenyl)pyrrolidin-2-one

A mixture of 1-amino-5-(2-chlorophenyl)pyrrolidin-2-one (3.3 g, 15.67 mmol) and ethyl 2-ethoxy-2-imino-acetate (4.6 g, 31.33 mmol) in ethanol (50 mL) was stirred at 70° C. for 18 h and concentrated under reduced pressure to give crude ethyl 2-[[2-(2-chlorophenyl)-5-oxo-pyrrolidin-1-yl]amino]-2-imino-acetate (4.8 g, 99%) as a brown oil. LCMS $R_T$=0.675 min, m/z=310.0 [M+H]$^+$.

LCMS (5 to 95% acetonitrile in water+0.03% trifluoacetic acid over 1.5 mins) retention time 0.675 min, ESI+ found [M+H]=310.0.

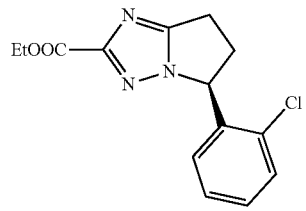 [SMILES: CCOC(=O)c1nc2n(n1)[C@H](c1ccccc1Cl)CC2]

Step 5: (S)-ethyl 5-(2-chlorophenyl)-6,7-dihydro-5H-pyrrolo[1,2-b][1,2,4]triazole-2-carboxylate A mixture of ethyl 2-[[2-(2-chlorophenyl)-5-oxo-pyrrolidin-1-yl]amino]-2-imino-acetate (4.8 g, 15.5 mmol) and phosphorus oxychloride (21.4 g, 139.5 mmol) was stirred at 100° C. for 3 h and cooled to 25° C. The mixture was carefully poured into water (100 mL) and extracted with ethyl acetate (3×50 ml). The combined organic layers were dried over sodium sulfate and concentrated. The residue was purified by column chromatography (silica gel, 100-200 mesh, 0 to 40% ethyl acetate in petroleum ether) to afford ethyl 5-(2-chlorophenyl)-6,7-dihydro-5H-pyrrolo[1,2-b][1,2,4]triazole-2-carboxylate (3.0 g, 66%) as a brown oil. LCMS $R_T$=0.741 min, m/z=292.1 [M+H]$^+$.

LCMS (5 to 95% acetonitrile in water+0.03% trifluoacetic acid over 1.5 mins) retention time 0.741 min, ESI+ found [M+H]=292.1.

The above racemic material (1.0 g, 3.43 mmol) was further separated by SFC to afford arbitrarily assigned:

(S)-ethyl 5-(2-chlorophenyl)-6,7-dihydro-5H-pyrrolo[1,2-b][1,2,4]triazole-2-carboxylate (peak 2, retention time=4.111 min) (400 mg, 40%) and (R)-ethyl 5-(2-chlorophenyl)-6,7-dihydro-5H-pyrrolo[1,2-b][1,2,4]triazole-2-carboxylate (peak 1, retention time=3.762 min) (400 mg, 40%), both as yellow solids.

SFC condition: Column: AD-3 (250 mm*30 mm, 5 μm); Condition: 0.1% NH$_3$H$_2$O EtOH; Begin B 30% End B 30%; Flow Rate (60 mL/min), Column temperature 40° C.

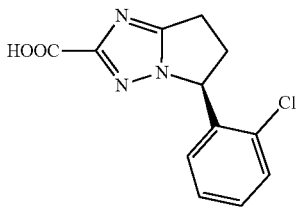 [SMILES: O=C(O)c1nc2n(n1)[C@H](c1ccccc1Cl)CC2]

Step 6: (S)-5-(2-chlorophenyl)-6,7-dihydro-5H-pyrrolo[1,2-b][1,2,4]triazole-2-carboxylic Acid A mixture of ethyl (S)-5-(2-chlorophenyl)-6,7-dihydro-5H-pyrrolo[1,2-b][1,2,4]triazole-2-carboxylate (400 mg, 1.37 mmol) and lithium hydroxide monohydrate (287 mg, 6.86 mmol) in ethanol (2 mL), water (2 mL) and tetrahydrofuran (2 mL) was stirred at 25° C. for 12 h and concentrated under reduced pressure. The residue was diluted with ice water (2 mL) and adjusted to pH=3 by addition of hydrochloric acid (2 M). The solid product was collected by filtration and washed with acetonitrile to afford crude (S)-5-(2-chlorophenyl)-6,7-dihydro-5H-pyrrolo[1,2-b][1,2,4]triazole-2-carboxylic acid (350 mg, 97%) as a white solid. LCMS R$_T$=0.642 min, m/z=264.0 [M+H]$^+$.

LCMS (5 to 95% acetonitrile in water+0.03% trifluoacetic acid over 1.5 mins) retention time 0.642 min, ESI+ found [M+H]=264.0.

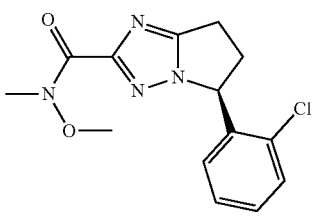 [SMILES: CON(C)C(=O)c1nc2n(n1)[C@H](c1ccccc1Cl)CC2]

Step 7: (S)-5-(2-chlorophenyl)-N-methoxy-N-methyl-6,7-dihydro-5H-pyrrolo[1,2-b][1,2,4]triazole-2-carboxamide A mixture of 1-hydroxybenzotriazole (215 mg, 1.59 mmol), N,O-dimethylhydroxylamine hydrochloride (194 mg, 1.99 mmol), (S)-5-(2-chlorophenyl)-6,7-dihydro-5H-pyrrolo[1,2-b][1,2,4]triazole-2-carboxylic acid (350 mg, 1.33 mmol), 1-(3-dimethylaminopropyl)-3-ethylcarbodiimide hydrochloride (305 mg, 1.59 mmol) and N,N-diisopropylethylamine (515 mg, 3.98 mmol) in dichloromethane (8 mL) was stirred at 25° C. for 12 h. The reaction was diluted with water (15 mL) and extracted with ethyl acetate (3×15 mL). The combined organic layers were washed with brine (2×25 mL), dried over sodium sulfate and concentrated under reduced pressure. The residue was purified by column chromatography (silica gel, 100-200 mesh, 10 to 35% ethyl acetate in petroleum ether) to afford (S)-5-(2-chlorophenyl)-N-methoxy-N-methyl-6,7-dihydro-5H-pyrrolo[1,2-b][1,2,4]triazole-2-carboxamide (300 mg, 74%) as a colorless oil. LCMS R$_T$=0.700 min, m/z=307.0 [M+H]$^+$.

LCMS (5 to 95% acetonitrile in water+0.03% trifluoacetic acid over 1.5 mins) retention time 0.700 min, ESI+ found [M+H]=307.0.

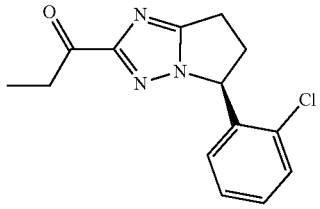 [SMILES: CCC(=O)c1nc2n(n1)[C@H](c1ccccc1Cl)CC2]

Step 8: 1-[(5S)-5-(2-chlorophenyl)-6,7-dihydro-5H-pyrrolo[1,2-b][1,2,4]triazol-2-yl]propan-1-one To a cooled (0° C.) solution of (S)-5-(2-chlorophenyl)-N-methoxy-N-methyl-6,7-dihydro-5H-pyrrolo[1,2-b][1,2,4]triazole-2-carboxamide (20 mg, 0.07 mmol) in tetrahydrofuran (5 mL) was added ethylmagnesium bromide (1.0 M in hexane, 0.42 mL, 0.42 mmol). The mixture was stirred at 0-5° C. for 1 h and quenched by addition of saturated aqueous ammonium chloride (5 mL). The mixture was extracted with ethyl acetate (2×20 mL). The combined organic layers were washed with brine (10 mL), dried over sodium sulfate and concentrated under reduced pressure. The residue was purified by RP-HPLC (acetonitrile 32-62%/0.2% formic acid in water) to afford 1-[(5S)-5-(2-chlorophenyl)-6,7-dihydro-5H-pyrrolo[1,2-b][1,2,4]triazol-2-yl]propan-1-one (5.7 mg, 31%) as a white solid. $^1$H NMR (400 MHz, CD$_3$OD) δ 7.52-7.50 (m, 1H), 7.38-7.33 (m, 2H), 6.96-6.94 (m, 1H), 5.99-5.96 (m, 1H), 3.40-3.33 (m, 1H), 3.14-3.11 (m, 2H), 3.07-3.03 (m, 2H), 2.68-2.65 (m, 1H), 1.18 (d, J=7.2 Hz, 3H). LCMS R$_T$=1.185 min, m/z=276.1 [M+H]$^+$.

LCMS (10 to 80% acetonitrile in water+0.03% trifluoacetic acid over 2 mins) retention time 1.185 min, ESI+ found [M+H]=276.1

Method 51

Example 72

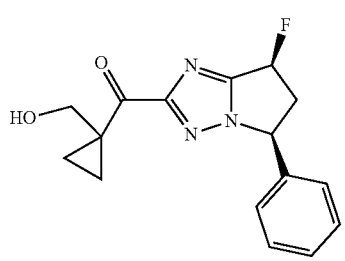

[1-(hydroxymethyl)cyclopropyl]-[(5S,7S)-7-fluoro-5-phenyl-6,7-dihydro-5H-pyrrolo[1,2-b][1,2,4]triazol-2-yl]methanone

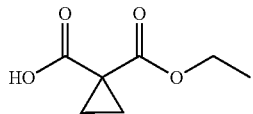

Step 1: 1-(ethoxycarbonyl)cyclopropanecarboxylic Acid

To a mixture of diethyl 1,1-cyclopropanedicarboxylate (10.0 g, 53.7 mmol) in ethanol (70 mL) and water (35 mL) was added sodium hydroxide (2.1 g, 53.7 mmol). The reaction was stirred at 25° C. for 16 h and diluted with ethyl acetate (60 mL). The organic layer was discarded. The aqueous phase was adjusted to pH=3 by addition of aqueous hydrochloric acid (4 M). The mixture was extracted with ethyl acetate (3×80 mL). The combined organic layers were washed with brine (30 mL), dried over sodium sulfate and concentrated under reduced pressure to give crude 1-ethoxycarbonylcyclopropanecarboxylic acid (6.6 g, 78%) as a colorless oil. $^1$H NMR (400 MHz, CDCl$_3$) δ 12.86 (br s, 1H), 4.31-4.17 (m, 2H), 1.87-1.81 (m, 2H), 1.77-1.69 (m, 2H), 1.32-1.24 (m, 3H).

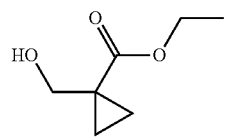

Step 2: Ethyl 1-(hydroxymethyl)cyclopropanecarboxylate

To a mixture of 1-ethoxycarbonylcyclopropanecarboxylic acid (6.6 g, 41.7 mmol) and triethylamine (6.98 mL, 50.1 mmol) in tetrahydrofuran (60 mL) was added isobutyl chloroformate (8.12 ml, 62.6 mmol) dropwise at 0° C. After addition, the reaction was stirred at 0° C. for 1 h and filtered. The filtrate was then added to a mixture of sodium borohydride (1.6 g, 41.7 mmol) in tetrahydrofuran (40 mL) and water (10 mL). The resulting mixture was stirred at 0° C. for 1 h and quenched by addition of 10% acetic acid (20 mL). The mixture was extracted with ethyl acetate (3×30 mL). The combined organic layers were washed with brine (30 mL), dried over anhydrous sodium sulfate and concentrated under reduced pressure. The residue was purified by column chromatography (silica gel, 100-200 mesh, 0 to 30% ethyl acetate in petroleum ether) to give ethyl 1-(hydroxymethyl)cyclopropanecarboxylate (3.8 g, 63%) as a colorless oil. $^1$H NMR (400 MHz, CDCl$_3$) δ 4.17-4.08 (m, 2H), 3.62 (s, 2H), 1.29-1.21 (m, 5H), 0.87-0.84 (m, 2H).

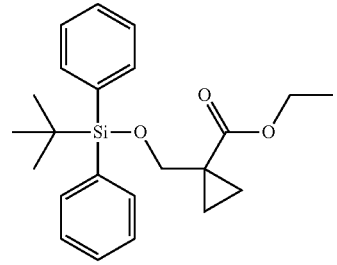 [SMILES: CCOC(=O)C1(CO[Si](c2ccccc2)(c2ccccc2)C(C)(C)C)CC1]

Step 3: Ethyl 1-(((tert-butyldiphenylsilyl)oxy)methyl)cyclopropanecarboxylate To stirred solution of ethyl 1-(hydroxymethyl)cyclopropane-1-carboxylate (1.0 g, 6.94 mmol) in N,N-dimethylformamide (20 mL) was added imidazole (1.4 g, 20.81 mmol) and tert-butyldiphenylchlorosilane (3.8 g, 13.87 mmol) at 0° C. The mixture was stirred at 25° C. for 18 h and poured into water (30 mL). The solution was extracted with dichloromethane (3×20 mL). The combined organic layers were dried over sodium sulfate and concentrated under reduced pressure. The residue was purified by column chromatography (silica gel, 100-200 mesh, 0 to 20% ethyl acetate in petroleum ether) to afford ethyl 1-[[tert-butyl(diphenyl)silyl]oxymethyl]cyclopropanecarboxylate (2.3 g, 87%) as a colorless oil. $^1$H NMR (400 MHz, CD$_3$OD) δ 7.70-7.61 (m, 4H), 7.46-7.35 (m, 6H), 4.15-4.06 (m, 2H), 3.85 (s, 2H), 1.23 (t, J=7.0 Hz, 3H), 1.17-1.11 (m, 2H), 1.04 (s, 9H), 0.93-0.87 (m, 2H).

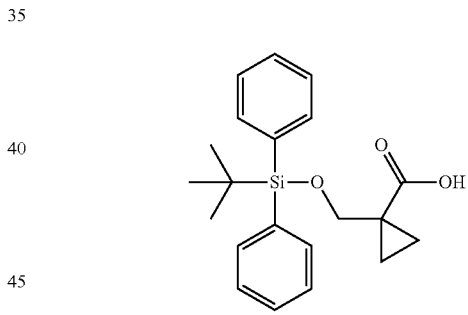

Step 4: 1-(((tert-butyldiphenylsilyl)oxy)methyl)cyclopropanecarboxylic Acid

A mixture of ethyl 1-[[tert-butyl(diphenyl)silyl]oxymethyl]cyclopropanecarboxylate (1.0 g, 2.61 mmol) and lithium hydroxide monohydrate (438 mg, 10.46 mmol) in tetrahydrofuran (16 mL), methyl alcohol (16 mL) and water (8 mL) was stirred at 25° C. for 18 h. The organic solvent was removed under reduced pressure. The aqueous residue was washed with ethyl acetate (15 mL) and adjusted to pH=3 by addition of aqueous hydrochloric acid (4 M) at 0° C. The resulting mixture was extracted with ethyl acetate (3×15 mL). The combined organic layers were washed with brine (10 mL), dried over sodium sulfate and concentrated under reduced pressure to give crude 1-[[tert-butyl(diphenyl)silyl]oxymethyl]cyclopropane carboxylic acid (950 mg, 100%) as a light stick white solid. This crude was used in next step without further purification.

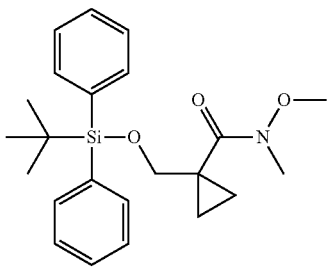 [SMILES: CON(C)C(=O)C1(CO[Si](c2ccccc2)(c2ccccc2)C(C)(C)C)CC1]

Step 5: 1-(((tert-butyldiphenylsilyl)oxy)methyl)-N-methoxy-N-methylcyclopropanecarboxamide A mixture of 1-[[tert-butyl(diphenyl)silyl]oxymethyl]cyclopropanecarboxylic acid (950 mg, 2.68 mmol), N,O-dimethylhydroxylamine hydrochloride (523 mg, 5.36 mmol), N,N-diisopropylethylamine (1.43 mL, 8.04 mmol), 1-hydroxybenzotriazole (217 mg, 1.61 mmol) and 1-(3-dimethylaminopropyl)-3-ethylcarbodiimidehydrochloride (771 mg, 4.02 mmol) in dichloromethane (20 mL) was stirred at 25° C. for 18 h. The resulting mixture was poured into water (20 mL) and extracted with dichloromethane (3×10 mL). The combined organic layers were dried over sodium sulfate and concentrated under reduced pressure. The residue was purified by preparative TLC (15% ethyl acetate in petroleum ether, $R_f$=0.4) to afford 1-[[tert-butyl(diphenyl)silyl]oxymethyl]-N-methoxy-N-methyl-cyclopropanecarboxamide (700 mg, 66%) as a colorless oil. $^1$H NMR (400 MHz, CDCl$_3$) δ 7.68-7.63 (m, 4H), 7.42-7.25 (m, 6H), 3.79 (s, 2H), 3.62 (s, 3H), 3.23 (s, 3H), 1.04-0.99 (m, 9H), 0.75-0.71 (m, 2H).

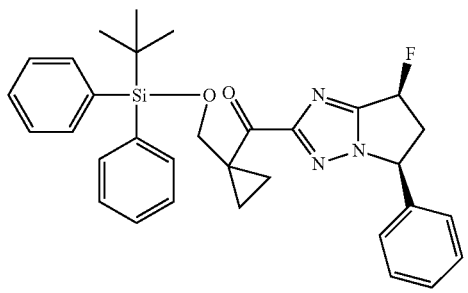 [SMILES: CC(C)(C)[Si](OCC1(C(=O)c2nc3n(n2)[C@H](c2ccccc2)C[C@@H]3F)CC1)(c1ccccc1)c1ccccc1]

Step 6: (1-(((tert-butyldiphenylsilyl)oxy)methyl)cyclopropyl)((5S,7S)-7-fluoro-5-phenyl-6,7-dihydro-5H-pyrrolo[1,2-b][1,2,4]triazol-2-yl)methanone To a mixture of (5S,7S)-2-bromo-7-fluoro-5-phenyl-6,7-dihydro-5H-pyrrolo[1,2-b][1,2,4]triazole (100 mg, 0.35 mmol) and 1-[[tert-butyl(diphenyl)silyl]oxymethyl]-N-methoxy-N-methyl-cyclopropanecarboxamide (282 mg, 0.71 mmol) in tetrahydrofuran (2 mL) was added n-butyllithium (2.5 M in hexanes, 0.43 mL, 1.06 mmol) dropwise under nitrogen atmosphere at −78° C. After addition, the mixture was stirred at −78° C. for 1 h and then quenched by addition of saturated aqueous ammonium chloride (10 mL). The mixture was extracted with ethyl acetate (2×10 mL). The combined organic layers were dried over sodium sulfate and concentrated under reduced pressure. The residue was purified by preparative TLC (50% ethyl acetate in petroleum ether, $R_f$=0.4) to afford [1-[[tert-butyl(diphenyl)silyl]oxymethyl]cyclopropyl]-[(5S,7S)-7-fluoro-5-phenyl-6,7-dihydro-5H-pyrrolo[1,2-b][1,2,4]triazol-2-yl]methanone (60 mg, 31%) as alight brown oil.

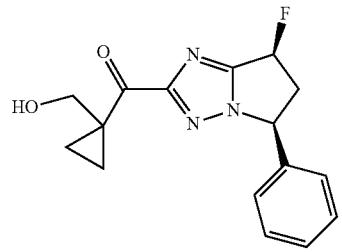 [SMILES: O=C(c1nc2n(n1)[C@H](c1ccccc1)C[C@@H]2F)C1(CO)CC1]

Step 7: [1-(hydroxymethyl)cyclopropyl]-[(5S,7S)-7-fluoro-5-phenyl-6,7-dihydro-5H-pyrrolo[1,2-b][1,2,4]triazol-2-yl]methanone To a solution of [1-[[tert-butyl(diphenyl)silyl]oxymethyl]cyclopropyl]-[(5S,7S)-7-fluoro-5-phenyl-6,7-dihydro-5H-pyrrolo[1,2-b][1,2,4]triazol-2-yl]methanone (60 mg, 0.11 mmol) in tetrahydrofuran (3 mL) was added tetrabutylammonium fluoride (1.0 M in tetrahydrofuran, 0.17 mL, 0.17 mmol). The mixture was stirred at 25° C. for 3 h and poured into water (10 mL). The resulting mixture was extracted with ethyl acetate (3×10 mL). The combined organic layers were washed with brine (30 mL), dried over sodium sulfate and concentrated under reduced pressure. The residue was purified by RP-HPLC (acetonitrile 25-55%/0.05% ammonia hydroxide in water) to afford arbitrarily assigned [1-(hydroxymethyl)cyclopropyl]-[(5S,7S)-7-fluoro-5-phenyl-6,7-dihydro-5H-pyrrolo[1,2-b][1,2,4]triazol-2-yl]methanone (7.8 mg, 18%) as a light brown oil. $^1$H NMR (400 MHz, CD$_3$OD) δ 7.44-7.38 (m, 3H), 7.30-7.26 (m, 2H), 6.19-6.16 (m, 0.5H), 6.05-6.02 (m, 0.5H), 5.65-5.61 (m, 1H), 3.97-3.85 (m, 2H), 3.84-3.68 (m, 1H), 2.87-2.80 (m, 1H), 1.72-1.67 (m, 2H), 1.11-1.08 (m, 2H). LC-MS $R_T$=0.695 min, m/z=302.1 [M+H]$^+$.

LCMS (5 to 95% acetonitrile in water+0.03% trifluoacetic acid over 1.5 mins) retention time 0.695 min, ESI+ found [M+H]=302.1.

Method 52

Example 73

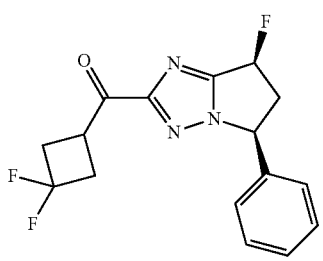

(3,3-difluorocyclobutyl)((5S,7S)-7-fluoro-5-phenyl-6,7-dihydro-5H-pyrrolo[1,2-b][1,2,4]triazol-2-yl)methanone

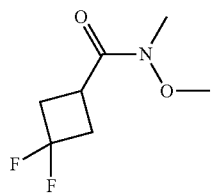

Step 1: 3,3-difluoro-N-methoxy-N-methylcyclobutanecarboxamide

A mixture of 1-hydroxybenzotriazole (297 mg, 2.20 mmol), 1-(3-dimethylaminopropyl)-3-ethylcarbodiimidehydrochloride (845 mg, 4.41 mmol), 3,3-difluorocyclobutanecarboxylic acid (500 mg, 3.67 mmol), N,O-dimethylhydroxylamine hydrochloride (537 mg, 5.51 mmol) and N,N-diisopropylethylamine (1187 mg, 9.18 mmol) in dichloromethane (8 mL) was stirred at 25° C. for 5 h and diluted with water (20 mL). The resulting mixture was extracted with ethyl acetate (3×20 mL). The combined organic layers were washed with water (2×20 mL), brine (20 mL), dried over sodium sulfate and concentrated under reduced pressure. The residue was purified by column chromatography (silica gel, 100-200 mesh, 0 to 30% ethyl acetate in petroleum ether) to give 3,3-difluoro-N-methoxy-N-methyl-cyclobutanecarboxamide (430 mg, 65%) as a colorless oil. $^1$H NMR (400 MHz, CDCl$_3$) δ 3.67 (s, 3H), 3.33-3.22 (m, 1H), 3.20 (s, 3H), 2.93-2.78 (m, 2H), 2.76-2.64 (m, 2H).

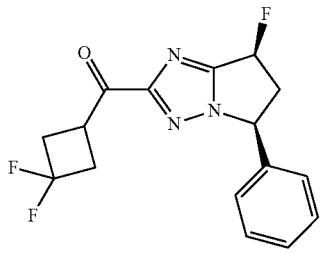 [SMILES: O=C(c1nc2n(n1)[C@H](c1ccccc1)C[C@@H]2F)C1CC(F)(F)C1]

Step 2: (3,3-difluorocyclobutyl)((5S,7S)-7-fluoro-5-phenyl-6,7-dihydro-5H-pyrrolo[1,2-b][1,2,4]triazol-2-yl)methanone To a solution of 3,3-difluoro-N-methoxy-N-methyl-cyclobutanecarboxamide (76 mg, 0.43 mmol) and (5S,7S)-2-bromo-7-fluoro-5-phenyl-6,7-dihydro-5H-pyrrolo[1,2-b][1,2,4]triazole (60 mg, 0.21 mmol) in tetrahydrofuran (13 mL) was added n-butyllithium (2.5 M in hexanes, 0.26 mL, 0.64 mmol) dropwise at −78° C. After addition, the mixture was stirred at −78° C. for 2 h and quenched by addition of saturated aqueous ammonium chloride (25 mL). The mixture was extracted with ethyl acetate (3×25 mL). The combined organic layers were dried over sodium sulfate and concentrated under reduced pressure. The residue was purified by RP-HPLC (acetonitrile 20-45°/0.225% hydrochloric acid in water) to give arbitrarily assigned (3,3-difluorocyclobutyl)-[(5S,7S)-7-fluoro-5-phenyl-6,7-dihydro-5H-pyrrolo[1,2-b][1,2,4]triazol-2-yl]methanone (12.4 mg, 18%) as a white solid. $^1$H NMR (400 MHz, CD$_3$OD) δ 7.44-7.39 (m, 3H), 7.30-7.28 (m, 2H), 6.20-6.17 (m, 0.5H), 6.06-6.03 (m, 0.5H), 5.66-5.64 (m, 1H), 3.97-3.80 (m, 1H), 3.78-3.74 (m, 1H), 2.91-2.83 (m, 5H). LCMS R$_T$=1.241 min, m/z=322.2 [M+H]$^+$.

LCMS (10 to 80% acetonitrile in water+0.03% trifluoacetic acid over 2 mins) retention time 1.241 min, ESI+ found [M+H]=322.2.

Method 53

Example 74

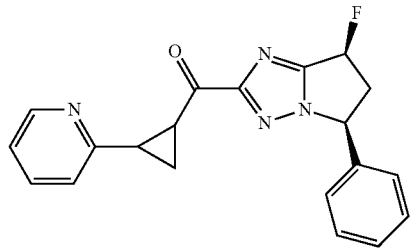

((5S,7S)-7-fluoro-5-phenyl-6,7-dihydro-5H-pyrrolo[1,2-b][1,2,4]triazol-2-yl)(2-(pyridin-2-yl)cyclopropyl)methanone

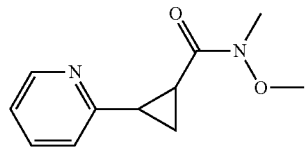

Step 1: N-methoxy-N-methyl-2-(pyridin-2-yl)cyclopropanecarboxamide

A mixture of 1-hydroxybenzotriazole (149 mg, 1.10 mmol), 1-(3-dimethylaminopropyl)-3-ethylcarbodiimidehydrochloride (423 mg, 2.21 mmol), 2-(pyridin-2-yl)cyclopropanecarboxylic acid (300 mg, 1.84 mmol), N,O-dimethylhydroxylamine hydrochloride (269 mg, 2.76 mmol) and N,N-diisopropylethylamine (594 mg, 4.60 mmol) in dichloromethane (10 mL) was stirred at 25° C. for 16 h and diluted with water (20 mL). The resulting mixture was extracted with ethyl acetate (3×20 mL). The combined organic layers were washed with water (20 mL), brine (20 mL) and concentrated under reduced pressure. The residue was purified by column chromatography (silica gel, 100-200 mesh, 0 to 30% ethyl acetate in petroleum ether) to give N-methoxy-N-methyl-2-(pyridin-2-yl)cyclopropanecarboxamide (300 mg, 79%) as a colorless oil. $^1$H NMR (400 MHz, CDCl$_3$) δ 8.47-8.43 (m, 1H), 7.57-7.51 (m, 1H), 7.27-7.22 (m, 1H), 7.10-7.02 (m, 1H), 3.68 (s, 3H), 3.21 (s, 3H), 2.76 (s, 1H), 2.61-2.52 (m, 1H), 1.63-1.55 (m, 2H).

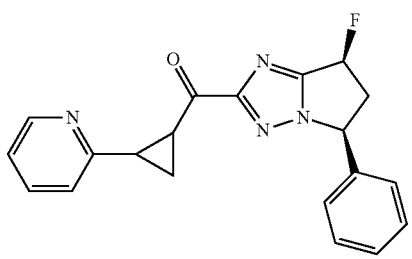 [SMILES: O=C(c1nc2n(n1)[C@H](c1ccccc1)C[C@@H]2F)C1CC1c1ccccn1]

Step 2: ((5S,7S)-7-fluoro-5-phenyl-6,7-dihydro-5H-pyrrolo[1,2-b][1,2,4]triazol-2-yl)(2-(pyridin-2-yl)cyclopropyl)methanone To a cooled (−78° C.) solution of (5S,7S)-2-bromo-7-fluoro-5-phenyl-6,7-dihydro-5H-pyrrolo[1,2-b][1,2,4]triazole (150 mg, 0.53 mmol) and N-methoxy-N-methyl-2-(2-pyridyl)cyclopropanecarboxamide (219 mg, 1.06 mmol) in 2-Methyltetrahydrofuran (3 mL) was added n-butyllithium (2.5 M in n-hexane, 0.64 mL, 1.6 mmol) under nitrogen atmosphere. The mixture was stirred at −78° C. for about 30 min and quenched by addition of saturated ammonium chloride solution (20 mL). The mixture was extracted with ethyl acetate (3×15 mL). The combined organic layers were concentrated under reduce pressure. The residue was purified by RP-HPLC (acetonitrile 32-62%/0.05% ammonia hydroxide in water) to give arbitrarily assigned [(5S,7S)-7-fluoro-5-phenyl-6,7-dihydro-5H-pyrrolo[1,2-b][1,2,4]triazol-2-yl]-[2-(2-pyridyl)cyclopropyl]methanone (11.0 mg, 6%) as a faint pink solid. $^1$H NMR (400 MHz, CD$_3$OD) δ 8.39-8.37 (m, 1H), 7.69-7.65 (m, 1H), 7.42-7.31 (m, 4H), 7.27-7.17 (m, 3H), 6.18-6.02 (m, 1H), 5.65-5.61 (m, 1H), 3.83-3.67 (m, 1H), 3.56-3.51 (m, 1H), 2.88-2.73 (m, 2H), 1.86-1.79 (m, 2H). LCMS R$_T$=0.745 min, m/z=348.9 [M+H]$^+$.

LCMS (10 to 80% acetonitrile in water+0.1% ammonia water over 3.0 mins) retention time 0.745 min, ESI+ found [M+H]=348.9.

Method 54

Example 75

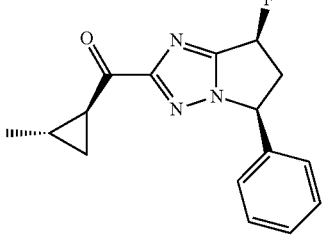

[(5S,7S)-7-fluoro-5-phenyl-6,7-dihydro-5H-pyrrolo[1,2-b][1,2,4]triazol-2-yl]-[rac-(1S,2S)-2-methylcyclopropyl]methanone To a solution of trans-N-methoxy-N,2-dimethyl-cyclopropanecarboxamide (137 mg, 0.96 mmol), (5S,7S)-2-bromo-7-fluoro-5-phenyl-6,7-dihydro-5H-pyrrolo[1,2-b][1,2,4]triazole (180 mg, 0.64 mmol) in tetrahydrofuran (5 mL) was added isopropylmagnesium bromide (3.0 M in tetrahydrofuran, 0.85 mL, 2.55 mmol) dropwise under nitrogen atmosphere at 0° C. After addition, the mixture was stirred at 0° C. for 1 h and quenched by addition of saturated aqueous ammonium chloride (20 mL). The resulting solution was extracted with ethyl acetate (2×15 mL). The combined organic layers were dried over sodium sulfate and concentrated under reduced pressure. The residue was purified by preparative TLC (30% ethyl acetate in petroleum ether, R$_f$=0.2) to afford arbitrarily assigned [(5S,7S)-7-fluoro-5-phenyl-6,7-dihydro-5H-pyrrolo[1,2-b][1,2,4]triazol-2-yl]-[rac-(1S,2S)-2-methylcyclopropyl]methanone (trans mixture methylcyclopropyl mixture) (80 mg, 44%) as a white solid. $^1$H NMR (400 MHz, CD$_3$OD) δ 7.42-7.37 (m, 3H), 7.28-7.26 (m, 2H), 6.20-6.16 (m, 0.5H), 6.05-6.02 (m, 0.5H), 5.65-5.63 (m, 1H), 3.78-3.68 (m, 1H), 2.83-2.75 (m, 2H), 1.59-1.52 (m, 1H), 1.45-1.37 (m, 1H), 1.19-1.14 (m, 3H), 1.01-0.91 (m, 1H). LC-MS R$_T$=0.793 min, m/z=286.1 [M+H]$^+$.

LCMS (5 to 95% acetonitrile in water+0.03% trifluoacetic acid over 1.5 mins) retention time 0.793 min, ESI+ found [M+H]=286.1.

Method 55

Example 76

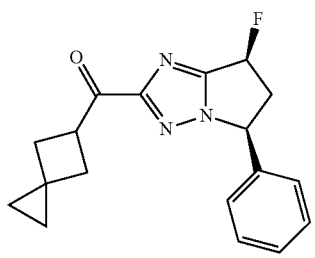

[(5S,7S)-7-fluoro-5-phenyl-6,7-dihydro-5H-pyrrolo[1,2-b][1,2,4]triazol-2-yl]-spiro[2.3]hexan-5-yl-methanone

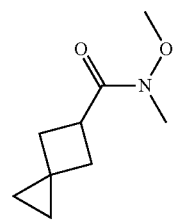

Step 1: N-methoxy-N-methyl-spiro[2.3]hexane-5-carboxamide

A mixture of spiro[2.3]hexane-5-carboxylic acid (150 mg, 1.19 mmol), N,N-diisopropylethylamine (0.5 mL, 2.97 mmol), 1-hydroxybenzotriazole (96.4 mg, 0.71 mmol) and N,O-dimethylhydroxylamine hydrochloride (174 mg, 1.78 mmol) in dichloromethane (10 mL) was stirred at 25° C. for 16 h and diluted with water (30 mL). The mixture was extracted with ethyl acetate (3×15 mL). The combined organic layers were washed with water (2×10 mL), brine (20 mL) and concentrated under reduced pressure. The residue was purified by column chromatography (silica gel, 100-200 mesh, 0 to 20% ethyl acetate in petroleum ether) to give N-methoxy-N-methyl-spiro[2.3]hexane-5-carboxamide (170 mg, 84%) as a colorless oil. ¹H NMR (400 MHz, CDCl₃) δ 3.66 (s, 3H), 3.20 (s, 3H), 2.60-2.54 (m, 2H), 2.17-2.12 (m, 2H), 0.50-0.40 (m, 4H).

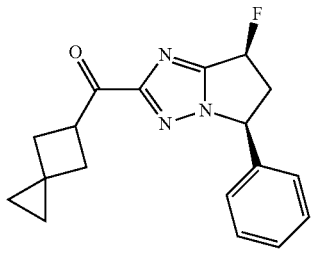 [SMILES: O=C(c1nc2n(n1)[C@H](c1ccccc1)C[C@@H]2F)C1CC2(CC2)C1]

Step 2: [(5S,7S)-7-fluoro-5-phenyl-6,7-dihydro-5H-pyrrolo[1,2-b][1,2,4]triazol-2-yl]-spiro[2.3]hexan-5-yl-methanone To a solution of N-methoxy-N-methyl-spiro[2.3]hexane-5-carboxamide (43 mg, 0.25 mmol), (5S,7S)-2-bromo-7-fluoro-5-phenyl-6,7-dihydro-5H-pyrrolo[1,2-b][1,2,4]triazole (50 mg, 0.18 mmol) in tetrahydrofuran (2 mL) was added isopropylmagnesium chloride (2.0 M in tetrahydrofuran, 0.21 mL, 0.42 mmol) dropwise at 0° C. The mixture was stirred at 0° C. for 1 h and quenched by addition of saturated aqueous ammonium chloride (5 mL). The solution was then extracted with ethyl acetate (3×20 mL). The combined organic layers were dried over sodium sulfate and concentrated under reduced pressure. The residue was purified by RP-HPLC (water (0.05% ammonia hydroxide v/v)-acetonitrile 45-70%) to afford arbitrarily assigned [(5S,7S)-7-fluoro-5-phenyl-6,7-dihydro-5H-pyrrolo[1,2-b][1,2,4]triazol-2-yl]-spiro[2.3]hexan-5-yl-methanone (42 mg, 75%) as a white solid. ¹H NMR (400 MHz, CDCl₃) δ 7.42-7.37 (m, 3H), 7.27-7.23 (m, 2H), 6.10-5.94 (m, 1H), 5.50-5.47 (m, 1H), 4.32-4.26 (m, 1H), 3.67-3.60 (m, 1H), 3.01-2.70 (m, 1H), 2.65-2.57 (m, 2H), 2.31-2.26 (m, 2H), 0.51-0.47 (m, 2H), 0.43-0.40 (m, 2H). LC-MS R$_T$=0.904 min, m/z=312.0 [M+H]⁺.

LCMS (5 to 95% acetonitrile in water+0.03% trifluoacetic acid over 1.5 mins) retention time 0.904 min, ESI+ found [M+H]=312.0.

Method 56 PGP-6-1

Example 77

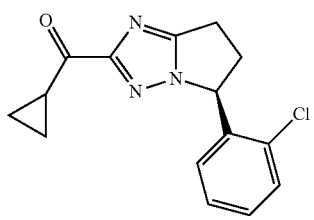

Cyclopropyl-[(5S)-5-(2-chlorophenyl)-6,7-dihydro-5H-pyrrolo[1,2-b][1,2,4]triazol-2-yl]methanone To a cooled (−78° C.) solution of (5S)-5-(2-chlorophenyl)-N-methoxy-N-methyl-6,7-dihydro-5H-pyrrolo[1,2-b][1,2,4]triazole-2-carboxamide (100 mg, 0.33 mmol) in tetrahydrofuran (10 mL) was added cyclopropylmagnesium bromide (0.5 M in tetrahydrofuran, 4.24 mL, 2.12 mmol) under nitrogen atmosphere. The mixture was stirred at −78° C. for 1 h and quenched by addition of saturated aqueous ammonium chloride (10 mL). The resulting mixture was extracted with ethyl acetate (2×10 mL). The combined organic layers were dried over sodium sulfate and concentrated under reduced pressure. The residue was purified by RP-HPLC (acetonitrile 38-68%/0.2% formic acid in water) to afford arbitrarily assigned cyclopropyl-[(5S)-5-(2-chlorophenyl)-6,7-dihydro-5H-pyrrolo[1,2-b][1,2,4]triazol-2-yl]methanone (23.5 mg, 25%) as colorless oil. ¹HNMR (400 MHz, CD₃OD) δ7.51 (d, J=1.6 Hz, 1H), 7.49-7.33 (m, 2H), 6.96 (d, J=7.6 Hz, 1H), 6.00-5.96 (m, 1H), 3.45-3.36 (m, 1H), 3.15-3.10 (m, 2H), 3.05-2.98 (m, 1H), 2.70-2.60 (m, 1H), 1.20-1.15 (m, 2H), 1.11-1.07 (m, 2H). LCMS R$_T$=1.187 min, m/z=288.1 [M+H]⁺.

LCMS (10 to 80% acetonitrile in water+0.03% trifluoacetic acid over 2 mins) retention time 1.187 min, ESI+ found [M+H]=288.1

Method 57

Example 78

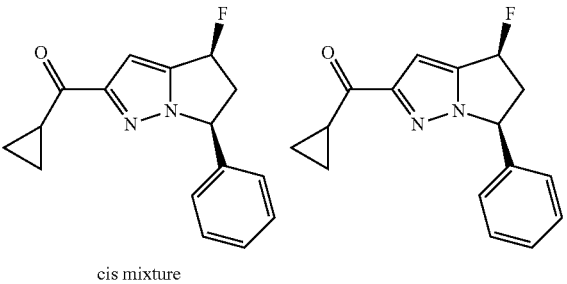

cis mixture

Cyclopropyl-[rac-(4S,6S)-4-fluoro-6-phenyl-5,6-dihydro-4H-pyrrolo[1,2-b]pyrazol-2-yl]methanone and cyclopropyl-[(4S,6S)-4-fluoro-6-phenyl-5,6-dihydro-4H-pyrrolo[1,2-b]pyrazol-2-yl]methanone

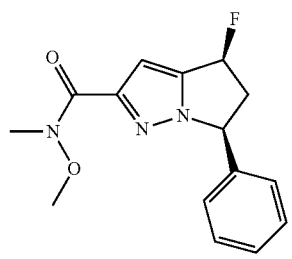

cis mixture

Step 1: rac-(4S,6S)-4-fluoro-N-methoxy-N-methyl-6-phenyl-5,6-dihydro-4H-pyrrolo[1,2-b]pyrazole-2-carboxamide A mixture of rac-(4S,6S)-4-fluoro-6-phenyl-5,6-dihydro-4H-pyrrolo[1,2-b]pyrazole-2-carboxylic acid (800 mg, 3.25 mmol), N,O-dimethylhydroxylamine hydrochloride (412 mg, 4.22 mmol), N,N-diisopropylethylamine (1.34 mL, 8.12 mmol) and 2-(3H-[1,2,3]triazolo[4,5-b]pyridin-3-yl)-1,1,3,3-tetramethylisouronium hexafluorophosphate(V) (1.6 g, 4.22 mmol) in N,N-dimethylformamide (20 mL) was stirred at 25° C. for 3 h. The mixture was diluted with water (30 mL) and extracted with ethyl acetate (3×20 mL). The combined organic layers were washed with brine (10 mL), dried over sodium sulfate and concentrated under reduce pressure. The residue was purified by column chromatography (silica gel, 100-200 mesh, 0 to 50% ethyl acetate in petroleum ether) to afford rac-(4S,6S)-4-fluoro-N-methoxy-N-methyl-6-phenyl-5,6-dihydro-4H-pyrrolo[1,2-b]pyrazole-2-carboxamide (800 mg, 85%) as a white solid. LCMS RT=0.707 min, m/z=290.1 [M+H]$^+$.

LCMS (5 to 95% acetonitrile in water+0.03% trifluoacetic acid over 1.5 mins) retention time 0.707 min, ESI+ found [M+H]=290.1.

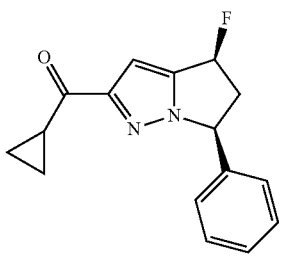 [SMILES: O=C(c1cc2n(n1)[C@H](c1ccccc1)C[C@@H]2F)C1CC1]

cis mixture

Step 2: Cyclopropyl-[rac-(4S,6S)-4-fluoro-6-phenyl-5,6-dihydro-4H-pyrrolo[1,2-b]pyrazol-2-yl]methanone To a cooled (0° C.) solution of rac-(4S,6S)-4-fluoro-N-methoxy-N-methyl-6-phenyl-5,6-dihydro-4H-pyrrolo[1,2-b]pyrazole-2-carboxamide (40 mg, 2.77 mmol) was added cyclopropylmagnesium bromide (0.5 M in tetrahydrofuran, 1.5 mL, 0.75 mmol) under nitrogen atmosphere. The mixture was stirred at 0° C. for 1 h and quenched by addition of saturated aqueous ammonium chloride (5 mL). The mixture was extracted with ethyl acetate (2×15 mL). The combined organic layers were washed with brine (20 mL), dried over sodium sulfate and concentrated under reduce pressure. The residue was purified by column chromatography (silica gel, 100-200 mesh, 0 to 30% ethyl acetate in petroleum ether) to afford arbitrarily assigned cyclopropyl-[rac-(4S,6S)-4-fluoro-6-phenyl-5,6-dihydro-4H-pyrrolo[1,2-b]pyrazol-2-yl]methanone (28.6 mg, 75%) as a white solid. $^1$H NMR (400 MHz, CDCl$_3$) δ 7.41-7.36 (m, 3H), 7.27-6.90 (m, 2H), 6.93 (s, 1H), 6.09-5.92 (m, 1H), 5.53-5.49 (m, 1H), 3.58-3.47 (m, 1H), 2.97-2.79 (m, 2H), 1.22-1.19 (m, 2H), 0.99-0.96 (m, 2H). LCMS R$_T$=0.870 min, m/z=270.9 [M+H]$^+$.

LCMS (5 to 95% acetonitrile in water+0.03% trifluoroacetic acid over 1.5 mins) retention time 0.870 min, ESI+ found [M+H]=270.9.

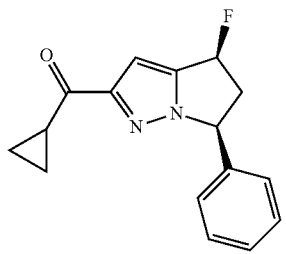

Step 3: Cyclopropyl-[(4S,6S)-4-fluoro-6-phenyl-5,6-dihydro-4H-pyrrolo[1,2-b]pyrazol-2-yl]methanone (G03280299)

The cyclopropyl-[rac-(4S,6S)-4-fluoro-6-phenyl-5,6-dihydro-4H-pyrrolo[1,2-b]pyrazol-2-yl]methanone (600 mg, 2.22 mmol, from another scale up batch) was further separated by chiral SFC to afford arbitrarily assigned: cyclopropyl-[(4S,6S)-4-fluoro-6-phenyl-5,6-dihydro-4H-pyrrolo[1,2-b]pyrazol-2-yl]methanone (peak 1, retention time=3.306 min) (250 mg, 41.7%) as a white solid. $^1$H NMR (400 MHz, CDCl$_3$) δ 7.39-7.37 (m, 3H), 7.23-7.21 (m, 2H), 6.93 (d, J=2.8 Hz, 1H), 6.09-6.07 (m, 0.5H), 5.95-5.93 (m, 0.5H), 5.51-5.49 (m, 1H), 3.54-3.45 (m, 1H), 2.96-2.92 (m, 1H), 2.85-2.82 (m, 1H), 1.23-1.20 (m, 2H), 0.99-0.96 (m, 2H). LCMS R$_T$=0.883 min, m/z=271.0 [M+H]$^+$.

LCMS (5 to 95% acetonitrile in water+0.03% trifluoacetic acid over 1.5 mins) retention time 0.883 min, ESI+ found [M+H]=271.0.

SFC condition: Column: OD-H (250 mm*30 mm, 5 μm); Condition: 0.1% NH$_3$H$_2$O EtOH; Begin B 30% End B 30%; Flow Rate (60 mL/min), Column temperature 40° C.

Method 58

Example 79

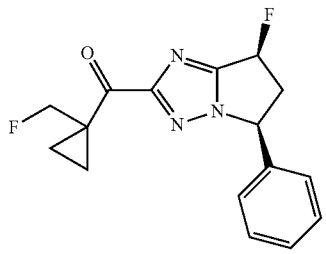

[1-(fluoromethyl)cyclopropyl]-[(5S,7S)-7-fluoro-5-phenyl-6,7-dihydro-5H-pyrrolo[1,2-b][1,2,4]triazol-2-yl]methanone

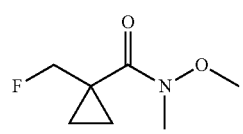

149

Step 1: 1-(fluoromethyl)-N-methoxy-N-methyl-cyclopropanecarboxamide

A mixture of 1-(fluoromethyl)cyclopropanecarboxylic acid (543 mg, 4.60 mmol), 1-(3-dimethylaminopropyl)-3-ethylcarbodiimidehydrochloride (1057 mg, 5.52 mmol), 1-hydroxybenzotriazole (372 mg, 2.76 mmol), N,O-dimethylhydroxylamine hydrochloride (897 mg, 9.19 mmol) and N,N-diisopropylethylamine (594 mg, 4.60 mmol) in dichloromethane (15 mL) was stirred at 30° C. for 18 h and quenched by addition of water (10 mL). The separated organic layer was washed with brine (30 mL), dried over sodium sulfate and concentrated under reduced pressure. The residue was purified by column chromatography (silica gel, 100-200 mesh, 0 to 50% ethyl acetate in petroleum ether) to afford 1-(fluoromethyl)-N-methoxy-N-methyl-cyclopropanecarboxamide (135 mg, 18%) as a brown oil. $^1$H NMR (400 MHz, CDCl$_3$) δ 4.63-4.47 (m, 2H), 3.74 (s, 3H), 3.26 (s, 3H), 1.30-1.23 (m, 2H), 0.95-0.85 (m, 2H).

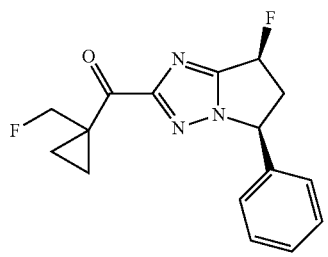 [SMILES: O=C(c1nc2n(n1)[C@H](c1ccccc1)C[C@@H]2F)C1(CF)CC1]

Step 2: [1-(fluoromethyl)cyclopropyl]-[(5S,7S)-7-fluoro-5-phenyl-6,7-dihydro-5H-pyrrolo [1,2-b][1,2,4]triazol-2-yl]methanone To a solution of 1-(fluoromethyl)-N-methoxy-N-methyl-cyclopropanecarboxamide (80 mg, 0.50 mmol) and (5S,7S)-2-bromo-7-fluoro-5-phenyl-6,7-dihydro-5H-pyrrolo[1,2-b][1,2,4]triazole (70 mg, 0.25 mmol) in tetrahydrofuran (5 mL) was added n-butyllithium (2.5 M in hexanes, 0.3 mL, 0.75 mmol) dropwise at −78° C. After addition, the mixture was stirred at −78° C. for 1 h and then quenched by addition of saturated aqueous ammonium chloride (20 mL). The mixture was extracted with ethyl acetate (3×15 mL). The combined organic layers were concentrated under reduced pressure. The residue was purified by preparative TLC (50% ethyl acetate in petroleum ether, R$_f$=0.4) to afford arbitrarily assigned [1-(fluoromethyl)cyclopropyl]-[(5S,7S)-7-fluoro-5-phenyl-6,7-dihydro-5H-pyrrolo [1,2-b][1,2,4]triazol-2-yl]methanone (15.6 mg, 20%) as brown oil. $^1$H NMR (400 MHz, CD$_3$OD) δ 7.43-7.33 (m, 3H), 7.26-7.23 (m, 2H), 6.17-6.12 (m, 0.5H), 6.01-5.98 (m, 0.5H), 5.62-5.60 (m, 1H), 4.83-4.76 (m, 1H), 4.73-4.63 (m, 1H), 3.76-3.65 (m, 1H), 2.85-2.77 (m, 1H), 1.86-1.79 (m, 2H), 1.23-1.16 (m, 2H). LC-MS R$_T$=1.188 min, m/z=304.2 [M+H]$^+$.

LCMS (5 to 95% acetonitrile in water+0.03% trifluoroacetic acid over 1.5 mins) retention time 1.188 min, ESI+ found [M+H]=304.2.

150

Method 59

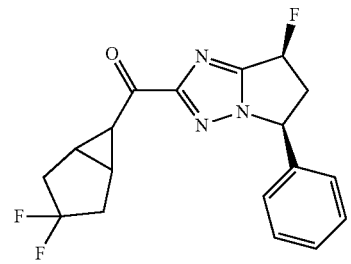

Example 80

(3,3-difluorobicyclo[3.1.0]hexan-6-yl)((5S,7S)-7-fluoro-5-phenyl-6,7-dihydro-5H-pyrrolo[1,2-b][1,2,4]triazol-2-yl)methanone

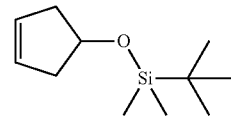

Step 1: tert-butyl(cyclopent-3-en-1-yloxy)dimethylsilane

To a solution of 3-cyclopentene-1-ol (10.0 g, 118.88 mmol) in tetrahydrofuran (130 mL) was added imidazole (16.0 g, 237.76 mmol) and tert-butyldimethylchlorosilane (23.0 g, 154.54 mmol). After addition, the reaction mixture was stirred at 30° C. for 16 h and quenched by addition of water (100 mL). The mixture was extracted with dichloromethane (2×200 mL). The combined organic layers were washed with brine (100 mL), dried over sodium sulfate and concentrated under reduced pressure. The residue was purified by column chromatography (silica gel, 100-200 mesh, 0 to 3% ethyl acetate in petroleum ether) to afford tert-butyl-cyclopent-3-en-1-yloxy-dimethyl-silane (22.0 g, 93%) as a colorless oil. $^1$H NMR (400 MHz, CDCl$_3$) δ 5.61 (s, 2H), 4.49-4.44 (m, 1H), 2.54-2.48 (m, 2H), 2.24-2.19 (m, 2H), 0.82 (s, 9H), 0.02 (s, 6H).

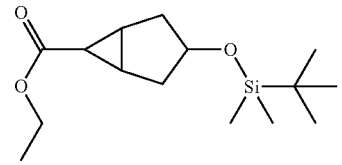 [SMILES: CCOC(=O)C1C2CC(O[Si](C)(C)C(C)(C)C)CC21]

Step 2: Ethyl 3-((tert-butyldimethylsilyl)oxy)bicyclo[3.1.0]hexane-6-carboxylate To a solution of tert-butyl-cyclopent-3-en-1-yloxy-dimethyl-silane (20.0 g, 100.82 mmol) in dichloromethane (160 mL) was added ethyl diazoacetate (13.8 g, 120.98 mmol). The reaction mixture was stirred for 12 h at 25° C. and concentrated under reduced pressure. The residue was purified by column chromatography (silica gel, 100-200 mesh, 0 to 5% ethyl acetate in petroleum ether) to afford ethyl 3-[tert-butyl(dimethyl)silyl]oxybicyclo[3.1.0]hexane-6-carboxylate (15.0 g, 52%) as a colorless oil. $^1$H NMR (400 MHz, CDCl$_3$) δ 4.49-4.44 (m, 2H), 2.53-2.48 (m, 2H), 2.24-2.19 (m, 2H), 1.65-1.24 (m, 2H), 1.25-1.22 (m, 2H), 0.83 (s, 9H), 0.00 (s, 6H).

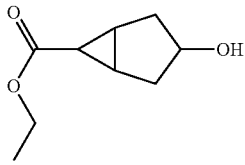

Step 3: Ethyl 3-hydroxybicyclo[3.1.0]hexane-6-carboxylate

To a solution of ethyl 3-[tert-butyl(dimethyl)silyl]oxybicyclo[3.1.0]hexane-6-carboxylate (15.0 g, 52.73 mmol) in tetrahydrofuran (200 mL) was added tetrabutylammonium fluoride (20.7 g, 79.09 mmol). The reaction mixture was stirred at 50° C. for 12 h and diluted with water (200 mL). The mixture was extracted with dichloromethane (3×100 mL). The combined organic layers were washed with brine (100 mL), dried over sodium sulfate and concentrated under reduced pressure to give crude ethyl 3-hydroxybicyclo[3.1.0]hexane-6-carboxylate (8.8 g, 98%) as a yellow oil.

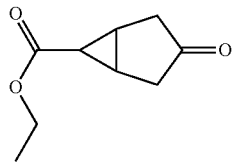

Step 4: Ethyl 3-oxobicyclo[3.1.0]hexane-6-carboxylate

To a solution of Dess-Martin periodinane (32.9 g, 77.55 mmol) in dichloromethane (200 mL) was added ethyl 3-hydroxybicyclo[3.1.0]hexane-6-carboxylate (8.8 g, 51.70 mmol). The reaction mixture was stirred at 25° C. for 12 h and diluted with water (200 mL). The resulting mixture was extracted with ethyl acetate (3×80 mL). The combined organic layers were washed with brine (100 mL), dried over sodium sulfate and concentrated under reduced pressure. The residue was purified by column chromatography (silica gel, 100-200 mesh, 0 to 30% ethyl acetate in petroleum ether) to give ethyl 3-oxobicyclo[3.1.0]hexane-6-carboxylate (8.0 g, 92%) as a yellow oil. $^1$H NMR (400 MHz, CDCl$_3$) δ 4.15-4.12 (m, 2H), 2.68-2.62 (m, 2H), 2.30-2.25 (m, 2H), 2.17-2.15 (m, 2H), 1.27-1.24 (m, 4H).

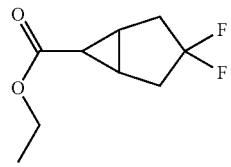

Step 5: Ethyl 3, 3-difluorobicyclo[3.1.0]hexane-6-carboxylate

To a solution of ethyl 3-oxobicyclo[3.1.0]hexane-6-carboxylate (2.0 g, 11.89 mmol) in dichloromethane (20 mL) was added diethylaminosulfur trifluoride (19.2 g, 118.91 mmol). The reaction mixture was stirred at 25° C. for 12 h and quenched by addition of water (100 mL) at 0° C. The mixture was extracted with dichloromethane (3×40 mL). The combined organic layers were washed with water (40 mL), brine (40 mL), dried over sodium sulfate and concentrated under reduced pressure. The residue was purified by column chromatography (silica gel, 100-200 mesh, 0 to 20% ethyl acetate in petroleum ether) to give ethyl 3, 3-difluorobicyclo[3.1.0]hexane-6-carboxylate (1.7 g, 75%) as a yellow oil. $^1$H NMR (400 MHz, CDCl$_3$) δ4.12-4.07 (m, 2H), 2.48-2.38 (m, 2H), 2.29-2.20 (m, 2H), 1.93-1.92 (m, 2H), 1.63-1.62 (m, 1H), 1.25-1.22 (m, 3H).

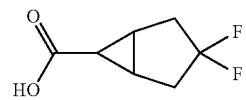 [SMILES: O=C(O)C1C2CC(F)(F)CC21]

Step 6: 3,3-difluorobicyclo[3.1.0]hexane-6-carboxylic Acid

To a solution of ethyl 3,3-difluorobicyclo[3.1.0]hexane-6-carboxylate (500 mg, 2.63 mmol) in tetrahydrofuran (24 mL) was added a solution of lithium hydroxide monohydrate (330 mg, 7.89 mmol) in water (7 mL). The mixture was stirred at 25° C. for 16 h and concentrated under reduced pressure. The aqueous residue was adjusted to pH=3 by addition of aqueous hydrochloric acid (4 M) at 0° C. The resulting mixture was extracted with ethyl acetate (3×15 mL). The combined organic layers were washed with brine (10 mL), dried over sodium sulfate and concentrated under reduced pressure to give crude 3,3-difluorobicyclo[3.1.0] hexane-6-carboxylic acid (250 mg, 59%) as a colorless oil.

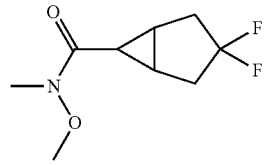

Step 7: 3,3-difluoro-N-methoxy-N-methylbicyclo[3.1.0]hexane-6-carboxamide

A mixture of 1-hydroxybenzotriazole (250 mg, 1.85 mmol), 1-(3-dimethylaminopropyl)-3-ethylcarbodiimidehydrochloride (426 mg, 2.22 mmol), 3,3-difluorobicyclo[3.1.0]hexane-6-carboxylic acid (300 mg, 1.85 mmol), N,O-dimethylhydroxylamine hydrochloride (271 mg, 2.78 mmol) and N,N-diisopropylethylamine (598 mg, 4.63 mmol) in dichloromethane (40 mL) was stirred at 25° C. for 16 h and diluted with water (20 mL). The mixture was extracted with dichloromethane (3×20 mL). The combined organic layers were washed with brine (20 mL), dried over sodium sulfate and concentrated under reduced pressure. The residue was purified by column chromatography (silica gel, 100-200 mesh, 0 to 20% ethyl acetate in petroleum ether) to give 3,3-difluoro-N-methoxy-N-methyl-bicyclo[3.1.0]hexane-6-carboxamide (102 mg, 27%) as a colorless oil. LCMS $R_T$=0.522 min, m/z=206.1 [M+H]$^+$.

LCMS (5 to 95% acetonitrile in water+0.03% trifluoacetic acid over 1.5 mins) retention time 0.522 min, ESI+ found [M+H]=206.1.

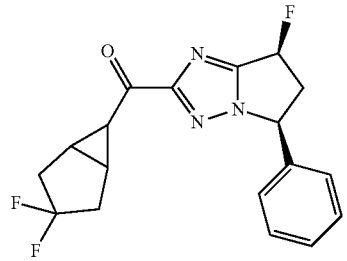 [SMILES: O=C(c1nc2n(n1)[C@H](c1ccccc1)C[C@@H]2F)C1C2CC(F)(F)CC21]

Step 8: (3,3-difluoro-6-bicyclo[3.1.0]hexanyl)-[(5S,7S)-7-fluoro-5-phenyl-6,7-dihydro-5H-pyrrolo[1,2-b][1,2,4]triazol-2-yl]methanone To a solution of 3,3-difluoro-N-methoxy-N-methyl-bicyclo[3.1.0]hexane-6-carboxamide (102 mg, 0.50 mmol) and (5S,7S)-2-bromo-7-fluoro-5-phenyl-6,7-dihydro-5H-pyrrolo[1,2-b][1,2,4]triazole (70 mg, 0.25 mmol) in tetrahydrofuran (10 mL) was added isopropylmagnesium chloride (2.0 M in tetrahydrofuran, 0.37 mL, 0.74 mmol) dropwise at −78° C. under nitrogen atmosphere. After addition, the mixture was stirred at −78° C. for 2 h and quenched by addition of saturated aqueous ammonium chloride (25 mL). The mixture was extracted with ethyl acetate (3×25 mL). The combined organic layers were dried over sodium sulfate and concentrated under reduced pressure. The residue was purified by RP-HPLC (acetonitrile 20-45°/0.225% hydrochloric acid in water) to afford arbitrarily assigned (3,3-difluoro-6-bicyclo[3.1.0]hexanyl)-[(5S,7S)-7-fluoro-5-phenyl-6,7-dihydro-5H-pyrrolo[1,2-b][1,2,4]triazol-2-yl]methanone (11 mg, 13%) as a white solid. $^1$H NMR (400 MHz, CD$_3$OD) δ 7.44-7.40 (m, 3H), 7.29-7.27 (m, 2H), 6.19-6.16 (m, 0.5H), 6.05-6.02 (m, 0.5H), 5.65-5.64 (m, 1H), 3.79-3.73 (m, 1H), 3.03-3.02 (m, 1H), 2.90-2.80 (m, 1H), 2.54-2.30 (m, 2H), 2.30-2.25 (m, 2H), 2.20-2.18 (m, 2H). LCMS $R_T$=1.255 min, m/z=348.2 [M+H]$^+$.

LCMS (10 to 80% acetonitrile in water+0.03% trifluoacetic acid over 2 mins) retention time 1.255 min, ESI+ found [M+H]=348.2.

Method 60

Example 81

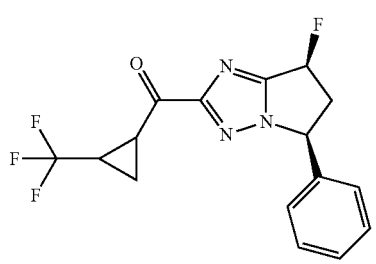

[(5S,7S)-7-fluoro-5-phenyl-6,7-dihydro-5H-pyrrolo[1,2-b][1,2,4]triazol-2-yl]-[2-(trifluoromethyl)cyclopropyl]methanone

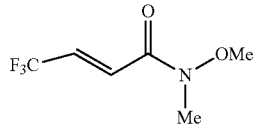 [SMILES: CON(C)C(=O)/C=C/C(F)(F)F]

Step 1: (E)-4,4,4-trifluoro-N-methoxy-N-methylbut-2-enamide

A mixture of N,O-dimethylhydroxylamine hydrochloride (4.42 g, 45.30 mmol), N,N-diisopropylethylamine (10.2 mL, 56.94 mmol), 4,4,4-trifluorobut-2-enoic acid (5.00 g, 35.70 mmol) and 1-(3-dimethylaminopropyl)-3-ethylcarbodiimide-hydrochloride (8.21 g, 42.84 mmol) in dichloromethane (50 mL) was stirred at 0° C. for 5 h. The mixture was washed with brine (2×50 mL), dried over sodium sulfate and concentrated under reduced pressure. The residue was purified by column chromatography (silica gel, 100-200 mesh, 0 to 20% ethyl acetate in petroleum ether) to afford (E)-4,4,4-trifluoro-N-methoxy-N-methyl-but-2-enamide (2.50 g, 38%) as colorless oil. LC-MS $R_T$=0.522 min, m/z=184.1 [M+H]$^+$.

LCMS (5 to 95% acetonitrile in water+0.03% trifluoacetic acid over 1.5 mins) retention time 0.522 min, ESI+ found [M+H]=184.1.

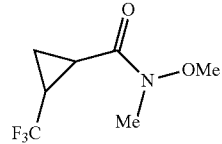

Step 2: N-methoxy-N-methyl-2-(trifluoromethyl)cyclopropanecarboxamide

To a solution of trimethylsulfoxonium iodide (6.01 g, 27.30 mmol)) in dimethyl sulfoxide (50 mL) was added sodium hydride (60%, 1.09 g, 27.30 mmol). The mixture was stirred for 1 h and a solution of (E)-4,4,4-trifluoro-N-methoxy-N-methyl-but-2-enamide (2.50 g, 13.65 mmol) in dimethyl sulfoxide (20 mL) was added. The resulting mixture was stirred at 25° C. for 16 h and diluted with saturated aqueous ammonium chloride (100 mL). The solution was extracted with ethyl acetate (3×100 mL). The combined organic layers were washed with brine (150 mL), dried over sodium sulfate and concentrated under reduced pressure. The residue was purified by RP-HPLC (35-65% acetonitrile/0.05% ammonia hydroxide in water) to afford N-methoxy-N-methyl-2-(trifluoromethyl)cyclopropanecarboxamide (700 mg, 26%) as a yellow oil. LC-MS $R_T$=0.722 min, m/z=197.9 [M+H]$^+$.

LCMS (5 to 95% acetonitrile in water+0.03% trifluoacetic acid over 1.5 mins) retention time 0.722 min, ESI+ found [M+H]=197.9.

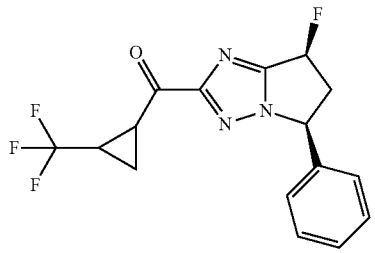

Step 3: [(5S,7S)-7-fluoro-5-phenyl-6,7-dihydro-5H-pyrrolo[1,2-b][1,2,4]triazol-2-yl]-[2-(trifluoromethyl)cyclopropyl]methanone To a solution of N-methoxy-N-methyl-2-(trifluoromethyl)cyclopropanecarboxamide (98 mg, 0.50 mmol) and (5S,7S)-2-bromo-7-fluoro-5-phenyl-6,7-dihydro-5H-pyrrolo[1,2-b][1,2,4]triazole (100 mg, 0.35 mmol) in tetrahydrofuran (2 mL) was added isopropylmagnesium chloride (2.0 M in tetrahydrofuran, 1.06 mL, 2.13 mmol) at 0° C. under nitrogen atmosphere. After addition, the mixture was stirred at 25° C. for 16 h and quenched by addition of saturated aqueous ammonium chloride (10 mL). The resulting mixture was extracted with ethyl acetate (3×10 mL). The combined organic layers were washed with brine (3×10 mL), dried over sodium sulfate and concentrated under reduced pressure. The residue was purified by column chromatography (silica gel, 100-200 mesh, 0-40% ethyl acetate in petroleum ether) to afford [(5S,7S)-7-fluoro-5-phenyl-6,7-dihydro-5H-pyrrolo[1,2-b][1,2,4]triazol-2-yl]-[2-(trifluoromethyl)cyclopropyl]methanone (30 mg, 24%) as a white solid. $^1$H NMR (400 MHz, CD$_3$OD) δ 7.45-7.39 (m, 3H), 7.32-7.29 (m, 2H), 6.22-6.05 (m, 1H), 5.70-5.65 (m, 1H), 3.84-3.71 (m, 1H), 3.41-3.37 (m, 1H), 2.90-2.79 (m, 1H), 2.45-2.40 (m, 1H), 1.53-1.46 (m, 2H). LC-MS R$_T$=0.904 min, m/z=339.9 [M+H]$^+$.

LCMS (5 to 95% acetonitrile in water+0.03% trifluoacetic acid over 1.5 mins) retention time 0.904 min, ESI+ found [M+H]=339.9.

Method 61

Example 82

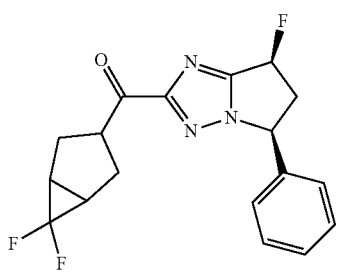

(6,6-difluoro-3-bicyclo[3.1.0]hexanyl)-[(5S,7S)-7-fluoro-5-phenyl-6,7-dihydro-5H-pyrrolo[1,2-b][1,2,4]triazol-2-yl]methanone

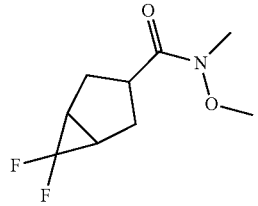

Step 1: 6,6-difluoro-N-methoxy-N-methylbicyclo[3.1.0]hexane-3-carboxamide

A mixture of 6,6-difluorobicyclo[3.1.0]hexane-3-carboxylic acid (150 mg, 0.93 mmol), 1-(3-dimethylaminopropyl)-3-ethylcarbodiimidehydrochloride (355 mg, 1.85 mmol), N,N-diisopropylethylamine (359 mg, 2.78 mmol), N,O-dimethylhydroxylamine hydrochloride (180 mg, 1.85 mmol) and 1-hydroxybenzotriazole (125 mg, 0.93 mmol) in dichloromethane (10 mL) was stirred at 25° C. for 18 h. The mixture was diluted with water (15 mL) and extracted with ethyl acetate (3×15 mL). The combined organic layers were washed with water (2×10 mL), brine (20 mL), dried over sodium sulfate and concentrated under reduced pressure. The residue was purified by column chromatography (silica gel, 100-200 mesh, 0-30% ethyl acetate in petroleum ether) to afford 6,6-difluoro-N-methoxy-N-methyl-bicyclo[3.1.0]hexane-3-carboxamide (100 mg, 53%) as colorless oil.

LCMS R$_T$=0.540 & 0.572 min, m/z=206.0 [M+H]$^+$.

LCMS (5 to 95% acetonitrile in water+0.03% trifluoacetic acid over 1.5 mins) retention time 0.540 & 0.572 min, ESI+ found [M+H]=206.0.

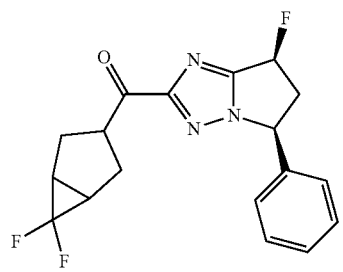 [SMILES: O=C(c1nc2n(n1)[C@H](c1ccccc1)C[C@@H]2F)C1CC2C(C1)C2(F)F]

Step 2: (6,6-difluoro-3-bicyclo[3.1.0]hexanyl)-[(5S,7S)-7-fluoro-5-phenyl-6,7-dihydro-5H-pyrrolo[1,2-b][1,2,4]triazol-2-yl]methanone To a solution of 6,6-difluoro-N-methoxy-N-methyl-bicyclo[3.1.0]hexane-3-carboxamide (33 mg, 0.16 mmol) and (5S,7S)-2-bromo-7-fluoro-5-phenyl-6,7-dihydro-5H-pyrrolo[1,2-b][1,2,4]triazole (30 mg, 0.11 mmol) in tetrahydrofuran (6 mL) was added isopropylmagnesium chloride (2.0 M in tetrahydrofuran, 0.16 mL, 0.32 mmol) under nitrogen at −78° C. The mixture was stirred at −78° C. for 2 h and then quenched by addition of saturated aqueous ammonium chloride (15 mL). The mixture was extracted with ethyl acetate (3×20 mL). The combined organic layers were washed with water (30 mL), brine (30 mL), dried over sodium sulfate and concentrated under reduced pressure. The residue was purified by RP-HPLC (40%-70% acetonitrile/0.05% ammonia hydroxide in water) to afford arbitrarily assigned (6,6-difluoro-3-bicyclo[3.1.0]hexanyl)-[(5S,7S)-7-fluoro-5-phenyl-6,7-dihydro-5H-pyrrolo[1,2-b][1,2,4]triazol-2-yl]methanone (3.9 mg, 11%) as a white solid. $^1$H NMR (400 MHz, CDCl$_3$) δ 7.42-7.39 (m, 3H), 7.26-7.23 (m, 2H), 6.12-5.94 (m, 1H), 5.52-5.48 (m, 1H), 4.19-4.15 (m, 0.5H), 3.88-3.85 (m, 0.5H), 3.68-3.59 (m, 1H), 3.02-2.91 (m, 1H), 2.39-2.30 (m, 4H), 2.08-2.04 (m, 2H). LCMS R$_T$=0.896 min, m/z=347.9 [M+H]$^+$.

LCMS (5 to 95% acetonitrile in water+0.03% trifluoacetic acid over 1.5 mins) retention time 0.896 min, ESI+ found [M+H]=347.9.

Method 63

Example 84

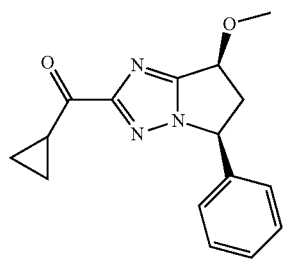

Cyclopropyl-[(5S,7S)-7-methoxy-5-phenyl-6,7-dihydro-5H-pyrrolo[1,2-b][1,2,4]triazol-2-yl]methanone

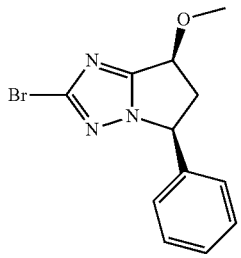

cix mixture

Step 1: cis-2-bromo-7-methoxy-5-phenyl-6,7-dihydro-5H-pyrrolo[1,2-b][1,2,4]triazole To a solution of 2-bromo-5-phenyl-6,7-dihydro-5H-pyrrolo[1,2-b][1,2,4]triazol-7-ol (1.20 g, 4.28 mmol) in tetrahydrofuran (50 mL) was added sodium hydride (60%, 342 mg, 8.57 mmol). The mixture was stirred for 20 min and iodomethane (3.00 g, 21.14 mmol) was added dropwise. After addition, the mixture was stirred for 2 h and poured into ice-water (70 ml). The resulting mixture was extracted with ethyl acetate (3×80 mL). The combined organic layers were washed with brine (2×70 mL), dried over sodium sulfate and concentrated under reduced pressure. The residue was purified by column chromatography (silica gel, 100-200 mesh, 8 to 12% ethyl acetate in petroleum ether) to afford cis-2-bromo-7-methoxy-5-phenyl-6,7-dihydro-5H-pyrrolo[1,2-b][1,2,4]triazole (330 mg, 26%) as a white solid. LCMS R$_T$=0.748 min, m/z=294.0 [M+H]$^+$.

LCMS (5 to 95% acetonitrile in water+0.03% trifluoacetic acid over 1.5 mins) retention time 0.748 min, ESI+ found [M+H]=294.0.

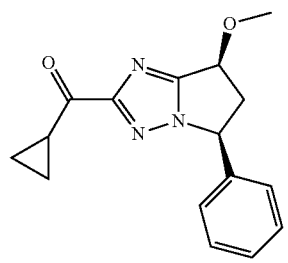 [SMILES: CO[C@H]1C[C@@H](c2ccccc2)n2nc(C(=O)C3CC3)nc21]

Step 2: Cyclopropyl-[(5S,7S)-7-methoxy-5-phenyl-6,7-dihydro-5H-pyrrolo[1,2-b][1,2,4]triazol-2-yl]methanone To a solution of cis-2-bromo-7-methoxy-5-phenyl-6,7-dihydro-5H-pyrrolo[1,2-b][1,2,4]triazole (220 mg, 0.75 mmol) and N-methoxy-N-methyl-cyclopropanecarboxamide (193 mg, 1.50 mmol) in tetrahydrofuran (6 mL) was added isopropylmagnesium chloride (2.0 M in tetrahydrofuran, 2.24 mL, 4.49 mmol) under nitrogen at 0° C. The mixture was stirred at 25° C. for 2 h and quenched by addition of saturated aqueous ammonium chloride (25 mL). The solution was extracted with ethyl acetate (3×15 mL). The combined organic layers were dried over sodium sulfate and concentrated under reduced pressure. The residue was purified by column chromatography (silica gel, 100-200 mesh, 0 to 40% ethyl acetate in petroleum ether) to afford cyclopropyl(cis-7-methoxy-5-phenyl-6,7-dihydro-5H-pyrrolo[1,2-b][1,2,4]triazol-2-yl) methanone (180 mg, 85%) as a brown oil.

This cis mixture was further separated by chiral SFC to afford arbitrarily assigned: cyclopropyl-[(5S,7S)-7-methoxy-5-phenyl-6,7-dihydro-5H-pyrrolo[1,2-b][1,2,4]triazol-2-yl]methanone (peak 1, retention time=4.247 min) (29.8 mg, 16%) as a yellow solid. $^1$H NMR (400 MHz, CD$_3$OD) δ 7.40-7.31 (m, 5H), 5.56-5.52 (m, 1H), 4.94-4.92 (m, 1H), 3.67-3.59 (m, 4H), 3.02-3.01 (m, 1H), 2.62-2.57 (m, 1H), 1.17-1.15 (m, 2H), 1.10-1.07 (m, 2H). LCMS R$_T$=0.709 min, m/z=284.1 [M+H]$^+$.

LCMS (5 to 95% acetonitrile in water+0.03% trifluoacetic acid over 1.5 mins) retention time 0.709 min, ESI+ found [M+H]=284.1.

SFC condition: Column: Lux Cellulose-2 150×4.6 mm I.D., 3 m Mobile phase: 40% of ethanol (0.05% DEA) in CO$_2$. Flow rate: 2.5 mL/min Column temperature: 40° C.

Method 64

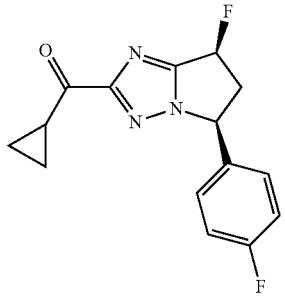

Example 85

Cyclopropyl-[(5S,7S)-7-fluoro-5-(4-fluorophenyl)-6,7-dihydro-5H-pyrrolo[1,2-b][1,2,4]triazol-2-yl]methanone

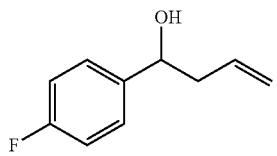

Step 1: 1-(4-fluorophenyl)but-3-en-1-ol

To a solution of 4-fluorobenzaldehyde (50.0 g, 402.87 mmol) in tetrahydrofuran (500 mL) was added allylmagnesium chloride (1.82 M in tetrahydrofuran, 288.0 mL, 523.73 mmol) at 0° C. under nitrogen. The reaction mixture was allowed to warm up to 25° C. and stirred for 2 h, before quenched by addition of saturated aqueous ammonium chloride (200 mL). The resulting mixture was extracted with ethyl acetate (3×300 mL). The combined organic layers were dried over sodium sulfate and concentrated under reduce pressure to give crude 1-(4-fluorophenyl)but-3-en-1-ol (66.8 g, 99%) as yellow oil. $^1$H NMR (400 MHz, CDCl$_3$) δ 7.32-7.28 (m, 2H), 7.04-7.00 (m, 2H), 5.80-5.73 (m, 1H), 5.17-5.12 (m, 2H), 4.70-4.67 (m, 1H), 2.48-2.46 (m, 2H), 2.44-2.31 (m, 1H).

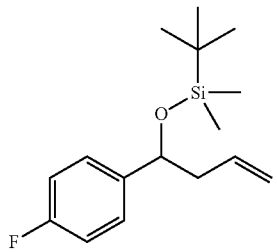 [SMILES: C=CCC(O[Si](C)(C)C(C)(C)C)c1ccc(F)cc1]

Step 2: Tert-Butyl((1-(4-fluorophenyl)but-3-en-1-yl)oxy)dimethylsilane

To a solution of 1-(4-fluorophenyl)but-3-en-1-ol (66.8 g, 401.95 mmol) in dichloromethane (500 mL) was added imidazole (54.7 g, 803.9 mmol) and tert-butylchlorodimethylsilane (72.7 g, 482.34 mmol). The reaction mixture was stirred at 25° C. for 16 h and diluted with water (500 mL). The resulting mixture was extracted with dichloromethane (2×300 mL). The combined organic layers were washed with brine (500 mL), dried over sodium sulfate and concentrated under reduced pressure to afford crude tert-butyl-[1-(4-fluorophenyl)but-3-enoxy]-dimethyl-silane (111.0 g, 98%) as light oil. $^1$H NMR (400 MHz, CDCl$_3$) δ 7.41-7.37 (m, 2H), 7.14-7.10 (m, 2H), 5.92-5.85 (m, 1H), 5.15-5.11 (m, 2H), 4.81-4.79 (m, 1H), 2.58-2.45 (m, 2H), 1.01 (s, 9H), 0.15 (s, 3H), 0.00 (s, 3H).

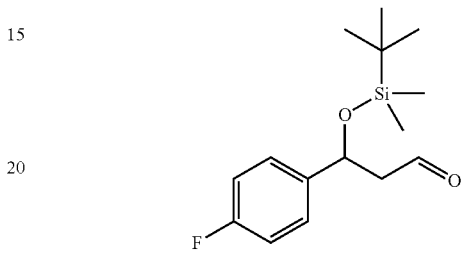

Step 3: 3-((tert-butyldimethylsilyl)oxy)-3-(4-fluorophenyl)propanal

To a solution of tert-butyl-[1-(4-fluorophenyl)but-3-enoxy]-dimethyl-silane (110.0 g, 392.23 mmol) in water (500 mL) and tetrahydrofuran (500 mL) was added osmium tetraoxide (0.5 g, 1.97 mmol). After stirred for 30 min at 25° C., sodium periodate (335.6 g, 1568.90 mmol) was added in small portions over 2 h and the resulting mixture was stirred for another 2 h at 25° C. The mixture was quenched by addition of cold saturated aqueous sodium thiosulfate (500 mL). The mixture was stirred for 30 min and then extracted with ethyl acetate (3×500 mL). The combined organic layers were washed with water (500 mL), brine (500 mL), dried over sodium sulfate and concentrated under reduced pressure. The residue was purified by column chromatography (silica gel, 100-200 mesh, 0 to 2% ethyl acetate in petroleum ether) to afford 3-[tert-butyl(dimethyl)silyl]oxy-3-(4-fluorophenyl)propanal (70.0 g, 63%) as a yellow oil. $^1$HNMR (400 Hz, CDCl$_3$) δ 9.95-9.90 (m, 1H), 7.48-7.44 (m, 2H), 7.19-7.15 (m, 2H), 5.37-5.34 (m, 1H), 3.02-2.95 (m, 1H), 2.79-2.77 (m, 1H), 1.01 (s, 9H), 0.19 (s, 3H), 0.00 (s, 3H).

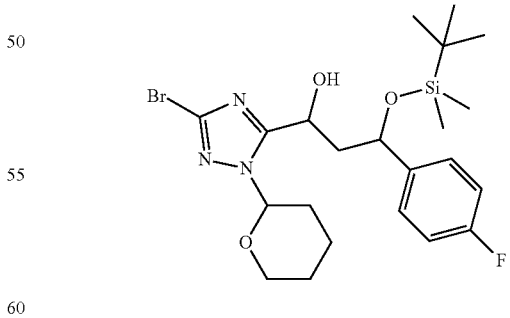

Step 4: 1-(3-bromo-1-(tetrahydro-2H-pyran-2-yl)-1H-1,2,4-triazol-5-yl)-3-((tert-butyldimethylsilyl)oxy)-3-(4-fluorophenyl)propan-1-ol To a cooled (−78° C.) solution of 3,5-dibromo-1-tetrahydropyran-2-yl-1,2,4-triazole (70.1 g, 225.32 mmol) in tetrahydrofuran (500 mL) was added n-butyllithium (2.5M in hexanes, 98.2 mL, 245.37 mmol) dropwise under nitrogen. The mixture was stirred at −78° C. for 30 min and a solution of 3-[tert-butyl(dimethyl)silyl]oxy-3-(4-fluorophenyl)propanal (63.0 g, 223.06 mmol) in tetrahydrofuran (50 mL) was added dropwise. After addition, the mixture was stirred at −78° C. for 1.5 h and quenched by addition of saturated aqueous ammonium chloride (500 mL). The resulting mixture was extracted with ethyl acetate (2×500 mL). The combined organic layers were dried over sodium sulfate and concentrated under reduce pressure. The residue was purified by column chromatography (silica gel, 100-200 mesh, 0 to 12% ethyl acetate in petroleum ether) to afford 1-(5-bromo-2-tetrahydropyran-2-yl-1,2,4-triazol-3-yl)-3-[tert-butyl(dimethyl)silyl]oxy-3-(4-fluorophenyl)propan-1-ol (95.0 g, 83%) as yellow oil.

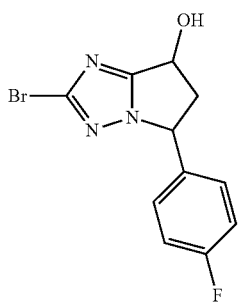 [SMILES: OC1CC(c2ccc(F)cc2)n2nc(Br)nc21]

Step 5: 2-bromo-5-(4-fluorophenyl)-6,7-dihydro-5H-pyrrolo[1,2-b][1,2,4]triazol-7-ol A mixture of 1-(5-bromo-2-tetrahydropyran-2-yl-1,2,4-triazol-3-yl)-3-[tert-butyl(dimethyl) silyl]oxy-3-(4-fluorophenyl)propan-1-ol (40.0 g, 77.75 mmol) and 2,2,2-trifluoroacetic acid (150 mL, 1554.9 mmol) was stirred at 55° C. for 8 h and concentrated under reduced pressure. The residue was diluted with ethyl acetate (300 mL) and adjusted to pH=9 by addition of saturated aqueous sodium bicarbonate. The resulting mixture was extracted with ethyl acetate (2×300 mL). The combined organic layers were washed with water (150 mL), brine (150 mL), dried over sodium sulfate and concentrated under reduced pressure. The residue was purified by column chromatography (silica gel, 100-200 mesh, 20 to 33% ethyl acetate in petroleum ether) to afford 2-bromo-5-(4-fluorophenyl)-6,7-dihydro-5H-pyrrolo[1,2-b][1,2,4]triazol-7-ol (23.5 g, 100%) as a yellow solid. LCMS $R_T$=0.679 min, m/z=300.0 [M+H]$^+$.

LCMS (5 to 95% acetonitrile in water+0.03% trifluoacetic acid over 1.5 mins) retention time 0.679 min, ESI+ found [M+H]=300.0.

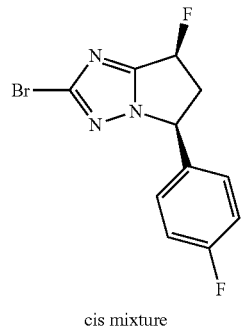 [SMILES: Fc1ccc([C@@H]2C[C@H](F)c3nc(Br)nn32)cc1]

cis mixture

Step 6: cis-2-bromo-7-fluoro-5-(4-fluorophenyl)-6,7-dihydro-5H-pyrrolo[1,2-b][1,2,4]triazole To a cooled (0° C.) solution of 2-bromo-5-(4-fluorophenyl)-6,7-dihydro-5H-pyrrolo[1,2-b][1,2,4]triazol-7-ol (6.0 g, 20.13 mmol) in dichloromethane (50 mL) was added diethylaminosulfur trifluoride (10.7 mL, 80.51 mmol) in dichloromethane (8 mL). After stirred for 30 min, the mixture poured into ice water (100 mL). The resulting mixture was extracted with dichloromethane (2×100 mL). The combined organic layers were dried over sodium sulfate and concentrated under reduced pressure. The residue was purified by column chromatography (silica gel, 100-200 mesh, 0 to 12% ethyl acetate in petroleum ether) to afford cis-2-bromo-7-fluoro-5-(4-fluorophenyl)-6,7-dihydro-5H-pyrrolo[1,2-b][1,2,4]triazole (2.1 g, 35%) as a light yellow solid. $^1$HNMR (CDCl$_3$, 400 MHz) δ 7.26-7.23 (m, 2H), 7.12-7.08 (m, 2H), 6.07-5.91 (m, 1H), 5.45-5.42 (m, 1H), 3.64-3.52 (m, 1H), 2.92-2.85 (m, 1H).

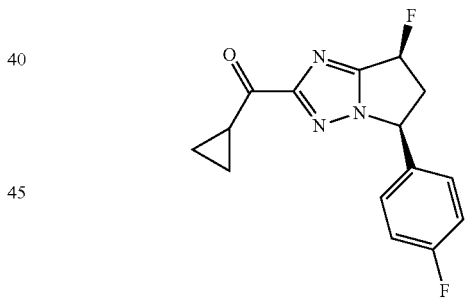

Step 7: Cyclopropyl-[(5S,7S)-7-fluoro-5-(4-fluorophenyl)-6,7-dihydro-5H-pyrrolo[1,2-b][1,2,4]triazol-2-yl]methanone To a solution of N-methoxy-N-methyl-cyclopropanecarboxamide (378 mg, 2.94 mmol) and cis-2-bromo-7-fluoro-5-(4-fluorophenyl)-6,7-dihydro-5H-pyrrolo[1,2-b][1,2,4]triazole (400 mg, 1.34 mmol) in tetrahydrofuran (15 mL) was added isopropylmagnesium chloride (2.0 M in tetrahydrofuran, 2.66 mL, 5.34 mmol) at 0° C. under a nitrogen atmosphere. The mixture was stirred at 0° C. for 8 h and quenched by addition of saturated aqueous ammonium chloride (10 mL). The mixture was extracted with ethyl acetate (3×50 mL). The combined organic layers were dried over sodium sulfate and concentrated under reduced pressure. The residue was purified by preparative TLC (30% ethyl acetate in petroleum ether, R_f=0.25) to give cyclopropyl-[cis-7-fluoro-5-(4-fluorophenyl)-6,7-dihydro-5H-pyrrolo[1,2-b][1,2,4]triazol-2-yl]methanone (180 mg, 47%) as yellow-pale solid. LCMS $R_T$=0.733 min, m/z=290.1 [M+H].

LCMS (5 to 95% acetonitrile in water+0.03% trifluoacetic acid over 1.5 mins) retention time 0.733 min, ESI+ found [M+H]=290.1.

This cis mixture was further separated by chiral SFC to arbitrarily assigned: cyclopropyl-[(5S,7S)-7-fluoro-5-(4-fluorophenyl)-6,7-dihydro-5H-pyrrolo[1,2-b][1,2,4]triazol-2-yl]methanone (peak 2, retention time=3.981 min) (71 mg, 39%) as a white solid. $^1$H NMR (400 MHz, CD$_3$OD) δ 7.36-7.32 (m, 2H), 7.19-7.14 (m, 2H), 6.20-6.04 (m, 1H), 5.65-5.65 (m, 1H), 3.83-3.69 (m, 1H), 3.10-2.97 (m, 1H), 2.89-2.77 (m, 1H), 1.20-1.09 (m, 4H). LCMS $R_T$=0.833 min, m/z=289.9 [M+H]$^+$.

LCMS (5 to 95% acetonitrile in water+0.03% trifluoacetic acid over 1.5 mins) retention time 0.833 min, ESI+ found [M+H]=289.9.

The 5R,7R-isomer was also collected (peak 1, retention time=3.439 min) (65 mg, 36%) as a white solid.

SFC condition: Column: ChiralPak AD-3 150×4.6 mm I.D., 3 μm Mobile phase: A: CO2 B:Ethanol (0.05% DEA) Gradient: from 5% to 40% of B in 5.5 min and hold 40% for 3 min, then 5% of B for 1.5 min Flow rate: 2.5 mL/min, Column temperature: 40° C.

Method 65

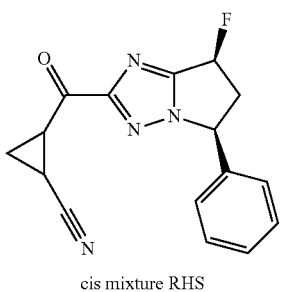 [SMILES: N#CC1CC1C(=O)c1nc2n(n1)[C@H](c1ccccc1)C[C@@H]2F]

cis mixture RHS

Example 86

2-(rac-(5S,7S)-7-fluoro-5-phenyl-6,7-dihydro-5H-pyrrolo[1,2-b][1,2,4]triazole-2-carbonyl) cyclopropanecarbonitrile

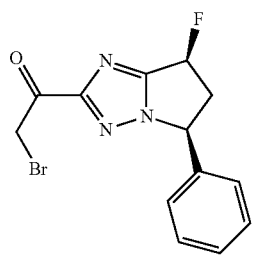

cis mixture RHS

Step 1: 2-bromo-1-(rac-(5S,7S)-7-fluoro-5-phenyl-6,7-dihydro-5H-pyrrolo[1,2-b][1,2,4]triazol-2-yl)ethanone To a mixture of 1-[rac-(5S,7S)-7-fluoro-5-phenyl-6,7-dihydro-5H-pyrrolo[1,2-b][1,2,4]triazol-2-yl]ethanone (250 mg, 1.02 mmol) in acetic acid (3 mL) was added pyridine hydrobromide perbromide (370 mg, 1.16 mmol). The mixture was stirred at 25° C. for 3 h and diluted with ethyl acetate (40 mL). The solution was washed with water (2×20 mL), dried over sodium sulfate and concentrated under reduced pressure. The residue was purified by column chromatography (silica gel, 100-200 mesh, 0 to 50% ethyl acetate in petroleum ether) to give 2-bromo-1-[rac-(5S,7S)-7-fluoro-5-phenyl-6,7-dihydro-5H-pyrrolo[1,2-b][1,2,4]triazol-2-yl]ethanone (185 mg, 56%) as a yellow oil. LCMS $R_T$=0.771 min, m/z=326.0 [M+H]$^+$.

LCMS (5 to 95% acetonitrile in water+0.03% trifluoacetic acid over 1.5 mins) retention time 0.771 min, ESI+ found [M+H]=326.0.

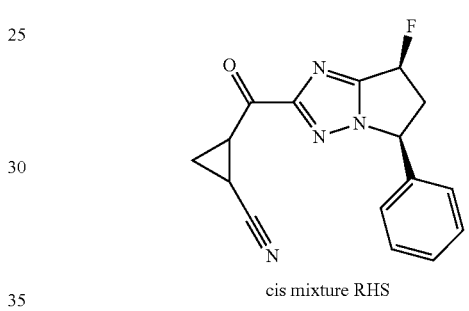

cis mixture RHS

Step 2: 2-(rac-(5S,7S)-7-fluoro-5-phenyl-6,7-dihydro-5H-pyrrolo[1,2-b][1,2,4]triazole-2-carbonyl) cyclopropanecarbonitrile To a mixture of 2-bromo-1-[rac-(5S,7S)-7-fluoro-5-phenyl-6,7-dihydro-5H-pyrrolo[1,2-b][1,2,4]triazol-2-yl]ethanone (120 mg, 0.37 mmol) in tetrahydrofuran (2 mL) and dimethyl sulfoxide (0.5 mL) was added 1,4-diazabicyclo[2.2.2.]octane (53 mg, 0.48 mmol). After stirred at 20° C. for 30 min, the mixture was added sodium carbonate (76 mg, 0.72 mmol) and acrylonitrile (6.2 mL, 94.23 mmol). The resulting mixture was stirred at 90° C. for 20 h and diluted with ethyl acetate (40 mL). The solution was washed with water (2×20 mL), dried over sodium sulfate and concentrated under reduced pressure. The residue was purified by RP-HPLC (water (0.05% ammonia hydroxide v/v)-acetonitrile 30-60%) to arbitrarily assigned 2-[rac-(5S,7S)-7-fluoro-5-phenyl-6,7-dihydro-5H-pyrrolo[1,2-b][1,2,4]triazole-2-carbonyl]cyclopropanecarbonitrile (3 mg, 3%) as a white solid. $^1$H NMR (400 MHz, CDCl$_3$) δ 7.46-7.42 (m, 3H), 7.31-7.27 (m, 2H), 6.15-5.99 (m, 1H), 5.56-5.53 (m, 1H), 3.72-3.67 (m, 2H), 3.07-3.03 (m, 1H), 2.21-2.08 (m, 1H), 1.75-1.70 (m, 1H), 1.68-1.57 (m, 1H). LCMS $R_T$=0.818 min, m/z=296.9 [M+H]$^+$.

LCMS (5 to 95% acetonitrile in water+0.03% trifluoacetic acid over 1.5 mins) retention time 0.771 min, ESI+ found [M+H]=296.9.

Method 66

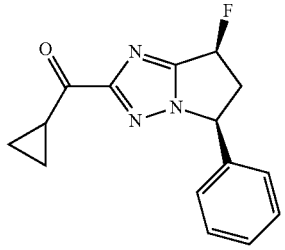

Example 87

Cyclopropyl-[(5S,7S)-7-hydroxy-5-phenyl-6,7-dihydro-5H-pyrrolo[1,2-b][1,2,4]triazol-2-yl]methanone

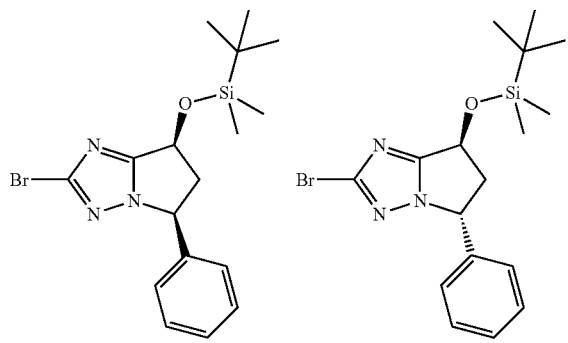 [SMILES: CC(C)(C)[Si](C)(C)O[C@H]1C[C@@H](c2ccccc2)n2nc(Br)nc21 ; CC(C)(C)[Si](C)(C)O[C@H]1C[C@H](c2ccccc2)n2nc(Br)nc21]

Step 1: (cis)-2-bromo-7-((tert-butyldimethylsilyl)oxy)-5-phenyl-6,7-dihydro-5H-pyrrolo [1,2-b][1,2,4]triazole and (trans)-2-bromo-7-((tert-butyldimethylsilyl)oxy)-5-phenyl-6,7-dihydro-5H-pyrrolo[1,2-b][1,2,4]triazole A mixture of 2-bromo-5-phenyl-6,7-dihydro-5H-pyrrolo [1,2-b][1,2,4]triazol-7-ol (1000 mg, 3.57 mmol) and triethylamine (1083 mg, 10.71 mmol) in dichloromethane (50 mL) was added tert-butyldimethylsilyl trifluoromethanesulfonate (1415 mg, 5.35 mmol). The mixture was stirred for 14 h at 25° C. and diluted with water (50 mL). The resulting solution was extracted with dichloromethane (2×100 mL). The combined organic layers were washed with brine (100 mL), dried over sodium sulfate and concentrated under reduced pressure. The residue was purified by column chromatography (silica gel, 100-200 mesh, 0 to 30% ethyl acetate in petroleum ether) to afford: (trans)-2-bromo-7-((tert-butyldimethylsilyl)oxy)-5-phenyl-6,7-dihydro-5H-pyrrolo[1,2-b][1,2,4]triazole (870 mg, 62%) as a yellow solid. $^1$H NMR (400 MHz, CDCl$_3$) δ 7.41-7.36 (m, 5H), 5.31-5.28 (m, 1H), 5.26-5.23 (m, 1H), 3.47-3.40 (m, 1H), 2.58-2.52 (m, 1H), 0.99 (s, 9H), 0.23 (s, 3H), 0.20 (s, 3H).

(cis)-2-bromo-7-((tert-butyldimethylsilyl)oxy)-5-phenyl-6,7-dihydro-5H-pyrrolo [1,2-b][1,2,4]triazole (430 mg, 31%) as a colorless oil. $^1$H NMR (400 MHz, CDCl$_3$) δ 7.49-7.35 (m, 3H), 7.11-7.10 (m, 2H), 5.61-5.58 (m, 1H), 5.33-5.30 (m, 1H), 3.00-2.96 (m, 1H), 2.90-2.83 (m, 1H), 0.93 (s, 9H), 0.23 (s, 3H), 0.19 (s, 3H).

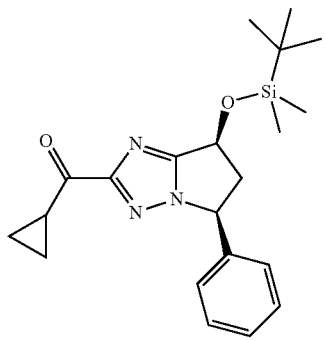 [SMILES: CC(C)(C)[Si](C)(C)O[C@H]1C[C@@H](c2ccccc2)n2nc(C(=O)C3CC3)nc21]

Step 2: [cis-7-[tert-butyl(dimethyl)silyl]oxy-5-phenyl-6,7-dihydro-5H-pyrrolo[1,2-b][1,2,4]triazol-2-yl]-cyclopropyl-methanone To a solution of N-methoxy-n-methyl-cyclopropanecarboxamide (242 mg, 1.88 mmol) and (cis)-2-bromo-7-((tert-butyldimethylsilyl)oxy)-5-phenyl-6,7-dihydro-5H-pyrrolo [1,2-b][1,2,4]triazole (370 mg, 0.94 mmol) in tetrahydrofuran (2 mL) was added isopropylmagnesium chloride (2.0 M in tetrahydrofuran, 1.41 mL, 2.81 mmol) at 0° C. under nitrogen atmosphere. The mixture was stirred at 0° C. for 1 h and quenched by addition of saturated aqueous ammonium chloride (50 mL). The resulting mixture was extracted with ethyl acetate (3×30 mL). The combined organic layers were dried over sodium sulfate and concentrated under reduced pressure. The residue was purified by column chromatography (silica gel, 100-200 mesh, 0 to 40% ethyl acetate in petroleum ether) to afford [cis-7-[tert-butyl(dimethyl)silyl] oxy-5-phenyl-6,7-dihydro-5H-pyrrolo[1,2-b][1,2,4]triazol-2-yl]-cyclopropyl-methanone (220 mg, 61%) as a yellow oil. $^1$H NMR (400 MHz, CDCl$_3$) δ 7.36-7.34 (m, 5H), 5.39-5.36 (m, 1H), 5.29-5.28 (m, 1H), 3.54-3.48 (m, 1H), 3.08-3.05 (m, 1H). 2.65-2.61 (m, 1H), 1.30-1.28 (m, 2H), 1.07-1.02 (m, 2H), 0.91 (s, 9H), 0.24 (s, 3H), 0.22 (s, 3H).

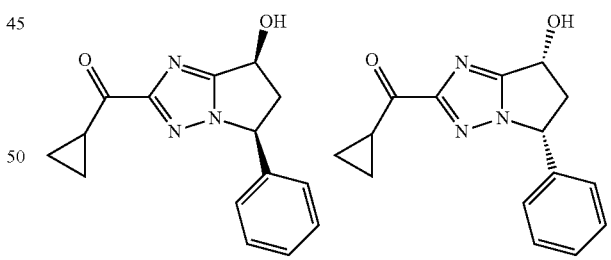

Step 3: Cyclopropyl-[(5S,7S)-7-hydroxy-5-phenyl-6,7-dihydro-5H-pyrrolo[1,2-b][1,2,4]triazol-2-yl] methanone and cyclopropyl-[(5R,7R)-7-hydroxy-5-phenyl-6,7-dihydro-5H-pyrrolo[1,2-b][1,2,4]triazol-2-yl]methanone To a solution of [cis-7-[tert-butyl(dimethyl)silyl]oxy-5-phenyl-6,7-dihydro-5H-pyrrolo[1,2-b][1,2,4]triazol-2-yl]-cyclopropyl-methanone (200 mg, 0.52 mmol) in tetrahydrofuran (10 mL) was added tetrabutylammonium fluoride (1.0

M in tetrahydrofuran, 2.09 mL, 2.09 mmol) at 25° C. The mixture was stirred at 25° C. for 14 h and diluted with dichloromethane (30 mL). The resulting mixture was washed with water (20 mL), brine (20 mL), dried over sodium sulfate and concentrated under reduced pressure. The residue was purified by column chromatography (silica gel, 100-200 mesh, 0 to 90% ethyl acetate in petroleum ether) to afford cyclopropyl-[cis-7-hydroxy-5-phenyl-6,7-dihydro-5H-pyrrolo[1,2-b][1,2,4]triazol-2-yl]methanone (95 mg, 67%) as a white solid. $^1$H NMR (400 MHz, CDCl$_3$) δ 7.42-7.36 (m, 5H), 5.46-5.40 (m, 2H), 4.79-4.78 (d, 1H), 3.64-3.58 (m, 1H). 3.00-2.98 (m, 1H), 2.81-2.76 (m, 1H), 1.31-1.27 (m, 2H), 1.07-1.03 (m, 2H).

This cis mixture was further separated by chiral SFC to afford arbitrarily assigned cyclopropyl-[(5S,7S)-7-hydroxy-5-phenyl-6,7-dihydro-5H-pyrrolo[1,2-b][1,2,4]triazol-2-yl]methanone (peak 1 retention time=3.345 min) (22.2 mg, 24%) as a white solid. $^1$H NMR (400 MHz, CDCl$_3$) δ 7.43-7.36 (m, 5H), 5.44-5.41 (m, 2H), 4.81 (s, 1H), 3.65-3.60 (m, 1H), 2.99-2.96 (m, 1H), 2.82-2.76 (m, 1H), 1.30-1.29 (m, 2H), 1.06-1.03 (m, 2H). LCMS R$_T$=2.061 min, m/z=270.2 [M+H]$^+$.

LCMS (10 to 80% acetonitrile in water+0.03% trifluoacetic acid over 7.0 mins) retention time 2.061 min, ESI+ found [M+H]=270.2.

cyclopropyl-[(5R,7R)-7-hydroxy-5-phenyl-6,7-dihydro-5H-pyrrolo[1,2-b][1,2,4]triazol-2-yl]methanone (peak 2, retention time=3.975 min) (32.2 mg, 35%) as a white solid. $^1$H NMR (400 MHz, CDCl$_3$) δ 7.43-7.34 (m, 5H), 5.44-5.39 (m, 2H), 3.65-3.57 (m, 1H), 3.07-3.00 (m, 1H), 2.79-2.74 (m, 1H), 1.31-1.28 (m, 2H), 1.07-1.04 (m, 2H). LCMS R$_T$=0.896 min, m/z=270.2 [M+H]$^+$.

LCMS (10 to 80% acetonitrile in water+0.03% trifluoacetic acid over 2.0 mins) retention time 0.896 min, ESI+ found [M+H]=270.2.

SFC condition: Column: OD (250 mm*30 mm, 5 μm) mobile phase: A: CO$_2$ B:0.1% NH$_3$H$_2$O EtOH Gradient: 40% of B. Flow rate: 60 mL/min; Column temp.: 40° C.

Method 67

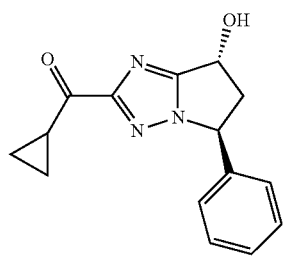

Example 88

Cyclopropyl-[(5S,7R)-7-hydroxy-5-phenyl-6,7-dihydro-5H-pyrrolo[1,2-b][1,2,4]triazol-2-yl]methanone

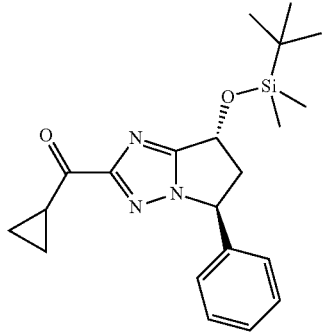 [SMILES: CC(C)(C)[Si](C)(C)O[C@@H]1C[C@@H](c2ccccc2)n2nc(C(=O)C3CC3)nc21]

Step 1: [trans-7-[tert-butyl(dimethyl)silyl]oxy-5-phenyl-6,7-dihydro-5H-pyrrolo[1,2-b][1,2,4]triazol-2-yl]-cyclopropyl-methanone To a solution of N-methoxy-N-methyl-cyclopropanecarboxamide (47 mg, 0.36 mmol) and [trans-2-bromo-5-phenyl-6,7-dihydro-5H-pyrrolo[1,2-b][1,2,4]triazol-7-yl]oxy-tert-butyl-dimethyl-silane (100 mg, 0.25 mmol) in tetrahydrofuran (10 mL) was added isopropylmagnesium chloride (2.0 M in tetrahydrofuran, 0.3 mL, 0.60 mmol) at 0° C. under nitrogen atmosphere. The mixture was stirred at 0° C. for 1 h and quenched by addition of saturated aqueous ammonium chloride (50 mL). The resulting mixture was extracted with ethyl acetate (3×30 mL). The combined organic layers were dried over sodium sulfate and concentrated under reduced pressure. The residue was purified by preparative TLC (30% ethyl acetate in petroleum ether, R$_f$=0.5) to afford [trans-7-[tert-butyl(dimethyl)silyl]oxy-5-phenyl-6,7-dihydro-5H-pyrrolo[1,2-b][1,2,4]triazol-2-yl]-cyclopropyl-methanone (50 mg, 51%) as a colorless oil. LCMS R$_T$=1.008 min, m/z=384.2 [M+H]$^+$.

LCMS (10 to 80% acetonitrile in water+0.03% trifluoacetic acid over 1.5 mins) retention time 1.008 min, ESI+ found [M+H]=384.2.

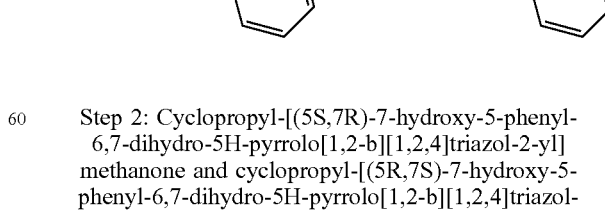

Step 2: Cyclopropyl-[(5S,7R)-7-hydroxy-5-phenyl-6,7-dihydro-5H-pyrrolo[1,2-b][1,2,4]triazol-2-yl]methanone and cyclopropyl-[(5R,7S)-7-hydroxy-5-phenyl-6,7-dihydro-5H-pyrrolo[1,2-b][1,2,4]triazol-2-yl]methanone To a solution of [trans-7-[tert-butyl(dimethyl)silyl]oxy-5-phenyl-6,7-dihydro-5H-pyrrolo[1,2-b][1,2,4]triazol-2-yl]- cyclopropyl-methanone (50 mg, 0.13 mmol) in tetrahydrofuran (5 mL) was added tetrabutylammonium fluoride (1.0 M in tetrahydrofuran, 0.52 mL, 0.52 mmol). The mixture was stirred at 25° C. for 14 h and diluted with dichloromethane (20 mL). The solution was washed with water (10 mL), brine (10 mL), dried over sodium sulfate and concentrated under reduced pressure. The residue was purified by preparative TLC (2.5% methanol in dichloromethane, $R_f$=0.5) to afford cyclopropyl-[(trans)-7-hydroxy-5-phenyl-6,7-dihydro-5H-pyrrolo[1,2-b][1,2,4]triazol-2-yl]methanone (20 mg, 57%) as a colorless oil. $^1$H NMR (400 MHz, CDCl$_3$) δ 7.43-7.38 (m, 3H), 7.19-7.17 (m, 2H), 5.76-5.73 (m, 1H), 5.54-5.52 (m, 1H), 3.29-3.25 (m, 1H), 3.03-3.00 (m, 2H), 1.31-1.28 (m, 2H), 1.06-1.03 (m, 2H).

This trans mixture (70 mg from another batch) was further separated by chiral SFC to afford arbitrarily assigned:

cyclopropyl-[(5S,7R)-7-hydroxy-5-phenyl-6,7-dihydro-5H-pyrrolo[1,2-b][1,2,4]triazol-2-yl]methanone (peak 1, retention time=3.515 min) (10.5 mg, 15%) as a white solid. $^1$H NMR (400 MHz, CDCl$_3$) δ 7.44-7.38 (m, 3H), 7.20-7.18 (m, 2H), 5.76-5.73 (m, 1H), 5.70-5.62 (m, 1H), 5.52-5.49 (m, 1H), 3.29-3.25 (m, 1H), 3.01-2.96 (m, 2H), 1.32-1.26 (m, 2H), 1.06-1.04 (m, 2H). LCMS $R_T$=0.906 min, m/z=270.2 [M+H]$^+$.

LCMS (10 to 80% acetonitrile in water+0.03% trifluoacetic acid over 2.0 mins) retention time 0.906 min, ESI+ found [M+H]=270.2.

cyclopropyl-[(5R,7S)-7-hydroxy-5-phenyl-6,7-dihydro-5H-pyrrolo[1,2-b][1,2,4]triazol-2-yl]methanone (peak 2, retention time=3.729 min) (17.0 mg, 24%) as a white solid. $^1$H NMR (400 MHz, CDCl$_3$) δ 7.44-7.38 (m, 3H), 7.20-7.18 (m, 2H), 5.76-5.73 (m, 1H), 5.65 (brs, 1H), 5.51-5.50 (m, 1H), 3.28-3.25 (m, 1H), 3.01-2.96 (m, 2H), 1.32-1.26 (m, 2H), 1.06-1.04 (m, 2H). LCMS $R_T$=0.905 min, m/z=270.2 [M+H]$^+$.

LCMS (10 to 80% acetonitrile in water+0.03% trifluoacetic acid over 2.0 mins) retention time 0.905 min, ESI+ found [M+H]=270.2.

SFC condition: Column: ChiralPak AD-3 150×4.6 mm I.D., 3 μm Mobile phase: A: CO$_2$ B: IPA (0.05% DEA) Gradient: from 5% to 40% of B in 5.5 min and hold 40% for 3 min, then 5% of B for 1.5 min Flow rate: 25 mL/min Column temp: 40° C.

Method 68

[(5S,7S)-7-fluoro-5-phenyl-6,7-dihydro-5H-pyrrolo[1,2-b][1,2,4]triazol-2-yl]-[(1S,2S)-2-methylcyclopropyl]methanone & [(5S,7S)-7-fluoro-5-phenyl-6,7-dihydro-5H-pyrrolo[1,2-b][1,2,4]triazol-2-yl]-[(1R,2R)-2-methylcyclopropyl]methanone The racemic [(5S,7S)-7-fluoro-5-phenyl-6,7-dihydro-5H-pyrrolo[1,2-b][1,2,4]triazol-2-yl]-[rac-(1S,2S)-2-methylcyclopropyl]methanone (trans mixture LHS) (80 mg) was further separated by chiral SFC to afford arbitrarily assigned:

[(5S,7S)-7-fluoro-5-phenyl-6,7-dihydro-5H-pyrrolo[1,2-b][1,2,4]triazol-2-yl]-[(1S,2S)-2-methylcyclopropyl]methanone (Peak 1, Retention time=3.714 min) (28 mg, 35%, ee: 96.1%) as a white solid. $^1$H NMR (400 MHz, CD$_3$OD) δ 7.45-7.38 (m, 3H), 7.29-7.26 (m, 2H), 6.19-6.17 (m, 0.5H), 6.05-6.03 (m, 0.5H), 5.67-5.62 (m, 1H), 3.81-3.71 (m, 1H), 2.89-2.75 (m, 2H), 1.62-1.54 (m, 1H), 1.45-1.39 (m, 1H), 1.18 (d, J=6.4 Hz, 3H), 0.99-0.96 (m, 1H). LC-MS $R_T$=0.756 min, m/z=286.1 [M+H].

LCMS (5 to 95% acetonitrile in water+0.03% trifluoacetic acid over 1.5 mins) retention time 0.756 min, ESI+ found [M+H]=286.1.

[(5S,7S)-7-fluoro-5-phenyl-6,7-dihydro-5H-pyrrolo[1,2-b][1,2,4]triazol-2-yl]-[(1R,2R)-2-methylcyclopropyl]methanone (Peak 2, Retention time=3.901 min) (48 mg, 60%, ee: 86%) as a white solid. $^1$H NMR (400 MHz, CD$_3$OD) δ 7.44-7.40 (m, 3H), 7.29-7.27 (m, 2H), 6.20-6.16 (m, 0.5H), 6.06-6.02 (m, 0.5H), 5.67-5.61 (m, 1H), 3.79-3.73 (m, 1H), 2.89-2.74 (m, 2H), 1.64-1.60 (m, 1H), 1.44-1.39 (m, 1H), 1.17 (d, J=6.0 Hz, 3H), 1.00-0.95 (m, 1H). LC-MS $R_T$=0.757 min, m/z=286.1 [M+H].

LCMS (5 to 95% acetonitrile in water+0.03% trifluoacetic acid over 1.5 mins) retention time 0.757 min, ESI+ found [M+H]=286.1

SFC condition: Column: AD (250 mm*30 mm, 5 μm); Mobile phase: A: CO$_2$ B:0.1% NH$_3$H$_2$O EtOH; Gradient: from 25% to 25% of B; Flow rate: 50 mL/min Column temperature: 40° C.

Method 69

Example 89

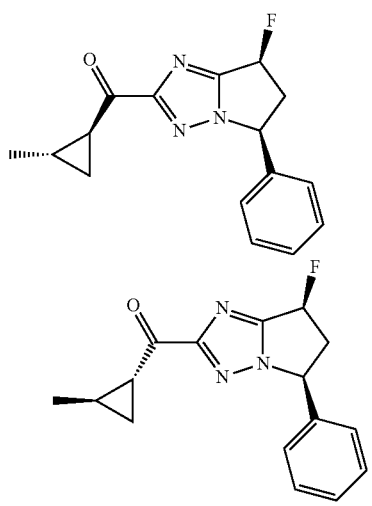

Example 90

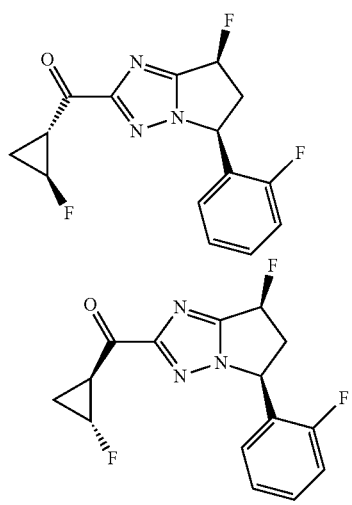

[(1R,2S)-2-fluorocyclopropyl]-[(5S,7S)-7-fluoro-5-(2-fluorophenyl)-6,7-dihydro-5H-pyrrolo[1,2-b][1,2,4]triazol-2-yl]methanone and [(1S,2R)-2-fluorocyclopropyl]-[(5S,7S)-7-fluoro-5-(2-fluorophenyl)-6,7-dihydro-5H-pyrrolo[1,2-b][1,2,4]triazol-2-yl]methanone To a solution of trans-2-fluoro-N-methoxy-N-methyl-cyclopropanecarboxamide (trans mixture) (245 mg, 1.65 mmol) and (5S,7S)-2-bromo-7-fluoro-5-(2-fluorophenyl)-6,7-dihydro-5H-pyrrolo[1,2-b][1,2,4]triazole (250 mg, 0.85 mmol) in tetrahydrofuran (10 mL) was added isopropylmagnesiumchloride (2.1 mL, 4.15 mmol, 2 M in tetrahydrofuran) at 0° C. under nitrogen atmosphere. The mixture was stirred at 0° C. for 1 hour. The reaction mixture was quenched by addition of water (10 mL) and extracted with ethyl acetate (3×20 mL). The organic layers were dried over sodium sulfate and concentrated under reduced pressure. The residue was purified by prep-TLC (33% ethyl acetate in petroleum ether, $R_f$=0.6) to afford [(1S,2R)-2-fluorocyclopropyl]-[(5S,7S)-7-fluoro-5-(2-fluorophenyl)-6,7-dihydro-5H-pyrrolo[1,2-b][1,2,4]triazol-2-yl]methanone (trans mixture) (105 mg, 41%) as a white solid. LCMS $R_T$=0.739 min, m/z=308.1 [M+H]$^+$.

LCMS (5 to 95% acetonitrile in water+0.03% trifluoacetic acid over 1.5 mins) retention time 0.739 min, ESI+ found [M+H]=308.1.

The above trans mixture was further separated by chiral SFC to afford arbitrarily assigned: [(1R,2S)-2-fluorocyclopropyl]-[(5S,7S)-7-fluoro-5-(2-fluorophenyl)-6,7-dihydro-5H-pyrrolo [1,2-b][1,2,4]triazol-2-yl]methanone (peak 1, retention time=2.773 min) (48.1 mg, 45%) as a white solid. $^1$H NMR (400 MHz, CD$_3$OD) δ 7.48-7.42 (m, 1H), 7.25-7.13 (m, 3H), 6.22-6.06 (m, 1H), 5.93-5.89 (m, 1H), 5.01-4.87 (m, 0.5H), 4.85-4.82 (m, 0.5H), 3.88-3.75 (m, 1H), 3.51-3.42 (m, 1H), 2.93-2.81 (m, 1H), 1.75-1.64 (m, 1H), 1.62-1.54 (m, 1H). LC-MS $R_T$=0.852 min, m/z=308.0 [M+H]$^+$.

LCMS (5 to 95% acetonitrile in water+0.03% trifluoacetic acid over 1.5 mins) retention time 0.852 min, ESI+ found [M+H]=308.0.

SFC condition:Column: Chiralcel OD-3 150×4.6 mm I.D., 3 μm Mobile phase: A: CO$_2$ B:ethanol (0.05% DEA) Gradient: from 5% to 40% of B in 5 min and hold 40% for 2.5 min, then 5% of B for 2.5 min Flow rate: 2.5 mL/min Column temp.: 35° C.

A larger batch of trans mixture (215 mg, 0.70 mmol) was separated by chiral SFC to give: [(1S,2R)-2-fluorocyclopropyl]-[(5S,7S)-7-fluoro-5-(2-fluorophenyl)-6,7-dihydro-5H-pyrrolo [1,2-b][1,2,4]triazol-2-yl]methanone (peak 1, retention time=2.445 min) (19.5 mg, 9%) as a white solid. $^1$H NMR (400 MHz, CDCl$_3$) δ 7.40-7.38 (m, 1H), 7.18-7.15 (m, 2H), 6.98-6.97 (m, 1H), 6.13-6.11 (m, 0.5H), 5.99-5.98 (m, 0.5H), 5.87-5.85 (m, 1H), 5.05-5.04 (m, 0.5H), 4.89-4.88 (m, 0.5H), 3.73-3.67 (m, 1H), 3.58-3.54 (m, 1H), 3.01-2.95 (m, 1H), 1.72-1.65 (m, 2H). LC-MS $R_T$=1.763 min, m/z=308.1 (M+H)+.

LCMS (10 to 80% acetonitrile in water+0.1% ammonia water over 3.0 mins) retention time 1.763 min, ESI+ found [M+H]=308.1. Note: the 1R,2S-isomer was peak 2 (retention time=2.728 min) under AD SFC conditions.

SFC condition:Column: Daicel Chiralpak AD-H (250 mm*30 mm, 5 μm) Mobile phase: A: CO2 B:ethanol (0.1% NH$_3$H$_2$O methanol) Gradient: from 15% to 15% of B in 5 min and hold 40% for 2.5 min, then 5% of B for 2.5 min Flow rate: 2.5 mL/min Column temp.: 35° C.

Method 70

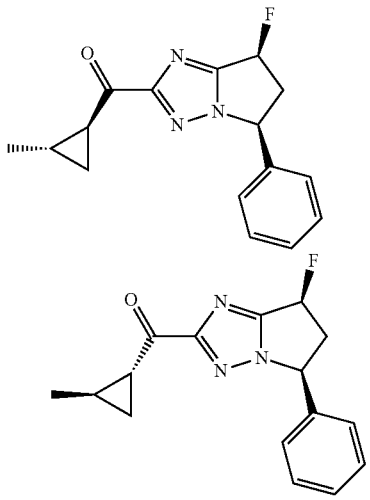

Example 91

[(5S,7S)-7-fluoro-5-phenyl-6,7-dihydro-5H-pyrrolo[1,2-b][1,2,4]triazol-2-yl]-[(1S,2S)-2-methylcyclopropyl]methanone & [(5S,7S)-7-fluoro-5-phenyl-6,7-dihydro-5H-pyrrolo[1,2-b][1,2,4]triazol-2-yl]-[(1R,2R)-2-methylcyclopropyl]methanone The racemic [(5S,7S)-7-fluoro-5-phenyl-6,7-dihydro-5H-pyrrolo[1,2-b][1,2,4]triazol-2-yl]-[rac-(1S,2S)-2-methylcyclopropyl]methanone (trans mixture LHS) (80 mg) was further separated by chiral SFC to afford arbitrarily assigned:

[(5S,7S)-7-fluoro-5-phenyl-6,7-dihydro-5H-pyrrolo[1,2-b][1,2,4]triazol-2-yl]-[(1S,2S)-2-methylcyclopropyl]methanone (Peak 1, Retention time=3.714 min) (28 mg, 35%, ee: 96.1%) as a white solid. $^1$H NMR (400 MHz, CD$_3$OD) δ 7.45-7.38 (m, 3H), 7.29-7.26 (m, 2H), 6.19-6.17 (m, 0.5H), 6.05-6.03 (m, 0.5H), 5.67-5.62 (m, 1H), 3.81-3.71 (m, 1H), 2.89-2.75 (m, 2H), 1.62-1.54 (m, 1H), 1.45-1.39 (m, 1H), 1.18 (d, J=6.4 Hz, 3H), 0.99-0.96 (m, 1H). LC-MS $R_T$=0.756 min, m/z=286.1 [M+H]$^+$.

LCMS (5 to 95% acetonitrile in water+0.03% trifluoacetic acid over 1.5 mins) retention time 0.756 min, ESI+ found [M+H]=286.1.

[(5S,7S)-7-fluoro-5-phenyl-6,7-dihydro-5H-pyrrolo[1,2-b][1,2,4]triazol-2-yl]-[(1R,2R)-2-methylcyclopropyl]methanone (Peak 2, Retention time=3.901 min) (48 mg, 60%, ee: 86%) as a white solid. $^1$H NMR (400 MHz, CD$_3$OD) δ 7.44-7.40 (m, 3H), 7.29-7.27 (m, 2H), 6.20-6.16 (m, 0.5H), 6.06-6.02 (m, 0.5H), 5.67-5.61 (m, 1H), 3.79-3.73 (m, 1H), 2.89-2.74 (m, 2H), 1.64-1.60 (m, 1H), 1.44-1.39 (m, 1H), 1.17 (d, J=6.0 Hz, 3H), 1.00-0.95 (m, 1H). LC-MS $R_T$=0.757 min, m/z=286.1 [M+H]$^+$.

LCMS (5 to 95% acetonitrile in water+0.03% trifluoacetic acid over 1.5 mins) retention time 0.757 min, ESI+ found [M+H]=286.1

SFC condition: Column: AD (250 mm*30 mm, 5 μm); Mobile phase: A: CO$_2$ B:0.1% NH$_3$H$_2$O EtOH; Gradient: from 25% to 25% of B; Flow rate: 50 mL/min Column temperature: 40° C.

Method 71

Example 92

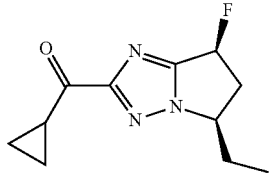

Cyclopropyl-[(5R,7S)-5-ethyl-7-fluoro-6,7-dihydro-5H-pyrrolo[1,2-b][1,2,4]triazol-2-yl]methanone

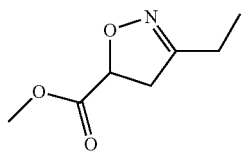

Step 1: Ethyl 3-ethyl-4,5-dihydroisoxazole-5-carboxylate

To a solution of ethyl acrylate (89.6 mL, 841.85 mmol), di-tert-butyldicarbonate (58.0 mL, 252.55 mmol) and 4-dimethylaminopyridine (2.1 g, 16.84 mmol) in acetonitrile (50 mL) was added a solution of 1-nitropropane (15.1 mL, 168.37 mmol) under 25° C. The mixture was stirred at 25° C. for 5 h and quenched by addition of saturated ammonium chloride solution (80 mL). The mixture was extracted with ethyl acetate (3×100 mL). The combined organic layers were dried over sodium sulfate and concentrated under reduced pressure. The residue was purified by flash chromatography (silica gel, 100-200 mesh, 0 to 10% ethyl acetate in petroleum ether) to afford ethyl 3-ethyl-4,5-dihydroisoxazole-5-carboxylate (25.5 g, 88%) as a colorless oil. $^1$H NMR (400 MHz, CDCl$_3$) δ 4.94-4.86 (m, 1H), 4.24-4.13 (m, 2H), 3.21-3.14 (m, 2H), 2.40-2.29 (m, 2H), 1.30-1.24 (m, 3H), 1.16-1.11 (m, 3H)

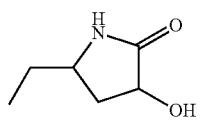

Step 2: 5-ethyl-3-hydroxy-pyrrolidin-2-one

A mixture of ethyl 3-ethyl-4,5-dihydroisoxazole-5-carboxylate (15.0 g, 87.62 mmol) and palladium (10% on carbon, 6.7 g) in ethanol (300 mL) was stirred under hydrogen atmosphere (50 psi) at 40° C. for 16 h and filtered. The filtrate was concentrated under reduced pressure to afford crude 5-ethyl-3-hydroxy-pyrrolidin-2-one (11.0 g, 97%) as a colorless oil.

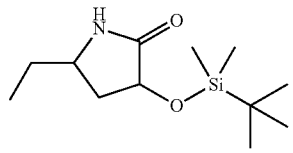 [SMILES: CCC1CC(O[Si](C)(C)C(C)(C)C)C(=O)N1]

Step 3: 3-[tert-butyl(dimethyl)silyl]oxy-5-ethyl-pyrrolidin-2-one

To a solution of 5-ethyl-3-hydroxy-pyrrolidin-2-one (11.0 g, 85.17 mmol) in dichloromethane (200 mL) was added imidazole (11.6 g, 170.33 mmol) and tert-butyldimethylchlorosilane (19.2 g, 127.75 mmol). The reaction mixture was stirred at 25° C. for 16 h and filtered. The filtrate was concentrated under reduced pressure. The residue was purified by column chromatography (silica gel, 100-200 mesh, 0 to 30% ethyl acetate in petroleum ether) to afford 3-[tert-butyl(dimethyl)silyl]oxy-5-ethyl-pyrrolidin-2-one (10.0 g, 48%) as a colorless oil.

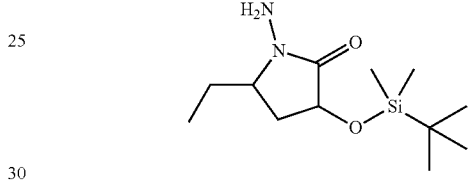

Step 4: 1-amino-3-[tert-butyl(dimethyl)silyl]oxy-5-ethyl-pyrrolidin-2-one

To a solution of 3-[tert-butyl(dimethyl)silyl]oxy-5-ethyl-pyrrolidin-2-one (10.0 g, 41.08 mmol) in N,N-dimethylformamide (200 mL) was added sodium hydride (60%, 2.5 g, 61.62 mmol). After stirred at 0° C. for 20 min, the mixture was added O-(diphenylphosphoryl) hydroxylamine (14.4 g, 61.62 mmol) and stirred at 25° C. for 16 h. The reaction mixture was filtered and the filtrate was concentrated under reduced pressure to afford crude (1-amino-3-[tert-butyl(dimethyl)silyl]oxy-5-ethyl-pyrrolidin-2-one (10.0 g, 94%) as a yellow oil. LCMS RT=1.130 min, m/z=259.2 [M+H]$^+$.

LCMS (10 to 80% acetonitrile in water+0.03% trifluoacetic acid over 2.0 mins) retention time 1.130 min, ESI+ found [M+H]=259.2.

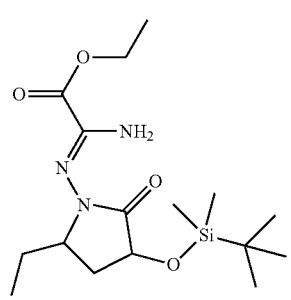 [SMILES: CCOC(=O)/C(N)=N/N1C(=O)C(O[Si](C)(C)C(C)(C)C)CC1CC]

Step 5: Ethyl 2-[[3-[tert-butyl(dimethyl)silyl]oxy-5-ethyl-2-oxo-pyrrolidin-1-yl]amino]-2-imino-acetate A mixture of 1-amino-3-[tert-butyl(dimethyl)silyl]oxy-5-ethyl-pyrrolidin-2-one (10.0 g, 38.7 mmol) and ethyl 2-ethoxy-2-imino-acetate (14.0 g, 96.74 mmol) in ethanol (250 mL) was stirred at 90° C. for 16 h and filtered. The filtrate was concentrated under reduced pressure to afford crude ethyl 2-[[3-[tert-butyl(dimethyl)silyl]oxy-5-ethyl-2-oxo-pyrrolidin-1-yl]amino]-2-imino-acetate (13.0 g, 94%) as a yellow oil. LCMS RT=1.148 min, m/z=358.3 [M+H]$^+$.

LCMS (10 to 80% acetonitrile in water+0.03% trifluoacetic acid over 2.0 mins) retention time 1.148 min, ESI+ found [M+H]=358.3.

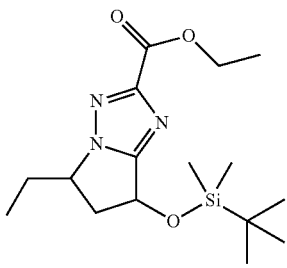 [SMILES: CCOC(=O)c1nc2n(n1)C(CC)CC2O[Si](C)(C)C(C)(C)C]

Step 6: Ethyl 7-[tert-butyl(dimethyl)silyl]oxy-5-ethyl-6,7-dihydro-5H-pyrrolo[1,2-b][1,2,4]triazole-2-carboxylate A mixture of ethyl 2-[[3-[tert-butyl(dimethyl)silyl]oxy-5-ethyl-2-oxo-pyrrolidin-1-yl]amino]-2-imino-acetate (13.0 g, 36.36 mmol) and p-toluenesulfonic acid (7.5 g, 43.63 mmol) in toluene (250 mL) was stirred at 120° C. for 16 h and filtered. The filtrate was concentrated under reduced pressure to afford crude ethyl 7-[tert-butyl(dimethyl)silyl]oxy-5-ethyl-6,7-dihydro-5H-pyrrolo[1,2-b][1,2,4]triazole-2-carboxylate (12.0 g, 97%) as a yellow oil. LCMS RT=0.823 min, m/z=340.2 [M+H]$^+$.

LCMS (5 to 95% acetonitrile in water+0.03% trifluoacetic acid over 1.5 mins) retention time 0.823 min, ESI+ found [M+H]=340.2.

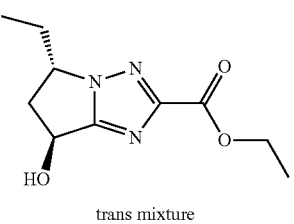 [SMILES: CCOC(=O)c1nc2n(n1)[C@@H](CC)C[C@@H]2O]

trans mixture

Step 7: Ethyl Trans-5-ethyl-7-hydroxy-6,7-dihydro-5H-pyrrolo[1,2-b][1,2,4]triazole-2-carboxylate To a solution of ethyl 7-[tert-butyl(dimethyl)silyl]oxy-5-ethyl-6,7-dihydro-5H-pyrrolo[1,2-b][1,2,4]triazole-2-carboxylate (12.0 g, 35.35 mmol) in tetrahydrofuran (200 mL) was added tetrabutylammonium fluoride (1.0 M in tetrahydrofuran, 35.35 mL, 35.35 mmol). The reaction mixture was stirred at 40° C. for 16 h and concentrated under reduced pressure. The residue was diluted with water (70 mL) and extracted with ethyl acetate (3×70 mL). The combined organic layers were concentrated under reduced pressure. The residue was purified by column chromatography (silica gel, 100-200 mesh, 0 to 100% ethyl acetate in petroleum ether) to afford ethyl trans-5-ethyl-7-hydroxy-6,7-dihydro-5H-pyrrolo[1,2-b][1,2,4]triazole-2-carboxylate (2.3 g, 29%) as pale red oil (along with cis isomer (2.8 g, 35%)). $^1$H NMR (400 MHz, CDCl$_3$) δ 5.32-5.27 (m, 1H), 4.49-4.43 (m, 3H), 3.24-3.17 (m, 1H), 2.41-2.36 (m, 1H), 2.21-2.12 (m, 1H), 1.94-1.84 (m, 1H), 1.36 (t, J=7.2 Hz, 3H), 1.03 (t, J=7.2 Hz, 3H).

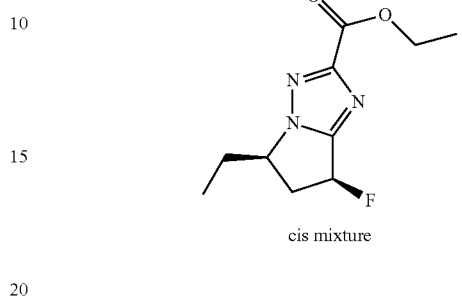

cis mixture

Step 8: Ethyl Cis-5-ethyl-7-fluoro-6,7-dihydro-5H-pyrrolo[1,2-b][1,2,4]triazole-2-carboxylate To a solution of ethyl trans-5-ethyl-7-hydroxy-6,7-dihydro-5H-pyrrolo[1,2-b][1,2,4]triazole-2-carboxylate (2.3 g, 10.21 mmol) in dichloromethane (50 mL) was added diethylaminosulfur trifluoride (6.6 g, 40.85 mmol) at 0° C. dropwise. The reaction mixture was stirred at 0° C. for 2 h and quenched by addition of saturated sodium bicarbonate solution (20 mL). The mixture was extracted with dichloromethane (3×50 mL). The combined organic layers were washed with brine (50 mL), dried over sodium sulfate and concentrated under reduced pressure. The residue was purified by column chromatography (silica gel, 100-200 mesh, 0 to 50% ethyl acetate in petroleum ether) to give ethyl cis-5-ethyl-7-fluoro-6,7-dihydro-5H-pyrrolo[1,2-b][1,2,4]triazole-2-carboxylate (800 mg, 34%) as a yellow oil. $^1$H NMR (400 MHz, CDCl$_3$) δ 6.00-5.78 (m, 1H), 4.53-4.37 (m, 3H), 3.35-3.16 (m, 1H), 2.69-2.54 (m, 1H), 2.13-2.05 (m, 1H), 1.98-1.91 (m, 1H), 1.43 (t, J=7.2 Hz, 3H), 1.02 (t, J=7.6 Hz, 3H).

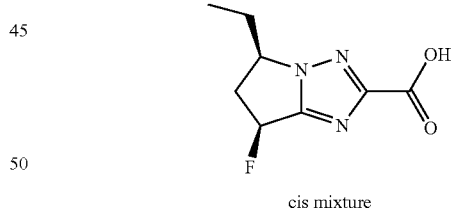

cis mixture

Step 9: cis-5-ethyl-7-fluoro-6,7-dihydro-5H-pyrrolo[1,2-b][1,2,4]triazole-2-carboxylic Acid A mixture of ethyl cis-5-ethyl-7-fluoro-6,7-dihydro-5H-pyrrolo[1,2-b][1,2,4]triazole-2-carboxylate (200 mg, 0.88 mmol) in tetrahydrofuran (3 mL), water (2 mL) and methanol (1 mL) was added lithium hydroxide monohydrate (148 mg, 3.52 mmol). The mixture was stirred at 25° C. for 16 h and concentrated under reduced pressure. The residue was diluted with ice water (20 mL) and adjusted to pH=3 by addition of aqueous hydrochloric acid (4 M). The mixture was extracted with ethyl acetate (3×20 mL). The combined organic layers were concentrated under reduced pressure to give crude cis-5-ethyl-7-fluoro-6,7-dihydro-5H-pyrrolo[1,2-b][1,2,4]triazole-2-carboxylic acid (150 mg, 86%) as a yellow oil.

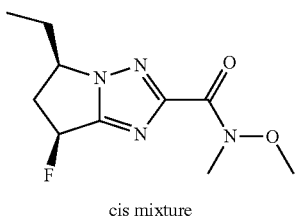 [SMILES: CC[C@@H]1C[C@H](F)c2nc(C(=O)N(C)OC)nn21]

cis mixture

Step 10: Cis-5-ethyl-7-fluoro-N-methoxy-N-methyl-6,7-dihydro-5H-pyrrolo[1,2-b][1,2,4]triazole-2-carboxamide, cis mixture A mixture of cis-5-ethyl-7-fluoro-6,7-dihydro-5H-pyrrolo[1,2-b][1,2,4]triazole-2-carboxylic acid (100 mg, 0.50 mmol), 1-hydroxybenzotriazole (34 mg, 0.25 mmol), N,N-diisopropylethylamine (0.21 mL, 1.26 mmol), N,O-dimethylhydroxylamine hydrochloride (74 mg, 0.75 mmol) and 1-(3-dimethylaminopropyl)-3-ethylcarbodiimidehydrochloride (116 mg, 0.60 mmol) in dichloromethane (5 mL) was stirred at 25° C. for 16 h. The mixture was diluted with water (20 mL) and extracted with ethyl acetate (3×20 mL). The combined organic layers were washed with brine (20 mL), dried over sodium sulfate and concentrated under reduced pressure. The residue was purified by column chromatography (silica gel, 100-200 mesh, 0 to 60% ethyl acetate in petroleum ether) to give cis-5-ethyl-7-fluoro-N-methoxy-N-methyl-6,7-dihydro-5H-pyrrolo[1,2-b][1,2,4]triazole-2-carboxamide (120 mg, 99%) as a colorless oil. $^1$H NMR (400 MHz, CDCl$_3$) δ 5.99-5.79 (m, 1H), 4.40-4.39 (m, 1H), 3.84 (s, 3H), 3.43 (s, 3H), 3.36-3.16 (m, 1H), 2.67-2.54 (m, 1H), 2.14-2.03 (m, 1H), 1.97-1.90 (m, 1H), 1.07-1.03 (m, 3H) LCMS R$_T$=0.481 min, m/z=243.1 [M+H]$^+$.

LCMS (5 to 95% acetonitrile in water+0.03% trifluoacetic acid over 1.5 mins) retention time 0.481 min, ESI+ found [M+H]=243.1.

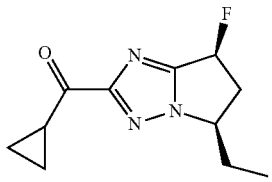 [SMILES: CC[C@@H]1C[C@H](F)c2nc(C(=O)C3CC3)nn21]

Step 11: Cyclopropyl-[(5R,7S)-5-ethyl-7-fluoro-6,7-dihydro-5H-pyrrolo[1,2-b][1,2,4]triazol-2-yl]methanone To a solution of cis-5-ethyl-7-fluoro-N-methoxy-N-methyl-6,7-dihydro-5H-pyrrolo[1,2-b][1,2,4]triazole-2-carboxamide (100 mg, 0.41 mmol) was added cyclopropylmagnesium bromide (0.5 M in tetrahydrofuran, 2.0 mL, 1.0 mmol) under nitrogen at 0° C. After addition, the mixture was stirred at 0° C. for 1 h and quenched by addition of saturated aqueous ammonium chloride (20 mL). The resulting mixture was extracted with ethyl acetate (3×20 mL). The combined organic layers were washed with brine (20 mL), dried over sodium sulfate and concentrated under reduced pressure. The residue was purified by preparative TLC (50% ethyl acetate in petroleum ether, R$_f$=0.4) to give cyclopropyl-[cis-5-ethyl-7-fluoro-6,7-dihydro-5H-pyrrolo[1,2-b][1,2,4]triazol-2-yl]methanone (80 mg, 87%) as a yellow oil. This cis mixture was further separated by chiral SFC to afford arbitrarily assigned:

cyclopropyl-[(5R,7S)-5-ethyl-7-fluoro-6,7-dihydro-5H-pyrrolo[1,2-b][1,2,4]triazol-2-yl]methanone (peak 1, retention time=3.928 min) (22.5 mg, 28%) as an orange solid (the (5S,7R)-isomer was also collected as peak 2 (retention time=4.391 min, 18.8 mg, 22%)). $^1$H NMR (400 MHz, CD$_3$OD) δ 6.09-5.89 (m, 1H), 4.55-4.45 (m, 1H), 3.43-3.36 (m, 1H), 3.15-3.06 (m, 1H), 2.67-2.53 (m, 1H), 2.09-1.93 (m, 2H), 1.23-1.18 (m, 2H), 1.17-1.11 (m, 2H), 1.05 (t, J=7.2 Hz, 3H). LCMS R$_T$=0.770 min, m/z=224.0 [M+H]$^+$.

LCMS (5 to 95% acetonitrile in water+0.03% trifluoacetic acid over 1.5 mins) retention time 0.770 min, ESI+ found [M+H]=224.0.

SFC condition: Column: Chiralcel IC 100×4.6 mm I.D., 3 μm Mobile phase: A: CO2 B:methanol (0.05% DEA) Gradient: from 5% to 40% of B in 3.5 min and hold 40% for 2.5 min, then 5% of B for 1.5 min Flow rate: 3 mL/min Column temperature:40° C.

Method 72

Example 93

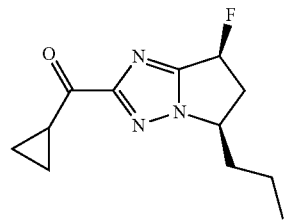

Cyclopropyl-[(5R,7S)-7-fluoro-5-propyl-6,7-dihydro-5H-pyrrolo[1,2-b][1,2,4]triazol-2-yl]methanone

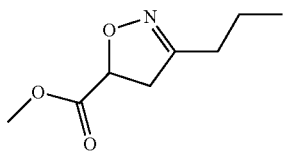

Step 1: Ethyl 3-propyl-4,5-dihydroisoxazole-5-carboxylate

To a solution of ethyl acrylate (10.32 mL, 96.97 mmol), di-tert-butyldicarbonate (6.68 mL, 29.09 mmol) and 4-dimethylaminopyridine (0.24 g, 1.94 mmol) in acetonitrile (20 mL) was added a solution of 1-nitrobutane (2.01 mL, 19.39 mmol) under 25° C. After addition, the mixture was stirred at 25° C. for 5 h and quenched by addition of saturated ammonium chloride solution (80 mL). The mixture was extracted with ethyl acetate (3×100 mL). The combined organic layers were dried over sodium sulfate and concentrated under reduced pressure. The residue was purified by flash chromatography on silica gel eluting with (silica gel, 100-200 mesh, 0 to 10% ethyl acetate in petroleum ether) to afford ethyl 3-propyl-4,5-dihydroisoxazole-5-carboxylate (3.2 g, 89%) as a colorless oil. $^1$H NMR (400 MHz, CDCl$_3$) δ 4.98-4.93 (m, 1H), 4.27-4.20 (m, 2H), 3.21-3.18 (m, 2H), 2.37-2.33 (m, 2H), 1.64-1.58 (m, 2H), 1.33-1.28 (m, 3H), 0.98-0.94 (m, 3H).

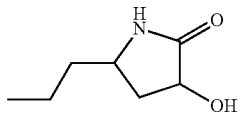

Step 2: Hydroxy-5-propyl-pyrrolidin-2-one

A mixture of ethyl 3-propyl-4,5-dihydroisoxazole-5-carboxylate (8.0 g, 43.19 mmol) and palladium (10% on carbon, 3.3 g) in ethanol (200 mL) was stirred under hydrogen atmosphere (50 psi) at 40° C. for 16 h and filtrated. The filtrate was concentrated under reduced pressure to afford crude 3-hydroxy-5-propyl-pyrrolidin-2-one (6.1 g, 99%) as a light yellow oil. LCMS R$_T$=0.263 min, m/z=144.3 [M+H]$^+$.

LCMS (10 to 80% acetonitrile in water+0.03% trifluoacetic acid over 2.0 mins) retention time 0.263 min, ESI+ found [M+H]=144.3.

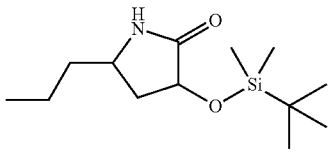 [SMILES: CCCC1CC(O[Si](C)(C)C(C)(C)C)C(=O)N1]

Step 3: 3-[tert-butyl(dimethyl)silyl]oxy-5-propyl-pyrrolidin-2-one

To a solution of 3-hydroxy-5-propyl-pyrrolidin-2-one (6.1 g, 42.60 mmol) in dichloromethane (200 mL) was added imidazole (5.8 g, 85.21 mmol) and tert-butyldimethylchlorosilane (9.6 g, 63.91 mmol). The reaction mixture was stirred at 25° C. for 16 h and filtered. The filtrate was concentrated under reduced pressure and the residue was purified by column chromatography (silica gel, 100-200 mesh, 0 to 20% ethyl acetate in petroleum ether) to afford 3-[tert-butyl(dimethyl)silyl]oxy-5-propyl-pyrrolidin-2-one (7.5 g, 68%) as a yellow oil. LCMS R$_T$=1.474 min, m/z=258.2 [M+H]$^+$.

LCMS (10 to 80% acetonitrile in water+0.03% trifluoacetic acid over 2.0 mins) retention time 1.474 min, ESI+ found [M+H]=258.2.

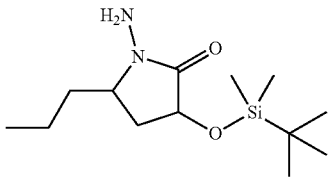 [SMILES: CCCC1CC(O[Si](C)(C)C(C)(C)C)C(=O)N1N]

Step 4: 1-amino-3-[tert-butyl(dimethyl)silyl]oxy-5-propyl-pyrrolidin-2-one

To a solution of 3-[tert-butyl(dimethyl)silyl]oxy-5-propyl-pyrrolidin-2-one (7.0 g, 27.19 mmol) in N,N-dimethylformamide (200 mL) was added sodium hydride (60%,1.6 g, 40.79 mmol, 60%). After stirred at 0° C. for 20 min, the mixture was added O-(diphenylphosphoryl) hydroxylamine (9.5 g, 40.79 mmol) and stirred at 25° C. for 16 h. The reaction mixture was filtered and the filtrate was concentrated under reduced pressure to afford crude (1-amino-3-[tert-butyl(dimethyl)silyl]oxy-5-propyl-pyrrolidin-2-one (6.8 g, 92%) as a yellow oil. This crude was used in next step without further purification. LCMS R$_T$=0.766 min, m/z=273.3 [M+H]$^+$.

LCMS (5 to 95% acetonitrile in water+0.03% trifluoacetic acid over 1.5 mins) retention time 0.766 min, ESI+ found [M+H]=273.3.

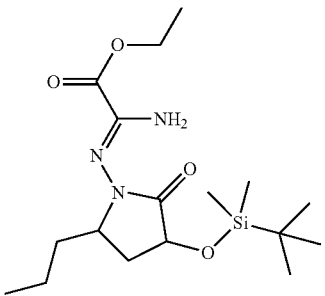 [SMILES: CCCC1CC(O[Si](C)(C)C(C)(C)C)C(=O)N1/N=C(\N)C(=O)OCC]

Step 5: Ethyl 2-[[3-[tert-butyl(dimethyl)silyl]oxy-2-oxo-5-propyl-pyrrolidin-1-yl]amino]-2-imino-acetate A mixture of 1-amino-3-[tert-butyl(dimethyl)silyl]oxy-5-propyl-pyrrolidin-2-one (6.6 g, 24.22 mmol) and ethyl 2-ethoxy-2-imino-acetate (8.8 g, 60.56 mmol) in ethanol (100 mL) was stirred at 90° C. for 16 h and filtered. The filtrate was concentrated under reduced pressure to afford crude ethyl 2-[[3-[tert-butyl(dimethyl)silyl]oxy-2-oxo-5-propyl-pyrrolidin-1-yl]amino]-2-imino-acetate (9.0 g, 100%) as a yellow oil. LCMS R$_T$=1.192 min, m/z=372.3 [M+H]$^+$.

LCMS (10 to 80% acetonitrile in water+0.03% trifluoacetic acid over 2.0 mins) retention time 1.192 min, ESI+ found [M+H]=372.3.

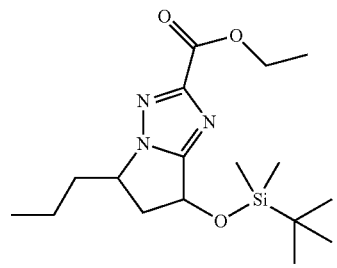 [SMILES: CCCC1CC(O[Si](C)(C)C(C)(C)C)c2nc(C(=O)OCC)nn21]

Step 6: Ethyl 7-[tert-butyl(dimethyl)silyl]oxy-5-propyl-6,7-dihydro-5H-pyrrolo[1,2-b][1,2,4]triazole-2-carboxylate A mixture of ethyl 2-[[3-[tert-butyl(dimethyl)silyl]oxy-2-oxo-5-propyl-pyrrolidin-1-yl]amino]-2-imino-acetate (9.0 g, 24.22 mmol) and p-toluenesulfonic acid (6.3 g, 36.33 mmol) in toluene (150 mL) was stirred at 120° C. for 16 h and filtered. The filtrate was concentrated under reduced pressure to afford crude ethyl 7-[tert-butyl(dimethyl)silyl]oxy-5-propyl-6,7-dihydro-5H-pyrrolo[1,2-b][1,2,4]triazole-2-carboxylate (8.3 g, 97%) as a yellow oil. LCMS $R_T$=0.803 min, m/z=240.2 [M-TBS]$^+$.

LCMS (10 to 80% acetonitrile in water+0.03% trifluoacetic acid over 2.0 mins) retention time 0.803 min, ESI+ found [M-TBS]=240.2.

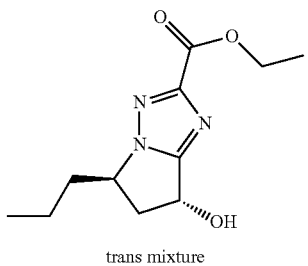 [SMILES: CCC[C@@H]1C[C@@H](O)c2nc(C(=O)OCC)nn21]

trans mixture

Step 7: Ethyl Trans-7-hydroxy-5-propyl-6,7-dihydro-5H-pyrrolo[1,2-b][1,2,4]triazole-2-carboxylate To a solution of ethyl 7-[tert-butyl(dimethyl)silyl]oxy-5-propyl-6,7-dihydro-5H-pyrrolo[1,2-b][1,2,4]triazole-2-carboxylate (8.30 g, 23.48 mmol) in tetrahydrofuran (150 mL) was added tetrabutylammonium fluoride in tetrahydrofuran (11.74 mL, 11.74 mmol). The reaction mixture was stirred at 40° C. for 15 h and concentrated under reduced pressure. The residue was diluted with water (70 mL) and extracted with ethyl acetate (3×70 mL). The combined organic layers were concentrated under reduced pressure. The residue was purified by flash chromatography (silica gel, 100-200 mesh, 0 to 60% ethyl acetate in petroleum ether) to afford ethyl trans-7-hydroxy-5-propyl-6,7-dihydro-5H-pyrrolo[1,2-b][1,2,4]triazole-2-carboxylate (1.0 g, 18%) as a yellow oil (along with same amount of cis product): $^1$H NMR (400 MHz, CDCl$_3$) δ 5.33-5.31 (m, 1H), 4.64-4.63 (m, 1H), 4.46-4.40 (m, 2H), 2.87-2.85 (m, 1H), 2.70-2.66 (m, 1H), 2.66-2.06 (m, 1H), 1.63-1.33 (m, 6H), 0.96-0.92 (m, 3H).

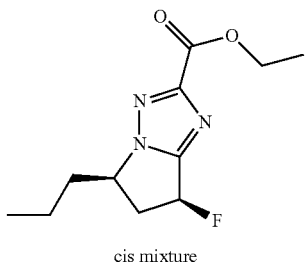 [SMILES: CCC[C@@H]1C[C@H](F)c2nc(C(=O)OCC)nn21]

cis mixture

Step 8: Ethyl Cis-7-fluoro-5-propyl-6,7-dihydro-5H-pyrrolo[1,2-b][1,2,4]triazole-2-carboxylate To a solution of ethyl trans-7-hydroxy-5-propyl-6,7-dihydro-5H-pyrrolo[1,2-b][1,2,4]triazole-2-carboxylate (800 mg, 3.34 mmol) in dichloromethane (30 mL) was added diethylaminosulfur trifluoride (2.2 g, 13.37 mmol) at 0° C.

The reaction mixture was stirred at 0° C. for 2 h and quenched by addition of saturated sodium bicarbonate solution (20 mL). The mixture was extracted with dichloromethane (3×50 mL). The combined organic layers were washed with brine (50 mL), dried over sodium sulfate and concentrated under reduced pressure. The residue was purified by column chromatography (silica gel, 100-200 mesh, 0 to 60% ethyl acetate in petroleum ether) to give ethyl cis-7-fluoro-5-propyl-6,7-dihydro-5H-pyrrolo[1,2-b][1,2,4]triazole-2-carboxylate (270 mg, 34%) as a yellow oil. $^1$H NMR (400 MHz, CDCl$_3$) δ 5.99-5.78 (m, 1H), 4.53-4.40 (m, 3H), 3.34-3.15 (m, 1H), 2.70-2.54 (m, 1H), 2.14-2.02 (m, 1H), 1.91-1.78 (m, 1H), 1.63-1.50 (m, 1H), 1.46-1.41 (m, 4H), 0.98 (t, J=7.2 Hz, 3H).

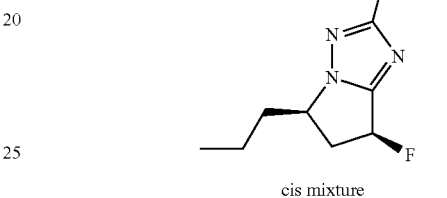

cis mixture

Step 9: Cis-7-fluoro-5-propyl-6,7-dihydro-5H-pyrrolo[1,2-b][1,2,4]triazole-2-carboxylic acid A mixture of ethyl cis-7-fluoro-5-propyl-6,7-dihydro-5H-pyrrolo[1,2-b][1,2,4]triazole-2-carboxylate (260 mg, 1.08 mmol) and lithium hydroxide monohydrate (135 mg, 3.23 mmol) in tetrahydrofuran (2 mL), water (1 mL) and methyl alcohol (0.5 mL) was stirred at 25° C. for 4 h and then concentrated under reduce pressure. The residue was diluted with ice water (20 mL) and adjusted to pH=3 by addition of aqueous hydrochloric acid (4 M). The mixture was extracted with ethyl acetate (3×20 mL). The combined organic layers were concentrated under reduced pressure to afford crude cis-7-fluoro-5-propyl-6,7-dihydro-5H-pyrrolo[1,2-b][1,2,4]triazole-2-carboxylic acid (225 mg, 98%) as a yellow solid.

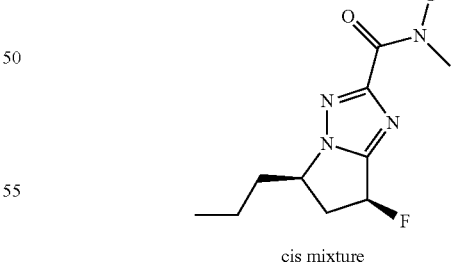

cis mixture

Step 10: Cyclopropyl-[cis-7-fluoro-5-propyl-6,7-dihydro-5H-pyrrolo[1,2-b][1,2,4]triazol-2-yl]methanone A mixture of cis-7-fluoro-5-propyl-6,7-dihydro-5H-pyrrolo[1,2-b][1,2,4]triazole-2-carboxylic acid (200 mg, 0.94 mmol), 1-hydroxybenzotriazole (63 mg, 0.47 mmol), N,O- dimethylhydroxylamine hydrochloride (137 mg, 1.41 mmol), N,N-diisopropylethylamine (0.39 mL, 2.35 mmol) and 1-(3-dimethylaminopropyl)-3-ethylcarbodiimidehydrochloride (215 mg, 1.13 mmol) was stirred at 25° C. for 3 h. The mixture was diluted with water (20 mL) and extracted with ethyl acetate (3×20 mL). The combined organic layers were washed with brine (20 mL), dried over sodium sulfate and concentrated reduced pressure. The residue was purified by column chromatography (silica gel, 100-200 mesh, 0 to 60% ethyl acetate in petroleum ether) to give cis-7-fluoro-N-methoxy-N-methyl-5-propyl-6,7-dihydro-5H-pyrrolo[1,2-b][1,2,4]triazole-2-carboxamide (180 mg, 75%) as a colorless oil. $^1$H NMR (400 MHz, CDCl$_3$) δ 6.00-5.76 (m, 1H), 4.51-4.37 (m, 1H), 3.84 (s, 3H), 3.43 (s, 2H), 3.33-3.17 (m, 1H), 2.70-2.53 (m, 1H), 2.11-1.97 (m, 1H), 1.89-1.77 (m, 1H), 1.66-1.53 (m, 1H), 1.51-1.38 (m, 1H), 0.98 (t, J=7.2 Hz, 3H).

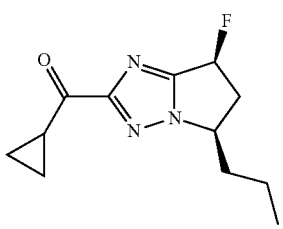 [SMILES: CCC[C@@H]1C[C@H](F)c2nc(C(=O)C3CC3)nn21]

Step 11: Cyclopropyl-[(5R,7S)-7-fluoro-5-propyl-6,7-dihydro-5H-pyrrolo[1,2-b][1,2,4]triazol-2-yl]methanone To a solution of cis-7-fluoro-N-methoxy-N-methyl-5-propyl-6,7-dihydro-5H-pyrrolo[1,2-b][1,2,4]triazole-2-carboxamide (170 mg, 0.66 mmol) was added cyclopropylmagnesium bromide (0.5 M in tetrahydrofuran, 3.21 mL, 1.61 mmol) under nitrogen at 0° C. After addition, the mixture was stirred at 0° C. for 1 h and quenched by addition of aqueous saturated ammonium chloride solution (20 mL). The resulting mixture was extracted with ethyl acetate (3×20 mL). The combined organic layers were washed with brine (20 mL), dried over sodium sulfate and concentrated under reduced pressure. The residue was purified by preparative TLC (50% ethyl acetate in petroleum ether, Rf=0.4) to give cyclopropyl-[cis-7-fluoro-5-propyl-6,7-dihydro-5H-pyrrolo[1,2-b][1,2,4]triazol-2-yl]methanone (100 mg, 64%) as a colorless oil. The cis mixture was further separated by chiral SFC to afford arbitrarily assigned: cyclopropyl-[(5R,7S)-7-fluoro-5-propyl-6,7-dihydro-5H-pyrrolo[1,2-b][1,2,4]triazol-2-yl]methanone (peak 1, retention time=3.997 min) (40.0 mg, 40%) as colorless oil. $^1$H NMR (400 MHz, CD$_3$OD) δ 6.07-5.91 (m, 1H), 4.59-4.53 (m, 1H), 3.42-3.33 (m, 1H), 3.11-3.07 (m, 1H), 2.67-2.52 (m, 1H), 2.02-1.98 (m, 1H), 1.91-1.80 (m, 1H), 1.69-1.57 (m, 1H), 1.52-1.38 (m, 1H), 1.23-1.11 (m, 4H), 1.01 (t, J=7.2 Hz, 3H). LCMS R$_T$=0.972 min, m/z=238.2 [M+H]$^+$.

LCMS (10 to 80% acetonitrile in water+0.03% trifluoacetic acid over 2.0 mins) retention time 0.972 min, ESI+ found [M+H]=238.2.

SFC condition: Column: Chiralcel IC 100×4.6 mm I.D., 3 μm Mobile phase: A: C$_{O2}$ B:methanol (0.05% DEA) Gradient: from 5% to 40% of B in 3.5 min and hold 40% for 2.5 min, then 5% of B for 1.5 min Flow rate: 3 mL/min Column temperature: 40° C.

Note: the 5S,7R-isomer was also collected as colorless oil. (peak 2, retention time=4.420 min) (42.0 mg, 42%)

Method 73

Example 94

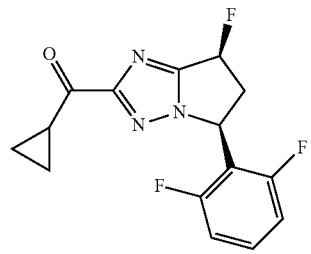

Cyclopropyl-[(5S,7S)-5-(2,6-difluorophenyl)-7-fluoro-6,7-dihydro-5H-pyrrolo[1,2-b][1,2,4]triazol-2-yl]methanone

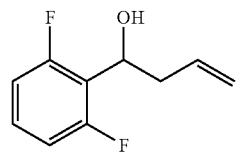

Step 1: 1-(2,6-difluorophenyl)but-3-en-1-ol

To a solution of 2,6-difluorobenzaldehyde (90.0 g, 633.36 mmol) in tetrahydrofuran (2000 mL) was added allylmagnesium bromide (1.0 M in tetrahydrofuran, 760.0 mL, 760.0 mmol) dropwise at 0° C. under nitrogen atmosphere. The mixture was allowed to warm to 25° C. and stirred for 2 h before quenched by addition of saturated aqueous ammonium chloride (2000 mL). The resulting mixture was extracted with ethyl acetate (2×2000 mL). The combined organic layers were washed with brine (1000 mL), dried over sodium sulfate and concentrated under reduced pressure to give crude 1-(2,6-difluorophenyl)but-3-en-1-ol (116 g, 99%) as colorless oil.

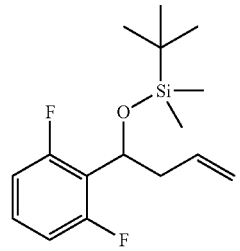 [SMILES: C=CCC(O[Si](C)(C)C(C)(C)C)c1c(F)cccc1F]

Step 2: Tert-Butyl((1-(2,6-difluorophenyl)but-3-en-1-yl)oxy)dimethylsilane

To a solution of 1-(2,6-difluorophenyl)but-3-en-1-ol (116.0 g, 629.82 mmol) in dichloromethane (2000 mL) was added imidazole (85.8 g, 1259.60 mmol) and tert-butyldimethylchlorosilane (113.9 g, 755.78 mmol). The reaction mixture was stirred at 25° C. for 4 h and filtered. The filtrate was washed with water (2×2000 mL), saturated aqueous sodium bicarbonate (2×2000 mL), brine (500 mL), dried over sodium sulfate and concentrated under reduced pressure to afford crude tert-butyl-[1-(2,6-difluorophenyl)but-3-enoxy]-dimethyl-silane (180.0 g, 96%) as a light yellow oil.

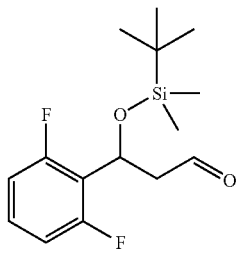 [SMILES: CC(C)(C)[Si](C)(C)OC(CC=O)c1c(F)cccc1F]

Step 3: 3-((tert-butyldimethylsilyl)oxy)-3-(2,6-difluorophenyl)propanal

To a solution of tert-butyl-[1-(2,6-difluorophenyl)but-3-enoxy]-dimethyl-silane (180.0 g, 603.14 mmol) in water (1000 mL) and tetrahydrofuran (1000 mL) was added osmium tetraoxide (0.88 g, 3.45 mmol). After stirred for 30 min at 15° C., sodium periodate (516.0 g, 2412.6 mmol) was added in small portions over 2 h. The resulting mixture was stirred for another 2 h at 25° C. and quenched by addition of cold saturated aqueous sodium thiosulfate (300 mL). The mixture was stirred for 30 min and extracted with ethyl acetate (3×2000 mL). The combined organic layers were washed with water (2000 mL), brine (2000 mL), dried over sodium sulfate and concentrated under reduced pressure to give crude product 3-[tert-butyl(dimethyl)silyl]oxy-3-(2,6-difluorophenyl)propanal (180.0 g, 99%) as a yellow oil.

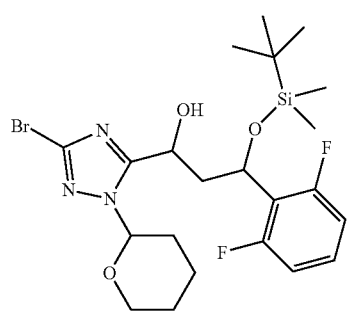 [SMILES: CC(C)(C)[Si](C)(C)OC(CC(O)c1nc(Br)nn1C1CCCCO1)c1c(F)cccc1F]

Step 4: 1-(3-bromo-1-(tetrahydro-2H-pyran-2-yl)-1H-1,2,4-triazol-5-yl)-3-((tert-butyldimethylsilyl)oxy)-3-(2,6-difluorophenyl)propan-1-ol To a cooled (−78° C.) solution of 3,5-dibromo-1-tetrahydropyran-2-yl-1,2,4-triazole (190.0 g, 610.99 mmol) in tetrahydrofuran (2000 mL) was slowly added n-butyllithium (2.5 M in hexanes, 268.8 mL, 672.09 mmol) under nitrogen atmosphere. The mixture was stirred at −78° C. for 30 min, then a solution of 3-[tert-butyl(dimethyl)silyl]oxy-3-(2,6-difluorophenyl)propanal (177.0 g, 589.17 mmol) in tetrahydrofuran (100 mL) was added dropwise. After addition, the mixture was stirred at −78° C. for 1.5 h and quenched by addition of saturated aqueous ammonium chloride (500 mL). The resulting mixture was extracted with ethyl acetate (3×2000 mL). The combined organic layers were dried over sodium sulfate and concentrated under reduced pressure. The residue was purified by column chromatography (silica gel, 100-200 mesh, 0 to 12% ethyl acetate in petroleum ether) to afford 1-(5-bromo-2-tetrahydropyran-2-yl-1,2,4-triazol-3-yl)-3-[tert-butyl(dimethyl)silyl]oxy-3-(2,6-difluorophenyl)propan-1-ol (160 g, 49%) as a yellow oil.

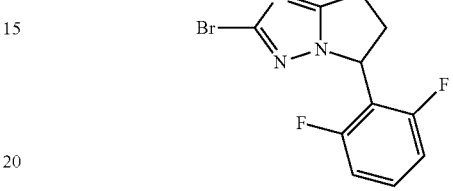

Step 5: 2-bromo-5-(2,6-difluorophenyl)-6,7-dihydro-H-pyrrolo[1,2-b][1,2,4]triazol-7-ol A mixture of 1-(5-bromo-2-tetrahydropyran-2-yl-1,2,4-triazol-3-yl)-3-[tert-butyl(dimethyl)silyl]oxy-3-(2,6-difluorophenyl)propan-1-ol (80.0 g, 150.24 mmol), trifluoroacetic acid (400 mL, 6009.5 mmol) and trifluoromethanesulfonic acid (40 mL, 600.95 mmol) was stirred at 50° C. for 12 h and concentrated under reduced pressure. The residue was adjusted to pH=9 by addition of saturated aqueous sodium bicarbonate and extracted with dichloromethane (2×700 mL). The combined organic layers were washed with water (2×300 mL), brine (100 mL), dried over sodium sulfate and concentrated under reduced pressure. The residue was washed with methyl tert-butyl ether (80 mL) to give crude 2-bromo-5-(2,6-difluorophenyl)-6,7-dihydro-5H-pyrrolo[1,2-b][1,2,4]triazol-7-ol (40 g, 84%) as a white solid. LCMS $R_T$=0.694&0.711 min, m/z=317.9 [M+H]$^+$.

LCMS (5 to 95% acetonitrile in water+0.03% trifluoacetic acid over 1.5 mins) retention time 0.694&0.711 min, ESI+ found [M+H]=317.9.

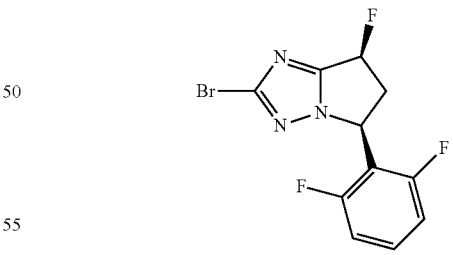

Step 6: (5S,7S)-2-bromo-5-(2,6-difluorophenyl)-7-fluoro-6,7-dihydro-5H-pyrrolo[1,2-b][1,2,4]triazole To a cooled (0° C.) solution of 2-bromo-5-(2,6-difluorophenyl)-6,7-dihydro-5H-pyrrolo[1,2-b][1,2,4]triazol-7-ol (1.5 g, 4.75 mmol) in dichloromethane (30 mL) was added diethylaminosulfur trifluoride (2.5 mL, 18.98 mmol). The mixture was stirred at 0° C. for 1 h and quenched by addition of saturated aqueous sodium bicarbonate (100 mL) at 0° C.

The mixture was extracted with dichloromethane (2×100 mL). The combined organic layers were washed with water (100 mL), brine (100 mL), dried over sodium sulfate and concentrated under reduced pressure. The residue was purified by column chromatography (silica gel, 100-200 mesh, 0 to 12% ethyl acetate in petroleum ether) to afford cis-2-bromo-5-(2,6-difluorophenyl)-7-fluoro-6,7-dihydro-5H-pyrrolo[1,2-b][1,2,4]triazole (0.25 g, 16%) as alight yellow solid. LCMS $R_T$=0.808 min, m/z=319.9 [M+H]$^+$. LCMS (5 to 95% acetonitrile in water+0.03% trifluoacetic acid over 1.5 mins) retention time 0.808 min, ESI+ found [M+H]=319.9.

This cis mixture was further separated by chiral SFC to afford arbitrarily assigned: (5S,7S)-2-bromo-5-(2,6-difluorophenyl)-7-fluoro-6,7-dihydro-5H-pyrrolo[1,2-b][1,2,4]triazole (peak 2, retention time=3.293 min) (115 mg, 46%) as a light yellow solid.

SFC condition: ChiralPak AD-3 150×4.6 mm I.D., 3 μm Mobile phase: A: $C_{O2}$ B:Ethanol (0.05% DEA) Gradient: from 5% to 40% of B in 5.5 min and hold 40% for 3 min, then 5% of B for 1.5 min.

Flow rate: 2.5 mL/min Column temperature: 40° C.

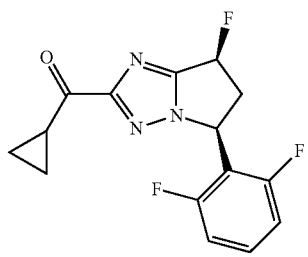 [SMILES: O=C(c1nc2n(n1)[C@H](c1c(F)cccc1F)C[C@@H]2F)C1CC1]

Step 7: Cyclopropyl-[(5S,7S)-5-(2,6-difluorophenyl)-7-fluoro-6,7-dihydro-5H-pyrrolo[1,2-b][1,2,4]triazol-2-yl]methanone To a solution of (5S,7S)-2-bromo-5-(2,6-difluorophenyl)-7-fluoro-6,7-dihydro-5H-pyrrolo[1,2-b][1,2,4]triazole (115 mg, 0.36 mmol) and N-methoxy-N-methyl-cyclopropanecarboxamide (93 mg, 0.72 mmol) in tetrahydrofuran (6 mL) was added isopropylmagnesium chloride (2.0 M in tetrahydrofuran, 0.36 mL, 0.72 mmol) at 0° C. under nitrogen atmosphere. The mixture was stirred at 0° C. for 1 h and quenched by addition of saturated aqueous ammonium chloride (10 mL). The mixture was extracted with ethyl acetate (3×20 mL). The combined organic layers were washed with water (20 mL), brine (20 mL), dried over sodium sulfate and concentrated under reduced pressure. The residue was purified by RP-HPLC (acetonitrile 37-67%/0.05% ammonia hydroxide in water) to afford cyclopropyl-[(5S,7S)-5-(2,6-difluorophenyl)-7-fluoro-6,7-dihydro-5H-pyrrolo[1,2-b][1,2,4]triazol-2-yl]methanone (32.6 mg, 29%) as a white solid. $^1$H NMR (400 MHz, CD$_3$OD) δ 7.54-7.48 (m, 1H), 7.10-7.06 (m, 2H), 6.24-6.21 (m, 0.5H), 6.10-6.07 (m, 0.5H), 5.98-5.94 (m, 1H), 3.89-3.81 (m, 1H), 3.03-2.91 (m, 2H), 1.18-1.16 (m, 2H), 1.11-1.08 (m, 2H). LCMS $R_T$=0.740 min, m/z=308.1 [M+H]$^+$.

LCMS (5 to 95% acetonitrile in water+0.03% trifluoacetic acid over 1.5 mins) retention time 0.740 min, ESI+ found [M+H]=308.1.

Method 74

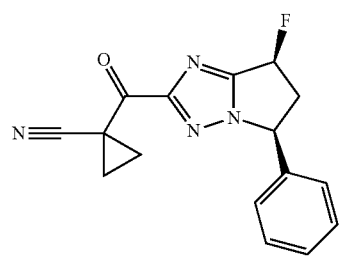

Example 95

1-[(5S,7S)-7-fluoro-5-phenyl-6,7-dihydro-5H-pyrrolo[1,2-b][1,2,4]triazole-2-carbonyl]cyclopropanecarbonitrile

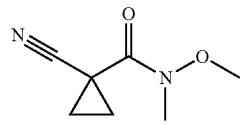

Step 1: 1-cyano-N-methoxy-N-methyl-cyclopropanecarboxamide

A mixture of 1-cyanocyclopropanecarboxylic acid (500 mg, 4.5 mmol), 1-hydroxybenzotriazole (365 mg, 2.7 mmol), 1-(3-dimethylaminopropyl)-3-ethylcarbodiimidehydrochloride (1.0 g, 5.4 mmol), N,O-dimethylhydroxylamine hydrochloride (878 mg, 9.0 mmol) and N,N-diisopropylethylamine (0.8 mL, 4.5 mmol) in dichloromethane (40 mL) was stirred at 25° C. for 16 h and quenched by addition of water (100 mL). The resulting mixture was extracted with dichloromethane (2×100 mL). The combined organic layers were washed with brine (100 mL), dried over sodium sulfate and concentrated under reduced pressure. The residue was purified by column chromatography (silica gel, 100-200 mesh, 50% to 60% ethyl acetate in petroleum ether) to afford 1-cyano-N-methoxy-N-methyl-cyclopropanecarboxamide (410 mg, 59%) as yellow oil.

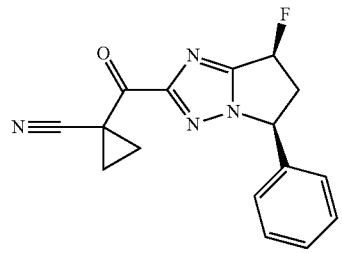 [SMILES: N#CC1(C(=O)c2nc3n(n2)[C@H](c2ccccc2)C[C@@H]3F)CC1]

Step 2: 1-[(5S,7S)-7-fluoro-5-phenyl-6,7-dihydro-5H-pyrrolo[1,2-b][1,2,4]triazole-2-carbonyl]cyclopropanecarbonitrile To a cooled (0° C.) mixture of (5S,7S)-2-bromo-7-fluoro-5-phenyl-6,7-dihydro-5H-pyrrolo[1,2-b][1,2,4]triazole (200 mg, 0.71 mmol) and 1-cyano-N-methoxy-N-methyl-cyclopropane carboxamide (164 mg, 1.06 mmol) in tetrahydrofuran (2 mL) was added isopropylmagnesium chloride (2.0 M in tetrahydrofuran, 1.06 mL, 2.13 mmol) dropwise under a nitrogen atmosphere. After addition, the mixture was stirred at 25° C. for 3 h and then quenched by addition of saturated aqueous ammonium chloride (10 mL). The mixture was extracted with ethyl acetate (2×10 mL). The combined organic layers were dried over sodium sulfate and concentrated under reduced pressure. The residue was purified by RP-HPLC (acetonitrile 35-65%/0.05% ammonia hydroxide in water) to afford arbitrarily assigned 1-[(5S,7S)-7-fluoro-5-phenyl-6,7-dihydro-5H-pyrrolo[1,2-b][1,2,4]triazole-2-carbonyl]cyclopropanecarbonitrile (20 mg, 9.2%) as a white solid. $^1$H NMR (400 MHz, CDCl$_3$) δ 7.43-7.40 (m, 3H), 7.78-7.27 (m, 2H), 6.15-5.99 (m, 1H), 5.57-5.55 (m, 1H), 3.69-3.61 (m, 1H), 3.06-2.96 (m, 1H), 2.10-2.03 (m, 2H), 1.84-1.81 (m, 2H). LCMS R$_T$=0.813 min, m/z=296.9 [M+H]$^+$.

LCMS (5 to 95% acetonitrile in water+0.03% trifluoroacetic acid over 1.5 mins) retention time 0.813 min, ESI+ found [M+H]=296.9.

Method 75

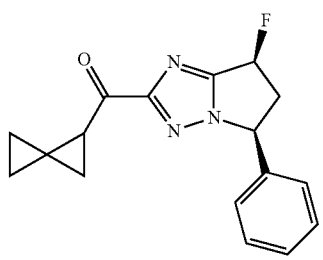

Example 96

[(5S,7S)-7-fluoro-5-phenyl-6,7-dihydro-5H-pyrrolo[1,2-b][1,2,4]triazol-2-yl]-spiro[2.2]pentan-2-yl-methanone

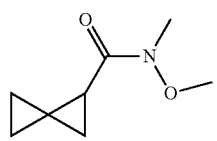

Step 1: N-methoxy-N-methylspiro[2.2]pentane-1-carboxamide

A mixture of spiro[2.2]pentane-2-carboxylic acid (0.5 g, 4.46 mmol), N,O-dimethylhydroxylamine hydrochloride (0.65 g, 6.69 mmol), 1-[Bis(dimethylamino)methylene]-1H-1,2,3-triazolo[4,5-b]pyridinium 3-oxide hexafluorophosphate (1.70 g, 4.46 mmol) and N,N-diisopropylethylamine (1.44 g, 11.15 mmol) in N,N-dimethylformamide (10 mL) was stirred at 25° C. for 5 h. The reaction was poured into water (30 mL) and extracted with dichloromethane (2×20 mL). The combined organic layers were washed with brine (20 mL) and concentrated under reduced pressure to give crude N-methoxy-N-methyl-spiro[2.2]pentane-2-carboxamide (690 mg, 100%) as a colorless oil. The crude was used in next step without further purification.

LC-MS R$_T$=0.638 min, m/z=156.1 [M+H]$^+$.

LCMS (5 to 95% acetonitrile in water+0.03% trifluoroacetic acid over 1.5 mins) retention time 0.638 min, ESI+ found [M+H]=156.1

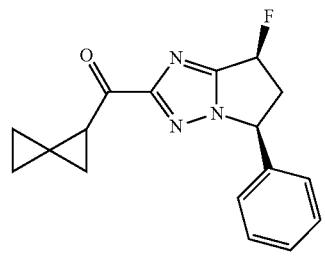 [SMILES: O=C(c1nc2n(n1)[C@H](c1ccccc1)C[C@@H]2F)C1CC12CC2]

Step 2: [(5S,7S)-7-fluoro-5-phenyl-6,7-dihydro-5H-pyrrolo[1,2-b][1,2,4]triazol-2-yl]-spiro[2.2]pentan-2-yl-methanone To a mixture of (5S,7S)-2-bromo-7-fluoro-5-phenyl-6,7-dihydro-5H-pyrrolo[1,2-b][1,2,4]triazole (100 mg, 0.35 mmol) and N-methoxy-N-methyl-spiro[2.2]pentane-2-carboxamide (110 mg, 0.71 mmol) in tetrahydrofuran (2 mL) was added isopropylmagnesium bromide (3.0 M in 2-methyl tetrahydrofuran, 0.71 mL, 2.13 mmol) under nitrogen atmosphere at 0° C. After addition, the mixture was stirred at 0° C. for 2 h and quenched by addition of saturated aqueous ammonium chloride (20 mL). The resulting mixture was extracted with ethyl acetate (2×30 mL). The combined organic layers were washed with brine (10 mL), dried over sodium sulfate and concentrated under reduced pressure. The residue was purified by RP-HPLC (acetonitrile 40-70%/0.05% ammonia hydroxide in water) to afford arbitrarily assigned [(5S,7S)-7-fluoro-5-phenyl-6,7-dihydro-5H-pyrrolo[1,2-b][1,2,4]triazol-2-yl]-spiro[2.2]pentan-2-yl-methanone (18.6 mg, 18%) as a white solid. $^1$H NMR (400 MHz, CDCl$_3$) δ 7.41-7.33 (m, 3H), 7.29-7.23 (m, 2H), 6.09-5.93 (m, 1H), 5.52-5.44 (m, 1H), 3.68-3.60 (m, 1H), 3.40-3.36 (m, 1H), 3.01-2.89 (m, 1H), 1.88-1.82 (m, 1H), 1.63-1.61 (m, 1H), 1.05-0.97 (m, 2H), 0.95-0.89 (m, 1H), 0.88-0.83 (m, 1H). LC-MS R$_T$=0.786 min, m/z=298.1 [M+H]$^+$.

LCMS (5 to 95% acetonitrile in water+0.03% trifluoroacetic acid over 1.5 mins) retention time 0.786 min, ESI+ found [M+H]=298.1

Method 76

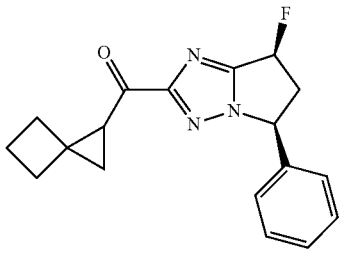

Example 97

[(5S,7S)-7-fluoro-5-phenyl-6,7-dihydro-5H-pyrrolo[1,2-b][1,2,4]triazol-2-yl]-spiro[2.3]hexan-2-yl-methanone

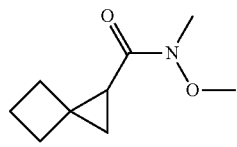

Step 1: N-methoxy-N-methylspiro[2.3]hexane-1-carboxamide

A mixture of spiro[2.3]hexane-2-carboxylic acid (300 mg, 2.38 mmol), N,O-dimethylhydroxylamine hydrochloride (464 mg, 4.76 mmol), N,N-diisopropylethylamine (922 mg, 7.13 mmol), 1-[Bis(dimethylamino)methylene]-1H-1,2,3-triazolo[4,5-b]pyridinium 3-oxide hexafluorophosphate (949 mg, 2.5 mmol) in N,N-dimethylformamide (10 mL) was stirred at 20° C. for 2 h. The mixture was poured into water (60 mL) and extracted with dichloromathane (2×30 mL). The combined organic layers were washed with water (2×20 mL), dried over sodium sulfate and concentrated under reduced pressure to afford crude N-methoxy-N-methyl-spiro[2.3]hexane-2-carboxamide (400 mg, 99%) as a light yellow oil which used in next step without further purification. LC-MS $R_T$=0.725 min, m/z=170.2 [M+H]$^+$.

LCMS (5 to 95% acetonitrile in water+0.03% trifluoacetic acid over 1.5 mins) retention time 0.725 min, ESI+ found [M+H]=170.2.

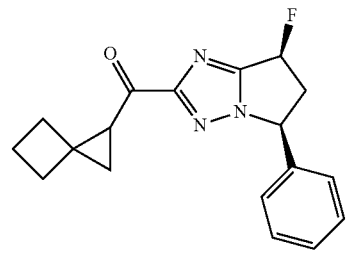 [SMILES: O=C(c1nc2n(n1)[C@H](c1ccccc1)C[C@@H]2F)C1CC12CCC2]

Step 2: [(5S,7S)-7-fluoro-5-phenyl-6,7-dihydro-5H-pyrrolo[1,2-b][1,2,4]triazol-2-yl]-spiro[2.3]hexan-2-yl-methanone To a solution of (5S,7S)-2-bromo-7-fluoro-5-phenyl-6,7-dihydro-5H-pyrrolo[1,2-b][1,2,4]triazole (100 mg, 0.35 mmol) and N-methoxy-N-methyl-spiro[2.3]hexane-2-carboxamide (120 mg, 0.71 mmol) in tetrahydrofuran (2 mL) was added isopropylmagnesium bromide (3.0 M in 2-methyl tetrahydrofuran, 0.71 mL, 2.13 mmol) dropwise under nitrogen atmosphere at 0° C. After addition, the mixture was stirred at 0° C. for 2 h and quenched by addition of saturated aqueous ammonium chloride (10 mL). The mixture was extracted with ethyl acetate (2×5 mL). The combined organic layers were washed with brine (20 mL), dried over sodium sulfate and concentrated under reduced pressure. The residue was purified by RP-HPLC (acetonitrile 45-75%/0.05% ammonia hydroxide in water) to afford arbitrarily assigned [(5S,7S)-7-fluoro-5-phenyl-6,7-dihydro-5H-pyrrolo[1,2-b][1,2,4]triazol-2-yl]-spiro[2.3]hexan-2-yl-methanone (21.6 mg, 19%) as a white solid. $^1$H NMR (400 MHz, CDCl$_3$) δ 7.42-7.38 (m, 3H), 7.29-7.26 (m, 2H), 6.11-5.95 (m, 1H), 5.51-5.48 (m, 1H), 3.69-3.60 (m, 1H), 3.10-3.03 (m, 1H), 3.02-2.90 (m, 1H), 2.38-2.13 (m, 4H), 2.08-1.99 (m, 1H), 1.98-1.89 (m, 1H), 1.56-1.52 (m, 1H), 1.29-1.24 (m, 1H). LC-MS $R_T$=0.821 min, m/z=312.1 [M+H]$^+$.

LCMS (5 to 95% acetonitrile in water+0.03% trifluoacetic acid over 1.5 mins) retention time 0.821 min, ESI+ found [M+H]=312.1

Method 77

Example 98

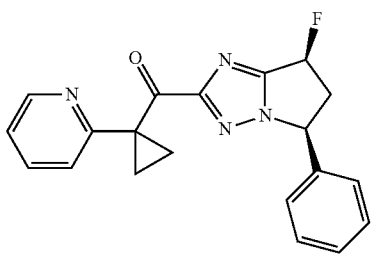

[1-(2-pyridyl)cyclopropyl]-[(5S,7S)-7-fluoro-5-phenyl-6,7-dihydro-5H-pyrrolo[1,2-b][1,2,4]triazol-2-yl]methanone

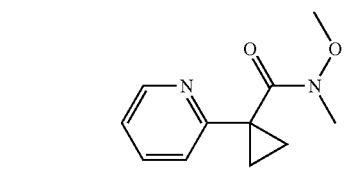

Step 1: N-methoxy-N-methyl-1-(2-pyridyl)cyclopropanecarboxamide

A mixture of 1-(2-pyridyl)cyclopropanecarboxylic acid (200 mg, 1.23 mmol), N,N-diisopropylethylamine (475 mg, 3.68 mmol), 1-hydroxybenzotriazole (198 mg, 1.47 mmol), 1-(3-dimethyaminopropyl)-3-ethylcarbodiimidehydrochloride (282 mg, 1.47 mmol) and N,O-dimethylhydroxylamine hydrochloride (179 mg, 1.84 mmol) in dichloromethane (10 mL) was stirred at 30° C. for 18 h and diluted with water (30 mL). The resulting mixture was extracted with ethyl acetate (3×15 mL). The combined organic layers were washed with water (2×10 mL), brine (20 mL) and concentrated under reduced pressure. The residue was purified by column chromatography (silica gel, 100-200 mesh, 0 to 20% ethyl acetate in petroleum ether) to give N-methoxy-N-methyl-1-(2-pyridyl)cyclopropanecarboxamide (200 mg, 79%) as a white solid. LC-MS $R_T$=0.733 min, m/z=207 (M+H)+.

LCMS (5 to 95% acetonitrile in water+0.03% trifluoacetic acid over 1.5 mins) retention time 0.733 min, ESI+ found [M+H]=207.

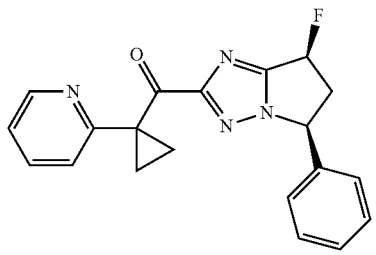 [SMILES: O=C(c1nc2n(n1)[C@H](c1ccccc1)C[C@@H]2F)C1(c2ccccn2)CC1]

Step 2: [1-(2-pyridyl)cyclopropyl]-[(5S,7S)-7-fluoro-5-phenyl-6,7-dihydro-5H-pyrrolo[1,2-b][1,2,4]triazol-2-yl]methanone To a solution of N-methoxy-N-methyl-1-(2-pyridyl)cyclopropanecarboxamide (55 mg, 0.27 mmol), (5S,7S)-2-bromo-7-fluoro-5-phenyl-6,7-dihydro-5H-pyrrolo[1,2-b][1,2,4]triazole (50 mg, 0.18 mmol) in tetrahydrofuran (3 mL) was added isopropylmagnesuim chloride (2.0 M in tetrahydrofuran, 0.4 mL, 0.80 mmol) dropwise at 0° C. The mixture was stirred at 0° C. for 1 h and quenched by addition of saturated aqueous ammonium chloride (5 mL). The resulting mixture was extracted with ethyl acetate (3×20 mL). The combined organic layers were dried over sodium sulfate and concentrated under reduced pressure. The residue was purified by RP-HPLC (water (0.05% ammonia hydroxide v/v)-acetonitrile 35-65%) to afford arbitrarily assigned [1-(2-pyridyl)cyclopropyl]-[(5S,7S)-7-fluoro-5-phenyl-6,7-dihydro-5H-pyrrolo[1,2-b][1,2,4]triazol-2-yl]methanone (15.4 mg, 24%) as a white solid. $^1$H NMR (400 MHz, CDCl$_3$) δ 8.42-8.40 (m, 1H), 7.50-7.47 (m, 1H), 7.34-7.32 (m, 3H), 7.26-7.10 (m, 1H), 7.06-7.02 (m, 3H), 6.00-5.83 (m, 1H), 5.40-5.35 (m, 1H), 3.60-3.49 (m, 1H), 2.92-2.81 (m, 1H), 2.02-1.90 (m, 1H), 1.83-1.78 (m, 2H), 1.60-1.50 (m, 1H). LCMS R$_T$=1.678 min, m/z=349.2 [M+H]$^+$.

LCMS (10 to 80% acetonitrile in water+0.1% ammonia water over 3.0 mins) retention time 1.678 min, ESI+ found [M+H]=349.2.

Method 78

Example 99

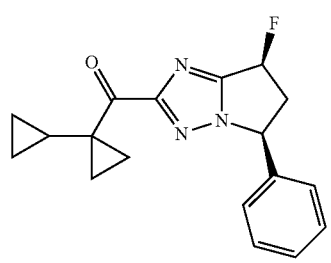 [SMILES: O=C(c1nc2n(n1)[C@H](c1ccccc1)C[C@@H]2F)C1(C2CC2)CC1]

(1-cyclopropylcyclopropyl)-[(5S,7S)-7-fluoro-5-phenyl-6,7-dihydro-5H-pyrrolo[1,2-b][1,2,4]triazol-2-yl]methanone

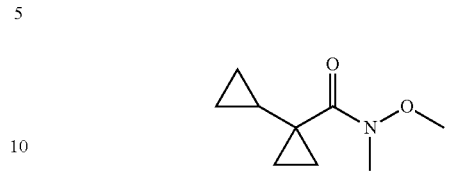

Step 1: 1-cyclopropyl-N-methoxy-N-methyl-cyclopropanecarboxamide

A mixture of 1-cyclopropylcyclopropanecarboxylic acid (500 mg, 3.96 mmol), 1-hydroxybenzotriazole (321 mg, 2.38 mmol), N,O-dimethylhydroxylamine hydrochloride (773 mg, 7.93 mmol), 1-(3-dimethylaminopropyl)-3-ethylcarbodiimidehydrochloride (912 mg, 4.76 mmol) and N,N-diisopropylethylamine (512 mg, 3.96 mmol) in dichloromethane (10 mL) was stirred at 25° C. for 18 h and quenched by addition of water (10 mL). The separated organic layer was washed with brine (10 mL), dried over sodium sulfate and concentrated under reduced pressure. The residue was purified by column chromatography (silica gel, 100-200 mesh, 50 to 60% ethyl acetate in petroleum ether) to give 1-cyclopropyl-N-methoxy-N-methyl-cyclopropanecarboxamide (370 mg, 55%) as a yellow oil.

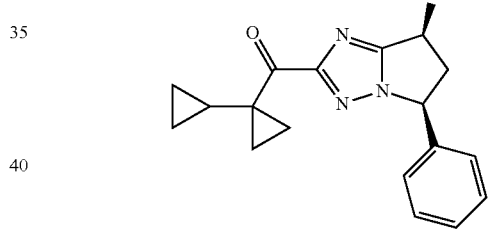

Step 2: (1-cyclopropylcyclopropyl)-[(5S,7S)-7-fluoro-5-phenyl-6,7-dihydro-5H-pyrrolo[1,2-b][1,2,4]triazol-2-yl]methanone To a solution of 1-cyclopropyl-N-methoxy-N-methyl-cyclopropanecarboxamide (340 mg, 2.01 mmol), (5S,7S)-2-bromo-7-fluoro-5-phenyl-6,7-dihydro-5H-pyrrolo[1,2-b][1,2,4]triazole (288 mg, 1.02 mmol) in tetrahydrofuran (20 mL) was added isopropylmagnesium chloride (2.0 M in tetrahydrofuran, 3.57 mL, 7.15 mmol) dropwise at 0° C. The reaction mixture was stirred at 0° C. for 1 h and quenched by addition of saturated aqueous ammonium chloride (10 mL). The mixture was extracted with ethyl acetate (3×20 mL). The combined organic layers were dried over sodium sulfate and concentrated under reduced pressure. The residue was purified by preparative TLC (20% ethyl acetate in petroleum ether, R$_f$=0.6) to afford arbitrarily assigned (1-cyclopropylcyclopropyl)-[(5S,7S)-7-fluoro-5-phenyl-6,7-dihydro-5H-pyrrolo[1,2-b][1,2,4]triazol-2-yl]methanone (100 mg, 31%) as a brown oil. $^1$H NMR (400 MHz, CDCl$_3$) δ 7.40-7.36 (m, 3H), 7.24-7.22 (m, 2H), 6.09-5.91 (m, 1H), 5.52-5.45 (m, 1H), 3.69-3.54 (m, 1H), 2.99-2.86 (m, 1H), 1.88-1.83 (m, 1H), 1.54-1.50 (m, 2H), 0.78-0.76 (m, 2H), 0.43-0.39 (m, 2H), 0.07-0.03 (m, 2H). LC-MS $R_T$=0.816 min, m/z=312.1 [M+H]$^+$.

LCMS (10 to 80% acetonitrile in water+0.03% ammonium bicarbonate over 3.0 mins) retention time 1.935 min, ESI+ found [M+H]=312.2.

Method 79

Example 100

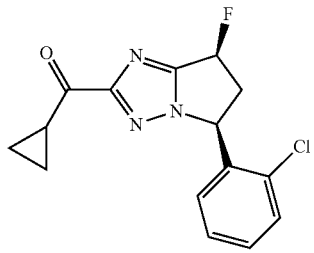

Cyclopropyl-[(5S,7S)-5-(2-chlorophenyl)-7-fluoro-6,7-dihydro-5H-pyrrolo[1,2-b][1,2,4]triazol-2-yl]methanone

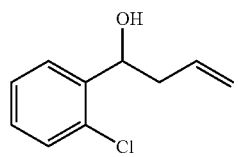

Step 1: 1-(2-chlorophenyl)but-3-en-1-ol

To a solution of 2-chlorobenzaldehyde (90.0 g, 640.25 mmol) in tetrahydrofuran (1000 mL) was added allylmagnesium chloride (2.0 M in tetrahydrofuran, 448.1 mL, 896.35 mmol) at −78° C. under nitrogen atmosphere. The resulting mixture was allowed to warm to 25° C. and stirred for 1 h before quenched by addition of saturated aqueous ammonium chloride (100 mL). The resulting mixture was extracted with ethyl acetate (2×500 mL). The combined organic layers were dried over sodium sulfate and concentrated under reduced pressure to give crude 1-(2-chlorophenyl)but-3-en-1-ol (116.0 g, 99%) as a yellow oil.

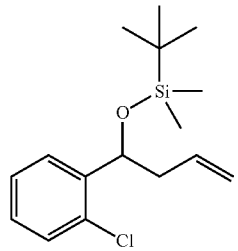 [SMILES: C=CCC(O[Si](C)(C)C(C)(C)C)c1ccccc1Cl]

Step 2: Tert-Butyl-[1-(2-chlorophenyl)but-3-enoxy]-dimethyl-silane

To a solution of 1-(2-chlorophenyl)but-3-en-1-ol (116.0 g, 634.55 mmol) in dichloromethane (1.5 L) was added imidazole (86.4 g, 1269.1 mmol) and tert-butyldimethylchlorosilane (124.3 g, 824.9 mmol). The reaction mixture was stirred at 25° C. for 16 h and quenched by addition of water (1 L). The mixture was extracted with ethyl acetate (2×1 L). The combined organic layers were washed with brine (1 L), dried over sodium sulfate and concentrated under reduced pressure to afford crude tert-butyl-[1-(2-chlorophenyl)but-3-enoxy]-dimethyl-silane (188.0 g, 99%) as a yellow oil. $^1$H NMR (400 MHz, CDCl$_3$) 7.59-7.54 (m, 1H), 7.31-7.23 (m, 2H), 7.20-7.14 (m, 1H), 5.92-5.79 (m, 1H), 5.17-5.12 (m, 1H), 5.07-5.00 (m, 2H), 2.49-2.42 (m, 1H), 2.40-2.32 (m, 1H), 0.89 (s, 9H), 0.05 (s, 3H), −0.10−−0.13 (m, 3H).

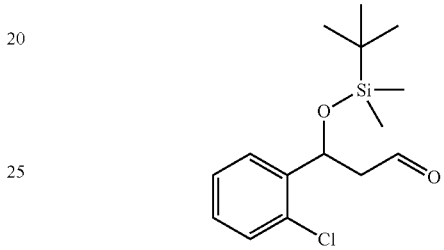

Step 3: 3-[tert-butyl(dimethyl)silyl]oxy-3-(2-chlorophenyl)propanal

To a solution of tert-butyl-[1-(2-chlorophenyl)but-3-enoxy]-dimethyl-silane (188.0 g, 633.19 mmol) in water (1.0 L) and tetrahydrofuran (1.0 L) was added osmium tetraoxide (0.04% in water, 41.55 mL, 6.65 mmol). After stirred for 30 min at 15° C., sodium periodate (541.7 g, 2532.8 mmol) was added in small portions over 2 h. The resulting mixture was stirred for another 2 h at 30° C. and quenched by addition of cold saturated aqueous sodium thiosulfate (500 mL). The mixture was stirred for 30 min and extracted with ethyl acetate (3×500 mL). The combined organic layers were washed with water (500 mL), brine (500 mL), dried over sodium sulfate and concentrated under reduced pressure. The residue was purified by column chromatography (silica gel, 100-200 mesh, 0 to 5% ethyl acetate in petroleum ether) to afford 3-[tert-butyl(dimethyl)silyl]oxy-3-(2-chlorophenyl)propanal (189.0 g, 99%) as a color oil. $^1$H NMR (400 MHz, CDCl$_3$) 9.84-9.81 (m, 1H), 7.63-7.59 (m, 1H), 7.35-7.28 (m, 2H), 7.25-7.19 (m, 1H), 5.66-5.62 (m, 1H), 2.76-2.69 (m, 2H), 0.89 (s, 9H), 0.09 (s, 3H), −0.10 (s, 3H).

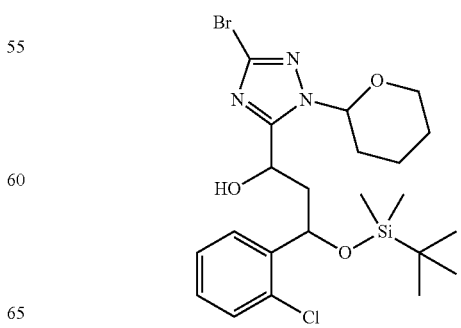

Step 4: 1-(5-bromo-2-tetrahydropyran-2-yl-1,2,4-triazol-3-yl)-3-[tert-butyl(dimethyl)silyl] oxy-3-(2-chlorophenyl)propan-1-ol To a cooled (−78° C.) solution of 3,5-dibromo-1-tetrahydropyran-2-yl-1,2,4-triazole (194.6 g, 626.04 mmol) in tetrahydrofuran (1100 mL) was slowly added n-butyllithium (2.5 M in hexanes, 278.2 mL, 695.6 mmol) under nitrogen atmosphere. The mixture was stirred at −78° C. for 30 min, then a solution of 3-[tert-butyl(dimethyl)silyl]oxy-3-(2-chlorophenyl)propanal (189.0 g, 632.4 mmol) in tetrahydrofuran (400 mL) was added dropwise. After addition, the mixture was stirred at −78° C. for 2 h and then quenched by addition of saturated aqueous ammonium chloride (200 mL). The resulting mixture was extracted with ethyl acetate (2×800 mL). The combined organic layers were dried over sodium sulfate and concentrated under reduced pressure. The residue was purified by column chromatography (silica gel, 100-200 mesh, 0 to 10% ethyl acetate in petroleum ether) to afford 1-(5-bromo-2-tetrahydropyran-2-yl-1,2,4-triazol-3-yl)-3-[tert-butyl(dimethyl)silyl]oxy-3-(2-chlorophenyl)propan-1-ol (202.0 g, 60%) as yellow oil. LC-MS $R_T$=2.657 min, m/z=446.1 [M+H]$^+$.

LCMS (10 to 80% acetonitrile in water+0.03% ammonium bicarbonate over 3.0 mins) retention time 2.657 min, ESI+ found [M+H]=446.1.

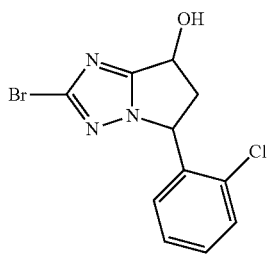 [SMILES: OC1CC(c2ccccc2Cl)n2nc(Br)nc21]

Step 5: 2-bromo-5-(2-chlorophenyl)-6,7-dihydro-5H-pyrrolo[1,2-b][1,2,4]triazol-7-ol A mixture of 1-(5-bromo-2-tetrahydropyran-2-yl-1,2,4-triazol-3-yl)-3-[tert-butyl(dimethyl)silyl] oxy-3-(2,3,6-trifluorophenyl)propan-1-ol (50.0 g, 94.17 mmol) and trifluoroacetic acid (280.7 mL, 3766.8 mmol) was stirred at 55° C. for 16 h and concentrated under reduced pressure. The residue was adjusted to pH=9 by addition of saturated aqueous sodium bicarbonate and extracted with ethyl acetate (3×300 mL). The combined organic layers were washed with water (100 mL), brine (100 mL), dried over sodium sulfate and concentrated under reduced pressure. The residue was purified by column chromatography (silica gel, 100-200 mesh, 0 to 50% ethyl acetate in petroleum ether) to afford 2-bromo-5-(2-chlorophenyl)-6,7-dihydro-5H-pyrrolo[1,2-b][1,2,4]triazol-7-ol (9.2 g, 31%) as a white solid. $^1$H NMR (400 MHz, CD$_3$Cl) δ 7.48-7.41 (m, 1H), 7.34-7.27 (m, 2H), 7.10-6.79 (m, 1H), 6.08-5.83 (m, 1H), 5.70-5.53 (m, 1H), 5.41 (br s, 1H), 3.74-3.57 (m, 0.5H), 3.35-3.21 (m, 0.5H), 2.99-2.84 (m, 1H), 2.67-2.52 (m, 0.5H). LC-MS $R_T$=0.614 min, m/z=314.0 [M+H]$^+$.

LCMS (5 to 95% acetonitrile in water+0.03% trifluoroacetic acid over 1.5 mins) retention time 0.614 min, ESI+ found [M+H]=314.0.

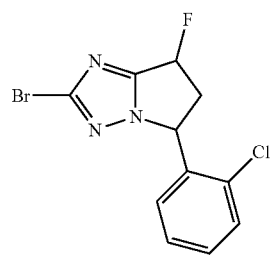 [SMILES: FC1CC(c2ccccc2Cl)n2nc(Br)nc21]

Step 6: 2-bromo-5-(2-chlorophenyl)-7-fluoro-6,7-dihydro-5H-pyrrolo[1,2-b][1,2,4]triazole To a cooled (0° C.) solution of 2-bromo-5-(2-chlorophenyl)-6,7-dihydro-5H-pyrrolo[1,2-b][1,2,4]triazol-7-ol (5.2 g, 16.53 mmol) in dichloromethane (80 mL) was added diethylaminosulfur trifluoride (8.8 mL, 66.12 mmol) in dichloromethane (20 mL). The reaction mixture was stirred at 0° C. for 1 h and quenched by addition of saturated aqueous sodium bicarbonate (300 mL) at 0° C. The mixture was extracted with dichloromethane (2×200 mL). The combined organic layers were washed with water (200 mL), brine (200 mL), dried over sodium sulfate and concentrated under reduced pressure. The residue was purified by column chromatography (silica gel, 100-200 mesh, 0 to 12% ethyl acetate in petroleum ether) to afford 2-bromo-5-(2-chlorophenyl)-7-fluoro-6,7-dihydro-5H-pyrrolo[1,2-b][1,2,4]triazole (3.9 g, 75%) as a deep yellow oil.

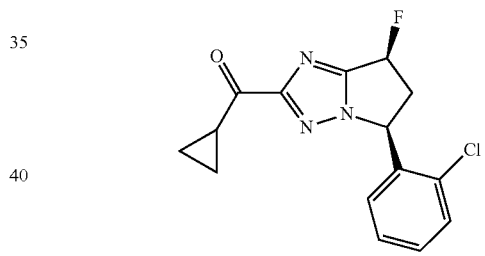

Step 7: cyclopropyl-[(5S,7S)-5-(2-chlorophenyl)-7-fluoro-6,7-dihydro-5H-pyrrolo[1,2-b][1,2,4]triazol-2-yl]methanone To a mixture of N-methoxy-N-methyl-cyclopropanecarboxamide (402 mg, 3.11 mmol), 2-bromo-5-(2-chlorophenyl)-7-fluoro-6,7-dihydro-5H-pyrrolo[1,2-b][1,2,4]triazole (500 mg, 1.58 mmol) in tetrahydrofuran (30 mL) was added isopropylmagnesium chloride (2.0 M in tetrahydrofuran, 5.5 mL, 11.06 mmol) dropwise at 0° C. The mixture was stirred at 0° C. for 1 h and quenched by addition of water (30 mL). The mixture was extracted with ethyl acetate (3×20 mL). The combined organic layers were dried over sodium sulfate and concentrated under reduced pressure. The residue was purified by preparative TLC (20% ethyl acetate in petroleum ether, $R_f$=0.5) to afford [5-(2-chlorophenyl)-7-fluoro-6,7-dihydro-5H-pyrrolo[1,2-b][1,2,4]triazol-2-yl]-cyclopropyl-methanone (250 mg, 52%) as a white solid. LC-MS $R_T$=0.685 min, m/z=306.1 [M+H]$^+$.

LCMS (5 to 95% acetonitrile in water+0.03% trifluoroacetic acid over 1.5 mins) retention time 0.685 min, ESI+ found [M+H]=306.1.

The above cis/trans mixture was further separated by chiral SFC to afford arbitrarily assigned: cyclopropyl-[(5S,7S)-5-(2-chlorophenyl)-7-fluoro-6,7-dihydro-5H-pyrrolo[1,2-b] [1,2,4]triazol-2-yl]methanone (peak 2, retention time=2.509 min) (50.6 mg, 12%) as a white solid. $^1$H NMR (400 MHz, CDCl$_3$) δ 7.45-7.43 (m, 1H), 7.34-7.28 (m, 1H), 7.26-7.24 (m, 1H), 6.76-6.72 (m, 1H), 6.10-6.06 (m, 0.5H), 6.01-5.95 (m, 1H), 5.95-5.93 (m, 0.5H), 3.78-3.62 (m, 1H), 3.12-3.04 (m, 1H), 2.93-2.80 (m, 1H), 1.37-1.32 (m, 2H), 1.14-1.09 (m, 2H). LC-MS R$_T$=1.049 min, m/z=306.1 [M+H]$^+$.

LCMS (10 to 80% acetonitrile in water+0.03% trifluoacetic acid over 2.0 mins) retention time 1.049 min, ESI+ found [M+H]=306.1.

cyclopropyl-[(5R,7R)-5-(2-chlorophenyl)-7-fluoro-6,7-dihydro-5H-pyrrolo[1,2-b] [1,2,4]triazol-2-yl]methanone (peak 4, retention time=3.571 min) (65.6 mg, 15%) as a white solid. $^1$H NMR (400 MHz, CDCl$_3$) δ 7.47-7.43 (m, 1H), 7.34-7.26 (m, 1.5H), 7.25-7.22 (m, 0.5H), 6.76-6.72 (m, 1H), 6.10-6.06 (m, 0.5H), 6.01-5.96 (m, 1H), 5.95-5.93 (m, 0.5H), 3.78-3.62 (m, 1H), 3.12-3.04 (m, 1H), 2.93-2.80 (m, 1H), 1.37-1.32 (m, 2H), 1.14-1.08 (m, 2H). LC-MS R$_T$=0.776 min, m/z=306.1 [M+H]$^+$.

LCMS (5 to 95% acetonitrile in water+0.03% trifluoacetic acid over 1.5 mins) retention time 0.776 min, ESI+ found [M+H]=306.1.

Note: Peak 1 and Peak 3 are Trans Isomers.

SFC method: Column: Chiralcel OJ-3 150×4.6 mm I.D., 3 μm Mobile phase: A: CO$_2$ B:ethanol (0.05% DEA) Gradient: from 5% to 40% of B in 5 min and hold 40% for 2.5 min, then 5% of B for 2.5 min Flow rate: 2.5 mL/min Column temp.: 35° C.

Method 80

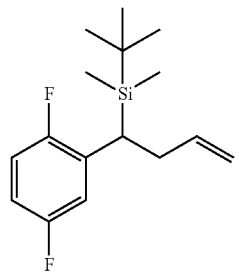

Cyclopropyl-[(5S,7S)-5-(2,5-difluorophenyl)-7-fluoro-6,7-dihydro-5H-pyrrolo[1,2-b][1,2,4]triazol-2-yl]methanone

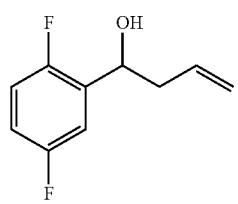

Step 1: 1-(2,5-difluorophenyl)but-3-en-1-ol

To a solution of 2,5-difluorobenzaldehyde (10.0 g, 70.4 mmol) in tetrahydrofuran (20 mL) was added allylmagnesium bromide (2.0 M in tetrahydrofuran, 49.3 mL, 98.5 mmol) at 0° C. under nitrogen atmosphere. After addition, the reaction mixture was allowed to warm to room temperature and stirred for 2 h. The mixture was quenched by addition of saturated aqueous ammonium chloride (10 mL) and extracted with ethyl acetate (3×20 mL). The combined organic layers were dried over sodium sulfate and concentrated under reduce pressure to afford crude 1-(2,5-difluorophenyl)but-3-en-1-ol (11.0 g, 85%) as a yellow oil.

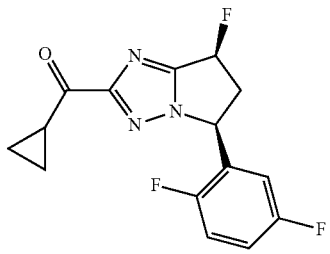 [SMILES: O=C(c1nc2n(n1)[C@H](c1cc(F)ccc1F)C[C@@H]2F)C1CC1]

Step 2: Tert-Butyl((1-(2,5-difluorophenyl)but-3-en-1-yl)oxy)dimethylsilane

To a solution of 1-(2,5-difluorophenyl)but-3-en-1-ol (11.0 g, 59.7 mmol) in dichloromethane (200 mL) was added imidazole (8.1 g, 119.5 mmol) and tert-butyldimethylchlorosilane (11.7 g, 77.6 mmol). After addition, the reaction mixture was stirred at 25° C. for 16 h and quenched by addition of water (100 mL). The mixture was extracted with dichloromethane (2×200 mL). The combined organic layers were washed with brine (100 mL), dried over sodium sulfate and concentrated under reduced pressure to afford crude tert-butyl-[1-(2,5-difluorophenyl)but-3-enoxy]-dimethyl-silane (17.0 g, 95%) as a light oil.

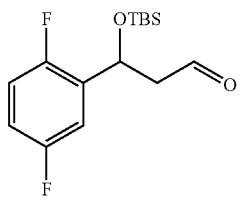 [SMILES: CC(C)(C)[Si](C)(C)OC(CC=O)c1cc(F)ccc1F]

Step 3: 3-((tert-butyldimethylsilyl)oxy)-3-(2,5-difluorophenyl)propanal

To a solution of tert-butyl-[1-(2,5-difluorophenyl)but-3-enoxy]-dimethyl-silane (17.0 g, 57.0 mmol) in tetrahydrofuran/water (100 mL, 1:1) was added osmium tetraoxide (80.0 mg, 0.33 mmol). After stirred for 30 min at 15° C., sodium periodate (48.7 g, 227.9 mmol) was added in small portions over 2 h and the resulting mixture was stirred for another 2 h at 30° C. The mixture was quenched by addition of cold saturated aqueous sodium thiosulfate (100 mL). The mixture was stirred for 30 min and then extracted with ethyl acetate (3×150 mL). The combined organic layers were washed with water (100 mL), brine (100 mL), dried over sodium sulfate and concentrated under reduced pressure. The residue was purified by column chromatography (silica gel, 100-200 mesh, 0 to 10% ethyl acetate in petroleum ether) to afford 3-[tert-butyl(dimethyl)silyl]oxy-3-(2,5-difluorophenyl)propanal (10.8 g, 63%) as a light yellow oil.

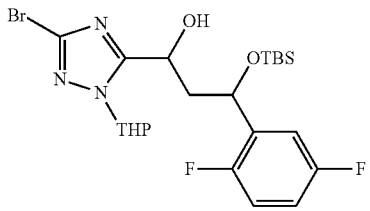

Step 4: 1-(3-bromo-1-(tetrahydro-2H-pyran-2-yl)-1H-1,2,4-triazol-5-yl)-3-((tert-butyldimethylsilyl)oxy)-3-(2,5-difluorophenyl)propan-1-ol To a cooled (−78° C.) solution of 3,5-dibromo-1-tetrahydropyran-2-yl-1,2,4-triazole (11.4 g, 36.6 mmol) in tetrahydrofuran (80 mL) was slowly added n-butyllithium (2.5 M in hexanes, 16.1 mL, 40.3 mmol) under nitrogen atmosphere. The mixture was stirred at −78° C. for 30 min, then a solution of 3-[tert-butyl(dimethyl)silyl]oxy-3-(2,3-difluorophenyl)propanal (10.8 g, 36.0 mmol) in tetrahydrofuran (100 mL) was added dropwise. After addition, the mixture was stirred at −78° C. for 1.5 h and quenched by addition of saturated aqueous ammonium chloride (100 mL). The resulting mixture was extracted with ethyl acetate (3×100 mL). The combined organic layers were dried over sodium sulfate and concentrated under reduce pressure. The residue was purified by column chromatography (silica gel, 100-200 mesh, 0 to 10% ethyl acetate in petroleum ether) to give 1-(5-bromo-2-tetrahydropyran-2-yl-1,2,4-triazol-3-yl)-3-[tert-butyl(dimethyl)silyl]oxy-3-(2,5-difluorophenyl)propan-1-ol (10.0 g, 52%) as a yellow oil.

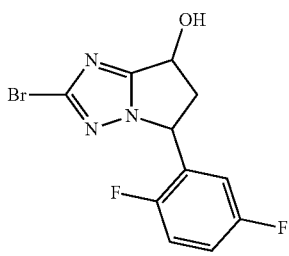 [SMILES: OC1CC(c2cc(F)ccc2F)n2nc(Br)nc21]

Step 5: 2-bromo-5-(2,3,6-trifluorophenyl)-6,7-dihydro-5H-pyrrolo[1,2-b][1,2,4]triazol-7-ol To a solution of 1-(3-bromo-1H-1,2,4-triazol-5-yl)-3-[tert-butyl(dimethyl)silyl]oxy-3-(2,5-difluorophenyl)propan-1-ol (3.96 g, 8.83 mmol) in trifluoroacetic acid (25 mL, 88.3 mmol) was added trifluoromethanesulfonic acid (2.5 mL, 8.83 mmol). The resulting mixture was heated at 60° C. for 2 h and concentrated under reduced pressure. The residue was adjusted to pH=9 by addition of saturated aqueous sodium bicarbonate and extracted with dichloromethane (3×100 mL). The combined organic layers were washed with water (100 mL), brine (100 mL), dried over sodium sulfate and concentrated under reduced pressure. The residue was purified by chromatography (silica gel, 100-200 mesh, 50 to 60% ethyl acetate in petroleum ether) to afford the crude product, which was washed with methyl t-butyl ether (20 mL) to give 2-bromo-5-(2,5-difluorophenyl)-6,7-dihydro-5H-pyrrolo[1,2-b][1,2,4]triazol-7-ol (1.1 g, 39%) as a brown solid. $^1$H NMR (400 MHz, CDCl$_3$) δ 7.11-7.03 (m, 1H), 6.98-6.75 (m, 1H), 5.84-5.68 (m, 1H), 5.47-5.30 (m, 2H), 3.64-3.18 (m, 1H), 3.02-2.63 (m, 1H). LCMS R$_T$=0.727 min, m/z=318.0 [M+H]+.

LCMS (5 to 95% acetonitrile in water+0.03% trifluoacetic acid over 1.5 mins) retention time 0.727 min, ESI+ found [M+H]=318.0.

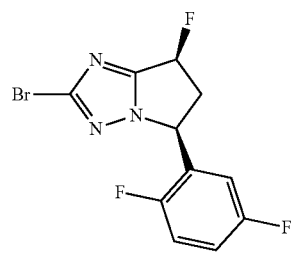 [SMILES: Fc1ccc(F)c([C@@H]2C[C@H](F)c3nc(Br)nn32)c1]

Step 6: (5S,7S)-2-bromo-5-(2,5-difluorophenyl)-7-fluoro-6,7-dihydro-5H-pyrrolo[1,2-b][1,2,4]triazole To a solution of 2-bromo-5-(2,5-difluorophenyl)-6,7-dihydro-5H-pyrrolo[1,2-b][1,2,4]triazol-7-ol (5.0 g, 15.8 mmol) in toluene (50 mL) was added diethylaminosulfur trifluoride (10.2 g, 63.3 mmol) dropwise at 0° C. The reaction mixture was stirred at 0° C. for 16 h and then slowly added into saturated aqueous sodium bicarbonate (100 mL) at 0° C. The mixture was extracted with dichloromethane (3×50 mL). The combined organic layers were washed with water (100 mL), brine (100 mL), dried over sodium sulfate and concentrated under reduced pressure. The residue was purified by column chromatography (silica gel, 100-200 mesh, 0 to 15% ethyl acetate in petroleum ether) to afford rac-(5S,7S)-2-bromo-5-(2,5-difluorophenyl)-7-fluoro-6,7-dihydro-5H-pyrrolo[1,2-b][1,2,4]triazole (1.3 g, 26%) as a brown solid. $^1$H NMR (400 MHz, CDCl$_3$) δ 7.15-7.05 (m, 2H), 6.72-6.68 (m, 1H), 6.07-5.91 (m, 1H), 5.78-5.74 (m, 1H), 3.68-3.55 (m, 1H), 2.90-2.79 (m, 1H). LCMS R$_T$=0.821 min, m/z=317.9 [M+H]$^+$.

LCMS (5 to 95% acetonitrile in water+0.03% trifluoacetic acid over 1.5 mins) retention time 0.821 min, ESI+ found [M+H]=317.9.

This cis mixture (500 mg, 1.7 mmol) was further separated by chiral SFC to afford arbitrarily assigned:

(5S,7S)-2-bromo-5-(2,5-difluorophenyl)-7-fluoro-6,7-dihydro-5H-pyrrolo[1,2-b][1,2,4]triazole (peak 2, retention time=2.600 min) (220 mg, 44%) as a brown solid. (Along with the 5R,7R-isomer (peak 1, retention time=2.295 min) (220 mg, 44%)).

SFC condition: Column: ChiralPak IC-3 150×4.6 mm I.D., 3 μm. Mobile phase: A: CO$_2$, B:Ethanol (0.05% DEA). Gradient: from 5% to 40% of B in 5.5 min and hold 40% for 3 min, then 5% of B for 1.5 min. Flow rate: 2.5 mL/min. Column temperature:40° C.

203

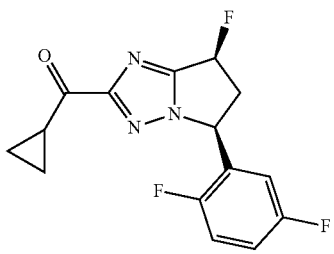 [SMILES: O=C(c1nc2n(n1)[C@H](c1cc(F)ccc1F)C[C@@H]2F)C1CC1]

Step 7: Cyclopropyl-[(5S,7S)-7-fluoro-5-(2,3,6-trifluorophenyl)-6,7-dihydro-5H-pyrrolo[1,2-b][1,2,4]triazol-2-yl]methanone To a mixture of (5S,7S)-2-bromo-5-(2,5-difluorophenyl)-7-fluoro-6,7-dihydro-5H-pyrrolo[1,2-b][1,2,4]triazole (100 mg, 0.31 mmol), N-methoxy-N-methyl-cyclopropanecarboxamide (81 mg, 0.63 mmol) in tetrahydrofuran (3 mL) was added isopropylmagnesium chloride (2.0 M in tetrahydrofuran, 0.31 mL, 0.63 mmol) dropwise at 0° C. The mixture was stirred at 0° C. for 0.5 h and quenched by addition of saturated aqueous ammonium chloride (10 mL). The mixture was extracted with ethyl acetate (3×10 mL). The combined organic layers were washed with water (20 mL), brine (20 mL), dried over sodium sulfate and concentrated under reduced pressure. The residue was purified by preparative TLC to give cyclopropyl-[(5S,7S)-5-(2,5-difluorophenyl)-7-fluoro-6,7-dihydro-5H-pyrrolo[1,2-b][1,2,4]triazol-2-yl]methanone (22.1 mg, 23%) as a white solid. $^1$H NMR (400 MHz, CD$_3$OD) δ 7.28-7.17 (m, 2H), 6.93-6.88 (m, 1H), 6.22-6.06 (m, 1H), 5.90-5.86 (m, 1H), 3.88-3.74 (m, 1H), 3.09-3.02 (m, 1H), 2.93-2.82 (m, 1H), 1.21-1.18 (m, 2H), 1.15-1.11 (m, 2H). LCMS R$_T$=1.007 min, m/z=308.1 [M+H]$^+$.

LCMS (10 to 80% acetonitrile in water+0.03% trifluoacetic acid over 2 mins) retention time 1.007 min, ESI+ found [M+H]=308.1.

Method 81

Example 102

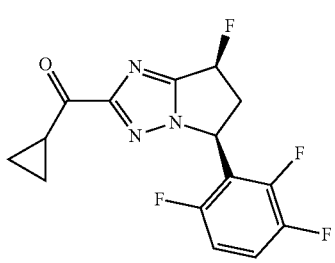

204

Cyclopropyl-[(5S,7S)-7-fluoro-5-(2,3,6-trifluorophenyl)-6,7-dihydro-5H-pyrrolo[1,2-b][1,2,4]triazol-2-yl]methanone

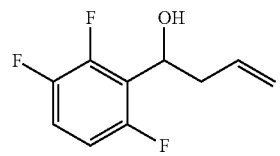

Step 1: 1-(2,3,6-trifluorophenyl)but-3-en-1-ol

To a solution of 2,3,6-trifluorobenzaldehyde (25.0 g, 156.2 mmol) in tetrahydrofuran (350 mL) was added allylmagnesium bromide (2.5 M in hexane, 93.7 mL, 187.4 mmol) at 0° C. under nitrogen atmosphere. The resulting mixture was allowed to warm to 25° C. and stirred for 1 h before quenched by addition of saturated aqueous ammonium chloride (100 mL). The resulting mixture was extracted with ethyl acetate (3×200 mL). The combined organic layers were dried over sodium sulfate and concentrated under reduce pressure to give crude 1-(2,3,6-trifluorophenyl)but-3-en-1-ol (30 g, 95%) as a light yellow oil. $^1$H NMR (400 MHz, CDCl$_3$) δ 7.01-7.17 (m, 1H), 6.79-6.92 (m, 1H), 5.72-5.91 (m, 1H), 5.07-5.26 (m, 3H), 2.74-2.88 (m, 1H), 2.65-2.69 (m, 1H), 2.44 (s, 1H).

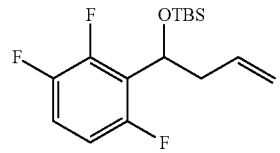 [SMILES: C=CCC(O[Si](C)(C)C(C)(C)C)c1c(F)ccc(F)c1F]

Step 2: Tert-Butyldimethyl((1-(2,3,6-trifluorophenyl)but-3-en-1-yl)oxy)silane To a solution of 1-(2,3,6-trifluorophenyl)but-3-en-1-ol (30.0 g, 148.4 mmol) in dichloromethane (250 mL) was added imidazole (20.2 g, 296.8 mmol) and tert-butyldimethylchlorosilane (29.1 g, 192.9 mmol). The reaction mixture was stirred at 25° C. for 16 h and then quenched by addition of water (100 mL). The mixture was extracted with dichloromethane (2×200 mL). The combined organic layers were washed with brine (100 mL), dried over sodium sulfate and concentrated under reduced pressure to afford crude tert-butyl-dimethyl-[1-(2,3,6-trifluorophenyl)but-3-enoxy]silane (46.0 g, 98%) as a light yellow oil. $^1$H NMR (400 MHz, CDCl$_3$) δ 7.26 (s, 1H), 7.07-6.95 (m, 1H), 6.97-6.77 (m, 1H), 5.58-5.82 (m, 1H), 4.97-5.11 (m, 3H), 2.84-2.64 (m, 1H), 2.62-2.44 (m, 1H), 0.83-0.86 (m, 9H), 0.03-0.07 (m, 3H), -0.17--0.13 (m, 3H).

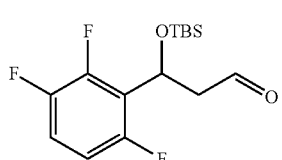

Step 3: 3-((tert-butyldimethylsilyl)oxy)-3-(2,3,6-trifluorophenyl)propanal

To a solution of tert-butyl-dimethyl-[1-(2,3,6-trifluorophenyl)but-3-enoxy]silane (5.0 g, 15.8 mmol) in water (30 mL) and tetrahydrofuran (30 mL) was added osmium tetroxide (0.5 g, 1.97 mmol). After stirred for 30 min at 15° C., sodium periodate (13.5 g, 63.2 mmol) was added in small portions over 2 h. The resulting mixture was stirred for another 2 h at 30° C. and then quenched by addition of cold saturated aqueous sodium thiosulfate (300 mL). The mixture was stirred for 30 min and then extracted with ethyl acetate (3×200 mL). The combined organic layers were washed with water (200 mL), brine (200 mL), dried over sodium sulfate and concentrated under reduced pressure to give crude product 3-[tert-butyl(dimethyl)silyl]oxy-3-(2,3,6-trifluorophenyl)propanal (5 g, 99%) as yellow oil.

Step 4: 1-(3-bromo-1-(tetrahydro-2H-pyran-2-yl)-1H-1,2,4-triazol-5-yl)-3-((tert-butyldimethylsilyl)oxy)-3-(2,3,6-trifluorophenyl)propan-1-ol To a cooled (−78° C.) solution of 3,5-dibromo-1-tetrahydropyran-2-yl-1,2,4-triazole (26.9 g, 86.4 mmol) in tetrahydrofuran (300 mL) was added n-butyllithium (2.5 M in hexanes, 38.0 mL, 95.0 mmol) under nitrogen atmosphere. The mixture was stirred at −78° C. for 30 min, then a solution of 3-[tert-butyl(dimethyl)silyl]oxy-3-(2,3,6-trifluorophenyl)propanal (27.0 g, 84.8 mmol) in tetrahydrofuran (100 mL) was added dropwise. After addition, the mixture was stirred at −78° C. for 1.5 h and quenched by addition of saturated aqueous ammonium chloride (100 mL). The resulting mixture was extracted with ethyl acetate (3×100 mL). The combined organic layers were dried over sodium sulfate and concentrated under reduce pressure. The residue was purified by column chromatography (silica gel, 100-200 mesh, 0 to 10% ethyl acetate in petroleum ether) to afford 1-(3-bromo-1-(tetrahydro-2H-pyran-2-yl)-1H-1,2,4-triazol-5-yl)-3-((tert-butyldimethylsilyl)oxy)-3-(2,3,6-trifluorophenyl)propan-1-ol (23 g, 49%) as a yellow oil.

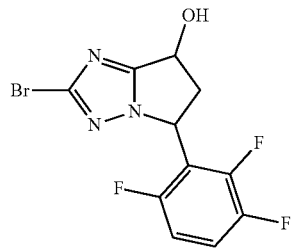 [SMILES: OC1CC(c2c(F)ccc(F)c2F)n2nc(Br)nc21]

Step 5: 2-bromo-5-(2,3,6-trifluorophenyl)-6,7-dihydro-5H-pyrrolo[1,2-b][1,2,4]triazol-7-ol A mixture of 1-(5-bromo-2-tetrahydropyran-2-yl-1,2,4-triazol-3-yl)-3-[tert-butyl(dimethyl)silyl] oxy-3-(2,3,6-trifluorophenyl)propan-1-ol (22.9 g, 41.6 mmol) and trifluoromethanesulfonic acid (12.2 mL, 138.4 mmol) in dichloromethane (200 mL) was heated at 55° C. for 4 d and concentrated under reduced pressure. The residue was diluted with water (100 mL) and adjusted to pH=9 with saturated aqueous sodium bicarbonate. The mixture was extracted with dichloromethane (3×200 mL). The combined organic layers were washed with water (100 mL), brine (100 mL), dried over sodium sulfate and concentrated under reduced pressure. The residue was purified by column chromatography (silica gel, 100-200 mesh, 0 to 30% ethyl acetate in petroleum ether) to afford the 2-bromo-5-(2,3,6-trifluorophenyl)-6,7-dihydro-5H-pyrrolo[1,2-b][1,2,4]triazol-7-ol (9.2 g, 66%) as a yellow solid. LCMS $R_T$=0.873&0.897 min, m/z=334.0/336.0 [M+H]$^+$.

LCMS (10 to 80% acetonitrile in water+0.03% trifluoacetic acid over 2.0 mins) retention time 0.873&0.897 min, ESI+ found [M+H]=334.0/336.0

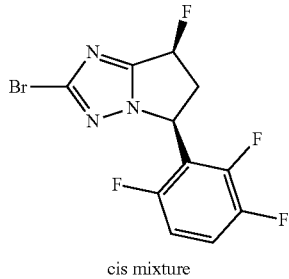 [SMILES: Fc1ccc(F)c([C@@H]2C[C@H](F)c3nc(Br)nn32)c1F]

cis mixture

Step 6: rac-(5S,7S)-2-bromo-7-fluoro-5-(2,3,6-trifluorophenyl)-6,7-dihydro-5H-pyrrolo[1,2-b][1,2,4]triazole To a cooled (0° C.) solution of 2-bromo-5-(2,3,6-trifluorophenyl)-6,7-dihydro-5H-pyrrolo[1,2-b][1,2,4]triazol-7-ol (9.2 g, 27.5 mmol) in toluene (100 mL) was added diethylaminosulfur trifluoride (14.6 mL, 110.2 mmol) in toluene (4 mL). The reaction mixture was stirred at 0° C. for 1 h and then slowly added into saturated aqueous sodium bicarbonate (100 mL) at 0° C. The mixture was extracted with dichloromethane (3×50 mL). The combined organic layers were washed with water (100 mL), brine (100 mL), dried over sodium sulfate and concentrated under reduced pressure. The residue was purified by column chromatography (silica gel, 100-200 mesh, 0 to 12% ethyl acetate in petroleum ether) to afford rac-(5S,7S)-2-bromo-7-fluoro-5-(2,3,6-trifluorophenyl)-6,7-dihydro-5H-pyrrolo[1,2-b][1,2,4]triazole (1.8 g, 19%) as a light yellow solid.

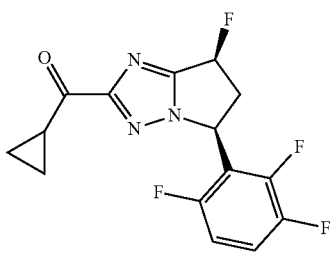 [SMILES: O=C(c1nc2n(n1)[C@H](c1c(F)ccc(F)c1F)C[C@@H]2F)C1CC1]

Step 7: Cyclopropyl-[(5S,7S)-7-fluoro-5-(2,3,6-trifluorophenyl)-6,7-dihydro-5H-pyrrolo[1,2-b][1,2,4]triazol-2-yl]methanone To a cooled (0° C.) solution of N-methoxy-N-methylcyclopropanecarboxamide (188 mg, 1.47 mmol) and rac-(5S,7S)-2-bromo-7-fluoro-5-(2,3,6-trifluorophenyl)-6,7-dihydro-5H-pyrrolo[1,2-b][1,2,4]triazole (150 mg, 0.72 mmol) in tetrahydrofuran (10 mL) was added isopropylmagnesium chloride (2.0 M in tetrahydrofuran, 0.73 ml, 1.46 mmol). The mixture was stirred at 0° C. for 1 h and quenched by addition of water (30 mL). The resulting mixture was extracted with ethyl acetate (2×20 mL). The combined organic layers were dried over sodium sulfate and concentrated under reduced pressure. The residue was purified by column chromatography (silica gel, 100-200 mesh, 0 to 5% ethyl acetate in petroleum ether) to afford cyclopropyl-[rac-(5S,7S)-7-fluoro-5-(2,3,6-trifluorophenyl)-6,7-dihydro-5H-pyrrolo[1,2-b][1,2,4]triazol-2-yl]methanone (95 mg, 40%) as a yellow solid. $^1$H NMR (400 MHz, CDCl$_3$) δ 7.25-7.16 (m, 1H), 6.92-6.89 (m, 1H), 6.23-5.96 (m, 1H), 5.91-5.77 (m, 1H), 3.87-3.72 (m, 1H), 3.14-2.97 (m, 2H), 1.37-1.27 (m, 2H), 1.14-1.03 (m, 2H). LCMS R$_T$=0.655 min, m/z=326.1 [M+H]+.

LCMS (5 to 95% acetonitrile in water+0.03% trifluoacetic acid over 1.5 mins) retention time 0.655 min, ESI+ found [M+H]=326.1.

This cis mixture was further separated by chiral SFC to afford arbitrarily assigned: cyclopropyl-[(5S,7S)-7-fluoro-5-(2,3,6-trifluorophenyl)-6,7-dihydro-5H-pyrrolo[1,2-b][1,2,4] triazol-2-yl]methanone (peak 1, retention time=2.856 min) (40 mg, 42%) as a white solid. $^1$H NMR (400 MHz, CDCl$_3$) δ 7.24-7.20 (m, 1H), 6.93-6.90 (m, 1H), 6.19-6.03 (m, 1H), 5.86-5.83 (m, 1H), 3.84-3.74 (m, 1H), 3.10-3.04 (m, 2H), 1.34-1.31 (m, 2H), 1.13-1.08 (m, 2H). LCMS R$_T$=0.864 min, m/z=325.9 [M+H]$^+$.

LCMS (5 to 95% acetonitrile in water+0.03% trifluoacetic acid over 1.5 mins) retention time 0.864 min, ESI+ found [M+H]=325.9.

SFC condition: Column: Chiralcel OJ-3 150×4.6 mm I.D., 3 μm. Mobile phase: A: CO$_2$ B: ethanol (0.05% DEA). Gradient: from 5% to 40% of B in 5 min and hold 40% for 2.5 min, then 5% of B for 2.5 min. Flow rate: 2.5 mL/min Column temp.: 35° C.

Method 82

Example 103

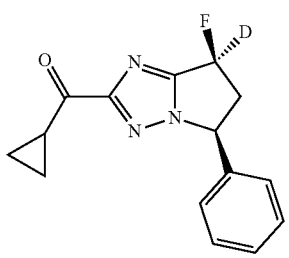

Cyclopropyl-[(5S,7S)-7-deuterio-7-fluoro-5-phenyl-5,6-dihydropyrrolo[1,2-b][1,2,4]triazol-2-yl]methanone

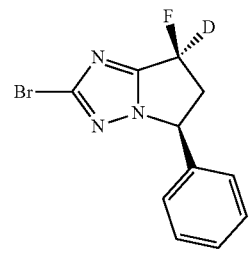

cis-mixture

Step 1: Cis-2-bromo-7-deuterio-7-fluoro-5-phenyl-5,6-dihydropyrrolo[1,2-b][1,2,4]triazole To a cooled (0° C.) solution of trans-2-bromo-7-deuterio-5-phenyl-5,6-dihydropyrrolo[1,2-b][1,2,4]triazol-7-ol (400 mg, 1.42 mmol) in toluene (10 mL) was added diethylaminosulfur trifluoride (917 mg, 5.69 mmol). The mixture was stirred at 0° C. for 1 h and quenched by addition of saturated sodium bicarbonate (30 mL) at 0° C. The mixture was extracted with dichloromethane (3×50 mL). The combined organic layers were washed with water (50 mL), brine (50 mL), dried over sodium sulfate and concentrated under reduced pressure. The residue was purified by column chromatography (silica gel, 100-200 mesh, 0 to 12% ethyl acetate in petroleum ether) to afford cis-2-bromo-7-deuterio-7-fluoro-5-phenyl-5,6-dihydropyrrolo[1,2-b][1,2,4]triazole (0.22 g, 55%) as a white solid. $^1$H NMR (400 MHz, CDCl$_3$) δ 7.43-7.38 (m, 3H), 7.27-7.24 (m, 2H), 5.47-5.42 (m, 1H), 3.63-3.51 (m, 1H), 2.94-2.84 (m, 1H).

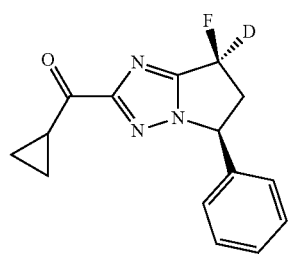 [SMILES: [2H][C@]1(F)C[C@@H](c2ccccc2)n2nc(C(=O)C3CC3)nc21]

Step 2: Cyclopropyl-[(5S,7S)-7-deuterio-7-fluoro-5-phenyl-5,6-dihydropyrrolo[1,2-b][1,2,4]triazol-2-yl]methanone To a solution of cis-2-bromo-7-deuterio-7-fluoro-5-phenyl-5,6-dihydropyrrolo[1,2-b][1,2,4] triazole (210 mg, 0.74 mmol) and N-methoxy-N-methyl-cyclopropanecarboxamide (192 mg, 1.48 mmol) in tetrahydrofuran (6 mL) was added isopropylmagnesium chloride (2.0 M in tetrahydrofuran, 0.74 mL, 1.48 mmol) at 0° C. under nitrogen. The mixture was stirred at 0° C. for 1 h and quenched by addition of saturated aqueous ammonium chloride (10 mL). The mixture was extracted with ethyl acetate (3×15 mL). The combined organic layers were washed with water (20 mL), brine (20 mL), dried over sodium sulfate and concentrated under reduced pressure. The residue was purified by RP-HPLC (acetonitrile 44-74%/0.05% ammonia hydroxide in water) to afford cyclopropyl-[cis-7-deuterio-7-fluoro-5-phenyl-5,6-dihydropyrrolo[1,2-b][1,2,4]triazol-2-yl]methanone (55 mg, 27%) as a white solid. LCMS $R_T$=0.646 min, m/z=273.2 [M+H]$^+$.

LCMS (5 to 95% acetonitrile in water+0.03% trifluoacetic acid over 1.5 mins) retention time: 0.646 min, ESI+ found [M+H]=273.2.

The above cis mixture was further separated by chiral SFC to afford arbitrarily assigned: cyclopropyl-[(5S,7S)-7-deuterio-7-fluoro-5-phenyl-5,6-dihydropyrrolo[1,2-b][1,2,4]triazol-2-yl]methanone (peak 2, retention time=4.354 min) (16.6 mg, 29%) as a white solid. $^1$HNMR (400 MHz, CD$_3$OD) δ 7.45-7.38 (m, 3H), 7.29-7.27 (m, 2H), 5.67-5.63 (m, 1H), 3.80-3.70 (m, 1H), 3.05-3.02 (m, 1H), 2.88-2.80 (m, 1H), 1.19-1.16 (m, 2H), 1.12-1.09 (m, 2H). LCMS $R_T$=0.738 min, m/z=273.1 [M+H]$^+$.

LCMS (5 to 95% acetonitrile in water+0.03% trifluoacetic acid over 1.5 mins) retention time: 0.738 min, ESI+ found [M+H]=273.1.

SFC condition: Column: Daicel Chiralpak AD-H (250 mm*30 mm, 5 μm) I.D., 5 μm mobile phase: A: CO2 B:ethanol (0.1% NH$_3$H$_2$O IPA) Gradient: from 30% to 30% of B in 5 min and hold 40% for 2.5 min, then 5% of B for 2.5 min Flow rate: 2.5 mL/min Column temp.: 35° C.

Method 83

Example 104

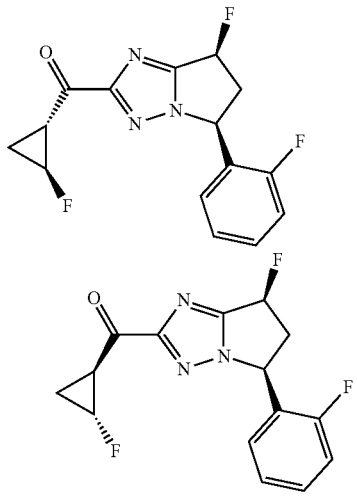

[(1R,2S)-2-fluorocyclopropyl]-[(5S,7S)-7-fluoro-5-(2-fluorophenyl)-6,7-dihydro-5H-pyrrolo[1,2-b][1,2,4]triazol-2-yl]methanone and [(1S,2R)-2-fluorocyclopropyl]-[(5S,7S)-7-fluoro-5-(2-fluorophenyl)-6,7-dihydro-5H-pyrrolo[1,2-b][1,2,4]triazol-2-yl]methanone To a solution of trans-2-fluoro-N-methoxy-N-methyl-cyclopropanecarboxamide (trans mixture) (245 mg, 1.65 mmol) and (5S,7S)-2-bromo-7-fluoro-5-(2-fluorophenyl)-6,7-dihydro-5H-pyrrolo[1,2-b][1,2,4]triazole (250 mg, 0.85 mmol) in tetrahydrofuran (10 mL) was added isopropylmagnesiumchloride (2.1 mL, 4.15 mmol, 2 M in tetrahydrofuran) at 0° C. under nitrogen atmosphere. The mixture was stirred at 0° C. for 1 hour. The reaction mixture was quenched by addition of water (10 mL) and extracted with ethyl acetate (3×20 mL). The organic layers were dried over sodium sulfate and concentrated under reduced pressure. The residue was purified by prep-TLC (33% ethyl acetate in petroleum ether, $R_f$=0.6) to afford [(1S,2R)-2-fluorocyclopropyl]-[(5S,7S)-7-fluoro-5-(2-fluorophenyl)-6,7-dihydro-5H-pyrrolo[1,2-b][1,2,4]triazol-2-yl]methanone (trans mixture) (105 mg, 41%) as a white solid. LCMS $R_T$=0.739 min, m/z=308.1 [M+H]$^+$.

LCMS (5 to 95% acetonitrile in water+0.03% trifluoacetic acid over 1.5 mins) retention time 0.739 min, ESI+ found [M+H]=308.1.

The above trans mixture was further separated by chiral SFC to afford arbitrarily assigned: [(1R,2S)-2-fluorocyclopropyl]-[(5S,7S)-7-fluoro-5-(2-fluorophenyl)-6,7-dihydro-5H-pyrrolo [1,2-b][1,2,4]triazol-2-yl]methanone (peak 1, retention time=2.773 min) (48.1 mg, 45%) as a white solid. $^1$H NMR (400 MHz, CD$_3$OD) δ 7.48-7.42 (m, 1H), 7.25-7.13 (m, 3H), 6.22-6.06 (m, 1H), 5.93-5.89 (m, 1H), 5.01-4.87 (m, 0.5H), 4.85-4.82 (m, 0.5H), 3.88-3.75 (m, 1H), 3.51-3.42 (m, 1H), 2.93-2.81 (m, 1H), 1.75-1.64 (m, 1H), 1.62-1.54 (m, 1H). LC-MS $R_T$=0.852 min, m/z=308.0 [M+H]$^+$.

LCMS (5 to 95% acetonitrile in water+0.03% trifluoacetic acid over 1.5 mins) retention time 0.852 min, ESI+ found [M+H]=308.0.

The 1S,2R-isomer was not isolated.

SFC condition:Column: Chiralcel OD-3 150×4.6 mm I.D., 3 μm Mobile phase: A: CO2 B:ethanol (0.05% DEA) Gradient: from 5% to 40% of B in 5 min and hold 40% for 2.5 min, then 5% of B for 2.5 min Flow rate: 2.5 mL/min Column temp.: 35° C.

A larger batch of trans mixture (215 mg, 0.70 mmol) was separated by chiral SFC to afford arbitrarily assigned:

[(1S,2R)-2-fluorocyclopropyl]-[(5S,7S)-7-fluoro-5-(2-fluorophenyl)-6,7-dihydro-5H-pyrrolo [1,2-b][1,2,4]triazol-2-yl]methanone (peak 1, retention time=2.445 min) (19.5 mg, 9%) as a white solid. $^1$H NMR (400 MHz, CDCl$_3$) δ 7.40-7.38 (m, 1H), 7.18-7.15 (m, 2H), 6.98-6.97 (m, 1H), 6.13-6.11 (m, 0.5H), 5.99-5.98 (m, 0.5H), 5.87-5.85 (m, 1H), 5.05-5.04 (m, 0.5H), 4.89-4.88 (m, 0.5H), 3.73-3.67 (m, 1H), 3.58-3.54 (m, 1H), 3.01-2.95 (m, 1H), 1.72-1.65 (m, 2H). LC-MS $R_T$=1.763 min, m/z=308.1 (M+H).

LCMS (10 to 80% acetonitrile in water+0.1% ammonia water over 3.0 mins) retention time 1.763 min, ESI+ found [M+H]=308.1. Note: the 1R,2S-isomer was peak 2 (retention time=2.728 min) under AD SFC conditions.

SFC condition:Column: Daicel Chiralpak AD-H (250 mm*30 mm, 5 μm) Mobile phase: A: CO2 B:ethanol (0.1% NH$_3$H$_2$O methanol) Gradient: from 15% to 15% of B in 5 min and hold 40% for 2.5 min, then 5% of B for 2.5 min Flow rate: 2.5 mL/min Column temp.: 35° C.

Method 84

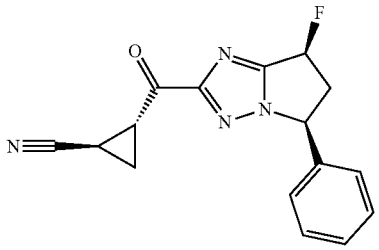

Example 105

Rac-(1R,2R)-2-[(5S,7S)-7-fluoro-5-phenyl-6,7-di-hydro-5H-pyrrolo[1,2-b][1,2,4]triazole-2-carbonyl]cyclopropanecarbonitrile

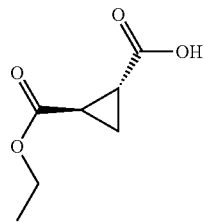

trans mixture

Step 1: trans-2-(ethoxycarbonyl)cyclopropanecarboxylic Acid

To a solution of diethyl trans-cyclopropane-1,2-dicarboxylate (2000 mg, 10.74 mmol) in ethanol (26 mL) was added a solution of sodium hydroxide (429 mg, 10.74 mmol) in water (3 mL). The mixture was stirred at 25° C. for 16 h and concentrated under reduced pressure. The aqueous residue was adjusted to pH=3 by addition of aqueous hydrochloric acid (4 M) at 0° C. The mixture was extracted with ethyl acetate (3×30 mL). The combined organic layers were washed with brine (10 mL), dried over sodium sulfate and concentrated under reduced pressure to give trans-2-ethoxycarbonylcyclopropanecarboxylic acid (820 mg, 48%) as a white solid. LCMS $R_T$=0.430 min, m/z=159.1 [M+H]$^+$.

LCMS (5 to 95% acetonitrile in water+0.03% trifluoacetic acid over 1.5 mins) retention time 0.430 min, ESI+ found [M+H]=159.1.

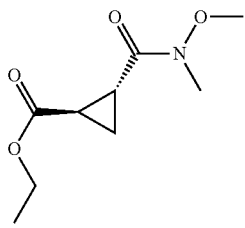

trans mixture

Step 2: Ethyl Trans-2-(methoxy(methyl)carbamoyl)cyclopropanecarboxylate

A mixture of 1-hydroxybenzotriazole (684 mg, 5.06 mmol), 1-(3-dimethylaminopropyl)-3-ethyl carbodiimide-hydrochloride (1164 mg, 6.07 mmol), trans-2-ethoxycarbonylcyclopropane carboxylic acid (800 mg, 5.06 mmol), N,O-dimethylhydroxylamine hydrochloride (740 mg, 7.59 mmol) and N,N-diisopropylethylamine (1634 mg, 12.65 mmol) in dichloromethane (20 mL) was stirred at 25° C. for 16 h and diluted with water (20 mL). The reaction mixture was extracted with dichloromethane (3×20 mL). The combined organic layers were washed with brine (20 mL), dried over sodium sulfate and concentrated under reduced pressure. The residue was purified by column chromatography (silica gel, 100-200 mesh, 0 to 20% ethyl acetate in petroleum ether) to give ethyl trans-2-[methoxy(methyl)carbamoyl]cyclopropanecarboxylate (600 mg, 59%) as a light yellow oil. LCMS $R_T$=0.525 min, m/z=202.2 [M+H]$^+$.

LCMS (5 to 95% acetonitrile in water+0.03% trifluoacetic acid over 1.5 mins) retention time 0.525 min, ESI+ found [M+H]=202.2.

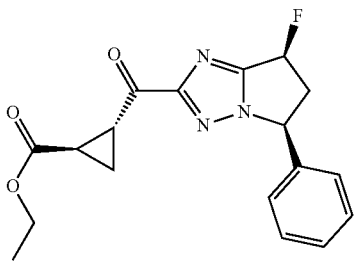

trans mixture

Step 3: Ethyl Trans-2-((5S,7S)-7-fluoro-5-phenyl-6,7-dihydro-5H-pyrrolo[1,2-b][1,2,4]triazole-2-carbonyl)cyclopropanecarboxylate To a solution of ethyl trans-2-[methoxy(methyl)carbamoyl]cyclopropanecarboxylate (571 mg, 2.84 mmol) and (5S,7S)-2-bromo-7-fluoro-5-phenyl-6,7-dihydro-5H-pyrrolo[1,2-b][1,2,4] triazole (400 mg, 1.42 mmol) in tetrahydrofuran (13 mL) was added isopropylmagnesium chloride (2.0 M in tetrahydrofuran, 2.84 mL, 5.67 mmol) dropwise at 0° C. under nitrogen atmosphere. After addition, the mixture was stirred at 0° C. for 2 h and quenched by addition of saturated aqueous ammonium chloride (10 mL). The resulting mixture was extracted with ethyl acetate (3×25 mL). The combined organic layers were dried over sodium sulfate and concentrated under reduced pressure. The residue was purified by column chromatography (silica gel, 100-200 mesh, 0 to 40% ethyl acetate in petroleum ether) to give ethyl trans-2-[(5S,7S)-7-fluoro-5-phenyl-6,7-dihydro-5H-pyrrolo[1,2-b][1,2,4]triazole-2-carbonyl]cyclo propanecarboxylate (350 mg, 72%) as a light yellow oil. LCMS $R_T$=0.693 min, m/z=344.1 [M+H]$^+$.

LCMS (5 to 95% acetonitrile in water+0.03% trifluoacetic acid over 1.5 mins) retention time 0.693 min, ESI+ found [M+H]=344.1.

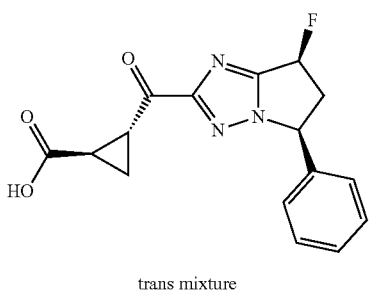 [SMILES: O=C(O)[C@@H]1C[C@H]1C(=O)c1nc2n(n1)[C@H](c1ccccc1)C[C@@H]2F]

trans mixture

Step 4: Trans-2-((5S,7S)-7-fluoro-5-phenyl-6,7-dihydro-5H-pyrrolo[1,2-b][1,2,4]triazole-2-carbonyl)cyclopropanecarboxylic Acid To a solution of ethyl trans-2-[(5S,7S)-7-fluoro-5-phenyl-6,7-dihydro-5H-pyrrolo[1,2-b][1,2,4]triazole-2-carbonyl]cyclopropanecarboxylate (100 mg, 0.29 mmol) in tetrahydrofuran (10 mL) was added a solution of lithium hydroxide (42 mg, 1.75 mmol) in water (2 mL). The mixture was stirred at 25° C. for 16 h and concentrated under reduced pressure. The aqueous residue was adjusted to pH=3 by addition of aqueous hydrochloric acid (4 M) at 0° C. The mixture was then extracted with ethyl acetate (3×15 mL). The combined organic layers were washed with brine (10 mL), dried over sodium sulfate and concentrated under reduced pressure to give crude trans-2-[(5S,7S)-7-fluoro-5-phenyl-6,7-dihydro-5H-pyrrolo[1,2-b][1,2,4]triazole-2-carbonyl]cyclopropanecarboxylic acid (90 mg, 98%) as a white solid. LCMS $R_T$=0.590 min, m/z=316.2 [M+H]$^+$.

LCMS (5 to 95% acetonitrile in water+0.03% trifluoacetic acid over 1.5 mins) retention time 0.590 min, ESI+ found [M+H]=316.2.

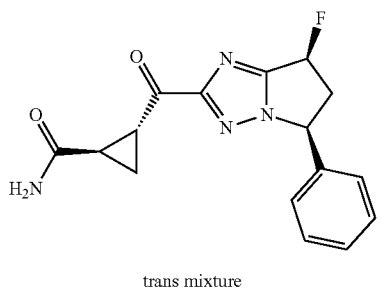 [SMILES: NC(=O)[C@@H]1C[C@H]1C(=O)c1nc2n(n1)[C@H](c1ccccc1)C[C@@H]2F]

trans mixture

Step 5: trans-2-((5S,7S)-7-fluoro-5-phenyl-6,7-dihydro-5H-pyrrolo[1,2-b][1,2,4]triazole-2-carbonyl)cyclopropanecarboxamide A mixture of 1-hydroxybenzotriazole (34 mg, 0.25 mmol), 1-(3-dimethylaminopropyl)-3-ethylcarbodiimidehydrochloride (49 mg, 0.25 mmol), ammonium chloride (27 mg, 0.51 mmol), N,N-diisopropylethylamine (98 mg, 0.76 mmol) and trans-2-[(5S,7S)-7-fluoro-5-phenyl-6,7-dihydro-5H-pyrrolo[1,2-b][1,2,4]triazole-2-carbonyl]cyclopropanecarboxylic acid (80 mg, 0.25 mmol) in N,N-dimethylformamide (3 mL) was stirred at 25° C. for 18 h and diluted with water (10 mL). The resulting mixture was extracted with ethyl acetate (3×20 mL). The combined organic layers were dried over sodium sulfate and concentrated under reduced pressure. The residue was purified by column chromatography (silica gel, 100-200 mesh, 0 to 10% ethyl acetate in methanol) to give trans-2-[(5S,7S)-7-fluoro-5-phenyl-6,7-dihydro-5H-pyrrolo[1,2-b][1,2,4]triazole-2-carbonyl]cyclopropanecarboxamide (75 mg, 94%) as a white solid. LCMS $R_T$=0.555 min, m/z=315.1 [M+H]$^+$.

LCMS (5 to 95% acetonitrile in water+0.03% trifluoacetic acid over 1.5 mins) retention time 0.555 min, ESI+ found [M+H]=315.1.

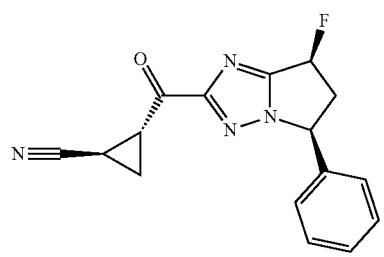 [SMILES: N#C[C@@H]1C[C@H]1C(=O)c1nc2n(n1)[C@H](c1ccccc1)C[C@@H]2F]

Step 6: Rac-(R,2R)-2-[(5S,7S)-7-fluoro-5-phenyl-6,7-dihydro-5H-pyrrolo[1,2-b][1,2,4] triazole-2-carbonyl]cyclopropanecarbonitrile To a solution of trans-2-[(5S,7S)-7-fluoro-5-phenyl-6,7-dihydro-5H-pyrrolo[1,2-b][1,2,4] triazole-2-carbonyl]cyclopropanecarboxamide (65 mg, 0.21 mmol) in 1,4-dioxane (3 mL) was added triethylamine (62 mg, 0.62 mmol) and trifluoroacetic anhydride (87 mg, 0.41 mmol). The reaction was stirred at 25° C. for 2 h and diluted with water (15 mL). The mixture was extracted with ethyl acetate (3×15 mL). The combined organic layers were washed with saturated aqueous sodium bicarbonate (20 mL), dried over sodium sulfate and concentrated under reduced pressure. The residue was purified by RP-HPLC (acetonitrile 15-45%/0.05% ammonia hydroxide in water) to afford arbitrarily assigned rac-(1R,2R)-2-[(5S,7S)-7-fluoro-5-phenyl-6,7-dihydro-5H-pyrrolo[1,2-b][1,2,4]triazole-2-carbonyl]cyclopropanecarbonitrile (24.0 mg, 38%) as a white solid. $^1$H NMR (400 MHz, CD$_3$OD) δ 7.45-7.39 (m, 3H), 7.32-7.30 (m, 2H), 6.22-6.20 (m, 0.5H), 6.08-6.06 (m, 0.5H), 5.70-5.67 (m, 1H), 3.81-3.75 (m, 1H), 3.62-3.31 (m, 1H), 2.90-2.75 (m, 1H), 2.28-2.24 (m, 1H), 1.68-1.63 (m, 2H). LCMS $R_T$=0.957 min, m/z=297.2 [M+H]$^+$.

LCMS (10 to 80% acetonitrile in water+0.03% ammonium bicarbonate over 2.0 mins) retention time 0.957 min, ESI+ found [M+H]=297.2.

Method 85

Example 106

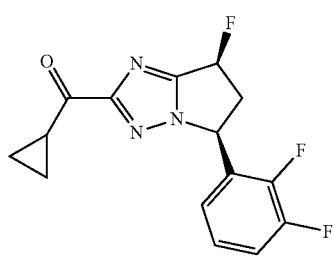

Cyclopropyl-[(5S,7S)-5-(2,3-difluorophenyl)-7-fluoro-6,7-dihydro-5H-pyrrolo[1,2-b][1,2,4]triazol-2-yl]methanone

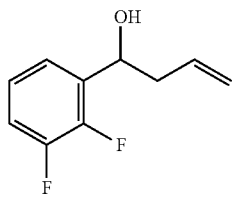

Step 1: 1-(2,3-difluorophenyl)but-3-en-1-ol

To a cooled (0° C.) solution of 2,3-difluorobenzaldehyde (10.0 g, 70.4 mmol) in tetrahydrofuran (100 mL) was added allylmagnesium chloride (2.0 M in tetrahydrofuran, 46.0 mL, 92.0 mmol) over 30 min. After addition, the reaction mixture was allowed to warm to room temperature and stirred for 2 h and then quenched by addition of saturated aqueous ammonium chloride (100 mL). The resulting mixture was extracted with ethyl acetate (3×200 mL). The combined organic layers were dried over sodium sulfate and concentrated under reduce pressure to give crude 1-(2,3-difluorophenyl)but-3-en-1-ol (12.9 g, 99%) as a light yellow oil. $^1$H NMR (400 MHz, CDCl$_3$) δ 7.27-7.24 (m, 1H), 7.11-7.06 (m, 2H), 5.87-5.77 (m, 1H), 5.20-5.08 (m, 3H), 2.62-2.47 (m, 2H).

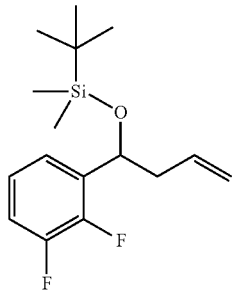 [SMILES: C=CCC(O[Si](C)(C)C(C)(C)C)c1cccc(F)c1F]

Step 2: Tert-Butyl((1-(3,4-difluorophenyl)but-3-en-1-yl)oxy)dimethylsilane

To a stirred solution of 1-(2,3-difluorophenyl)but-3-en-1-ol (12.9 g, 70.6 mmol) in dichloromethane (20 mL) was added imidazole (9.6 g, 141.2 mmol) and tert-butyldimethylchlorosilane (12.8 g, 84.7 mmol). After addition, the reaction mixture was stirred at 25° C. for 16 h and quenched by addition of water (100 mL). The mixture was extracted with dichloromethane (2×200 mL). The combined organic layers were washed with brine (100 mL), dried over sodium sulfate and concentrated under reduced pressure to afford crude tert-butyl-[1-(2,3-difluorophenyl)but-3-enoxy]-dimethyl-silane (21.0 g, 99%) as colorless oil. $^1$H NMR (400 MHz, CDCl$_3$) δ 7.25-7.22 (m, 1H), 7.08-7.03 (m, 2H), 5.82-5.75 (m, 1H), 5.10-4.99 (m, 3H), 2.49-2.42 (m, 2H), 0.89 (s, 9H), 0.67 (s, 3H), −0.08 (s, 3H).

Step 3: 3-((tert-butyldimethylsilyl)oxy)-3-(3,4-difluorophenyl)propanal

To a solution of tert-butyl-[1-(2,3-difluorophenyl)but-3-enoxy]-dimethyl-silane (21.0 g, 70.4 mmol) in tetrahydrofuran/water (200 mL, 1:1) was added osmium tetraoxide (0.1 g, 0.39 mmol). After stirred for 30 min at 15° C., the mixture wad added sodium periodate (60.2 g, 281.5 mmol) in small portions over 2 h. The resulting mixture was stirred for another 2 h at 30° C. and then quenched by addition of cold saturated aqueous sodium thiosulfate (300 mL). The mixture was stirred for 30 min and then extracted with ethyl acetate (3×200 mL). The combined organic layers were washed with water (200 mL), brine (200 mL), dried over sodium sulfate and concentrated under reduced pressure. The residue was purified by column chromatography (silica gel, 100-200 mesh, 0 to 3% ethyl acetate in petroleum ether) to afford 3-[tert-butyl(dimethyl)silyl]oxy-3-(2,3-difluorophenyl)propanal (15.0 g, 71%) as yellow oil.

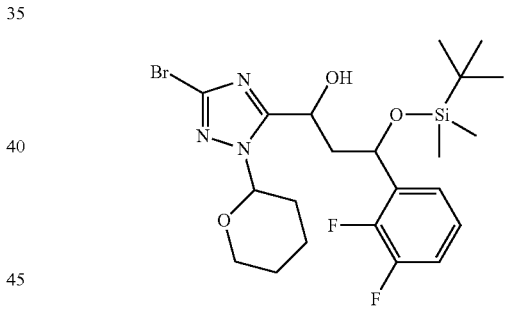

Step 4: 1-(3-bromo-1-(tetrahydro-2H-pyran-2-yl)-1H-1,2,4-triazol-5-yl)-3-((tert-butyldimethylsilyl)oxy)-3-(3,4-difluorophenyl)propan-1-ol To a cooled (−78° C.) solution of 3,5-dibromo-1-tetrahydropyran-2-yl-1,2,4-triazole (15.7 g, 50.4 mmol) in tetrahydrofuran (150 mL) was added n-butyllithium (2.5 M in hexanes, 22.0 mL, 54.9 mmol) dropwise under nitrogen atmosphere. The mixture was stirred at −78° C. for 30 min, then a solution of 3-[tert-butyl(dimethyl)silyl]oxy-3-(2,3-difluorophenyl)propanal (15.0 g, 49.9 mmol) in tetrahydrofuran (20 mL) was added dropwise. After addition, the mixture was stirred at −78° C. for 1.5 h and then quenched by addition of saturated aqueous ammonium chloride (100 mL). The resulting mixture was extracted with ethyl acetate (3×100 mL). The combined organic layers were dried over sodium sulfate and concentrated under reduce pressure. The residue was purified by column chromatography (silica gel, 100-200 mesh, 0 to 12% ethyl acetate in petroleum ether) to afford 1-(5-bromo-2-tetrahydropyran-2-yl-1,2,4-triazol-3-yl)-3-[tert-butyl(dimethyl)silyl]oxy-3-(2,3-difluorophenyl)propan-1-ol (12.0 g, 45%) as yellow oil.

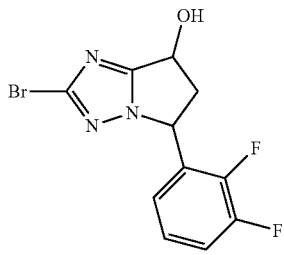 [SMILES: OC1CC(c2cccc(F)c2F)n2nc(Br)nc21]

Step 5: 2-bromo-5-(2,3-difluorophenyl)-6,7-dihydro-5H-pyrrolo[1,2-b][1,2,4]triazol-7-ol A solution of 1-(5-bromo-2-tetrahydropyran-2-yl-1,2,4-triazol-3-yl)-3-[tert-butyl(dimethyl)silyl] oxy-3-(3,4-difluorophenyl)propan-1-ol (56.0 g, 105.2 mmol) in trifluoroacetic acid (150 mL) was heated at 55° C. for 16 h and concentrated under reduced pressure. The residue was adjusted to pH=9 by addition of saturated aqueous sodium bicarbonate and extracted with dichloromethane (3×200 mL). The combined organic layers were washed with water (100 mL), brine (100 mL), dried over sodium sulfate and concentrated under reduced pressure to afford crude 2-bromo-5-(2,3-difluorophenyl)-6,7-dihydro-5H-pyrrolo[1,2-b][1,2,4]triazol-7-ol (22.0 g, 66%) as a white solid.

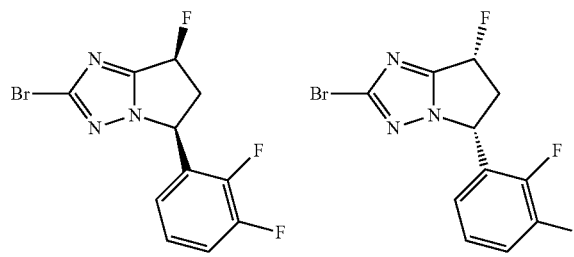

Step 6: (5S,7S)-2-bromo-5-(2,3-difluorophenyl)-7-fluoro-6,7-dihydro-5H-pyrrolo[1,2-b][1,2,4]triazole and (5R,7R)-2-bromo-5-(2,3-difluorophenyl)-7-fluoro-6,7-dihydro-5H-pyrrolo[1,2-b][1,2,4]triazole To a stirred solution of 2-bromo-5-(2,3-difluorophenyl)-6,7-dihydro-5H-pyrrolo[1,2-b][1,2,4]triazol-7-ol (30.0 g, 94.9 mmol) in toluene (200 mL) was slowly added diethylaminosulfur trifluoride (45.9 g, 284.7 mmol) at 0° C. The reaction mixture was stirred at 0° C. for 16 h and then slowly added into stirred aqueous saturated sodium bicarbonate (200 mL) at 0° C. The mixture was extracted with dichloromethane (3×150 mL). The combined organic layers were washed with water (100 mL), brine (100 mL), dried over sodium sulfate and concentrated under reduced pressure. The residue was purified by column chromatography (silica gel, 100-200 mesh, 0 to 15% ethyl acetate in petroleum ether) to afford cis-2-bromo-5-(2,3-difluorophenyl)-7-fluoro-6,7-dihydro-5H-pyrrolo[1,2-b][1,2,4]triazole. This cis material was further separated by chiral SFC to afford arbitrarily assigned: (5S,7S)-2-bromo-5-(2,3-difluorophenyl)-7-fluoro-6,7-dihydro-5H-pyrrolo[1,2-b][1,2,4]triazole (peak 1, retention time=2.828 min) (1.1 g, 3.7%) as a white solid and (5R,7R)-2-bromo-5-(2,3-difluorophenyl)-7-fluoro-6,7-dihydro-5H-pyrrolo[1,2-b][1,2,4]triazole (peak 2, retention time=2.935 min) (1.1 g, 3.7%) as a white solid.

SFC condition: Column: Chiral Cel OJ-H 150×4.6 mm I.D., 5 μm Mobile phase: A: $CO_2$ B:Ethanol (0.05% DEA) Gradient: from 5% to 40% of B in 5.5 min and hold 40% for 3 min, then 5% of B for 1.5 min Flow rate: 2.5 mL/min. Column temp.: 40° C.

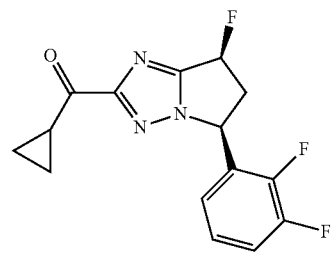 [SMILES: O=C(c1nc2n(n1)[C@H](c1cccc(F)c1F)C[C@@H]2F)C1CC1]

Step 7: Cyclopropyl-[(5S,7S)-5-(2,3-difluorophenyl)-7-fluoro-6,7-dihydro-5H-pyrrolo[1,2-b][1,2,4]triazol-2-yl]methanone To a solution of (5S,7S)-2-bromo-5-(2,3-difluorophenyl)-7-fluoro-6,7-dihydro-5H-pyrrolo[1,2-b][1,2,4]triazole (150 mg, 0.47 mmol), N-methoxy-N-methyl-cyclopropanecarboxamide (122 mg, 0.94 mmol) in tetrahydrofuran (3 mL) was added isopropylmagnesium chloride (2.0 M in tetrahydrofuran, 0.47 mL, 0.94 mmol) dropwise at 0° C. After addition, the mixture was stirred at 0° C. for 0.5 h and quenched by addition of saturated aqueous ammonium chloride (10 mL). The mixture was extracted with ethyl acetate (3×10 mL). The combined organic layers were washed with water (20 mL), brine (20 mL), dried over sodium sulfate and concentrated under reduced pressure. The residue was purified by RP-HPLC (acetonitrile 40-70%/0.225% formic acid in water) to afford arbitrarily assigned cyclopropyl-[(5S,7S)-5-(2,3-difluorophenyl)-7-fluoro-6,7-dihydro-5H-pyrrolo[1,2-b][1,2,4]triazol-2-yl]methanone (49.1 mg, 34%) as a white solid. $^1$H NMR (400 MHz, CDCl$_3$) δ 7.22-7.16 (m, 1H), 7.14-7.08 (m, 1H), 6.75-6.72 (m, 1H), 6.13-6.10 (m, 0.5H), 5.99-5.96 (m, 0.5H), 5.88-5.84 (m, 1H), 3.74-3.67 (m, 1H), 3.09-3.04 (m, 1H), 2.99-2.92 (m, 1H), 1.36-1.31 (m, 2H), 1.14-1.09 (m, 2H). LC-MS $R_T$=0.666 min, m/z=308.1 [M+H]$^+$.

LCMS (5 to 95% acetonitrile in water+0.03% trifluoacetic acid over 1.5 mins) retention time 0.666 min, ESI+ found [M+H]=308.1.

Method 86

Example 107

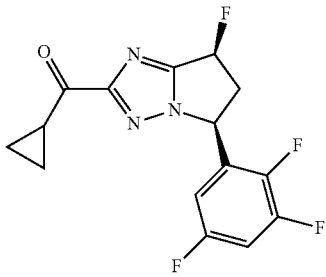

Cyclopropyl-[(5S,7S)-7-fluoro-5-(2,3,5-trifluorophenyl)-6,7-dihydro-5H-pyrrolo[1,2-b][1,2,4]triazol-2-yl]methanone

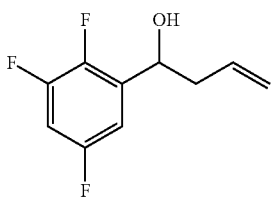

Step 1: 1-(2,3,5-trifluorophenyl)but-3-en-1-ol

To a solution of 2,3,5-trifluorobenzaldehyde (20.0 g, 124.93 mmol) in dichloromethane (120 mL) and water (120 mL) was added tetrabutylammonium iodide (4.6 g, 12.49 mmol) and potassium allyltrifluoroborate (40.7 g, 137.42 mmol) at 25° C. The mixture was stirred for 2 h at 25° C. and extracted with dichloromethane (2×100 mL). The combined organic layers were washed with brine (50 mL) and concentrated under reduced pressure to afford crude 1-(2,3,5-trifluorophenyl)but-3-en-1-ol (29.0 g, 100%) as a yellow oil.

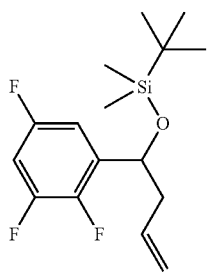 [SMILES: C=CCC(O[Si](C)(C)C(C)(C)C)c1cc(F)cc(F)c1F]

Step 2: Tert-Butyldimethyl((1-(2,3,5-trifluorophenyl)but-3-en-1-yl)oxy)silane To a mixture of 1-(2,3,5-trifluorophenyl)but-3-en-1-ol (20.5 g, 101.4 mmol) and imidazole (13.8 g, 202.7 mmol) in dichloromethane (120 mL) was added tert-butyldimethylchlorosilane (19.9 g, 131.9 mmol). The mixture was stirred at 35° C. for 16 h and diluted with dichloromethane (50 mL). The mixture was washed with water (2×50 mL), brine (50 mL), dried over sodium sulfate and concentrated under reduced pressure. The residue was purified by column chromatography (silica gel, 100-200 mesh, 0 to 10% ethyl acetate in petroleum ether) to afford tert-butyldimethyl((1-(2,3,5-trifluorophenyl)but-3-en-1-yl)oxy)silane (28.0 g, 87%) as a colorless oil.

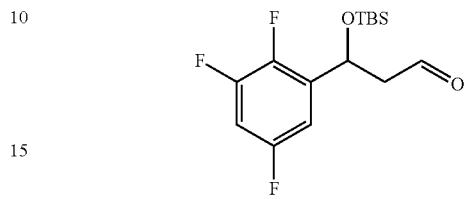

Step 3: 3-((tert-butyldimethylsilyl)oxy)-3-(2,3,5-trifluorophenyl)propanal

A mixture of tert-butyl-dimethyl-[1-(2,3,5-trifluorophenyl)but-3-enoxy]silane (5.0 g, 15.8 mmol) and osmium tetroxide (5.0 g, 19.7 mmol) in tetrahydrofuran (20 mL) and water (20 mL) was stirred at 20° C. for 0.5 h and then sodium periodate (13.5 g, 63.2 mmol) was added in 3 portions over 0.5 h. After addition, the reaction mixture was stirred at 20° C. for 3 h and quenched by addition of saturated aqueous sodium thiosulfate (30 mL). The solid was removed by filtration. The filtrate was extracted with ethyl acetate (3×20 mL). The combined organic layers were washed with brine and concentrated under reduced pressure. The residue was purified by column chromatography (silica gel, 100-200 mesh, 0 to 5% ethyl acetate in petroleum ether) to afford 3-[tert-butyl(dimethyl)silyl]oxy-3-(2,3,5-trifluorophenyl)propanal (1.6 g, 32%) as a brown oil. $^1$H NMR (400 MHz, CDCl$_3$) δ 9.78 (t, J=2.2 Hz, 1H), 7.04-7.01 (m, 1H), 6.87-6.83 (m, 1H), 5.56-5.53 (m, 1H), 2.85-2.79 (m, 1H), 2.71-2.66 (m, 1H), 0.89 (s, 1H), 0.11 (s, 1H), −0.05 (s, 1H).

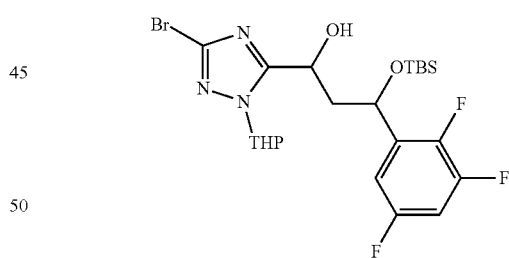

Step 4: 1-(3-bromo-1-(tetrahydro-2H-pyran-2-yl)-1H-1,2,4-triazol-5-yl)-3-((tert-butyldimethylsilyl)oxy)-3-(2,3,5-trifluorophenyl)propan-1-ol To a mixture of 3,5-dibromo-1-tetrahydropyran-2-yl-1,2,4-triazole (1.6 g, 5.2 mmol) in tetrahydrofuran (20 mL) was added n-butyllithium (2.5 M in hexane, 2.1 mL, 5.2 mmol) dropwise under nitrogen at −78° C. After addition, the mixture was stirred at −78° C. for 0.5 h and a solution of 3-[tert-butyl(dimethyl)silyl]oxy-3-(2,3,5-trifluorophenyl) propanal (1.5 g, 4.71 mmol) in tetrahydrofuran (10 mL) was added dropwise. The resulting mixture was stirred at −78° C. for 4 h and quenched by addition of saturated aqueous ammonium chloride (10 mL). The mixture was extracted with ethyl acetate (2×20 mL). The combined organic layers were washed with brine and concentrated under reduced pressure. The residue was purified by column chromatography (silica gel, 100-200 mesh, 0 to 15% ethyl acetate in petroleum ether) to afford 1-(5-bromo-2-tetrahydropyran-2-yl-1,2,4-triazol-3-yl)-3-[tert-butyl(dimethyl)silyl]oxy-3-(2,3,5-trifluorophenyl)propan-1-ol (1.78 g, 69%) as a yellow gum. LCMS $R_T$=1.056 min, m/z=466.0 [M+H]$^+$.

LCMS (5 to 95% acetonitrile in water+0.03% trifluoacetic acid over 1.5 mins) retention time 1.056 min, ESI+ found [M+H]=466.0.

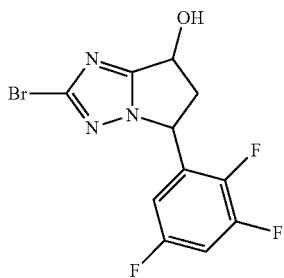 [SMILES: OC1CC(c2cc(F)cc(F)c2F)n2nc(Br)nc21]

Step 5: 2-bromo-5-(2,3,5-trifluorophenyl)-6,7-dihydro-5H-pyrrolo[1,2-b][1,2,4]triazol-7-ol A solution of 1-(5-bromo-2-tetrahydropyran-2-yl-1,2,4-triazol-3-yl)-3-[tert-butyl(dimethyl)silyl] oxy-3-(2,3,5-trifluorophenyl)propan-1-ol (1.8 g, 3.2 mmol) in trifluoroacetic acid (250 mL, 32.3 mmol) was stirred at 50° C. for 1 h, and then trifluoromethanesulfonic acid (1 mL, 3.2 mmol) was added. The resulting mixture was stirred at 50° C. for 3 h and then concentrated under reduced pressure. The residue was diluted with ethyl acetate (50 mL) and adjusted to pH=8 by addition of aqueous sodium hydroxide (20%). The separated organic layer was washed with water (2×50 mL), brine, dried over sodium sulfate and concentrated under reduced pressure. The residue was purified by column chromatography (silica gel, 100-200 mesh, 40 to 60% ethyl acetate in petroleum ether) to afford a crude product. This crude was washed with methyl t-butyl ether (20 mL) to give 2-bromo-5-(2,3,5-trifluorophenyl)-6,7-dihydro-5H-pyrrolo[1,2-b][1,2,4]triazol-7-ol (0.55 g, 51%) as a brown solid. $^1$H NMR (400 MHz, CDCl$_3$) δ 7.01-6.94 (m, 1H), 6.980-6.56 (m, 1H), 5.88-5.60 (m, 2H), 5.47-5.40 (m, 1H), 3.66-3.22 (m, 1H), 3.01-3.64 (m, 1H).

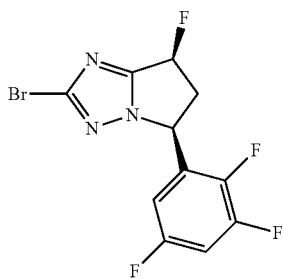 [SMILES: Fc1cc(F)c(F)c([C@@H]2C[C@H](F)c3nc(Br)nn32)c1]

Step 6: (5S,7S)-2-bromo-7-fluoro-5-(2,3,5-trifluorophenyl)-6,7-dihydro-5H-pyrrolo[1,2-b][1,2,4]triazole To a mixture of 2-bromo-5-(2,3,5-trifluorophenyl)-6,7-dihydro-5H-pyrrolo[1,2-b][1,2,4]triazol-7-ol (550 mg, 1.65 mmol) in toluene (10 mL) was added diethylaminosulfur trifluoride (1.06 g, 6.6 mmol) dropwise at 0° C. The reaction mixture was stirred at 0° C. for 16 h and then quenched by addition of saturated aqueous sodium bicarbonate (50 mL). The resulting mixture was extracted with dichloromethane (3×30 mL). The combined organic layers were washed with water (20 mL), brine (20 mL), dried over sodium sulfate and concentrated under reduced pressure. The residue was purified by column chromatography (silica gel, 100-200 mesh, 15 to 20% ethyl acetate in petroleum ether) to afford rac-(5S,7S)-2-bromo-7-fluoro-5-(2,3,5-trifluorophenyl)-6,7-dihydro-5H-pyrrolo[1,2-b][1,2,4]triazole (197 mg, 36%) as a brown solid. $^1$H NMR (400 MHz, CDCl$_3$) δ 7.00-6.95 (m, 1H), 6.52-6.48 (m, 1H), 6.08-5.92 (m, 1H), 5.81-5.77 (m, 1H), 3.71-3.57 (m, 1H), 2.90-2.80 (m, 1H).

This racemate was further separated by chiral SFC to afford arbitrarily assigned: (5S,7S)-2-bromo-7-fluoro-5-(2,3,5-trifluorophenyl)-6,7-dihydro-5H-pyrrolo[1,2-b][1,2,4] triazole (peak 2, retention time=2.866 min) (80 mg, 41%) as a brown solid (along with 5R,7R-isomer (peak 1, retention time=2.345 min) (80 mg, 41%)).

SFC condition: Column: Chiralpak IC-3 150×4.6 mm I.D., 3 μm. Mobile phase: A: CO$_2$, B:iso-propanol (0.05% DEA). Gradient: from 5% to 40% of B in 5 min and hold 40% for 2.5 min, then 5% of B for 2.5 min. Flow rate: 2.5 mL/min. Column temp.: 35° C.

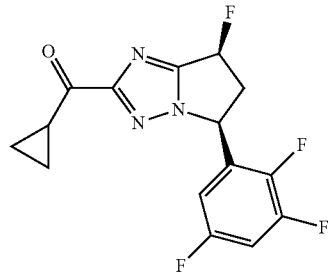 [SMILES: O=C(c1nc2n(n1)[C@H](c1cc(F)cc(F)c1F)C[C@@H]2F)C1CC1]

Step 7: Cyclopropyl-((5S,7S)-7-fluoro-5-(2,3,5-trifluorophenyl)-6,7-dihydro-5H-pyrrolo[1,2-b][1,2,4]triazol-2-yl)methanone To a mixture of (5S,7S)-2-bromo-7-fluoro-5-(2,3,5-trifluorophenyl)-6,7-dihydro-5H-pyrrolo[1,2-b][1,2,4]triazole (80 mg, 0.24 mmol), N-methoxy-N-methyl-cyclopropanecarboxamide (62 mg, 0.48 mmol) in tetrahydrofuran (3 mL) was added isopropylmagnesium chloride (2.0 M in tetrahydrofuran, 0.24 mL, 0.48 mmol) dropwise at 0° C. The mixture was stirred at 0° C. for 1 h and quenched by addition of saturated aqueous ammonium chloride (10 mL). The mixture was extracted with ethyl acetate (2×20 mL). The combined organic layers were washed with brine (15 mL), dried over sodium sulfate and concentrated under reduced pressure. The residue was purified by RP-HPLC (acetonitrile 40-70/0.05% ammonia hydroxide in water) to afford arbitrarily assigned cyclopropyl-[(5S,7S)-7-fluoro-5-(2,3,5-trifluorophenyl)-6,7-dihydro-5H-pyrrolo[1,2-b][1,2,4] triazol-2-yl]methanone (11 mg, 14%) as a white solid. $^1$H NMR (400 MHz, CD$_3$OD) δ 7.29-7.26 (m, 1H), 6.78-6.75 (m, 1H), 6.23-6.06 (m, 1H), 5.96-5.93 (m, 1H), 3.88-3.80 (m, 1H), 3.07-3.04 (m, 1H), 2.96-2.89 (m, 1H), 1.22-1.11 (m, 4H). LCMS $R_T$=1.029 min, m/z=326.2 [M+H]$^+$.

LCMS (5 to 95% acetonitrile in water+0.03% trifluoacetic acid over 1.5 mins) retention time 1.029 min, ESI+ found [M+H]=326.2.

Method 87

Example 109

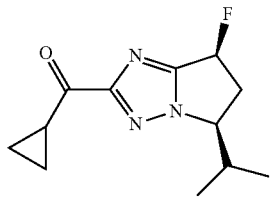

Cyclopropyl-[(5S,7S)-7-fluoro-5-isopropyl-6,7-dihydro-5H-pyrrolo[1,2-b][1,2,4]triazol-2-yl]methanone

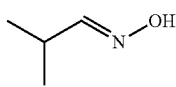

Step 1: (1E)-2-methylpropanal Oxime

To a solution of isobutyraldehyde (200.0 g, 2773.5 mmol) in water (2.0 L) was added hydroxylamine hydrochloride (231.3 g, 3328.3 mmol) and sodium carbonate (587.9 g, 5547.1 mmol). After addition, the reaction mixture was stirred at 20° C. for 4 h and filtered. The filtrate was extracted with ethyl acetate (3×1 L). The combined organic layers were washed with brine (2×1 L), dried over sodium sulfate and concentrated under reduced pressure to give crude (1E)-2-methylpropanal oxime (220 g, 91%) as a colorless oil.

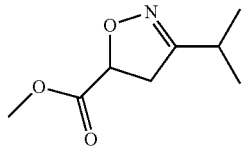

Step 2: Methyl 3-isopropyl-4,5-dihydroisoxazole-5-carboxylate

To a solution of n-chlorosuccinimide (268.2 g, 2008.7 mmol) in chloroform (1500 mL) was added pyridine (9.73 mL, 120.5 mmol) and (1E)-2-methylpropanal oxime (175.0 g, 2008.7 mmol) at 25° C. After stirred for 0.5 h at 25° C., a solution of methyl acrylate (227.2 mL, 2506.9 mmol) and triethylamine (292.4 mL, 2109.2 mmol) in chloroform (100 mL) was added dropwise over 30 min at 25° C. The reaction mixture was stirred at 25° C. for 16 h and diluted with dichloromethane (1000 mL). The separated organic layer was washed with water (3×500 mL), dried over sodium sulfate and concentrated under reduced pressure. The residue was purified by column chromatography (silica gel, 100-200 mesh, 0 to 20% ethyl acetate in petroleum ether) to afford methyl 3-isopropyl-4,5-dihydroisoxazole-5-carboxylate (240 g, 70%) as a colorless oil. $^1$H NMR (400 MHz, CDCl$_3$) δ 4.98-4.93 (m, 1H), 3.76 (s, 3H), 3.21-3.19 (m, 2H), 2.75-2.66 (m, 1H), 1.16 (d, J=6.8 Hz, 6H).

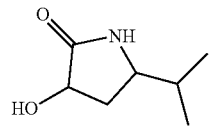

Step 3: 3-hydroxy-5-isopropyl-pyrrolidin-2-one

A mixture of methyl 3-isopropyl-4,5-dihydroisoxazole-5-carboxylate (240.0 g, 1402 mmol) and palladium (10% on carbon, 14.9 g) in ethanol (2 L) was hydrogenated (50 psi) at 45° C. for 16 h and filtered. The filtrate was concentrated under reduced pressure to give crude 3-hydroxy-5-isopropyl-pyrrolidin-2-one (70 g, 35%) as a white solid.

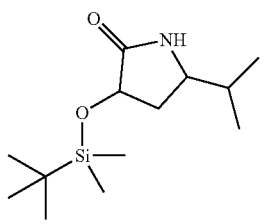 [SMILES: CC(C)C1CC(O[Si](C)(C)C(C)(C)C)C(=O)N1]

Step 4: 3-[tert-butyl(dimethyl)silyl]oxy-5-isopropyl-pyrrolidin-2-one

To a cooled (0° C.) mixture of 3-hydroxy-5-isopropyl-pyrrolidin-2-one (49.0 g, 342.2 mmol) and imidazole (69.9 g, 1026.7 mmol) in dichloromethane (1120 mL) was added tert-butyldimethylchlorosilane (77.4 g, 513.3 mmol). After addition, the mixture was stirred at 25° C. for 16 h and poured into water (1000 mL). The separated organic layer was washed with brine (500 mL), dried over sodium sulfate and concentrated under reduced pressure. The residue was purified by column chromatography (silica gel, 100-200 mesh, 0 to 10% ethyl acetate in petroleum ether) to afford 3-[tert-butyl(dimethyl)silyl]oxy-5-isopropyl-pyrrolidin-2-one (35.0 g, 40%) as colorless oil. $^1$H NMR (400 MHz, CDCl$_3$) δ 6.63 (s, 1H), 4.32-4.28 (m, 1H), 3.17-3.11 (m, 1H), 2.46-2.40 (m, 1H), 1.66-1.60 (m, 2H), 0.92-0.89 (m, 14H), 0.15 (d, J=10.4 Hz, 6H).

Step 5: 1-amino-3-[tert-butyl(dimethyl)silyl]oxy-5-isopropyl-pyrrolidin-2-one To a cooled (0° C.) solution of 3-[tert-butyl(dimethyl)silyl]oxy-5-isopropyl-pyrrolidin-2-one (5.0 g, 19.42 mmol) in N,N-dimethylformamide (200 mL) was added sodium hydride (60%, 1.2 g, 29.13 mmol). After addition, the mixture was stirred at 0° C. for 30 min then o-(diphenylphosphoryl)hydroxylamine (6.8 g, 29.13 mmol) was added. The resulting mixture was stirred at 20° C. for 16 h and filtered. The filtrate was concentrated under reduced pressure to afford crude (1-amino-3-[tert-butyl(dimethyl)silyl]oxy-5-isopropyl-pyrrolidin-2-one (5.3 g, 100%) as a yellow oil. LCMS $R_T$=1.178 min, m/z=273.3 [M+H]$^+$.

LCMS (10 to 80% acetonitrile in water+0.03% trifluoroacetic acid over 2 mins) retention time 1.178 min, ESI+ found [M+H]=273.3.

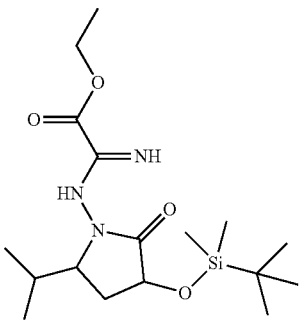 [SMILES: CCOC(=O)C(=N)NN1C(=O)C(O[Si](C)(C)C(C)(C)C)CC1C(C)C]

Step 6: Ethyl 2-[[3-[tert-butyl(dimethyl)silyl]oxy-5-isopropyl-2-oxo-pyrrolidin-1-yl]amino]-2-imino-acetate To a solution of 1-amino-3-[tert-butyl(dimethyl)silyl]oxy-5-isopropyl-pyrrolidin-2-one (5.28 g, 19.38 mmol) in ethanol (250 mL) was added ethyl 2-ethoxy-2-imino-acetate (8.44 g, 58.14 mmol). The reaction mixture was stirred at 90° C. for 16 h and filtered. The filtrate was concentrated under reduced pressure to afford ethyl 2-[[3-[tert-butyl(dimethyl)silyl]oxy-5-isopropyl-2-oxo-pyrrolidin-1-yl]amino]-2-imino-acetate (7.10 g, 98%) as a yellow oil. LCMS $R_T$=0.948 min, m/z=372.2 [M+H]$^+$.

LCMS (5 to 95% acetonitrile in water+0.03% trifluoroacetic acid over 1.5 mins) retention time 0.948 min, ESI+ found [M+H]=372.2.

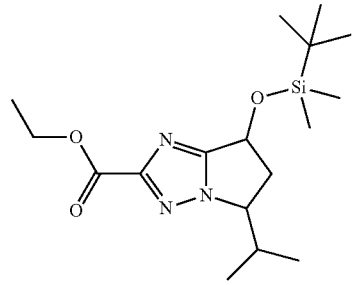 [SMILES: CCOC(=O)c1nc2n(n1)C(C(C)C)CC2O[Si](C)(C)C(C)(C)C]

Step 7: Ethyl 7-[tert-butyl(dimethyl)silyl]oxy-5-isopropyl-6,7-dihydro-5H-pyrrolo [1,2-b][1,2,4]triazole-2-carboxylate To a solution of ethyl 2-[[3-[tert-butyl(dimethyl)silyl]oxy-5-isopropyl-2-oxo-pyrrolidin-1-yl]amino]-2-imino-acetate (7.1 g, 19.11 mmol) in toluene (140 mL) was added p-toluenesulfonic acid monohydrate (4.4 g, 22.93 mmol). The reaction mixture was stirred at 120° C. for 16 h and filtered. The filtrate was concentrated under reduced pressure to afford ethyl 7-[tert-butyl(dimethyl)silyl]oxy-5-isopropyl-6,7-dihydro-5H-pyrrolo[1,2-b][1,2,4]triazole-2-carboxylate (6.6 g, 98%) as a yellow oil. LCMS $R_T$=0.952 min, m/z=354.2 [M+H]$^+$.

LCMS (5 to 95% acetonitrile in water+0.03% trifluoroacetic acid over 1.5 mins) retention time 0.952 min, ESI+ found [M+H]=354.2.

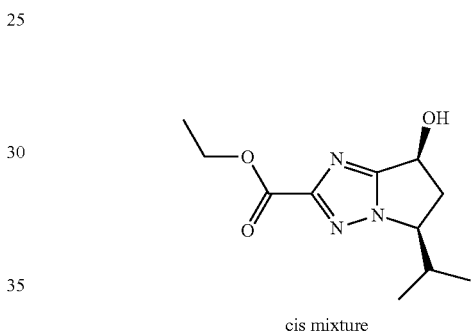

cis mixture

Step 7: Ethyl Cis-7-hydroxy-5-isopropyl-6,7-dihydro-5H-pyrrolo[1,2-b] [1,2,4]triazole-2-carboxylate To a solution of ethyl 7-[tert-butyl(dimethyl)silyl]oxy-5-isopropyl-6,7-dihydro-5H-pyrrolo[1,2-b][1,2,4]triazole-2-carboxylate (6.6 g, 18.67 mmol) in tetrahydrofuran (50 mL) was added tetrabutylammonium fluoride (1.0 M in tetrahydrofuran, 18.67 mL, 18.67 mmol) at 25° C. The reaction mixture was stirred at 40° C. for 16 h and concentrated. The residue was diluted with water (100 mL) and extracted with ethyl acetate (3×50 mL). The combined organic layers were concentrated under reduced pressure. The residue was purified by column chromatography (silica gel, 100-200 mesh, 0 to 70% ethyl acetate in petroleum ether) to afford ethyl cis-7-hydroxy-5-isopropyl-6,7-dihydro-5H-pyrrolo[1,2-b][1,2,4]triazole-2-carboxylate (2.8 g, 62.7%) as a yellow solid. $^1$H NMR (400 MHz, CDCl$_3$) δ 5.34-5.31 (m, 1H), 4.47-4.43 (m, 2H), 4.26-4.24 (m, 1H), 3.14-3.09 (m, 1H), 2.48-2.42 (m, 2H), 1.43-1.39 (m, 3H), 1.07 (d, J=7.2 Hz, 3H), 0.92 (d, J=7.2 Hz, 3H).

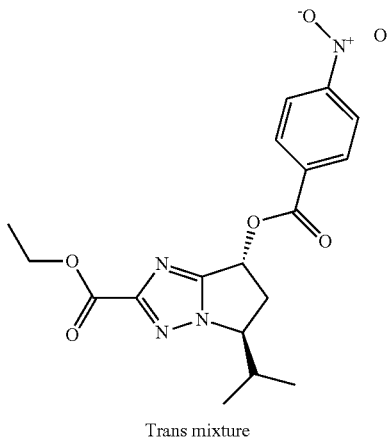

Trans mixture

Step 8: Ethyl Trans-5-isopropyl-7-(4-nitrobenzoyl)oxy-6,7-dihydro-5H-pyrrolo[1,2-b][1,2,4]triazole-2-carboxylate To a mixture of ethyl cis-7-hydroxy-5-isopropyl-6,7-dihydro-5H-pyrrolo [1,2-b][1,2,4]triazole-2-carboxylate (2.0 g, 8.36 mmol), 4-nitrobenzoic acid (2.1 g, 12.54 mmol) and triphenylphosphine (6.6 g, 25.08 mmol) in tetrahydrofuran (40 mL) was added diisopropyl azodicarboxylate (5.0 mL, 25.08 mmol) at 0° C. under nitrogen atmosphere. The mixture was stirred at 25° C. for 16 h and concentrated under reduced pressure. The residue was purified by column chromatography (silica gel, 100-200 mesh, 0 to 17% ethyl acetate in petroleum ether) to give ethyl trans-5-isopropyl-7-(4-nitrobenzoyl)oxy-6,7-dihydro-5H-pyrrolo[1,2-b][1,2,4]triazole-2-carboxylate (2.5 g, 77%) as a yellow solid.

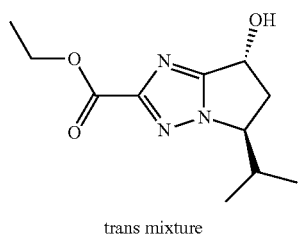 [SMILES: CCOC(=O)c1nc2n(n1)[C@H](C(C)C)C[C@H]2O]

trans mixture

Step 9: Ethyl Trans-7-hydroxy-5-isopropyl-6,7-dihydro-5H-pyrrolo[1,2-b] [1,2,4]triazole-2-carboxylate A mixture of potassium carbonate (1.23 g, 8.88 mmol) and ethyl trans-5-isopropyl-7-(4-nitrobenzoyl)oxy-6,7-dihydro-5H-pyrrolo[1,2-b][1,2,4]triazole-2-carboxylate (2.3 g, 5.92 mmol) in ethanol (10 mL)/tetrahydrofuran (5 mL)/water (5 mL) was stirred at 25° C. for 1 h and concentrated under reduced pressure. The residue was diluted with water (50 mL) and extracted with ethyl acetate (2×30 mL). The combined organic layers were dried over sodium sulfate and concentrated under reduced pressure to give crude ethyl trans-7-hydroxy-5-isopropyl-6,7-dihydro-5H-pyrrolo[1,2-b][1,2,4]triazole-2-carboxylate (1.10 g, 78%) as a colorless oil.

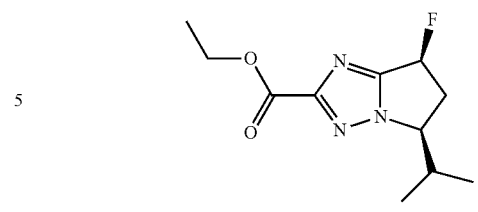

cis mixture

Step 10: Ethyl Cis-7-fluoro-5-isopropyl-6,7-dihydro-5H-pyrrolo[1,2-b][1,2,4] triazole-2-carboxylate To a mixture of ethyl trans-7-hydroxy-5-isopropyl-6,7-dihydro-5H-pyrrolo [1,2-b][1,2,4]triazole-2-carboxylate (1.0 g, 4.18 mmol) in dichloromethane (20 mL) was added diethylaminosulfur trifluoride (2.23 mL, 16.72 mmol) at 0° C. under nitrogen atmosphere. The mixture was stirred at 0° C. for 1 h and quenched by addition of saturated aqueous sodium bicarbonate (200 mL). The solution was extracted with dichloromethane (3×100 mL). The combined organic layers were washed with brine (2×100 mL), dried over sodium sulfate and concentrated under reduced pressure. The residue was purified by column chromatography (silica gel, 100-200 mesh, 0 to 7% ethyl acetate in petroleum ether) to give ethyl cis-7-fluoro-5-isopropyl-6,7-dihydro-5H-pyrrolo[1,2-b][1,2,4]triazole-2-carboxylate (550 mg, 55%) as colorless oil.

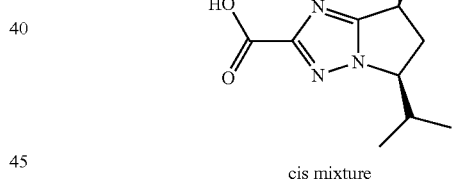

cis mixture

Step 11: Cis-7-fluoro-5-isopropyl-6,7-dihydro-5H-pyrrolo[1,2-b][1,2,4] triazole-2-carboxylic acid A mixture of ethyl cis-7-fluoro-5-isopropyl-6,7-dihydro-5H-pyrrolo[1,2-b][1,2,4]triazole-2-carboxylate (550 mg, 2.28 mmol) and lithium hydroxide hydrate (191 mg, 4.56 mmol) in methanol (10 mL)/tetrahydrofuran (5 mL)/water (5 mL) was stirred at 20° C. for 1 h and concentrated under reduced pressure. The residue was diluted with water (20 mL) and washed with ethyl acetate (20 mL). The aqueous phase was adjusted to pH=6 by addition of hydrochloric acid (1 M) and then extracted with ethyl acetate (2×20 mL). The combined organic layers were dried over sodium sulfate and concentrated under reduced pressure to give crude cis-7-fluoro-5-isopropyl-6,7-dihydro-5H-pyrrolo[1,2-b][1,2,4] triazole-2-carboxylic acid (420 mg, 86%) as a colorless oil.

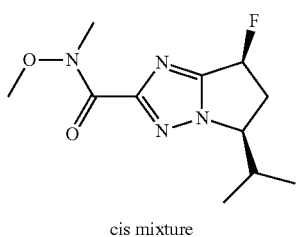 [SMILES: CON(C)C(=O)c1nc2n(n1)[C@H](C(C)C)C[C@@H]2F]

cis mixture

Step 12: Cis-7-fluoro-5-isopropyl-N-methoxy-N-methyl-6,7-dihydro-5H-pyrrolo[1,2-b][1,2,4]triazole-2-carboxamide A mixture of cis-7-fluoro-5-isopropyl-6,7-dihydro-5H-pyrrolo[1,2-b] [1,2,4]triazole-2-carboxylic acid (420 mg, 1.97 mmol), N,N-diisopropylethylamine (1.05 mL, 5.91 mmol), 1-(3-dimethylaminopropyl)-3-ethylcarbodiimidehydrochloride (453 mg, 2.36 mmol), 1-hydroxybenzotriazole (160 mg, 1.18 mmol) and N,O-dimethylhydroxylamine hydrochloride (384 mg, 3.94 mmol) in dichloromethane (10 mL) was stirred at 25° C. for 16 h and quenched by addition of water (20 mL). The mixture was extracted with dichloromethane (2×50 mL). The combined organic layers were washed with brine (2×50 mL), dried over sodium sulfate and concentrated under reduced pressure. The residue was purified by column chromatography (silica gel, 100-200 mesh, 50 to 60% to give cis-7-fluoro-5-isopropyl-N-methoxy-N-methyl-6,7-dihydro-5H-pyrrolo[1,2-b][1,2,4]triazole-2-carboxamide (200 mg, 40%) as yellow oil. LCMS $R_T$=0.692 min, m/z=257.1 [M+H]$^+$.

LCMS (5 to 95% acetonitrile in water+0.03% trifluoroacetic acid over 1.5 mins) retention time 0.692 min, ESI+ found [M+H]=257.1.

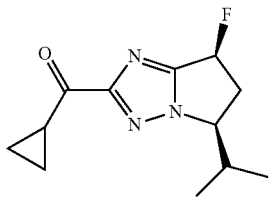 [SMILES: CC(C)[C@@H]1C[C@H](F)c2nc(C(=O)C3CC3)nn21]

Step 13: Cyclopropyl-[(5S,7S)-7-fluoro-5-isopropyl-6,7-dihydro-5H-pyrrolo [1,2-b][1,2,4]triazol-2-yl]methanone To a cooled (0° C.) solution of cis-7-fluoro-5-isopropyl-N-methoxy-N-methyl-6,7-dihydro-5H-pyrrolo[1,2-b][1,2,4] triazole-2-carboxamide (200 mg, 0.78 mmol) in tetrahydrofuran (5 mL) was added cyclopropylmagnesium bromide (0.5 M in tetrahydrofuran, 1.0 mL, 0.50 mmol) under nitrogen atmosphere. The mixture was stirred at 25° C. for 1 h and quenched by addition of saturated aqueous ammonium chloride (20 mL). The resulting mixture was extracted with ethyl acetate (3×10 mL). The combined organic layers were washed with brine (2×10 mL), dried over sodium sulfate and concentrated under reduced pressure. The residue was purified by column chromatography (silica gel, 100-200 mesh, 0 to 40% ethyl acetate in petroleum ether) to give cyclopropyl-[cis-7-fluoro-5-isopropyl-6,7-dihydro-5H-pyrrolo[1,2-b][1,2,4]triazol-2-yl] methanone (100 mg, 52%) as a white solid. This cis mixture was further separated by chiral SFC to afford arbitrarily assigned: cyclopropyl-[(5S,7S)-7-fluoro-5-isopropyl-6,7-dihydro-5H-pyrrolo[1,2-b][1,2,4]triazol-2-yl]methanone (peak 2, retention time=5.136 min) (24 mg, 23%) as a white solid. $^1$H NMR (400 MHz, CDCl$_3$) δ 5.99-5.83 (m, 1H), 4.39-4.34 (m, 1H), 3.22-3.18 (m, 1H), 3.12-3.08 (m, 1H), 2.72-2.62 (m, 1H), 2.42-2.38 (m, 1H), 1.34-1.33 (m, 2H), 1.13-1.10 (m, 2H), 1.08 (d, J=6.8 Hz, 3H), 0.94 (d, J=6.8 Hz, 3H). LCMS $R_T$=0.822 min, m/z=238.0 [M+H]$^+$.

LCMS (5 to 95% acetonitrile in water+0.03% trifluoroacetic acid over 1.5 mins) retention time 0.822 min, ESI+ found [M+H]=238.0.

SFC condition: Column: Lux 3u Cellulose-2 150×4.6 mm, Mobile phase: A: CO$_2$ B:methanol (0.05% DEA) Gradient: from 5% to 40% of B in 5 min and hold 40% for 2.5 min, then 5% of B for 2.5 min Flow rate: 2.5 mL/min Column temp. 35° C.

Method 88

Example 110

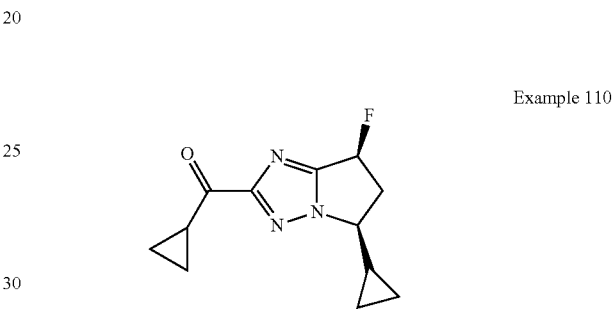

Cyclopropyl-[(5S,7S)-5-cyclopropyl-7-fluoro-6,7-dihydro-5H-pyrrolo[1,2-b][1,2,4]triazol-2-yl]methanone

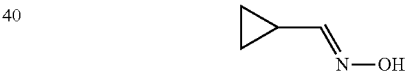

Step 1: (E)-cyclopropanecarbaldehyde Oxime

To a solution of cyclopropanecarboxaldehyde (50.0 g, 713.37 mmol) in ethanol (500 mL) was added sodium carbonate (166.3 g, 1569.4 mmol) and hydroxylamine hydrochloride (59.5 g, 856.04 mmol). The reaction mixture was stirred at 25° C. for 3 h and filtered. The filtrate was concentrated under reduced pressure. The residue was diluted with water (1000 mL) and extracted with ethyl acetate (3×600 mL). The combined organic layers were washed with brine (1000 mL), dried over sodium sulfate and concentrated under reduced pressure to afford crude (E)-cyclopropanecarbaldehyde oxime (40 g, 66%) as a colorless oil.

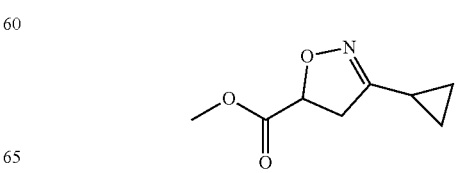

Step 2: Methyl 3-cyclopropyl-4, 5-dihydroisoxazole-5-carboxylate

A mixture of pyridine (2.85 mL, 35.25 mmol), N-chlorosuccinimide (78.5 g, 587.54 mmol) and (E)-cyclopropanecarbaldehyde oxime (50 g, 587.54 mmol) in chloroform (500 mL) was stirred at 25° C. for 2 h, then a solution of methyl acrylate (66.45 mL, 733.25 mmol) and triethylamine (85.35 mL, 615.75 mmol) in chloroform (100 mL) was added. The reaction mixture was stirred at 25° C. for 12 h and quenched by addition of water (200 mL). The resulting mixture was extracted with ethyl acetate (2×200 mL). The combined organic layers were dried over sodium sulfate and concentrated under reduced pressure. The residue was purified by column chromatography (silica gel, 100-200 mesh, 0 to 50% ethyl acetate in petroleum ether) to afford methyl 3-cyclopropyl-4, 5-dihydroisoxazole-5-carboxylate (75.0 g, 76%) as colorless oil.

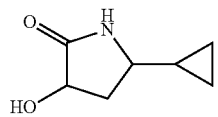

Step 3: 5-cyclopropyl-3-hydroxy-pyrrolidin-2-one

A mixture of methyl 3-cyclopropyl-4, 5-dihydroisoxazole-5-carboxylate (35.0 g, 206.88 mmol) and platinum oxide (6.1 g, 26.89 mmol) in ethylene glycol (300 mL) was stirred at 25° C. under hydrogen atmosphere (30 psi) for 48 h and filtered. The filtrate was concentrated under reduced pressure. The residue was purified by column chromatography (silica gel, 100-200 mesh, 0 to 100% ethyl acetate in petroleum ether) to afford 5-cyclopropyl-3-hydroxy-pyrrolidin-2-one (15.5 g, 53%) as colorless oil. LCMS $R_T$=0.297 min, m/z=142.1 [M+H]$^+$.

LCMS (10 to 80% acetonitrile in water+0.1% ammonia water over 3.0 mins) retention time 0.297 min, ESI+ found [M+H]=142.1.

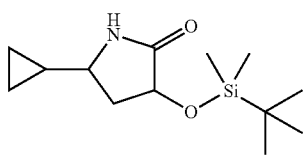 [SMILES: CC(C)(C)[Si](C)(C)OC1CC(C2CC2)NC1=O]

Step 4: 3-[tert-butyl (dimethyl) silyl] oxy-5-cyclopropyl-pyrrolidin-2-one

To a cooled (0° C.) mixture of 5-cyclopropyl-3-hydroxy-pyrrolidin-2-one (13.0 g, 92.09 mmol) and imidazole (18.8 g, 276.26 mmol) in dichloromethane (150 mL) was added tert-butyldimethylchlorosilane (20.8 g, 138.13 mmol). The mixture was stirred at 25° C. for 16 h, and then washed with water (2×50 mL), brine (50 mL), dried over sodium sulfate and concentrated under reduced pressure. The residue was purified by column chromatography (silica gel, 100-200 mesh, 0 to 20% ethyl acetate in petroleum ether) to afford 3-[tert-butyl (dimethyl) silyl] oxy-5-cyclopropyl-pyrrolidin-2-one (10.2 g, 43%) as a colorless oil.

Step 5: 1-amino-3-[tert-butyl (dimethyl) silyl] oxy-5-cyclopropyl-pyrrolidin-2-one To a cooled (0° C.) solution of 3-[tert-butyl (dimethyl) silyl] oxy-5-cyclopropyl-pyrrolidin-2-one (10.2 g, 39.93 mmol) in N,N-dimethylformamide (150 mL) was added sodium hydride (60% in mineral oil, 2.4 g, 59.9 mmol). The mixture was stirred at 0° C. for 30 min, and then O-(diphenylphosphoryl) hydroxylamine (14.0 g, 59.9 mmol) was added. The resulting mixture was stirred at 10° C. for 16 h and filtered. The filtrate was concentrated under reduced pressure to afford crude (1-amino-3-[tert-butyl (dimethyl) silyl] oxy-5-cyclopropyl-pyrrolidin-2-one (10.5 g, 97%) as a yellow oil. LCMS $R_T$=0.810 min, m/z=271.2 [M+H]$^+$.

LCMS (5 to 95% acetonitrile in water+0.03% trifluoacetic acid over 1.5 mins) retention time 0.810 min, ESI+ found [M+H]=271.2.

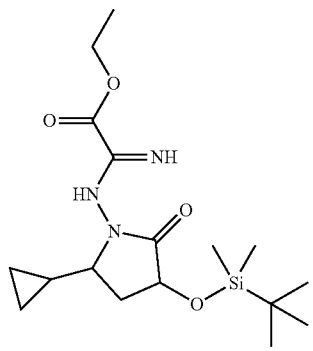 [SMILES: CCOC(=O)C(=N)NN1C(=O)C(O[Si](C)(C)C(C)(C)C)CC1C1CC1]

Step 6: Ethyl 2-[[3-[tert-butyl (dimethyl) silyl] oxy-5-cyclopropyl-2-oxo-pyrrolidin-1-yl] amino]-2-imino-acetate A mixture of 1-amino-3-[tert-butyl (dimethyl) silyl] oxy-5-cyclopropyl-pyrrolidin-2-one (10.5 g, 38.83 mmol) and ethyl 2-ethoxy-2-imino-acetate (14.1 g, 97.06 mmol) in ethanol (150 mL) was stirred at 90° C. for 12 h and concentrated under reduced pressure to afford crude ethyl 2-[[3-[tert-butyl (dimethyl) silyl] oxy-5-cyclopropyl-2-oxo-pyrrolidin-1-yl] amino]-2-imino-acetate (10.0 g, 70%) as a yellow oil. LCMS $R_T$=0.804 min, m/z=370.2 [M+H]$^+$.

LCMS (5 to 95% acetonitrile in water+0.03% trifluoacetic acid over 1.5 mins) retention time 0.804 min, ESI+ found [M+H]=370.2.

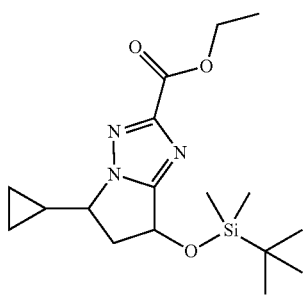 [SMILES: CCOC(=O)c1nc2n(n1)C(C1CC1)CC2O[Si](C)(C)C(C)(C)C]

Step 7: Ethyl 7-[tert-butyl(dimethyl)silyl]oxy-5-cyclopropyl-6,7-dihydro-5H-pyrrolo[1,2-b][1,2,4]triazole-2-carboxylate To a solution of ethyl (2Z)-2-amino-2-[3-[tert-butyl (dimethyl) silyl] oxy-5-cyclopropyl-2-oxo-pyrrolidin-1-yl] imino-acetate (10.0 g, 27.06 mmol) in toluene (120 mL) was added p-toluenesulfonic acid (5.6 g, 32.47 mmol). The reaction mixture was stirred at 120° C. for 16 h and concentrated under reduced pressure. The residue was diluted with water (200 mL) and extracted with ethyl acetate (3×200 mL). The combined organic layers were concentrated under reduced pressure to afford crude ethyl 7-[tert-butyl(dimethyl)silyl]oxy-5-cyclopropyl-6,7-dihydro-5H-pyrrolo[1,2-b][1,2,4]triazole-2-carboxylate (9.5 g, 99%) as a red oil. LCMS $R_T$=0.928 min, m/z=352.2 [M+H]$^+$.

LCMS (5 to 95% acetonitrile in water+0.03% trifluoacetic acid over 1.5 mins) retention time 0.928 min, ESI+ found [M+H]=352.2.

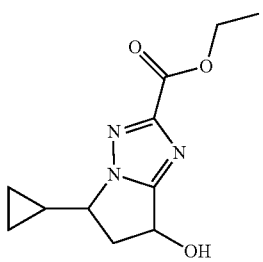 [SMILES: CCOC(=O)c1nc2n(n1)C(C1CC1)CC2O]

Step 8: Ethyl 5-cyclopropyl-7-hydroxy-6,7-dihydro-5H-pyrrolo[1,2-b][1,2,4]triazole-2-carboxylate To a solution of ethyl 7-[tert-butyl (dimethyl) silyl] oxy-5-cyclopropyl-6,7-dihydro-5H-pyrrolo [1,2-b][1,2,4]triazole-2-carboxylate (9.5 g, 27.03 mmol) in tetrahydrofuran (100 mL) was added tetrabutylammonium fluoride (1.0 M in tetrahydrofuran, 27.0 mL, 27.0 mmol). The reaction mixture was stirred at 40° C. for 12 h and concentrated under reduced pressure. The residue was diluted with water (200 mL) and extracted with ethyl acetate (3×200 mL). The combined organic layers were concentrated under reduced pressure. The residue was purified by column chromatography (silica gel, 100-200 mesh, 0 to 100% ethyl acetate in petroleum ether) to afford ethyl 5-cyclopropyl-7-hydroxy-6,7-dihydro-5H-pyrrolo[1,2-b][1,2,4]triazole-2-carboxylate (2.2 g, 34%) as yellow oil. LCMS $R_T$=0.521 min, m/z=238.1 [M+H]$^+$.

LCMS (5 to 95% acetonitrile in water+0.03% trifluoacetic acid over 1.5 mins) retention time 0.521 min, ESI+ found [M+H]=238.1.

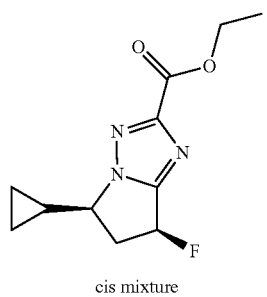 [SMILES: CCOC(=O)c1nc2n(n1)[C@H](C1CC1)C[C@@H]2F]

cis mixture

Step 9: Ethyl Cis-5-cyclopropyl-7-fluoro-6,7-dihydro-5H-pyrrolo[1,2-b][1,2,4] triazole-2-carboxylate To a cooled (0° C.) solution of ethyl 5-cyclopropyl-7-hydroxy-6,7-dihydro-5H-pyrrolo[1,2-b][1,2,4]triazole-2-carboxylate (2.0 g, 8.43 mmol) in dichloromethane (20 mL) was added diethylaminosulfur trifluoride (3.26 mL, 25.29 mmol). The reaction mixture was stirred for 12 h at 0° C. and quenched by addition of water (5.0 mL). The resulting mixture was extracted with dichloromethane (3×50 mL). The combine organic layers were washed with brine (50 mL), dried over sodium sulfate and concentrated under reduced pressure. The resulting residue was purified by column chromatography (silica gel, 100-200 mesh, 0 to 50% ethyl acetate in petroleum ether) to give ethyl cis-5-cyclopropyl-7-fluoro-6,7-dihydro-5H-pyrrolo[1,2-b][1,2,4] triazole-2-carboxylate (220 mg, 11%) as yellow oil. LCMS $R_T$=0.701 min, m/z=240.1 [M+H]$^+$.

LCMS (5 to 95% acetonitrile in water+0.03% trifluoacetic acid over 1.5 mins) retention time 0.701 min, ESI+ found [M+H]=240.1.

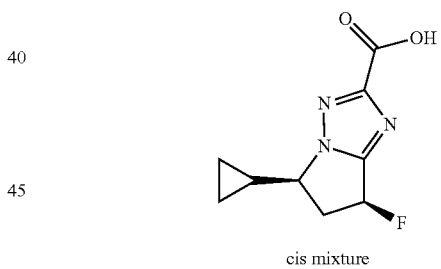

cis mixture

Step 10: Cis-5-cyclopropyl-7-fluoro-6,7-dihydro-5H-pyrrolo[1,2-b][1,2,4]triazole-2-carboxylic Acid A mixture of lithium hydroxide monohydrate (105 mg, 2.51 mmol) and ethyl cis-5-cyclopropyl-7-fluoro-6,7-dihydro-5H-pyrrolo[1,2-b][1,2,4]triazole-2-carboxylate (200 mg, 0.84 mmol) in ethanol (0.50 mL)/water (0.50 mL)/tetrahydrofuran (0.50 mL) was stirred at 25° C. for 2 h and concentrated under reduced pressure. The aqueous residue was adjusted to pH=7 by addition of aqueous hydrochloric acid (1 M) and concentrated under reduced pressure to afford crude cis-5-cyclopropyl-7-fluoro-6,7-dihydro-5H-pyrrolo [1,2-b][1,2,4]triazole-2-carboxylic acid (175 mg, 99%) as yellow oil. LCMS $R_T$=0.452 min, m/z=212.1 [M+H]$^+$.

LCMS (5 to 95% acetonitrile in water+0.03% trifluoacetic acid over 1.5 mins) retention time 0.452 min, ESI+ found [M+H]=212.1.

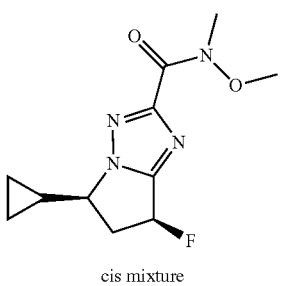 [SMILES: CON(C)C(=O)c1nc2n(n1)[C@H](C1CC1)C[C@@H]2F]

cis mixture

Step 11: Cis-5-cyclopropyl-7-fluoro-N-methoxy-N-methyl-6,7-dihydro-5H-pyrrolo[1,2-b][1,2,4]triazole-2-carboxamide A mixture of cis-5-cyclopropyl-7-fluoro-6,7-dihydro-5H-pyrrolo[1,2-b][1,2,4]triazole-2-carboxylic acid (175 mg, 0.83 mmol), 1-hydroxybenzotriazole (56 mg, 0.41 mmol), N,O-dimethylhydroxylamine hydrochloride (121 mg, 1.24 mmol), N,N-diisopropylethylamine (0.34 mL, 2.07 mmol) and 1-(3-dimethylaminopropyl)-3-ethylcarbodiimidehydrochloride (190.6 mg, 0.99 mmol) in dichloromethane (5 mL) was stirred at 25° C. for 16 h and quenched by addition of water (10 mL). The mixture was extracted with ethyl acetate (3×20 mL). The combined organic layers were washed with brine (10 mL), dried over sodium sulfate and concentrated under reduced pressure. The residue was purified by column chromatography (silica gel, 100-200 mesh, 0 to 60% ethyl acetate in petroleum ether) to give cis-5-cyclopropyl-7-fluoro-N-methoxy-N-methyl-6,7-dihydro-5H-pyrrolo[1,2-b][1,2,4]triazole-2-carboxamide (75 mg, 36%) as a colorless oil. LCMS $R_T$=0.604 min, m/z=255.1 [M+H]$^+$.

LCMS (5 to 95% acetonitrile in water+0.03% trifluoacetic acid over 1.5 mins) retention time 0.604 min, ESI+ found [M+H]=255.1.

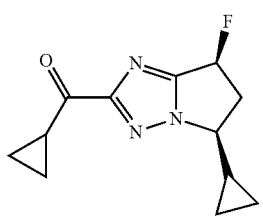 [SMILES: O=C(c1nc2n(n1)[C@H](C1CC1)C[C@@H]2F)C1CC1]

Step 12: Cyclopropyl-[(5S,7S)-5-cyclopropyl-7-fluoro-6,7-dihydro-5H-pyrrolo[1,2-b][1,2,4]triazol-2-yl]methanone To a cooled (0° C.) solution of cis-5-cyclopropyl-7-fluoro-N-methoxy-N-methyl-6,7-dihydro-5H-pyrrolo[1,2-b][1,2,4]triazole-2-carboxamide (65 mg, 0.26 mmol) in tetrahydrofuran (5 mL) was added cyclopropylmagnesium bromide (0.5 M in tetrahydrofuran, 1.24 mL, 0.62 mmol) under nitrogen atmosphere. After addition, the mixture was stirred at 0° C. for 1 h and quenched by addition of saturated aqueous ammonium chloride (3 mL). The resulting mixture was extracted with ethyl acetate (3×5 mL). The combined organic layers were washed with brine (5 mL), dried over sodium sulfate and concentrated under reduced pressure. The residue was purified by preparative TLC (50% ethyl acetate in petroleum ether, $R_f$=0.4) to give cyclopropyl-[cis-5-cyclopropyl-7-fluoro-6,7-dihydro-5H-pyrrolo[1,2-b][1,2,4]triazol-2-yl]methanone (50 mg, 83%) as a yellow oil. LCMS $R_T$=0.676 min, m/z=236.1 [M+H]$^+$.

LCMS (5 to 95% acetonitrile in water+0.03% trifluoacetic acid over 1.5 mins) retention time 0.676 min, ESI+ found [M+H]=236.1.

This cis mixture was further separated by chiral SFC to afford arbitrarily assigned: cyclopropyl-[(5S,7S)-5-cyclopropyl-7-fluoro-6,7-dihydro-5H-pyrrolo[1,2-b][1,2,4]triazol-2-yl]methanone (Peak 1, Retention time=2.841 min) (3.1 mg, 6%) as a colorless oil. $^1$H NMR (400 MHz, CD$_3$OD) δ 6.05-5.89 (m, 1H), 4.02-3.95 (m, 1H), 3.51-3.35 (m, 1H), 3.14-3.10 (m, 1H), 2.78-2.70 (m, 1H), 1.26-1.12 (m, 5H), 0.79-0.67 (m, 3H), 0.58-0.52 (m, 1H). LCMS $R_T$=0.677 min, m/z=236.1 [M+H]$^+$.

LCMS (5 to 95% acetonitrile in water+0.03% trifluoacetic acid over 1.5 mins) retention time 0.677 min, ESI+ found [M+H]=236.1.

SFC condition: Column: DAICEL CHIRALPAK IC (250 mm*30 mm, 5 μm) Mobile phase: A: CO2, B: 0.1% NH3H$_2$O IPA Begin B 40% End B 40% Gradient Time: Gradient: from 40% to 40% of B in 5 min and hold 40% for 2.5 min, Flow rate: 60 mL/min Column temp: 35° C.

Method 89

Example 111

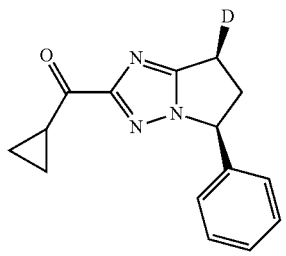

Cyclopropyl-[(5S,7S)-7-deuterio-5-phenyl-6,7-dihydro-5H-pyrrolo[1,2-b][1,2,4]triazol-2-yl]methanone To a solution of cyclopropyl-[(5S,7S)-7-chloro-7-deuterio-5-phenyl-5,6-dihydropyrrolo[1,2-b][1,2,4]triazol-2-yl]methanone (50 mg, 0.17 mmol) in methanol (2.0 mL) was added nickel (10 mg, 0.17 mmol). The mixture was stirred at 20° C. under hydrogen atmosphere (15 psi) for 2 h and filtered. The filtrate was concentrated under reduced pressure. The residue was purified by RP-HPLC (water (0.05% ammonia hydroxide v/v)-acetonitrile: 33-63%) to afford arbitrarily assigned cyclopropyl-[(5S,7S)-7-deuterio-5-phenyl-6,7-dihydro-5H-pyrrolo[1,2-b][1,2,4]triazol-2-yl]methanone (14.8 mg, 33%) as a white solid. $^1$H NMR (400 MHz, CDCl$_3$) δ 7.41-7.36 (m, 3H), 7.14-7.11 (m, 2H), 5.52-5.48 (m, 1H), 3.28-3.21 (m, 1H), 3.06-3.00 (m, 2H), 2.70-2.65 (m, 1H), 1.30-1.27 (m, 2H), 1.06-1.03 (m, 2H). LCMS $R_T$=1.551 min, m/z=255.1 [M+H]$^+$.

LCMS (10 to 80% acetonitrile in water+0.1% ammonia water over 3.0 mins) retention time 1.551 min, ESI+ found [M+H]=255.1.

Method 90

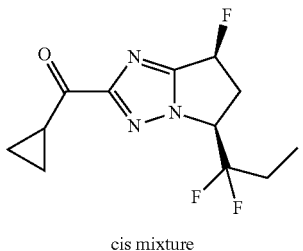

cis mixture

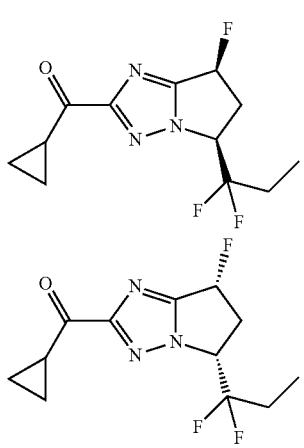

Cyclopropyl-[rac-(5S,7S)-5-(1,1-difluoropropyl)-7-fluoro-6,7-dihydro-5H-pyrrolo[1,2-b][1,2,4]triazol-2-yl]methanone, cyclopropyl-[(5S,7S)-5-(1,1-difluoropropyl)-7-fluoro-6,7-dihydro-5H-pyrrolo[1,2-b][1,2,4]triazol-2-yl]methanone and cyclopropyl-[(5R,7R)-5-(1,1-difluoropropyl)-7-fluoro-6,7-dihydro-5H-pyrrolo[1,2-b][1,2,4]triazol-2-yl]methanone

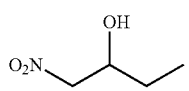

Step 1: 1-nitrobutan-2-ol

To a mixture of nitromethane (52.6 g, 860.9 mmol), hexadecyltrimethylammonium chloride (27.6 g, 86.1 mmol), sodium hydroxide (34.4 g, 860.9 mmol) in water (2.5 L) was added propionaldehyde (50.0 g, 860.9 mmol) at 25° C. The mixture was stirred at 25° C. for 4 h, then added sodium chloride (700 g) and extracted with ethyl acetate (2×300 mL). The combined organic layers were dried over sodium sulfate and concentrated under reduced pressure to give crude 1-nitrobutan-2-ol (80.0 g, 78%) as light brown oil. The crude was used in next step directly without further purification.

Example 112

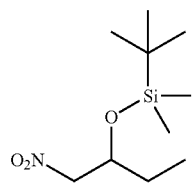

Step 2:
Tert-Butyldimethyl((1-nitrobutan-2-yl)oxy)silane

To a stirred solution of 1-nitrobutan-2-ol (40.0 g, 335.8 mmol) and imidazole (48.0 g, 705.2 mmol) in N,N-dimethylformamide (300 mL) was added tert-butyldimethylchlorosilane (53.2 g, 352.6 mmol) under nitrogen at 25° C. After addition, the reaction mixture was stirred at 25° C. for 15 h. The mixture was then diluted with water (400 mL) and extracted with ethyl acetate (2×200 mL). The combined organic layers were washed with water (200 mL), brine (200 mL), dried over sodium sulfate and concentrated under reduced pressure. The residue was purified by column chromatography (silica gel, 100-200 mesh, 0 to 10% ethyl acetate in petroleum ether) to afford tert-butyl-dimethyl-[1-(nitromethyl)propoxy]silane (28.0 g, 36%) as a light brown oil.

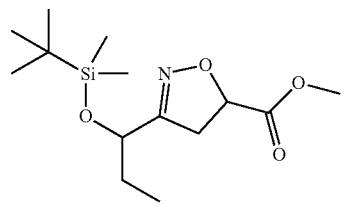 [SMILES: CCC(O[Si](C)(C)C(C)(C)C)C1=NOC(C(=O)OC)C1]

Step 3: Methyl 3-(1-((tert-butyldimethylsilyl)oxy)propyl)-4,5-dihydroisoxazole-5-carboxylate To a mixture of methyl acrylate (54.4 mL, 599.9 mmol), di-tert-butyldicarbonate (39.3 g, 179.9 mmol) and 4-dimethylaminopyridine (1.5 g, 12.0 mmol) in acetonitrile (500 mL) was added a solution of tert-butyl-dimethyl-[1-(nitromethyl)propoxy]silane (28.0 g, 119.9 mmol) in acetonitrile (10 mL). The mixture was stirred at 25° C. for 5 h and then concentrated under reduced pressure. The residue was purified by column chromatography (silica gel, 100-200 mesh, 0 to 10% ethyl acetate in petroleum ether) to afford methyl 3-[1-[tert-butyl(dimethyl)silyl]oxypropyl]-4,5-dihydroisoxazole-5-carboxylate (17.0 g, 47%) as a brown oil.

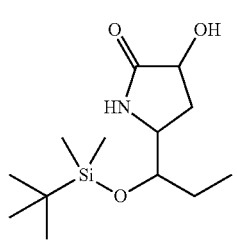 [SMILES: CCC(O[Si](C)(C)C(C)(C)C)C1CC(O)C(=O)N1]

Step 4: 5-(1-((tert-butyldimethylsilyl)oxy)propyl)-3-hydroxypyrrolidin-2-one A mixture of ethyl 3-[1-[tert-butyl(dimethyl)silyl]oxypropyl]-4,5-dihydroisoxazole-5-carboxylate (17.0 g, 53.89 mmol) and palladium (10% on carbon, 3.0 g) in ethanol (500 mL) was stirred at 40° C. under hydrogen atmosphere (50 psi) for 48 h and filtered. The filtrate was concentrated under reduced pressure to give crude 5-[1-[tert-butyl(dimethyl)silyl]oxypropyl]-3-hydroxy-pyrrolidin-2-one (12.0 g, 82%) as a white solid.

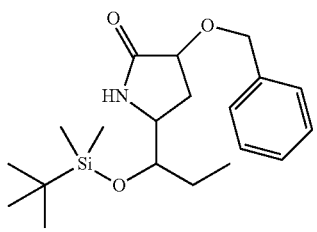 [SMILES: CCC(O[Si](C)(C)C(C)(C)C)C1CC(OCc2ccccc2)C(=O)N1]

Step 5: 3-(benzyloxy)-5-(1-((tert-butyldimethylsilyl)oxy)propyl)pyrrolidin-2-one To a solution of 5-[1-[tert-butyl(dimethyl)silyl]oxypropyl]-3-hydroxy-pyrrolidin-2-one (8.8 g, 32.2 mmol) in dichloromethane (440 mL) was added tetrabutylammonium bromide (519 mg, 1.6 mmol), aqueous sodium hydroxide (30%, 60 mL) and benzyl bromide (8.3 g, 48.3 mmol). After addition, the mixture was stirred at 40° C. for 18 h. The mixture was then poured into water (200 mL) and extracted with dichloromethane (2×100 mL). The combined organic layers were dried over sodium sulfate and concentrated under reduced pressure. The residue was purified by column chromatography (silica gel, 100-200 mesh, 0 to 80% ethyl acetate in petroleum ether) to afford 3-benzyloxy-5-[1-[tert-butyl(dimethyl)silyl]oxypropyl]pyrrolidin-2-one (6.8 g, 58%) as a colorless oil.

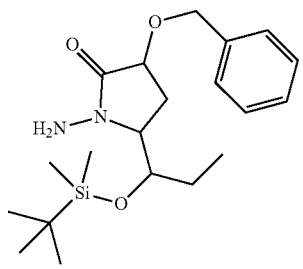 [SMILES: CCC(O[Si](C)(C)C(C)(C)C)C1CC(OCc2ccccc2)C(=O)N1N]

Step 6: 1-amino-3-(benzyloxy)-5-(1-((tert-butyldimethylsilyl)oxy)propyl)pyrrolidin-2-one To a solution of 3-benzyloxy-5-[1-[tert-butyl(dimethyl)silyl]oxypropyl]pyrrolidin-2-one (6.80 g, 18.7 mmol) in N,N-dimethylformamide (150 mL) was added sodium hydride (60% in mineral oil, 1.12 g, 28.1 mmol) at 0° C. After stirred at 25° C. for 20 min, the mixture was added o-(diphenylphosphoryl) hydroxylamine (6.50 g, 28.1 mmol) and stirred for another 18 h at 25° C. The mixture was filtered and the filtrate was concentrated under reduced pressure to afford crude 1-amino-3-benzyloxy-5-[1-[tert-butyl (dimethyl)silyl]oxypropyl]pyrrolidin-2-one (7.10 g, 100%) as a light yellow solid. LC-MS $R_T$=0.876 min, m/z=379.3 [M+H]$^+$.

LCMS (5 to 95% acetonitrile in water+0.03% trifluoacetic acid over 1.5 mins) retention time 0.876 min, ESI+ found [M+H]=379.3.

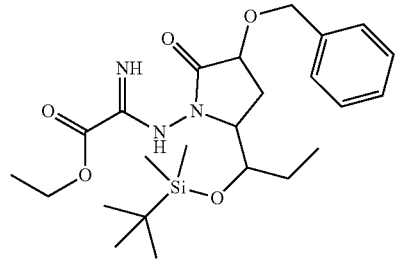 [SMILES: CCOC(=O)C(=N)NN1C(=O)C(OCc2ccccc2)CC1C(CC)O[Si](C)(C)C(C)(C)C]

Step 7: Ethyl 2-((3-(benzyloxy)-5-(1-((tert-butyldimethylsilyl)oxy)propyl)-2-oxopyrrolidin-1-yl)amino)-2-iminoacetate A mixture of 1-amino-3-benzyloxy-5-[1-[tert-butyl(dimethyl)silyl]oxypropyl]pyrrolidin-2-one (1.87 g, 4.94 mmol) and ethyl 2-ethoxy-2-imino-acetate (1.79 g, 12.35 mmol) in ethanol (25 mL) was stirred at 90° C. for 33 h and concentrated under reduced pressure to afford crude ethyl 2-((3-(benzyloxy)-5-(1-((tert-butyldimethylsilyl)oxy)propyl)-2-oxopyrrolidin-1-yl)amino)-2-iminoacetate (2.36 g, 99%) as a yellow oil. The crude product was used next step without further purification. LC-MS $R_T$=1.037&1.061 min, m/z=478.2 [M+H]$^+$.

LCMS (5 to 95% acetonitrile in water+0.03% trifluoacetic acid over 1.5 mins) retention time 1.037& 1.061 min, ESI+ found [M+H]=478.2.

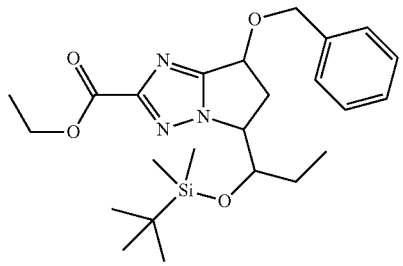 [SMILES: CCOC(=O)c1nc2n(n1)C(C(CC)O[Si](C)(C)C(C)(C)C)CC2OCc1ccccc1]

Step 8: Ethyl 7-(benzyloxy)-5-(1-((tert-butyldimethylsilyl)oxy)propyl)-6,7-dihydro-5H-pyrrolo[1,2-b][1,2,4]triazole-2-carboxylate To a solution of ethyl 2-[[3-benzyloxy-5-[1-[tert-butyl (dimethyl)silyl]oxypropyl]-2-oxo-pyrrolidin-1-yl]amino]-2-imino-acetate (2.2 g, 4.61 mmol) in toluene (50 mL) was added p-toluenesulfonic acid monohydrate (1.1 g, 5.53 mmol). The reaction mixture was stirred at 120° C. for 16 h and filtered. The filtrate was concentrated under reduced pressure. The residue was purified by column chromatography (silica gel, 100-200 mesh, 0 to 50% ethyl acetate in petroleum ether) to afford ethyl 7-benzyloxy-5-[1-[tert-butyl (dimethyl)silyl]oxypropyl]-6,7-dihydro-5H-pyrrolo[1,2-b]

[1,2,4]triazole-2-carboxylate (0.9 g, 43%) as a colorless oil. LC-MS $R_T$=0.935 min, m/z=460.3 [M+H]$^+$.

LCMS (5 to 95% acetonitrile in water+0.03% trifluoacetic acid over 1.5 mins) retention time 0.935 min, ESI+ found [M+H]=460.3.

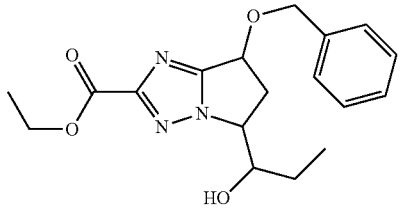 [SMILES: CCOC(=O)c1nc2n(n1)C(C(O)CC)CC2OCc1ccccc1]

Step 9: Ethyl 7-(benzyloxy)-5-(1-hydroxypropyl)-6,7-dihydro-5H-pyrrolo[1,2-b][1,2,4]triazole-2-carboxylate To a solution of ethyl 7-benzyloxy-5-[1-[tert-butyl(dimethyl)silyl]oxypropyl]-6,7-dihydro-5H-pyrrolo[1,2-b][1,2,4]triazole-2-carboxylate (800 mg, 1.74 mmol) in tetrahydrofuran (10 mL) was added tetrabutylammonium fluoride (1.0 M in tetrahydrofuran, 5.22 mL, 5.22 mmol). The mixture was stirred at 25° C. for 18 h and diluted with water (20 mL). The resulting mixture was extracted with ethyl acetate (2×50 mL). The combined organic layers were washed with brine (50 mL), dried over sodium sulfate and concentrated under reduced pressure to afford crude ethyl 7-benzyloxy-5-(1-hydroxypropyl)-6,7-dihydro-5H-pyrrolo[1,2-b][1,2,4]triazole-2-carboxylate (70 mg, 93%) as a brown oil. This crude was used in the next step without further purification.

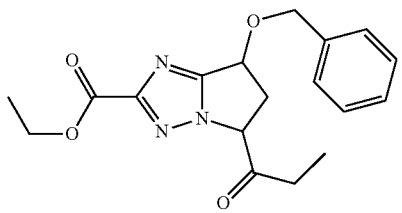 [SMILES: CCOC(=O)c1nc2n(n1)C(C(=O)CC)CC2OCc1ccccc1]

Step 10: Ethyl 7-(benzyloxy)-5-propionyl-6,7-dihydro-5H-pyrrolo[1,2-b][1,2,4]triazole-2-carboxylate To a mixture of ethyl 7-benzyloxy-5-(1-hydroxypropyl)-6,7-dihydro-5H-pyrrolo[1,2-b][1,2,4]triazole-2-carboxylate (600 mg, 1.74 mmol) and sodium bicarbonate (584 mg, 6.95 mmol) in dichloromethane (20 mL) was added Dess-Martin periodinane (1473 mg, 3.47 mmol) at 0° C. The reaction mixture was stirred at 0° C. for 40 min and then quenched by addition of saturated aqueous sodium sulfite (20 mL). The separated organic layer was washed with brine (10 mL), dried over sodium sulfate and concentrated under reduced pressure. The residue was purified by preparative TLC (50% ethyl acetate in petroleum ether, $R_f$=0.3) to give ethyl 7-benzyloxy-5-propanoyl-6,7-dihydro-5H-pyrrolo[1,2-b][1,2,4]triazole-2-carboxylate (590 mg, 99%) as a light brown oil. LC-MS $R_T$=0.834 min, m/z=344.1 [M+H].

LCMS (5 to 95% acetonitrile in water+0.03% trifluoacetic acid over 1.5 mins) retention time 0.834 min, ESI+ found [M+H]=344.1

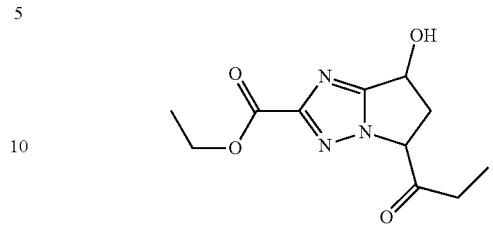

Step 11: Ethyl 7-hydroxy-5-propionyl-6,7-dihydro-5H-pyrrolo[1,2-b][1,2,4]triazole-2-carboxylate A mixture of ethyl 7-benzyloxy-5-propanoyl-6,7-dihydro-5H-pyrrolo[1,2-b][1,2,4]triazole-2-carboxylate (450 mg, 1.31 mmol) in 2,2,2-trifluoroacetic acid (20 mL) was heated at 120° C. for 3 h and concentrated under reduced pressure. The residue was re-dissolved in dichloromethane (30 mL), washed with saturated aqueous sodium bicarbonate (15 mL) and concentrated under reduced pressure. The residue was purified by preparative TLC (60% ethyl acetate in petroleum ether, $R_f$=0.3) to afford ethyl 7-hydroxy-5-propanoyl-6,7-dihydro-5H-pyrrolo[1,2-b][1,2,4]triazole-2-carboxylate (220 mg, 66%) as a brown oil. $^1$H NMR (400 MHz, CDCl$_3$) δ 5.43-5.39 (m, 1H), 5.25-5.21 (m, 1H), 4.50-4.43 (m, 2H), 3.05-3.01 (m, 2H), 2.75-2.55 (m, 2H), 1.44-1.40 (m, 3H), 1.13-1.08 (m, 3H). LC-MS $R_T$=0.530& 0.564 min, m/z=254.1 [M+H]$^+$.

LCMS (5 to 95% acetonitrile in water+0.03% trifluoacetic acid over 1.5 mins) retention time 0.530&0.564 min, ESI+ found [M+H]=254.1.

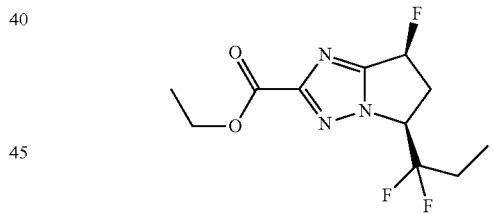

Step 12: Ethyl Cis-5-(1,1-difluoropropyl)-7-fluoro-6,7-dihydro-5H-pyrrolo[1,2-b][1,2,4]triazole-2-carboxylate A mixture of ethyl 7-hydroxy-5-propanoyl-6,7-dihydro-5H-pyrrolo[1,2-b][1,2,4]triazole-2-carboxylate (220 mg, 0.87 mmol) and diethylaminosulfur trifluoride (140 mg, 0.87 mmol) was stirred at 10° C. for 2 h and then quenched by addition of saturated aqueous sodium bicarbonate (15 mL). The resulting mixture was extracted with dichloromethane (2×10 mL). The combined organic layers were washed with brine (20 mL), dried over sodium sulfate and concentrated under reduced pressure. The residue was purified by preparative TLC (50% ethyl acetate in petroleum ether, $R_f$=0.4 for cis isomer and $R_f$=0.6 for trans isomer) to afford ethyl trans-5-(1,1-difluoropropyl)-7-fluoro-6,7-dihydro-5H-pyrrolo[1,2-b][1,2,4]triazole-2-carboxylate (60 mg, 25%) and ethyl cis-5-(1,1-difluoropropyl)-7-fluoro-6,7-dihydro-5H-pyrrolo[1,2-b][1,2,4]triazole-2-carboxylate (60 mg, 25%), both as brown oils.

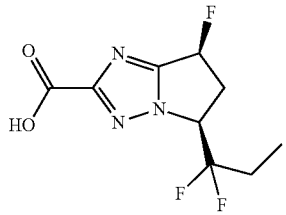 [SMILES: CCC(F)(F)[C@@H]1C[C@H](F)c2nc(C(=O)O)nn21]

Step 13: Cis-5-(1,1-difluoropropyl)-7-fluoro-6,7-dihydro-5H-pyrrolo[1,2-b][1,2,4]triazole-2-carboxylic Acid To a solution of ethyl cis-5-(1,1-difluoropropyl)-7-fluoro-6,7-dihydro-5H-pyrrolo[1,2-b][1,2,4]triazole-2-carboxylate (55 mg, 0.20 mmol) in tetrahydrofuran (2 mL), ethanol (2 mL) and water (0.5 mL) was added with lithium hydroxide monohydrate (83 mg, 1.98 mmol). The reaction mixture was stirred at 25° C. for 2 h and then concentrated under reduce pressure. The residue was diluted with ice water (20 mL) and adjusted to pH=3 by addition of aqueous hydrochloric acid (4 M). The mixture was extracted with ethyl acetate (2×5 mL). The combined organic layers were dried over sodium sulfate and concentrated under reduced pressure to afford crude cis-5-(1,1-difluoropropyl)-7-fluoro-6,7-dihydro-5H-pyrrolo[1,2-b][1,2,4]triazole-2-carboxylic acid (40 mg, 81%) as a light pink solid.

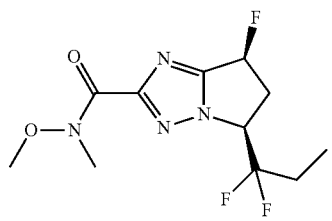 [SMILES: CCC(F)(F)[C@@H]1C[C@H](F)c2nc(C(=O)N(C)OC)nn21]

Step 14: Cis-5-(1,1-difluoropropyl)-7-fluoro-N-methoxy-N-methyl-6,7-dihydro-5H-pyrrolo[1,2-b][1,2,4]triazole-2-carboxamide A mixture of cis-5-(1,1-difluoropropyl)-7-fluoro-6,7-dihydro-5H-pyrrolo[1,2-b][1,2,4]triazole-2-carboxylic acid (40 mg, 0.16 mmol), N,O-dimethylhydroxylamine hydrochloride (31 mg, 0.32 mmol), 1-[Bis(dimethylamino)methylene]-1H-1,2,3-triazolo[4,5-b]pyridinium 3-oxide hexafluorophosphate (64 mg, 0.17 mmol) and N,N-diisopropylethylamine (0.08 mL, 0.48 mmol) in N,N-dimethylformamide (1 mL) was stirred at 20° C. for 2 h and concentrated under reduced pressure. The residue was purified by preparative TLC (50% ethyl acetate in petroleum ether, $R_f$=0.3) to afford cis-5-(1,1-difluoropropyl)-7-fluoro-N-methoxy-N-methyl-6,7-dihydro-5H-pyrrolo[1,2-b][1,2,4]triazole-2-carboxamide (27 mg, 58%) as a colorless oil. LC-MS $R_T$=0.7.14 min, m/z=293.1 [M+H].

LCMS (5 to 95% acetonitrile in water+0.03% trifluoacetic acid over 1.5 mins) retention time 0.714 min, ESI+ found [M+H]=293.1

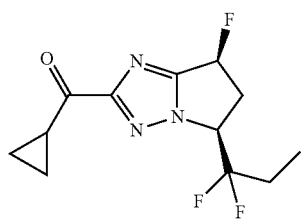 [SMILES: CCC(F)(F)[C@@H]1C[C@H](F)c2nc(C(=O)C3CC3)nn21]

Step 15: Cyclopropyl-[rac-(5S,7S)-5-(1,1-difluoropropyl)-7-fluoro-6,7-dihydro-5H-pyrrolo[1,2-b][1,2,4]triazol-2-yl]methanone To a solution of cis-5-(1,1-difluoropropyl)-7-fluoro-N-methoxy-N-methyl-6,7-dihydro-5H-pyrrolo[1,2-b][1,2,4]triazole-2-carboxamide (27 mg, 0.09 mmol) in tetrahydrofuran (0.5 mL) was added cyclopropylmagnesium bromide (0.5 M in tetrahydrofuran, 0.92 mL, 0.46 mmol) under nitrogen atmosphere. After addition, the mixture was stirred at 0° C. for 1 h and quenched by addition of methanol (10 mL). The resulting mixture was concentrated under reduced pressure and the residue was purified by preparative TLC (50% ethyl acetate in petroleum ether, $R_f$=0.6) to afford cyclopropyl-[rac-(5S,7S)-5-(1,1-difluoropropyl)-7-fluoro-6,7-dihydro-5H-pyrrolo[1,2-b][1,2,4]triazol-2-yl]methanone (cis mixture) (9.9 mg, 35%) as a white solid. $^1$H NMR (400 MHz, CD$_3$OD) δ 5.97-5.80 (m, 1H), 4.90-4.78 (m, 1H), 3.45-3.25 (m, 1H), 3.05-2.95 (m, 1H), 2.95-2.75 (m, 1H), 2.28-2.00 (m, 2H), 1.20-1.11 (m, 2H), 1.07-0.98 (m, 5H). LC-MS $R_T$=0.766 min, m/z=274.1 [M+H].

LCMS (5 to 95% acetonitrile in water+0.03% trifluoacetic acid over 1.5 mins) retention time 0.766 min, ESI+ found [M+H]=274.1.

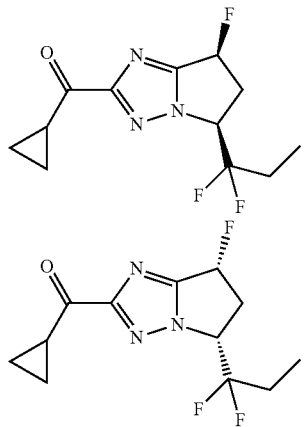

Step 16: Cyclopropyl-[(5S,7S)-5-(1,1-difluoropropyl)-7-fluoro-6,7-dihydro-5H-pyrrolo[1,2-b][1,2,4]triazol-2-yl]methanone and cyclopropyl-[(5R,7R)-5-(1,1-difluoropropyl)-7-fluoro-6,7-dihydro-5H-pyrrolo[1,2-b][1,2,4]triazol-2-yl]methanone Cyclopropyl-[rac-(5S,7S)-5-(1,1-difluoropropyl)-7-fluoro-6,7-dihydro-5H-pyrrolo[1,2-b][1,2,4]triazole-2-yl]methanone (58 mg) was separated by chiral SFC to afford arbitrarily assigned: cyclopropyl-[(5S,7S)-5-(1,1-difluoropropyl)-7-fluoro-6,7-dihydro-5H-pyrrolo[1,2-b][1,2,4] triazol-2-yl]methanone (Peak 2, retention time=5.085 min) (8.2 mg, 14%) as a white solid. $^1$H NMR (400 MHz, CDCl$_3$) δ 6.02-5.84 (m, 1H), 4.71-4.66 (m, 1H), 3.33-3.23 (m, 1H), 3.19-3.07 (m, 2H), 2.34-2.26 (m, 1H), 2.18-2.01 (m, 1H), 1.35-1.25 (m, 2H), 1.18 (s, 1H), 1.17-1.15 (m, 2H), 1.14-1.11 (m, 2H). LC-MS R$_T$=0.818 min, m/z=273.9 [M+H]+.

LCMS (5 to 95% acetonitrile in water+0.03% trifluoroacetic acid over 1.5 mins) retention time 0.818 min, ESI+ found [M+H]=273.9.

cyclopropyl-[(5R,7R)-5-(1,1-difluoropropyl)-7-fluoro-6,7-dihydro-5H-pyrrolo[1,2-b][1,2,4] triazol-2-yl]methanone (Peak 1, retention time=3.815 min) (13.9 mg, 23%) as a white solid. $^1$H NMR (400 MHz, CDCl3) δ 6.04-5.81 (m, 1H), 4.69-4.61 (m, 1H), 3.43-3.23 (m, 1H), 3.20-3.00 (m, 2H), 2.43-2.22 (m, 1H), 2.20-2.00 (m, 1H), 1.35-1.25 (m, 2H), 1.18 (s, 1H), 1.16-1.15 (m, 2H), 1.15-1.12 (m, 2H). LC-MS R$_T$=0.815 min, m/z=273.9 [M+H]$^+$.

LCMS (5 to 95% acetonitrile in water+0.03% trifluoroacetic acid over 1.5 mins) retention time 0.815 min, ESI+ found [M+H]=273.9.

Method 91

Example 113

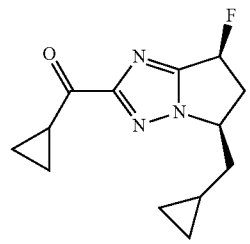

Cyclopropyl-[(5R,7S)-5-(cyclopropylmethyl)-7-fluoro-6,7-dihydro-5H-pyrrolo[1,2-b][1,2,4]triazol-2-yl]methanone

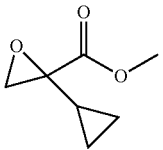

Step 1: Methyl 2-cyclopropyloxirane-2-carboxylate

A mixture of sodium methoxide (40.5 g, 749.04 mmol) in methanol (250 mL) was added cyclopropanecarboxaldehyde (35.0 g, 499.36 mmol) at −10° C., then methyl chloroacetate (81.3 g, 749.04 mmol) was added dropwise over 2 h. After addition, the mixture was stirred at 25° C. for 16 h and quenched by addition of acetic acid. The resulting mixture was diluted with water (300 mL) and extracted with ethyl acetate (3×300 mL). The combined organic layers were washed with brine (500 mL), dried over sodium sulfate and concentrated under reduced pressure to give crude methyl 2-cyclopropyloxirane-2-carboxylate as a brown oil. The oil was distilled under reduced pressure to afford methyl 2-cyclopropyloxirane-2-carboxylate (38 g, 53%) as colorless oil.

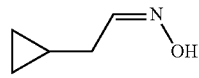

Step 2: (Z)-2-cyclopropylacetaldehyde Oxime

To a solution of sodium hydroxide (19.9 g, 498.07 mmol) in water (70 mL) was added methyl 2-cyclopropyloxirane-2-carboxylate (59.0 g, 415.05 mmol) at 25° C. over 2 h. The reaction mixture was stirred at 25° C. for 1 h and hydroxylamine sulfate (37.5 g, 228.28 mmol) was added over 30 min at 25° C. The mixture was stirred at 25° C. for 2 h and diluted with water (300 mL). The solution was extracted with ethyl acetate (3×300 mL). The combined organic layers were washed with brine (300 mL), dried over sodium sulfate and concentrated under reduced pressure. The residue was purified by column chromatography (silica gel, 100-200 mesh, 50% ethyl acetate in petroleum ether) to afford (Z)-2-cyclopropylacetaldehyde oxime (23.5 g, 57%) as a white solid. LC-MS R$_T$=0.265 min, m/z=100.1 [M+H]$^+$.

LCMS (5 to 95% acetonitrile in water+0.03% trifluoacetic acid over 1.5 mins) retention time 0.265 min, ESI+ found [M+H]=100.1.

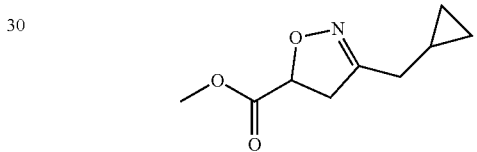

Step 3: Methyl 3-(cyclopropylmethyl)-4,5-dihydroisoxazole-5-carboxylate

A solution of pyridine (0.85 mL, 10.59 mmol), N-chlorosuccinimide (28.3 g, 211.84 mmol) and (Z)-2-cyclopropylacetaldehyde oxime (21.0 g, 211.84 mmol) in chloroform (200 mL) was stirred at 25° C. for 2 h and then a solution of methyl acrylate (23.96 mL, 264.38 mmol) and triethylamine (30.77 mL, 222.01 mmol) in chloroform (30 mL) was added. The mixture was stirred at 25° C. for 16 h and diluted with water (300 mL). The mixture was extracted with ethyl acetate (3×100 mL). The combined organic layers were dried over sodium sulfate and concentrated under reduced pressure. The residue was purified by column chromatography (silica gel, 100-200 mesh, 0-50% ethyl acetate in petroleum ether) to afford methyl 3-(cyclopropylmethyl)-4,5-dihydroisoxazole-5-carboxylate (21.0 g, 54%) as colorless oil. LC-MS R$_T$=0.565 min, m/z=184.1 [M+H]$^+$.

LCMS (5 to 95% acetonitrile in water+0.03% trifluoacetic acid over 1.5 mins) retention time 0.565 min, ESI+ found [M+H]=184.1.

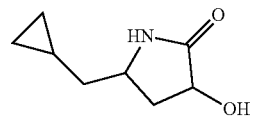 [SMILES: O=C1NC(CC2CC2)CC1O]

Step 4: 5-(cyclopropylmethyl)-3-hydroxypyrrolidin-2-one

A mixture of methyl 3-(cyclopropylmethyl)-4,5-dihydroisoxazole-5-carboxylate (18.0 g, 98.25 mmol) in methanol and palladium (10% on carbon, 10.5 g,) was stirred at 25° C. under hydrogen (15 psi) for 16 h and filtered. The filtrate was concentrated under reduced pressure and the residue was purified by column chromatography (silica gel, 100-200 mesh, 0-100% ethyl acetate in petroleum ether) to afford 5-(cyclopropylmethyl)-3-hydroxy-pyrrolidin-2-one (6.2 g, 41%) as a colorless oil. LC-MS $R_T$=0.272 min, m/z=165.2 [M+H]$^+$.

LCMS (5 to 95% acetonitrile in water+0.03% trifluoacetic acid over 1.5 mins) retention time 0.272 min, ESI+ found [M+H]=165.2.

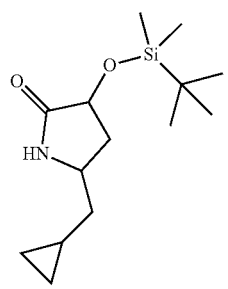 [SMILES: CC(C)(C)[Si](C)(C)OC1CC(CC2CC2)NC1=O]

Step 5: 3-((tert-butyldimethylsilyl)oxy)-5-(cyclopropylmethyl)pyrrolidin-2-one To a solution of 5-(cyclopropylmethyl)-3-hydroxy-pyrrolidin-2-one (5.7 g, 36.73 mmol) and imidazole (5.5 g, 80.80 mmol) in dichloromethane (50 mL) was added tert-butyldimethylchlorosilane (11.1 g, 73.46 mmol). The mixture was stirred at 20° C. for 16 h and filtered. The filtrate was concentrated under reduced pressure. The residue was purified by column chromatography (silica gel, 100-200 mseh, 0-50% ethyl acetate in petroleum ether) to afford 3-[tert-butyl(dimethyl)silyl]oxy-5-(cyclopropylmethyl)pyrrolidin-2-one (7.7 g, 78%) as a white solid. LC-MS $R_T$=0.872 min, m/z=270.2 [M+H]$^+$.

LCMS (5 to 95% acetonitrile in water+0.03% trifluoacetic acid over 1.5 mins) retention time 0.872 min, ESI+ found [M+H]=270.2.

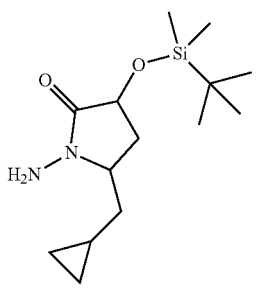 [SMILES: CC(C)(C)[Si](C)(C)OC1CC(CC2CC2)N(N)C1=O]

Step 6: 1-amino-3-((tert-butyldimethylsilyl)oxy)-5-(cyclopropylmethyl)pyrrolidin-2-one To a solution of 3-[tert-butyl(dimethyl)silyl]oxy-5-(cyclopropylmethyl)pyrrolidin-2-one (7.2 g, 26.72 mmol) in N,N-dimethylformamide (10 mL) was added sodium hydride (60%, 1.6 g, 40.08 mmol) at 0° C. After stirred at 0° C. for 30 min, O-(diphenylphosphoryl)hydroxylamine (9.3 g, 40.08 mmol) was added and the mixture was stirred at 10° C. for 16 h. The reaction mixture was filtered and the filtrate was concentrated under reduced pressure to afford crude 1-amino-3-[tert-butyl(dimethyl)silyl]oxy-5-(cyclopropylmethyl)pyrrolidin-2-one (7.5 g, 99%) as a yellow oil. LC-MS $R_T$=0.772 min, m/z=285.2 [M+H]$^+$.

LCMS (5 to 95% acetonitrile in water+0.03% trifluoacetic acid over 1.5 mins) retention time 0.772 min, ESI+ found [M+H]=285.2.

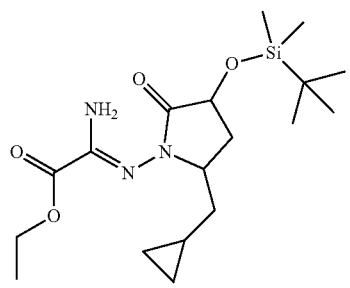 [SMILES: CCOC(=O)/C(N)=N/N1C(=O)C(O[Si](C)(C)C(C)(C)C)CC1CC1CC1]

Step 7: (Z)-ethyl 2-amino-2-((3-((tert-butyldimethylsilyl)oxy)-5-(cyclopropylmethyl)-2-oxopyrrolidin-1-yl)imino)acetate A mixture of 1-amino-3-[tert-butyl(dimethyl)silyl]oxy-5-(cyclopropylmethyl)pyrrolidin-2-one (7.1 g, 24.96 mmol) and ethyl 2-ethoxy-2-imino-acetate (9.1 g, 62.4 mmol) in ethanol (150 mL) was stirred at 90° C. for 12 h and concentrated under reduced pressure to afford crude (Z)-ethyl 2-amino-2-((3-((tert-butyldimethylsilyl)oxy)-5-(cyclopropylmethyl)-2-oxopyrrolidin-1-yl)imino) acetate (9.2 g, 96%) as yellow oil. LC-MS $R_T$=0.783 min, m/z=384.3 [M+H]$^+$.

LCMS (5 to 95% acetonitrile in water+0.03% trifluoacetic acid over 1.5 mins) retention time 0.783 min, ESI+ found [M+H]=384.3.

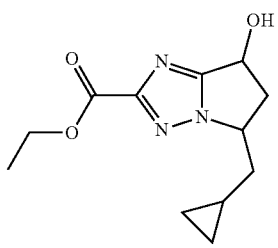 [SMILES: CCOC(=O)c1nc2n(n1)C(CC1CC1)CC2O]

Step 8: Ethyl 5-(cyclopropylmethyl)-7-hydroxy-6,7-dihydro-5H-pyrrolo[1,2-b][1,2,4]triazole-2-carboxylate A mixture of (Z)-ethyl 2-amino-2-[3-[tert-butyl(dimethyl)silyl]oxy-5-(cyclopropylmethyl)-2-oxo-pyrrolidin-1-yl]imino-acetate (9.2 g, 23.99 mmol) and p-toluenesulfonic acid (5.0 g, 28.78 mmol) in toluene (100 mL) was stirred at 120° C. for 16 h and diluted with water (200 mL). The mixture was extracted with ethyl acetate (3×200 mL). The combined organic layers were concentrated under reduced pressure to afford crude ethyl 5-(cyclopropylmethyl)-7-hydroxy-6,7-dihydro-5H-pyrrolo[1,2-b][1,2,4]triazole-2-carboxylate (4.9 g, 82%) as red oil. LC-MS $R_T$=0.540 min, m/z=252.2 [M+H]$^+$. LCMS (5 to 95% acetonitrile in water+ 0.03% trifluoacetic acid over 1.5 mins) retention time 0.540 min, ESI+ found [M+H]=252.2.

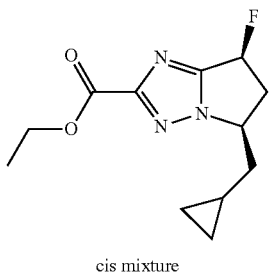 [SMILES: CCOC(=O)c1nc2n(n1)[C@H](CC1CC1)C[C@@H]2F]

cis mixture

Step 9: Ethyl Cis-5-(cyclopropylmethyl)-7-fluoro-6,7-dihydro-5H-pyrrolo[1,2-b][1,2,4] triazole-2-carboxylate To a solution of ethyl 5-(cyclopropylmethyl)-7-hydroxy-6,7-dihydro-5H-pyrrolo[1,2-b][1,2,4]triazole-2-carboxylate (3.0 g, 11.98 mmol) in dichloromethane (150 mL) was added diethylaminosulfur trifluoride (5.8 g, 35.94 mmol). The mixture was stirred at 0° C. for 16 h and quenched by addition of saturated aqueous sodium bicarbonate (200 mL). The resulting mixture was extracted with ethyl acetate (3×100 mL). The combined organic layers were dried over sodium sulfate and concentrated under reduced pressure. The residue was purified by column chromatography (silica gel, 100-200 mesh, 0-30% ethyl acetate in petroleum ether) to afford ethyl trans-5-(cyclopropylmethyl)-7-fluoro-6,7-dihydro-5H-pyrrolo[1,2-b][1,2,4]triazole-2-carboxylate (650 mg, 21%) and ethyl cis-5-(cyclopropylmethyl)-7-fluoro-6,7-dihydro-5H-pyrrolo[1,2-b][1,2,4]triazole-2-carboxylate (850 mg, 28%), both as yellow oils. (TLC: 33% ethyl acetate in petroleum ether, $R_f$=0.35 for cis isomer and $R_f$=0.85 for trans isomer).

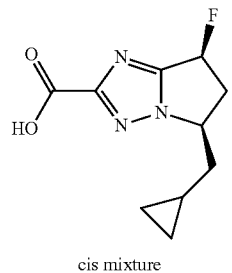

cis mixture

Step 10: Cis-5-(cyclopropylmethyl)-7-fluoro-6,7-dihydro-5H-pyrrolo[1,2-b][1,2,4]triazole-2-carboxylic Acid A mixture of ethyl cis-5-(cyclopropylmethyl)-7-fluoro-6,7-dihydro-5H-pyrrolo[1,2-b][1,2,4]triazole-2-carboxylate (750 mg, 2.96 mmol) and lithium hydroxide monohydrate (1.2 g, 29.61 mmol) in ethanol (3 mL) and water (1 mL) was stirred at 20° C. for 16 h and concentrated under reduced pressure. The residue was diluted with ice water (2 mL) and adjusted to pH=3 by addition of hydrochloric acid (2 M). The mixture was extracted with ethyl acetate (3×20 mL). The combined organic layers were dried over sodium sulfate and concentrated under reduced pressure to afford crude cis-5-(cyclopropylmethyl)-7-fluoro-6,7-dihydro-5H-pyrrolo[1,2-b][1,2,4]triazole-2-carboxylic acid (660 mg, 99%) as clear oil. LC-MS $R_T$=0.491 min, m/z=226.2 [M+H]$^+$.

LCMS (5 to 95% acetonitrile in water+0.03% trifluoacetic acid over 1.5 mins) retention time 0.491 min, ESI+ found [M+H]=226.2.

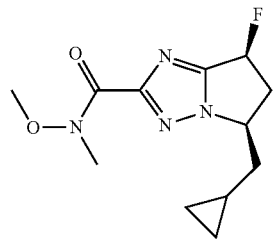

cis mixture

Step 11: Cis-5-(cyclopropylmethyl)-7-fluoro-N-methoxy-N-methyl-6,7-dihydro-5H-pyrrolo [1,2-b][1,2,4]triazole-2-carboxamide A mixture of cis-5-(cyclopropylmethyl)-7-fluoro-6,7-dihydro-5H-pyrrolo[1,2-b][1,2,4]triazole-2-carboxylic acid (660 mg, 3.11 mmol), N,N-diisopropylethylamine (3.32 mL, 18.65 mmol), N,O-dimethylhydroxylamine hydrochloride (606 mg, 6.22 mmol) and 1-[Bis(dimethylamino) methylene]-1H-1,2,3-triazolo[4,5-b]pyridinium 3-oxide hexafluorophosphate (1536 mg, 4.04 mmol) in N,N-dimethylformamide (10 mL) was stirred at 25° C. for 3 h and diluted with water (50 mL). The resulting mixture was extracted with ethyl acetate (3×50 mL). The combined organic layers were washed with brine (2×50 mL), dried over sodium sulfate and concentrated under reduced pressure to afford crude cis-5-(cyclopropylmethyl)-7-fluoro-N-methoxy-N-methyl-6,7-dihydro-5H-pyrrolo[1,2-b][1,2,4]triazole-2-carboxamide (670 mg, 80%) as a brown solid. LC-MS $R_T$=0.706 min, m/z=269.2 [M+H]$^+$.

LCMS (5 to 95% acetonitrile in water+0.03% trifluoacetic acid over 1.5 mins) retention time 0.706 min, ESI+ found [M+H]=269.2.

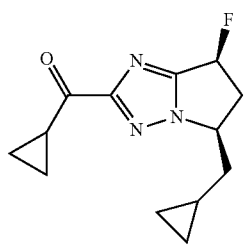 [SMILES: O=C(c1nc2n(n1)[C@H](CC1CC1)C[C@@H]2F)C1CC1]

Step 12: Cyclopropyl-[(5R,7S)-5-(cyclopropylmethyl)-7-fluoro-6,7-dihydro-5H-pyrrolo[1,2-b][1,2,4]triazol-2-yl]methanone To a solution of cis-5-(cyclopropylmethyl)-7-fluoro-N-methoxy-N-methyl-6,7-dihydro-5H-pyrrolo[1,2-b][1,2,4]

triazole-2-carboxamide (150 mg, 0.56 mmol) in tetrahydrofuran (1 mL) was added cyclopropylmagnesium bromide (0.5 M in tetrahydrofuran, 3.35 mL, 1.68 mmol) at 0° C. The mixture was stirred at 0° C. for 5 h and quenched by addition of water (5 mL). The resulting mixture was extracted with ethyl acetate (3×5 mL). The combined organic layers were dried over sodium sulfate and concentrated under reduced pressure. The residue was purified by RP-HPLC (acetonitrile 30-60%/0.225% formic acid in water) and further purified by chiral SFC to afford arbitrarily assigned:

cyclopropyl-[(5R,7S)-5-(cyclopropylmethyl)-7-fluoro-6,7-dihydro-5H-pyrrolo[1,2-b][1,2,4] triazol-2-yl]methanone (peak 2, retention time=3.498 min) (13.6 mg, 9.5%) as colorless oil. $^1$H NMR (400 MHz, CD$_3$OD) δ 6.02-6.00 (m, 0.5H), 5.88-5.86 (m, 0.5H), 4.60-4.55 (m, 1H), 3.37-3.23 (m, 1H), 3.05-3.01 (m, 1H), 2.75-2.60 (m, 1H), 2.00-1.95 (m, 1H), 1.68-1.65 (m, 1H), 1.16-1.06 (m, 4H), 0.90-0.77 (m, 1H), 0.49-0.47 (m, 2H), 0.10-0.02 (m, 2H). LC-MS $R_T$=0.635 min, m/z=250.2 [M+H]$^+$.

LCMS (5 to 95% acetonitrile in water+0.03% trifluoroacetic acid over 1.5 mins) retention time 0.635 min, ESI+ found [M+H]=250.2.

The 5S,7R-isomer (peak 1, retention time=3.041 min) (13.5 mg, 9%) was also obtained as a colorless oil.

SFC condition: Column: ChiralPak AD-3 150×4.6 mm I.D., 3 μm Mobile phase: A: CO$_2$ B: Ethanol (0.05% DEA) Gradient: from 5% to 40% of B in 5.5 min and hold 40% for 3 min, then 5% of B for 1.5 min Flow rate: 25 mL/min Column temp: 40° C.

SFC condition: Column: Lux Cellulose-2 150×4.6 mm I.D., 3 m, Mobile phase: A: CO2 B: ethanol (0.05% DEA), Gradient: from 5% to 40% of B in 5.5 min and hold 40% for 3 min, then 5% of B for 1.5 min, Flow rate: 2.5 mL/min Column temperature: 40° C.

Method 92

Example 114

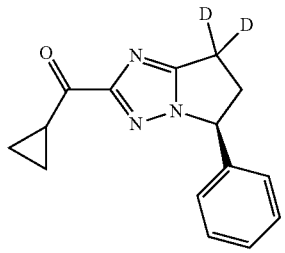

Cyclopropyl-[(5S)-7,7-dideuterio-5-phenyl-5,6-dihydropyrrolo[1,2-b][1,2,4]triazol-2-yl]methanone

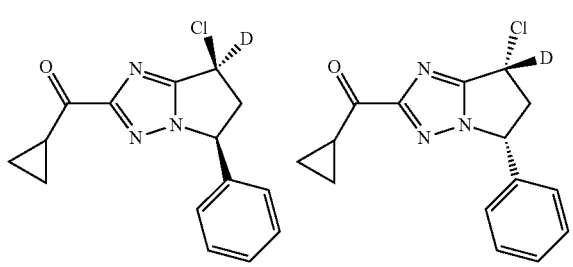

Step 1: Cyclopropyl-[(5S,7S)-7-chloro-7-deuterio-5-phenyl-5,6-dihydropyrrolo[1,2-b][1,2,4]triazol-2-yl]methanone and cyclopropyl-[(5R,7R)-7-chloro-7-deuterio-5-phenyl-5,6-dihydropyrrolo[1,2-b][1,2,4]triazol-2-yl]methanone cyclopropyl-[rac-(5S,7S)-7-chloro-7-deuterio-5-phenyl-5,6-dihydropyrrolo[1,2-b][1,2,4]triazol-2-yl]methanone (350 mg, from another scale up batch) was separated by chiral SFC to arbitrarily assigned:

cyclopropyl-[(5R,7R)-7-chloro-7-deuterio-5-phenyl-5,6-dihydropyrrolo[1,2-b][1,2,4]triazol-2-yl]methanone (peak 1: retention time=3.132 min, 100 mg, 10%) and cyclopropyl-[(5S,7S)-7-chloro-7-deuterio-5-phenyl-5,6-dihydropyrrolo[1,2-b][1,2,4]triazol-2-yl]methanone (peak 2: retention time=4.124 min, 100 mg, 10%), both as white solids.

SFC condition: Column: OJ-H (250 mm*30 mm, 10 μm); Condition: 0.1% NH$_3$H$_2$O EtOH; Begin B 30% End B 30%; Flow Rate (80 mL/min), Column temperature 40° C.

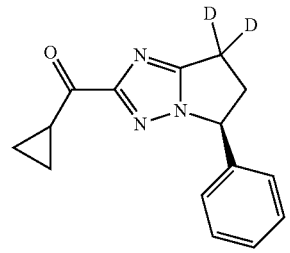 [SMILES: [2H]C1([2H])C[C@@H](c2ccccc2)n2nc(C(=O)C3CC3)nc21]

Step 2: Cyclopropyl-[(5S)-7,7-dideuterio-5-phenyl-5,6-dihydropyrrolo[1,2-b][1,2,4]triazol-2-yl]methanone A solution of cyclopropyl-[(5S,7S)-7-chloro-7-deuterio-5-phenyl-5,6-dihydropyrrolo[1,2-b][1,2,4]triazol-2-yl]methanone (40 mg, 0.14 mmol) and zinc (40 mg, 0.61 mmol) in formic acid-D$_2$ (2.0 mL, 0.14 mmol) was stirred at 20° C. for 48 h. The mixture was diluted with ethyl acetate (20 mL), washed with water (2×10 mL) and concentrated under reduced pressure. The residue was purified by RP-HPLC (0.05% ammonia hydroxide v/v-acetonitrile 36-66%) to afford arbitrarily assigned cyclopropyl-[(5S)-7,7-dideuterio-5-phenyl-5,6-dihydropyrrolo[1,2-b][1,2,4]triazol-2-yl]methanone (13.2 mg, 36%) as a white solid. $^1$H NMR (400 MHz, CDCl$_3$) δ 7.41-7.36 (m, 3H), 7.14-7.11 (m, 2H), 5.52-5.48 (m, 1H), 3.28-3.21 (m, 1H), 3.04-3.00 (m, 1H), 2.70-2.65 (m, 1H), 1.30-1.27 (m, 2H), 1.06-1.03 (m, 2H). LCMS $R_T$=1.549 min, m/z=256.2 [M+H]$^+$.

LCMS (10 to 80% acetonitrile in water+0.1% ammonia water over 3.0 mins) retention time 1.549 min, ESI+ found [M+H]=256.2.

Method 93

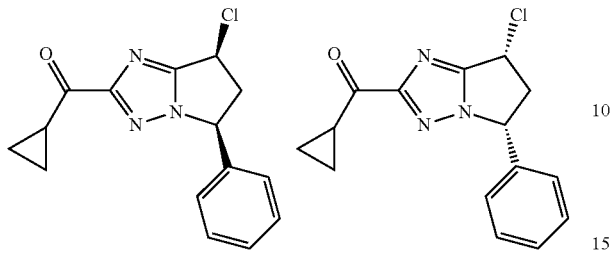

Example 115

Cyclopropyl-[(5S,7S)-7-chloro-5-phenyl-6,7-dihydro-5H-pyrrolo[1,2-b][1,2,4]triazol-2-yl]methanone and cyclopropyl-[(5R,7R)-7-chloro-5-phenyl-6,7-dihydro-5H-pyrrolo[1,2-b][1,2,4]triazol-2-yl]methanone A mixture of thionyl chloride (441 mg, 3.71 mmol) and cyclopropyl-[trans-7-hydroxy-5-phenyl-6,7-dihydro-5H-pyrrolo[1,2-b][1,2,4]triazol-2-yl]methanone (400 mg, 1.49 mmol) was stirred at 0° C. for 0.5 h and quenched by addition of water (100 mL). The mixture was extracted with ethyl acetate (2×200 mL). The combined organic layers were dried over sodium sulfate and concentrated under reduced pressure. The residue was purified by column chromatography (silica gel, 100-200 mesh, 0 to 20% ethyl acetate in petroleum ether) to afford cyclopropyl-[cis-7-chloro-5-phenyl-6,7-dihydro-5H-pyrrolo[1,2-b][1,2,4]triazol-2-yl]methanone (220 mg, 52%) as a yellow solid. LC-MS RT=0.692 min, m/z=288.1 [M+H]$^+$.

LCMS (5 to 95% acetonitrile in water+0.03% trifluoroacetic acid over 1.5 mins) retention time 0.692 min, [M+H]=288.1.

This cis mixture was further separated by chiral SFC to afford arbitrarily assigned: cyclopropyl-[(5S,7S)-7-chloro-5-phenyl-6,7-dihydro-5H-pyrrolo[1,2-b][1,2,4]triazol-2-yl]methanone (peak 1, retention time=3.711 min) (72.9 mg, 33%) as a white solid. $^1$H NMR (400 MHz, CDCl$_3$) δ 7.43-7.39 (m, 2H), 7.33-7.28 (m, 3H), 5.56-5.51 (m, 1H), 5.40-5.35 (m, 1H), 3.95-3.88 (m, 1H), 3.07-2.99 (m, 2H), 1.34-1.31 (m, 2H), 1.11-1.07 (m, 2H). LCMS R$_T$=1.034 min, m/z=288.2 [M+H]$^+$.

LCMS (10 to 80% acetonitrile in water+0.03% trifluoroacetic acid over 2.0 mins) retention time 1.034 min, ESI+ found [M+H]=288.2.

cyclopropyl-[(5R,7R)-7-chloro-5-phenyl-6,7-dihydro-5H-pyrrolo[1,2-b][1,2,4]triazol-2-yl]methanone (peak 2, retention time=3.949 min) (84.6 mg, 38%) as a white solid. $^1$H NMR (400 MHz, CDCl$_3$) δ 7.43-7.39 (m, 2H), 7.33-7.28 (m, 3H), 5.56-5.51 (m, 1H), 5.40-5.35 (m, 1H), 3.96-3.86 (m, 1H), 3.10-2.99 (m, 2H), 1.35-1.28 (m, 2H), 1.10-1.06 (m, 2H). LCMS R$_T$=1.033 min, m/z=288.2 [M+H]$^+$.

LCMS (10 to 80% acetonitrile in water+0.03% trifluoroacetic acid over 2.0 mins) retention time 1.033 min, ESI+ found [M+H]=288.2.

SFC method: column: Chiralcel OJ-3 150×4.6 mm I.D., 3 μm Mobile phase: A: CO$_2$ B:ethanol (0.05% DEA) Gradient: from 5% to 40% of B in 5 min and hold 40% for 2.5 min, then 5% of B for 2.5 min Flow rate: 2.5 mL/min Column temp.: 35° C.

Method 94

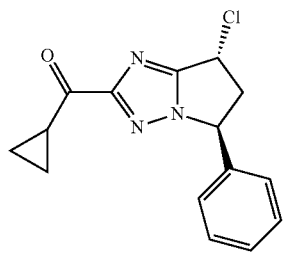

Example 117

Cyclopropyl-[(5S,7R)-7-chloro-5-phenyl-6,7-dihydro-5H-pyrrolo[1,2-b][1,2,4]triazol-2-yl]methanone

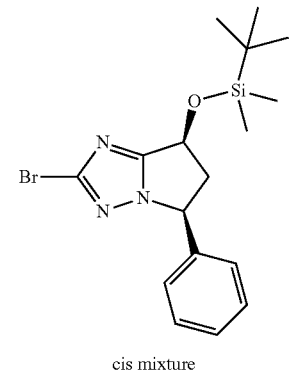 [SMILES: CC(C)(C)[Si](C)(C)O[C@H]1C[C@@H](c2ccccc2)n2nc(Br)nc21]

cis mixture

Step 1: [rac-(5S,7S)-2-bromo-5-phenyl-6,7-dihydro-5H-pyrrolo[1,2-b][1,2,4]triazol-7-yl]oxy-tert-butyl-dimethyl-silane A mixture of rac-(5S,7S)-2-bromo-5-phenyl-6,7-dihydro-5H-pyrrolo[1,2-b][1,2,4]triazol-7-ol (800 mg, 2.86 mmol), imidazole (389 mg, 5.71 mmol) and tert-butyldimethylchlorosilane (646 mg, 4.28 mmol) in dichloromethane (20 mL) was stirred at 15° C. for 1.5 h and filtered. The filtrate was concentrated under reduced pressure. The residue was purified by column chromatography (silica gel, 100-200 mesh, 0 to 10% ethyl acetate in petroleum ether) to afford [rac-(5S,7S)-2-bromo-5-phenyl-6,7-dihydro-5H-pyrrolo[1,2-b][1,2,4]triazol-7-yl]oxy-tert-butyl-dimethyl-silane (900 mg, 80%) as a colorless oil.

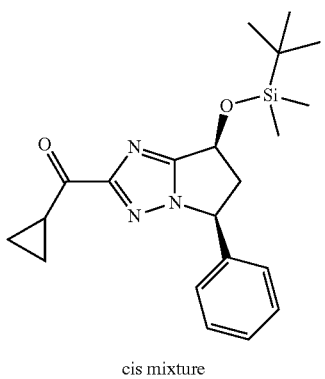 [SMILES: CC(C)(C)[Si](C)(C)O[C@H]1C[C@@H](c2ccccc2)n2nc(C(=O)C3CC3)nc21]

cis mixture

Step 2: Cyclopropyl-[(rac-5S,7S)-7-[tert-butyl(dimethyl)silyl]oxy-5-phenyl-6,7-dihydro-5H-pyrrolo[1,2-b][1,2,4]triazol-2-yl]methanone To a solution of N-methoxy-N-methyl-cyclopropanecarboxamide (589 mg, 4.56 mmol) and [rac-(5S,7S)-2-bromo-5-phenyl-6,7-dihydro-5H-pyrrolo[1,2-b][1,2,4]triazol-7-yl]oxy-tert-butyl-dimethyl-silane (900 mg, 2.28 mmol) in tetrahydrofuran (20 mL) was added isopropylmagnesium chloride (2.0 M in tetrahydrofuran, 3.42 mL, 6.85 mmol) dropwise at 0° C. The mixture was stirred at 0° C. for 1 h and diluted with ethyl acetate (100 mL). The separated organic layer was washed with saturated aqueous ammonium chloride (50 mL), dried over sodium sulfate and concentrated under reduced pressure. The residue was purified by column chromatography (silica gel, 100-200 mesh, 0 to 20% ethyl acetate in petroleum ether) to give cyclopropyl-[(rac-5S,7S)-7-[tert-butyl(dimethyl)silyl]oxy-5-phenyl-6,7-dihydro-5H-pyrrolo[1,2-b][1,2,4]triazol-2-yl]methanone (450 mg, 51%) as a colorless oil.

LCMS $R_T$=1.016 min, m/z=384.3 [M+H]$^+$.

LCMS (5 to 95% acetonitrile in water+0.03% trifluoacetic acid over 1.5 mins) retention time 1.016 min, ESI+ found [M+H]=384.3.

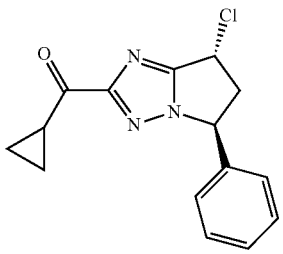 [SMILES: O=C(c1nc2n(n1)[C@H](c1ccccc1)C[C@H]2Cl)C1CC1]

Step 3: Cyclopropyl-[(5S,7R)-7-chloro-5-phenyl-6,7-dihydro-5H-pyrrolo[1,2-b][1,2,4]triazol-2-yl]methanone To a solution of cyclopropyl-[(rac-5S,7S)-7-[tert-butyl(dimethyl)silyl]oxy-5-phenyl-6,7-dihydro-5H-pyrrolo[1,2-b][1,2,4]triazol-2-yl]methanone (450 mg, 1.17 mmol) in dichloromethane (10 mL) was added thionylchloride (0.43 mL, 5.87 mmol). The mixture was stirred at 25° C. for 40 h and concentrated under reduced pressure. The residue was diluted with water (20 mL) and extracted with ethyl acetate (3×20 mL). The combined organic layers were washed with brine (20 mL), dried over sodium sulfate and concentrated under reduced pressure. The residue was purified by column chromatography (silica gel, 100-200 mesh, 0 to 20% ethyl acetate in petroleum ether) to afford cyclopropyl-[rac-(5S,7R)-7-chloro-5-phenyl-6,7-dihydro-5H-pyrrolo[1,2-b][1,2,4]triazol-2-yl]methanone (200 mg, 59%) as a colorless oil. LCMS RT=0.803 min, m/z=288.2 [M+H]+ LCMS (5 to 95% acetonitrile in water+0.03% trifluoacetic acid over 1.5 mins) retention time 0.803 min, ESI+ found [M+H]=288.2.

This racemate was further separated by chiral SFC to afford arbitrarily assigned: cyclopropyl-[(5S,7R)-7-chloro-5-phenyl-6,7-dihydro-5H-pyrrolo[1,2-b][1,2,4]triazol-2-yl]methanone (peak 2, retention time=4.690 min) (60 mg, 40%) as a white solid. $^1$H NMR (400 MHz, CD$_3$OD) δ 7.45-7.38 (m, 3H), 7.34-7.32 (m, 2H), 5.85 (t, J=7.2 Hz, 1H), 5.69-5.67 (m, 1H), 3.40-3.31 (m, 2H), 3.03-3.00 (m, 1H), 1.19-1.16 (m, 2H), 1.11-1.08 (m, 2H). LCMS $R_T$=1.028 min, m/z=288.2 [M+H]$^+$.

LCMS (10 to 80% acetonitrile in water+0.03% trifluoacetic acid over 2.0 mins) retention time 1.028 min, ESI+ found [M+H]=288.2.

SFC condition: Column: Chiralcel OJ-H 100×4.6 mm I.D., 3 μm Mobile phase: A: C$_{02}$ B:methanol (0.05% DEA) Gradient: from 30% to 30% of B, temperature:40° C.

Method 95

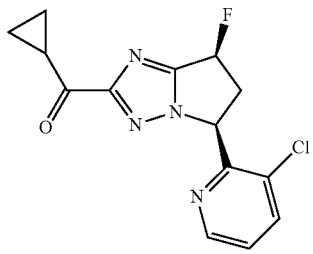

Example 118 cis mixture

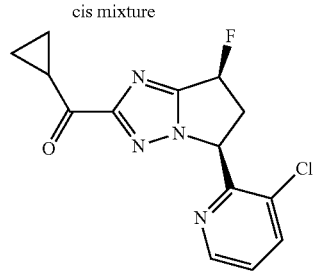

Cyclopropyl-[rac-(5S,7S)-5-(3-chloro-2-pyridyl)-7-fluoro-6,7-dihydro-5H-pyrrolo[1,2-b][1,2,4]triazol-2-yl]methanone and cyclopropyl-[(5S,7S)-5-(3-chloro-2-pyridyl)-7-fluoro-6,7-dihydro-5H-pyrrolo[1,2-b][1,2,4]triazol-2-yl]methanone

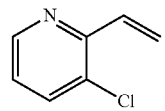

Step 1: Ethyl 3-chloro-2-vinylpyridine

A mixture of 2-bromo-3-chloropyridine (62.5 g, 324.78 mmol), potassium vinyltrifluoroborate (47.9 g, 357.25 mmol), [1,1'-Bis(diphenylphosphino)ferrocene]dichloropalladium(II) (13.2 g, 16.24 mmol) and sodium bicarbonate (68.2 g, 811.94 mmol) in 1,4-dioxane (600 mL) and water (150 mL) was stirred at 100° C. for 24 h and concentrated under reduced pressure. The residue was diluted petroleum ether (500 mL) and filtered. The filtrate was concentrated under reduced pressure. The residue was purified by column chromatography (silica gel, 100-200 mesh, 0 to 10% ethyl acetate in petroleum ether) to afford 3-chloro-2-vinyl-pyridine (40.0 g, 88%) as a green oil. LCMS $R_T$=0.554 min, m/z=140.1/142.1 [M+H]$^+$.

LCMS (5 to 95% acetonitrile in water+0.03% trifluoacetic acid over 1.5 mins) retention time 0.554 min, ESI+ found [M+H]=140.1&142.1.

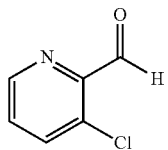

Step 2: 3-Chloropicolinaldehyde

To a solution of 3-chloro-2-vinyl-pyridine (35.0 g, 250.75 mmol) in water (200 mL) and tetrahydrofuran (200 mL) was added osmium tetroxide (0.89 g, 3.51 mmol). The black solution was stirred for 30 min at 25° C., and added sodium periodate (214.5 g, 1003 mmol). The resulting mixture was stirred at 25° C. for 2 h and quenched by addition of saturated aqueous sodium sulfite (200 mL). The solution was extracted with ethyl acetate (2×100 mL). The combined organic layers were dried over sodium sulfate and concentrated under reduced pressure. The residue was purified by column chromatography (silica gel, 100-200 mesh, 0 to 10% ethyl acetate in petroleum ether) to afford 3-chloropyridine-2-carbaldehyde (18.5 g, 52%) as a yellow solid. $^1$H NMR (400 MHz, CDCl$_3$) δ 10.45-10.18 (m, 1H), 8.73-8.70 (m, 1H), 7.86-7.84 (m, 1H), 7.48-7.44 (m, 1H).

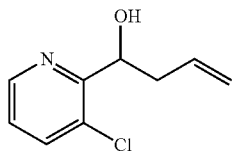

Step 3: 1-(3-chloropyridin-2-yl)but-3-en-1-ol

To a solution of 3-chloropyridine-2-carboxaldehyde (18.5 g, 130.7 mmol) in tetrahydrofuran (200 mL) was added allylmagnesium bromide (1.0 M in n-hexane, 162.2 mL, 162.2 mmol) dropwise over min at 0° C. After addition, the reaction was allowed to warm up to 20° C. and stirred for 2 h. The mixture was quenched by addition of saturated aqueous ammonium chloride (100 mL) and extracted with ethyl acetate (2×100 mL). The combined organic layers were washed with brine (100 mL), dried over sodium sulfate and concentrated under reduced pressure. The residue was purified by column chromatography (silica gel, 100-200 mesh, 0 to 30% ethyl acetate in petroleum ether) to afford 1-(3-chloro-2-pyridyl)but-3-en-1-ol (10.0 g, 42%) as a colorless oil. LCMS $R_T$=0.524 min, m/z=184.1/186.1 [M+H]$^+$.

LCMS (5 to 95% acetonitrile in water+0.03% trifluoacetic acid over 1.5 mins) retention time 0.524 min, ESI+ found [M+H]=184.1&186.1.

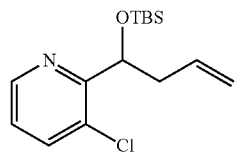 [SMILES: C=CCC(O[Si](C)(C)C(C)(C)C)c1ncccc1Cl]

Step 4: 2-(1-((tert-butyldimethylsilyl)oxy)but-3-en-1-yl)-3-chloropyridine

To a solution of 1-(3-chloro-2-pyridyl)but-3-en-1-ol (10.0 g, 54.46 mmol) in dichloromethane (100 mL) was added imidazole (7.4 g, 108.91 mmol) and tert-butyldimethylchlorosilane (12.3 g, 81.69 mmol). The reaction mixture was stirred at 10° C. for 16 h and diluted with water (50 mL). The separated organic layer was washed with brine (50 mL), dried over sodium sulfate and concentrated under reduced pressure. The residue was purified by column chromatography (silica gel, 100-200 mesh, 0 to 10% ethyl acetate in petroleum ether) to afford tert-butyl-[1-(3-chloro-2-pyridyl)but-3-enoxy]-dimethyl-silane (10 g, 62%) as a light oil.

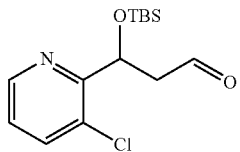 [SMILES: CC(C)(C)[Si](C)(C)OC(CC=O)c1ncccc1Cl]

Step 5: 3-((tert-butyldimethylsilyl)oxy)-3-(3-chloropyridin-2-yl)propanal

To a solution of tert-butyl-[1-(3-chloro-2-pyridyl)but-3-enoxy]-dimethyl-silane (10.0 g, 33.57 mmol) in water (100 mL) and tetrahydrofuran (100 mL) was added osmium tetroxide (0.11 g, 0.44 mmol). After stirred for 30 min at 15° C., the mixture was added sodium periodate (28.7 g, 134.27 mmol) in small portions over 30 min and stirred at 25° C. for another 2 h. The mixture was quenched by addition of saturated aqueous sodium sulfite (1.50 L) and extracted with ethyl acetate (3×300 mL). The combined organic layers were washed with brine (300 mL), dried over sodium sulfate and concentrated under reduced pressure. The residue was purified by column chromatography (silica gel, 100-200 mesh, 0 to 20% ethyl acetate in petroleum ether) to afford 3-[tert-butyl(dimethyl)silyl]oxy-3-(3-chloro-2-pyridyl)propanal (6.5 g, 65%) as a yellow oil. LCMS $R_T$=0.719 min, m/z=300.1/302.1 [M+H]$^+$.

LCMS (5 to 95% acetonitrile in water+0.03% trifluoacetic acid over 1.5 mins) retention time 0.719 min, ESI+ found [M+H]=300.1&302.1.

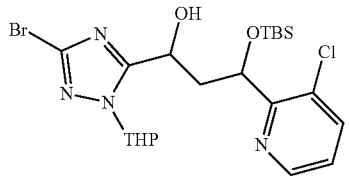

Step 6: 1-(3-bromo-1-(tetrahydro-2H-pyran-2-yl)-1H-1,2,4-triazol-5-yl)-3-((tert-butyldimethylsilyl)oxy)-3-(3-chloropyridin-2-yl)propan-1-ol To a cooled (−78° C.) solution of 3,5-dibromo-1-tetrahydropyran-2-yl-1,2,4-triazole (8.1 g, 26.01 mmol) in tetrahydrofuran (50 mL) was added n-butyllithium (2.5 M in n-hexene, 9.97 mL, 24.93 mmol) dropwise under nitrogen atmosphere. The mixture was stirred at −78° C. for 30 min and then added a solution of 3-[tert-butyl(dimethyl)silyl]oxy-3-(3-chloro-2-pyridyl)propanal (6.5 g, 21.68 mmol) in tetrahydrofuran (15 mL). The resulting mixture was stirred at −78° C. for 1.5 h and quenched by addition of saturated aqueous ammonium chloride (50 mL). The solution was extracted with ethyl acetate (2×50 mL). The combined organic layers were dried over sodium sulfate and concentrated under reduced pressure. The residue was purified by column chromatography (silica gel, 100-200 mesh, 0 to 50% ethyl acetate in petroleum ether) to afford 1-(5-bromo-2-tetrahydropyran-2-yl-1,2,4-triazol-3-yl)-3-[tert-butyl(dimethyl)silyl]oxy-3-(3-chloro-2-pyridyl)propan-1-ol (10.0 g, 87%) as yellow oil. LCMS R$_T$=0.941 min, m/z=533.2 [M+H]$^+$.

LCMS (5 to 95% acetonitrile in water+0.03% trifluoroacetic acid over 1.5 mins) retention time 0.941 min, ESI+ found [M+H]=533.2.

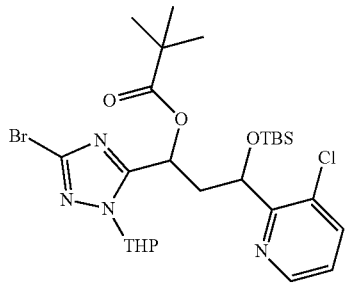

Step 7: [1-(3-bromo-1-(tetrahydro-2H-pyran-2-yl)-1H-1,2,4-triazol-5-yl)-3-((tert-butyldimethylsilyl)oxy)-3-(3-chloropyridin-2-yl)propyl] 2,2-dimethylpropanoate To a mixture of 4-dimethylaminopyridine (321 mg, 2.63 mmol), 1-(5-bromo-2-tetrahydropyran-2-yl-1,2,4-triazol-3-yl)-3-[tert-butyl(dimethyl)silyl]oxy-3-(3-chloro-2-pyridyl)propan-1-ol (14.0 g, 26.32 mmol) and triethylamine (7.01 mL, 52.64 mmol) in dichloromethane (100 mL) was added pivaloyl chloride (4.8 g, 39.48 mmol). The mixture was stirred at 20° C. for 2 h and quenched by addition of water (50 mL). The solution was extracted with dichloromethane (2×100 mL). The combined organic layers were dried over sodium sulfate and concentrated under reduced pressure. The residue was purified by column chromatography (silica gel, 100-200 mesh, 0 to 20% ethyl acetate in petroleum ether) to afford [1-(5-bromo-2-tetrahydropyran-2-yl-1,2,4-triazol-3-yl)-3-[tert-butyl(dimethyl)silyl]oxy-3-(3-chloro-2-pyridyl)propyl] 2,2-dimethylpropanoate (12.5 g, 77%) as a colorless oil.

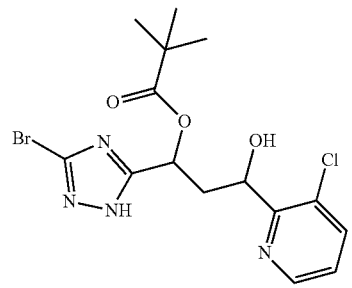 [SMILES: CC(C)(C)C(=O)OC(CC(O)c1ncccc1Cl)c1nc(Br)n[nH]1]

Step 8: 1-(3-bromo-1H-1,2,4-triazol-5-yl)-3-(3-chloropyridin-2-yl)-3-hydroxypropyl 2,2-dimethylpropanoate A mixture of [1-(5-bromo-2-tetrahydropyran-2-yl-1,2,4-triazol-3-yl)-3-[tert-butyl(dimethyl)silyl] oxy-3-(3-chloro-2-pyridyl)propyl] 2,2-dimethylpropanoate (12.0 g, 19.48 mmol) and p-toluenesulfonic acid (4.0 g, 23.37 mmol) in methanol (100 mL) was stirred at 50° C. for 2 h and then concentrated under reduced pressure. The residue was purified by RP-HPLC (acetonitrile 17-47%/0.05% ammonium hydroxide in water) to afford [1-(3-bromo-1H-1,2,4-triazol-5-yl)-3-(3-chloro-2-pyridyl)-3-hydroxy-propyl] 2,2-dimethylpropanoate (6.8 g, 83%) as a white solid. LCMS R$_T$=0.760&0.768 min, m/z=417.1/419.0 [M+H]$^+$.

LCMS (5 to 95% acetonitrile in water+0.03% trifluoroacetic acid over 1.5 mins) retention time 0.760&0.768 min, ESI+ found [M+H]=417.1&419.0.

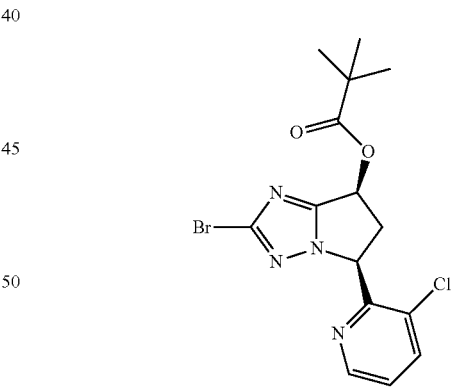

Step 9: Rac-[(5S,7S)-2-bromo-5-(3-chloropyridin-2-yl)-6,7-dihydro-5H-pyrrolo[1,2-b][1,2,4]triazol-7-yl] 2,2-dimethylpropanoate A mixture of [1-(3-bromo-1H-1,2,4-triazol-5-yl)-3-(3-chloro-2-pyridyl)-3-hydroxy-propyl] 2,2-dimethylpropanoate (6.2 g, 14.84 mmol), triphenylphosphine (4.7 g, 17.81 mmol) in tetrahydrofuran (50 mL) was added a solution of diisopropyl azodicarboxylate (3.6 g, 17.81 mmol) in tetrahydrofuran (50 mL). The mixture was stirred at 25° C. for 12 h and then concentrated under reduced pressure. The residue was purified by column chromatography (silica gel, 100-200 mesh, 0 to 30% ethyl acetate in petroleum ether) to afford rac-[(5S,7S)-2-bromo-5-(3-chloro-2-pyridyl)-6,7-dihydro-5H-pyrrolo[1,2-b][1,2,4]triazol-7-yl] 2,2-dimethylpropanoate (2.3 g, 39%) as a colorless oil. LCMS $R_T$=0.753&0.781 min, m/z=399.0/401.0 [M+H]$^+$.

LCMS (5 to 95% acetonitrile in water+0.03% trifluoacetic acid over 1.5 mins) retention time 0.753&0.781 min, ESI+ found [M+H]=399.0&401.0.

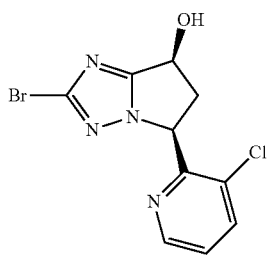 [SMILES: O[C@H]1C[C@@H](c2ncccc2Cl)n2nc(Br)nc21]

Step 10: Rac-(5S,7S)-2-bromo-5-(3-chloropyridin-2-yl)-6,7-dihydro-5H-pyrrolo[1,2-b][1,2,4]triazol-7-ol A mixture of rac-[(5S,7S)-2-bromo-5-(3-chloro-2-pyridyl)-6,7-dihydro-5H-pyrrolo[1,2-b][1,2,4]triazol-7-yl] 2,2-dimethylpropanoate (2.3 g, 5.75 mmol), lithium hydroxide monohydrate (2.4 g, 57.55 mmol) in tetrahydrofuran (10 mL) and water (10 mL) was stirred at 25° C. for 12 h and then extracted with ethyl acetate (2×10 mL). The combined organic layers were dried over sodium sulfate and concentrated under reduced pressure to afford rac-(5S,7S)-2-bromo-5-(3-chloro-2-pyridyl)-6,7-dihydro-5H-pyrrolo[1,2-b][1,2,4]triazol-7-ol (1.7 g, 94%) as a white solid. LCMS $R_T$=0.639 min, m/z=315.0/317.0 [M+H]$^+$.

LCMS (5 to 95% acetonitrile in water+0.03% trifluoacetic acid over 1.5 mins) retention time 0.639 min, ESI+ found [M+H]=315.0 & 317.0.

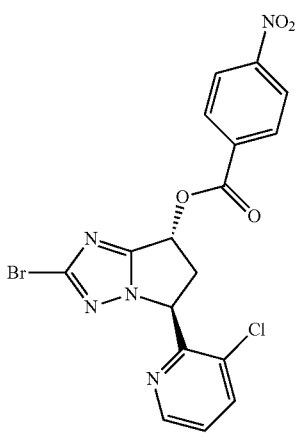 [SMILES: O=C(O[C@@H]1C[C@@H](c2ncccc2Cl)n2nc(Br)nc21)c1ccc([N+](=O)[O-])cc1]

Step 11: Rac-(5S,7R)-2-bromo-5-(3-chloropyridin-2-yl)-6,7-dihydro-5H-pyrrolo[1,2-b][1,2,4]triazol-7-yl 4-nitrobenzoate To a mixture of triphenylphosphine (1.25 g, 4.75 mmol), rac-(5S,7S)-2-bromo-5-(3-chloro-2-pyridyl)-6,7-dihydro-5H-pyrrolo[1,2-b][1,2,4]triazol-7-ol (1.2 g, 3.80 mmol) and 4-nitrobenzoic acid (790 mg, 4.75 mmol) in tetrahydrofuran (5 mL) was added diisopropyl azodicarboxylate (0.77 mL, 4.75 mmol) dropwise at 0° C. under nitrogen atmosphere. The solution was stirred at 0° C. for 12 h and filtered to give crude rac-[(5S,7R)-2-bromo-5-(3-chloro-2-pyridyl)-6,7-dihydro-5H-pyrrolo[1,2-b][1,2,4]triazol-7-yl] 4-nitrobenzoate (1.6 g, 91%) as a white solid.

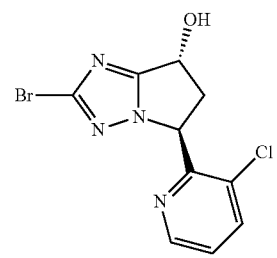 [SMILES: O[C@@H]1C[C@@H](c2ncccc2Cl)n2nc(Br)nc21]

Step 12: Rac-(5S,7R)-2-bromo-5-(3-chloropyridin-2-yl)-6,7-dihydro-5H-pyrrolo[1,2-b][1,2,4]triazol-7-ol A mixture of potassium carbonate (713 mg, 5.16 mmol) and rac-[(5S,7R)-2-bromo-5-(3-chloro-2-pyridyl)-6,7-dihydro-5H-pyrrolo[1,2-b][1,2,4]triazol-7-yl] 4-nitrobenzoate (1.6 g, 3.44 mmol) in methanol (5 mL) and water (5 mL) was stirred at 70° C. for 1 h and concentrated under reduced pressure. The residue was diluted with water (10 mL) and filtered. The solid product was washed with acetonitrile (5 mL) to afford crude rac-(5S,7R)-2-bromo-5-(3-chloro-2-pyridyl)-6,7-dihydro-5H-pyrrolo[1,2-b][1,2,4]triazol-7-ol (800 mg, 74%) as a white solid. LCMS $R_T$=0.649 min, m/z=315.0/317.0 [M+H]$^+$.

LCMS (5 to 95% acetonitrile in water+0.03% trifluoacetic acid over 1.5 mins) retention time 0.649 min, ESI+ found [M+H]=315.0 & 317.0.

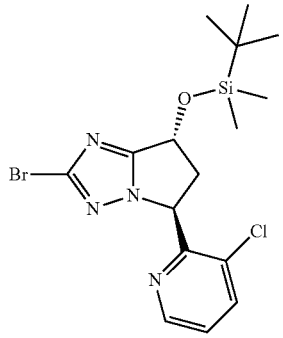 [SMILES: CC(C)(C)[Si](C)(C)O[C@@H]1C[C@@H](c2ncccc2Cl)n2nc(Br)nc21]

Step 13: Rac-(5S,7R)-2-bromo-7-((tert-butyldimethylsilyl)oxy)-5-(3-chloropyridin-2-yl)-6,7-dihydro-5H-pyrrolo[1,2-b][1,2,4]triazole A mixture of rac-(5S,7R)-2-bromo-5-(3-chloro-2-pyridyl)-6,7-dihydro-5H-pyrrolo[1,2-b][1,2,4]triazol-7-ol (350 mg, 1.11 mmol), imidazole (151 mg, 2.22 mmol) in dichloromethane (20 mL) was added tert-butyldimethylchlorosilane (251 mg, 1.66 mmol) at 0° C. The mixture was stirred at 0° C. for 1 h and concentrated under reduced pressure. The residue was purified by column chromatography (silica gel, 100-200 mesh, 0 to 50% ethyl acetate in petroleum ether) to afford rac-(5S,7R)-2-bromo-7-((tert-butyldimethylsilyl)oxy)-5-(3-chloropyridin-2-yl)-6,7-dihydro-5H-pyrrolo[1,2-b][1,2,4]triazole (450 mg, 94%) as a white solid. $^1$H NMR (400 MHz, CDCl3) δ 8.43-8.41 (m, 1H), 7.73 (d, J=8.4 Hz, 1H), 7.25-7.21 (m, 1H), 6.22-6.19 (m, 1H), 5.49-5.46 (m, 1H), 3.12-3.08 (m, 1H), 2.97-2.93 (m, 1H), 0.95 (s, 9H), 0.24-0.19 (m, 6H).

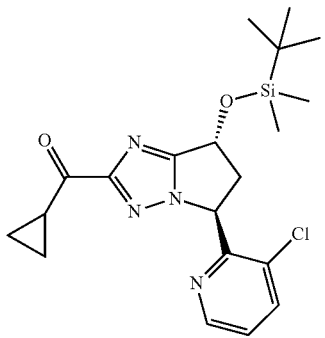 [SMILES: CC(C)(C)[Si](C)(C)O[C@@H]1C[C@@H](c2ncccc2Cl)n2nc(C(=O)C3CC3)nc21]

Step 14: Rac-((5S,7R)-7-((tert-butyldimethylsilyl)oxy)-5-(3-chloropyridin-2-yl)-6,7-dihydro-5H-pyrrolo[1,2-b][1,2,4]triazol-2-yl)(cyclopropyl)methanone To a solution of rac-(5S,7R)-2-bromo-7-((tert-butyldimethylsilyl)oxy)-5-(3-chloropyridin-2-yl)-6,7-dihydro-5H-pyrrolo[1,2-b][1,2,4]triazole (450 mg, 1.05 mmol) and N-methoxy-N-methyl-cyclopropanecarboxamide (270 mg, 2.09 mmol) in tetrahydrofuran (20 mL) was added isopropylmagnesium chloride (2.0 M in tetrahydrofuran, 2.62 mL, 5.23 mmol) at 0° C. After addition, the reaction mixture was stirred at 0° C. for 1 h and quenched by addition of water (20 mL). The resulting mixture was extracted with ethyl acetate (3×30 mL). The combined organic layers were washed with brine (20 mL), dried over sodium sulfate and concentrated under reduced pressure. The residue was purified by column chromatography (silica gel, 100-200 mesh, 0 to 50% ethyl acetate in petroleum ether) to afford rac-((5S,7R)-7-((tert-butyldimethylsilyl)oxy)-5-(3-chloropyridin-2-yl)-6,7-dihydro-5H-pyrrolo[1,2-b][1,2,4]triazol-2-yl)(cyclopropyl)methanone (125 mg, 28%) as a colorless oil. $^1$H NMR (400 MHz, CDCl3) δ 8.41-8.40 (m, 1H), 7.75-7.73 (m, 1H), 7.24-7.22 (m, 1H), 6.28-6.25 (m, 1H), 5.53-5.50 (m, 1H), 3.15-3.12 (m, 1H), 3.10-3.06 (m, 1H), 3.04-3.02 (m, 1H), 1.06-1.04 (m, 2H), 0.96 (s, 9H), 0.91-0.86 (m, 2H), 0.25 (d, J=6.8 Hz, 6H). LCMS $R_T$=0.857 min, m/z=419.1 [M+H]$^+$.

LCMS (5 to 95% acetonitrile in water+0.03% trifluoacetic acid over 1.5 mins) retention time 0.857 min, ESI+ found [M+H]=419.1.

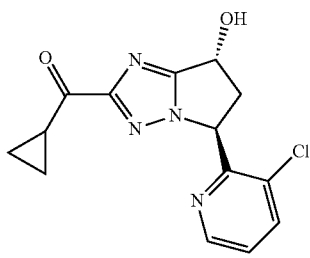 [SMILES: O=C(c1nc2n(n1)[C@H](c1ncccc1Cl)C[C@H]2O)C1CC1]

Step 15: Rac-((5S,7R)-5-(3-chloropyridin-2-yl)-7-hydroxy-6,7-dihydro-5H-pyrrolo[1,2-b][1,2,4]triazol-2-yl)(cyclopropyl)methanone A mixture of rac-((5S,7R)-7-((tert-butyldimethylsilyl)oxy)-5-(3-chloropyridin-2-yl)-6,7-dihydro-5H-pyrrolo[1,2-b][1,2,4]triazol-2-yl)(cyclopropyl)methanone (120 mg, 0.29 mmol) and hydrochloric acid (4.0 M in methanol, 3.60 mL, 14.40 mmol) in methanol (10 mL) was a stirred at 20° C. for 1 ho and then concentrated under reduced pressure. The residue was diluted with water (10 mL) and adjusted to pH=7 by addition of saturated aqueous sodium bicarbonate. The mixture was extracted with dichloromethane (2×20 mL). The combined organic layers were concentrated under reduced pressure to afford crude rac-((5S,7R)-5-(3-chloropyridin-2-yl)-7-hydroxy-6,7-dihydro-5H-pyrrolo[1,2-b][1,2,4]triazol-2-yl)(cyclopropyl)methanone (52 mg, 60%) as a yellow solid. LCMS $R_T$=0.567 min, m/z=305.0 [M+H]$^+$.

LCMS (5 to 95% acetonitrile in water+0.03% trifluoacetic acid over 1.5 mins) retention time 0.567 min, ESI+ found [M+H]=305.0.

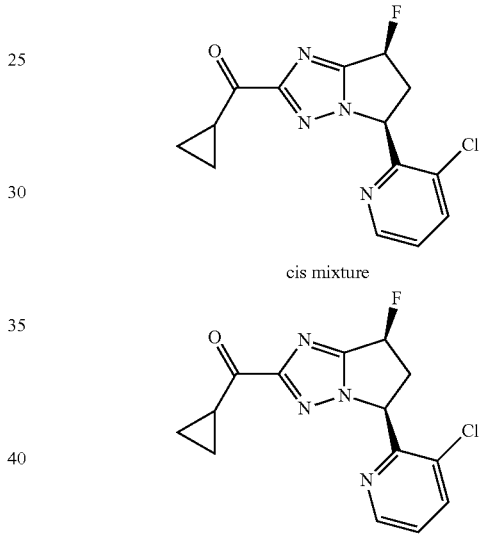

cis mixture

Step 16: cyclopropyl-[rac-(5S,7S)-5-(3-chloro-2-pyridyl)-7-fluoro-6,7-dihydro-5H-pyrrolo[1,2-b][1,2,4]triazol-2-yl]methanone and cyclopropyl-[(5S,7S)-5-(3-chloro-2-pyridyl)-7-fluoro-6,7-dihydro-5H-pyrrolo[1,2-b][1,2,4]triazol-2-yl]methanone To a mixture of rac-((5S,7R)-5-(3-chloropyridin-2-yl)-7-hydroxy-6,7-dihydro-5H-pyrrolo[1,2-b][1,2,4]triazol-2-yl)(cyclopropyl)methanone (90 mg, 0.28 mmol) in dichloromethane (2 mL) was added diethylaminosulfur trifluoride (40 mg, 0.25 mmol) at 0° C. The mixture was stirred for 1 h and then quenched by addition of water (5 mL). The resulting mixture was extracted with dichloromethane (3×5 mL). The combine organic layers were washed with brine (5 mL), dried over sodium sulfate and concentrated under reduced pressure. The residue was purified by RP-HPLC (acetonitrile 32-62/0.05% ammonia hydroxide in water) to afford cyclopropyl-[rac-(5S,7S)-5-(3-chloro-2-pyridyl)-7-fluoro-6,7-dihydro-5H-pyrrolo[1,2-b][1,2,4]triazol-2-yl]methanone (G03345456) (15.0 mg, 28.7%) as a white solid. $^1$H NMR (400 MHz, CD$_3$OD) δ 8.45 (d, J=4.8 Hz, 1H), 7.97-7.95 (m, 1H), 7.42-7.38 (m, 1H), 6.24-6.03 (m, 2H), 3.83-3.72 (m, 1H), 3.04-2.89 (m, 2H), 1.18-1.15 (m, 2H), 1.11-1.08 (m, 2H). LCMS $R_T$=0.780 min, m/z=306.9 [M+H]$^+$.

LCMS (5 to 95% acetonitrile in water+0.03% trifluoacetic acid over 1.5 mins) retention time 0.780 min, ESI+ found [M+H]=306.9.

A cis mixture was further separated by SFC to afford arbitrarily assigned: cyclopropyl-[(5S,7S)-5-(3-chloro-2-pyridyl)-7-fluoro-6,7-dihydro-5H-pyrrolo[1,2-b][1,2,4] triazol-2-yl]methanone (G03348054) (peak 1, retention time=3.920 min) (5.2 mg, 34%) as a white solid. $^1$H NMR (400 MHz, CDCl$_3$) δ 8.47 (d, J=4.8 Hz, 1H), 7.79-7.76 (m, 1H), 7.29-7.27 (m, 1H), 6.14-6.12 (m, 1H), 6.11-6.10 (m, 0.5H), 5.99-5.98 (m, 0.5H), 3.71-3.64 (m, 1H), 3.13-3.02 (m, 2H), 1.34-1.32 (m, 2H), 1.11-1.08 (m, 2H). LCMS $R_T$=0.617 min, m/z=307.0 [M+H]$^+$.

LCMS (5 to 95% acetonitrile in water+0.03% trifluoacetic acid over 1.5 mins) retention time 0.617 min, ESI+ found [M+H]=307.0.

SFC condition: Column: OJ-H (250 mm*30 mm, 5 μm); Condition: 0.1% NH$_3$H$_2$O EtOH; Begin B 35% End B 35%; Flow Rate (50 mL/min), Column temperature 40° C.

Method 96

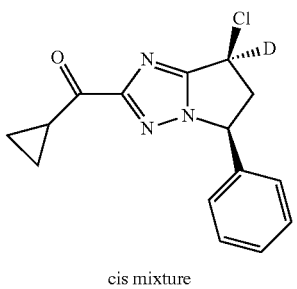

Example 119 cis mixture

Cyclopropyl-[rac-(5S,7S)-7-chloro-7-deuterio-5-phenyl-5,6-dihydropyrrolo[1,2-b][1,2,4] triazol-2-yl] methanone

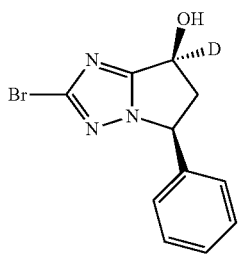

cis mixture

Step 1: Cis-2-bromo-7-deuterio-5-phenyl-5,6-dihydropyrrolo[1,2-b][1,2,4]triazol-7-ol To a solution of 2-bromo-5-phenyl-5,6-dihydropyrrolo[1,2-b][1,2,4]triazol-7-one (3.0 g, 10.79 mmol) in methanol (100 mL) was added sodium borodeuteride (1.4 g, 32.36 mmol). The mixture was stirred at 20° C. for 1 h and concentrated under reduced pressure. The residue was diluted with water (50 mL), aqueous hydrochloric acid (1.0 M, 2 mL) and extracted with ethyl acetate (3×30 mL). The combined organic layers were washed with brine (40 mL), dried over sodium sulfate and concentrated under reduced pressure to afford crude cis-2-bromo-7-deuterio-5-phenyl-5,6-dihydropyrrolo[1,2-b][1,2,4]triazol-7-ol (3.0 g, 99%) as a yellow solid. LCMS $R_T$=0.681 min, m/z=283.0 [M+H]$^+$. LCMS (5 to 95% acetonitrile in water+0.03% trifluoacetic acid over 1.5 mins) retention time 0.681 min, ESI+ found [M+H]=283.0.

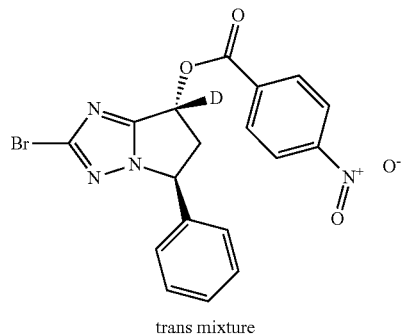

trans mixture

Step 2: [trans-2-bromo-7-deuterio-5-phenyl-5,6-dihydropyrrolo[1,2-b][1,2,4]triazol-7-yl] 4-nitrobenzoate To a mixture of 4-nitrobenzoic acid (1.0 g, 6.24 mmol), triphenylphosphine (1.9 g, 7.21 mmol) and cis-2-bromo-7-deuterio-5-phenyl-5,6-dihydropyrrolo[1,2-b][1,2,4]triazol-7-ol (1.4 g, 4.8 mmol) in tetrahydrofuran (20 mL) was added diisopropyl azodicarboxylate (1.5 g, 7.21 mmol) dropwise under nitrogen at 0° C. This mixture was stirred for 1.5 h and filtered. The solid was washed with tetrahydrofuran (10 mL) and methyl tert-butyl ether (10 mL) to give [trans-2-bromo-7-deuterio-5-phenyl-5,6-dihydropyrrolo[1,2-b][1,2,4]triazol-7-yl] 4-nitrobenzoate (800 mg, 39%) as a white solid. LCMS $R_T$=0.904 min, m/z=432.0 [M+H]$^+$. LCMS (5 to 95% acetonitrile in water+0.03% trifluoacetic acid over 1.5 mins) retention time 0.904 min, ESI+ found [M+H]=432.0.

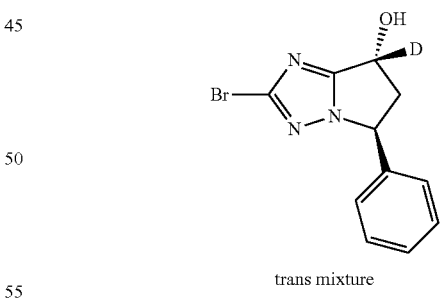

trans mixture

Step 3: Trans-2-bromo-7-deuterio-5-phenyl-5,6-dihydropyrrolo[1,2-b][1,2,4]triazol-7-ol A mixture of potassium carbonate (514 mg, 3.72 mmol) and [trans-2-bromo-7-deuterio-5-phenyl-5,6-dihydropyrrolo[1,2-b][1,2,4]triazol-7-yl] 4-nitrobenzoate (800 mg, 1.86 mmol) in methanol (10 mL)/water (5 mL) was stirred at 25° C. for 16 h and diluted with water (20 mL). The mixture was extracted with ethyl acetate (3×30 mL). The combined organic layers were washed with brine (2×20 mL), dried over sodium sulfate and concentrated under reduced pressure. The residue was purified by column chromatography (silica gel, 100-200 mesh, 0 to 35% ethyl acetate in petroleum ether) to afford trans-2-bromo-7-deuterio-5-phenyl-5,6-dihydropyrrolo[1,2-b][1,2,4]triazol-7-ol (300 mg, 57%) as a faint yellow solid. LCMS $R_T$=0.689 min, m/z=281.0 [M+H]$^+$. LCMS (5 to 95% acetonitrile in water+0.03% trifluoacetic acid over 1.5 mins) retention time 0.689 min, ESI+ found [M+H]=281.0.

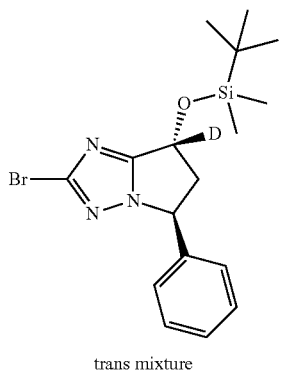 [SMILES: [2H][C@@]1(O[Si](C)(C)C(C)(C)C)C[C@@H](c2ccccc2)n2nc(Br)nc21]

trans mixture

Step 4: [trans-2-bromo-7-deuterio-5-phenyl-5,6-dihydropyrrolo[1,2-b][1,2,4]triazol-7-yl]oxy-tert-butyl-dimethyl-silane To a solution of trans-2-bromo-7-deuterio-5-phenyl-5,6-dihydropyrrolo[1,2-b][1,2,4]triazol-7-ol (300 mg, 1.07 mmol) and imidazole (145 mg, 2.13 mmol) in dichloromethane (20 mL) was added tert-butyldimethylchlorosilane (241 mg, 1.6 mmol). The mixture was stirred at 25° C. for 18 h and diluted with water (30 mL). The solution was extracted with dichloromethane (2×30 mL). The combined organic layers were washed with brine (20 mL), dried over sodium sulfate and concentrated under reduced pressure. The residue was purified by column chromatography (silica gel, 100-200 mesh, 0 to 10% ethyl acetate in petroleum ether) to afford [trans-2-bromo-7-deuterio-5-phenyl-5,6-dihydropyrrolo[1,2-b][1,2,4]triazol-7-yl]oxy-tert-butyl-dimethyl-silane 350 mg, 83%) as a yellow oil. LCMS $R_T$=0.931 min, m/z=397.1 [M+H]$^+$. LCMS (5 to 95% acetonitrile in water+0.03% trifluoacetic acid over 1.5 mins) retention time 0.931 min, ESI+ found [M+H]=397.1.

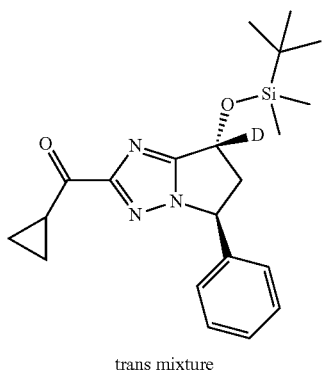 [SMILES: [2H][C@@]1(O[Si](C)(C)C(C)(C)C)C[C@@H](c2ccccc2)n2nc(C(=O)C3CC3)nc21]

trans mixture

Step 5: [trans-7-[tert-butyl(dimethyl)silyl]oxy-7-deuterio-5-phenyl-5,6-dihydropyrrolo[1,2-b][1,2,4]triazol-2-yl]-cyclopropyl-methanone To a solution of N-methoxy-N-methyl-cyclopropanecarboxamide (457 mg, 3.54 mmol) and [trans-2-bromo-7-deuterio-5-phenyl-5,6-dihydropyrrolo[1,2-b][1,2,4]triazol-7-yl]oxy-tert-butyl-dimethyl-silane (350 mg, 0.89 mmol) in tetrahydrofuran (20 mL) was added isopropylmagnesium chloride (2.0 M in tetrahydrofuran, 1.33 mL, 2.66 mmol) at 0° C. under nitrogen atmosphere. The mixture was stirred at 0° C. for 1 h and quenched by addition of saturated aqueous ammonium chloride (20 mL). The resulting mixture was extracted with ethyl acetate (3×30 mL). The combined organic layers were dried over sodium sulfate and concentrated under reduced pressure. The residue was purified by column chromatography (silica gel, 100-200 mesh, 0 to 30% ethyl acetate in petroleum ether) to give [trans-7-[tert-butyl (dimethyl)silyl]oxy-7-deuterio-5-phenyl-5,6-dihydropyrrolo[1,2-b][1,2,4]triazol-2-yl]-cyclopropyl-methanone (200 mg, 59%) as a yellow oil. LCMS $R_T$=0.935 min, m/z=385.3 [M+H]$^+$. LCMS (5 to 95% acetonitrile in water+0.03% trifluoacetic acid over 1.5 mins) retention time 0.935 min, ESI+ found [M+H]=385.3.

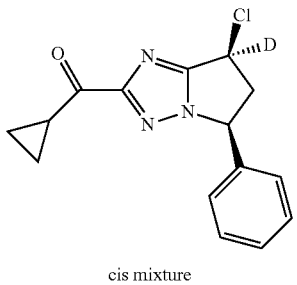 [SMILES: [2H][C@]1(Cl)C[C@@H](c2ccccc2)n2nc(C(=O)C3CC3)nc21]

cis mixture

Step 6: Cyclopropyl-[rac-(5S,7S)-7-chloro-7-deuterio-5-phenyl-5,6-dihydropyrrolo[1,2-b][1,2,4]triazol-2-yl]methanone To a mixture of [trans-7-[tert-butyl(dimethyl)silyl]oxy-7-deuterio-5-phenyl-5,6-dihydropyrrolo[1,2-b][1,2,4]triazol-2-yl]-cyclopropyl-methanone (200 mg, 0.52 mmol) in dichloromethane (3 mL) was added thionyl chloride (0.19 mL, 2.6 mmol) and 2 drops of dimethyl formamide. The mixture was stirred at 25° C. for 16 h and concentrated under reduced pressure. The residue was diluted with water (30 mL) and extracted with ethyl acetate (3×30 mL). The combined organic layers were washed with brine (30 mL), dried over sodium sulfate and concentrated under reduced pressure. The residue was purified first by column chromatography (silica gel, 100-200 mesh, 0 to 30% ethyl acetate in petroleum ether), then by RP-HPLC (acetonitrile 54-84/ 0.05% ammonia hydroxide in water) to afford cyclopropyl-[rac-(5S,7S)-7-chloro-7-deuterio-5-phenyl-5,6-dihydropyrrolo[1,2-b][1,2,4]triazol-2-yl]methanone (35.0 mg, 23%) as a yellow solid. $^1$H NMR (400 MHz, CD$_3$OD) δ 7.46-7.38 (m, 3H), 7.33-7.31 (m, 2H), 5.69-5.65 (m, 1H), 4.02-3.96 (m, 1H), 3.07-2.99 (m, 1H), 2.91-2.86 (m, 1H), 1.21-1.16 (m, 2H), 1.13-1.09 (m, 2H). LCMS $R_T$=1.033 min, m/z=289.1 [M+H]$^+$. LCMS (10 to 80% acetonitrile in water+0.03% trifluoacetic acid over 2.0 mins) retention time 1.033 min, ESI+ found [M+H]=289.1.

Method 97

Example 120

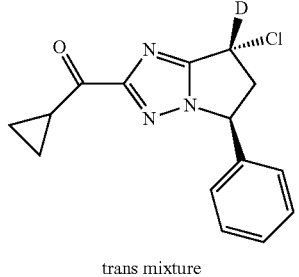

trans mixture

Cyclopropyl-[rac-(5S,7R)-7-chloro-7-deuterio-5-phenyl-5,6-dihydropyrrolo[1,2-b][1,2,4]triazol-2-yl]methanone

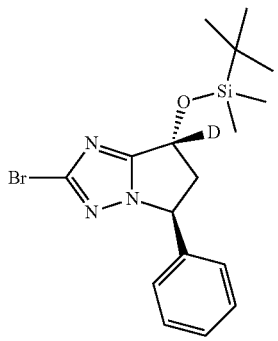

trans mixture

Step 1: [cis-2-bromo-7-deuterio-5-phenyl-5,6-dihydropyrrolo[1,2-b][1,2,4]triazol-7-yl]oxy-tert-butyl-dimethyl-silane To a solution of cis-2-bromo-7-deuterio-5-phenyl-5,6-dihydropyrrolo[1,2-b][1,2,4]triazol-7-ol (1.5 g, 5.34 mmol) and imidazole (726 mg, 10.67 mmol) in dichloromethane (50 mL) was added tert-butyldimethylchlorosilane (1.2 g, 8.00 mmol). The mixture was stirred at 15° C. for 16 h and diluted with water (20 mL). The resulting mixture was extracted with dichloromethane (2×30 mL). The combined organic layers were washed with brine (20 mL), dried over sodium sulfate and concentrated under reduced pressure. The residue was purified by column chromatography (silica gel, 100-200 mesh, 0 to 10% ethyl acetate in petroleum ether) to afford [cis-2-bromo-7-deuterio-5-phenyl-5,6-dihydropyrrolo[1,2-b][1,2,4]triazol-7-yl]oxy-tert-butyl-dimethyl-silane (1.8 g, 85%) as a colorless oil. LCMS $R_T$=1.029 min, m/z=395.1 [M+H]$^+$. LCMS (5 to 95% acetonitrile in water+0.03% trifluoacetic acid over 1.5 mins) retention time 1.029 min, ESI+ found [M+H]=395.1.

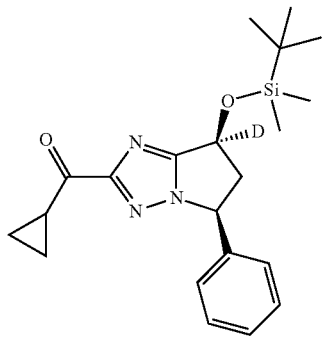

cis mixture

Step 2: [cis-7-[tert-butyl(dimethyl)silyl]oxy-7-deuterio-5-phenyl-5,6-dihydropyrrolo[1,2-b][1,2,4]triazol-2-yl]-cyclopropyl-methanone To a solution of N-methoxy-N-methyl-cyclopropanecarboxamide (1.2 g, 9.10 mmol) and [cis-2-bromo-7-deuterio-5-phenyl-5,6-dihydropyrrolo[1,2-b][1,2,4]triazol-7-yl]oxy-tert-butyl-dimethyl-silane (1.8 g, 4.55 mmol) in tetrahydrofuran (40 mL) was added isopropylmagnesium chloride (2.0 M in tetrahydrofuran, 6.83 mL, 13.66 mmol) dropwise at 0° C. The mixture was stirred at 0° C. for 1.5 h and quenched by addition of saturated aqueous ammonium chloride (50 mL). The mixture was extracted with ethyl acetate (3×50 mL). The combined organic layers were dried over sodium sulfate and concentrated under reduced pressure. The residue was purified by column chromatography (silica gel, 100-200 mesh, 0 to 20% ethyl acetate in petroleum ether) to give [cis-7-[tert-butyl(dimethyl)silyl]oxy-7-deuterio-5-phenyl-5,6-dihydropyrrolo[1,2-b][1,2,4] triazol-2-yl]-cyclopropyl-methanone (450 mg, 26%) as a colorless oil. LCMS $R_T$=1.030 min, m/z=384.2 [M+H]$^+$. LCMS (5 to 95% acetonitrile in water+0.03% trifluoacetic acid over 1.5 mins) retention time 1.030 min, ESI+ found [M+H]=384.2.

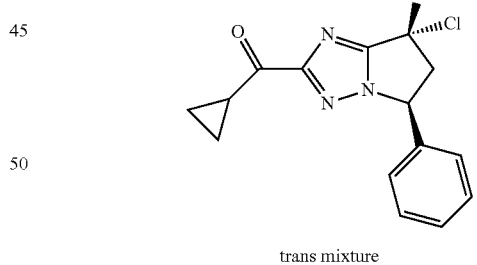

trans mixture

Step 3: Cyclopropyl-[rac-(5S,7R)-7-chloro-7-deuterio-5-phenyl-5,6-dihydropyrrolo[1,2-b][1,2,4]triazol-2-yl]methanone A mixture of [cis-7-[tert-butyl(dimethyl)silyl]oxy-7-deuterio-5-phenyl-5,6-dihydropyrrolo[1,2-b][1,2,4]triazol-2-yl]-cyclopropyl-methanone (450 mg, 1.17 mmol) in dichloromethane (4 mL) was added thionyl chloride (1.47 mL, 20.23 mmol). The mixture was stirred at 25° C. for 25 h and concentrated under reduced pressure. The residue was diluted with water (50 mL) and extracted with ethyl acetate (3×30 mL). The combined organic layers were washed with brine (40 mL), dried over sodium sulfate and concentrated under reduced pressure. The residue was purified first by column chromatography on silica (solvent gradient: 0-30% ethyl acetate in petroleum ether), then by RP-HPLC (acetonitrile 40-70/0.05% ammonia hydroxide in water) to afford arbitrarily assigned cyclopropyl-[rac-(5S,7R)-7-chloro-7-deuterio-5-phenyl-5,6-dihydropyrrolo[1,2-b][1,2,4]triazol-2-yl]methanone (110 mg, 32.2% yield) as a white solid. $^1$H NMR (400 MHz, CD$_3$OD) δ 7.74-7.69 (m, 3H), 7.63-7.61 (m, 2H), 6.14 (t, J=6.8 Hz, 1H), 3.73-3.62 (m, 2H), 3.61-3.59 (m, 1H), 1.48-1.45 (m, 2H), 1.40-1.37 (m, 2H). LCMS R$_T$=1.033 min, m/z=289.2 [M+H]$^+$. LCMS (10 to 80% acetonitrile in water+0.03% trifluoacetic acid over 2.0 mins) retention time 1.033 min, ESI+ found [M+H]=289.2.

Method 98

Example 122

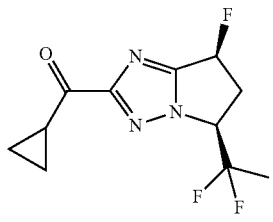

cis mixture

Cyclopropyl-[rac-(5S,7S)-5-(1,1-difluoroethyl)-7-fluoro-6,7-dihydro-5H-pyrrolo[1,2-b][1,2,4]triazol-2-yl]methanone

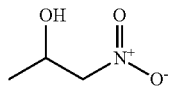

Step 1: 1-nitropropan-2-ol

To a cooled (0° C.) solution of acetaldehyde (45.9 mL, 819.13 mmol) and nitromethane (44.4 mL, 819.13 mmol) in sodium hydroxide (32.8 g, 819.13 mmol) in water (1000 mL) was added hexadecyltrimethylammonium chloride (26.2 g, 81.91 mmol). The reaction mixture was stirred at 15° C. for 16 h and adjusted to pH=7 by addition of acetic acid. The mixture was extracted with ethyl acetate (2×500 mL). The combined organic layers were wash with brine, dried over sodium sulfate and concentrated under reduced pressure to give crude 1-nitropropan-2-ol (61.0 g, 71%) as a light brown oil.

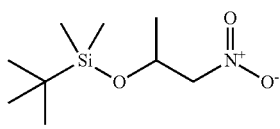

Step 2: Tert-butyl-dimethyl-(1-methyl-2-nitro-ethoxy)silane

To a mixture of imidazole (83.0 g, 1219 mmol) and 1-nitropropan-2-ol (61.0 g, 580.45 mmol) in dichloromethane (1.00 L) was added tert-butyldimethylchlorosilane (104.9 g, 696.55 mmol) at 0° C. The mixture was stirred at 20° C. for 16 h and diluted with water (200 mL). The solution was extracted with dichloromethane (2×200 mL). The combined organic layers were washed with brine (200 mL), dried over sodium sulfate and concentrated under reduced pressure. The residue was purified by column chromatography (silica gel, 100-200 mesh, 0 to 10% ethyl acetate in petroleum ether) to give tert-butyl-dimethyl-(1-methyl-2-nitro-ethoxy)silane (115.0 g, 90%) as a light yellow oil. $^1$H NMR (400 MHz, CDCl$_3$) δ 4.53-4.68 (m, 1H), 4.24-4.53 (m, 2H), 1.25-1.32 (m, 3H), 0.87-0.90 (m, 9H), 0.07-0.12 (m, 6H).

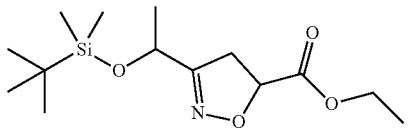 [SMILES: CCOC(=O)C1CC(C(C)O[Si](C)(C)C(C)(C)C)=NO1]

Step 3: Ethyl 3-[1-[tert-butyl(dimethyl)silyl]oxyethyl]-4,5-dihydroisoxazole-5-carboxylate To a mixture of ethyl acrylate (242.6 mL, 2279.5 mmol), di-tert-butyldicarbonate (157.1 mL, 683.84 mmol) and 4-dimethylaminopyridine (5.6 g, 45.59 mmol) in acetonitrile (1 L) was added tert-butyl-dimethyl-(1-methyl-2-nitro-ethoxy)silane (100.0 g, 455.89 mmol) at 20° C. The mixture was stirred at 20° C. for 16 h and concentrated under reduced pressure. The residue was purified by column chromatography (silica gel, 100-200 mesh, 0 to 10% ethyl acetate in petroleum ether) to afford ethyl 3-[1-[tert-butyl(dimethyl)silyl]oxyethyl]-4,5-dihydroisoxazole-5-carboxylate (40.0 g, 29%) as brown oil. $^1$H NMR (400 MHz, CDCl$_3$) δ 4.89-5.07 (m, 1H), 4.66-4.84 (m, 1H), 4.16-4.33 (m, 2H), 3.21-3.41 (m, 2H), 1.32-1.37 (m, 3H), 1.26-1.30 (m, 3H), 0.86-0.87 (m, 9H), 0.03-0.10 (m, 6H).

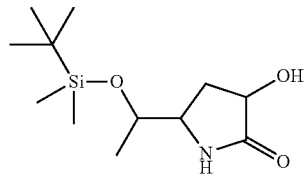 [SMILES: CC(O[Si](C)(C)C(C)(C)C)C1CC(O)C(=O)N1]

Step 4: 5-[1-[tert-butyl(dimethyl)silyl]oxyethyl]-3-hydroxy-pyrrolidin-2-one

A mixture of ethyl 3-[1-[tert-butyl(dimethyl)silyl]oxyethyl]-4,5-dihydroisoxazole-5-carboxylate (40.0 g, 132.69 mmoL) and palladium (10% on carbon, 7.06 g) in ethanol (1.0 L) was hydrogenated (50 psi) at 40° C. for 48 h and filtered. The filtrate was concentrated under reduced pressure to give crude 5-[1-[tert-butyl(dimethyl)silyl]oxyethyl]-3-hydroxy-pyrrolidin-2-one (37.0 g, 92%) as a white solid.

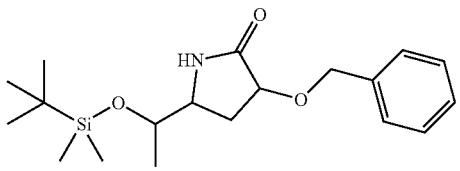 [SMILES: CC(O[Si](C)(C)C(C)(C)C)C1CC(OCc2ccccc2)C(=O)N1]

Step 5: 3-benzyloxy-5-[1-[tert-butyl(dimethyl)silyl]oxyethyl]pyrrolidin-2-one To a solution of 5-[1-[tert-butyl(dimethyl)silyl]oxyethyl]-3-hydroxy-pyrrolidin-2-one (31.2 g, 120.27 mmol) in dichloromethane (500 mL) was added tetrabutylammonium bromide (1.94 g, 6.01 mmol), sodium hydroxide (30% in water, 80.2 g, 601.34 mmol,) and benzyl bromide (30.9 g, 180.4 mmol). The mixture was stirred at 40° C. for 18 h and cooled to 25° C. The separated organic layer was dried over sodium sulfate and concentrated under reduced pressure. The residue was purified by column chromatography (silica gel, 100-200 mesh, 0 to 80% ethyl acetate in petroleum ether) to afford 3-benzyloxy-5-[1-[tert-butyl(dimethyl) silyl]oxyethyl]pyrrolidin-2-one (22.0 g, 52%) as colorless oil. LC-MS $R_T$=0.957 min, m/z=350.2 [M+H]$^+$. LCMS (5 to 95% acetonitrile in water+0.03% trifluoacetic acid over 1.5 mins) retention time 0.957 min, ESI+ found [M+H]=350.2.

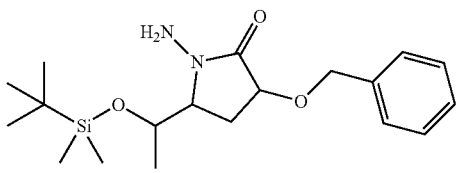 [SMILES: CC(O[Si](C)(C)C(C)(C)C)C1CC(OCc2ccccc2)C(=O)N1N]

Step 6: 1-amino-3-benzyloxy-5-[1-[tert-butyl(dimethyl)silyl]oxyethyl]pyrrolidin-2-one To the solution of 3-benzyloxy-5-[1-[tert-butyl(dimethyl) silyl]oxyethyl]pyrrolidin-2-one (22.0 g, 62.94 mmol) in N,N-dimethylformamide (400 mL) was added sodium hydride (60% in mineral oil, 3.78 g, 94.41 mmol) at 0° C. After stirred at 20° C. for 30 min, t o-(diphenylphosphoryl) hydroxylamine (19.1 g, 81.82 mmol) was added. The mixture was stirred at 20° C. for 18 h and filtered. The filtrate was concentrated under reduced pressure to afford crude 1-amino-3-benzyloxy-5-[1-[tert-butyl(dimethyl) silyl]oxyethyl]pyrrolidin-2-one (22.9 g, 99%) a s brown oil.

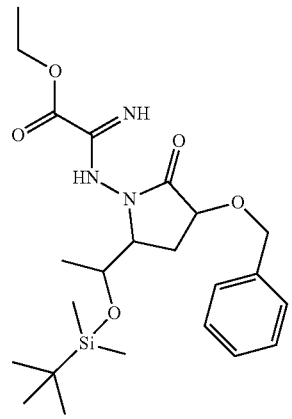 [SMILES: CCOC(=O)C(=N)NN1C(=O)C(OCc2ccccc2)CC1C(C)O[Si](C)(C)C(C)(C)C]

Step 7: Ethyl 2-((3-(benzyloxy)-5-(1-((tert-butyldimethylsilyl)oxy)ethyl)-2-oxopyrrolidin-1-yl)amino)-2-iminoacetate A mixture of 1-amino-3-benzyloxy-5-[1-[tert-butyl(dimethyl)silyl]oxyethyl] pyrrolidin-2-one (22.0 g, 60.4 mmol) and ethyl 2-ethoxy-2-imino-acetate (20.3 mL, 150.9 mmol) in ethanol (220 mL) was stirred at 90° C. for 33 h and concentrated under reduced pressure to afford crude ethyl 2-((3-(benzyloxy)-5-(1-((tert-butyldimethylsilyl)oxy)ethyl)-2-oxopyrrolidin-1-yl)amino)-2-iminoacetate (27.9 g, 99%) as a yellow oil. LC-MS $R_T$=0.840 min, m/z=365.3 [M+15]+. LCMS (5 to 95% acetonitrile in water+0.03% trifluoacetic acid over 1.5 mins) retention time 0.840 min, ESI+ found [M+15]=365.3.

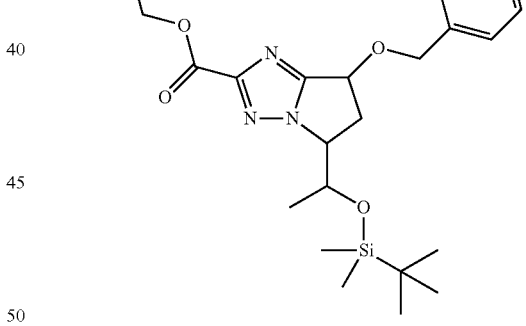

Step 8: Ethyl 7-benzyloxy-5-[1-[tert-butyl(dimethyl)silyl]oxyethyl]-6,7-dihydro-5H-pyrrolo[1,2-b][1,2,4]triazole-2-carboxylate To a solution of ethyl 2-[[3-benzyloxy-5-[1-[tert-butyl (dimethyl)silyl]oxyethyl]-2-oxo-pyrrolidin-1-yl]amino]-2-imino-acetate (27.0 g, 58.2 mmol) in toluene (500 mL) was added p-toluenesulfonic acid monohydrate (13.3 g, 69.9 mmol). The reaction mixture was stirred at 130° C. for 16 h and filtered. The filtrate was concentrated under reduced pressure. The residue was purified by column chromatography (silica gel, 100-200 mesh, 0 to 50% ethyl acetate in petroleum ether) to afford ethyl 7-benzyloxy-5-[1-[tert-butyl (dimethyl)silyl]oxyethyl]-6,7-dihydro-5H-pyrrolo[1,2-b][1,2,4]triazole-2-carboxylate (11.2 g, 43%) as a yellow oil.

LC-MS $R_T$=1.029 min, m/z=446.3 [M+H]⁺. LCMS (5 to 95% acetonitrile in water+0.03% trifluoacetic acid over 1.5 mins) retention time 1.029 min, ESI+ found [M+H]=446.3.

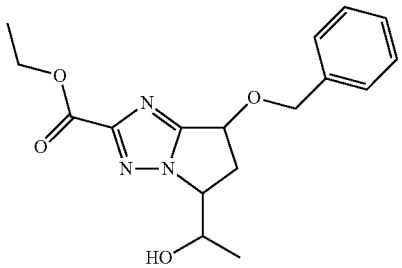 [SMILES: CCOC(=O)c1nc2n(n1)C(C(C)O)CC2OCc1ccccc1]

Step 9: Ethyl 7-benzyloxy-5-(1-hydroxyethyl)-6,7-dihydro-5H-pyrrolo[1,2-b][1,2,4] triazole-2-carboxylate To a solution of ethyl 7-benzyloxy-5-[1-[tert-butyl(dimethyl)silyl]oxyethyl]-6,7-dihydro-5H-pyrrolo[1,2-b][1,2,4]triazole-2-carboxylate (5.1 g, 11.44 mmol) in tetrahydrofuran (100 mL) was added tetrabutylammonium fluoride (1.0 M in tetrahydrofuran, 34.33 mL, 34.33 mmol). The mixture was stirred at 25° C. for 18 h and diluted with water (50 mL). The resulting mixture was extracted with ethyl acetate (2×50 mL). The combined organic layers were washed with aqueous hydrochloric acid (1 N, 15 mL) and brine (50 mL), dried over sodium sulfate and concentrated under reduced pressure to afford crude ethyl 7-benzyloxy-5-(1-hydroxyethyl)-6,7-dihydro-5H-pyrrolo[1,2-b][1,2,4]triazole-2-carboxylate (3.8 g, 100%) as brown oil.

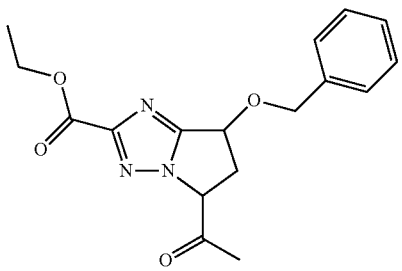 [SMILES: CCOC(=O)c1nc2n(n1)C(C(C)=O)CC2OCc1ccccc1]

Step 10: Ethyl 5-acetyl-7-benzyloxy-6,7-dihydro-5H-pyrrolo[1,2-b][1,2,4]triazole-2-carboxylate To a cooled (0° C.) solution of ethyl 7-benzyloxy-5-(1-hydroxyethyl)-6,7-dihydro-5H-pyrrolo[1,2-b][1,2,4]triazole-2-carboxylate (3.8 g, 11.44 mmol) in dichloromethane (25 mL) was added sodium bicarbonate (3.8 g, 45.75 mmol) and Dess-Martin periodinane (9.7 g, 22.87 mmol). The mixture was stirred at 0° C. for 2 h and filtered. The filtrate was diluted with water (20 mL) and extracted with dichloromethane (3×20 mL). The combined organic layers were dried over sodium sulfate and concentrated under reduced pressure. The residue was purified by preparative TLC (50% ethyl acetate in petroluem ether, $R_f$=0.5) to afford ethyl 5-acetyl-7-benzyloxy-6,7-dihydro-5H-pyrrolo[1,2-b][1,2,4] triazole-2-carboxylate (1.5 g, 40%) as light brown oil. LC-MS $R_T$=0.655 min, m/z=330.2 [M+H]⁺. LCMS (5 to 95% acetonitrile in water+0.03% trifluoacetic acid over 1.5 mins) retention time 0.655 min, ESI+ found [M+H]=330.2.

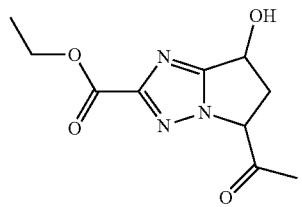 [SMILES: CCOC(=O)c1nc2n(n1)C(C(C)=O)CC2O]

Step 11: Ethyl 5-acetyl-7-hydroxy-6,7-dihydro-5H-pyrrolo[1,2-b][1,2,4]triazole-2-carboxylate A mixture of ethyl 5-acetyl-7-benzyloxy-6,7-dihydro-5H-pyrrolo[1,2-b][1,2,4] triazole-2-carboxylate (1.5 g, 4.6 mmol) in 2,2,2-trifluoroacetic acid (3 mL) was heated at 120° C. for 3 h and concentrated under reduced pressure. The residue was purified by preparative TLC (5% methanol and 45% ethyl acetate in petroleum ether, $R_f$=0.2) to afford ethyl 5-acetyl-7-hydroxy-6,7-dihydro-5H-pyrrolo[1,2-b][1,2,4]triazole-2-carboxylate (350 mg, 32%) as light brown oil. LC-MS $R_T$=0.278 min, m/z=240.2 [M+H]⁺. LCMS (5 to 95% acetonitrile in water+0.03% trifluoacetic acid over 1.5 mins) retention time 0.278 min, ESI+ found [M+H]=240.2.

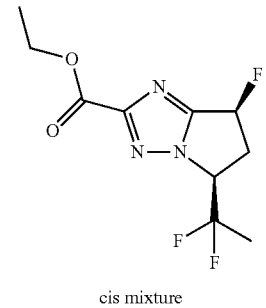 [SMILES: CCOC(=O)c1nc2n(n1)[C@H](C(C)(F)F)C[C@@H]2F]

cis mixture

Step 12: Ethyl Cis-5-(1,1-difluoroethyl)-7-fluoro-6,7-dihydro-5H-pyrrolo [1,2-b][1,2,4] triazole-2-carboxylate A mixture of ethyl 5-acetyl-7-hydroxy-6,7-dihydro-5H-pyrrolo[1,2-b] [1,2,4]triazole-2-carboxylate (350 mg, 1.46 mmol) and diethylaminosulfur trifluoride (5.0 mL, 1.46 mmol) in dichloromethane (10 mL) was stirred at 10° C. for 2 h and quenched by addition of ice cooled saturated aqueous sodium bicarbonate (20 mL). The mixture was extracted with dichloromethane (3×10 mL). The combined organic layers were washed with brine (20 mL), dried over sodium sulfate and concentrated under reduced pressure. The residue was purified by preparative TLC (50% ethyl acetate in petroleum ether, $R_f$=0.4) to afford ethyl cis-5-(1,1-difluoroethyl)-7-fluoro-6,7-dihydro-5H-pyrrolo[1,2-b][1,2,4]triazole-2-carboxylate (37 mg, 10%) as a colorless oil. LC-MS $R_T$=0.694 min, m/z=264.1 [M+H]⁺. LCMS (5 to 95% acetonitrile in water+0.03% trifluoacetic acid over 1.5 mins) retention time 0.694 min, ESI+ found [M+H]=264.1.

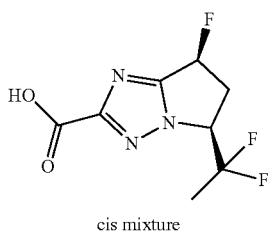 [SMILES: CC(F)(F)[C@@H]1C[C@H](F)c2nc(C(=O)O)nn21]

cis mixture

Step 13: Cis-5-(1,1-difluoroethyl)-7-fluoro-6,7-dihydro-5H-pyrrolo [1,2-b][1,2,4]triazole-2-carboxylic Acid A mixture of ethyl cis-5-(1,1-difluoroethyl)-7-fluoro-6,7-dihydro-5H-pyrrolo [1,2-b][1,2,4]triazole-2-carboxylate (27 mg, 0.10 mmol), lithium hydroxide monohydrate (22 mg, 0.51 mmol) in methanol (0.7 mL)/water (0.7 mL)/tetrahydrofuran (0.7 mL) was stirred at 10° C. for 2 h and concentrated under reduce pressure. The residue was diluted with ice water (2 mL) and adjusted to pH=4 by addition of aqueous hydrochloric acid (1 M). The mixture was concentrated to dryness under reduce pressure to afford crude cis-5-(1,1-difluoroethyl)-7-fluoro-6,7-dihydro-5H-pyrrolo [1,2-b][1,2,4]triazole-2-carboxylic acid with lithium chloride salt (28 mg, 98%).

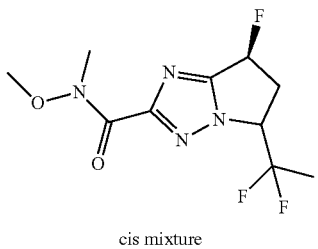 [SMILES: CON(C)C(=O)c1nc2n(n1)C(C(C)(F)F)C[C@@H]2F]

cis mixture

Step 14: Cis-5-(1,1-difluoroethyl)-7-fluoro-N-methoxy-N-methyl-6,7-dihydro-5H-pyrrolo [1,2-b][1,2,4]triazole-2-carboxamide A mixture of cis-5-(1,1-difluoroethyl)-7-fluoro-6,7-dihydro-5H-pyrrolo [1,2-b][1,2,4]triazole-2-carboxylic acid (28 mg, 0.12 mmol), N,O-dimethylhydroxylamine hydrochloride (23 mg, 0.24 mmol), 1-[Bis(dimethylamino)methylene]-1H-1,2,3-triazolo[4,5-b]pyridinium 3-oxide hexafluorophosphate (48 mg, 0.13 mmol) and N,N-diisopropylethylamine (62 mg, 0.48 mmol) in N,N-dimethylformamide (2 mL) was stirred at 20° C. for 3 h and concentrated under reduced pressure. The residue was purified by preparative TLC (70% ethyl acetate in petroleum ether, $R_f$=0.3) to afford give cis-5-(1,1-difluoroethyl)-7-fluoro-N-methoxy-N-methyl-6,7-dihydro-5H-pyrrolo[1,2-b][1,2,4]triazole-2-carboxamide (15 mg, 45%) as a white solid. $^1$H NMR (400 MHz, CDCl$_3$) δ 6.05-5.73 (m, 1H), 4.62 (br s, 1H), 3.86-3.82 (m, 3H), 3.54-3.21 (m, 5H), 3.14-2.99 (m, 1H), 1.96-1.75 (m, 3H).

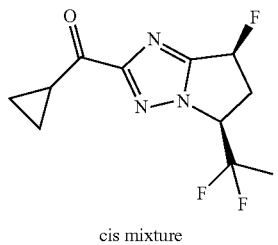 [SMILES: CC(F)(F)[C@@H]1C[C@H](F)c2nc(C(=O)C3CC3)nn21]

cis mixture

Step 15: Cyclopropyl-[rac-(5S,7S)-5-(1,1-difluoroethyl)-7-fluoro-6,7-dihydro-5H-pyrrolo[1,2-b][1,2,4]triazol-2-yl]methanone To a cooled (0° C.) solution of cis-5-(1,1-difluoroethyl)-7-fluoro-N-methoxy-N-methyl-6,7-dihydro-5H-pyrrolo[1,2-b][1,2,4]triazole-2-carboxamide (10 mg, 0.04 mmol) in tetrahydrofuran (1 mL) was added with cyclopropylmagnesium bromide (0.5 M in tetrahydrofuran, 0.5 mL, 0.25 mmol) dropwise under nitrogen atmosphere. After stirred at 0° C. for 1 h, the mixture was quenched by addition of saturated aqueous ammonium chloride (0.5 mL) and concentrated under reduced pressure. The residue was re-dissolved in dichloromethane (50 mL), filtered to remove solid, the filtrate was concentrated under reduce pressure. The residue was purified by RP-HPLC (acetonitrile 36-66%/0.05% ammonia hydroxide in water) to afford cyclopropyl-[rac-(5S,7S)-5-(1,1-difluoroethyl)-7-fluoro-6,7-dihydro-5H-pyrrolo[1,2-b][1,2,4]triazol-2-yl] methanone (2.2 mg, 23%) as a white solid. $^1$H NMR (400 MHz, CDCl$_3$) δ 6.00-5.84 (m, 1H), 4.75-4.55 (m, 1H), 3.38-3.29 (m, 1H), 3.18-2.99 (m, 2H), 1.86 (t, J=19.2 Hz, 3H), 1.36-1.33 (m, 2H), 1.16-1.12 (m, 2H). LC-MS $R_T$=0.828 min, m/z=259.9 [M+H]$^+$. LCMS (5 to 95% acetonitrile in water+0.03% trifluoacetic acid over 1.5 mins) retention time 0.828 min, ESI+ found [M+H]=259.9.

Method 99

Example 124

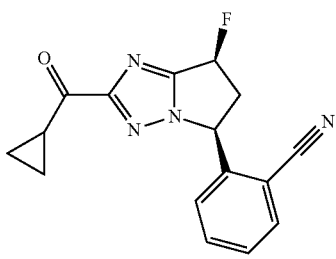

2-[(5S,7S)-2-(cyclopropanecarbonyl)-7-fluoro-6,7-dihydro-5H-pyrrolo[1,2-b][1,2,4]triazol-5-yl]benzonitrile A mixture of [(5S,7S)-5-(2-chlorophenyl)-7-fluoro-6,7-dihydro-5H-pyrrolo[1,2-b][1,2,4]triazol-2-yl]-cyclopropylmethanone (40 mg, 0.13 mmol), potassium hexacyanoferrate(II) trihydrate (28 mg, 0.07 mmol), potassium acetate (2 mg, 0.02 mmol), t-BuXPhos Phos palladium(II) biphenyl-2-amine mesylate (10 mg, 0.01 mmol) and 2-di-tert-butylphosphino-2',4',6'-triisopropylbiphenyl (6 mg, 0.01 mmol) in water (5 mL) and 1,4-dioxane (5 mL) was stirred at 100° C. for 6 h under nitrogen atmosphere. The reaction mixture was filtered and the filtrate was concentrated under reduced pressure. The residue was purified by RP-HPLC (40-70/0.04% $NH_3H_2O+10$ mM $NH_4HCO_3$ in water) to afford 2-[(5S,7S)-2-(cyclopropanecarbonyl)-7-fluoro-6,7-dihydro-5H-pyrrolo[1,2-b][1,2,4]triazol-5-yl]benzonitrile (6.1 mg, 16%) as a white solid. $^1$H NMR (400 MHz, $CDCl_3$) δ 7.79-7.76 (m, 1H), 7.64-7.60 (m, 1H), 7.53-7.50 (m, 1H), 7.01 (d, J=8.0 Hz, 1H), 6.15-6.12 (m, 0.5H), 6.00-5.98 (m, 1.5H), 3.90-3.74 (m, 1H), 3.10-3.06 (m, 1H), 2.99-2.85 (m, 1H), 1.39-1.33 (m, 2H), 1.17-1.09 (m, 2H). LC-MS $R_T$=0.915 min, m/z=397.2 [M+H]$^+$.

LCMS (10 to 80% acetonitrile in water+0.03% ammonium bicarbonate over 3.0 mins) retention time 0.915 min, ESI+ found [M+H]=397.2.

Method 100

Example 125

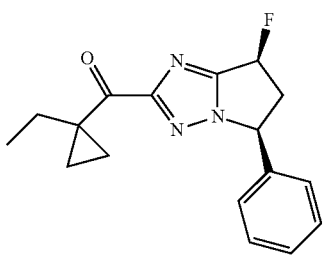

(1-ethylcyclopropyl)((5S,7S)-7-fluoro-5-phenyl-6,7-dihydro-5H-pyrrolo[1,2-b][1,2,4]triazol-2-yl)methanone

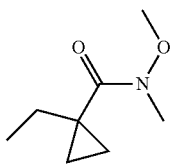

Step 1: 1-ethyl-N-methoxy-N-methylcyclopropane-1-carboxamide

Prepared from 1-ethylcyclopropanecarboxylic acid using Method 5. The crude reaction mixture was purified by flash column chromatography (silica gel, 0-100% isopropyl acetate/heptane) to afford 1-ethyl-N-methoxy-N-methylcyclopropane-1-carboxamide (435 mg, 63% yield). $^1$H NMR (400 MHz, Chloroform-d) δ 3.71 (s, 3H), 3.24 (s, 3H), 1.60 (q, J=7.4 Hz, 2H), 0.97 (d, J=2.0 Hz, 2H), 0.96 (t, J=7.4 Hz, 3H), 0.59-0.52 (m, 2H). LCMS $R_T$=0.92 min, m/z=157.9 [M+H]$^+$. LCMS (5 to 100% acetonitrile in water+0.1% formic acid over 1.6 min) retention time 0.92 min, ESI+ found [M+H]=157.9.

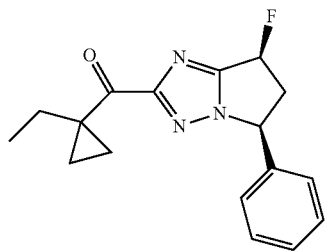 [SMILES: CCC1(C(=O)c2nc3n(n2)[C@H](c2ccccc2)C[C@@H]3F)CC1]

Step 2: (1-ethylcyclopropyl)((5S,7S)-7-fluoro-5-phenyl-6,7-dihydro-5H-pyrrolo[1,2-b][1,2,4]triazol-2-yl)methanone Prepared from 1-ethyl-N-methoxy-N-methylcyclopropane-1-carboxamide using Method 2. The crude reaction mixture was purified by RP-HPLC (30-70% acetonitrile/0.1% formic acid in water, 10 min) to afford (1-ethylcyclopropyl)((5S,7S)-7-fluoro-5-phenyl-6,7-dihydro-5H-pyrrolo[1,2-b][1,2,4]triazol-2-yl)methanone (134 mg, 72% yield). $^1$H NMR (400 MHz, DMSO-$d_6$) δ 7.46-7.34 (m, 3H), 7.25-7.19 (m, 2H), 6.20 (ddd, J=56.5, 7.1, 1.9 Hz, 1H), 5.69 (ddd, J=8.5, 6.6, 3.0 Hz, 1H), 3.72 (dddd, J=26.1, 15.4, 8.5, 7.1 Hz, 1H), 2.68 (dddd, J=26.6, 15.3, 3.1, 1.9 Hz, 1H), 1.73 (qd, J=7.2, 1.7 Hz, 2H), 1.58 (dq, J=4.4, 1.7, 1.2 Hz, 2H), 0.93 (q, J=3.2, 2.6 Hz, 2H), 0.86 (t, J=7.3 Hz, 3H). LCMS $R_T$=5.29 min, m/z=300.1 [M+H]$^+$. LCMS (2 to 98% acetonitrile in water+0.1% formic acid over 7 min) retention time 5.29 min, ESI+ found [M+H]=300.1.

Method 101

Example 126

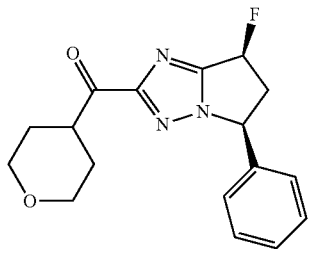

((5S,7S)-7-fluoro-5-phenyl-6,7-dihydro-5H-pyrrolo[1,2-b][1,2,4]triazol-2-yl)(tetrahydro-2H-pyran-4-yl)methanone

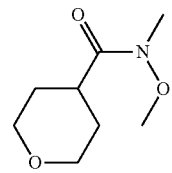

Step 1: N-methoxy-N-methyltetrahydro-2H-pyran-4-carboxamide

Prepared from tetrahydropyran-4-carboxylic acid using Method 5. The crude reaction mixture was purified by flash column chromatography (silica gel, 0-100% isopropyl acetate/heptane) to afford N-methoxy-N-methyltetrahydro-2H-pyran-4-carboxamide (721 mg, quantitative yield). ¹H NMR (400 MHz, Chloroform-d) δ 4.08-3.95 (m, 2H), 3.71 (s, 3H), 3.46 (td, J=11.8, 2.3 Hz, 2H), 3.18 (s, 3H), 2.91 (tt, J=11.4, 3.8 Hz, 1H), 1.94-1.78 (m, 2H), 1.73-1.59 (m, 2H). LCMS $R_T$=0.70 min, m/z=173.9 [M+H]⁺. LCMS (5 to 100% acetonitrile in water+0.1% formic acid over 1.6 min) retention time 0.70 min, ESI+ found [M+H]=173.9.

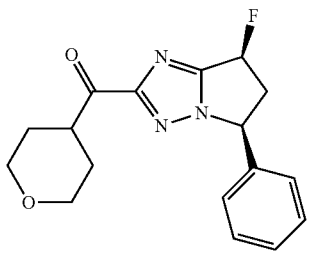 [SMILES: O=C(c1nc2n(n1)[C@H](c1ccccc1)C[C@@H]2F)C1CCOCC1]

Step 2: ((5S,7S)-7-fluoro-5-phenyl-6,7-dihydro-5H-pyrrolo[1,2-b][1,2,4]triazol-2-yl)(tetrahydro-2H-pyran-4-yl)methanone Prepared from N-methoxy-N-methyltetrahydro-2H-pyran-4-carboxamide using Method 2. The crude reaction mixture was purified by RP-HPLC (20-60% acetonitrile/0.1% NH₄OH in water, 10 min) to afford ((5S,7S)-7-fluoro-5-phenyl-6,7-dihydro-5H-pyrrolo[1,2-b][1,2,4]triazol-2-yl)(tetrahydro-2H-pyran-4-yl)methanone (167 mg, 85% yield). ¹H NMR (400 MHz, DMSO-d₆) δ 7.47-7.35 (m, 3H), 7.28-7.21 (m, 2H), 6.23 (ddd, J=56.4, 7.2, 1.9 Hz, 1H), 5.73 (ddd, J=8.9, 6.5, 3.0 Hz, 1H), 3.88 (ddt, J=11.0, 4.6, 2.4 Hz, 2H), 3.74 (dddd, J=26.1, 15.5, 8.6, 7.2 Hz, 1H), 3.60 (tt, J=11.5, 3.8 Hz, 1H), 3.42 (tdd, J=11.4, 3.6, 2.2 Hz, 2H), 2.70 (dddd, J=26.7, 15.2, 3.1, 1.9 Hz, 1H), 1.76 (tdt, J=10.8, 4.5, 2.2 Hz, 2H), 1.58 (dtdd, J=13.3, 11.7, 8.8, 4.5 Hz, 2H). LCMS $R_T$=4.22 min, m/z=316.1 [M+H]⁺. LCMS (2 to 98% acetonitrile in water+0.1% formic acid over 7 min) retention time 4.22 min, ESI+ found [M+H]=316.1.

Method 102

Example 127

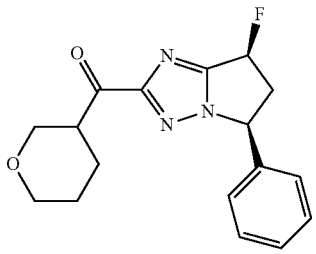 [SMILES: O=C(c1nc2n(n1)[C@H](c1ccccc1)C[C@@H]2F)C1CCCOC1]

((5S,7S)-7-fluoro-5-phenyl-6,7-dihydro-5H-pyrrolo[1,2-b][1,2,4]triazol-2-yl)(tetrahydro-2H-pyran-3-yl)methanone

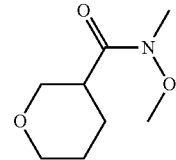

Step 1: N-methoxy-N-methyltetrahydro-2H-pyran-3-carboxamide

Prepared from tetrahydropyran-3-carboxylic acid using Method 5. The crude reaction mixture was purified by flash column chromatography (silica gel, 0-100% isopropyl acetate/heptane) to afford N-methoxy-N-methyltetrahydro-2H-pyran-3-carboxamide (697 mg, quantitative yield). ¹H NMR (400 MHz, Chloroform-d) δ 4.03-3.96 (m, 1H), 3.96-3.89 (m, 1H), 3.71 (s, 3H), 3.49 (t, J=10.9 Hz, 1H), 3.45-3.37 (m, 1H), 3.16 (s, 3H), 3.07-2.94 (m, 1H), 1.94 (dtd, J=11.1, 3.7, 1.9 Hz, 1H), 1.86-1.61 (m, 3H). LCMS $R_T$=0.73 min, m/z=173.9 [M+H]⁺. LCMS (5 to 100% acetonitrile in water+0.1% formic acid over 1.6 min) retention time 0.73 min, ESI+ found [M+H]=173.9.

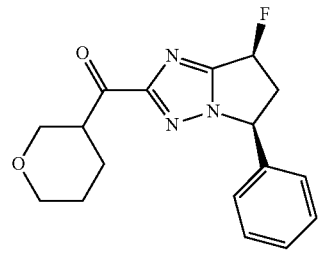

Step 2: ((5S,7S)-7-fluoro-5-phenyl-6,7-dihydro-5H-pyrrolo[1,2-b][1,2,4]triazol-2-yl)(tetrahydro-2H-pyran-3-yl)methanone Prepared from N-methoxy-N-methyltetrahydro-2H-pyran-3-carboxamide using Method 2. The crude reaction mixture was purified by RP-HPLC (20-60% acetonitrile/0.1% NH₄OH in water, 10 min) to afford ((5S,7S)-7-fluoro-5-phenyl-6,7-dihydro-5H-pyrrolo[1,2-b][1,2,4]triazol-2-yl)(tetrahydro-2H-pyran-3-yl)methanone (169 mg, 86% yield). ¹H NMR (400 MHz, DMSO-d₆) δ 7.49-7.34 (m, 3H), 7.25 (dt, J=7.8, 1.4 Hz, 2H), 6.23 (dddd, J=56.4, 7.2, 2.0, 0.9 Hz, 1H), 5.73 (ddd, J=8.8, 6.4, 3.0 Hz, 1H), 4.01 (tdd, J=10.5, 3.9, 1.8 Hz, 1H), 3.84-3.65 (m, 2H), 3.57 (tdd, J=9.8, 3.8, 1.9 Hz, 1H), 3.45 (ddd, J=10.9, 9.5, 2.6 Hz, 1H), 3.41-3.33 (m, 1H), 2.79-2.62 (m, 1H), 2.05-1.89 (m, 1H), 1.78-1.47 (m, 3H). LCMS $R_T$=4.42 min, m/z=316.1 [M+H]⁺. LCMS (2 to 98% acetonitrile in water+0.1% formic acid over 7 min) retention time 4.42 min, ESI+ found [M+H]=316.1.

Method 103

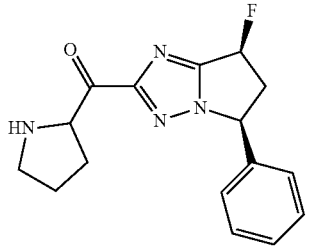

Example 128

(5S,7S)-2-(D-prolyl)-7-fluoro-5-phenyl-6,7-dihydro-5H-pyrrolo[1,2-b][1,2,4]triazole

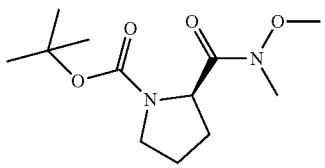 [SMILES: CON(C)C(=O)[C@H]1CCCN1C(=O)OC(C)(C)C]

Step 1: Tert-Butyl (R)-2-(methoxy(methyl)carbamoyl)pyrrolidine-1-carboxylate Prepared from N-Boc-D-proline using Method 1 (1.23 g, quantitative yield). The product was used without purification. $^1$H NMR (400 MHz, Chloroform-d) δ 4.65 (ddd, J=42.4, 8.5, 3.5 Hz, 1H), 3.74 (d, J=25.4 Hz, 3H), 3.57 (dddd, J=15.0, 10.5, 7.8, 5.0 Hz, 1H), 3.44 (ddt, J=28.9, 10.3, 6.9 Hz, 1H), 3.19 (s, 3H), 2.27-2.08 (m, 1H), 2.08-1.74 (m, 3H), 1.43 (d, J=17.9 Hz, 9H). LCMS $R_T$=1.03 min, m/z=158.9 [(M-Boc)+H]$^+$. LCMS (5 to 100% acetonitrile in water+0.1% formic acid over 1.6 min) retention time 1.03 min, ESI+ found [(M-Boc)+H]=158.9.

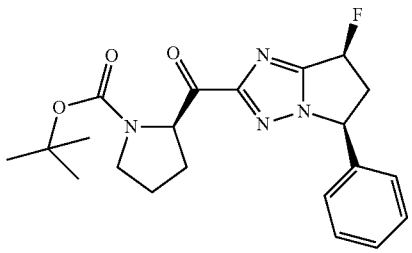 [SMILES: CC(C)(C)OC(=O)N1CCC[C@@H]1C(=O)c1nc2n(n1)[C@H](c1ccccc1)C[C@@H]2F]

Step 2: Tert-Butyl (R)-2-((5S,7S)-7-fluoro-5-phenyl-6,7-dihydro-5H-pyrrolo[1,2-b][1,2,4]triazole-2-carbonyl)pyrrolidine-1-carboxylate Prepared from tert-butyl (R)-2-(methoxy(methyl)carbamoyl)pyrrolidine-1-carboxylate using Method 3. The product was used without purification. LCMS $R_T$=1.30 min, m/z=300.9 [(M-Boc)+H]$^+$. LCMS (5 to 100% acetonitrile in water+0.1% formic acid over 1.6 min) retention time 1.30 min, ESI+ found [(M-Boc)+H]=300.9.

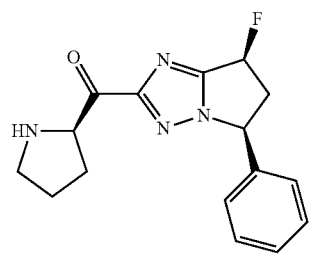 [SMILES: O=C(c1nc2n(n1)[C@H](c1ccccc1)C[C@@H]2F)[C@H]1CCCN1]

Step 3: (5S,7S)-2-(D-prolyl)-7-fluoro-5-phenyl-6,7-dihydro-5H-pyrrolo[1,2-b][1,2,4]triazole tert-butyl (R)-2-((5S,7S)-7-fluoro-5-phenyl-6,7-dihydro-5H-pyrrolo[1,2-b][1,2,4]triazole-2-carbonyl)pyrrolidine-1-carboxylate was dissolved in dichloromethane (2 mL) and cooled to 0° C. Trifluoroacetic acid (2 mL) was added and the reaction mixture was stirred at 0° C. The reaction mixture was concentrated and purified by SFC (5-60% methanol/carbon dioxide, pyridyl amide column, 12 min) to afford (5S,7S)-2-(D-prolyl)-7-fluoro-5-phenyl-6,7-dihydro-5H-pyrrolo[1,2-b][1,2,4]triazole (3.7 mg, 3% yield). $^1$H NMR (400 MHz, DMSO-d$_6$) δ 7.48-7.29 (m, 3H), 7.23 (ddt, J=11.8, 6.1, 1.6 Hz, 2H), 6.35-5.99 (m, 1H), 5.82-5.52 (m, 1H), 4.37-3.89 (m, 1H), 3.88-3.45 (m, 1H), 3.12-2.51 (m, 3H), 2.40-0.29 (m, 4H). LCMS $R_T$=0.88 min, m/z=300.9 [M+H]$^+$. LCMS (5 to 100% acetonitrile in water+0.1% formic acid over 1.6 min) retention time 0.88 min, ESI+ found [M+H]=300.9.

Method 104

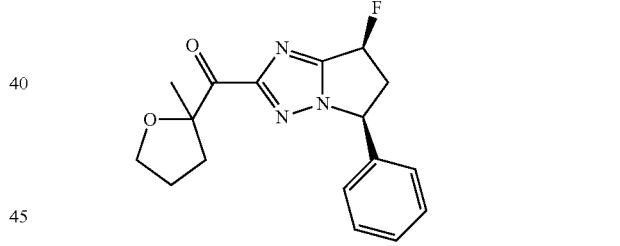

Example 129

((5S,7S)-7-fluoro-5-phenyl-6,7-dihydro-5H-pyrrolo[1,2-b][1,2,4]triazol-2-yl)(2-methyltetrahydrofuran-2-yl)methanone

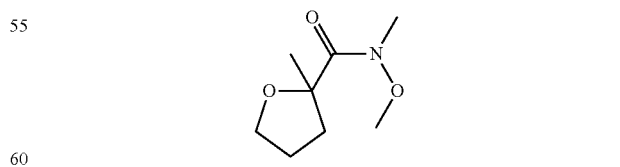

Step 1: N-methoxy-N,2-dimethyltetrahydrofuran-2-carboxamide

Prepared from 2-methyltetrahydrofuran-2-carboxylic acid using Method 2 (76 mg, 38% yield). The product was used without purification. LCMS $R_T$=0.82 min, m/z=174.0 [M+H]⁺. LCMS (5 to 100% acetonitrile in water+0.1% formic acid over 1.6 min) retention time 0.82 min, ESI+ found [M+H]=174.0.

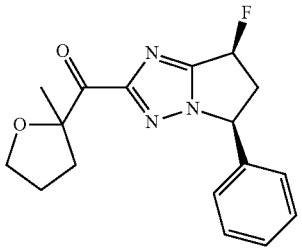 [SMILES: CC1(C(=O)c2nc3n(n2)[C@H](c2ccccc2)C[C@@H]3F)CCCO1]

Step 2: ((5S,7S)-7-fluoro-5-phenyl-6,7-dihydro-5H-pyrrolo[1,2-b][1,2,4]triazol-2-yl)(2-methyltetrahydrofuran-2-yl)methanone Prepared from N-methoxy-N,2-dimethyltetrahydrofuran-2-carboxamide using Method 3. The crude reaction mixture was purified by RP-HPLC (20-60% acetonitrile/0.1% formic acid in water, 10 min) to afford ((5S,7S)-7-fluoro-5-phenyl-6,7-dihydro-5H-pyrrolo[1,2-b][1,2,4]triazol-2-yl)(2-methyltetrahydrofuran-2-yl)methanone (24 mg, 17% yield). ¹H NMR (400 MHz, DMSO-d₆) δ 7.48-7.35 (m, 3H), 7.28-7.19 (m, 2H), 6.23 (ddt, J=56.5, 7.2, 2.0 Hz, 1H), 5.72 (ddt, J=8.9, 6.3, 2.8 Hz, 1H), 3.93-3.82 (m, 1H), 3.82-3.65 (m, 2H), 2.71 (dddd, J=26.6, 15.2, 3.1, 1.9 Hz, 1H), 2.52 (m, 1H), 1.99-1.85 (m, 2H), 1.85-1.72 (m, 1H), 1.53 (d, J=3.6 Hz, 3H). LCMS $R_T$=4.66 min, m/z=316.1 [M+H]⁺. LCMS (2 to 98% acetonitrile in water+0.1% formic acid over 7 min) retention time 4.66 min, ESI+ found [M+H]=316.1.

Method 105

Example 130

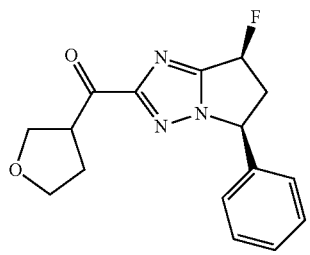 [SMILES: O=C(c1nc2n(n1)[C@H](c1ccccc1)C[C@@H]2F)C1CCOC1]

((5S,7S)-7-fluoro-5-phenyl-6,7-dihydro-5H-pyrrolo[1,2-b][1,2,4]triazol-2-yl)(tetrahydrofuran-3-yl)methanone

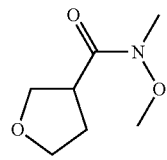

Step 1:
N-methoxy-N-methyltetrahydrofuran-3-carboxamide

Prepared from tetrahydrofuran-3-carboxylic acid using Method 3 (97 mg, 47% yield). The product was used without purification. LCMS $R_T$=0.80 min, m/z=160.0 [M+H]⁺. LCMS (5 to 100% acetonitrile in water+0.1% formic acid over 1.6 min) retention time 0.80 min, ESI+ found [M+H]=160.0.

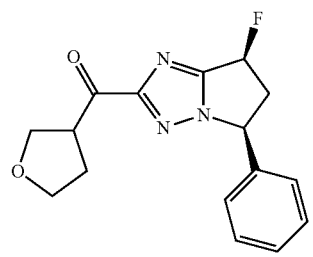

Step 2: ((5S,7S)-7-fluoro-5-phenyl-6,7-dihydro-5H-pyrrolo[1,2-b][1,2,4]triazol-2-yl)(tetrahydrofuran-3-yl)methanone Prepared from N-methoxy-N-methyltetrahydrofuran-3-carboxamide using Method 3. The crude reaction mixture was purified by RP-HPLC (20-60% acetonitrile/0.1% formic acid in water, 10 min) to afford the diastereomeric mixture of ((5S,7S)-7-fluoro-5-phenyl-6,7-dihydro-5H-pyrrolo[1,2-b][1,2,4]triazol-2-yl)(tetrahydrofuran-3-yl)methanone (49 mg, 37% yield). ¹H NMR (400 MHz, DMSO-d₆) δ 7.49-7.35 (m, 3H), 7.30-7.21 (m, 2H), 6.24 (ddd, J=56.2, 7.1, 1.9 Hz, 1H), 5.74 (ddd, J=9.2, 6.6, 3.1 Hz, 1H), 4.14-4.05 (m, 1H), 3.93 (dt, J=11.3, 8.4 Hz, 1H), 3.87-3.65 (m, 4H), 2.72 (dddd, J=26.7, 15.3, 3.1, 1.9 Hz, 1H), 2.19-2.00 (m, 2H). LCMS $R_T$=4.33 min, m/z=302.2 [M+H]⁺. LCMS (2 to 98% acetonitrile in water+0.1% formic acid over 7 min) retention time 4.33 min, ESI+ found [M+H]=302.2.

Method 106

Examples 131 and 132

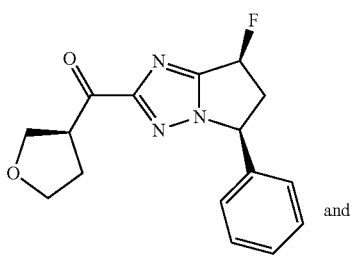

and

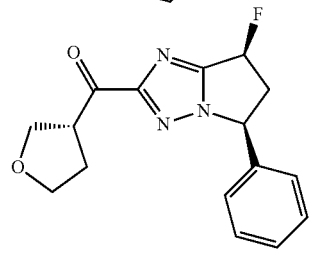

((5S,7S)-7-fluoro-5-phenyl-6,7-dihydro-5H-pyrrolo[1,2-b][1,2,4]triazol-2-yl)((S)-tetrahydrofuran-3-yl)methanone The diastereomeric mixture of ((5S,7S)-7-fluoro-5-phenyl-6,7-dihydro-5H-pyrrolo[1,2-b][1,2,4]triazol-2-yl)(tetrahydrofuran-3-yl)methanone was purified by chiral SFC (retention time=1.241 min) to afford the arbitrarily assigned ((5S,7S)-7-fluoro-5-phenyl-6,7-dihydro-5H-pyrrolo[1,2-b][1,2,4]triazol-2-yl)((S)-tetrahydrofuran-3-yl)methanone (15 mg, 11% yield). $^1$H NMR (400 MHz, DMSO-$d_6$) δ 7.49-7.35 (m, 3H), 7.30-7.21 (m, 2H), 6.24 (ddd, J=56.2, 7.1, 1.9 Hz, 1H), 5.74 (ddd, J=9.2, 6.6, 3.1 Hz, 1H), 4.14-4.05 (m, 1H), 3.93 (dt, J=11.3, 8.4 Hz, 1H), 3.87-3.65 (m, 4H), 2.72 (dddd, J=26.7, 15.3, 3.1, 1.9 Hz, 1H), 2.19-2.00 (m, 2H). LCMS $R_T$=4.33 min, m/z=302.2 [M+H]$^+$. LCMS (2 to 98% acetonitrile in water+0.1% formic acid over 7 min) retention time 4.33 min, ESI+ found [M+H]=302.2.

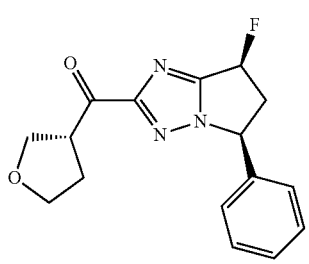 [SMILES: O=C(c1nc2n(n1)[C@H](c1ccccc1)C[C@@H]2F)[C@@H]1CCOC1]

((5S,7S)-7-fluoro-5-phenyl-6,7-dihydro-5H-pyrrolo[1,2-b][1,2,4]triazol-2-yl)((R)-tetrahydrofuran-3-yl)methanone The diastereomeric mixture of ((5S,7S)-7-fluoro-5-phenyl-6,7-dihydro-5H-pyrrolo[1,2-b][1,2,4]triazol-2-yl)(tetrahydrofuran-3-yl)methanone was purified by chiral SFC (retention time=1.627 min) to afford the arbitrarily assigned ((5S,7S)-7-fluoro-5-phenyl-6,7-dihydro-5H-pyrrolo[1,2-b][1,2,4]triazol-2-yl)((R)-tetrahydrofuran-3-yl)methanone (23 mg, 17% yield). $^1$H NMR (400 MHz, DMSO-$d_6$) δ 7.49-7.35 (m, 3H), 7.30-7.21 (m, 2H), 6.24 (ddd, J=56.2, 7.1, 1.9 Hz, 1H), 5.74 (ddd, J=9.2, 6.6, 3.1 Hz, 1H), 4.14-4.05 (m, 1H), 3.93 (dt, J=11.3, 8.4 Hz, 1H), 3.87-3.65 (m, 4H), 2.72 (dddd, J=26.7, 15.3, 3.1, 1.9 Hz, 1H), 2.19-2.00 (m, 2H). LCMS $R_T$=4.33 min, m/z=302.2 [M+H]$^+$. LCMS (2 to 98% acetonitrile in water+0.1% formic acid over 7 min) retention time 4.33 min, ESI+ found [M+H]=302.2.

SFC condition: Column: Chiralpak IA (150 mm*21.2 mm, 5 μm); Condition: 0.1% NH$_4$OH MeOH; Begin B 10% End B 10%; Flow Rate (70 mL/min); Column temperature 40° C. SFC condition: Column: Chiralpak IA (150 mm*21.2 mm, 5 μm); Condition: 0.1% NH$_4$OH MeOH; Begin B 10% End B 10%; Flow Rate (70 mL/min); Column temperature 40° C.

Method 107

Example 133

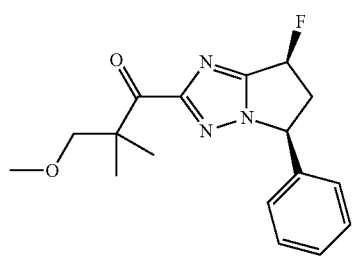 [SMILES: COCC(C)(C)C(=O)c1nc2n(n1)[C@H](c1ccccc1)C[C@@H]2F]

1-((5S,7S)-7-fluoro-5-phenyl-6,7-dihydro-5H-pyrrolo[1,2-b][1,2,4]triazol-2-yl)-3-methoxy-2,2-dimethylpropan-1-one

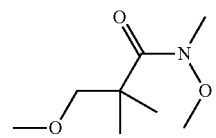

Step 1: N,3-dimethoxy-N,2,2-trimethylpropanamide

Prepared from 3-methoxy-2,2-dimethylpropanoic acid using Method 2 (184 mg, 46% yield). The product was used without purification. LCMS $R_T$=0.93 min, m/z=176.0 [M+H]$^+$. LCMS (5 to 100% acetonitrile in water+0.1% formic acid over 1.6 min) retention time 0.93 min, ESI+ found [M+H]=176.0.

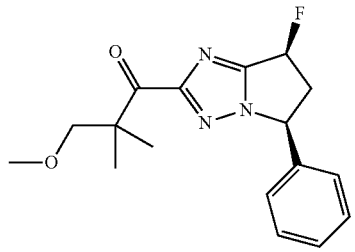

Step 2: 1-((5S,7S)-7-fluoro-5-phenyl-6,7-dihydro-5H-pyrrolo[1,2-b][1,2,4]triazol-2-yl)-3-methoxy-2,2-dimethylpropan-1-one Prepared from N,3-dimethoxy-N,2,2-trimethylpropanamide using Method 3. The crude reaction mixture was purified by RP-HPLC (20-60% acetonitrile/0.1% formic acid in water, 10 min) to afford 1-((5S,7S)-7-fluoro-5-phenyl-6,7-dihydro-5H-pyrrolo[1,2-b][1,2,4]triazol-2-yl)-3-methoxy-2,2-dimethylpropan-1-one (16 mg, 18% yield). $^1$H NMR (400 MHz, DMSO-$d_6$) δ 7.48-7.34 (m, 3H), 7.25-7.18 (m, 2H), 6.23 (ddd, J=56.5, 7.1, 1.9 Hz, 1H), 5.74 (ddd, J=8.9, 6.5, 2.9 Hz, 1H), 3.84-3.71 (m, 2H), 3.79-3.66 (m, 1H), 3.07 (s, 3H), 2.71 (dddd, J=26.6, 15.2, 3.1, 1.9 Hz, 1H), 1.25 (d, J=6.0 Hz, 6H). LCMS $R_T$=5.44 min, m/z=318.2

[M+H]⁺. LCMS (2 to 98% acetonitrile in water+0.1% formic acid over 7 min) retention time 5.44 min, ESI+ found [M+H]=318.2.

Method 108

Example 134

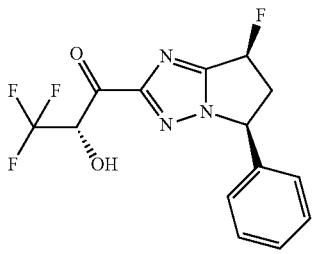

(S)-3,3,3-trifluoro-1-((5S,7S)-7-fluoro-5-phenyl-6,7-dihydro-5H-pyrrolo[1,2-b][1,2,4]triazol-2-yl)-2-hydroxypropan-1-one

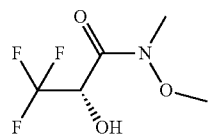

Step 1: (S)-3,3,3-trifluoro-2-hydroxy-N-methoxy-N-methylpropanamide

Prepared from (S)-3,3,3-trifluoro-2-hydroxypropanoic acid using Method 2 (52 mg, 13% yield). The product was used without purification. LCMS $R_T$=0.72 min, m/z=187.9 [M+H]⁺. LCMS (5 to 100% acetonitrile in water+0.1% formic acid over 1.6 min) retention time 0.72 min, ESI+ found [M+H]=187.9.

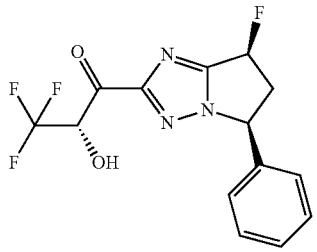 [SMILES: O=C(c1nc2n(n1)[C@H](c1ccccc1)C[C@@H]2F)[C@H](O)C(F)(F)F]

Step 2: (S)-3,3,3-trifluoro-1-((5S,7S)-7-fluoro-5-phenyl-6,7-dihydro-5H-pyrrolo[1,2-b][1,2,4]triazol-2-yl)-2-hydroxypropan-1-one Prepared from (S)-3,3,3-trifluoro-2-hydroxy-N-methoxy-N-methylpropanamide using Method 3. The crude reaction mixture was purified by RP-HPLC (20-60% acetonitrile/0.1% formic acid in water, 10 min) to afford arbitrarily assigned (S)-3,3,3-trifluoro-1-((5S,7S)-7-fluoro-5-phenyl-6,7-dihydro-5H-pyrrolo[1,2-b][1,2,4]triazol-2-yl)-2-hydroxy-propan-1-one (7.5 mg, 9% yield). ¹H NMR (400 MHz, DMSO-d₆) δ 7.42 (dddd, J=9.2, 7.4, 6.3, 3.3 Hz, 3H), 7.26 (td, J=8.3, 7.8, 1.6 Hz, 2H), 6.27 (dddd, J=56.3, 7.3, 3.5, 2.0 Hz, 1H), 5.77 (ddd, J=9.0, 6.3, 3.1 Hz, 1H), 5.62 (dd, J=10.2, 4.0 Hz, 1H), 3.77 (dddd, J=25.7, 15.5, 8.5, 7.2 Hz, 1H), 2.80-2.65 (m, 1H). LCMS $R_T$=4.82 min, m/z=330.1 [M+H]⁺. LCMS (2 to 98% acetonitrile in water+0.1% formic acid over 7 min) retention time 4.82 min, ESI+ found [M+H]=330.1.

Method 109

Example 135

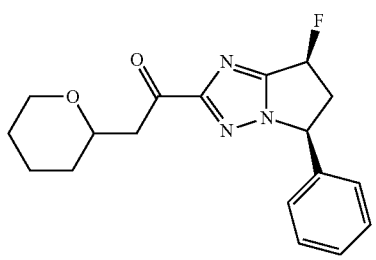

1-((5S,7S)-7-fluoro-5-phenyl-6,7-dihydro-5H-pyrrolo[1,2-b][1,2,4]triazol-2-yl)-2-(tetrahydro-2H-pyran-2-yl)ethan-1-one

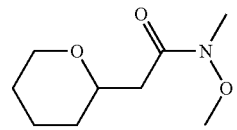

Step 1: N-methoxy-N-methyl-2-(tetrahydro-2H-pyran-2-yl)acetamide

Prepared from 2-tetrahydropyran-2-ylacetic acid using Method 2 (200 mg, 77% yield). The product was used without purification. LCMS $R_T$=0.84 min, m/z=188.0 [M+H]⁺. LCMS (5 to 100% acetonitrile in water+0.1% formic acid over 1.6 min) retention time 0.84 min, ESI+ found [M+H]=188.0.

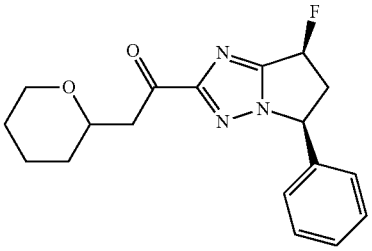 [SMILES: O=C(CC1CCCCO1)c1nc2n(n1)[C@H](c1ccccc1)C[C@@H]2F]

Step 2: 1-((5S,7S)-7-fluoro-5-phenyl-6,7-dihydro-5H-pyrrolo[1,2-b][1,2,4]triazol-2-yl)-2-(tetrahydro-2H-pyran-2-yl)ethan-1-one Prepared from N-methoxy-N-methyl-2-(tetrahydro-2H-pyran-2-yl)acetamide using Method 3. The crude reaction mixture was purified by RP-HPLC (5-85% acetonitrile/0.1% formic acid in water, 10 min) to afford 1-((5S,7S)-7-fluoro-5-phenyl-6,7-dihydro-5H-pyrrolo[1,2-b][1,2,4]triazol-2-yl)-2-(tetrahydro-2H-pyran-2-yl)ethan-1-one (2.5 mg, 3% yield). LCMS $R_T$=4.94 min, m/z=330.2 [M+H]⁺. LCMS (2 to 98% acetonitrile in water+0.1% formic acid over 7 min) retention time 4.94 min, ESI+ found [M+H]=330.2.

Method 110

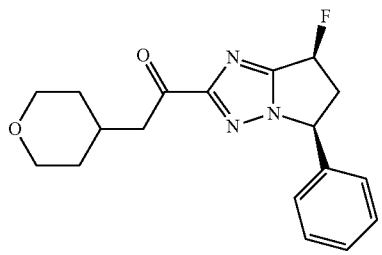 [SMILES: O=C(CC1CCOCC1)c1nc2n(n1)[C@H](c1ccccc1)C[C@@H]2F]

Example 136

1-((5S,7S)-7-fluoro-5-phenyl-6,7-dihydro-5H-pyrrolo[1,2-b][1,2,4]triazol-2-yl)-2-(tetrahydro-2H-pyran-4-yl)ethan-1-one

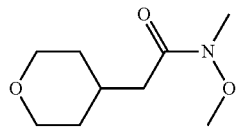

Step 1: N-methoxy-N-methyl-2-(tetrahydro-2H-pyran-4-yl)acetamide

Prepared from 2-tetrahydropyran-4-ylacetic acid using Method 2 (154 mg, 59% yield). The product was used without purification. LCMS $R_T$=0.78 min, m/z=188.0 [M+H]⁺. LCMS (5 to 100% acetonitrile in water+0.1% formic acid over 1.6 min) retention time 0.78 min, ESI+ found [M+H]=188.0.

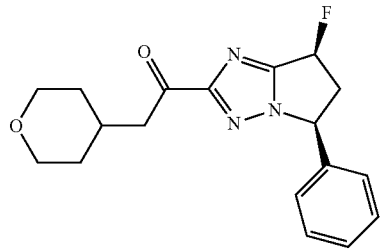

Step 2: 1-((5S,7S)-7-fluoro-5-phenyl-6,7-dihydro-5H-pyrrolo[1,2-b][1,2,4]triazol-2-yl)-2-(tetrahydro-2H-pyran-4-yl)ethan-1-one Prepared from N-methoxy-N-methyl-2-(tetrahydro-2H-pyran-4-yl)acetamide using Method 3. The crude reaction mixture was purified by RP-HPLC (20-60% acetonitrile/ 0.1% formic acid in water, 10 min) to afford 1-((5S,7S)-7-fluoro-5-phenyl-6,7-dihydro-5H-pyrrolo[1,2-b][1,2,4]triazol-2-yl)-2-(tetrahydro-2H-pyran-4-yl)ethan-1-one (46 mg, 52% yield). ¹H NMR (400 MHz, DMSO-d₆) δ 7.46-7.34 (m, 3H), 7.28-7.22 (m, 2H), 6.22 (ddd, J=56.4, 7.2, 1.9 Hz, 1H), 5.71 (ddd, J=8.5, 6.5, 3.1 Hz, 1H), 3.84-3.63 (m, 3H), 3.28-3.21 (m, 1H), 2.94 (dd, J=6.8, 2.1 Hz, 2H), 2.71 (dddd, J=26.7, 15.2, 3.2, 2.0 Hz, 1H), 2.10 (ttt, J=11.0, 7.1, 3.9 Hz, 1H), 1.55 (ddd, J=12.9, 4.2, 2.0 Hz, 2H), 1.23 (qd, J=12.4, 4.4 Hz, 2H), 0.87-0.65 (m, 1H). LCMS $R_T$=2.51 min, m/z=330.2 [M+H]⁺. LCMS (2 to 98% acetonitrile in water+0.1% formic acid over 7 min) retention time 2.51 min, ESI+ found [M+H]=330.2.

Method 111

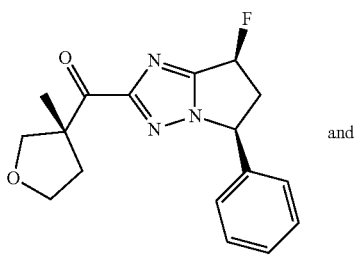

Examples 137 and 138 and

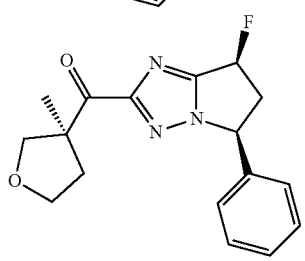

((5S,7S)-7-fluoro-5-phenyl-6,7-dihydro-5H-pyrrolo[1,2-b][1,2,4]triazol-2-yl)((R)-3-methyltetrahydrofuran-3-yl)methanone and ((5S,7S)-7-fluoro-5-phenyl-6,7-dihydro-5H-pyrrolo[1,2-b][1,2,4]triazol-2-yl)((S)-3-methyltetrahydrofuran-3-yl)methanone

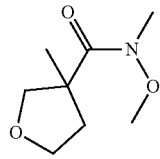

Step 1: N-methoxy-N,3-dimethyltetrahydrofuran-3-carboxamide

Prepared from 3-methyltetrahydrofuran-3-carboxylic acid using Method 2 (386 mg, 58% yield). The product was used without purification. LCMS $R_T$=0.89 min, m/z=173.9 [M+H]⁺. LCMS (5 to 100% acetonitrile in water+0.1% formic acid over 1.6 min) retention time 0.89 min, ESI+ found [M+H]=173.9.

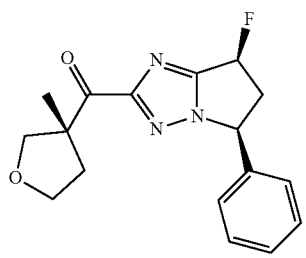 [SMILES: C[C@@]1(C(=O)c2nc3n(n2)[C@H](c2ccccc2)C[C@@H]3F)CCOC1]

((5S,7S)-7-fluoro-5-phenyl-6,7-dihydro-5H-pyrrolo[1,2-b][1,2,4]triazol-2-yl)((R)-3-methyltetrahydrofuran-3-yl)methanone Prepared from N-methoxy-N,3-dimethyltetrahydrofuran-3-carboxamide using Method 3. The crude reaction mixture was purified by RP-HPLC (20-60% acetonitrile/0.1% formic acid in water, 10 min) to afford the diastereomeric mixture of ((5S,7S)-7-fluoro-5-phenyl-6,7-dihydro-5H-pyrrolo[1,2-b][1,2,4]triazol-2-yl)(3-methyltetrahydrofuran-3-yl)methanone (31 mg, 28% yield). The diastereomeric mixture of ((5S,7S)-7-fluoro-5-phenyl-6,7-dihydro-5H-pyrrolo[1,2-b][1,2,4]triazol-2-yl)(3-methyltetrahydrofuran-3-yl)methanone was purified by chiral SFC (retention time=0.785 min) to afford the arbitrarily assigned ((5S,7S)-7-fluoro-5-phenyl-6,7-dihydro-5H-pyrrolo[1,2-b][1,2,4]triazol-2-yl)((R)-3-methyltetrahydrofuran-3-yl)methanone (11 mg, 10%). $^1$H NMR (400 MHz, DMSO-$d_6$) δ 7.46-7.35 (m, 3H), 7.28-7.21 (m, 2H), 6.24 (ddd, J=56.4, 7.1, 2.0 Hz, 1H), 5.73 (ddd, J=8.9, 6.4, 3.1 Hz, 1H), 4.18 (d, J=8.9 Hz, 1H), 3.84-3.66 (m, 3H), 3.64 (d, J=8.9 Hz, 1H), 2.71 (dddd, J=26.6, 15.2, 3.1, 2.0 Hz, 1H), 2.56 (ddd, J=12.6, 8.2, 6.8 Hz, 1H), 1.85 (ddd, J=13.0, 7.6, 5.6 Hz, 1H), 1.48 (s, 3H). LCMS $R_T$=4.68 min, m/z=316.2 [M+H]$^+$. LCMS (2 to 98% acetonitrile in water+0.1% formic acid over 7 min) retention time 4.68 min, ESI+ found [M+H]=316.2.

SFC condition: Column: Chiralpak IG (150 mm*21.2 mm, 5 μm); Condition: 0.1% NH$_4$OH MeOH; Begin B 20% End B 20%; Flow Rate (70 mL/min); Column temperature 40° C.

((5S,7S)-7-fluoro-5-phenyl-6,7-dihydro-5H-pyrrolo[1,2-b][1,2,4]triazol-2-yl)((S)-3-methyltetrahydrofuran-3-yl)methanone The diastereomeric mixture of ((5S,7S)-7-fluoro-5-phenyl-6,7-dihydro-5H-pyrrolo[1,2-b][1,2,4]triazol-2-yl)(3-methyltetrahydrofuran-3-yl)methanone was purified by chiral SFC (retention time=0.966 min) to afford the arbitrarily assigned ((5S,7S)-7-fluoro-5-phenyl-6,7-dihydro-5H-pyrrolo[1,2-b][1,2,4]triazol-2-yl)((S)-3-methyltetrahydrofuran-3-yl)methanone (12 mg, 11% yield).

$^1$H NMR (400 MHz, DMSO-$d_6$) δ 7.47-7.34 (m, 3H), 7.28-7.21 (m, 2H), 6.24 (ddd, J=56.3, 7.1, 1.9 Hz, 1H), 5.73 (ddd, J=8.9, 6.5, 3.1 Hz, 1H), 4.21 (d, J=89. Hz, 1H), 3.83-3.64 (m, 3H), 3.67 (d, J=8.9 Hz, 1H), 2.71 (dddd, J=26.6, 15.2, 3.1, 2.0 Hz, 1H), 2.59-2.52 (m, 1H), 1.82 (ddd, J=12.6, 7.6, 5.7 Hz, 1H), 1.47 (s, 3H). LCMS $R_T$=4.68 min, m/z=316.2 [M+H]$^+$. LCMS (2 to 98% acetonitrile in water+0.1% formic acid over 7 min) retention time 4.68 min, ESI+ found [M+H]=316.2.

SFC condition: Column: Chiralpak IG (150 mm*21.2 mm, 5 μm); Condition: 0.1% NH$_4$OH MeOH; Begin B 25% End B 25%; Flow Rate (70 mL/min); Column temperature 40° C.

Method 112

Examples 139, 140 and 141

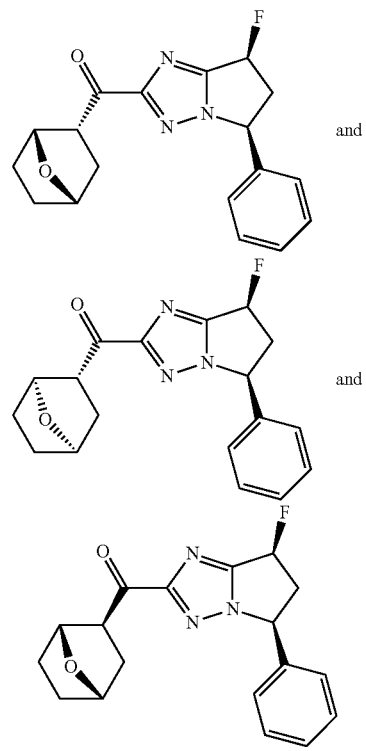

((1R,2R,4S)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone and ((1S,2R,4R)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone and ((1R,2S,4S)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone

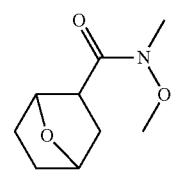

Step 1: N-methoxy-N-methyl-7-oxabicyclo[2.2.1]heptane-2-carboxamide

Prepared from 7-oxabicyclo[2.2.1]heptane-2-carboxylic acid using Method 2 (184 mg, 70% yield). The product was used without purification. LCMS $R_T$=0.76 min, m/z=185.8 [M+H]$^+$. LCMS (5 to 100% acetonitrile in water+0.1% formic acid over 1.6 min) retention time 0.76 min, ESI+ found [M+H]=185.8.

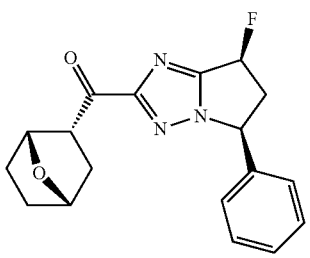 [SMILES: O=C(c1nc2n(n1)[C@H](c1ccccc1)C[C@@H]2F)[C@@H]1C[C@@H]2CC[C@H]1O2]

Step 2: ((1R,2R,4S)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone Prepared from N-methoxy-N-methyl-7-oxabicyclo[2.2.1]heptane-2-carboxamide using Method 3. The crude reaction mixture was purified by RP-HPLC (20-60% acetonitrile/0.1% formic acid in water, 10 min) to afford the diastereomeric mixture of (7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone (41 mg, 31% yield). The diastereomeric mixture of (7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone was purified by chiral SFC (retention time=0.442 min) to afford arbitrarily assigned ((1R,2R,4S)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone (3 mg, 2% yield). $^1$H NMR (400 MHz, DMSO-d$_6$) δ 7.47-7.35 (m, 3H), 7.29-7.22 (m, 2H), 6.25 (ddd, J=56.4, 7.2, 2.0 Hz, 1H), 5.74 (ddd, J=9.1, 6.4, 3.1 Hz, 1H), 4.91 (t, J=4.9 Hz, 1H), 4.59 (t, J=5.2 Hz, 1H), 3.96-3.87 (m, 1H), 3.75 (dddd, J=25.8, 15.5, 8.5, 7.2 Hz, 1H), 2.72 (dddd, J=26.7, 15.1, 3.1, 2.0 Hz, 1H), 2.00 (dd, J=11.9, 4.6 Hz, 1H), 1.75 (dddd, J=12.0, 10.9, 5.3, 2.8 Hz, 1H), 1.66-1.52 (m, 1H), 1.50-1.36 (m, 2H), 1.29-1.17 (m, 1H). LCMS R$_T$=4.61 min, m/z=328.2 [M+H]$^+$. LCMS (2 to 98% acetonitrile in water+0.1% formic acid over 7 min) retention time 4.61 min, ESI+ found [M+H]=328.2.

SFC condition: Column: Chiralpak ID (250 mm*21.2 mm, 5 μm); Condition: 0.1% NH4OH MeOH; Begin B 25% End B 25%; Flow Rate (70 mL/min); Column temperature 40° C.

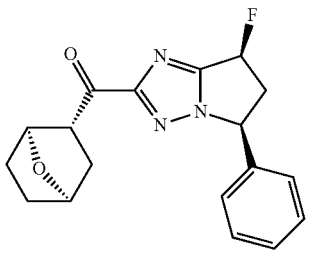 [SMILES: O=C(c1nc2n(n1)[C@H](c1ccccc1)C[C@@H]2F)[C@@H]1C[C@H]2CC[C@@H]1O2]

((1S,2R,4R)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone The diastereomeric mixture of (7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone was purified by chiral SFC (retention time=0.523 min) to afford arbitrarily assigned ((1S,2R,4R)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone (3 mg, 2% yield). $^1$H NMR (400 MHz, Chloroform-d) δ 7.43-7.34 (m, 3H), 7.25-7.19 (m, 2H), 6.03 (ddd, J=55.8, 7.1, 1.7 Hz, 1H), 5.50 (ddd, J=8.8, 6.2, 2.8 Hz, 1H), 4.83 (d, J=4.7 Hz, 1H), 4.70 (t, J=4.8 Hz, 1H), 3.77-3.51 (m, 2H), 2.95 (dddd, J=25.0, 15.4, 2.8, 1.7 Hz, 1H), 2.32 (dtd, J=12.2, 5.0, 2.1 Hz, 1H), 1.90-1.63 (m, 5H). LCMS R$_T$=4.54 min, m/z=328.2 [M+H]$^+$. LCMS (2 to 98% acetonitrile in water+0.1% formic acid over 7 min) retention time 4.54 min, ESI+ found [M+H]=328.2.

SFC condition: Column: Chiralpak ID (250 mm*21.2 mm, 5 μm); Condition: 0.1% NH$_4$OH MeOH; Begin B 25% End B 25%; Flow Rate (70 mL/min); Column temperature 40° C.

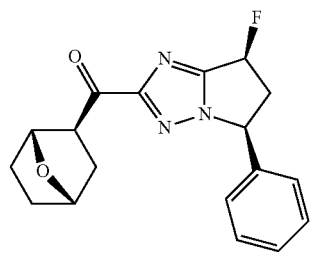 [SMILES: O=C(c1nc2n(n1)[C@H](c1ccccc1)C[C@@H]2F)[C@H]1C[C@@H]2CC[C@H]1O2]

((1R,2S,4S)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone The diastereomeric mixture of (7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone was purified by chiral SFC (retention time=1.220 min) to afford arbitrarily assigned ((1R,2S,4S)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone (21 mg, 16% yield). $^1$H NMR (400 MHz, DMSO-d$_6$) δ 7.47-7.35 (m, 3H), 7.31-7.24 (m, 2H), 6.23 (ddd, J=56.3, 7.2, 1.9 Hz, 1H), 5.74 (ddd, J=8.9, 6.5, 3.1 Hz, 1H), 4.94 (t, J=4.9 Hz, 1H), 4.59 (t, J=5.2 Hz, 1H), 3.93-3.83 (m, 1H), 3.75 (dddd, J=26.1, 15.5, 8.5, 7.2 Hz, 1H), 2.72 (dddd, J=26.6, 15.2, 3.1, 1.9 Hz, 1H), 1.99 (dd, J=12.0, 4.6 Hz, 1H), 1.73 (dddd, J=11.9, 10.8, 5.3, 2.8 Hz, 1H), 1.59 (ddt, J=12.8, 8.5, 4.8 Hz, 1H), 1.51-1.37 (m, 2H), 1.28-1.17 (m, 1H). LCMS R$_T$=4.61 min, m/z=328.2 [M+H]$^+$. LCMS (2 to 98% acetonitrile in water+0.1% formic acid over 7 min) retention time 4.61 min, ESI+ found [M+H]=328.2.

SFC condition: Column: Chiralpak ID (250 mm*21.2 mm, 5 μm); Condition: 0.1% NH$_4$OH MeOH; Begin B 25% End B 25%; Flow Rate (70 mL/min); Column temperature 40° C.

Method 113

Example 142

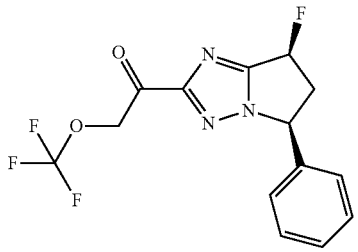 [SMILES: O=C(COC(F)(F)F)c1nc2n(n1)[C@H](c1ccccc1)C[C@@H]2F]

1-((5S,7S)-7-fluoro-5-phenyl-6,7-dihydro-5H-pyrrolo[1,2-b][1,2,4]triazol-2-yl)-2-(trifluoromethoxy)ethan-1-one

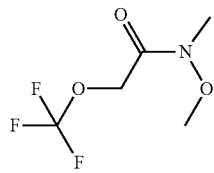

Step 1: N-methoxy-N-methyl-2-(trifluoromethoxy)acetamide

Prepared from 2-(trifluoromethoxy)acetic acid using Method 2 (129 mg, 20% yield). The product was used without purification. LCMS $R_T$=0.88 min, m/z=187.8 [M+H]$^+$. LCMS (5 to 100% acetonitrile in water+0.1% formic acid over 1.6 min) retention time 0.88 min, ESI+ found [M+H]=187.8.

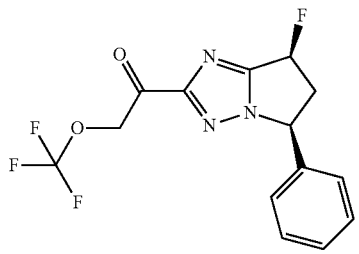

Step 2: 1-((5S,7S)-7-fluoro-5-phenyl-6,7-dihydro-5H-pyrrolo[1,2-b][1,2,4]triazol-2-yl)-2-(trifluoromethoxy)ethan-1-one Prepared from N-methoxy-N-methyl-2-(trifluoromethoxy)acetamide using Method 3. The crude reaction mixture was purified by RP-HPLC (20-60% acetonitrile/0.1% formic acid in water, 10 min) to afford 1-((5S,7S)-7-fluoro-5-phenyl-6,7-dihydro-5H-pyrrolo[1,2-b][1,2,4]triazol-2-yl)-2-(trifluoromethoxy)ethan-1-one (2 mg, 2% yield). $^1$H NMR (400 MHz, DMSO-d$_6$) δ 7.47-7.36 (m, 3H), 7.30-7.24 (m, 2H), 6.26 (ddd, J=56.2, 7.2, 1.9 Hz, 1H), 5.75 (ddd, J=8.8, 6.5, 3.1 Hz, 1H), 5.50 (d, J=1.2 Hz, 2H), 3.84-3.63 (m, 1H), 2.74 (dddd, J=26.8, 15.3, 3.2, 1.9 Hz, 1H). LCMS $R_T$=5.39 min, m/z=330.1 [M+H]$^+$. LCMS (2 to 98% acetonitrile in water+0.1% formic acid over 7 min) retention time 5.39 min, ESI+ found [M+H]=330.1.

Method 114

Examples 143 and 144

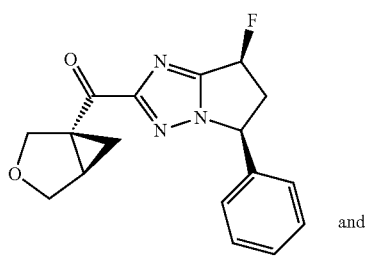

and

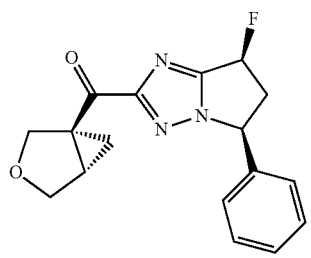

((1R,5R)-3-oxabicyclo[3.1.0]hexan-1-yl)((5S,7S)-7-fluoro-5-phenyl-6,7-dihydro-5H-pyrrolo[1,2-b][1,2,4]triazol-2-yl)methanone and ((1S,5S)-3-oxabicyclo[3.1.0]hexan-1-yl)((5S,7S)-7-fluoro-5-phenyl-6,7-dihydro-5H-pyrrolo[1,2-b][1,2,4]triazol-2-yl)methanone

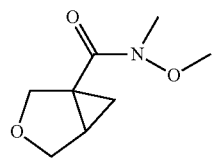

Step 1: N-methoxy-N-methyl-3-oxabicyclo[3.1.0]hexane-1-carboxamide

Prepared from 3-oxabicyclo[3.1.0]hexane-1-carboxylic acid using Method 3 (150 mg, 56% yield). The product was used without purification. LCMS $R_T$=0.72 min, m/z=171.9 [M+H]$^+$. LCMS (5 to 100% acetonitrile in water+0.1% formic acid over 1.6 min) retention time 0.72 min, ESI+ found [M+H]=171.9.

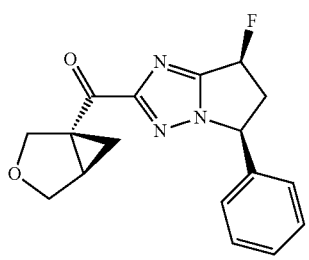 [SMILES: O=C(c1nc2n(n1)[C@H](c1ccccc1)C[C@@H]2F)[C@@]12COC[C@@H]1C2]

Step 2: ((1R,5R)-3-oxabicyclo[3.1.0]hexan-1-yl)
((5S,7S)-7-fluoro-5-phenyl-6,7-dihydro-5H-pyrrolo
[1,2-b][1,2,4]triazol-2-yl)methanone Prepared from N-methoxy-N-methyl-3-oxabicyclo[3.1.0]hexane-1-carboxamide using Method 3. The crude reaction mixture was purified by RP-HPLC (20-60% acetonitrile/0.1% formic acid in water, 10 min) to afford the diastereomeric mixture of (3-oxabicyclo[3.1.0]hexan-1-yl)((5S,7S)-7-fluoro-5-phenyl-6,7-dihydro-5H-pyrrolo[1,2-b][1,2,4]triazol-2-yl)methanone (30 mg, 27% yield). The diastereomeric mixture of (3-oxabicyclo[3.1.0]hexan-1-yl)((5S,7S)-7-fluoro-5-phenyl-6,7-dihydro-5H-pyrrolo[1,2-b][1,2,4]triazol-2-yl)methanone was purified by chiral SFC (retention time=0.736 min) to afford arbitrarily assigned ((1R,5R)-3-oxabicyclo[3.1.0]hexan-1-yl)((5S,7S)-7-fluoro-5-phenyl-6,7-dihydro-5H-pyrrolo[1,2-b][1,2,4]triazol-2-yl)methanone (28 mg, 25% yield). $^1$H NMR (400 MHz, DMSO-$d_6$) δ 7.48-7.33 (m, 3H), 7.24 (dt, J=7.8, 1.5 Hz, 2H), 6.22 (dddd, J=56.4, 7.2, 3.5, 1.9 Hz, 1H), 5.76-5.65 (m, 1H), 4.11-4.04 (m, 1H), 4.00 (dd, J=8.7, 1.7 Hz, 1H), 3.81-3.64 (m, 3H), 2.83-2.61 (m, 2H), 1.84 (td, J=8.3, 3.9 Hz, 1H), 1.13 (dd, J=5.7, 4.0 Hz, 1H). LCMS $R_T$=4.58 min, m/z=314.1 [M+H]$^+$.

LCMS (2 to 98% acetonitrile in water+0.1% formic acid over 7 min) retention time 4.58 min, ESI+ found [M+H]= 314.1.

SFC condition: Column: Chiralcel OX (50 mm*4.6 mm, 3 μm); Condition: 0.1% NH$_4$OH MeOH; Begin B 25% End B 25%; Flow Rate (4 mL/min); Column temperature 40° C.

((1S,5S)-3-oxabicyclo[3.1.0]hexan-1-yl)((5S,7S)-7-fluoro-5-phenyl-6,7-dihydro-5H-pyrrolo[1,2-b][1,2,4]triazol-2-yl)methanone The diastereomeric mixture of (3-oxabicyclo[3.1.0]hexan-1-yl)((5S,7S)-7-fluoro-5-phenyl-6,7-dihydro-5H-pyrrolo[1,2-b][1,2,4]triazol-2-yl)methanone was purified by chiral SFC (retention time=0.914 min) to afford arbitrarily assigned ((1S,5S)-3-oxabicyclo[3.1.0]hexan-1-yl)((5S,7S)-7-fluoro-5-phenyl-6,7-dihydro-5H-pyrrolo[1,2-b][1,2,4]triazol-2-yl)methanone (0.5 mg, 0.05% yield). LCMS $R_T$=4.58 min, m/z=314.2 [M+H]$^+$. LCMS (2 to 98% acetonitrile in water+0.1% formic acid over 7 min) retention time 4.58 min, ESI+ found [M+H]=314.2.

SFC condition: Column: Chiralcel OX (50 mm*4.6 mm, 3 μm); Condition: 0.1% NH$_4$OH MeOH; Begin B 25% End B 25%; Flow Rate (4 mL/min); Column temperature 40° C.

Method 115

Examples 145 and 146

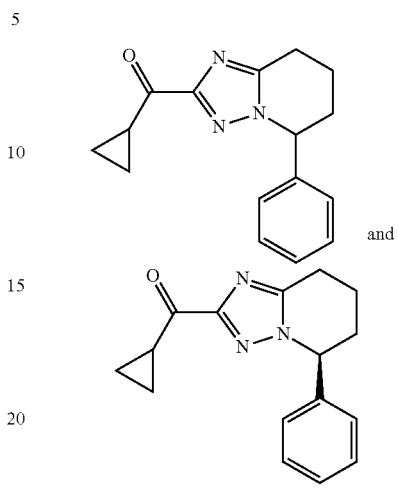

Cyclopropyl-(5-phenyl-5,6,7,8-tetrahydro-[1,2,4]triazolo[1,5-a]pyridin-2-yl)methanone and (S)-cyclopropyl(5-phenyl-5,6,7,8-tetrahydro-[1,2,4]triazolo[1,5-a]pyridin-2-yl)methanone

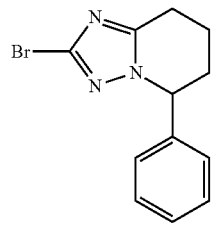 [SMILES: Brc1nc2n(n1)C(c1ccccc1)CCC2]

Step 1: 2-bromo-5-phenyl-5,6,7,8-tetrahydro-[1,2,4]triazolo[1,5-a]pyridine

Hydrogen was bubbled through a solution of 5-phenyl-[1,2,4]triazolo[1,5-a]pyridin-2-amine (0.90 g, 4.28 mmol) and platinum(IV) oxide (97.2 mg, 0.428 mmol) in acetic acid (43 mL). After 5 min, the needle was removed from the solution and the reaction was allowed to stir under a hydrogen atmosphere for 48 h (50% conversion). The reaction was filtered through a plug of celite using methanol. The filtrate was concentrated under reduced pressure and the crude residue was submitted to the next step without further purification.

To a solution of copper(II) bromide (1.72 g, 7.61 mmol) and tert-butyl nitrite (0.750 mL, 5.71 mmol) in acetonitrile (7.6 mL) at 60° C. was added the crude 5-phenyl-[1,2,4]triazolo[1,5-a]pyridin-2-amine (0.80 g, 3.81 mmol). The reaction was then heated at 75° C. for 1h. After cooling to rt, 1M HCl was added. The aqueous layer was extracted with isopropyl acetate. The combined organic layers were dried over sodium sulfate, concentrated, and the crude residue was purified by flash column chromatography (silica, 0% to 50% isopropyl acetate-heptane) to give 2-bromo-5-phenyl-5,6,7, 8-tetrahydro-[1,2,4]triazolo[1,5-a]pyridine (0.354 g, 1.27 mmol, 33% yield). LCMS $R_T$=1.15 min, m/z=277.8 [M=H]+.

Step 2: Cyclopropyl-(5-phenyl-5,6,7,8-tetrahydro-[1,2,4]triazolo[1,5-a]pyridin-2-yl)methanone (S)-cyclopropyl(5-phenyl-5,6,7,8-tetrahydro-[1,2,4]triazolo[1,5-a]pyridin-2-yl)methanone Isopropylmagnesium chloride (2.0 M in THF, 0.27 mL, 0.540 mmol) was added dropwise to a solution of 2-bromo-5-phenyl-5,6,7,8-tetrahydro-[1,2,4]triazolo[1,5-a]pyridine (50 mg, 0.180 mmol) and N-methoxy-N-methylcyclopropanecarboxamide (71 mg, 0.54 mmol) in THF (1.8 mL) at 0° C. over 15 min. After 1 h, saturated aqueous ammonium chloride was added. The aqueous layer was extracted with isopropyl acetate (2×20 mL). The combined organic layers were dried over sodium sulfate, concentrated and the crude residue was purified by prep TLC (100% isopropyl acetate) to give cyclopropyl-(5-phenyl-5,6,7,8-tetrahydro-[1,2,4]triazolo[1,5-a]pyridin-2-yl)methanone (20.9 mg, 0.078 mmol, 44% Yield). The crude material was further purified by prep SFC to provide arbitrarily assigned (S)-cyclopropyl(5-phenyl-5,6,7,8-tetrahydro-[1,2,4]triazolo[1,5-a]pyridin-2-yl)methanone.

cyclopropyl-(5-phenyl-5,6,7,8-tetrahydro-[1,2,4]triazolo[1,5-a]pyridin-2-yl)methanone: $^1$H NMR (400 MHz, DMSO-$d_6$) δ 7.41-7.27 (m, 3H), 7.12-7.04 (m, 2H), 5.62 (t, J=5.9 Hz, 1H), 3.12-2.83 (m, 3H), 2.46-2.35 (m, 1H), 2.13-2.01 (m, 1H), 1.93-1.81 (m, 2H), 1.04-0.92 (m, 4H). LCMS $R_T$=4.37 min, m/z=268.1 [M+H]+.

(S)-cyclopropyl(5-phenyl-5,6,7,8-tetrahydro-[1,2,4]triazolo[1,5-a]pyridin-2-yl)methanone: $^1$H NMR (400 MHz, DMSO-d) δ 7.42-7.23 (m, 3H), 7.12-7.04 (m, 2H), 5.62 (t, J=6.0 Hz, 1H), 3.12-2.85 (m, 3H), 2.45-2.35 (m, 1H), 2.13-2.00 (m, 1H), 1.96-1.82 (m, 2H), 1.05-0.93 (m, 4H). LCMS $R_T$=4.39 min, m/z=268.1 [M+H]+.

Prep SFC Information: Column: Chiralcel OJ 5 μm, (250×21.2 mm), Mobile Phase: Carbon Dioxide (A)/0.1% Ammonium Hydroxide in Methanol (B), Elution Program Isocratic: 15% B Flow Rate: 70 mL/min, Column Temperature: 30° C., Wavelength: 220 nm Method 116

Examples 147, 148 and 149

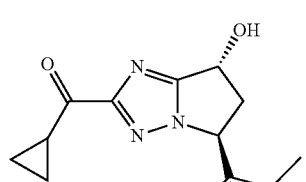

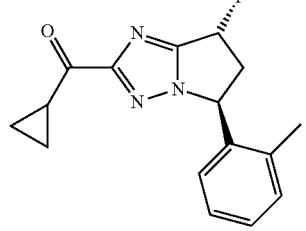

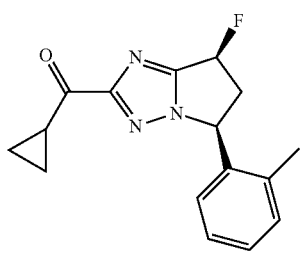

Cyclopropyl((5S,7R)-7-hydroxy-5-(o-tolyl)-6,7-dihydro-5H-pyrrolo[1,2-b][1,2,4]triazol-2-yl)methanone and cyclopropyl-[rac-(5S,7R)-7-fluoro-5-(o-tolyl)-6,7-dihydro-5H-pyrrolo[1,2-b][1,2,4]triazol-2-yl]methanone and cyclopropyl-[rac-(5S,7S)-7-fluoro-5-(o-tolyl)-6,7-dihydro-5H-pyrrolo[1,2-b][1,2,4]triazol-2-yl]methanone

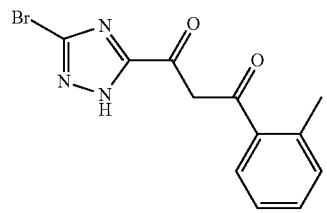 [SMILES: Cc1ccccc1C(=O)CC(=O)c1nc(Br)n[nH]1]

Step 1: 1-(3-bromo-H-1,2,4-triazol-5-yl)-3-(o-tolyl)propane-1,3-dione

Lithium bis(trimethylsilyl)amide (1.0 M in THF, 26 mL, 26 mmol) was added to a solution of 1-(o-tolyl)ethanone (1.9 mL, 15 mmol) and methyl 3-bromo-1H-1,2,4-triazole-5-carboxylate (2.0 g, 9.7 mmol) in THF (32 mL) at −78° C. After, the reaction was warmed to rt and stirred for 1h. The reaction was diluted with water and isopropyl acetate. A 5% citric acid solution (100 mL) was added and the aqueous layer was extracted with isopropyl acetate (3×100 mL). The combined organic layers were dried with sodium sulfate, concentrated and the crude residue was purified by flash column chromatography (silica, 0% to 80% isopropyl acetate-heptane) to give 1-(3-bromo-1H-1,2,4-triazol-5-yl)-3-(o-tolyl)propane-1,3-dione (2.03 g, 6.59 mmol, 68% yield). LCMS $R_T$=1.28 min, m/z=307.8 [M+H]+.

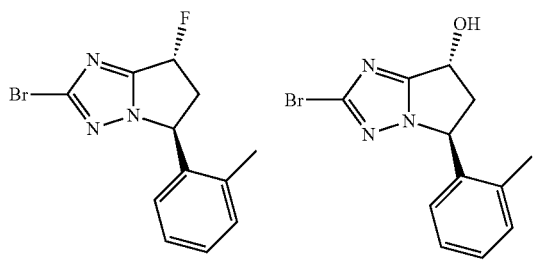

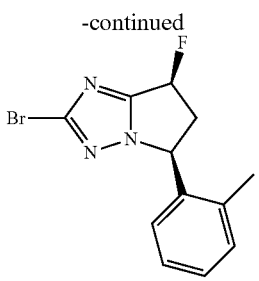

Step 2: (5S,7R)-2-bromo-7-fluoro-5-(o-tolyl)-6,7-dihydro-5H-pyrrolo[1,2-b][1,2,4]triazole and (5S,7R)-2-bromo-5-(o-tolyl)-6,7-dihydro-5H-pyrrolo[1,2-b][1,2,4]triazol-7-ol and (5S,7S)-2-bromo-7-fluoro-5-(o-tolyl)-6,7-dihydro-5H-pyrrolo[1,2-b][1,2,4]triazole Sodium borohydride (3.84 g, 97.4 mmol) was added to a solution of 1-(3-bromo-H-1,2,4-triazol-5-yl)-3-(o-tolyl)propane-1,3-dione (2.00 g, 6.49 mmol) in ethanol (130 mL) at rt. After 1h, a saturated aqueous solution of ammonium chloride was added and the reaction was concentrated under reduced pressure. The crude residue was dissolved in isopropyl acetate and water. The aqueous layer was extracted with isopropyl acetate (6×50 mL). The combined organic layers were dried over sodium sulfate, concentrated and the crude residue was submitted to the next step without further purification. LCMS $R_T$=0.96 min, m/z=311.8 [M+H]+. Trifluoroacetic acid (65 mL) was added to a solution of the crude residue in dichloromethane (65 mL) at rt. After 30 min, the reaction was concentrated under reduced pressure. The crude residue was dissolved in dichloromethane. Water and saturated aqueous sodium bicarbonate were added. The aqueous layer was extracted with dichloromethane (4×50 mL). The combined organic layers were dried over sodium sulfate, concentrated and the crude residue was submitted to the next step without further purification. LCMS $R_T$=1.08 min, m/z=293.8 [M+H]+ and LCMS $R_T$=0.98 min, m/z=293.8 [M+H]+. Diethylaminosulfur trifluoride (3.60 mL, 26.0 mmol) was added to a solution of the crude residue in dichloromethane (65 mL) at rt. After 30 min, saturated aqueous sodium bicarbonate was carefully added. The aqueous layer was extracted with dichloromethane (4×50 mL). The combined organic layers were dried over sodium sulfate, concentrated and the crude residue was purified by flash column chromatography (silica, 10% to 100% isopropyl acetate-heptane then 10% methanol-dichloromethane) to give a 2:1 mixture of (5S,7R)-2-bromo-5-(o-tolyl)-6,7-dihydro-5H-pyrrolo[1,2-b][1,2,4]triazol-7-ol and (5S,7R)-2-bromo-7-fluoro-5-(o-tolyl)-6,7-dihydro-5H-pyrrolo[1,2-b][1,2,4]triazole (0.470 g) and (5S,7S)-2-bromo-7-fluoro-5-(o-tolyl)-6,7-dihydro-5H-pyrrolo[1,2-b][1,2,4]triazole (0.350 g, 1.18 mmol, 18% yield).

(5S,7R)-2-bromo-7-fluoro-5-(o-tolyl)-6,7-dihydro-5H-pyrrolo[1,2-b][1,2,4]triazole: $^1$H NMR (400 MHz, DMSO-$d_6$) δ 7.30-7.18 (m, 3H), 6.88 (d, J=7.6 Hz, 1H), 6.30 (ddd, J=56.2, 6.8, 1.6 Hz, 1H), 6.11 (td, J=6.8, 3.8 Hz, 1H), 3.44-3.27 (m, 1H), 2.92 (ddt, J=27.9, 15.2, 6.5 Hz, 1H), 2.36 (s, 3H). LCMS $R_T$=1.26 min, m/z=295.8 [M+H]+.

(5S,7S)-2-bromo-7-fluoro-5-(o-tolyl)-6,7-dihydro-5H-pyrrolo[1,2-b][1,2,4]triazole: $^1$H NMR (400 MHz, DMSO-$d_6$) δ 7.38-7.09 (m, 3H), 6.78-6.69 (m, 1H), 6.20 (ddd, J=56.4, 7.2, 1.9 Hz, 1H), 5.95-5.80 (m, 1H), 3.69 (dddd, J=25.4, 15.4, 8.5, 7.2 Hz, 1H), 2.66-2.51 (m, 1H), 2.39 (s, 3H). LCMS $R_T$=1.25 min, m/z=295.7 [M+H]+.

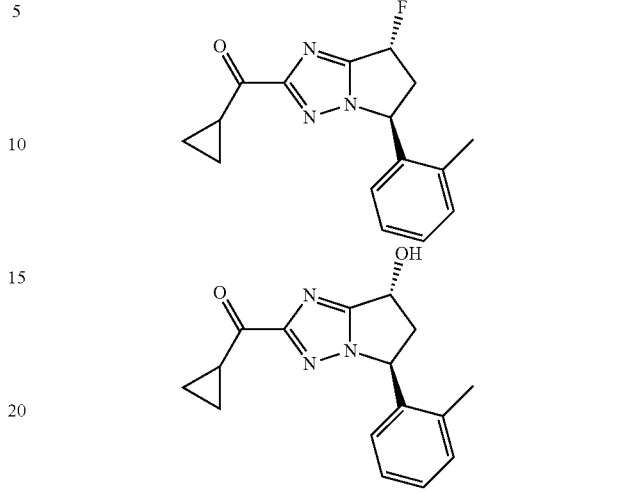

Step 3: Cyclopropyl((5S,7R)-7-fluoro-5-(o-tolyl)-6,7-dihydro-5H-pyrrolo[1,2-b][1,2,4]triazol-2-yl)methanone and cyclopropyl((5S,7R)-7-hydroxy-5-(o-tolyl)-6,7-dihydro-5H-pyrrolo[1,2-b][1,2,4]triazol-2-yl)methanone Isopropylmagnesium chloride (2.0 M in THF, 2.4 mL, 4.76 mmol) was added dropwise to a solution of a 2:1 mixture of (5S,7R)-2-bromo-5-(o-tolyl)-6,7-dihydro-5H-pyrrolo[1,2-b][1,2,4]triazol-7-ol and (5S,7R)-2-bromo-7-fluoro-5-(o-tolyl)-6,7-dihydro-5H-pyrrolo[1,2-b][1,2,4]triazole (0.470 g) and N-methoxy-N-methylcyclopropanecarboxamide (0.634 g, 4.76 mmol) in THF (15.9 mL) at 0° C. over 15 min. After 1h, saturated aqueous ammonium chloride was added. The aqueous layer was extracted with isopropyl acetate (2×20 mL). The combined organic layers were dried over sodium sulfate, concentrated and the crude residue was purified by prep HPLC/SFC to afford arbitrarily assigned cyclopropyl((5S,7R)-7-fluoro-5-(o-tolyl)-6,7-dihydro-5H-pyrrolo[1,2-b][1,2,4]triazol-2-yl)methanone (137 mg, 0.480 mmol) and cyclopropyl((5S,7R)-7-hydroxy-5-(o-tolyl)-6,7-dihydro-5H-pyrrolo[1,2-b][1,2,4]triazol-2-yl)methanone (33.8 mg, 0.119 mmol).

cyclopropyl((5S,7R)-7-fluoro-5-(o-tolyl)-6,7-dihydro-5H-pyrrolo[1,2-b][1,2,4]triazol-2-yl)methanone: $^1$H NMR (400 MHz, DMSO-$d_6$) δ 7.33-7.14 (m, 3H), 6.89 (d, J=7.5 Hz, 1H), 6.35 (ddd, J=56.2, 6.8, 1.6 Hz, 1H), 6.19 (td, J=6.9, 3.2 Hz, 1H), 3.59-3.27 (m, 1H), 3.11-2.91 (m, 2H), 2.38 (s, 3H), 1.14-1.01 (m, 4H). LCMS $R_T$=4.81 min, m/z=286.1 [M+H]+. Prep SFC Information: Column: Torus Diol 5 μm, (150×30 mm), Mobile Phase: Carbon Dioxide (A)/0.1% Ammonium Hydroxide in Methanol (B), Elution Program Isocratic: 5% B Flow Rate: 150 mL/min, Column Temperature: 25° C., Wavelength: 220 nm cyclopropyl((5S,7R)-7-hydroxy-5-(o-tolyl)-6,7-dihydro-5H-pyrrolo[1,2-b][1,2,4]triazol-2-yl)methanone: $^1$H NMR (400 MHz, DMSO-$d_6$) δ 7.30-7.13 (m, 3H), 7.01-6.94 (m, 1H), 6.25 (bs, 1H), 5.75 (dd, J=8.1, 5.8 Hz, 1H), 5.23 (dd, J=7.9, 4.6 Hz, 1H), 3.63-3.52 (m, 1H), 3.03-2.92 (m, 1H), 2.38 (s, 3H), 2.31-2.14 (m, 1H), 1.09-0.96 (m, 4H). LCMS RT=4.08 min, m/z=284.1 [M+H]+.

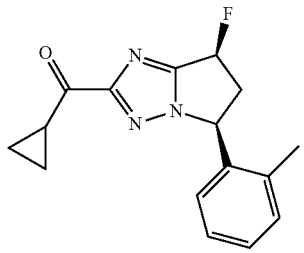 [SMILES: Cc1ccccc1[C@@H]1C[C@H](F)c2nc(C(=O)C3CC3)nn21]

Step 4: Cyclopropyl((5S,7S)-7-fluoro-5-(o-tolyl)-6, 7-dihydro-5H-pyrrolo[1,2-b][1,2,4]triazol-2-yl) methanone Isopropylmagnesium chloride (2.0 M in THF, 1.80 mL, 3.55 mmol) was added dropwise to a solution of (5S,7S)-2-bromo-7-fluoro-5-(o-tolyl)-6,7-dihydro-5H-pyrrolo[1,2-b][1,2,4]triazole (0.350 g, 1.18 mmol) and N-methoxy-N-methylcyclopropanecarboxamide (0.472 g, 3.55 mmol) in THF (11.8 mL) at 0° C. over 15 min. After 1h, saturated aqueous ammonium chloride was added. The aqueous layer was extracted with isopropyl acetate (2×20 mL). The combined organic layers were dried over sodium sulfate, concentrated and the crude residue was purified by prep SFC to afford arbitrarily assigned cyclopropyl((5S,7S)-7-fluoro-5-(o-tolyl)-6,7-dihydro-5H-pyrrolo[1,2-b][1,2,4]triazol-2-yl) methanone (0.179 g, 0.627 mmol, 53% yield).

$^1$H NMR (400 MHz, DMSO-d$_6$) δ 7.35-7.14 (m, 3H), 6.76-6.66 (m, 1H), 6.26 (ddd, J=56.3, 7.2, 1.9 Hz, 1H), 5.94 (ddd, J=8.5, 6.6, 3.2 Hz, 1H), 3.94-3.48 (m, 1H), 3.01 (ddt, J=7.6, 6.1, 5.2 Hz, 1H), 2.66 (dddd, J=26.8, 15.1, 3.2, 2.0 Hz, 1H), 2.42 (s, 3H), 1.18-0.99 (m, 4H). LCMS R$_T$=4.80 min, m/z=286.1 [M+H]$^+$.

Prep SFC Information: Column: Torus Diol 5 μm, (150×30 mm), Mobile Phase: Carbon Dioxide (A)/0.1% Ammonium Hydroxide in Methanol (B), Elution Program Isocratic: 5% B Flow Rate: 150 mL/min, Column Temperature: 25° C., Wavelength: 220 nm.

Method 117

Examples 150 and 151

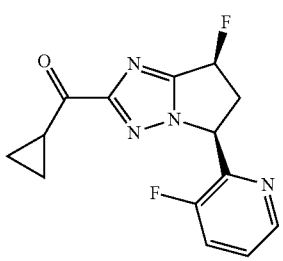

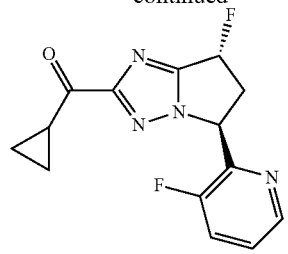

Cyclopropyl((5S,7S)-7-fluoro-5-(3-fluoropyridin-2-yl)-6,7-dihydro-5H-pyrrolo[1,2-b][1,2,4]triazol-2-yl) methanone and cyclopropyl((5S,7R)-7-fluoro-5-(3-fluoropyridin-2-yl)-6,7-dihydro-5H-pyrrolo[1,2-b][1,2,4]triazol-2-yl)methanone

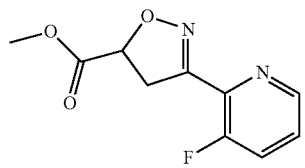 [SMILES: COC(=O)C1CC(c2ncccc2F)=NO1]

Step 1: Methyl 3-(3-fluoropyridin-2-yl)-4,5-dihydroisoxazole-5-carboxylate

Triethylamine (9.8 mL, 70 mmol) was added to a solution of (2Z)-3-fluoro-N-hydroxy-pyridine-2-carboximidoyl chloride (12.0 g, 68.7 mmol) and methyl acrylate (6.3 mL, 70 mmol) in dichloromethane (460 mL) at 0° C. The reaction was warmed to rt and stirred for an additional 4h. Water was added and the aqueous layer was extracted with dichloromethane (3×200 mL). The combined organic layers were dried with sodium sulfate, concentrated and the crude residue was purified by flash column chromatography (silica, 0% to 100% isopropyl acetate-heptane) to give methyl 3-(3-fluoro-2-pyridyl)-4,5-dihydroisoxazole-5-carboxylate (10.6 g, 47.3 mmol, 68% Yield).

For the preparation of (2Z)-3-fluoro-N-hydroxy-pyridine-2-carboximidoyl chloride see: WO2006/114706, 2006, A1. LCMS R$_T$=0.89 min, m/z=224.8 [M+H]+.

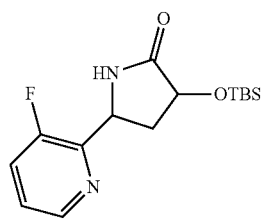 [SMILES: CC(C)(C)[Si](C)(C)OC1CC(c2ncccc2F)NC1=O]

Step 2: 3-((tert-butyldimethylsilyl)oxy)-5-(3-fluoropyridin-2-yl)pyrrolidin-2-one Nickel(II) chloride hexa hydrate (21.6 g, 89.2 mmol) and methyl 3-(3-fluoro-2-pyridyl)-4,5-dihydroisoxazole-5-carboxylate (10.0 g, 44.6 mmol) were dissolved in methanol (372 mL) and cooled to −30° C. under nitrogen. Sodium borohydride (8.79 g, 223 mmol) was added portion-wise over 10 min. After, the reaction was warmed to rt and stirred for an additional 1h. Ammonia hydroxide (100 ml) was added and the reaction was allowed to stir at rt overnight. The precipitate was filtered off. The filtrate was concentrated and the crude residue was submitted to the next step without further purification. LCMS $R_T$=0.75 min, m/z=196.8 [M=H]+. 4-Dimethylaminopyridine (0.545 g, 4.46 mmol) was added to a solution of the crude substrate and imidazole (9.11 g, 134 mmol) and tert-butyldimethylchlorosilane (13.9 g, 89.2 mmol) in dimethyl sulfoxide (89 mL) at 40° C. After 24 h, the reaction as diluted with water and isopropyl acetate. The aqueous layer was extracted with isopropyl acetate (4×200 mL). The combined organic layers were dried with sodium sulfate, concentrated and the crude residue was purified by flash column chromatography (silica, 0% to 100% isopropyl acetate-heptane) to give 3-[tert-butyl(dimethyl)silyl]oxy-5-(3-fluoro-2-pyridyl)pyrrolidin-2-one (9.6 g, 31 mmol, 69% yield).

$^1$H NMR (400 MHz, Chloroform-d) 1:1 mixture of diastereomers δ 8.41-8.36 (m, 1H), 7.45-7.35 (m, 1H), 7.31-7.22 (m, 1H), 6.21 (s, 0.5H), 5.87 (s, 0.5H), 5.18-5.10 (m, 0.5H), 4.90 (ddd, J=9.5, 6.3, 1.3 Hz, 0.5H), 4.59-4.47 (m, 1H), 3.01-2.90 (m, 0.5H), 2.61 (ddd, J=13.0, 7.5, 3.7 Hz, 0.5H), 2.48 (ddd, J=13.2, 8.1, 6.5 Hz, 0.5H), 2.21 (dt, J=12.3, 9.5 Hz, 0.5H), 0.93 (s, 4.5H), 0.91 (s, 4.5H), 0.22-0.13 (m, 6H). LCMS $R_T$=1.38 min, m/z=311.0 [M+H]+.

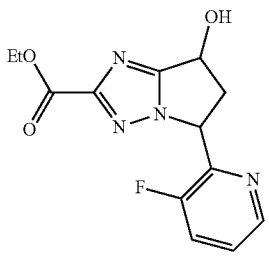 [SMILES: CCOC(=O)c1nc2n(n1)C(c1ncccc1F)CC2O]

Step 3: Ethyl 5-(3-fluoropyridin-2-yl)-7-hydroxy-6,7-dihydro-5H-pyrrolo[1,2-b][1,2,4]triazole-2-carboxylate Sodium hydride (60% in oil, 0.390 g, 9.7 mmol) was added to a solution of 3-[tert-butyl(dimethyl)silyl]oxy-5-(3-fluoro-2-pyridyl)pyrrolidin-2-one (2.0 g, 6.4 mmol) in N,N-dimethylformamide (64 mL) at 0° C. After 30 min, O-diphenylphosphorylhydroxylamine (2.3 g, 9.7 mmol) was added. The reaction was warmed to rt and stirred for 16h. The reaction was filtered and the filtrate was evaporated under reduced pressure. The crude residue was submitted to the next reaction without further purification. LCMS $R_T$=1.34 min, m/z=326.0 [M+H]+ and LCMS $R_T$=1.30 min, m/z=326.0 [M+H]+. Ethyl 2-ethoxy-2-iminoacetate (2.50 g, 16 mmol) and the crude residue were dissolved in ethanol (23 mL) and the reaction was heated at 90° C. for 16h. After cooling to rt, the reaction was filtered and the filtrate was concentrated under reduced pressure. The crude residue was submitted to the next reaction without further purification. LCMS $R_T$=1.38 min, m/z=425.0 [M+H]$^+$ and LCMS $R_T$=1.34 min, m/z=425.0 [M+H]+. p-Toluenesulfonic acid monohydrate (1.5 g, 7.7 mmol) was added to a solution of the crude residue in toluene (25 mL). The reaction was heated at 120° C. for 16 h. After cooling to rt the reaction was filtered and the filtrate was concentrated under reduced pressure. The crude residue was submitted to the next reaction without further purification. LCMS $R_T$=1.55 min, m/z=407.0 [M+H] and LCMS $R_T$=1.50 min, m/z=407.1 [M+H]+. Tetrabutylammonium fluoride (1.0 M in THF, 6.4 mL, 6.4 mmol) was added to a solution of the crude residue in THF (21 mL) and the reaction was heated at 40° C. for 1 h. After cooling to rt saturated aqueous ammonium chloride was added. The aqueous layer was extracted with isopropyl acetate (4×50 mL). The combined organic layers were dried over sodium sulfate, concentrated and the crude residue was purified by flash column chromatography (silica 0% to 10% methanol/dichloromethane) to give ethyl 5-(3-fluoro-2-pyridyl)-7-hydroxy-6,7-dihydro-5H-pyrrolo[1,2-b][1,2,4]triazole-2-carboxylate (0.800 g, 2.74 mmol, 42% yield). $^1$H NMR (400 MHz, Chloroform-d) 1:1 mixture of diastereomers δ 8.41-8.29 (m, 1H), 7.63-7.26 (m, 2H), 6.12 (dd, J=8.1, 4.4 Hz, 0.5H), 6.07 (d, J=8.2 Hz, 0.5H), 5.64 (dd, J=7.6, 4.0 Hz, 0.5H), 5.21 (d, J=6.5 Hz, 0.5H), 4.51-4.38 (m, 2H), 3.45 (ddd, J=14.7, 8.3, 6.6 Hz, 0.5H), 3.29 (ddd, J=13.8, 7.5, 4.3 Hz, 0.5H), 3.10 (ddd, J=13.8, 8.1, 4.0 Hz, 0.5H), 2.74 (d, J=14.4 Hz, 0.5H), 1.40 (t, J=7.1 Hz, 3H). LCMS $R_T$=0.89 min, m/z=292.9 [M+H]$^+$.

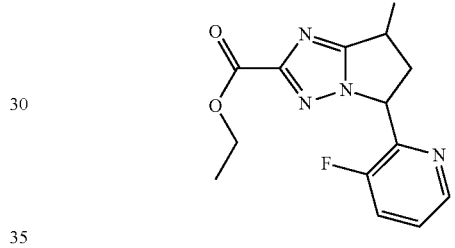

Step 4: Ethyl 7-fluoro-5-(3-fluoropyridin-2-yl)-6,7-dihydro-5H-pyrrolo[1,2-b][1,2,4]triazole-2-carboxylate Diethylaminosulfur trifluoride (1.53 mL, 10.9 mmol) was added to a solution of ethyl 5-(3-fluoro-2-pyridyl)-7-hydroxy-6,7-dihydro-5H-pyrrolo[1,2-b][1,2,4]triazole-2-carboxylate (0.800 g, 2.74 mmol) in dichloromethane (27.4 mL) at rt. After 20 min saturated aqueous sodium bicarbonate was added. The aqueous layer was extracted with dichloromethane (4×30 mL). The combined organic layers were dried with sodium sulfate, concentrated and the crude residue was purified by flash column chromatography (silica, 0% to 10% DCM-methanol) to give ethyl 7-fluoro-5-(3-fluoro-2-pyridyl)-6,7-dihydro-5H-pyrrolo[1,2-b][1,2,4]triazole-2-carboxylate (0.800 g, 2.72 mmol, 99% Yield). LCMS $R_T$=1.01 min, m/z=294.8 [M+H]$^+$.

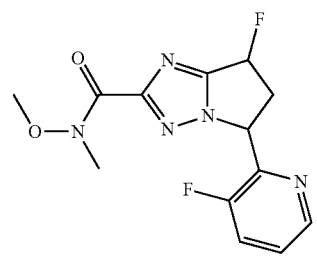 [SMILES: CON(C)C(=O)c1nc2n(n1)C(c1ncccc1F)CC2F]

Step 5: 7-fluoro-5-(3-fluoropyridin-2-yl)-N-methoxy-N-methyl-6,7-dihydro-5H-pyrrolo[1,2-b][1,2,4]triazole-2-carboxamide Lithium hydroxide monohydrate (1.20 g, 27 mmol) was added to a solution of ethyl 7-fluoro-5-(3-fluoro-2-pyridyl)-6,7-dihydro-5H-pyrrolo[1,2-b][1,2,4]triazole-2-carboxylate (0.80 g, 2.7 mmol) in THF (9.1 mL), water (4.5 mL), and methanol (9.1 mL) at rt. After 1h, the reaction was neutralized with 1 M HCl (27 mL). The reaction was extracted with isopropyl acetate (10×20 mL). The combined organic layers were dried with sodium sulfate, concentrated and the crude residue was submitted to the next reaction without further purification. LCMS $R_T$=0.83 min, m/z=266.8 [M+H]$^+$. Triethylamine (1.5 mL, 11 mmol), was added to a solution of 1-(3-dimethylaminopropyl)-3-ethylcarbodiimide hydrochloride (0.790 g, 4.1 mmol), 1-hydroxybenzotriazole (0.370 g, 2.7 mmol), N,O-dimethylhydroxylamine hydrochloride (0.540 g, 5.4 mmol) and the crude residue in N,N-dimethylformamide (9.1 mL) at rt. After 2h, the reaction was filtered and the filtrate was concentrated under reduced pressure. The crude residue was purified by flash column chromatography (0% to 10% methanol-dichloromethane) to give 7-fluoro-5-(3-fluoro-2-pyridyl)-N-methoxy-N-methyl-6,7-dihydro-5H-pyrrolo[1,2-b][1,2,4]triazole-2-carboxamide (0.224 g, 0.724 mmol, 27% Yield). LCMS $R_T$=0.85 min, m/z=309.9 [M+H]$^+$.

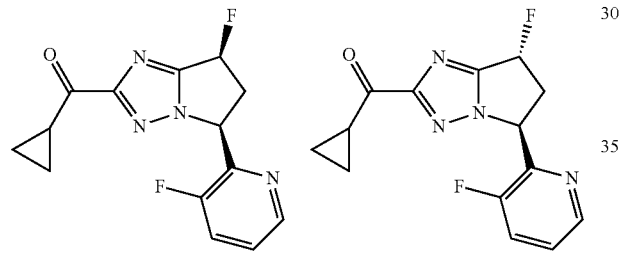

Step 6: Cyclopropyl((5S,7S)-7-fluoro-5-(3-fluoropyridin-2-yl)-6,7-dihydro-5H-pyrrolo[1,2-b][1,2,4]triazol-2-yl)methanone and cyclopropyl((5S,7R)-7-fluoro-5-(3-fluoropyridin-2-yl)-6,7-dihydro-5H-pyrrolo[1,2-b][1,2,4]triazol-2-yl)methanone Cyclopropylmagnesium bromide (0.5 M in THF, 5.7 mL, 2.85 mmol) was added to a solution of 7-fluoro-5-(3-fluoro-2-pyridyl)-N-methoxy-N-methyl-6,7-dihydro-5H-pyrrolo[1,2-b][1,2,4]triazole-2-carboxamide (0.220 g, 0.711 mmol) in THF (2.4 mL) at −50° C. After 20 min, the reaction was placed in a rt bath and stirred for 3 min. Water was added and the reaction was diluted with isopropyl acetate. The aqueous layer was extracted with isopropyl acetate (4×20 mL). The combined organic layers were dried with sodium sulfate, concentrated and the crude residue was purified by prep SFC to afford arbitrarily assigned cyclopropyl((5S,7S)-7-fluoro-5-(3-fluoropyridin-2-yl)-6,7-dihydro-5H-pyrrolo[1,2-b][1,2,4]triazol-2-yl)methanone (16.59 mg, 0.057 mmol, 8% Yield) and cyclopropyl((5S,7R)-7-fluoro-5-(3-fluoropyridin-2-yl)-6,7-dihydro-5H-pyrrolo[1,2-b][1,2,4]triazol-2-yl)methanone (23.7 mg, 0.082 mmol, 12% Yield).

cyclopropyl((5S,7S)-7-fluoro-5-(3-fluoropyridin-2-yl)-6,7-dihydro-5H-pyrrolo[1,2-b][1,2,4]triazol-2-yl)methanone: $^1$H NMR (400 MHz, DMSO-d$_6$) δ 8.45 (dt, J=4.6, 1.5 Hz, 1H), 7.89 (ddd, J=10.0, 8.4, 1.3 Hz, 1H), 7.57 (dt, J=8.6, 4.4 Hz, 1H), 6.26 (ddd, J=56.6, 7.7, 2.7 Hz, 1H), 6.10-5.99 (m, 1H), 3.74 (dddd, J=19.7, 14.7, 8.5, 7.7 Hz, 1H), 3.16-2.84 (m, 2H), 1.18-0.93 (m, 4H). LCMS $R_T$=3.64 min, m/z=291.1 [M+H]+.

Prep SFC Information: Column: Chiralcel OJ 5 μm, (250×21.2 mm), Mobile Phase: Carbon Dioxide (A)/Methanol (B), Elution Program Isocratic: 15% B Flow Rate: 70 mL/min, Column Temperature: 35° C., Wavelength: 261 nm cyclopropyl((5S,7R)-7-fluoro-5-(3-fluoropyridin-2-yl)-6,7-dihydro-5H-pyrrolo[1,2-b][1,2,4]triazol-2-yl)methanone: $^1$H NMR (400 MHz, DMSO-d$_6$) δ 8.42 (dt, J=4.6, 1.5 Hz, 1H), 7.89 (ddd, J=10.0, 8.5, 1.3 Hz, 1H), 7.56 (dt, J=8.6, 4.4 Hz, 1H), 6.58-6.32 (m, 2H), 3.55-3.19 (m, 2H), 2.95 (tt, J=7.5, 4.9 Hz, 1H), 1.13-0.98 (m, 4H). LCMS $R_T$=3.82 min, m/z=291.1 [M+H]+.

Prep SFC Information: Column: Chiralcel OJ 5 μm, (250×21.2 mm), Mobile Phase: Carbon Dioxide (A)/Methanol (B), Elution Program Isocratic: 15% B Flow Rate: 70 mL/min, Column Temperature: 35° C., Wavelength: 261 nm.

Method 118

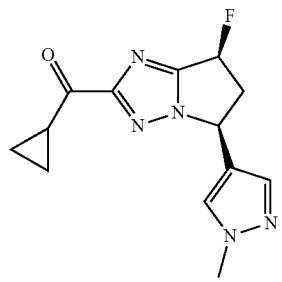 [SMILES: Cn1cc([C@@H]2C[C@H](F)c3nc(C(=O)C4CC4)nn32)cn1]

Example 152

Cyclopropyl((5S,7S)-7-fluoro-5-(1-methyl-1H-pyrazol-4-yl)-6,7-dihydro-5H-pyrrolo[1,2-b][1,2,4]triazol-2-yl)methanone

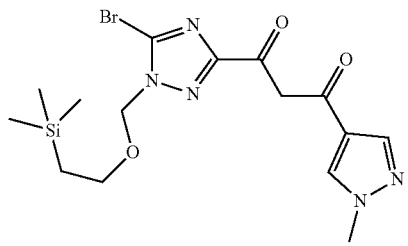 [SMILES: Cn1cc(C(=O)CC(=O)c2nc(Br)n(COCC[Si](C)(C)C)n2)cn1]

Step 1: 1-(5-bromo-1-((2-(trimethylsilyl)ethoxy)methyl)-1H-1,2,4-triazol-3-yl)-3-(1-methyl-1H-pyrazol-4-yl)propane-1,3-dione Lithium bis(trimethylsilyl)amide (1.0 M in THF, 9.5 mL, 9.5 mmol) was added to a solution of methyl 5-bromo-1-(2-trimethylsilylethoxymethyl)-1,2,4-triazole-3-carboxylate (2.0 g, 5.9 mmol) and 1-(1-methylpyrazol-4-yl)ethanone (1.20 g, 9.5 mmol) in THF (40 mL) at 0° C. After, the reaction was warmed to rt and stirred for 1 h. The reaction was diluted with water and isopropyl acetate. A 5% citric acid solution was added and the aqueous layer was extracted with isopropyl acetate (4×100 mL). The combined organic layers were dried with sodium sulfate, concentrated and the crude residue was purified by flash column chromatography (silica, 0% to 100% isopropyl acetate-heptane) to give 1-[5-bromo-1l-(2-trimethylsilylethoxymethyl)-1,2,4-triazol-3-yl]-3-(1-methylpyrazol-4-yl)propane-1,3-dione (2.40 g, 5.60 mmol, 94% yield). LCMS $R_T$=1.57 min, m/z=427.9 [M+H]+.

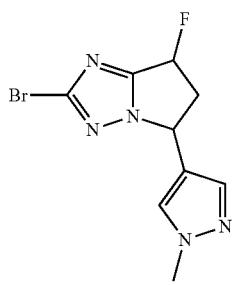 [SMILES: Cn1cc(C2CC(F)c3nc(Br)nn32)cn1]

Step 2: 2-bromo-7-fluoro-5-(1-methyl-1H-pyrazol-4-yl)-6,7-dihydro-5H-pyrrolo[1,2-b][1,2,4]triazole Sodium borohydride (3.30 g, 84 mmol) was added to a solution of 1-[5-bromo-1-(2-trimethylsilylethoxymethyl)-1,2,4-triazol-3-yl]-3-(1-methylpyrazol-4-yl)propane-1,3-dione (2.4 g, 5.6 mmol) in ethanol (110 mL) at rt. After 30 min, the reaction was quenched with saturated aqueous ammonium chloride and the volatiles were removed under reduced pressure. The crude residue was dissolved in isopropyl acetate and diluted with water. The aqueous layer was extracted with isopropyl acetate (4×100 mL). The combined organic layers were dried with sodium sulfate, concentrated, and the crude residue was submitted to the next step without further purification. LCMS $R_T$=1.17 min, m/z=431.9 [M+H]+. Trifluoroacetic acid (56 mL) and dichloromethane (56 mL) were added to the crude residue and the reaction was heated at 50° C. for 16 h. After cooling to rt, the reaction was concentrated under reduced pressure. The crude residue was dissolved in dichloromethane and a saturated aqueous of sodium bicarbonate was added. The aqueous layer was extracted with dichloromethane (4×100 mL). The combined organic layers were dried with sodium sulfate, concentrated and the crude residue was submitted to the next step without further purification. LCMS $R_T$=0.82 min, m/z=283.8 [M+H]+. Diethylaminosulfur trifluoride (3.1 mL, 22 mmol) was added to a solution of the crude residue in dichloromethane (56 mL) at rt. After 20 min, the reaction sodium bicarbonate (5.0 g) was added. The reaction was diluted with water and isopropyl acetate. Brine was added and the aqueous layer was extracted with isopropyl acetate (4×100 mL). The combined organic layers were dried with sodium sulfate, concentrated and the crude residue was purified by flash column chromatography (50% to 100% isopropyl acetate-heptane) to give 2-bromo-7-fluoro-5-(1-methylpyrazol-4-yl)-6,7-dihydro-5H-pyrrolo[1,2-b][1,2,4]triazole (0.379 g, 1.32 mmol, 24% yield). $^1$H NMR (400 MHz, DMSO-$d_6$) 1:1 mixture of diastereomers δ 7.84 (s, 0.5H), 7.78 (s, 0.5H), 7.52 (d, J=0.8 Hz, 0.5H), 7.45 (d, J=0.8 Hz, 0.5H), 6.33-6.03 (m, 1H), 5.88-5.74 (m, 0.5H), 5.63-5.51 (m, 0.5H), 3.83 (s, 1.5H), 3.82 (s, 1.5H), 3.65-3.47 (m, 0.5H), 3.25-3.00 (m, 1H), 2.81-2.64 (m, 0.5H). LCMS $R_T$=0.92 min, m/z=285.8 [M+H]+.

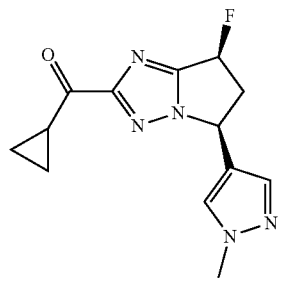 [SMILES: Cn1cc([C@@H]2C[C@H](F)c3nc(C(=O)C4CC4)nn32)cn1]

Step 3: Cyclopropyl((5S,7S)-7-fluoro-5-(1-methyl-H-pyrazol-4-yl)-6,7-dihydro-5H-pyrrolo[1,2-b][1,2,4]triazol-2-yl)methanone Isopropylmagnesium chloride (2.0 M in THF, 2.0 mL, 3.97 mmol) was added to a solution of 2-bromo-7-fluoro-5-(1-methylpyrazol-4-yl)-6,7-dihydro-5H-pyrrolo[1,2-b][1,2,4]triazole (0.379 g, 1.32 mmol) and N-methoxy-N-methylcyclopropanecarboxamide (0.529 g, 3.97 mmol) in THF (13.2 mL) at 0° C. After 5 min, the reaction was warmed to rt and stirred for an additional 1h. Water was added and the reaction was diluted with isopropyl acetate. Brine was added and the aqueous layer was extracted with isopropyl acetate (4×50 mL). The combined organic layers were dried with sodium sulfate, concentrated and the crude residue was purified by prep SFC to afford arbitrarily assigned cyclopropyl((5S,7S)-7-fluoro-5-(1-methyl-1H-pyrazol-4-yl)-6,7-dihydro-5H-pyrrolo[1,2-b][1,2,4]triazol-2-yl)methanone (44.23 mg, 0.161 mmol, 12% yield). $^1$H NMR (400 MHz, DMSO-$d_6$) δ 7.80 (d, J=0.8 Hz, 1H), 7.48 (d, J=0.8 Hz, 1H), 6.21 (ddd, J=56.4, 7.0, 2.4 Hz, 1H), 5.66 (ddd, J=8.2, 6.0, 3.6 Hz, 1H), 3.81 (s, 3H), 3.73-3.55 (m, 1H), 2.99 (tt, J=7.5, 4.9 Hz, 1H), 2.80 (dddd, J=26.4, 14.9, 3.7, 2.4 Hz, 1H), 1.14-0.95 (m, 4H). LCMS $R_T$=3.10 min, m/z=276.1 [M+H]+.

Prep SFC Information: Column: Whelko-01 5 µm, (150× 21.2 mm), Mobile Phase: Carbon Dioxide (A)/0.1% Ammonium Hydroxide in Methanol (B), Elution Program Isocratic: 35% B Flow Rate: 70 mL/min, Column Temperature: 40° C., Wavelength: 220 nm.

Method 119

Example 153

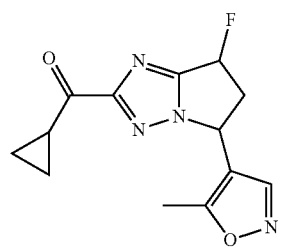

313

Cyclopropyl(7-fluoro-5-(5-methylisoxazol-4-yl)-6,7-dihydro-5H-pyrrolo[1,2-b][1,2,4]triazol-2-yl)methanone

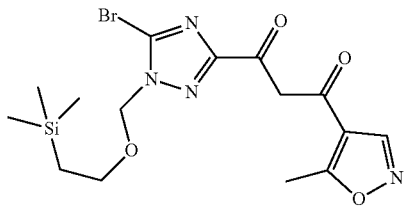 [SMILES: Cc1oncc1C(=O)CC(=O)c1nc(Br)n(COCC[Si](C)(C)C)n1]

Step 1: 1-(5-bromo-1-((2-(trimethylsilyl)ethoxy)methyl)-1H-1,2,4-triazol-3-yl)-3-(5-methylisoxazol-4-yl)propane-1,3-dione Lithium bis(trimethylsilyl)amide (1.0 M in THF, 7.1 mL, 7.1 mmol) was added to a solution of methyl 5-bromo-1-(2-trimethylsilylethoxymethyl)-1,2,4-triazole-3-carboxylate (1.5 g, 4.5 mmol) and 1-(5-methylisoxazol-4-yl)ethanone (0.890 g, 7.1 mmol) in THF (30 mL) at 0° C. After 5 min, the reaction was warmed to rt and stirred for an additional 30 min. Water was added and the reaction was diluted with isopropyl acetate. A 10% aqueous citric acid solution was added to adjust the pH to 2. The aqueous layer was extracted with isopropyl acetate (2×200 mL). The combined organic layers were dried with sodium sulfate, concentrated and the crude residue was purified by flash column chromatography (silica 0% to 100% isopropyl acetate-heptane) to give 1-[5-bromo-1-(2-trimethylsilylethoxymethyl)-1,2,4-triazol-3-yl]-3-(5-methylisoxazol-4-yl)propane-1,3-dione (1.6 g, 3.7 mmol, 84% Yield). LCMS $R_T$=1.35 min, m/z=428.9 [M+H]$^+$.

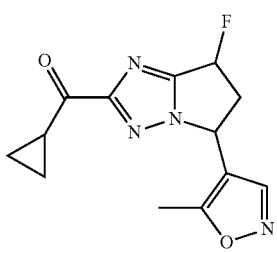 [SMILES: Cc1oncc1C1CC(F)c2nc(C(=O)C3CC3)nn21]

Step 2: Cyclopropyl(7-fluoro-5-(5-methylisoxazol-4-yl)-6,7-dihydro-5H-pyrrolo[1,2-b][1,2,4]triazol-2-yl)methanone Sodium borohydride (3.30 g, 84 mmol) was added to a solution of 1-[5-bromo-1-(2-trimethylsilylethoxymethyl)-1,2,4-triazol-3-yl]-3-(5-methylisoxazol-4-yl)propane-1,3-dione (2.4 g, 5.6 mmol) in ethanol (110 mL) at rt. After 30 min, the reaction was quenched with saturated aqueous ammonium chloride. The volatiles were removed under reduced pressure. The crude residue was dissolved in isopropyl acetate and diluted with water. The aqueous layer was extracted with isopropyl acetate (4×100 mL). The combined organic layers were dried with sodium sulfate, concentrated and the crude residue was submitted to the next step without further purification. LCMS $R_T$=1.27 min, m/z=432.9 [M+H]$^+$. Sulfuric acid (10 mL) was added to the crude residue and the reaction was heated at 100° C. for 2h. After cooling to rt, the reaction was diluted with water. Sodium hydroxide (3 M in water) was added until the aqueous layer became basic. The aqueous layer was extracted with isopropyl acetate (3×100 mL). The combined organic layers were dried with sodium sulfate, concentrated and the crude residue was submitted to the next step without further purification. Diethylaminosulfur trifluoride (0.470 mL, 3.37 mmol) was added to a solution of the crude residue in dichloromethane (8.4 mL) at rt. After 20 min, sodium bicarbonate (2.0 g) was added. The reaction was diluted with water and isopropyl acetate. Brine was added and the aqueous layer was extracted with isopropyl acetate (4×20 mL). The combined organic layers were dried with sodium sulfate, concentrated and the crude residue (0.110 g, 0.383 mmol) was submitted to the next reaction without further purification. LCMS $R_T$=1.02 min, m/z=286.8 [M+H]+. Isopropylmagnesium chloride (2.0 M in THF, 0.38 mL, 0.766 mmol) was added to a solution of the crude residue and N-methoxy-N-methylcyclopropanecarboxamide (0.153 g, 1.15 mmol) in THF (3.8 mL) at 0° C. After 5 min, the reaction was warmed to rt and stirred for an additional 20 min. Water was added and the reaction was diluted with isopropyl acetate. The aqueous layer was extracted with isopropyl acetate (4×20 mL). The combined organic layers were dried with sodium sulfate, concentrated and the crude residue was purified by prep SFC to give diasteromeric mixture of cyclopropyl(7-fluoro-5-(5-methylisoxazol-4-yl)-6,7-dihydro-5H-pyrrolo[1,2-b][1,2,4]triazol-2-yl)methanone (1.26 mg, 0.0046 mmol). LCMS $R_T$=3.63 min, m/z=277.1 [M+H]$^+$.

Prep SFC Information: Column: Chiracel OX 5 μm, (150×21.2 mm), Mobile Phase: Carbon Dioxide (A)/Methanol (B) Elution Program Isocratic: 20% B Flow Rate: 70 mL/min, Column Temperature: 40° C., Wavelength: 220 nm Method 120

Examples 154 and 155

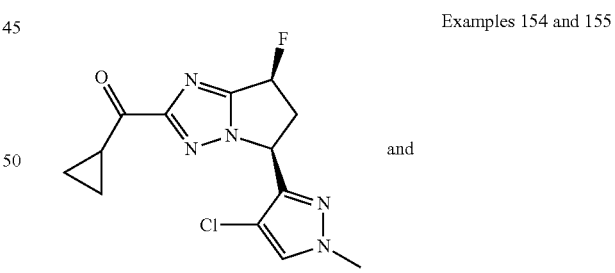

and

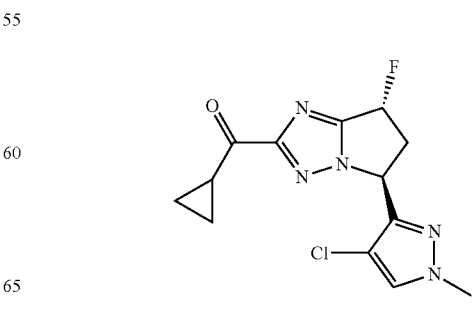

((5S,7S)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone and ((5S,7R)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone

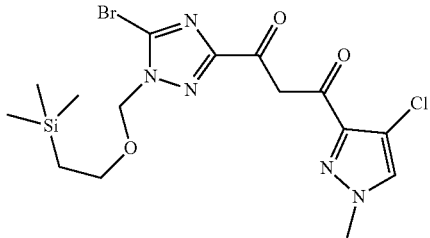 [SMILES: Cn1cc(Cl)c(C(=O)CC(=O)c2nc(Br)n(COCC[Si](C)(C)C)n2)n1]

Step 1: 1-(5-bromo-1-((2-(trimethylsilyl)ethoxy)methyl)-1H-1,2,4-triazol-3-yl)-3-(4-chloro-1-methyl-1H-pyrazol-3-yl)propane-1,3-dione Lithium bis(trimethylsilyl)amide (1.0 M in THF, 5.9 mL, 5.9 mmol) was added to a solution of methyl 5-bromo-1-(2-trimethylsilylethoxymethyl)-1,2,4-triazole-3-carboxylate (2.0 g, 5.9 mmol) and 1-(4-chloro-1-methyl-pyrazol-3-yl)ethanone (0.940 g, 5.9 mmol) in THF (40 mL) at 0° C. After 5 min, the reaction was warmed to rt and stirred for an additional 30 min. Water was added and the reaction was diluted with isopropyl acetate. A 10% aqueous citric acid solution was added to adjust the pH to 2. The aqueous layer was extracted with isopropyl acetate (2×200 mL). The combined organic layers were dried with sodium sulfate, concentrated and the crude residue was purified by flash column chromatography (silica 0% to 100% isopropyl acetate-heptane) to give 1-[5-bromo-1-(2-trimethylsilylethoxymethyl)-1,2,4-triazol-3-yl]-3-(4-chloro-1-methyl-pyrazol-3-yl)propane-1,3-dione (2.40 g, 5.19 mmol, 87% yield). LCMS $R_T$=1.68 min, m/z=461.9[M+H]$^+$.

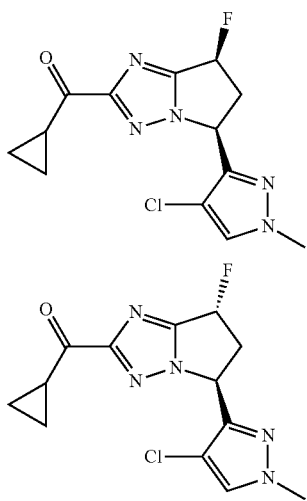

Step 2: ((5S,7S)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone and ((5S,7R)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone Sodium borohydride (3.10 g, 78 mmol) was added to a solution of 1-[5-bromo-1-(2-trimethylsilylethoxymethyl)-1,2,4-triazol-3-yl]-3-(4-chloro-1-methyl-pyrazol-3-yl)propane-1,3-dione (2.4 g, 5.2 mmol) in ethanol (100 mL) at rt. After 30 min, the reaction was quenched with saturated aqueous ammonium chloride. The volatiles were removed under reduced pressure. The solution was dissolved in isopropyl acetate and diluted with water. The aqueous layer was extracted with isopropyl acetate (4×100 mL). The combined organic layers were dried with sodium sulfate, concentrated and the crude residue was submitted to the next step without further purification. Sulfuric acid (10 mL) was added to the crude residue and the reaction was heated at 100° C. for 2h. After cooling to rt, the reaction was diluted with water. Sodium hydroxide (3M in water) was added until the aqueous layer became basic. The aqueous layer was extracted with isopropyl acetate (3×100 mL). The combined organic layers were dried with sodium sulfate, concentrated and the crude residue was submitted to the next step without further purification.

Diethylaminosulfur trifluoride (1.5 mL, 10 mmol) was added to a solution of the crude residue in dichloromethane (26 mL) at rt. After 20 min, sodium bicarbonate (2.0 g) was added. The reaction was diluted with water and isopropyl acetate. Brine was added and the aqueous layer was extracted with isopropyl acetate (4×50 mL). The combined organic layers were dried with sodium sulfate, concentrated and the crude residue (0.40 g, 1.25 mmol) was submitted to the next reaction without further purification. Isopropylmagnesium chloride (2.0 M in THF, 1.2 mL, 2.50 mmol) was added to a solution of the crude residue and N-methoxy-N-methylcyclopropanecarboxamide (0.498 g, 3.74 mmol) in THF (12.5 mL) at 0° C. After 5 min, the reaction was warmed to rt and stirred for an additional 20 min. Water was added and the reaction was diluted with isopropyl acetate. The aqueous layer was extracted with isopropyl acetate (4×20 mL). The combined organic layers were dried with sodium sulfate, concentrated and the crude residue was purified by prep SFC afford arbitrarily assigned ((5S,7S)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone (8.4 mg, 0.027 mmol) and ((5S,7R)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone (38.8 mg, 0.125 mmol).

((5S,7S)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone. $^1$H NMR (400 MHz, DMSO-d$_6$) δ 8.03 (s, 1H), 6.23 (ddd, J=56.8, 7.8, 3.3 Hz, 1H), 5.70 (ddd, J=8.4, 6.5, 5.0 Hz, 1H), 3.82 (s, 3H), 3.72 (ddt, J=16.3, 14.6, 8.1 Hz, 1H), 3.02-2.82 (m, 2H), 1.14-0.99 (m, 4H). LCMS $R_T$=3.86 min, m/z=310.0 [M+H]+.

Prep SFC Information: Column: Chiralpak IB-N 5 μm, (150×21.2 mm), Mobile Phase: Carbon Dioxide (A)/0.1% Ammonium Hydroxide in Methanol (B), Elution Program Isocratic: 20% B Flow Rate: 70 mL/min, Column Temperature: 40° C., Wavelength: 225 nm ((5S,7R)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone. $^1$H NMR (400 MHz, DMSO-d$_6$) δ

8.03 (s, 1H), 6.58-6.22 (m, 1H), 6.04 (ddd, J=7.4, 6.1, 3.1 Hz, 1H), 3.81 (s, 3H), 3.46-3.21 (m, 2H), 2.97 (tt, J=7.6, 4.8 Hz, 1H), 1.14-1.00 (m, 4H). LCMS $R_T$=4.01 min, m/z=310.0 [M+H]$^+$.

Prep SFC Information: Column: Chiralpak IB-N 5 μm, (150×21.2 mm), Mobile Phase: Carbon Dioxide (A)/0.1% Ammonium Hydroxide in Methanol (B), Elution Program Isocratic: 20% B Flow Rate: 70 mL/min, Column Temperature: 40° C., Wavelength: 225 nm.

Method 121

Example 156

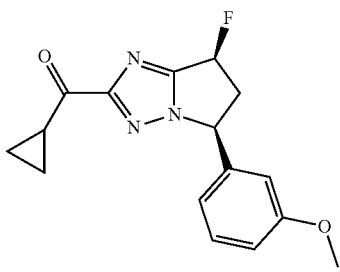

Cyclopropyl((5S,7S)-7-fluoro-5-(3-methoxyphenyl)-6,7-dihydro-5H-pyrrolo[1,2-b][1,2,4]triazol-2-yl)methanone

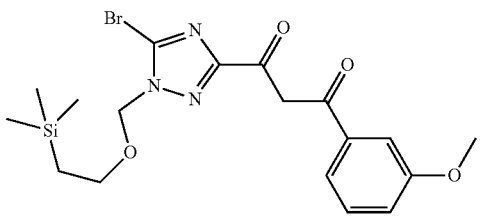

Step 1: 1-(5-bromo-1-((2-(trimethylsilyl)ethoxy)methyl)-1H-1,2,4-triazol-3-yl)-3-(3-methoxyphenyl)propane-1,3-dione Lithium bis(trimethylsilyl)amide (1.0 M in THF, 14 mL, 14 mmol) was added to a solution of methyl 5-bromo-1-(2-trimethylsilylethoxymethyl)-1,2,4-triazole-3-carboxylate (3.00 g, 8.9 mmol) and 1-(3-methoxyphenyl)ethanone (2.0 mL, 14 mmol) in THF (59 mL) at 0° C. After 5 min, the reaction was warmed to rt and stirred for an additional 30 min. Water was added and the reaction was diluted with isopropyl acetate. A 10% aqueous citric acid solution was added to adjust the pH to 2. The aqueous layer was extracted with isopropyl acetate (2×200 mL). The combined organic layers were dried with sodium sulfate, concentrated and the crude residue was purified by flash column chromatography (silica 0% to 100% isopropyl acetate-heptane) 1-[5-bromo-1-(2-trimethylsilylethoxymethyl)-1,2,4-triazol-3-yl]-3-(3-methoxyphenyl)propane-1,3-dione (4.10 g, 9.02 mmol, 100% Yield—The product was contaminated with 1-(3-methoxyphenyl)ethenone). LCMS $R_T$=1.80 min, m/z=453.9 [M+H]$^+$.

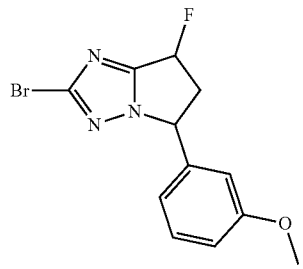 [SMILES: COc1cccc(C2CC(F)c3nc(Br)nn32)c1]

Step 2: 2-bromo-7-fluoro-5-(3-methoxyphenyl)-6,7-dihydro-5H-pyrrolo[1,2-b][1,2,4]triazole Sodium borohydride (5.30 g, 140 mmol) was added to a solution of 1-[5-bromo-1-(2-trimethylsilylethoxymethyl)-1,2,4-triazol-3-yl]-3-(3-methoxyphenyl)propane-1,3-dione (4.1 g, 9.0 mmol) in ethanol (180 mL) at rt. After 30 min, saturated aqueous ammonium chloride was added. The volatiles were removed under reduced pressure. The crude residue was dissolved in isopropyl acetate and diluted with water. The aqueous layer was extracted with isopropyl acetate (4×100 mL). The combined organic layers were dried with sodium sulfate, concentrated and the crude residue was submitted to the next step without further purification. LCMS $R_T$=1.40 min, m/z=357.9 [M+H]$^+$. Sulfuric acid (10 mL) was added to a solution of the crude residue and the reaction was heated at 100° C. for 2h. After cooling to rt, the reaction was diluted with water. Sodium hydroxide (3M in water) was added until the aqueous layer became basic. The aqueous layer was extracted with isopropyl acetate (3×100 mL). The combined organic layers were dried with sodium sulfate, concentrated and the crude residue was submitted to the next step without further purification. LCMS $R_T$=1.02 min, m/z=309.8 [M+H]$^+$. Diethylaminosulfur trifluoride (2.50 mL, 17.9 mmol) was added to a solution of the crude residue in dichloromethane (89 mL) at rt. After 20 min, sodium bicarbonate (5.0 g) was added. The reaction was diluted with water and isopropyl acetate. Brine was added and the aqueous layer was extracted with isopropyl acetate (4×100 mL). The combined organic layers were dried with sodium sulfate, concentrated and the crude residue was purified by flash column chromatography (silica, 0% to 100% isopropyl acetate-heptane) to give 2-bromo-7-fluoro-5-(3-methoxyphenyl)-6,7-dihydro-5H-pyrrolo[1,2-b][1,2,4]triazole (50 mg, 0.160 mmol, 1.79% yield). $^1$H NMR (400 MHz, Chloroform-d) δ 7.35-7.26 (m, 1H), 6.90 (ddd, J=8.3, 2.5, 0.9 Hz, 1H), 6.83 (dd, J=7.6, 1.6 Hz, 1H), 6.76 (t, J=2.1 Hz, 1H), 5.97 (ddd, J=56.0, 7.1, 1.8 Hz, 1H), 5.39 (t, J=9.1 Hz, 1H), 3.79 (s, 3H), 3.64-3.46 (m, 1H), 2.96-2.80 (m, 1H). LCMS $R_T$=1.16 min, m/z=311.8 [M+H]$^+$.

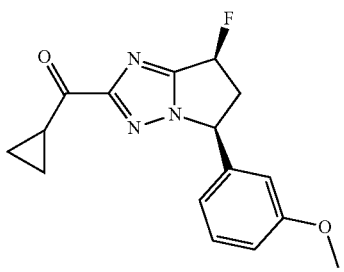 [SMILES: COc1cccc([C@@H]2C[C@H](F)c3nc(C(=O)C4CC4)nn32)c1]

Step 3: Cyclopropyl((5S,7S)-7-fluoro-5-(3-methoxyphenyl)-6,7-dihydro-5H-pyrrolo[1,2-b][1,2,4]triazol-2-yl)methanone Isopropylmagnesium chloride (2.0 M in THF, 0.24 mL, 0.481 mmol) was added dropwise to a solution of (5S,7S)-2-bromo-7-fluoro-5-(3-methoxyphenyl)-6,7-dihydro-5H-pyrrolo[1,2-b][1,2,4]triazole (50 mg, 0.160 mmol) and N-methoxy-N-methylcyclopropanecarboxamide (64 mg, 0.481 mmol) in THF (1.6 mL) at 0° C. over 15 min. After, the reaction was allowed to stir at this temperature for 1 h. Saturated aqueous ammonium chloride was added. The aqueous layer was extracted with isopropyl acetate (2×20 mL). The combined organic layers were dried over sodium sulfate, concentrated and the crude residue was purified by prep SFC to afford arbitrarily assigned cyclopropyl-[(5S,7S)-7-fluoro-5-(3-methoxyphenyl)-6,7-dihydro-5H-pyrrolo[1,2-b][1,2,4]triazol-2-yl]methanone (2.35 mg, 0.0078 mmol, 5% yield). LCMS $R_T$=4.92 min, m/z=302.1 [M+H]$^+$.

Prep SFC Information: Column: Cellulose-1 5 μm, (150× 21.2 mm), Mobile Phase: Carbon Dioxide (A)/Methanol (B), Elution Program, Isocratic: 15% B Flow Rate: 70 mL/min, Column Temperature: 40° C., Wavelength: 220 nm

Method 122

Example 157

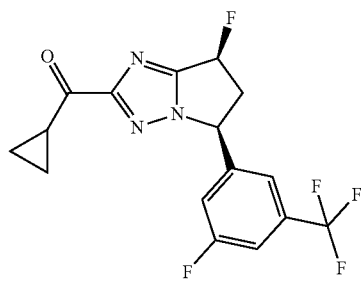

Cyclopropyl((5S,7S)-7-fluoro-5-(3-fluoro-5-(trifluoromethyl)phenyl)-6,7-dihydro-5H-pyrrolo[1,2-b][1,2,4]triazol-2-yl)methanone

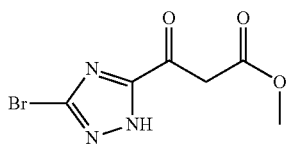

Step 1: Methyl 3-(3-bromo-H-1,2,4-triazol-5-yl)-3-oxo-propanoate

Lithium bis(trimethylsilyl)amide (1.0 M in THF, 194 mL, 194 mmol) was added to a solution of methyl 3-bromo-1H-1,2,4-triazole-5-carboxylate (20.0 g, 97.1 mmol) and methyl acetate (15.5 mL, 194 mmol) in THF (324 mL) at −20° C. After addition, the reaction was allowed to warm to rt and stir overnight. The reaction pH of the reaction was adjusted to pH 1 by addition of 10% aqueous citric acid. The aqueous layer was extracted with isopropyl acetate (3×200 mL). The combined organic layers were dried with sodium sulfate, concentrated and the crude residue was purified by flash column chromatography (silica, 0% to 100% isopropyl acetate-heptane) to give methyl 3-(3-bromo-1H-1,2,4-triazol-5-yl)-3-oxo-propanoate (15.4 g, 62.1 mmol, 64.0% Yield). LCMS $R_T$=0.91 min, m/z=247.7 [M+H]$^+$.

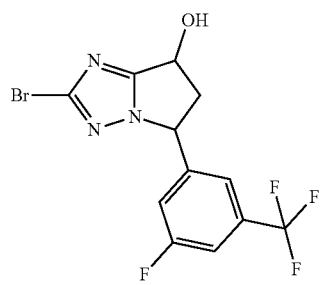 [SMILES: OC1CC(c2cc(F)cc(C(F)(F)F)c2)n2nc(Br)nc21]

Step 2: 2-bromo-5-(3-fluoro-5-(trifluoromethyl)phenyl)-6,7-dihydro-5H-pyrrolo[1,2-b][1,2,4]triazol-7-ol Piperidinium acetate (0.250 g, 1.6 mmol) was added a solution of methyl 3-(3-bromo-1H-1,2,4-triazol-5-yl)-3-oxo-propanoate (2.00 g, 8.1 mmol) and 3-fluoro-5-(trifluoromethyl)benzaldehyde (1.2 mL 8.1 mmol) in benzene (8.1 mL). The reaction was equipped with a Dean-Stark trap and a reflux condenser and was heated at reflux for 3h. After cooling to rt, the reaction was diluted with water and isopropyl acetate. The aqueous layer was extracted with isopropyl acetate (3×50 mL). The combined organic layers were dried with sodium sulfate, concentrated and the crude residue was purified by flash column chromatography (silica 0% to 100% isopropyl acetate-heptane) to give methyl 2-bromo-5-[3-fluoro-5-(trifluoromethyl)phenyl]-7-hydroxy-5H-pyrrolo[1,2-b][1,2,4]triazole-6-carboxylate (0.60 g, 1.4 mmol, 18% Yield) which was immediately used in the next reaction. LCMS $R_T$=1.28 min, m/z=421.8 [M+H]$^+$.

Sodium chloride (0.830 g, 14 mmol) was added to a solution of the crude residue in dimethyl sulfoxide (4.7 mL) and water (0.47 mL). The reaction was then heated at 120° C. for 15 min, at which point the reaction was placed in a rt water bath and sodium borohydride (0.270 g, 7.1 mmol) was added. After 10 min, saturated aqueous ammonium chloride was added and the reaction was diluted with water and isopropyl acetate. The aqueous layer was extracted with isopropyl acetate (3×20 mL). The combined organic layers were dried with sodium sulfate, concentrated and the crude residue was purified by flash column chromatography (silica, 0% to 100% isopropyl acetate-heptane) to give 2-bromo-5-[3-fluoro-5-(trifluoromethyl)phenyl]-6,7-dihydro-5H-pyrrolo[1,2-b][1,2,4]triazol-7-ol (0.320 g, 0.874 mmol, 61% yield). $^1$H NMR (400 MHz, Chloroform-d) 3:1 mixture of diastereomers δ 7.45 (s, 1H), 7.39-7.25 (m, 2H), 5.46-5.35 (m, 2H), 3.63-3.49 (m, 0.75H), 3.18 (ddd, J=14.3, 7.5, 2.5 Hz, 0.25H), 2.90 (ddd, J=14.2, 7.1, 6.1 Hz, 0.25H), 2.66 (ddd, J=14.5, 3.9, 3.0 Hz, 0.75H). LCMS $R_T$=1.19 min, m/z=365.8 [M+H]$^+$.

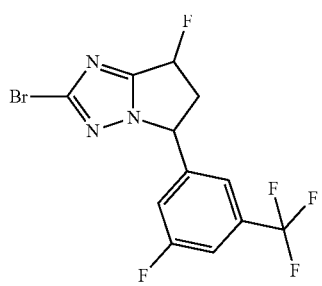 [SMILES: Fc1cc(C2CC(F)c3nc(Br)nn32)cc(C(F)(F)F)c1]

Step 3: 2-bromo-7-fluoro-5-(3-fluoro-5-(trifluoromethyl)phenyl)-6,7-dihydro-5H-pyrrolo[1,2-b][1,2,4]triazole Diethylaminosulfur trifluoride (0.230 mL, 1.75 mmol) was added to a solution of 2-bromo-5-[3-fluoro-5-(trifluoromethyl)phenyl]-6,7-dihydro-5H-pyrrolo[1,2-b][1,2,4]triazol-7-ol (0.320 g, 0.874 mmol) in dichloromethane (17.5 mL) at 40° C. After 10 min, saturated aqueous sodium bicarbonate was added. The reaction was diluted with water and dichloromethane. The aqueous layer was extracted with dichloromethane (3×20 mL). The combined organic layers were dried with sodium sulfate, concentrated and the crude residue was purified by flash column chromatography (silica, 0% to 100% isopropyl acetate-heptane) to give 2-bromo-7-fluoro-5-[3-fluoro-5-(trifluoromethyl)phenyl]-6,7-dihydro-5H-pyrrolo[1,2-b][1,2,4]triazole (0.250 g, 0.679 mmol, 78% yield). $^1$H NMR (400 MHz, Chloroform-d) 3:1 mixture of diastereomers δ 7.42-7.33 (m, 1H), 7.27 (d, J=12.2 Hz, 1H), 7.15-7.04 (m, 1H), 6.14-5.88 (m, 1H), 5.72 (td, J=6.8, 3.6 Hz, 0.75H), 5.60-5.44 (m, 0.25H), 3.70-3.52 (m, 0.25H), 3.41 (dddd, J=22.4, 15.3, 7.0, 1.3 Hz, 0.75H), 3.01-2.80 (m, 1H). LCMS $R_T$=1.35 min, m/z=367.7 [M+H]$^+$.

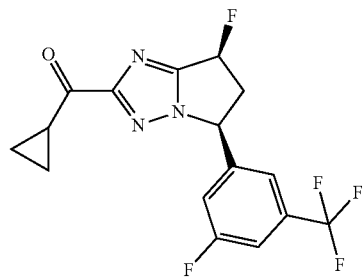 [SMILES: O=C(c1nc2n(n1)[C@H](c1cc(F)cc(C(F)(F)F)c1)C[C@@H]2F)C1CC1]

Step 4: Cyclopropyl((5S,7S)-7-fluoro-5-(3-fluoro-5-(trifluoromethyl)phenyl)-6,7-dihydro-5H-pyrrolo[1,2-b][1,2,4]triazol-2-yl)methanone Isopropylmagnesium chloride (2.0 M in THF, 1.0 mL, 2.04 mmol) was added dropwise to a solution of N-methoxy-N-methylcyclopropanecarboxamide (0.271 g, 2.04 mmol) and 2-bromo-7-fluoro-5-[3-fluoro-5-(trifluoromethyl)phenyl]-6,7-dihydro-5H-pyrrolo[1,2-b][1,2,4]triazole (0.250 g, 0.679 mmol) in THF (6.8 mL) at 0° C. over 15 min. After 1h saturated aqueous ammonium chloride was added. The aqueous layer was extracted with isopropyl acetate (2×20 mL). The combined organic layers were dried over sodium sulfate, concentrated and the crude residue was purified by prep SFC to afford arbitrarily assigned cyclopropyl-[7-fluoro-5-[3-fluoro-5-(trifluoromethyl)phenyl]-6,7-dihydro-5H-pyrrolo[1,2-b][1,2,4]triazol-2-yl]methanone (3.47 mg, 0.0097 mmol, 1.4% yield). $^1$H NMR (400 MHz, DMSO-d$_6$) δ 7.76 (dt, J=8.8, 2.1 Hz, 1H), 7.61 (s, 1H), 7.47 (dt, J=9.4, 1.9 Hz, 1H), 6.26 (ddd, J=56.2, 7.0, 2.1 Hz, 1H), 5.89 (ddd, J=8.9, 6.2, 3.4 Hz, 1H), 3.86-3.66 (dddd, J=25.2, 15.4, 8.5, 7.1 Hz, 1H), 3.09-2.93 (m, 1H), 2.83 (dddd, J=26.1, 15.2, 3.4, 2.2 Hz, 1H), 1.16-0.99 (m, 4H). LCMS $R_T$=5.51 min, m/z=358.1 [M+H]$^+$.

Prep SFC Information: Column: Whelko-01 5 μm, (150× 21.2 mm), Mobile Phase: Carbon Dioxide (A)/Methanol (B), Elution Program Isocratic: 20% B Flow Rate: 70 mL/min, Column Temperature: 40° C., Wavelength: 220 nm.

Method 123

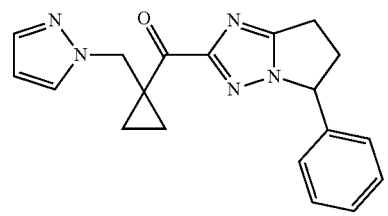

Example 158

(1-((1H-pyrazol-1-yl)methyl)cyclopropyl)(5-phenyl-6,7-dihydro-5H-pyrrolo[1,2-b][1,2,4]triazol-2-yl)methanone (1-((1H-pyrazol-1-yl)methyl)cyclopropyl)(5-phenyl-6,7-dihydro-5H-pyrrolo[1,2-b][1,2,4]triazol-2-yl)methanone was prepared from (1R,2R)-2-(1-methylpyrazol-4-yl)cyclopropanecarboxylic acid according to Methods 2 and 3. The crude residue was further purified by prep-HPLC (Gemini-NX C18 50×30 mm, 5 μm, 20-60% of 0.1% Formic Acid in Water/Acetonitrile) to afford final product (20.2 mg, 32%) as a white solid. $^1$H NMR (400 MHz, DMSO-d$_6$) δ 7.57 (d, J=2.2 Hz, 1H), 7.44-7.30 (m, 4H), 7.26-7.18 (m, 2H), 6.16 (d, J=2.2 Hz, 1H), 5.60 (dd, J=8.3, 5.8 Hz, 1H), 4.63 (q, J=14.4 Hz, 2H), 3.22-2.81 (m, 2H), 2.61-2.28 (m, 1H), 1.70-1.53 (m, 2H), 1.35-1.13 (m, 3H). LCMS $R_T$=4.31 min, m/z=334.2 (M+H)$^+$. LCMS (5 to 95% acetonitrile in water+ 0.1% formic acid over 10 mins) retention time 4.31 min, ESI+ found [M+H]=334.2

Additional SFC Purification and Analytical Conditions

SFC 1

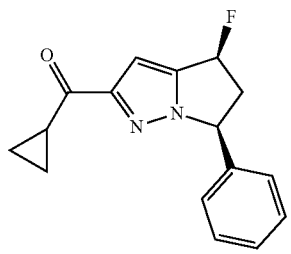

Example 159

Cyclopropyl((4S,6S)-4-fluoro-6-phenyl-5,6-dihydro-4H-pyrrolo[1,2-b]pyrazol-2-yl)methanone Arbitrarily assigned cyclopropyl((4S,6S)-4-fluoro-6-phenyl-5,6-dihydro-4H-pyrrolo[1,2-b]pyrazol-2-yl)methanone (7.9 mg, 55% yield). 1H NMR (400 MHz, DMSO-d6) δ 7.46-7.28 (m, 3H), 7.28-7.07 (m, 2H), 6.94 (d, J=2.6 Hz, 1H), 6.34-5.96 (m, 1H), 5.88-5.51 (m, 1H), 2.94-2.75 (m, 1H), 2.76-2.55 (m, 1H), 2.07 (s, 1H), 1.04-0.74 (m, 4H). LC-MS $R_T$=5.11 min, m/z=271.1 (M+H).

SFC2

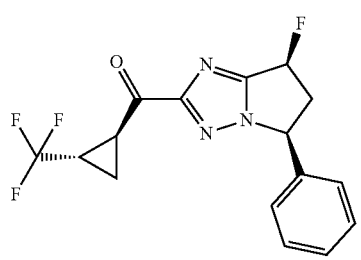

Example 160

[rac-(5S,7S)-7-fluoro-5-phenyl-6,7-dihydro-5H-pyrrolo[1,2-b][1,2,4]triazol-2-yl]-[rac-(1S,2S)-2-(trifluoromethyl)cyclopropyl]methanone Arbitrarily assigned [rac-(5S,7S)-7-fluoro-5-phenyl-6,7-dihydro-5H-pyrrolo[1,2-b][1,2,4]triazol-2-yl]-[rac-(1S,2S)-2-(trifluoromethyl)cyclopropyl]methanone (4.2 mg, 31% yield). 1H NMR (400 MHz, DMSO-d6) δ 7.59-7.08 (m, 5H), 6.50-6.06 (m, 1H), 5.93-5.55 (m, 1H), 3.76-3.25 (m, 1H), 2.58 (d, J=2.5 Hz, 1H), 1.88-1.15 (m, 2H). LC-MS $R_T$=5.36 min, m/z=340.1 (M+H)$^+$.

SFC3

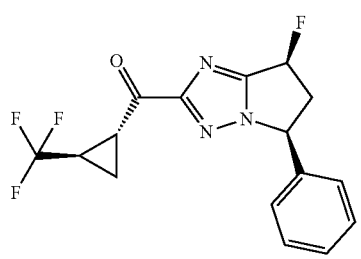

Example 161

[rac-(5S,7S)-7-fluoro-5-phenyl-6,7-dihydro-5H-pyrrolo[1,2-b][1,2,4]triazol-2-yl]-[rac-(1R,2R)-2-(trifluoromethyl)cyclopropyl]methanone Arbitrarily assigned [rac-(5S,7S)-7-fluoro-5-phenyl-6,7-dihydro-5H-pyrrolo[1,2-b][1,2,4]triazol-2-yl]-[rac-(1R,2R)-2-(trifluoromethyl)cyclopropyl]methanone (12.2 mg, 89% yield). 1H NMR (400 MHz, DMSO-d6) δ 7.50-7.13 (m, 5H), 6.51-6.05 (m, 1H), 5.93-5.49 (m, 1H), 3.90-3.54 (m, 1H), 2.84-2.59 (m, 1H), 2.62-2.53 (m, 1H), 2.07 (s, 1H), 1.64-1.26 (m, 2H). LC-MS $R_T$=5.40 min, m/z=340.1 (M+H)$^+$.

SFC 4

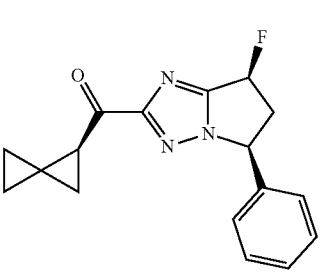

Example 162

[rac-(5S,7S)-7-fluoro-5-phenyl-6,7-dihydro-5H-pyrrolo[1,2-b][1,2,4]triazol-2-yl]-[rac-(2S)-spiro[2.2]pentan-2-yl]methanone Arbitrarily assigned [rac-(5S,7S)-7-fluoro-5-phenyl-6,7-dihydro-5H-pyrrolo[1,2-b][1,2,4]triazol-2-yl]-[rac-(2S)-spiro[2.2]pentan-2-yl]methanone (3.2 mg, 39% yield). LC-MS $R_T$=4.95 min, m/z=298.1 (M+H)$^+$.

SFC 5

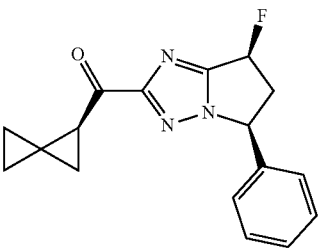

Example 163

[rac-(5S,7S)-7-fluoro-5-phenyl-6,7-dihydro-5H-pyrrolo[1,2-b] [1,2,4]triazol-2-yl]-[rac-(2R)-spiro[2.2]pentan-2-yl]methanone Arbitrarily assigned [rac-(5S,7S)-7-fluoro-5-phenyl-6,7-dihydro-5H-pyrrolo[1,2-b][1,2,4]triazol-2-yl]-[rac-(2R)-spiro[2.2]pentan-2-yl]methanone (x mg, x % yield). LC-MS $R_T$=4.94 min, m/z=298.1 (M+H).

| Method* | Instrument | Solvent A | Solvent B | initial % B | Final % B | λ/nM | column | col. dimensions | flow rate |
|---|---|---|---|---|---|---|---|---|---|
| SFC 1 Analytical Peak 1 R.T = 0.693 min | Waters UPC | Carbon Dioxide | MeOH w/ 0.1% NH4OH | 10 | 10 | 220 | Chiralpak IB-N | | |
| SFC 1 Prep Peak 1 | PIC 200 Chiral | Carbon Dioxide | MeOH w/ 0.1% NH4OH | 15 | 15 | 236 | Chiralpak IB-N | 150 × 21.2 mm, 5 µM | 70 |
| SFC 2 Analytical Peak 2 0.900 min | Waters UPC | Carbon Dioxide | MeOH w/ 0.1% NH4OH | 25 | 25 | 220 | Whelk-O1 S,S | | |
| SFC 2 Prep Peak 2 | PIC 200 Chiral | Carbon Dioxide | MeOH w/ 0.1% NH4OH | 30 | 30 | 220 | Whelk-O1 S,S | 150 × 21.2 mm, 5 µM | 70 |
| SFC 3 Analytical Peak 1 0.790 min | Waters UPC | Carbon Dioxide | MeOH w/ 0.1% NH4OH | 25 | 25 | 220 | Whelk-O1 S,S | | |
| SFC 3 Prep Peak 1 | PIC 200 Chiral | Carbon Dioxide | MeOH w/0.1% NH4OH | 30 | 30 | 220 | Whelk-O1 S,S | 150 × 21.2 mm, 5 µM | 70 |
| SFC 4 Prep Peak 1 | PIC 200 Chiral | Carbon Dioxide | MeOH | 15 | 15 | 230 | Cellulose-1 | 150 × 21.2 mm, 5 µM | 70 |
| SFC 5 Prep Peak 2 | PIC 200 Chiral | Carbon Dioxide | MeOH | 15 | 15 | 230 | Chiralpak AD | 150 × 21.2 mm, 5 µM | 70 |

*All column temperatures 40° C. with the exception of SFC 1 Prep, which was 30° C.

RIP1 Kinase Inhibition Assays (Biochemical Assay)

The compounds of the present invention were tested for their capacity to inhibit RIP1K activity as described below.

Enzyme assay: The ability of the receptor interacting protein kinase (RIPK1) to catalyze the hydrolysis of adenosine-5'-triphosphate (ATP) is monitored using the Transcreener ADP (adenosine-5'-diphosphate) assay (BellBrook Labs). Purified human RIP1 kinase domain (2-375) (50 nM) derived from a baculovirus-infected insect cell expression system is incubated with test compounds for 2 hours in 50 mM Hepes buffer (pH 7.5) containing 30 mM $MgCl_2$, 1 mM dithiothreitol, 50 µM ATP, 0.002% Brij-35, and 0.5% dimethyl sulfoxide (DMSO). Reactions are quenched by the addition of 1X Bell Brooks Stop buffer B (20 mM Hepes (ph7.5), 40 mM ethylenediaminetetraacetic acid and 0.02% Brij-35) containing an additional 12 mM EDTA and 55 ug/mL ADP2 antibody and 4 nM ADP-AlexaFluor® 633 tracer. The tracer bound to the antibody is displaced by the ADP generated during the RIP1K reaction, which causes a decrease in fluorescence polarization that is measured by laser excitation at 633 nm with a FP microplate reader M1000. Fractional activity was plotted against test article concentration. Using Genedata Screener software (Genedata; Basel, Switzerland), the data were fit to the tight-binding apparent inhibition constant ($K_i^{app}$) Morrison equation [Williams, J. W. and Morrison, J. F. (1979) The kinetics of reversible tight-binding inhibition. Methods Enzymol 63: 437-67]. The following equation was used to calculate fractional activity and $K_i^{app}$:

$$\text{Fractional activity} = \frac{v_i}{v_o} = 1 - \frac{([E]_T + [I]_T + K_i^{app}) - \sqrt{([E]_T + [I]_T + K_i^{app})^2 - 4[E]_T[I]_T}}{2[E]_T}$$

where $[E]_T$ and $[I]_T$ are the total concentrations of active enzyme and test article, respectively.

Exemplary compounds of the present invention are provided in Tables 1 and 2 along with their physiochemical characterization and in vitro RIP1 kinase inhibitory activity data. "Method" in the first column of each table refers to the synthetic method(s) used to prepare each compound as shown in the Examples above. In certain examples, chiral column retention times (min) are provided for certain stereoisomers. Unless otherwise specified, the stereochemistry shown in each structure represents relative configuration of a single stereoisomer, and absolute configuration (i.e., "R" and/or "S") is arbitrarily assigned. In some embodiments, where the Method is described to include the separation of stereoisomers, a single stereoisomer of a compound of Table 1 or Table 2 is provided.

TABLE 1

| K_i (uM) Method | Ex # | Structure | ¹H NMR | MS (m/z) R.T. |
|---|---|---|---|---|
| 0.014 Method 1 | 1 | ((5S,7S)-7-fluoro-5-phenyl-6,7-dihydro-5H-pyrrolo[1,2-b][1,2,4]triazol-2-yl)((1R,2R)-2-fluorocyclopropyl)methanone | ¹H NMR (400 MHz, CD₃OD) δ 7.44-7.39 (m, 3H), 7.30-7.28 (m, 2H), 6.20-6.18 (m, 0.5H), 6.06-6.04 (m, 0.5H), 5.65-5.64 (m, 1H), 5.04-5.02 (m, 0.5H), 4.90-4.87 (m, 0.5H), 3.80-3.74 (m, 1H), 3.25-3.21 (m, 1H), 2.88-2.81 (m, 1H), 2.03-1.96 (m, 1H), 1.34-1.28 (m, 1H). | 290.1 1.654 min |
| 0.053 Method 1 | 2 | ((5S,7S)-7-fluoro-5-phenyl-6,7-dihydro-5H-pyrrolo[1,2-b][1,2,4]triazol-2-yl)((1S,2S)-2-fluorocyclopropyl)methanone | ¹H NMR (400 MHz, CD₃OD) δ 7.44-7.38 (m, 3H), 7.30-7.28 (m, 2H), 6.21-6.18 (m, 0.5H), 6.06-6.05 (m, 0.5H), 5.66-5.65 (m, 1H), 5.05-5.04 (m, 0.5H), 4.90-4.87 (m, 0.5H), 3.82-3.74 (m, 1H), 3.23-3.20 (m, 1H), 2.88-2.82 (m, 1H), 2.02-1.96 (m, 1H), 1.34-1.30 | 290.1 1.662 min, |
| >10 Method 2 | 3 | ((5R,7R)-7-fluoro-5-phenyl-6,7-dihydro-5H-pyrrolo[1,2-b][1,2,4]triazol-2-yl)((1R,2R)-2-fluorocyclopropyl)methanone | ¹H NMR (400 MHz, CDCl₃) δ 7.44-7.37 (m, 3H), 7.28-7.27 (m, 2H), 6.13-6.11 (m, 1H), 5.99-5.97 (m, 1H), 5.53-5.50 (m, 1H), 3.69-3.63 (m, 1H), 3.27-3.23 (m, 1H), 3.03-2.96 (m, 1H), 2.23-2.16 (m, 1H), 1.29-1.24 (m, 1H). | 289.9 0.849 min |
| >10 Method 2 | 4 | ((5R,7R)-7-fluoro-5-phenyl-6,7-dihydro-5H-pyrrolo[1,2-b][1,2,4]triazol-2-yl)((1S,2S)-2-fluorocyclopropyl)methanone | ¹H NMR (400 MHz, CDCl₃) δ 7.44-7.39 (m, 3H), 7.28-7.27 (m, 2H), 6.13-6.11 (m, 1H), 5.99-5.97 (m, 1H), 5.53-5.49 (m, 1H), 3.69-3.61 (m, 1H), 3.27-3.24 (m, 1H), 3.03-2.96 (m, 1H), 2.23-2.15 (m, 1H), 1.29-1.24 (m, 1H). | 289.9 0.846 min, |

TABLE 1-continued

| $K_i$ (uM) Method | Ex # | Structure | $^1$H NMR | MS (m/z) R.T. |
|---|---|---|---|---|
| 0.023 Method SP 5 | 5 | 2-hydroxy-2-methyl-1-[rac-(5R,7R)-7-fluoro-5-phenyl-6,7-dihydro-5H-pyrrolo[1,2-b][1,2,4]triazol-2-yl]propan-1-one (relative, not absolute stereochemistry known) | $^1$H NMR (400 MHz, DMSO-d$_6$) δ 7.50-7.33 (m, 2H), 7.29-7.14 (m, 2H), 6.40-6.05 (m, 1H), 5.81-5.63 (m, 1H), 5.23 (s, 1H), 2.98-2.56 (m, 1H), 1.51 (s, 3H), 1.48 (s, 3H). | 290.1 4.029 min |
| 3.4 Method SP 6 | 6 | 2-hydroxy-2-methyl-1-[rac-(5S,7S)-7-fluoro-5-phenyl-6,7-dihydro-5H-pyrrolo[1,2-b][1,2,4]triazol-2-yl]propan-1-one (relative, not absolute stereochemistry known) | $^1$H NMR (400 MHz, DMSO-d$_6$) δ 7.47-7.31 (m, 3H), 7.30-7.12 (m, 2H), 6.37-6.01 (m, 1H), 5.82-5.53 (m, 1H), 5.23 (s, 1H), 285-2.59 (m, 1H), 152-1.47 (m, 6H). | 290.1 4.029 min |
| 0.0122 Method 3 | 7 | 2-phenyl-1-[rac-(5S,7S)-7-fluoro-5-phenyl-6,7-dihydro-5H-pyrrolo[1,2-b][1,2,4]triazol-2-yl]ethanone | 1H NMR (400 MHz, DMSO-d6) δ 7.57-7.15 (m, 10H), 6.25 (ddd, J = 56.4, 7.2, 1.9 Hz, 1H), 5.75 (ddd, J = 9.1, 6.5, 3.0 Hz, 1H), 4.34 (s, 2H), 3.75 (dddd, J = 26.1, 15.5, 8.5, 7.1 Hz, 1H), 2.72 (dddd, J = 26.9, 15.4, 3.2, 1.9 Hz, 1H). | 322.1 5.24 min |
| >10 Method 4 | 8 | ((5R,7R)-7-fluoro-5-phenyl-6,7-dihydro-5H-pyrrolo[1,2-b][1,2,4]triazol-2-yl)((1R,2S)-2-fluorocyclopropyl)methanone | $^1$H NMR (400 MHz, CDCl$_3$) δ 7.43-7.39 (m, 3H), 7.28-7.27 (m, 2H), 6.12-5.97 (m, 1H), 5.54-5.50 (m, 1H), 5.03-4.87 (m, 1H), 3.69-3.51 (m, 2H), 3.04-2.97 (m, 1H), 1.70-1.62 (m, 2H). | 289.9 0.865 min |

TABLE 1-continued

| $K_i$ (uM) Method | Ex # | Structure | $^1$H NMR | MS (m/z) R.T. |
|---|---|---|---|---|
| >10 Method 4 | 9 | ((5R,7R)-7-fluoro-5-phenyl-6,7-dihydro-5H-pyrrolo[1,2-b][1,2,4]triazol-2-yl)((1S,2R)-2-fluorocyclopropyl)methanone | 1H NMR (400 MHz, CDCl$_3$) δ 7.43-7.39 (m, 3H), 7.28-7.27 (m, 2H), 6.13-5.97 (m, 1H), 5.54-5.51 (m, 1H), 5.02-4.84 (m, 1H), 3.69-3.53 (m, 2H), 3.03-2.97 (m, 1H), 1.70-1.63 (m, 2H). | 289.9 0.866 min, |
| 0.116 Method 5 | 10 | (7-fluoro-5-phenyl-6,7-dihydro-5H-pyrrolo[1,2-b][1,2,4]triazol-2-yl)-[rac-(1S,2S)-2-fluorocyclopropyl]methanone | $^1$H NMR (400 MHz, CD$_3$OD) δ 7.44-7.37 (m, 3H), 7.29-7.27 (m, 2H), 6.19-6.18 (m, 0.5H), 6.04-6.03 (m, 0.5H), 5.67-5.61 (m, 1H), 5.08-4.89 (m, 1H), 3.81-3.70 (m, 1H), 3.26-3.16 (m, 1H), 2.91-2.75 (m, 1H), 2.07-1.90 (m, 1H), 1.36-1.29 (m, 1H) | 290.1 1.038 min |
| 0.078 Method 6 | 11 | (2,2-difluorocyclopropyl)-(7-fluoro-5-phenyl-6,7-dihydro-5H-pyrrolo[1,2-b][1,2,4]triazol-2-yl)methanone | $^1$H NMR (400 MHz, CD$_3$OD) δ 7.44-7.39 (m, 3H), 7.30-7.29 (m, 2H), 6.21-6.05 (m, 1H), 5.69-5.64 (m, 1H), 3.84-3.74 (m, 2H), 2.90-2.82 (m, 1H), 2.32-2.27 (m, 1H), 1.97-1.90 (m, 1H). | 307.9 0.875 min |
| 0.0212 Method 7 | 12 | phenyl-[rac-(5S,7S)-7-fluoro-5-phenyl-6,7-dihydro-5H-pyrrolo[1,2-b][1,2,4]triazol-2-yl]methanone | $^1$H NMR (400 MHz, DMSO-d$_6$) δ 8.20-8.12 (m, 2H), 7.74-7.65 (m, 1H), 7.61-7.52 (m, 2H), 7.48-7.33 (m, 3H), 7.32-7.24 (m, 2H), 6.28 (ddd, J = 56.4, 7.2, 1.9 Hz, 1H), 5.78 (ddd, J = 8.5, 6.5, 3.1 Hz, 1H), 3.78 (dddd, J = 25.8, 15.4, 8.5, 7.1 Hz, 1H), 2.74 (dddd, J = 26.7, 15.2, 3.2, 2.0 Hz, 1H). | 308.1 5.04 min |

TABLE 1-continued

| K$_i$ (uM) Method | Ex # | Structure | $^1$H NMR | MS (m/z) R.T. |
|---|---|---|---|---|
| 0.193 Method 8 | 13 | 1-[rac-(5R,7S)-7-fluoro-5-phenyl-6,7-dihydro-5H-pyrrolo[1,2-b][1,2,4]triazol-2-yl]propan-1-one | $^1$H NMR (400 MHz, CD$_3$OD) δ 7.44-7.38 (m, 3H), 7.30-7.26 (m, 2H), 6.27-6.26 (m, 0.5H), 6.14-6.12 (m, 0.5H), 5.87-5.84 (m, 1H), 3.44-3.41 (m, 1H), 3.12-3.02 (m, 3H), 1.16 (t, J = 12 Hz, 3H). | 260.1 0.840 min |
| 0.0112 Method 9 | 14 | (rac-(5S,7S)-7-fluoro-5-phenyl-6,7-dihydro-5H-pyrrolo[1,2-b][1,2,4]triazol-2-yl)-[1-(trifluoromethyl)cyclopropyl]methanone | $^1$H NMR (400 MHz, CD$_3$OD) δ 7.43-7.35 (m, 3H), 7.24-7.22 (m, 2H), 6.15-5.99 (m, 1H), 5.61-5.60 (m, 1H), 3.77-3.68 (m, 1H), 2.84-2.77 (m, 1H), 2.27-2.17 (m, 2H), 1.60-1.55 (m, 2H). | 339.9 0.933 min, |
| 0.030 Method 10 | 15 | (rac-(5S,7S)-7-fluoro-5-phenyl-6,7-dihydro-5H-pyrrolo[1,2-b][1,2,4]triazol-2-yl)-(3-methyloxetan-3-yl)methanone | $^1$H NMR (400 MHz, CD$_3$OD) δ 7.43-7.37 (m, 3H), 7.26-7.23 (m, 2H), 6.17-6.01 (m, 1H), 5.65-5.63 (m, 1H), 5.08-5.03 (m, 2H), 4.52-4.48 (m, 2H), 3.78-3.70 (m, 1H), 2.86-2.76 (m, 1H), 1.75 (s, 3H). | 302.0 0.816 min |
| 0.0236 Method 11 | 16 | (rac-(5S,7S)-7-fluoro-5-phenyl-6,7-dihydro-5H-pyrrolo[1,2-b][1,2,4]triazol-2-yl)-[rac-(1S,2R)-2-fluorocyclopropyl]methanone | $^1$H NMR (400 MHz, CDCl$_3$) δ 7.42-7.37 (m, 3H), 7.28-7.27 (m, 2H), 6.13-5.97 (m, 1H), 5.54-5.52 (m, 1H), 5.03-4.85 (m, 1H), 3.71-3.51 (m, 2H), 3.04-2.94 (m, 1H), 1.70-1.62 (m, 2H). | 289.9 0.862 min |

TABLE 1-continued

| K$_i$ (uM) Method | Ex # | Structure | $^1$H NMR | MS (m/z) R.T. |
|---|---|---|---|---|
| 0.94 Method 12 | 17 | 1-(7-phenyl-6,7-dihydro-5H-pyrrolo[1,2-a]imidazol-2-yl)propan-1-one | $^1$H NMR (400 MHz, CD$_3$OD) δ 7.86 (s, 1H), 7.35-7.31 (m, 2H), 7.30-7.21 (m, 3H), 4.42-4.38 (m, 1H), 4.25-4.23 (m, 1H), 4.20-4.11 (m, 1H), 3.12-3.10 (m, 1H), 2.89-2.83 (m, 2H), 2.58-2.50 (m, 1H), 1.14-1.10 (m, 3H) | 241.1 0.634 min |
| 0.235 Method 13 | 18 | cyclopropyl-[rac-(5R,7S)-7-fluoro-5-phenyl-6,7-dihydro-5H-pyrrolo[1,2-b][1,2,4]triazol-2-yl]methanone | $^1$H NMR (400 MHz, CD$_3$OD) δ 7.44-7.40 (m, 3H), 7.30-7.26 (m, 2H), 6.29-6.26 (m, 0.5H), 6.14-6.12 (m, 0.5H), 5.92-5.87 (m, 1H), 3.44-3.41 (m, 1H), 3.01-3.02 (m, 2H), 1.19-1.16 (m, 2H), 1.12-1.09 (m, 2H). | 272.0 0.849 min |
| 0.0442 Method 14 | 19 | 1-(6-phenyl-5,6-dihydro-4H-pyrrolo[1,2-b]pyrazol-2-yl)propan-1-one | $^1$H NMR (400 MHz, CD$_3$OD) δ 7.39-7.30 (m, 3H), 7.11-7.09 (m, 2H), 6.60 (s, 1H), 5.54-5.50 (m, 1H), 3.11-3.01 (m, 3H), 2.95-2.89 (m, 2H), 2.52-2.48 (m, 1H), 1.11 (t, J = 7.2 Hz, 3H) | 241.2 1.858 min |
| >10 Method 15 | 20 | 1-[rac-(4R)-4-(2-fluorophenyl)-6,7-dihydro-4H-pyrazolo[5,1-c][1,4]oxazin-2-yl]propan-1-one | $^1$H NMR(400 MHz, CD$_3$OD) δ 7.40-7.34 (m, 2H), 7.16-7.14 (m, 2H), 6.22 (s, 1H), 6.08 (s, 1H), 4.41-4.15 (m, 4H), 3.00-2.92 (m, 2H), 1.10 (t, J = 7.2 Hz, 3H). | 275.2 1.755 min |

TABLE 1-continued

| $K_i$ (uM) Method | Ex # | Structure | $^1$H NMR | MS (m/z) R.T. |
|---|---|---|---|---|
| 0.198 Method 15 | 21 | 1-[rac-(4S)-4-(2-fluorophenyl)-6,7-dihydro-4H-pyrazolo[5,1-c][1,4]oxazin-2-yl]propan-1-one | $^1$H NMR (400 MHz, CD$_3$OD) δ 7.40-7.34 (m, 2H), 7.16-7.14 (m, 2H), 6.22 (s, 1H), 6.07 (s, 1H), 4.42-4.18 (m, 4H), 2.96-2.92 (m, 2H), 1.10 (t, J = 7.2 Hz, 3H). | 275.2 1.761 min |
| 0.0331 Method 16 | 22 | 3-(rac-(5S,7S)-7-fluoro-5-phenyl-6,7-dihydro-5H-pyrrolo[1,2-b][1,2,4]triazol-2-yl)-2,2-dimethyl-3-oxo-propanenitrile | $^1$H NMR (400 MHz, CDCl$_3$) δ 7.44-7.38 (m, 3H), 7.27-7.25 (m, 2H), 6.15-6.13 (m, 0.5H), 6.01-5.99 (m, 0.5H), 5.57-5.56 (m, 1H), 3.74-3.63 (m, 1H), 3.06-2.95 (m, 1H), 1.81 (s, 3H), 1.78 (s, 3H). | 299.2 1.734 min |
| 2.18 Method 17 | 23 | (S)-1-(4-phenyl-5,6-dihydro-4H-pyrrolo[1,2-b]pyrazol-2-yl)propan-1-one | $^1$H NMR (400 MHz, CD$_3$OD) δ 7.35-7.22 (m, 5H), 6.43 (s, 1H), 4.51-4.38 (m, 1H), 4.37-4.33 (m, 1H), 4.25-4.22 (m, 1H), 3.14-3.12 (m, 1H), 3.02-2.96 (m, 2H), 2.58-2.54 (m, 1H), 1.16 (t, J = 7.2 Hz, 3H). | 241.0 0.838 min |
| >10 Method 17 | 24 | (R)-1-(4-phenyl-5,6-dihydro-4H-pyrrolo[1,2-b]pyrazol-2-yl)propan-1-one | $^1$H NMR (400 MHz, CD$_3$OD) δ 7.32-7.21 (m, 5H), 6.43 (s, 1H), 4.50-4.37 (m, 1H), 4.36-4.33 (m, 1H), 4.24-4.22 (m, 1H), 3.13-3.10 (m, 1H), 2.99-2.95 (m, 2H), 2.57-2.53 (m, 1H), 1.15 (t, J = 7.2 Hz, 3H). | 240.9 0.843 min |

TABLE 1-continued

| $K_i$ (uM) Method | Ex # | Structure | $^1$H NMR | MS (m/z) R.T. |
|---|---|---|---|---|
| 0.0899 Method 18 | 25 | 1-(rac-(5S,7S)-7-fluoro-5-phenyl-6,7-dihydro-5H-pyrrolo[1,2-b][1,2,4]triazol-2-yl)-2-hydroxy-2-methyl-propan-1-one | $^1$H NMR (400 MHz, CD$_3$OD) δ 7.43-7.37 (m, 3H), 7.27-7.25 (m, 2H), 6.20-6.03 (m, 1H), 5.66-5.57 (m, 1H), 3.79-3.71 (m, 1H), 2.87-2.77 (m, 1H), 1.60 (s, 3H), 1.56 (s, 3H). | 290.1 0.771 min |
| 0.038 Method 19 | 26 | (rac-(5S,7S)-7-fluoro-5-phenyl-6,7-dihydro-5H-pyrrolo[1,2-b][1,2,4]triazol-2-yl)-(1-methylcyclopropyl)methanone | $^1$H NMR (400 MHz, CD$_3$OD) δ 7.41-7.37 (m, 3H), 7.24-7.23 (m, 2H), 6.15-6.13 (m, 0.5H), 6.01-5.99 (m, 0.5H), 5.60-5.59 (m, 1H), 3.76-3.68 (m, 1H), 2.84-2.74 (m, 1H), 1.82-1.76 (m, 2H), 1.41 (s, 3H), 0.97-0.92 (m, 2H) | 286.1 1.068 min |
| >10 Method 20 | 27 | 1-[rac-(4R)-4-phenyl-6,7-dihydro-4H-pyrazolo[5,1-c][1,4]oxazin-2-yl]propan-1-one | $^1$H NMR (400 MHz, CD$_3$OD) δ 7.39-7.37 (m, 5H), 6.21 (s, 1H), 5.82 (s, 1H), 4.42-4.36 (m, 2H), 4.31-4.25 (m, 1H), 4.21-4.19 (m, 1H), 3.00-2.92 (m, 2H), 1.13 (t, J = 7.2 Hz, 3H). | 257.1 1.023 min |
| 0.237 Method 20 | 28 | 1-[rac-(4S)-4-phenyl-6,7-dihydro-4H-pyrazolo[5,1-c][1,4]oxazin-2-yl]propan-1-one | $^1$H NMR (400 MHz, CD$_3$OD) δ 7.39-7.37 (m, 5H), 6.21 (s, 1H), 5.82 (s, 1H), 4.42-4.36 (m, 2H), 4.30-4.28 (m, 1H), 4.21-4.18 (m, 1H), 3.00-2.95 (m, 2H), 1.13 (t, J = 7.2 Hz, 3H). | 257.1 1.026 min |

TABLE 1-continued

| K$_i$ (uM) Method | Ex # | Structure | $^1$H NMR | MS (m/z) R.T. |
|---|---|---|---|---|
| 0.134 Method 21 | 29 | 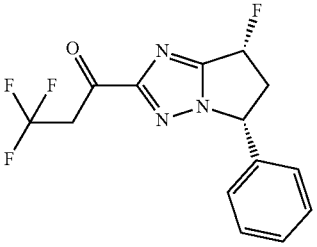 [SMILES: O=C(CC(F)(F)F)c1nc2n(n1)[C@@H](c1ccccc1)C[C@H]2F] 3,3,3-trifluoro-1-[rac-(5R,7R)-7-fluoro-5-phenyl-6,7-dihydro-5H-pyrrolo[1,2-b][1,2,4]triazol-2-yl]propan-1-one | $^1$H NMR (400 MHz, CD$_3$OD) δ 7.40-7.37 (m, 3H), 7.28-7.26 (m, 2H), 6.19-6.17 (m, 0.5H), 6.05-6.03 (m, 0.5H), 5.65-5.63 (m, 1H), 4.09-4.01 (m, 2H), 3.78-3.29 (m, 1H), 2.89-2.77 (m, 1H). | 314.1 1.072 min |
| 0.0215 Method 22 | 30 | 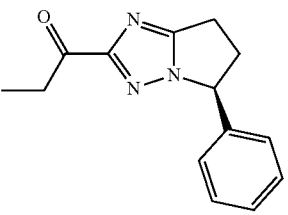 [SMILES: CCC(=O)c1nc2n(n1)[C@H](c1ccccc1)CC2] 1-[rac-(5S)-5-phenyl-6,7-dihydro-5H-pyrrolo[1,2-b][1,2,4]triazol-2-yl]propan-1-one | $^1$H NMR (400 MHz, CDCl$_3$) δ 7.42-7.32 (m, 3H), 7.12-7.10 (m, 2H), 5.49 (dd, J = 5.6, 8.4 Hz, 1H), 3.31-3.21 (m, 1H), 3.17-3.01 (m, 4H), 2.72-2.64 (m, 1H), 1.21 (t, J = 7.2 Hz, 3H). | 242.2 1.523 min |
| 0.00739 Method 23 | 31 | 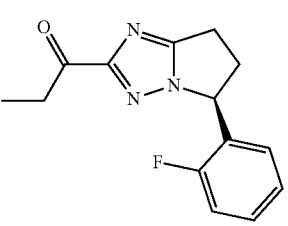 [SMILES: CCC(=O)c1nc2n(n1)[C@H](c1ccccc1F)CC2] 1-[rac-(5S)-5-(2-fluorophenyl)-6,7-dihydro-5H-pyrrolo[1,2-b][1,2,4]triazol-2-yl]propan-1-one | $^1$H NMR (400 MHz, CD$_3$OD) δ 7.45-7.35 (m, 1H), 7.20-7.12 (m, 3H), 5.80-5.75 (m, 1H), 3.30-3.28 (m, 1H), 3.15-3.05 (m, 2H), 3.01-2.97 (m, 2H), 2.72-2.66 (m, 1H), 1.12 (t, J = 7.2 Hz, 3H). | 260.1 0.977 min |
| 0.737 Method 24 | 32 | 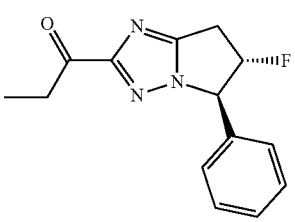 [SMILES: CCC(=O)c1nc2n(n1)[C@H](c1ccccc1)[C@@H](F)C2] 1-[rac-(5R,6S)-6-fluoro-5-phenyl-6,7-dihydro-5H-pyrrolo[1,2-b][1,2,4]triazol-2-yl]propan-1-one | $^1$H NMR (400 MHz, CDCl$_3$) δ 7.34-7.31 (m, 3H), 6.90-6.87 (m, 2H), 5.63-5.61 (m, 0.5H), 5.59-5.57 (m, 1H), 5.46-5.44 (m, 0.5H), 3.42-3.28 (m, 1H), 3.26-3.21 (m, 1H), 3.03-3.01 (m, 2H), 1.16 (t, J = 7.2 Hz, 3H). | 260.1 0.977 min |

TABLE 1-continued

| $K_i$ (uM) Method | Ex # | Structure | $^1$H NMR | MS (m/z) R.T. |
|---|---|---|---|---|
| 2.36 Method 25 | 33 | (rac-(5S,7S)-7-fluoro-5-phenyl-6,7-dihydro-5H-pyrrolo[1,2-b][1,2,4]triazol-2-yl)-(2-pyridyl)methanone | $^1$H NMR (400 MHz, DMSO-d$_6$) δ 8.69-8.65 (m, 1H), 8.00-7.90 (m, 2H), 7.62-7.59 (m, 1H), 7.42-7.30 (m, 3H), 7.25-7.20 (m, 2H), 6.30-6.22 (m, 0.5H), 6.18-6.14 (m, 0.5H), 5.75-5.55 (m, 1H), 3.77-3.67 (m, 1H), 2.74-2.45 (m, 1H). | 309.1 1.510 min |
| 0.0036 Method 26 | 34 | cyclopropyl-[rac-(5S,7S)-7-fluoro-5-phenyl-6,7-dihydro-5H-pyrrolo[1,2-b][1,2,4]triazol-2-yl]methanone | $^1$H NMR (400 MHz, CD$_3$OD) δ 7.44-7.27 (m, 5H), 6.20-6.17 (m, 0.5H), 6.06-6.03 (m, 0.5H), 5.66-5.64 (m, 1H), 3.79-3.71 (m, 1H), 3.05-3.02 (m, 1H), 3.01-2.81 (m, 1H), 1.19-1.09 (m, 4H). | 272.0 0.817 min |
| >9.4 Method 26 | 35 | cyclopropyl-[rac-(5R,7R)-7-fluoro-5-phenyl-6,7-dihydro-5H-pyrrolo[1,2-b][1,2,4]triazol-2-yl]methanone | $^1$H NMR (400 MHz, CD$_3$OD) δ 7.44-7.38 (m, 3H), 7.29-7.27 (m, 2H), 6.19 (d, J = 5.6 Hz, 0.5H), 6.05 (d, J = 5.2 Hz, 0.5H), 5.66-5.62 (m, 1H), 3.79-3.71 (m, 1H), 3.05-3.02 (m, 1H), 3.01-2.81 (m, 1H), 1.29-1.09 (m, 4H) | 271.9 0.816 min |
| 0.0188 Method 27 | 36 | cyclopentyl-(rac-(5S,7S)-7-fluoro-5-phenyl-6,7-dihydro-5H-pyrrolo[1,2-b][1,2,4]triazol-2-yl)methanone | $^1$H NMR (400 MHz, CD$_3$OD) δ 7.44-7.40 (m, 3H), 7.28-7.26 (m, 2H), 6.19-6.17 (m, 0.5H), 6.05-6.03 (m, 0.5H), 5.64-5.63 (m, 1H), 3.89-3.68 (m, 2H), 2.88-2.75 (m, 1H), 2.02-1.60 (m, 8H). | 300.2 2.070 min |

TABLE 1-continued

| $K_i$ (uM) Method | Ex # | Structure | $^1$H NMR | MS (m/z) R.T. |
|---|---|---|---|---|
| 2.83 Method SP 37 | 37 | 2,2-dimethyl-1-[rac-(5S,7S)-7-fluoro-5-phenyl-6,7-dihydro-5H-pyrrolo[1,2-b][1,2,4]triazol-2-yl]propan-1-one (relative, not absolute stereochemistry known) | no NMR generated | 288.1 5.26 min |
| 0.00417 Method SP 38 | 38 | 2,2-dimethyl-1-[rac-(5R,7R)-7-fluoro-5-phenyl-6,7-dihydro-5H-pyrrolo[1,2-b][1,2,4]triazol-2-yl]propan-1-one (relative, not absolute stereochemistry known) | no NMR generated | 288.1 5.26 min |
| 0.225 Method SP 39 | 39 | (1-methylpyrazol-4-yl)-[rac-(5R,7R)-7-fluoro-5-phenyl-6,7-dihydro-5H-pyrrolo[1,2-b][1,2,4]triazol-2-yl]methanone (relative, not absolute stereochemistry known) | $^1$H NMR (400 MHz, DMSO-d$_6$) δ 8.69 (s, 1H), 8.18 (d, J = 0.7 Hz, 1H), 7.48-7.34 (m, 3H), 7.30-7.22 (m, 2H), 6.43-6.09 (m, 1H), 5.88-5.62 (m, 1H), 3.93 (s, 3H), 3.87-3.58 (m, 1H). | 312.1 3.99 min |

TABLE 1-continued

| K$_i$ (uM) Method | Ex # | Structure | $^1$H NMR | MS (m/z) R.T. |
|---|---|---|---|---|
| >10 Method SP 40 | 40 | (1-methylpyrazol-4-yl)-[rac-(5S,7S)-7-fluoro-5-phenyl-6,7-dihydro-5H-pyrrolo[1,2-b][1,2,4]triazol-2-yl]methanone (relative, not absolute stereochemistry known) | $^1$H NMR (400 MHz, DMSO-d$_6$) δ 8.68 (s, 1H), 8.18 (s, 1H), 7.48-7.33 (m, 3H), 7.32-7.06 (m, 2H), 6.43-6.08 (m, 1H), 5.92-5.62 (m, 1H), 3.93 (s, 3H), 2.96-2.57 (m, 1H). | 312.1 3.99 min |
| 0.0267 Method 28 | 41 | (rac-(5S,7S)-7-fluoro-5-phenyl-6,7-dihydro-5H-pyrrolo[1,2-b][1,2,4]triazol-2-yl)-(2-thienyl)methanone | $^1$H NMR (400 MHz, CD$_3$OD) δ 8.50-8.49 (m, 1H). 7.96-7.94 (m, 1H), 7.49-7.35 (m, 3H), 7.35-7.27 (m, 2H), 7.26-7.20 (m, 1H), 6.24-6.22 (m, 0.5H), 6.10-6.08 (m, 0.5H), 5.74-5.68 (m, 1H), 3.86-3.72 (m, 1H), 2.91-2.79 (m, 1H). | 314.1 0.891 min |
| 0.0468 Method 26 | 42 | cyclopropyl-(rac-(5S,7S)-7-fluoro-5-phenyl-6,7-dihydro-5H-pyrrolo[1,2-b][1,2,4]triazol-2-yl)methanone | $^1$H NMR (400 MHz, CD$_3$OD) δ 7.45-7.35 (m, 3H), 7.27-7.25 (m, 2H), 6.18-6.15 (m, 0.5H), 6.05-6.00 (m, 0.5H), 5.65-5.60 (m, 1H), 3.77-3.65 (m, 1H), 3.05-2.95 (m, 1H), 2.90-2.70 (m, 1H), 1.17-1.13 (m, 2H), 1.10-1.05 (m, 2H) | 272.3 1.031 min |
| 0.012 Method 29 | 43 | cyclobutyl-[rac-(5R,7R)-7-fluoro-5-phenyl-6,7-dihydro-5H-pyrrolo[1,2-b][1,2,4]triazol-2-yl]methanone | $^1$H NMR (400 MHz, CD$_3$OD) δ 7.40-7.30 (m, 3H), 7.25-7.21 (m, 2H), 6.15-6.10 (m, 0.5H), 6.01-5.95 (m, 0.5H), 5.60-5.55 (m, 1H), 4.15-4.07 (m, 1H), 3.74-3.65 (m, 1H), 2.80-2.70 (m, 1H), 2.35-2.20 (m, 3H), 2.20-2.15 (m, 1H), 2.12-2.00 (m, 1H), 1.90-1.85 (m, 1H). | 286.0 0.883 min |

TABLE 1-continued

| K$_i$ (uM) Method | Ex # | Structure | $^1$H NMR | MS (m/z) R.T. |
|---|---|---|---|---|
| 0.0115 Method 30 | 44 | 1-(7-fluoro-5-phenyl-6,7-dihydro-5H-pyrrolo[1,2-b][1,2,4]triazol-2-yl)-2,2-dimethyl-propan-1-one | $^1$H NMR (400 MHz, CD$_3$OD) δ 7.42-7.36 (m, 3H), 7.36-7.23 (m, 2H), 6.16-6.13 (m, 0.5H), 6.02-5.99 (m, 0.5H), 5.65-5.61 (m, 1H), 3.77-3.68 (m, 1H), 2.85-2.73 (m, 1H), 1.35 (s, 9H). | 288.0 0.907 min |
| 0.0143 Method 31 | 45 | 1-(7-fluoro-5-phenyl-6,7-dihydro-5H-pyrrolo[1,2-b][1,2,4]triazol-2-yl)-2-methyl-propan-1-one | $^1$H NMR (400 MHz, CD$_3$OD) δ 7.46-7.36 (m, 3H), 7.28-7.26 (m, 2H), 6.18-6.16 (m, 0.5H), 6.05-6.02 (m, 0.5H), 5.65-5.61 (m, 1H), 3.78-3.72 (m, 1H), 3.64-3.61 (m, 1H), 2.87-2.76 (m, 1H), 1.19 (d, J = 7.2 Hz, 3H), 1.17 (d, J = 6.8 Hz, 3H). | 274.2 1.971 min, |
| 1.21 Method 32 | 46 | 1-[rac-(5R,7R)-7-fluoro-5-phenyl-6,7-dihydro-5H-pyrrolo[1,2-b][1,2,4]triazol-2-yl]propan-1-one | $^1$H NMR (400 MHz, CD$_3$OD) δ 7.42-7.32 (m, 3H), 7.27-7.23 (m, 2H), 6.17-6.14 (m, 0.5H), 6.03-6.00 (m, 0.5H), 5.62-5.58 (m, 1H), 3.80-3.70 (m, 1H), 3.06-3.00 (m, 2H), 2.82-2.78 (m, 1H), 1.13 (t, J = 7.2 Hz, 3H). | 260.0 0.817 min, |
| 0.00356 Method 32 | 47 | 1-[rac-(5S,7S)-7-fluoro-5-phenyl-6,7-dihydro-5H-pyrrolo[1,2-b][1,2,4]triazol-2-yl]propan-1-one | 1H NMR (400 MHz, CD$_3$OD) δ 7.43-7.32 (m, 3H), 7.27-7.23 (m, 2H), 6.17-6.14 (m, 0.5H), 6.02-6.00 (m, 0.5H), 5.65-5.58 (m, 1H), 3.84-3.64 (m, 1H), 3.06-3.00 (m, 2H), 2.88-2.69 (m, 1H), 1.13 (t, J = 7.2 Hz, 3H) | 260.0 0.822 min |

TABLE 1-continued

| K$_i$ (uM) Method | Ex # | Structure | $^1$H NMR | MS (m/z) R.T. |
|---|---|---|---|---|
| 0.416 Method 33 | 48 | (1-methylpyrazol-4-yl)-[rac-(5R,7R)-7-fluoro-5-phenyl-6,7-dihydro-5H-pyrrolo[1,2-b][1,2,4]triazol-2-yl]methanone | $^1$H NMR (400 MHz, CD$_3$OD) δ 8.61 (s, 1H), 8.24 (s, 1H), 7.46-7.34 (m, 3H), 7.32-7.25 (m, 2H), 6.22-6.19 (m, 0.5H), 6.08-6.05 (m, 0.5H), 5.72-5.65 (m, 1H), 3.93 (s, 3H), 3.85-3.70 (m, 1H), 2.90-2.75 (m, 1H). | 311.9 0.791 min, |
| 0.0236 Method 32 | 49 | 1-[rac-(5R,7R)-7-fluoro-5-phenyl-6,7-dihydro-5H-pyrrolo[1,2-b][1,2,4]triazol-2-yl]propan-1-one | $^1$H NMR(400 MHz, CD$_3$OD) δ 7.38-7.35 (m, 3H), 7.25-7.23 (m, 2H), 6.15-6.13 (m, 0.5H), 6.01-5.99 (m, 0.5H), 5.59-5.53 (m, 1H), 3.77-3.67 (m, 1H), 3.05-2.99 (m, 2H), 2.84-2.73 (m, 1H), 1.13 (t, J = 7.2 Hz, 3H). | 260.2 1.038 min, |
| 0.0767 Method 34 | 50 | 1-[rac-(5R,7R)-7-fluoro-5-phenyl-6,7-dihydro-5H-pyrrolo[1,2-b][1,2,4]triazol-2-yl]ethanone | $^1$H NMR (400 MHz, CD$_3$OD) δ 7.41-7.35 (m, 3H), 7.26-7.24 (m, 2H), 6.16-6.14 (m, 0.5H), 6.01-6.00 (m, 0.5H), 5.62-5.58 (m, 1H), 3.77-3.68 (m, 1H), 2.85-2.74 (m, 1H), 2.55 (s, 3H). | 246.2 0.954 min |
| 0.003 Method 35 | 51 | ((5S,7S)-7-fluoro-5-phenyl-6,7-dihydro-5H-pyrrolo[1,2-b][1,2,4]triazol-2-yl)((1R,2S)-2-fluorocyclopropyl)methanone | 1H NMR (400 MHz, CD3OD) δ 7.51-7.33 (m, 3H), 7.32-7.20 (m, 2H), 6.21-6.04 (m, 1H), 5.70-5.62 (m, 1H), 5.00-4.82 (m, 1H), 3.83-3.70 (m, 1H), 3.47-3.42 (m, 1H), 2.90-2.77 (m, 1H), 1.74-1.63 (m, 1H), 1.60-1.52 (m, 1H). | 290.1 1.756 min |

TABLE 1-continued

| $K_i$ (uM) Method | Ex # | Structure | $^1$H NMR | MS (m/z) R.T. |
|---|---|---|---|---|
| 0.005 Method 35 | 52 | ((5S,7S)-7-fluoro-5-phenyl-6,7-dihydro-5H-pyrrolo[1,2-b][1,2,4]triazol-2-yl)((1S,2R)-2-fluorocyclopropyl)methanone | 1H NMR (400 MHz, CD3OD) δ 7.51-7.33 (m, 3H), 7.30-7.28 (m, 2H), 6.21-6.03 (m, 1H), 5.68-5.64 (m, 1H), 5.02-4.94 (m, 1H), 4.84-4.80 (m, 1H), 3.84-3.70 (m, 1H), 3.47-3.44 (m, 1H), 2.90-2.78 (m, 1H), 1.73-1.62 (m, 1H), 1.60-1.52 (m, 1H). | 290.1 1.765 min |
| 0.0224 Method 36 | 53 | (1-fluorocyclopropyl)-(rac-(5S,7S)-7-fluoro-5-phenyl-6,7-dihydro-5H-pyrrolo[1,2-b][1,2,4]triazol-2-yl)methanone | 1H NMR (400 MHz, CDCl3) δ 7.41-7.37 (m, 3H), 7.23-7.21 (m, 2H), 6.09-6.07 (m, 0.5H), 5.96-5.93 (m, 0.5H), 5.51-5.50 (m, 1H), 3.67-3.58 (m, 1H), 3.00-2.90 (m, 1H), 1.92-1.88 (m, 2H), 1.62-1.58 (m, 2H). | 290.1 1.726 min |
| 0.028 Method 37 | 54 | (3-methyloxetan-3-yl)-[(5S,7S)-7-fluoro-5-phenyl-6,7-dihydro-5H-pyrrolo[1,2-b][1,2,4]triazol-2-yl]methanone | 1H NMR (400 MHz, CD3OD) δ 7.43-7.37 (m, 3H), 7.25-7.23 (m, 2H), 6.17-6.15 (m, 0.5H), 6.03-6.01 (m, 0.5H), 5.65-5.62 (m, 1H), 5.09-5.02 (m, 2H), 4.52-4.26 (m, 2H), 3.78-3.70 (m, 1H), 2.86-2.76 (m, 1H), 1.74 (s, 3H). | 302.1 0.675 min |
| >10 Method 38 | 55 | (3-methyloxetan-3-yl)-[(5R,7R)-7-fluoro-5-phenyl-6,7-dihydro-5H-pyrrolo[1,2-b][1,2,4]triazol-2-yl]methanone | 1H NMR (400 MHz, CD3OD) δ 7.43-7.37 (m, 3H), 7.25-7.23 (m, 2H), 6.17-6.15 (m, 0.5H), 6.03-6.01 (m, 0.5H), 5.65-5.62 (m, 1H), 5.09-5.02 (m, 2H), 4.52-4.26 (m, 2H), 3.78-3.70 (m, 1H), 2.86-2.76 (m, 1H), 1.74 (s, 3H). | 302.1 0.678 min, |

TABLE 1-continued

| K$_i$ (uM) Method | Ex # | Structure | $^1$H NMR | MS (m/z) R.T. |
|---|---|---|---|---|
| 0.221 Method 39 | 56 | 3-oxabicyclo[3.1.0]hexan-6-yl-[rac-(5S,7S)-7-fluoro-5-phenyl-6,7-dihydro-5H-pyrrolo[1,2-b][1,2,4]triazol-2-yl]methanone | 1H NMR (400 MHz, CDCl3) δ 7.43-7.39 (m, 3H), 7.27-7.26 (m, 2H), 6.12-5.96 (m, 1H), 5.53-5.49 (m, 1H), 4.02-3.99 (m, 2H), 3.82-3.80 (m, 2H), 3.70-3.61 (m, 1H), 3.07-3.05 (m, 1H), 3.02-2.95 (m, 1H), 2.45-2.43 (m, 2H). | 313.9 0.821 min |
| 0.0423 Method 40 | 57 | oxetan-3-yl-[rac-(5S,7S)-7-fluoro-5-phenyl-6,7-dihydro-5H-pyrrolo[1,2-b][1,2,4]triazol-2-yl]methanone | 1H NMR (400 MHz, CDCl3) δ 7.43-7.40 (m, 3H), 7.27-7.23 (m, 2H), 6.11-5.95 (m, 1H), 5.50-5.49 (m, 1H), 4.97-4.90 (m, 4H), 4.72-4.68 (m, 1H), 3.68-3.59 (m, 1H), 3.03-2.92 (m, 1H). | 287.9 0.782 min, |
| 0.0287 Method 41 | 58 | [1-(hydroxymethyl)cyclopropyl]-[rac-(5S,7S)-7-fluoro-5-phenyl-6,7-dihydro-5H-pyrrolo[1,2-b][1,2,4]triazol-2-yl]methanone | 1H NMR (400 MHz, CD3OD) δ 7.43-7.37 (m, 3H), 7.27-7.25 (m, 2H), 6.17-6.15 (m, 0.5H), 6.03-6.01 (m, 0.5H), 5.63-5.61 (m, 1H), 3.96-3.85 (m, 2H), 3.77-3.71 (m, 1H), 2.86-2.75 (m, 1H), 1.71-1.67 (m, 2H), 1.10-1.07 (m, 2H). | 302.1 0.648 min |
| 0.0032 Method 42 | 59 | [(1R)-2,2-difluorocyclopropyl]-[(5S,7S)-7-fluoro-5-phenyl-6,7-dihydro-5H-pyrrolo[1,2-b][1,2,4]triazol-2-yl]methanone | 1H NMR (400 MHz, CD3OD) δ 7.45-7.41 (m, 3H), 7.30-7.28 (m, 2H), 6.21-6.19 (m, 0.5H), 6.07-6.05 (m, 0.5H), 5.66-5.65 (m, 1H), 3.87-3.74 (m, 2H), 2.89-2.79 (m, 1H), 2.33-2.28 (m, 1H), 1.98-1.97 (m, 1H). | 308.1 1.822 min |

TABLE 1-continued

| $K_i$ (uM) Method | Ex # | Structure | $^1$H NMR | MS (m/z) R.T. |
|---|---|---|---|---|
| 0.0183 Method 42 | 60 | [(1S)-2,2-difluorocyclopropyl]-[(5S,7S)-7-fluoro-5-phenyl-6,7-dihydro-5H-pyrrolo[1,2-b][1,2,4]triazol-2-yl]methanone | 1H NMR (400 MHz, CD3OD) δ 7.42-7.38 (m, 3H), 7.31-7.29 (m, 2H), 6.21-6.19 (m, 0.5H), 6.07-6.05 (m, 0.5H), 5.68-5.66 (m, 1H), 3.85-3.76 (m, 2H), 2.86-2.83 (m, 1H), 2.32-2.28 (m, 1H), 1.96-1.93 (m, 1H). | 308.1 1.834 min |
| 0.0003 Method 43 | 61 | (1-fluorocyclopropyl)-[(5S,7S)-7-fluoro-5-phenyl-6,7-dihydro-5H-pyrrolo[1,2-b][1,2,4]triazol-2-yl]methanone | 1H NMR (400 MHz, CDCl3) δ 7.40-7.37 (m, 3H), 7.23-7.21 (m, 2H), 6.09-6.07 (m, 0.5H), 5.96-5.94 (m, 0.5H), 5.51-5.49 (m, 1H), 3.67-3.58 (m, 1H), 3.00-2.90 (m, 1H), 1.92-1.88 (m, 2H), 1.62-1.60 (m, 2H). | 290.1 1.736 min |

TABLE 2

| $K_i$ (uM) Method | Ex # | Structure | $^1$H NMR | MS (m/z) R.T. |
|---|---|---|---|---|
| 0.004 Method 44 | 62 | cyclopropyl-[(5S,7S)-7-fluoro-5-(2-fluorophenyl)-6,7-dihydro-5H-pyrrolo[1,2-b][1,2,4]triazol-2-yl]methanone | $^1$H NMR (400 MHz, CD$_3$OD) δ 7.47-7.41 (m, 1H), 7.25-7.18 (m, 2H), 7.16-7.13 (m, 1H), 6.22-6.06 (m, 1H), 5.92-5.88 (m, 1H), 3.85-3.78 (m, 1H), 3.08-3.02 (m, 1H), 2.93-2.78 (m, 1H), 1.22-1.17 (m, 2H), 1.15-1.09 (m, 2H). | 290.2 1.043 min |
| 0.01 Method 45 | 63 | cyclopropyl-[rac-(5S)-5-(2-fluorophenyl)-6,7-dihydro-5H-pyrrolo[1,2-b][1,2,4]triazol-2-yl]methanone | $^1$H NMR (400 MHz, CD$_3$OD) δ 7.44-7.35 (m, 1H), 7.23-7.16 (m, 3H), 5.81-5.77 (m, 1H), 3.37-3.29 (m, 1H), 3.21-3.03 (m, 2H), 2.99-2.93 (m, 1H), 2.77-2.65 (m, 1H), 1.16-1.09 (m, 2H), 1.09-1.00 (m, 2H). | 272.1 0.699 min |

TABLE 2-continued

| K$_i$ (uM) Method | Ex # | Structure | $^1$H NMR | MS (m/z) R.T. |
|---|---|---|---|---|
| 0.78 Method 46 | 64 | (3,3-difluorocyclobutyl)-[(5R,7R)-7-fluoro-5-phenyl-6,7-dihydro-5H-pyrrolo[1,2-b][1,2,4]triazol-2-yl]methanone | $^1$H NMR (400 MHz, CD$_3$OD) δ 7.43-7.38 (m, 3H), 7.29-7.27 (m, 2H), 6.19-6.17 (m, 0.5H), 6.05-6.03 (m, 0.5H), 5.64-5.63 (m, 1H), 3.94-3.93 (m, 1H), 3.79-3.75 (m, 1H), 2.90-2.82 (m, 5H). | 322.1 1.904 min |
| 0.68 Method 35 | 65 | [(1S,2R)-2-fluorocyclopropyl]-[(5R,7R)-7-fluoro-5-phenyl-6,7-dihydro-5H-pyrrolo[1,2-b][1,2,4]triazol-2-yl]methanone | $^1$H NMR (400 MHz, CD$_3$OD) δ 7.51-7.33 (m, 3H), 7.30-7.28 (m, 2H), 6.21-6.03 (m, 1H), 5.68-5.64 (m, 1H), 5.02-4.94 (m, 1H), 4.84-4.80 (m, 1H), 3.84-3.70 (m, 1H), 3.47-3.44 (m, 1H), 2.90-2.78 (m, 1H), 1.73-1.62 (m, 1H), 1.60-1.52 (m, 1H). | 290.1 1.765 min |
| 0.0033 Method 47 | 66 | [(5S)-7,7-difluoro-5-phenyl-5,6-dihydropyrrolo[1,2-b][1,2,4]triazol-2-yl]-[(1S,2R)-2-fluorocyclopropyl]methanone | $^1$H NMR (400 MHz, CD$_3$OD) δ 7.49-7.44 (m, 3H), 7.33-7.30 (m, 2H), 5.99-5.92 (m, 1H), 5.02-5.00 (m, 0.5H), 4.86-4.82 (m, 0.5H), 3.89-3.86 (m, 1H), 3.51-3.47 (m, 1H), 3.34-3.33 (m, 0.5H), 3.32-3.22 (m, 0.5H), 1.78-1.70 (m, 1H), 1.63-1.57 (m, 1H). | 308.0 0.822 min |
| 0.027 Method 47 | 67 | [(5S)-7,7-difluoro-5-phenyl-5,6-dihydropyrrolo[1,2-b][1,2,4]triazol-2-yl]-[(1R,2S)-2-fluorocyclopropyl]methanone | $^1$H NMR (400 MHz, CD$_3$OD) δ 7.47-7.43 (m, 3H), 7.31-7.29 (m, 2H), 5.98-5.94 (m, 1H), 5.05-4.99 (m, 0.5H), 4.86-4.83 (m, 0.5H), 3.91-3.86 (m, 1H), 3.47-3.45 (m, 1H), 3.34-3.26 (m, 1H), 1.74-1.68 (m, 1H), 1.62-1.56 (m, 1H). | 308.1 0.818 min, |

TABLE 2-continued

| $K_i$ (uM) Method | Ex # | Structure | $^1$H NMR | MS (m/z) R.T. |
|---|---|---|---|---|
| 0.013 Method 48 | 68 | cyclopropyl-[(5S)-7,7-difluoro-5-phenyl-5,6-dihydropyrrolo[1,2-b][1,2,4]triazol-2-yl]methanone | $^1$H NMR (400 MHz, CDCl$_3$) δ 7.45-7.41 (m, 3H), 7.23-7.21 (m, 2H), 5.73-5.68 (m, 1H), 3.75-3.70 (m, 1H), 3.31-3.19 (m, 1H), 3.09-3.04 (m, 1H), 1.37-1.32 (m, 2H), 1.14-1.09 (m, 2H). | 290.2 1.238 min |
| 0.790 Method 35 | 69 | [(1R,2S)-2-fluorocyclopropyl]-[(5R,7R)-7-fluoro-5-phenyl-6,7-dihydro-5H-pyrrolo[1,2-b][1,2,4]triazol-2-yl]methanone | $^1$H NMR (400 MHz, CD$_3$OD) δ 7.51-7.33 (m, 3H), 7.32-7.20 (m, 2H), 6.21-6.04 (m, 1H), 5.70-5.62 (m, 1H), 5.00-4.82 (m, 1H), 3.83-3.70 (m, 1H), 3.47-3.42 (m, 1H), 2.90-2.77 (m, 1H), 1.74-1.63 (m, 1H), 1.60-1.52 (m, 1H). | 290.1 1.756 min |
| 0.017 Method 49 | 70 | (2,2-difluorospiro[2.3]hexan-5-yl)-[(5S,7S)-7-fluoro-5-phenyl-6,7-dihydro-5H-pyrrolo[1,2-b][1,2,4]triazol-2-yl]methanone (mixture of diastereomers) | $^1$H NMR (400 MHz, CD$_3$OD) δ 7.43-7.38 (m, 3H), 7.28-7.26 (m, 2H), 6.18-6.02 (m, 1H), 5.64-5.62 (m, 1H), 4.24-4.08 (m, 1H), 3.87-3.64 (m, 1H), 2.91-2.74 (m, 1H), 268-228 (m, 4H), 1.32-1.23 (m, 2H). | 348.1 1.281 & 1.298 min, |
| 0.014 Method 50 | 71 | 1-[(5S)-5-(2-chlorophenyl)-6,7-dihydro-5H-pyrrolo[1,2-b][1,2,4]triazol-2-yl]propan-1-one | $^1$H NMR (400 MHz, CD$_3$OD) δ 7.52-7.50 (m, 1H), 7.38-7.33 (m, 2H), 6.96-6.94 (m, 1H), 5.99-5.96 (m, 1H), 3.40-3.33 (m, 1H), 3.14-3.11 (m, 2H), 3.07-3.03 (m, 2H), 2.68-2.65 (m, 1H), 1.18 (d, J = 7.2 Hz, 3H). | 276.1 1.185 min |

TABLE 2-continued

| K_i (uM) Method | Ex # | Structure | $^1$H NMR | MS (m/z) R.T. |
|---|---|---|---|---|
| 0.0049 Method 51 | 72 | [1-(hydroxymethyl)cyclopropyl]-[(5S,7S)-7-fluoro-5-phenyl-6,7-dihydro-5H-pyrrolo[1,2-b][1,2,4]triazol-2-yl]methanone | $^1$H NMR (400 MHz, CD$_3$OD) δ 7.44-7.38 (m, 3H), 7.30-7.26 (m, 2H), 6.19-6.16 (m, 0.5H), 6.05-6.02 (m, 0.5H), 5.65-5.61 (m, 1H), 3.97-3.85 (m, 2H), 3.84-3.68 (m, 1H), 2.87-2.80 (m, 1H), 1.72-1.67 (m, 2H), 1.11-1.08 (m, 2H). | 0.695 min, 302.1 |
| 0.0034 Method 52 | 73 | (3,3-difluorocyclobutyl)-[(5S,7S)-7-fluoro-5-phenyl-6,7-dihydro-5H-pyrrolo[1,2-b][1,2,4]triazol-2-yl]methanone | $^1$H NMR (400 MHz, CD$_3$OD) δ 7.44-7.39 (m, 3H), 7.30-7.28 (m, 2H), 6.20-6.17 (m, 0.5H), 6.06-6.03 (m, 0.5H), 5.66-5.64 (m, 1H), 3.97-3.80 (m, 1H), 3.78-3.74 (m, 1H), 2.91-2.83 (m, 5H). | 322.2 1.241 min |
| 0.018 Method 53 | 74 | [2-(2-pyridyl)cyclopropyl]-[(5S,7S)-7-fluoro-5-phenyl-6,7-dihydro-5H-pyrrolo[1,2-b][1,2,4]triazol-2-yl]methanone | $^1$H NMR (400 MHz, CD$_3$OD) δ 8.39-8.37 (m, 1H), 7.69-7.65 (m, 1H), 7.42-7.31 (m, 4H), 7.27-7.17 (m, 3H), 6.18-6.02 (m, 1H), 5.65-5.61 (m, 1H), 3.83-3.67 (m, 1H), 3.56-3.51 (m, 1H), 2.88-2.73 (m, 2H), 1.86-1.79 (m, 2H). | 348.9 0.745 min |
| 0.0037 Method 54 | 75 | [(5S,7S)-7-fluoro-5-phenyl-6,7-dihydro-5H-pyrrolo[1,2-b][1,2,4]triazol-2-yl]-[rac-(1S,2S)-2-methylcyclopropyl]methanone (mixture of diastereomers) | $^1$H NMR (400 MHz, CD$_3$OD) δ 7.42-7.37 (m, 3H), 7.28-7.26 (m, 2H), 6.20-6.16 (m, 0.5H), 6.05-6.02 (m, 0.5H), 5.65-5.63 (m, 1H), 3.78-3.68 (m, 1H), 2.83-2.75 (m, 2H), 1.59-1.52 (m, 1H), 1.45-1.37 (m, 1H), 1.19-1.14 (m, 3H), 1.01-0.91 (m, 1H). | 286.1 0.793 min |

TABLE 2-continued

| K$_i$ (uM) Method | Ex # | Structure | $^1$H NMR | MS (m/z) R.T. |
|---|---|---|---|---|
| 0.0035 Method 55 | 76 | [(5S,7S)-7-fluoro-5-phenyl-6,7-dihydro-5H-pyrrolo[1,2-b][1,2,4]triazol-2-yl]-spiro[2.3]hexan-5-yl-methanone | $^1$H NMR (400 MHz, CDCl$_3$) δ 7.42-7.37 (m, 3H), 7.27-7.23 (m, 2H), 6.10-5.94 (m, 1H), 5.50-5.47 (m, 1H), 4.32-4.26 (m, 1H), 3.67-3.60 (m, 1H), 3.01-2.70 (m, 1H), 2.65-2.57 (m, 2H), 2.31-2.26 (m, 2H), 0.51-0.47 (m, 2H), 0.43-0.40 (m, 2H). | 312.0 0.904 min |
| 0.014 Method 56 | 77 | cyclopropyl-[(5S)-5-(2-chlorophenyl)-6,7-dihydro-5H-pyrrolo[1,2-b][1,2,4]triazol-2-yl]methanone | $^1$H NMR (400 MHz, CD$_3$OD) δ 7.51 (d, J = 1.6 Hz, 1H), 7.49-7.33 (m, 2H), 6.96 (d, J = 7.6 Hz, 1H), 6.00-5.96 (m, 1H), 3.45-3.36 (m, 1H), 3.15-3.10 (m, 2H), 3.05-2.98 (m, 1H), 2.70-2.60 (m, 1H), 1.20-1.15 (m, 2H), 1.11-1.07 (m, 2H). | 288.1 1.187 min |
| 0.020 Method 57 | 78 | cyclopropyl-[rac-(4S,6S)-4-fluoro-6-phenyl-5,6-dihydro-4H-pyrrolo[1,2-b]pyrazol-2-yl]methanone (mixture of enantiomers) | $^1$H NMR (400 MHz, CDCl$_3$) δ 7.41-7.36 (m, 3H), 7.27-6.90 (m, 2H), 6.93 (s, 1H), 6.09-5.92 (m, 1H), 5.53-5.49 (m, 1H), 3.58-3.47 (m, 1H), 2.97-2.79 (m, 2H), 1.22-1.19 (m, 2H), 0.99-0.96 (m, 2H). | 270.0 0.870 min |
| 0.0034 Method 58 | 79 | [1-(fluoromethyl)cyclopropyl]-[(5S,7S)-7-fluoro-5-phenyl-6,7-dihydro-5H-pyrrolo[1,2-b][1,2,4]triazol-2-yl]methanone | $^1$H NMR (400 MHz, CD$_3$OD) δ 7.43-7.33 (m, 3H), 7.26-7.23 (m, 2H), 6.17-6.12 (m, 0.5H), 6.01-5.98 (m, 0.5H), 5.62-5.60 (m, 1H), 4.83-4.76 (m, 1H), 4.73-4.63 (m, 1H), 3.76-3.65 (m, 1H), 2.85-2.77 (m, 1H), 1.86-1.79 (m, 2H), 1.23-1.16 (m, 2H). | 304.2 1.188 min |

TABLE 2-continued

| $K_i$ (uM) Method | Ex # | Structure | ¹H NMR | MS (m/z) R.T. |
|---|---|---|---|---|
| 0.033 Method 59 | 80 | 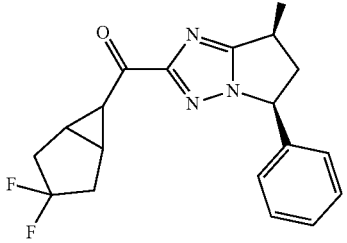<br>(3,3-difluoro-6-bicyclo[3.1.0]hexanyl)-[(5S,7S)-7-fluoro-5-phenyl-6,7-dihydro-5H-pyrrolo[1,2-b][1,2,4]triazol-2-yl]methanone<br>(mixture of diastereomers) | ¹H NMR (400 MHz, CD₃OD) δ 7.44-7.40 (m, 3H), 7.29-7.27 (m, 2H), 6.19-6.16 (m, 0.5H), 6.05-6.02 (m, 0.5H), 5.65-5.64 (m, 1H), 3.79-3.73 (m, 1H), 3.03-3.02 (m, 1H), 2.90-2.80 (m, 1H), 2.54-2.30 (m, 2H), 2.30-2.25 (m, 2H), 2.20-2.18 (m, 2H). | 348.2 1.255 min |
| 0.028 Method 60 | 81 | 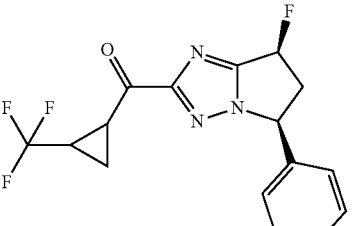<br>[(5S,7S)-7-fluoro-5-phenyl-6,7-dihydro-5H-pyrrolo[1,2-b][1,2,4]triazol-2-yl]-[2-(trifluoromethyl)cyclopropyl]methanone<br>(mixture of diastereomers) | ¹H NMR (400 MHz, CD₃OD) δ 7.45-7.39 (m, 3H), 7.32-7.29 (m, 2H), 6.22-6.05 (m, 1H), 5.70-5.65 (m, 1H), 3.84-3.71 (m, 1H), 3.41-3.37 (m, 1H), 2.90-2.79 (m, 1H), 2.45-2.40 (m, 1H), 1.53-1.46 (m, 2H). | 339.9 0.904 min |
| 0.010 Method 61 | 82 | 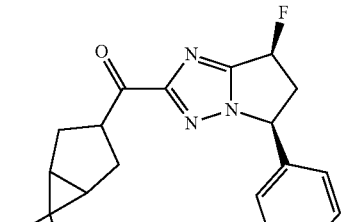<br>(6,6-difluoro-3-bicyclo[3.1.0]hexanyl)-[(5S,7S)-7-fluoro-5-phenyl-6,7-dihydro-5H-pyrrolo[1,2-b][1,2,4]triazol-2-yl]methanone<br>(mixture of diastereomers) | ¹H NMR (400 MHz, CDCl₃) δ 7.42-7.39 (m, 3H), 7.26-7.23 (m, 2H), 6.12-5.94 (m, 1H), 5.52-5.48 (m, 1H), 4.19-4.15 (m, 0.5H), 3.88-3.85 (m, 0.5H), 3.68-3.59 (m, 1H), 3.02-2.91 (m, 1H), 2.39-2.30 (m, 4H), 2.08-2.04 (m, 2H). | 347.9 0.896 min |
| 0.0037 Method 62 | 83 | 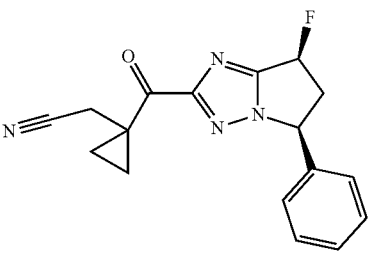 [SMILES: N#CCC1(C(=O)c2nc3n(n2)[C@H](c2ccccc2)C[C@@H]3F)CC1]<br>2-[1-[(5S,7S)-7-fluoro-5-phenyl-6,7-dihydro-5H-pyrrolo[1,2-b][1,2,4]triazole-2-carbonyl]cyclopropyl]acetonitrile | ¹H NMR (400 MHz, CD₃OD) δ 7.43-7.35 (m, 3H), 7.26-7.23 (m, 2H), 6.17-6.14 (m, 0.5H), 6.03-6.00 (m, 0.5H), 5.65-5.59 (m, 1H), 3.81-3.67 (m, 1H), 2.92 (s, 2H), 2.87-2.72 (m, 1H), 2.14-1.99 (m, 2H), 1.27-1.21 (m, 2H). | 311.1 0.717 min |

TABLE 2-continued

| K<sub>i</sub> (uM) Method | Ex # | Structure | ¹H NMR | MS (m/z) R.T. |
|---|---|---|---|---|
| 0.15 Method 63 | 84 | cyclopropyl-[(5S,7S)-7-methoxy-5-phenyl-6,7-dihydro-5H-pyrrolo[1,2-b][1,2,4]triazol-2-yl]methanone | 1H NMR (400 MHz, CD₃OD) δ 7.40-7.31 (m, 5H), 5.56-5.52 (m, 1H), 4.94-4.92 (m, 1H), 3.67-3.59 (m, 4H), 3.02-3.01 (m, 1H), 2.62-2.57 (m, 1H), 1.17-1.15 (m, 2H), 1.10-1.07 (m, 2H). | 284.1 0.709 min |
| 0.009 Method 64 | 85 | cyclopropyl-[(5S,7S)-7-fluoro-5-(4-fluorophenyl)-6,7-dihydro-5H-pyrrolo[1,2-b][1,2,4]triazol-2-yl]methanone | ¹H NMR (400 MHz, CD₃OD) δ 7.36-7.32 (m, 2H), 7.19-7.14 (m, 2H), 6.20-6.04 (m, 1H), 5.65-5.65 (m, 1H), 3.83-3.69 (m, 1H), 3.10-2.97 (m, 1H), 2.89-2.77 (m, 1H), 1.20-1.09 (m, 4H). | 289.9 0.833 min |
| 0.16 Method 65 | 86 | 2-[rac-(5S,7S)-7-fluoro-5-phenyl-6,7-dihydro-5H-pyrrolo[1,2-b][1,2,4]triazole-2-carbonyl]-cyclopropanecarbonitrile (mixture of diastereomers) | ¹H NMR (400 MHz, CDCl₃) δ 7.46-7.42 (m, 3H), 7.31-7.27 (m, 2H), 6.15-5.99 (m, 1H), 5.56-5.53 (m, 1H), 3.72-3.67 (m, 2H), 3.07-3.03 (m, 1H), 2.21-2.08 (m, 1H), 1.75-1.70 (m, 1H), 1.68-1.57 (m, 1H). | 296.9 0.818 min |
| 0.013 Method 66 | 87 | cyclopropyl-[(5S,7S)-7-hydroxy-5-phenyl-6,7-dihydro-5H-pyrrolo[1,2-b][1,2,4]triazol-2-yl]methanone | ¹H NMR (400 MHz, CDCl₃) δ 7.43-7.36 (m, 5H), 5.44-5.41 (m, 2H), 4.81 (s, 1H), 3.65-3.60 (m, 1H), 2.99-2.96 (m, 1H), 2.82-2.76 (m, 1H), 1.30-1.29 (m, 2H), 1.06-1.03 (m, 2H). | 270.2 2.061 min |

TABLE 2-continued

| $K_i$ (uM) Method | Ex # | Structure | $^1$H NMR | MS (m/z) R.T. |
|---|---|---|---|---|
| 0.180 Method 67 | 88 | cyclopropyl-[(5S,7R)-7-hydroxy-5-phenyl-6,7-dihydro-5H-pyrrolo[1,2-b][1,2,4]triazol-2-yl]methanone | $^1$H NMR (400 MHz, CDCl$_3$) δ 7.44-7.38 (m, 3H), 7.20-7.18 (m, 2H), 5.76-5.73 (m, 1H), 5.70-5.62 (m, 1H), 5.52-5.49 (m, 1H), 3.29-3.25 (m, 1H), 3.01-2.96 (m, 2H), 1.32-1.26 (m, 2H), 1.06-1.04 (m, 2H). | 270.2 0.906 min |
| 0.015 Method 68 | 89 | [(5S,7S)-7-fluoro-5-phenyl-6,7-dihydro-5H-pyrrolo[1,2-b][1,2,4]triazol-2-yl]-[(1S,2S)-2-methylcyclopropyl]methanone | $^1$H NMR (400 MHz, CD$_3$OD) δ 7.45-7.38 (m, 3H), 7.29-7.26 (m, 2H), 6.19-6.17 (m, 0.5H), 6.05-6.03 (m, 0.5H). 5.67-5.62 (m, 1H), 3.81-3.71 (m, 1H), 2.89-2.75 (m, 2H), 1.62-1.54 (m, 1H), 1.45-1.39 (m, 1H), 1.18 (d, J = 6.4 Hz, 3H), 0.99-0.96 (m, 1H). | 286.1 0.756 min |
| 0.0034 Method 69 | 90 | [(1R,2S)-2-fluorocyclopropyl]-[(5S,7S)-7-fluoro-5-(2-fluorophenyl)-6,7-dihydro-5H-pyrrolo[1,2-b][1,2,4]triazol-2-yl]methanone | $^1$H NMR (400 MHz, CD$_3$OD) δ 7.48-7.42 (m, 1H), 7.25-7.13 (m, 3H), 6.22-6.06 (m, 1H), 5.93-5.89 (m, 1H), 5.01-4.87 (m, 0.5H), 4.85-4.82 (m, 0.5H), 3.88-3.75 (m, 1H), 3.51-3.42 (m, 1H), 2.93-2.81 (m, 1H), 1.75-1.64 (m, 1H), 1.62-1.54 (m, 1H). | 308.0 0.852 min |
| 0.0034 Method 70 | 91 | [(5S,7S)-7-fluoro-5-phenyl-6,7-dihydro-5H-pyrrolo[1,2-b][1,2,4]triazol-2-yl]-[(1R,2R)-2-methylcyclopropyl]methanone | $^1$H NMR (400 MHz, CD$_3$OD) δ 7.44-7.40 (m, 3H), 7.29-7.27 (m, 2H), 6.20-6.16 (m, 0.5H), 6.06-6.02 (m, 0.5H), 5.67-5.61 (m, 1H), 3.79-3.73 (m, 1H), 2.89-2.74 (m, 2H), 1.64-1.60 (m, 1H), 1.44-1.39 (m, 1H), 1.17 (d, J = 6.0 Hz, 3H), 1.00-0.95 (m, 1H). | 286.1 0.757 min |

TABLE 2-continued

| K$_i$ (uM) Method | Ex # | Structure | $^1$H NMR | MS (m/z) R.T. |
|---|---|---|---|---|
| 0.870 Method 71 | 92 | cyclopropyl-[(5R,7S)-5-ethyl-7-fluoro-6,7-dihydro-5H-pyrrolo[1,2-b][1,2,4]triazol-2-yl]methanone | $^1$H NMR (400 MHz, CD$_3$OD) δ 6.09-5.89 (m, 1H), 4.55-4.45 (m, 1H), 3.43-3.36 (m, 1H), 3.15-3.06 (m, 1H), 2.67-2.53 (m, 1H), 2.09-1.93 (m, 2H), 1.23-1.18 (m, 2H), 1.17-1.11 (m, 2H), 1.05 (t, J = 7.2 Hz, 3H). | 224.0 0.770 min |
| 0.041 Method 72 | 93 | cyclopropyl-[(5R,7S)-7-fluoro-5-propyl-6,7-dihydro-5H-pyrrolo[1,2-b][1,2,4]triazol-2-yl]methanone | $^1$H NMR (400 MHz, CD$_3$OD) δ 6.07-5.91 (m, 1H), 4.59-4.53 (m, 1H), 3.42-3.33 (m, 1H), 3.11-3.07 (m, 1H), 2.67-2.52 (m, 1H), 2.02-1.98 (m, 1H), 1.91-1.80 (m, 1H), 1.69-1.57 (m, 1H), 1.52-1.38 (m, 1H), 1.23-1.11 (m, 4H), 1.01 (t, J = 7.2 Hz, 3H). | 238.2 0.972 min |
| 0.0031 Method 73 | 94 | cyclopropyl-[(5S,7S)-5-(2,6-difluorophenyl)-7-fluoro-6,7-dihydro-5H-pyrrolo[1,2-b][1,2,4]triazol-2-yl]methanone | $^1$H NMR (400 MHz, CD$_3$OD) δ 7.54-7.48 (m, 1H), 7.10-7.06 (m, 2H), 6.24-6.21 (m, 0.5H), 6.10-6.07 (m, 0.5H), 5.98-5.94 (m, 1H), 3.89-3.81 (m, 1H), 3.03-2.91 (m, 2H), 1.18-1.16 (m, 2H), 1.11-1.08 (m, 2H). | 308.1 0.740 min |
| 0.0027 Method 74 | 95 | 1-[(5S,7S)-7-fluoro-5-phenyl-6,7-dihydro-5H-pyrrolo[1,2-b][1,2,4]triazole-2-carbonyl]cyclopropanecarbonitrile | $^1$H NMR (400 MHz, CDCl$_3$) δ 7.43-7.40 (m, 3H), 7.78-7.27 (m, 2H), 6.15-5.99 (m, 1H), 5.57-5.55 (m, 1H), 3.69-3.61 (m, 1H), 3.06-2.96 (m, 1H), 2.10-2.03 (m, 2H), 1.84-1.81 (m, 2H). | 296.9 0.813 min |

TABLE 2-continued

| K<sub>i</sub> (uM) Method | Ex # | Structure | ¹H NMR | MS (m/z) R.T. |
|---|---|---|---|---|
| 0.0036 Method 75 | 96 | [(5S,7S)-7-fluoro-5-phenyl-6,7-dihydro-5H-pyrrolo[1,2-b][1,2,4]triazol-2-yl]-spiro[2.2]pentan-2-yl-methanone (mixture of diastereomers) | ¹H NMR (400 MHz, CDCl₃) δ 7.41-7.33 (m, 3H), 7.29-7.23 (m, 2H), 6.09-5.93 (m, 1H), 5.52-5.44 (m, 1H), 3.68-3.60 (m, 1H), 3.40-3.36 (m, 1H), 3.01-2.89 (m, 1H), 1.88-1.82 (m, 1H), 1.63-1.61 (m, 1H), 1.05-0.97 (m, 2H), 0.95-0.89 (m, 1H), 0.88-0.83 (m, 1H). | 298.1 0.786 min |
| 0.0084 Method 76 | 97 | [(5S,7S)-7-fluoro-5-phenyl-6,7-dihydro-5H-pyrrolo[1,2-b][1,2,4]triazol-2-yl]-spiro[2.3]hexan-2-yl-methanone (mixture of diastereomers) | ¹H NMR (400 MHz, CDCl₃) δ 7.42-7.38 (m, 3H), 7.29-7.26 (m, 2H), 6.11-5.95 (m, 1H), 5.51-5.48 (m, 1H), 3.69-3.60 (m, 1H), 3.10-3.03 (m, 1H), 3.02-2.90 (m, 1H), 2.38-2.13 (m, 4H), 2.08-1.99 (m, 1H), 1.98-1.89 (m, 1H), 1.56-1.52 (m, 1H), 1.29-1.24 (m, 1H). | 312.1 0.821 min |
| 0.11 Method 77 | 98 | [1-(2-pyridyl)cyclopropyl]-[(5S,7S)-7-fluoro-5-phenyl-6,7-dihydro-5H-pyrrolo[1,2-b][1,2,4]triazol-2-yl]methanone | ¹H NMR (400 MHz, CDCl₃) δ 8.42-8.40 (m, 1H), 7.50-7.47 (m, 1H), 7.34-7.32 (m, 3H), 7.26-7.10 (m, 1H), 7.06-7.02 (m, 3H), 6.00-5.83 (m, 1H), 5.40-5.35 (m, 1H), 3.60-3.49 (m, 1H), 2.92-2.81 (m, 1H), 2.02-1.90 (m, 1H), 1.83-1.78 (m, 2H), 1.60-1.50 (m, 1H). | 349.2 1.678 min |
| 0.0029 Method 78 | 99 | (1-cyclopropylcyclopropyl)-[(5S,7S)-7-fluoro-5-phenyl-6,7-dihydro-5H-pyrrolo[1,2-b][1,2,4]triazol-2-yl]methanone | ¹H NMR (400 MHz, CDCl₃) δ 7.40-7.36 (m, 3H), 7.24-7.22 (m, 2H), 6.09-5.91 (m, 1H), 5.52-5.45 (m, 1H), 3.69-3.54 (m, 1H), 2.99-2.86 (m, 1H), 1.88-1.83 (m, 1H), 1.54-1.50 (m, 2H), 0.78-0.76 (m, 2H), 0.43-0.39 (m, 2H), 0.07-0.03 (m, 2H). | 312.1 0.816 min |

TABLE 2-continued

| $K_i$ (uM) Method | Ex # | Structure | $^1$H NMR | MS (m/z) R.T. |
|---|---|---|---|---|
| 0.0035 Method 79 | 100 | cyclopropyl-[(5S,7S)-5-(2-chlorophenyl)-7-fluoro-6,7-dihydro-5H-pyrrolo[1,2-b][1,2,4]triazol-2-yl]methanone | $^1$H NMR (400 MHz, CDCl$_3$) δ 7.45-7.43 (m, 1H), 7.34-7.28 (m, 1H), 7.26-7.24 (m, 1H), 6.76-6.72 (m, 1H), 6.10-6.06 (m, 0.5H), 6.01-5.95 (m, 1H), 5.95-5.93 (m, 0.5H), 3.78-3.62 (m, 1H), 3.12-3.04 (m, 1H), 2.93-2.80 (m, 1H), 1.37-1.32 (m, 2H), 1.14-1.09 (m, 2H). | 306.1 1.049 min |
| 0.0036 Method 80 | 101 | cyclopropyl-[(5S,7S)-5-(2,5-difluorophenyl)-7-fluoro-6,7-dihydro-5H-pyrrolo[1,2-b][1,2,4]triazol-2-yl]methanone | $^1$H NMR (400 MHz, CD$_3$OD) δ 7.28-7.17 (m, 2H), 6.93-6.88 (m, 1H), 6.22-6.06 (m, 1H), 5.90-5.86 (m, 1H), 3.88-3.74 (m, 1H), 3.09-3.02 (m, 1H), 2.93-2.82 (m, 1H), 1.21-1.18 (m, 2H), 1.15-1.11 (m, 2H). | 308.1 1.007 min |
| 0.0036 Method 81 | 102 | cyclopropyl-[(5S,7S)-7-fluoro-5-(2,3,6-trifluorophenyl)-6,7-dihydro-5H-pyrrolo[1,2-b][1,2,4]triazol-2-yl]methanone | $^1$H NMR (400 MHz, CDCl$_3$) δ 7.24-7.20 (m, 1H), 6.93-6.90 (m, 1H), 6.19-6.03 (m, 1H), 5.86-5.83 (m, 1H), 3.84-3.74 (m, 1H), 3.10-3.04 (m, 2H), 1.34-1.31 (m, 2H), 1.13-1.08 (m, 2H). | 325.9 0.864 min |
| 0.0079 Method 82 | 103 | cyclopropyl-[(5S,7S)-7-deuterio-7-fluoro-5-phenyl-5,6-dihydropyrrolo[1,2-b][1,2,4]triazol-2-yl]methanone | $^1$H NMR (400 MHz, CD$_3$OD) δ 7.45-7.38 (m, 3H), 7.29-7.27 (m, 2H), 5.67-5.63 (m, 1H), 3.80-3.70 (m, 1H), 3.05-3.02 (m, 1H), 2.88-2.80 (m, 1H), 1.19-1.16 (m, 2H), 1.12-1.09 (m, 2H). | 273.1 0.738 min |

TABLE 2-continued

| K$_i$ (uM) Method | Ex # | Structure | $^1$H NMR | MS (m/z) R.T. |
|---|---|---|---|---|
| 0.0032 Method 83 | 104 | [(1S,2R)-2-fluorocyclopropyl]-[(5S,7S)-7-fluoro-5-(2-fluorophenyl)-6,7-dihydro-5H-pyrrolo[1,2-b][1,2,4]triazol-2-yl]methanone | $^1$H NMR (400 MHz, CDCl$_3$) δ 7.40-7.38 (m, 1H), 7.18-7.15 (m, 2H), 6.98-6.97 (m, 1H), 6.13-6.11 (m, 0.5H), 5.99-5.98 (m, 0.5H), 5.87-5.85 (m, 1H), 5.05-5.04 (m, 0.5H), 4.89-4.88 (m, 0.5H), 3.73-3.67 (m, 1H), 3.58-3.54 (m, 1H), 3.01-2.95 (m, 1H), 1.72-1.65 (m. 2H). | 308.1 1.763 min |
| 0.013 Method 84 | 105 | rac-(1R,2R)-2-[(5S,7S)-7-fluoro-5-phenyl-6,7-dihydro-5H-pyrrolo[1,2-b][1,2,4]triazole-2-carbonyl]cyclopropanecarbonitrile (mixture of diastereomers) | $^1$H NMR (400 MHz, CD$_3$OD) δ 7.45-7.39 (m, 3H), 7.32-7.30 (m, 2H), 6.22-6.20 (m, 0.5H), 6.08-6.06 (m, 0.5H), 5.70-5.67 (m, 1H), 3.81-3.75 (m, 1H), 3.62-3.31 (m, 1H), 2.90-2.75 (m, 1H), 2.28-2.24 (m, 1H), 1.68-1.63 (m, 2H). | 297.2 0.957 min |
| 0.0031 Method 85 | 106 | cyclopropyl-[(5S,7S)-5-(2,3-difluorophenyl)-7-fluoro-6,7-dihydro-5H-pyrrolo[1,2-b][1,2,4]triazol-2-yl]methanone | $^1$H NMR (400 MHz, CDCl$_3$) δ 7.22-7.16 (m, 1H), 7.14-7.08 (m, 1H), 6.75-6.72 (m, 1H), 6.13-6.10 (m, 0.5H), 5.99-5.96 (m, 0.5H), 5.88-5.84 (m, 1H), 3.74-3.67 (m, 1H), 3.09-3.04 (m, 1H), 2.99-2.92 (m, 1H), 1.36-1.31 (m, 2H), 1.14-1.09 (m, 2H). | 308.1 0.666 min |
| 0.0039 Method 86 | 107 | cyclopropyl-[(5S,7S)-7-fluoro-5-(2,3,5-trifluorophenyl)-6,7-dihydro-5H-pyrrolo[1,2-b][1,2,4]triazol-2-yl]methanone | $^1$H NMR (400 MHz, CD$_3$OD) δ 7.29-7.26 (m, 1H), 6.78-6.75 (m, 1H), 6.23-6.06 (m, 1H), 5.96-5.93 (m, 1H), 3.88-3.80 (m, 1H), 3.07-3.04 (m, 1H), 2.96-2.89 (m, 1H), 1.22-1.11 (m, 4H). | 326.2 1.029 min |

TABLE 2-continued

| K$_i$ (μM) Method | Ex # | Structure | $^1$H NMR | MS (m/z) R.T. |
|---|---|---|---|---|
| 0.0037 Method 57 | 108 | cyclopropyl-[(4S,6S)-4-fluoro-6-phenyl-5,6-dihydro-4H-pyrrolo[1,2-b]pyrazol-2-yl]methanone | $^1$H NMR (400 MHz, CDCl$_3$) δ 7.39-7.37 (m, 3H), 7.23-7.21 (m, 2H), 6.93 (d, J = 2.8Hz, 1H), 6.09-6.07 (m, 0.5H), 5.95-5.93 (m, 0.5H), 5.51-5.49 (m, 1H), 3.54-3.45 (m, 1H), 2.96-2.92 (m, 1H), 2.85-2.82 (m, 1H), 1.23-1.20 (m, 2H), 0.99-0.96 (m, 2H). | 271.0 0.883 min |
| 0.150 Method 87 | 109 | cyclopropyl-[(5S,7S)-7-fluoro-5-isopropyl-6,7-dihydro-5H-pyrrolo[1,2-b][1,2,4]triazol-2-yl]methanone | $^1$H NMR (400 MHz, CDCl$_3$) δ 5.99-5.83 (m, 1H), 4.39-4.34 (m, 1H), 3.22-3.18 (m, 1H), 3.12-3.08 (m, 1H), 2.72-2.62 (m, 1H), 2.42-2.38 (m, 1H), 1.34-1.33 (m, 2H), 1.13-1.10 (m, 2H), 1.08 (d, J = 6.8 Hz, 3H), 0.94 (d, J = 6.8 Hz, 3H). | 238.0 0.822 min |
| 0.310 Method 88 | 110 | cyclopropyl-[(5S,7S)-5-cyclopropyl-7-fluoro-6,7-dihydro-5H-pyrrolo[1,2-b][1,2,4]triazol-2-yl]methanone | $^1$H NMR (400 MHz, CD$_3$OD) δ 6.05-5.89 (m, 1H), 4.02-3.95 (m, 1H), 3.51-3.35 (m, 1H), 3.14-3.10 (m, 1H), 2.78-2.70 (m, 1H), 1.26-1.12 (m, 5H), 0.79-0.67 (m, 3H), 0.58-0.52 (m, 1H). | 236.1 0.677 min |
| 0.0082 Method 89 | 111 | cyclopropyl-[(5S,7S)-7-deuterio-5-phenyl-6,7-dihydro-5H-pyrrolo[1,2-b][1,2,4]triazol-2-yl]methanone | $^1$H NMR (400 MHz, CDCl$_3$) δ 7.41-7.36 (m, 3H), 7.14-7.11 (m, 2H), 5.52-5.48 (m, 1H), 3.28-3.21 (m, 1H), 3.06-3.00 (m, 2H), 2.70-2.65 (m, 1H), 1.30-1.27 (m, 2H), 1.06-1.03 (m, 2H). | 255.1 1.551 min |

TABLE 2-continued

| K_i (uM) Method | Ex # | Structure | $^1$H NMR | MS (m/z) R.T. |
|---|---|---|---|---|
| 0.071 Method 90 | 112 | cyclopropyl-[rac-(5S,7S)-5-(1,1-difluoropropyl)-7-fluoro-6,7-dihydro-5H-pyrrolo[1,2-b][1,2,4]triazol-2-yl]methanone (mixture of enantiomers) | $^1$H NMR (400 MHz, CD$_3$OD) δ 5.97-5.80 (m, 1H), 4.90-4.78 (m, 1H), 3.45-3.25 (m, 1H), 3.05-2.95 (m, 1H), 2.95-2.75 (m, 1H), 2.28-2.00 (m, 2H), 1.20-1.11 (m, 2H), 1.07-0.98 (m, 5H). | 274.1 0.766 min |
| 0.043 Method 91 | 113 | cyclopropyl-[(5R,7S)-5-(cyclopropylmethyl)-7-fluoro-6,7-dihydro-5H-pyrrolo[1,2-b][1,2,4]triazol-2-yl]methanone | $^1$H NMR (400 MHz, CD$_3$OD) δ 6.02-6.00 (m, 0.5H), 5.88-5.86 (m, 0.5H), 4.60-4.55 (m, 1H), 3.37-3.23 (m, 1H), 3.05-3.01 (m, 1H), 2.75-2.60 (m, 1H), 2.00-1.95 (m, 1H), 1.68-1.65 (m, 1H), 1.16-1.06 (m, 4H), 0.90-0.77 (m, 1H), 0.49-0.47 (m, 2H), 0.10-0.02 (m, 2H). | 250.2 0.635 min |
| 0.018 Method 92 | 114 | cyclopropyl-[(5S)-7,7-dideuterio-5-phenyl-5,6-dihydropyrrolo[1,2-b][1,2,4]triazol-2-yl]methanone | $^1$H NMR (400 MHz, CDCl$_3$) δ 7.41-7.36 (m, 3H), 7.14-7.11 (m, 2H), 5.52-5.48 (m, 1H), 3.28-3.21 (m, 1H), 3.04-3.00 (m, 1H), 2.70-2.65 (m, 1H), 1.30-1.27 (m, 2H), 1.06-1.03 (m, 2H). | 256.2 1.549 min |
| 0.790 Method 93 | 115 | cyclopropyl-[(5R,7R)-7-chloro-5-phenyl-6,7-dihydro-5H-pyrrolo[1,2-b][1,2,4]triazol-2-yl]methanone | $^1$H NMR (400 MHz, CDCl$_3$) δ 7.43-7.39 (m, 2H), 7.33-7.28 (m, 3H), 5.56-5.51 (m, 1H), 5.40-5.35 (m, 1H), 3.96-3.86 (m, 1H), 3.10-2.99 (m, 2H), 1.35-1.28 (m, 2H), 1.10-1.06 (m, 2H). | 288.2 1.033 min |

TABLE 2-continued

| K$_i$ (uM) Method | Ex # | Structure | $^1$H NMR | MS (m/z) R.T. |
|---|---|---|---|---|
| 0.004 Method 93 | 116 | cyclopropyl-[(5S,7S)-7-chloro-5-phenyl-6,7-dihydro-5H-pyrrolo[1,2-b][1,2,4]triazol-2-yl]methanone | $^1$H NMR (400 MHz, CDCl$_3$) δ 7.43-7.39 (m, 2H), 7.33-7.28 (m, 3H), 5.56-5.51 (m, 1H), 5.40-5.35 (m, 1H), 3.95-3.88 (m, 1H), 3.07-2.99 (m, 2H), 1.34-1.31 (m, 2H), 1.11-1.07 (m, 2H). | 288.2 1.034 min |
| 0.56 Method 94 | 117 | cyclopropyl-[(5S,7R)-7-chloro-5-phenyl-6,7-dihydro-5H-pyrrolo[1,2-b][1,2,4]triazol-2-yl]methanone | $^1$H NMR (400 MHz, CD$_3$OD) δ 7.45-7.38 (m, 3H), 7.34-7.32 (m, 2H), 5.85 (t, J = 7.2 Hz, 1H), 5.69-5.67 (m, 1H), 3.40-3.31 (m, 2H), 3.03-3.00 (m, 1H), 1.19-1.16 (m, 2H), 1.11-1.08 (m, 2H). | 288.2 1.028 min |
| 0.032 Method 95 | 118 | cyclopropyl-[rac-(5S,7S)-5-(3-chloro-2-pyridyl)-7-fluoro-6,7-dihydro-5H-pyrrolo[1,2-b][1,2,4]triazol-2-yl]methanone (mixture of enantiomers) | 1H NMR (400 MHz, CD$_3$OD) δ 8.45 (d, J = 4.8 Hz, 1H), 7.97-7.95 (m, 1H), 7.42-7.38 (m, 1H), 6.24-6.03 (m, 2H), 3.83-3.72 (m, 1H), 3.04-2.89 (m, 2H), 1.18-1.15 (m, 2H), 1.11-1.08 (m, 2H). | 306.9 0.780 min |
| 0.036 Method 96 | 119 | cyclopropyl-[rac-(5S,7S)-7-chloro-7-deuterio-5-phenyl-5,6-dihydropyrrolo[1,2-b][1,2,4]triazol-2-yl]methanone (mixture of enantiomers) | $^1$H NMR (400 MHz, CD$_3$OD) δ 7.46-7.38 (m, 3H), 7.33-7.31 (m, 2H), 5.69-5.65 (m, 1H), 4.02-3.96 (m, 1H), 3.07-2.99 (m, 1H), 2.91-2.86 (m, 1H), 1.21-1.16 (m, 2H), 1.13-1.09 (m, 2H). | 289.1 1.033 min |

TABLE 2-continued

| K$_i$ (uM) Method | Ex # | Structure | $^1$H NMR | MS (m/z) R.T. |
|---|---|---|---|---|
| 0.910 Method 97 | 120 | cyclopropyl-[rac-(5S,7R)-7-chloro-7-deuterio-5-phenyl-5,6-dihydropyrrolo[1,2-b][1,2,4]triazol-2-yl]methanone (mixture of enantiomers) | $^1$H NMR (400 MHz, CD$_3$OD) δ 7.74-7.69 (m, 3H), 7.63-7.61 (m, 2H), 6.14 (t, J = 6.8 Hz, 1H), 3.73-3.62 (m, 2H), 3.61-3.59 (m, 1H), 1.48-1.45 (m, 2H), 1.40-1.37 (m, 2H). | 289.2 1.033 min |
| <0.005 Method 90 | 121 | cyclopropyl-[(5S,7S)-5-(1,1-difluoropropyl)-7-fluoro-6,7-dihydro-5H-pyrrolo[1,2-b][1,2,4]triazol-2-yl]methanone | $^1$H NMR (400 MHz, CDCl$_3$) δ 6.02-5.84 (m, 1H), 4.71-4.66 (m, 1H), 3.33-3.23 (m, 1H), 3.19-3.07 (m, 2H), 2.34-2.26 (m, 1H), 2.18-2.01 (m, 1H), 1.35-1.25 (m, 2H), 1.18 (s, 1H), 1.17-1.15 (m, 2H), 1.14-1.11 (m, 2H). | 273.9 0.818 min |
| 0.360 Method 98 | 122 | cyclopropyl-[rac-(5S,7S)-5-(1,1-difluoroethyl)-7-fluoro-6,7-dihydro-5H-pyrrolo[1,2-b][1,2,4]triazol-2-yl]methanone (mixture of enantiomers) | $^1$H NMR (400 MHz, CDCl$_3$) δ 6.00-5.84 (m, 1H), 4.75-4.55 (m, 1H), 3.38-3.29 (m, 1H), 3.18-2.99 (m, 2H), 1.86 (t, J = 19.2 Hz, 3H), 1.36-1.33 (m, 2H), 1.16-1.12 (m, 2H). | 259.9 0.828 min |
| 0.010 Method 95 | 123 | cyclopropyl-[(5S,7S)-5-(3-chloro-2-pyridyl)-7-fluoro-6,7-dihydro-5H-pyrrolo[1,2-b][1,2,4]triazol-2-yl]methanone | $^1$H NMR (400 MHz, CDCl$_3$) δ 8.47 (d, J = 4.8 Hz, 1H), 7.79-7.76 (m, 1H), 7.29-7.27 (m, 1H), 6.14-6.12 (m, 1H), 6.11-6.10 (m, 0.5H), 5.99-5.98 (m, 0.5H), 3.71-3.64 (m, 1H), 3.13-3.02 (m, 2H), 1.34-1.32 (m, 2H), 1.11-1.08 (m, 2H). | 307.0 0.617 min |

TABLE 2-continued

| K$_i$ (uM) Method | Ex # | Structure | $^1$H NMR | MS (m/z) R.T. |
|---|---|---|---|---|
| 0.061 Method 99 | 124 | 2-[(5S,7S)-2-(cyclopropanecarbonyl)-7-fluoro-6,7-dihydro-5H-pyrrolo[1,2-b][1,2,4]triazol-5-yl]benzonitrile | $^1$H NMR (400 MHz, CDCl$_3$) δ 7.79-7.76 (m, 1H), 7.64-7.60 (m, 1H), 7.53-7.50 (m, 1H), 7.01 (d, J = 8.0 Hz, 1H), 6.15-6.12 (m, 0.5H), 6.00-5.98 (m, 1.5H), 3.90-3.74 (m, 1H), 3.10-3.06 (m, 1H), 2.99-2.85 (m, 1H), 1.39-1.33 (m, 2H), 1.17-1.09 (m, 2H). | 397.2 0.915 min |
| 0.004 Method 100 | 125 | (1-ethylcyclopropyl)-[rac-(5S,7S)-7-fluoro-5-phenyl-6,7-dihydro-5H-pyrrolo[1,2-b][1,2,4]triazol-2-yl]methanone | 1H NMR (400 MHz, DMSO-d$_6$) δ 7.46-7.34 (m, 3H), 7.25-7.19 (m, 2H), 6.20 (ddd, J = 56.5, 7.1, 1.9 Hz, 1H), 5.69 (ddd, J = 8.5, 6.6, 3.0 Hz, 1H), 3.72 (dddd, J = 26.1, 15.4, 8.5, 7.1 Hz, 1H), 2.68 (dddd, J = 26.6, 15.3, 3.1, 1.9 Hz, 1H), 1.73 (qd, J = 7.2, 1.7 Hz, 2H), 1.58 (dq, J = 4.4, 1.7, 1.2 Hz, 2H), 0.93 (q, J = 3.2, 2.6 Hz, 2H), 0.86 (t, J = 7.3 Hz, 3H). | 300.1 5.29 min |
| 0.057 Method 101 | 126 | [rac-(5S,7S)-7-fluoro-5-phenyl-6,7-dihydro-5H-pyrrolo[1,2-b][1,2,4]triazol-2-yl]-tetrahydropyran-4-yl-methanone | 1H NMR (400 MHz, DMSO-d$_6$) δ 7.47-7.35 (m, 3H), 7.28-7.21 (m, 2H), 6.23 (ddd, J = 56.4, 7.2, 1.9 Hz, 1H), 5.73 (ddd, J = 8.9, 6.5, 3.0 Hz, 1H), 3.88 (ddt, J = 11.0, 4.6, 2.4 Hz, 2H), 3.74 (dddd, J = 26.1, 15.5, 8.6, 7.2 Hz, 1H), 3.60 (tt, J = 11.5, 3.8 Hz, 1H), 3.42 (tdd, J = 11.4, 3.6, 2.2 Hz, 2H), 2.70 (dddd, J = 26.7, 15.2, 3.1, 1.9 Hz, 1H), 1.76 (tdt, J = 10.8, 4.5, 2.2 Hz, 2H), 1.58 (dtdd, J = 13.3, 11.7, 8.8, 4.5 Hz, 2H). | 316.1 4.22 min |
| 0.016 Method 102 | 127 | [rac-(5S,7S)-7-fluoro-5-phenyl-6,7-dihydro-5H-pyrrolo[1,2-b][1,2,4]triazol-2-yl]-tetrahydropyran-3-yl-methanone (mixture of diastereomers) | 1H NMR (400 MHz, DMSO-d$_6$) δ 7.49-7.34 (m, 3H), 7.25 (dt, J = 7.8, 1.4 Hz, 2H), 6.23 (dddd, J = 56.4, 7.2, 2.0, 0.9 Hz, 1H), 5.73 (ddd, J = 8.8, 6.4, 3.0 Hz, 1H), 4.01 (tdd, J = 10.5, 3.9, 1.8 Hz, 1H), 3.84-3.65 (m, 2H), 3.57 (tdd, J = 9.8, 3.8, 1.9 Hz, 1H), 3.45 (ddd, J = 10.9, 9.5, 2.6 Hz, 1H), 3.41-3.33 (m, 1H), 2.79-2.62 (m, 1H), 2.05-1.89 (m, 1H), 1.78-1.47 (m, 3H). | 316.1 4.42 min |

TABLE 2-continued

| K$_i$ (uM) Method | Ex # | Structure | $^1$H NMR | MS (m/z) R.T. |
|---|---|---|---|---|
| 0.65 Method 103 | 128 | [rac-(5S,7S)-7-fluoro-5-phenyl 6,7-dihydro-5H-pyrrolo[1,2-b][1,2,4]triazol-2-yl]-[rac-(2R)-pyrrolidin-2-yl]methanone | 1H NMR (400 MHz, DMSO-d6) δ 7.48-7.29 (m, 3H), 7.23 (ddt, J = 11.8, 6.1, 1.6 Hz, 2H), 6.35-5.99 (m, 1H), 5.82-5.52 (m, 1H), 4.37-3.89 (m, 1H), 3.88-3.45 (m, 1H), 3.12-2.51 (m, 3H), 2.40-0.29 (m, 4H). | 300.9 0.88 min |
| 0.047 Method 104 | 129 | (2-methyltetrahydrofuran-2-yl)-[rac-(5S,7S)-7-fluoro-5-phenyl-6,7-dihydro-5H-pyrrolo[1,2-b][1,2,4]triazol-2-yl]methanone (mixture of diastereomers) | 1H NMR (400 MHz, DMSO-d6) δ 7.48-7.35 (m, 3H), 7.28-7.19 (m, 2H), 6.23 (ddt, J = 56.5, 7.2, 2.0 Hz, 1H), 5.72 (ddt, J = 8.9, 6.3, 2.8 Hz, 1H), 3.93-3.82 (m, 1H), 3.82-3.65 (m, 2H), 2.71 (dddd, J = 26.6, 15.2, 3.1, 1.9 Hz, 1H), 2.52 (m, 1H), 1.99-1.85 (m, 2H), 1.85-1.72 (m, 1H), 1.53 (d, J = 3.6 Hz, 3H). | 316.1 4.66 min |
| 0.008 Method 105 | 130 | [rac-(5S,7S)-7-fluoro-5-phenyl-6,7-dihydro-5H-pyrrolo[1,2-b][1,2,4]triazol-2-yl]-tetrahydrofuran-3-yl-methanone (mixture of diastereomers) | 1H NMR (400 MHz, DMSO-d6) δ 7.49-7.35 (m, 3H), 7.30-7.21 (m, 2H), 6.24 (ddd, J = 56.2, 7.1, 1.9 Hz, 1H), 5.74 (ddd, J = 9.2, 6.6, 3.1 Hz, 1H), 4.14-4.05 (m, 1H), 3.93 (dt, J = 11.3, 8.4 Hz, 1H), 3.87-3.65 (m, 4H), 2.72 (dddd, J = 26.7, 15.3, 3.1, 1.9 Hz, 1H), 2.19-2.00 (m, 2H). | 302.2 4.33 min |
| <0.005 Method 106 | 131 | [rac-(5S,7S)-7-fluoro-5-phenyl-6,7-dihydro-5H-pyrrolo[1,2-b][1,2,4]triazol-2-yl]-[rac-(3S)-tetrahydrofuran-3-yl]methanone | 1H NMR (400 MHz, DMSO-d6) δ 7.49-7.35 (m, 3H), 7.30-7.21 (m, 2H), 6.24 (ddd, J = 56.2, 7.1, 1.9 Hz, 1H), 5.74 (ddd, J = 9.2, 6.6, 3.1 Hz, 1H), 4.14-4.05 (m, 1H), 3.93 (dt, J = 11.3, 8.4 Hz, 1H), 3.87-3.65 (m, 4H), 2.72 (dddd, J = 26.7, 15.3, 3.1, 1.9 Hz, 1H), 2.19-2.00 (m, 2H). | 302.2 4.33 min |

TABLE 2-continued

| K$_i$ (uM) Method | Ex # | Structure | $^1$H NMR | MS (m/z) R.T. |
|---|---|---|---|---|
| <0.005 Method 106 | 132 | [rac-(5S,7S)-7-fluoro-5-phenyl-6,7-dihydro-5H-pyrrolo[1,2-b][1,2,4]triazol-2-yl]-[rac-(3R)-tetrahydrofuran-3-yl] methanone | 1H NMR (400 MHz, DMSO-d6) δ 7.49-7.35 (m, 3H), 7.30-7.21 (m, 2H), 6.24 (ddd, J = 56.2, 7.1, 1.9 Hz, 1H), 5.74 (ddd, J = 9.2, 6.6, 3.1 Hz, 1H), 4.14-4.05 (m, 1H), 3.93 (dt, J = 11.3, 8.4 Hz, 1H), 3.87-3.65 (m, 4H), 2.72 (dddd, J = 26.7, 15.3, 3.1, 1.9 Hz, 1H), 2.19-2.00 (m, 2H). | 302.2 4.33 min |
| <0.005 Method 107 | 133 | 3-methoxy-2,2-dimethyl-1-[rac-(5S,7S)-7-fluoro-5-phenyl-6,7-dihydro-5H-pyrrolo[1,2-b][1,2,4]triazol-2-yl]propan-1-one | 1H NMR (400 MHz, DMSO-d6) δ 7.48-7.34 (m, 3H), 7.25-7.18 (m, 2H), 6.23 (ddd, J = 56.5, 7.1, 1.9 Hz, 1H), 5.74 (ddd, J = 8.9, 6.5, 2.9 Hz, 1H), 3.84-3.71 (m, 2H), 3.79-3.66 (m, 1H), 3.07 (s, 3H), 2.71 (dddd, J = 26.6, 15.2, 3.1, 1.9 Hz, 1H), 1.25 (d, J = 6.0 Hz, 6H). | 318.2 5.44 min |
| 0.220 Method 108 | 134 | rac-(2S)-3,3,3-trifluoro-2-hydroxy-1-[rac-(5S,7S)-7-fluoro-5-phenyl-6,7-dihydro-5H-pyrrolo[1,2-b][1,2,4]triazol-2-yl]propan-1-one | 1H NMR (400 MHz, DMSO-d6) δ 7.42 (dddd, J = 9.2, 7.4, 6.3, 3.3 Hz, 3H), 7.26 (td, J = 8.3, 7.8, 1.6 Hz, 2H), 6.27 (dddd, J = 56.3, 7.3, 3.5, 2.0 Hz, 1H), 5.77 (ddd, J = 9.0, 6.3, 3.1 Hz, 1H), 5.62 (dd, J = 10.2, 4.0 Hz, 1H), 3.77 (dddd, J = 25.7, 15.5, 8.5, 7.2 Hz, 1H), 2.80-2.65 (m, 1H). | 330.1 4.82 min |
| 0.180 Method 109 | 135 | 1-[rac-(5S,7S)-7-fluoro-5-phenyl-6,7-dihydro-5H-pyrrolo[1,2-b][1,2,4]triazol-2-yl]-2-tetrahydropyran-2-yl-ethanone (mixture of diastereomers) | no NMR generated | 330.2 4.94 min |

TABLE 2-continued

| K$_i$ (uM) Method | Ex # | Structure | $^1$H NMR | MS (m/z) R.T. |
|---|---|---|---|---|
| 0.032 Method 110 | 136 | 1-[rac-(5S,7S)-7-fluoro-5-phenyl-6,7-dihydro-5H-pyrrolo[1,2-b][1,2,4]triazol-2-yl]-2-tetrahydropyran-4-yl-ethanone | 1H NMR (400 MHz, DMSO-d6) δ 7.46-7.34 (m, 3H), 7.28-7.22 (m, 2H), 6.22 (ddd, J = 56.4, 7.2, 1.9 Hz, 1H), 5.71 (ddd, J = 8.5, 6.5, 3.1 Hz, 1H), 3.84-3.63 (m, 3H), 3.28-3.21 (m, 1H), 2.94 (dd, J = 6.8, 2.1 Hz, 2H), 2.71 (dddd, J = 26.7, 15.2, 3.2, 2.0 Hz, 1H), 2.10 (ttt, J = 11.0, 7.1, 3.9 Hz, 1H), 1.55 (ddd, J = 12.9, 4.2, 2.0 Hz, 2H), 1.23 (qd, J = 12.4, 4.4 Hz, 2H), 0.87-0.65 (m, 1H). | 330.2 2.51 min |
| <0.005 Method 111 | 137 | [rac-(5S,7S)-7-fluoro-5-phenyl-6,7-dihydro-5H-pyrrolo[1,2-b][1,2,4]triazol-2-yl]-[rac-(3R)-3-methyltetrahydrofuran-3-yl]methanone | 1H NMR (400 MHz, DMSO-d6) δ 7.46-7.35 (m, 3H), 7.28-7.21 (m, 2H), 6.24 (ddd, J = 56.4, 7.1, 2.0 Hz, 1H), 5.73 (ddd, J = 8.9, 6.4, 3.1 Hz, 1H), 4.18 (d, J = 8.9 Hz, 1H), 3.84-3.66 (m, 3H), 3.64 (d, J = 8.9 Hz, 1H), 2.71 (dddd, J = 26.6, 15.2, 3.1, 2.0 Hz, 1H), 2.56 (ddd, J = 12.6, 8.2, 6.8 Hz, 1H), 1.85 (ddd, J = 13.0, 7.6, 5.6 Hz, 1H), 1.48 (s, 3H). | 316.2 4.68 min |
| <0.005 Method 111 | 138 | [rac-(5S,7S)-7-fluoro-5-phenyl-6,7-dihydro-5H-pyrrolo[1,2-b][1,2,4]triazol-2-yl]-[rac-(3S)-3-methyltetrahydrofuran-3-yl]methanone | 1H NMR (400 MHz, DMSO-d6) δ 7.47-7.34 (m, 3H), 7.28-7.21 (m, 2H), 6.24 (ddd, J = 56.3, 7.1, 1.9 Hz, 1H), 5.73 (ddd, J = 8.9, 6.5, 3.1 Hz, 1H), 4.21 (d, J = 89. Hz, 1H), 3.83-3.64 (m, 3H), 3.67 (d, J = 8.9 Hz, 1H), 2.71 (dddd, J = 26.6, 15.2, 3.1, 2.0 Hz, 1H), 2.59-2.52 (m, 1H), 1.82 (ddd, J = 12.6, 7.6, 5.7 Hz, 1H), 1.47 (s, 3H). | 316.2 4.68 min |
| 0.140 Method 112 | 139 | [rac-(5S,7S)-7-fluoro-5-phenyl-6,7-dihydro-5H-pyrrolo[1,2-b][1,2,4]triazol-2-yl]-[rac-(1R,2R,4S)-7-oxabicyclo[2.2.1]heptan-2-yl]methanone | 1H NMR (400 MHz, DMSO-d6) δ 7.47-7.35 (m, 3H), 7.29-7.22 (m, 2H), 6.25 (ddd, J = 56.4, 7.2, 2.0 Hz, 1H), 5.74 (ddd, J = 9.1, 6.4, 3.1 Hz, 1H), 4.91 (t, J = 4.9 Hz, 1H), 4.59 (t, J = 5.2 Hz, 1H), 3.96-3.87 (m, 1H), 3.75 (dddd, J = 25.8, 15.5, 8.5, 7.2 Hz, 1H), 2.72 (dddd, J = 26.7, 15.1, 3.1, 2.0 Hz, 1H), 2.00 (dd, J = 11.9, 4.6 Hz, 1H), 1.75 (dddd, J = 12.0, 10.9, 5.3, 2.8 Hz, 1H), 1.66-1.52 (m, 1H), 1.50-1.36 (m, 2H), 1.29-1.17 (m, 1H). | 328.2 4.61 min |

TABLE 2-continued

| K$_i$ (uM) Method | Ex # | Structure | $^1$H NMR | MS (m/z) R.T. |
|---|---|---|---|---|
| 0.150 Method 112 | 140 | ((1S,2R,4R)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone | 1H NMR (400 MHz, Chloroform-d) δ 7.43-7.34 (m, 3H), 7.25-7.19 (m, 2H), 6.03 (ddd, J = 55.8, 7.1, 1.7 Hz, 1H), 5.50 (ddd, J = 8.8, 6.2, 2.8 Hz, 1H), 4.83 (d, J = 4.7 Hz, 1H), 4.70 (t, J = 4.8 Hz, 1H), 3.77-3.51 (m, 2H), 2.95 (dddd, J = 25.0, 15.4, 2.8, 1.7 Hz, 1H), 2.32 (dtd, J = 12.2, 5.0, 2.1 Hz, 1H), 1.90-1.63 (m, 5H). | 328.2 4.54 min |
| 0.009 Method 112 | 141 | ((1R,2S,4S)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone | 1H NMR (400 MHz, DMSO-d6) δ 7.47-7.35 (m, 3H), 7.31-7.24 (m, 2H), 6.23 (ddd, J = 56.3, 7.2, 1.9 Hz, 1H), 5.74 (ddd, J = 8.9, 6.5, 3.1 Hz, 1H), 4.94 (t, J = 4.9 Hz, 1H), 4.59 (t, J = 5.2 Hz, 1H), 3.93-3.83 (m, 1H), 3.75 (dddd, J = 26.1, 15.5, 8.5, 7.2 Hz, 1H), 2.72 (dddd, J = 26.6, 15.2, 3.1, 1.9 Hz, 1H), 1.99 (dd, J = 12.0, 4.6 Hz, 1H), 1.73 (dddd, J = 11.9, 10.8, 5.3, 2.8 Hz, 1H), 1.59 (ddt, J = 12.8, 8.5, 4.8 Hz, 1H), 1.51-1.37 (m, 2H), 1.28-1.17 (m, 1H). | 328.2 4.61 min |
| 0.009 Method 113 | 142 | 1-[rac-(5S,7S)-7-fluoro-5-phenyl-6,7-dihydro-5H-pyrrolo[1,2-b][1,2,4]triazol-2-yl]-2-(trifluoromethoxy)ethanone | 1H NMR (400 MHz, DMSO-d6) δ 7.47-7.36 (m, 3H), 7.30-7.24 (m, 2H), 6.26 (ddd, J = 56.2, 7.2, 1.9 Hz, 1H), 5.75 (ddd, J = 8.8, 6.5, 3.1 Hz, 1H), 5.50 (d, J = 1.2 Hz, 2H), 3.84-3.63 (m, 1H), 2.74 (dddd, J = 26.8, 15.3, 3.2, 1.9 Hz, 1H). | 330.1 5.39 min |
| <0.005 Method 114 | 143 | [rac-(5S,7S)-7-fluoro-5-phenyl-6,7-dihydro-5H-pyrrolo[1,2-b][1,2,4]triazol-2-yl]-[rac-(1R,5R)-3-oxabicyclo[3.1.0]hexan-1-yl]methanone | 1H NMR (400 MHz, DMSO-d6) δ 7.48-7.33 (m, 3H), 7.24 (dt, J = 7.8, 1.5 Hz, 2H), 6.22 (dddd, J = 56.4, 7.2, 3.5, 1.9 Hz, 1H), 5.76-5.65 (m, 1H), 4.11-4.04 (m, 1H), 4.00 (dd, J = 8.7, 1.7 Hz, 1H), 3.81-3.64 (m, 3H), 2.83-2.61 (m, 2H), 1.84 (td, J = 8.3, 3.9 Hz, 1H), 1.13 (dd, J = 5.7, 4.0 Hz, 1H). | 314.1 4.58 min |

TABLE 2-continued

| K$_i$ (uM) Method | Ex # | Structure | $^1$H NMR | MS (m/z) R.T. |
|---|---|---|---|---|
| 0.230 Method 114 | 144 | [rac-(5S,7S)-7-fluoro-5-phenyl-6,7-dihydro-5H-pyrrolo[1,2-b][1,2,4]triazol-2-yl]-[rac-(1S,5S)-3-oxabicyclo[3.1.0]hexan-1-yl]methanone | no NMR generated | 314.2 4.58 min |
| 0.26 Method 115 | 145 | cyclopropyl-(5-phenyl-5,6,7,8-tetrahydro-[1,2,4]triazolo[1,5-a]pyridin-2-yl)methanone (mixture of diastereomers) | 1H NMR (400 MHz, DMSO-d6) δ 7.41-7.27 (m, 3H), 7.12-7.04 (m, 2H), 5.62 (t, J = 5.9 Hz, 1H), 3.12-2.83 (m, 3H), 2.46-2.35 (m, 1H), 2.13-2.01 (m, 1H), 1.93-1.81 (m, 2H), 1.04-0.92 (m, 4H). | 268.1 4.37 min |
| 0.07 Method 115 | 146 | (S)-cyclopropyl(5-phenyl-5,6,7,8-tetrahydro-[1,2,4]triazolo[1,5-a]pyridin-2-yl)methanone | 1H NMR (400 MHz, DMSO-d6) δ 7.42-7.23 (m, 3H), 7.12-7.04 (m, 2H), 5.62 (t, J = 6.0 Hz, 1H), 3.12-2.85 (m, 3H), 2.45-2.35 (m, 1H), 2.13-2.00 (m, 1H), 1.96-1.82 (m, 2H), 1.05-0.93 (m, 4H). | 268.1 4.39 min |
| 0.45 Method 116 | 147 | cyclopropyl((5S,7R)-7-hydroxy-5-(o-tolyl)-6,7-dihydro-5H-pyrrolo[1,2-b][1,2,4]triazol-2-yl)methanone (mixture of diastereomers) | 1H NMR (400 MHz, DMSO-d6) δ 7.30-7.13 (m, 3H), 7.01-6.94 (m, 1H), 6.25 (bs, 1H), 5.75 (dd, J = 8.1, 5.8 Hz, 1H), 5.23 (dd, J = 7.9, 4.6 Hz, 1H), 3.63-3.52 (m, 1H), 3.03-2.92 (m, 1H), 2.38 (s, 3H), 2.31-2.14 (m, 1H), 1.09-0.96 (m, 4H). | 284.1 4.08 min |

TABLE 2-continued

| K$_i$ (uM) Method | Ex # | Structure | $^1$H NMR | MS (m/z) R.T. |
|---|---|---|---|---|
| 0.73 Method 116 | 148 | cyclopropyl-[rac-(5S,7R)-7-fluoro-5-(o-tolyl)-6,7-dihydro-5H-pyrrolo[1,2-b][1,2,4]triazol-2-yl]methanone (mixture of diastereomers) | 1H NMR (400 MHz, DMSO-d6) δ 7.33-7.14 (m, 3H), 6.89 (d, J = 7.5 Hz, 1H), 6.35 (ddd, J = 56.2, 6.8, 1.6 Hz, 1H), 6.19 (td, J = 6.9, 3.2 Hz, 1H), 3.59-3.27 (m, 1H), 3.11-2.91 (m, 2H), 2.38 (s, 3H), 1.14-1.01 (m, 4H). | 286.1 4.81 min |
| 0.039 Method 116 | 149 | cyclopropyl-[rac-(5S,7S)-7-fluoro-5-(o-tolyl)-6,7-dihydro-5H-pyrrolo[1,2-b][1,2,4]triazol-2-yl]methanone (mixture of diastereomers) | 1H NMR (400 MHz, DMSO-d6) δ 7.35-7.14 (m, 3H), 6.76-6.66 (m, 1H), 6.26 (ddd, J = 56.3, 7.2, 1.9 Hz, 1H), 5.94 (ddd, J = 8.5, 6.6, 3.2 Hz, 1H), 3.94-3.48 (m, 1H), 3.01 (ddt, J = 7.6, 6.1, 5.2 Hz, 1H), 2.66 (dddd, J = 26.8, 15.1, 3.2, 2.0 Hz, 1H), 2.42 (s, 3H), 1.18-0.99 (m, 4H). | 286.1 4.80 min |
| 0.010 Method 117 | 150 | cyclopropyl((5S,7S)-7-fluoro-5-(3-fluoropyridin-2-yl)-6,7-dihydro-5H-pyrrolo[1,2-b][1,2,4]triazol-2-yl)methanone | 1H NMR (400 MHz, DMSO-d6) δ 8.45 (dt, J = 4.6, 1.5 Hz, 1H), 7.89 (ddd, J = 10.0, 8.4, 1.3 Hz, 1H), 7.57 (dt, J = 8.6, 4.4 Hz, 1H), 6.26 (ddd, J = 56.6, 7.7, 2.7 Hz, 1H), 6.10-5.99 (m, 1H), 3.74 (dddd, J = 19.7, 14.7, 8.5, 7.7 Hz, 1H), 3.16-2.84 (m, 2H), 1.18-0.93 (m, 4H). | 291.1 3.64 min |
| 0.230 Method 117 | 151 | cyclopropyl((5S,7R)-7-fluoro-5-(3-fluoropyridin-2-yl)-6,7-dihydro-5H-pyrrolo[1,2-b][1,2,4]triazol-2-yl)methanone | 1H NMR (400 MHz, DMSO-d6) δ 8.42 (dt, J = 4.6, 1.5 Hz, 1H), 7.89 (ddd, J = 10.0, 8.5, 1.3 Hz, 1H), 7.56 (dt, J = 8.6, 4.4 Hz, 1H), 6.58-6.32 (m, 2H), 3.55-3.19 (m, 2H), 2.95 (tt, J = 7.5, 4.9 Hz, 1H), 1.13-0.98 (m, 4H). | 291.1 3.82 min |

TABLE 2-continued

| K$_i$ (uM) Method | Ex # | Structure | $^1$H NMR | MS (m/z) R.T. |
|---|---|---|---|---|
| 0.030 Method 118 | 152 | cyclopropyl((5S,7S)-7-fluoro-5-(1-methyl-1H-pyrazol-4-yl)-6,7-dihydro-5H-pyrrolo[1,2-b][1,2,4]triazol-2-yl)methanone | 1H NMR (400 MHz, DMSO-d6) δ 7.80 (d, J = 0.8 Hz, 1H), 7.48 (d, J = 0.8 Hz, 1H), 6.21 (ddd, J = 56.4, 7.0, 2.4 Hz, 1H), 5.66 (ddd, J = 8.2, 6.0, 3.6 Hz, 1H), 3.81 (s, 3H), 3.73-3.55 (m, 1H), 2.99 (tt, J = 7.5, 4.9 Hz, 1H), 2.80 (dddd, J = 26.4, 14.9, 3.7, 2.4 Hz, 1H), 1.14-0.95 (m, 4H). | 276.1 3.10 min |
| 0.380 Method 119 | 153 | cyclopropyl(7-fluoro-5-(5-methylisoxazol-4-yl)-6,7-dihydro-5H-pyrrolo[1,2-b][1,2,4]triazol-2-yl)methanone (mixture of diastereomers) | no NMR generated | 277.1 3.63 min |
| 0.032 Method 120 | 154 | ((5S,7S)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone | 1H NMR (400 MHz, DMSO-d6) δ 8.03 (s, 1H), 6.23 (ddd, J = 56.8, 7.8, 3.3 Hz, 1H), 5.70 (ddd, J = 8.4, 6.5, 5.0 Hz, 1H), 3.82 (s, 3H), 3.72 (ddt, J = 16.3, 14.6, 8.1 Hz, 1H), 3.02-2.82 (m, 2H), 1.14-0.99 (m, 4H). | 310.0 3.86 min |
| 0.970 Method 120 | 155 | ((5S,7R)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone | 1H NMR (400 MHz, DMSO-d6) δ 8.03 (s, 1H), 6.58-6.22 (m, 1H), 6.04 (ddd, J = 7.4, 6.1, 3.1 Hz, 1H), 3.81 (s, 3H), 3.46-3.21 (m, 2H), 2.97 (tt, J = 7.6, 4.8 Hz, 1H), 1.14-1.00 (m, 4H). | 310.0 4.01 min |

TABLE 2-continued

| K$_i$ (uM) Method | Ex # | Structure | $^1$H NMR | MS (m/z) R.T. |
|---|---|---|---|---|
| 0.020 Method 121 | 156 | cyclopropyl((5S,7S)-7-fluoro-5-(3-methoxyphenyl)-6,7-dihydro-5H-pyrrolo[1,2-b][1,2,4]triazol-2-yl)methanone | no NMR generated | 302.1 4.92 min |
| 0.117 Method 122 | 157 | cyclopropyl((5S,7S)-7-fluoro-5-(3-fluoro-5-(trifluoromethyl)phenyl)-6,7-dihydro-5H-pyrrolo[1,2-b][1,2,4]triazol-2-yl)methanone | 1H NMR (400 MHz, DMSO-d6) δ 7.76 (dt, J = 8.8, 2.1 Hz, 1H), 7.61 (s, 1H), 7.47 (dt, J = 9.4, 1.9 Hz, 1H), 6.26 (ddd, J = 56.2, 7.0, 2.1 Hz, 1H), 5.89 (ddd, J = 8.9, 6.2, 3.4 Hz, 1H), 3.86-3.66 (dddd, J = 25.2, 15.4, 8.5, 7.1 Hz, 1H), 3.09-2.93 (m, 1H), 2.83 (dddd, J = 26.1, 15.2, 3.4, 2.2 Hz, 1H), 1.16-0.99 (m, 4H). | 358.1 5.51 min |
| 0.650 Method 123 | 158 | (5-phenyl-6,7-dihydro-5H-pyrrolo[1,2-b][1,2,4]triazol-2-yl)-[1-(pyrazol-1-ylmethyl)cyclopropyl]methanone (mixture of diastereomers) | $^1$H NMR (400 MHz, DMSO-d6) δ 7.57 (d, J = 2.2 Hz, 1H), 7.44-7.30 (m, 4H), 7.26-7.18 (m, 2H), 6.16 (d, J = 2.2 Hz, 1H), 5.60 (dd, 8.3, 5.8 Hz, 1H), 4.63 (q, J = 14.4 Hz, 2H), 3.22-2.81 (m, 2H), 2.61-2.28 (m, 1H), 1.70-1.53 (m, 2H), 1.35-1.13 (m, 3H). | 334.2 4.31 min |
| 0.005 SFC 1 | 159 | cyclopropyl((4S,6S)-4-fluoro-6-phenyl-5,6-dihydro-4H-pyrrolo[1,2-b]pyrazol-2-yl)methanone | 1H NMR (400 MHz, DMSO-d6) δ 7.46-7.28 (m, 3H), 7.28-7.07 (m, 2H), 6.94 (d, J = 2.6 Hz, 1H), 6.34-5.96 (m, 1H), 5.88-5.51 (m, 1H), 2.94-2.75 (m, 1H), 2.76-2.55 (m, 1H), 2.07 (s, 1H), 1.04-0.74 (m, 4H). | 271.1 5.11 min |

TABLE 2-continued

| K_i (uM) Method | Ex # | Structure | ¹H NMR | MS (m/z) R.T. |
|---|---|---|---|---|
| 0.003 SFC 2 | 160 | [rac-(5S,7S)-7-fluoro-5-phenyl-6,7-dihydro-5H-pyrrolo[1,2-b][1,2,4]triazol-2-yl]-[rac-(1S,2S)-2-(trifluoromethyl)cyclopropyl]methanone | 1H NMR (400 MHz, DMSO-d6) δ 7.59-7.08 (m, 5H), 6.50-6.06 (m, 1H), 5.93-5.55 (m, 1H), 3.76-3.25 (m, 1H), 2.58 (d, J = 2.5 Hz, 1H), 1.88-1.15 (m, 2H). | 340.1 5.36 min |
| 0.050 SFC 3 | 161 | [rac-(5S,7S)-7-fluoro-5-phenyl-6,7-dihydro-5H-pyrrolo[1,2-b][1,2,4]triazol-2-yl]-[rac-(1R,2R)-2-(trifluoromethyl)cyclopropyl]methanone | 1H NMR (400 MHz, DMSO-d6) δ 7.50-7.13 (m, 5H), 6.51-6.05 (m, 1H), 5.93-5.49 (m, 1H), 3.90-3.54 (m, 1H), 2.84-2.59 (m, 1H), 2.62-2.53 (m, 1H), 2.07 (s, 1H), 1.64-1.26 (m, 2H). | 340.1 5.40 min |
| 0.016 SFC 4 | 162 | [rac-(5S,7S)-7-fluoro-5-phenyl-6,7-dihydro-5H-pyrrolo[1,2-b][1,2,4]triazol-2-yl]-[rac-(2S)-spiro[2.2]pentan-2-yl]methanone | no NMR generated | 298.1 4.95 min |
| 0.004 SFC 5 | 163 | [rac-(5S,7S)-7-fluoro-5-phenyl-6,7-dihydro-5H-pyrrolo[1,2-b][1,2,4]triazol-2-yl]-[rac-(2R)-spiro[2.2]pentan-2-yl]methanone | no NMR generated | 298.1 4.94 min |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:

1. A method for the treatment of a disease or disorder in a human, the method comprising administration to the human of an effective treatment amount of a compound of formula (I):

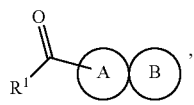

or a pharmaceutically acceptable salt thereof, wherein:

$R^1$ is selected from the group consisting of $C_1$-$C_6$ alkyl, $C_3$-$C_6$ cycloalkyl, $C_1$-$C_6$ haloalkyl, $C_1$-$C_6$ alkyl-N($R^N$)$_2$, phenyl, benzyl, 4 to 8 membered heterocyclyl and 5 to 6 membered heteroaryl; wherein $R^1$ is bound to the adjacent carbonyl by a carbon atom, and wherein $R^1$ is optionally substituted by one or two substituents selected from the group consisting of F, Cl, Br, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-N($R^N$)$_2$, hydroxyl, hydroxymethyl, cyano, cyanomethyl, cyanoethyl, C(O) $C_1$-$C_6$ alkyl, phenyl, benzyl, CH$_2$—($C_3$-$C_6$ cycloalkyl), 5 to 6 membered heteroaryl, and CH$_2$-(5 to 6 membered heteroaryl);

each $R^N$ is independently selected from the group consisting of H, $C_1$-$C_6$ alkyl, $C_3$-$C_6$ cycloalkyl, $C_1$-$C_6$ alkoxy, and $C_1$-$C_6$ haloalkyl; or two $R^N$ may together with the adjacent N form a 4-6 membered ring; and the A ring and the B ring together are selected from the group consisting of:

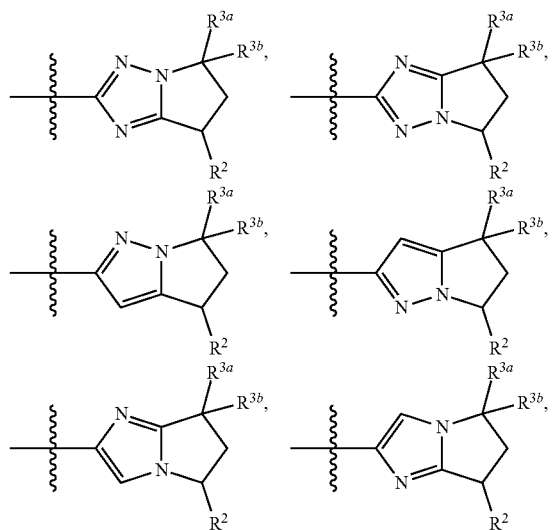

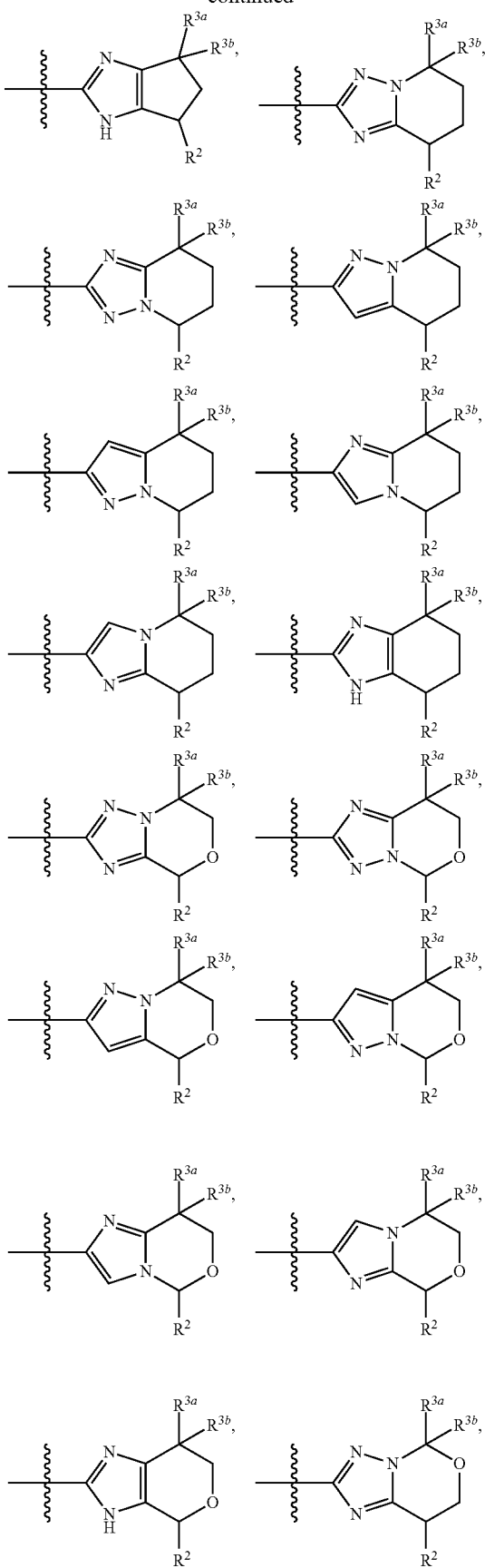

-continued

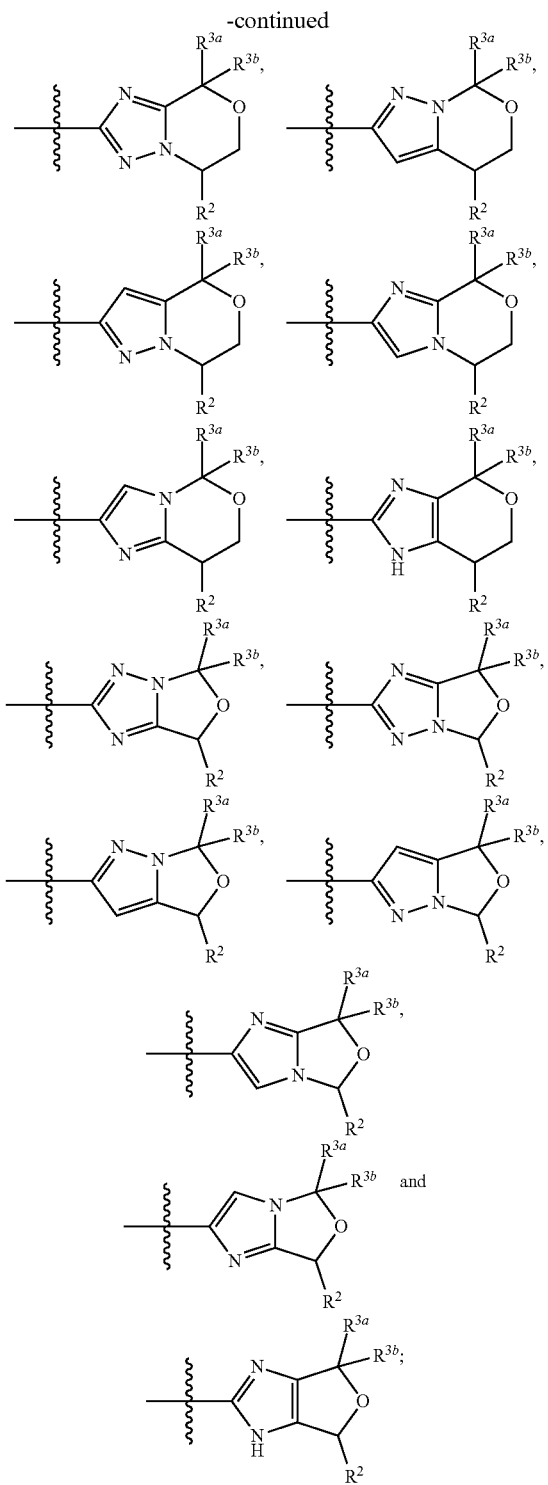

wherein:
R₂ is selected from the group consisting of $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2$ $CH_2$-(4 to 6 membered heterocyclyl), 5 to 6 membered heteroaryl, and $CH_2$-(5 to 6 membered heteroaryl); wherein when a phenyl ring or 5 to 6 membered heteroaryl ring is present it may be substituted by 1 to 3 substituents selected from the group consisting of halogen, $C_1$-$C_6$ alkyl, $C_1$-$C_6$ haloalkyl, $C_1$-$C_6$ alkoxy, $C_1$-$C_6$ haloalkoxy, cyclopropyl, and cyano; and $R^{3a}$ and $R^{3b}$ are selected as follows:
(i) one of $R^{3a}$ and $R^{3b}$ is H, and the other is selected from the group consisting of D, halogen, OH, CN, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, and $C_1$-$C_6$ alkyl-$N(R^N)_2$;
(ii) each of $R^{3a}$ and $R^{3b}$ is selected from the group consisting of D, F, Cl, OH, CN and methyl, provided that $R^{3a}$ and $R^{3b}$ cannot both be OH or CN; or
(iii) $R^{3a}$ and $R^{3b}$ together form cyclopropyl; and
wherein the disease or disorder is selected from the group consisting of Parkinson's Disease, Lewy body dementia, multiple system atrophy, Parkinson-plus syndrome, tauopathy, Alzheimer's Disease, frontotemporal dementia, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathy, progressive supranuclear palsy, corticobasal degeneration, multiple sclerosis, inflammatory bowel disease, Crohn's disease, ulcerative colitis, glaucoma, psoriasis, psoriatic arthritis, rheumatoid arthritis, spondyloarthritis, juvenile idiopathic arthritis, and osteoarthritis.

2. The method of claim 1, wherein the disease or disorder is selected from the group consisting of inflammatory bowel disease, Crohn's disease, ulcerative colitis, glaucoma, psoriasis, psoriatic arthritis, rheumatoid arthritis, spondyloarthritis, juvenile idiopathic arthritis, and osteoarthritis.

3. The method of claim 1, wherein the disease or disorder is Alzheimer's disease, multiple sclerosis, Parkinson's disease, amyotrophic lateral sclerosis, Huntington's disease, ischemia, spinal muscular atrophy, an inflammatory bowel disease, Crohn's disease, ulcerative colitis, psoriasis, psoriatic arthritis, rheumatoid arthritis, spondyloarthritis, and juvenile idiopathic arthritis.

4. The method of claim 1, wherein the compound is selected from the group consisting of:
((5S,7S)-7-fluoro-5-phenyl-6,7-dihydro-5H-pyrrolo[1,2-b][1,2,4]triazol-2-yl)((1R,2R)-2-fluorocyclopropyl)methanone;
phenyl-[rac-(5S,7S)-7-fluoro-5-phenyl-6,7-dihydro-5H-pyrrolo[1,2-b][1,2,4]triazol-2-yl]methanone;
(rac-(5S,7S)-7-fluoro-5-phenyl-6,7-dihydro-5H-pyrrolo[1,2-b][1,2,4]triazol-2-yl)-(1-methylcyclopropyl)methanone;
cyclopropyl((5S,7S)-7-fluoro-5-phenyl-6,7-dihydro-5H-pyrrolo[1,2-1)][1,2,4]triazol-2-yl)methanone;
[(1R,2S)-2-fluorocyclopropyl]-[(5S,7S)-7-fluoro-5-(2-fluorophenyl)-6,7-dihydro-5H-pyrrolo[1,2-1)][1,2,4]triazol-2-yl]methanone;
cyclopropyl-[(5S,7S)-5-(2,6-difluorophenyl)-7-fluoro-6,7-dihydro-5H-pyrrolo[1,2-b][1,2,4]triazol-2-yl]methanone;
cyclopropyl-[(5S,7S)-5-(2-chlorophenyl)-7-fluoro-6,7-dihydro-5H-pyrrolo[1,2-b][1,2,4]triazol-2-yl]methanone;
cyclopropyl-[(5S,7S)-7-chloro-5-phenyl-6,7-dihydro-5H-pyrrolo[1,2-b][1,2,4]triazol-2-yl]methanone; and cyclopropyl((5S,7S)-7-fluoro-5-(3-methoxyphenyl)-6,7-dihydro-5H-pyrrolo[1,2-b][1,2,4]triazol-2-yl)methanone.

5. The method of claim 1, wherein the compound is selected from the group consisting of:

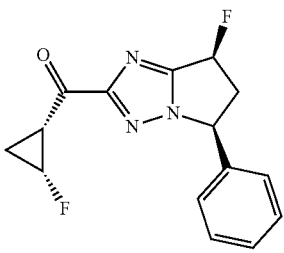 [SMILES: O=C(c1nc2n(n1)[C@H](c1ccccc1)C[C@@H]2F)[C@H]1C[C@H]1F]

((5S,7S)-7-fluoro-5-phenyl-6,7-dihydro-5H-pyrrolo[1,2-1)][1,2,4]triazol-2-yl)((1R,2R)-2-fluorocyclopropyl)methanone;

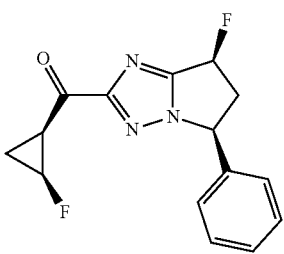 [SMILES: O=C(c1nc2n(n1)[C@H](c1ccccc1)C[C@@H]2F)[C@@H]1C[C@@H]1F]

((5S,7S)-7-fluoro-5-phenyl-6,7-dihydro-5H-pyrrolo[1,2-b][1,2,4]triazol-2-yl)((1S,2S)-2-fluorocyclopropyl)methanone;

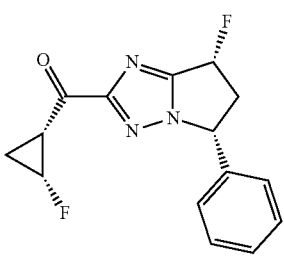 [SMILES: O=C(c1nc2n(n1)[C@@H](c1ccccc1)C[C@H]2F)[C@H]1C[C@H]1F]

((5R,7R)-7-fluoro-5-phenyl-6,7-dihydro-5H-pyrrolo[1,2-b][1,2,4]triazol-2-yl)((1R,2R)-2-fluorocyclopropyl)methanone;

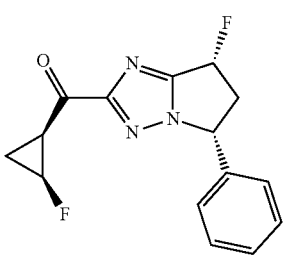

((5R,7R)-7-fluoro-5-phenyl-6,7-dihydro-5H-pyrrolo[1,2-b][1,2,4]triazol-2-yl)((1S,2S)-2-fluorocyclopropyl)methanone;

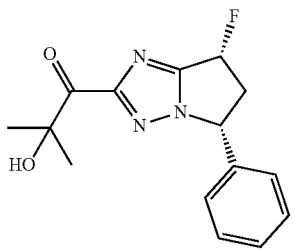 [SMILES: CC(C)(O)C(=O)c1nc2n(n1)[C@@H](c1ccccc1)C[C@H]2F]

2-hydroxy-2-methyl-1-[rac-(5R,7R)-7-fluoro-5-phenyl-6,7-dihydro-5H-pyrrolo[1,2-b][1,2,4]triazol-2-yl]propan-1-one;

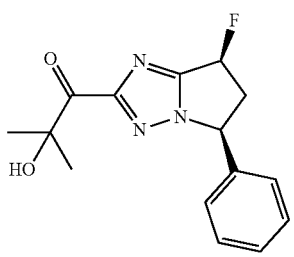 [SMILES: CC(C)(O)C(=O)c1nc2n(n1)[C@H](c1ccccc1)C[C@@H]2F]

2-hydroxy-2-methyl-1-[rac-(5S,7S)-7-fluoro-5-phenyl-6,7-dihydro-5H-pyrrolo[1,2-b][1,2,4]triazol-2-yl]propan-1-one;

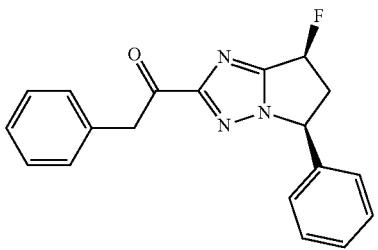 [SMILES: O=C(Cc1ccccc1)c1nc2n(n1)[C@H](c1ccccc1)C[C@@H]2F]

2-phenyl-1-[rac-(5S,7S)-7-fluoro-5-phenyl-6,7-dihydro-5H-pyrrolo[1,2-b][1,2,4]triazol-2-yl]ethanone;

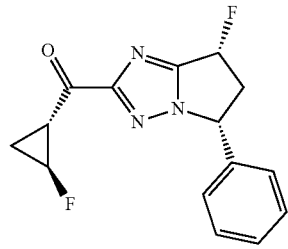 [SMILES: O=C(c1nc2n(n1)[C@@H](c1ccccc1)C[C@H]2F)[C@H]1C[C@@H]1F]

((5R,7R)-7-fluoro-5-phenyl-6,7-dihydro-5H-pyrrolo[1,2-b][1,2,4]triazol-2-yl)((1R,2S)-2-fluorocyclopropyl)methanone;

415

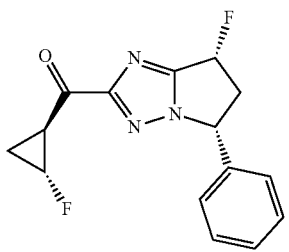 [SMILES: O=C(c1nc2n(n1)[C@@H](c1ccccc1)C[C@H]2F)[C@@H]1C[C@H]1F]

((5R,7R)-7-fluoro-5-phenyl-6,7-dihydro-5H-pyrrolo[1,2-b][1,2,4]triazol-2-yl)((1S,2R)-2-fluorocyclopropyl)methanone;

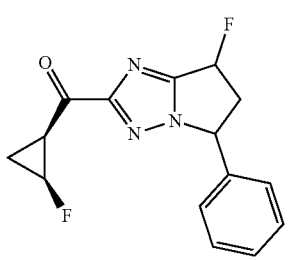 [SMILES: O=C(c1nc2n(n1)C(c1ccccc1)CC2F)[C@@H]1C[C@@H]1F]

(7-fluoro-5-phenyl-6,7-dihydro-5H-pyrrolo[1,2-b][1,2,4]triazol-2-yl)-[rac-(1S,2S)-2-fluorocyclopropyl]methanone;

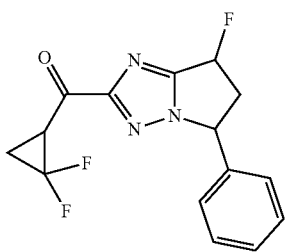 [SMILES: O=C(c1nc2n(n1)C(c1ccccc1)CC2F)C1CC1(F)F]

(2,2-difluorocyclopropyl)-(7-fluoro-5-phenyl-6,7-dihydro-5H-pyrrolo[1,2-b][1,2,4]triazol-2-yl)methanone;

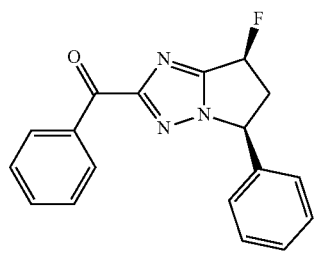 [SMILES: O=C(c1ccccc1)c1nc2n(n1)[C@H](c1ccccc1)C[C@@H]2F]

phenyl-[rac-(5S,7S)-7-fluoro-5-phenyl-6,7-dihydro-5H-pyrrolo[1,2-b][1,2,4]triazol-2-yl]methanone;

416

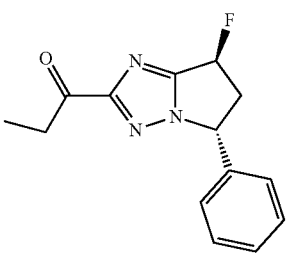 [SMILES: CCC(=O)c1nc2n(n1)[C@@H](c1ccccc1)C[C@@H]2F]

1-[rac-(5R,7S)-7-fluoro-5-phenyl-6,7-dihydro-5H-pyrrolo[1,2-b][1,2,4]triazol-2-yl]propan-1-one;

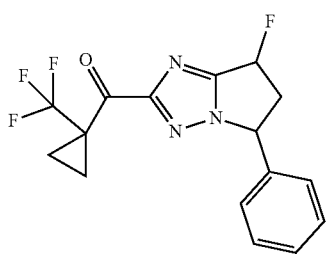 [SMILES: O=C(c1nc2n(n1)C(c1ccccc1)CC2F)C1(C(F)(F)F)CC1]

(rac-(5S,7S)-7-fluoro-5-phenyl-6,7-dihydro-5H-pyrrolo[1,2-b][1,2,4]triazol-2-yl)-[1-(trifluoromethyl)cyclopropyl]methanone;

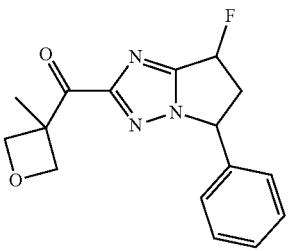 [SMILES: CC1(C(=O)c2nc3n(n2)C(c2ccccc2)CC3F)COC1]

(rac-(5S,7S)-7-fluoro-5-phenyl-6,7-dihydro-5H-pyrrolo[1,2-b][1,2,4]triazol-2-yl)-(3-methyloxetan-3-yl)methanone;

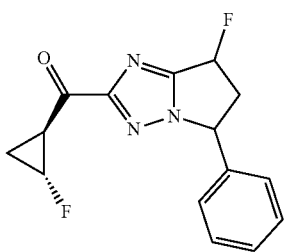

(rac-(5S,7S)-7-fluoro-5-phenyl-6,7-dihydro-5H-pyrrolo[1,2-b][1,2,4]triazol-2-yl)-[rac-(1S,2R)-2-fluorocyclopropyl]methanone;

417

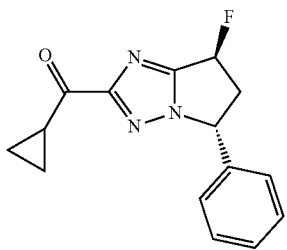 [SMILES: O=C(c1nc2n(n1)[C@@H](c1ccccc1)C[C@@H]2F)C1CC1]

cyclopropyl-[rac-(5R,7S)-7-fluoro-5-phenyl-6,7-dihydro-5H-pyrrolo[1,2-b][1,2,4]triazol-2-yl]methanone;

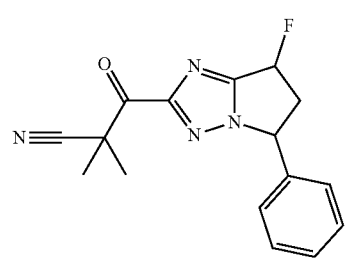 [SMILES: CC(C)(C#N)C(=O)c1nc2n(n1)C(c1ccccc1)CC2F]

3-(rac-(5S,7S)-7-fluoro-5-phenyl-6,7-dihydro-5H-pyrrolo[1,2-b][1,2,4]triazol-2-yl)-2,2-dimethyl-3-oxo-propanenitrile;

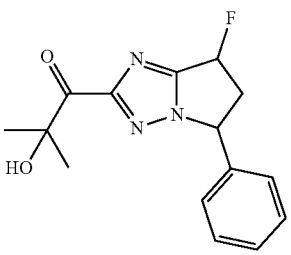 [SMILES: CC(C)(O)C(=O)c1nc2n(n1)C(c1ccccc1)CC2F]

1-(rac-(5S,7S)-7-fluoro-5-phenyl-6,7-dihydro-5H-pyrrolo[1,2-b][1,2,4]triazol-2-yl)-2-hydroxy-2-methyl-propan-1-one;

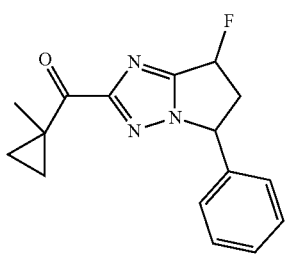 [SMILES: CC1(C(=O)c2nc3n(n2)C(c2ccccc2)CC3F)CC1]

(rac-(5S,7S)-7-fluoro-5-phenyl-6,7-dihydro-5H-pyrrolo[1,2-b][1,2,4]triazol-2-yl)-(1-methylcyclopropyl)methanone;

418

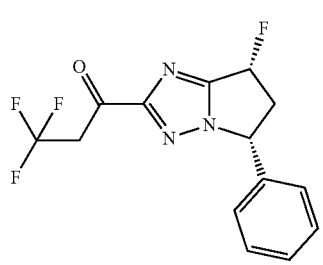 [SMILES: O=C(CC(F)(F)F)c1nc2n(n1)[C@@H](c1ccccc1)C[C@H]2F]

3,3,3-trifluoro-1-[rac-(5R,7R)-7-fluoro-5-phenyl-6,7-dihydro-5H-pyrrolo[1,2-b][1,2,4]triazol-2-yl]propan-1-one;

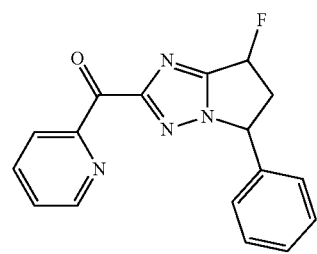 [SMILES: O=C(c1ccccn1)c1nc2n(n1)C(c1ccccc1)CC2F]

(rac-(5S,7S)-7-fluoro-5-phenyl-6,7-dihydro-5H-pyrrolo[1,2-b][1,2,4]triazol-2-yl)-(2-pyridyl)methanone;

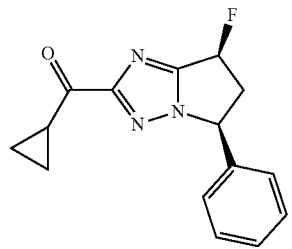

cyclopropyl-[rac-(5S,7S)-7-fluoro-5-phenyl-6,7-dihydro-5H-pyrrolo[1,2-b][1,2,4]triazol-2-yl]methanone;

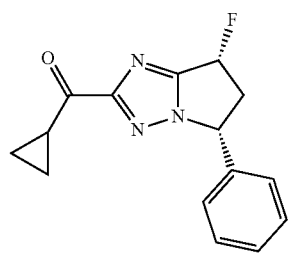

cyclopropyl-[rac-(5R,7R)-7-fluoro-5-phenyl-6,7-dihydro-5H-pyrrolo[1,2-b][1,2,4]triazol-2-yl]methanone;

419

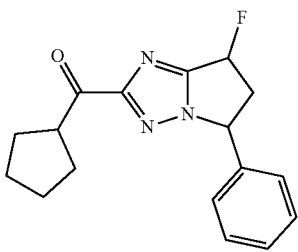 [SMILES: O=C(c1nc2n(n1)C(c1ccccc1)CC2F)C1CCCC1]

cyclopentyl-(rac-(5S,7S)-7-fluoro-5-phenyl-6,7-dihydro-5H-pyrrolo[1,2-b][1,2,4]triazol-2-yl)methanone;

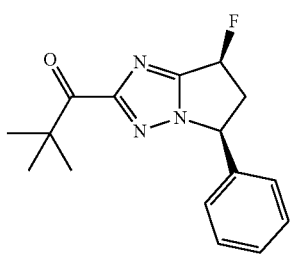 [SMILES: CC(C)(C)C(=O)c1nc2n(n1)[C@H](c1ccccc1)C[C@@H]2F]

2,2-dimethyl-1-[rac-(5S,7S)-7-fluoro-5-phenyl-6,7-dihydro-5H-pyrrolo[1,2-b][1,2,4]triazol-2-yl]propan-1-one;

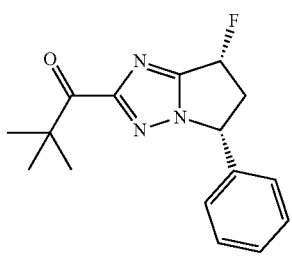 [SMILES: CC(C)(C)C(=O)c1nc2n(n1)[C@@H](c1ccccc1)C[C@H]2F]

2,2-dimethyl-1-[rac-(5R,7R)-7-fluoro-5-phenyl-6,7-dihydro-5H-pyrrolo[1,2-b][1,2,4]triazol-2-yl]propan-1-one;

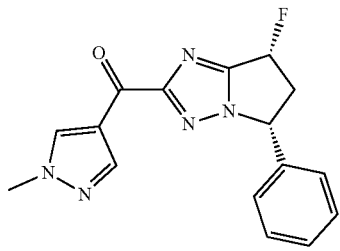 [SMILES: Cn1cc(C(=O)c2nc3n(n2)[C@@H](c2ccccc2)C[C@H]3F)cn1]

(1-methylpyrazol-4-yl)-[rac-(5R,7R)-7-fluoro-5-phenyl-6,7-dihydro-5H-pyrrolo[1,2-b][1,2,4]triazol-2-yl]methanone;

420

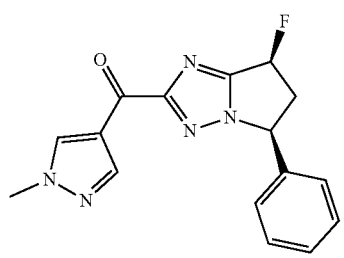 [SMILES: Cn1cc(C(=O)c2nc3n(n2)[C@H](c2ccccc2)C[C@@H]3F)cn1]

(1-methylpyrazol-4-yl)-[rac-(5S,7S)-7-fluoro-5-phenyl-6,7-dihydro-5H-pyrrolo[1,2-b][1,2,4]triazol-2-yl]methanone;

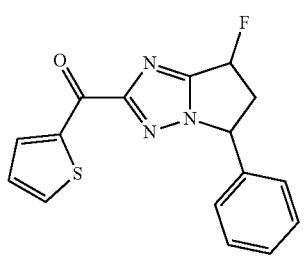 [SMILES: O=C(c1nc2n(n1)C(c1ccccc1)CC2F)c1cccs1]

(rac-(5S,7S)-7-fluoro-5-phenyl-6,7-dihydro-5H-pyrrolo[1,2-b][1,2,4]triazol-2-yl)-(2-thienyl)methanone;

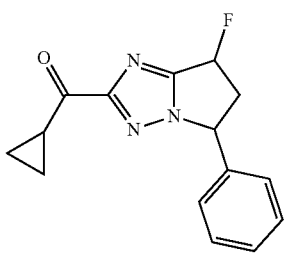 [SMILES: O=C(c1nc2n(n1)C(c1ccccc1)CC2F)C1CC1]

cyclopropyl-(rac-(5S,7S)-7-fluoro-5-phenyl-6,7-dihydro-5H-pyrrolo[1,2-b][1,2,4]triazol-2-yl)methanone;

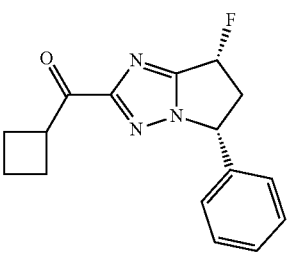 [SMILES: O=C(c1nc2n(n1)[C@@H](c1ccccc1)C[C@H]2F)C1CCC1]

cyclobutyl-[rac-(5R,7R)-7-fluoro-5-phenyl-6,7-dihydro-5H-pyrrolo[1,2-b][1,2,4]triazol-2-yl]methanone;

421

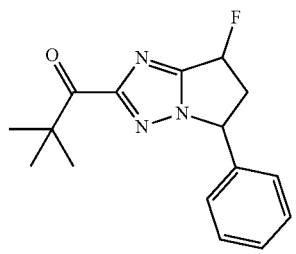 [SMILES: CC(C)(C)C(=O)c1nc2n(n1)C(c1ccccc1)CC2F]

1-(7-fluoro-5-phenyl-6,7-dihydro-5H-pyrrolo[1,2-b][1,2,4]triazol-2-yl)-2,2-dimethyl-propan-1-one;

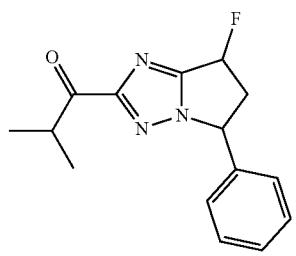 [SMILES: CC(C)C(=O)c1nc2n(n1)C(c1ccccc1)CC2F]

1-(7-fluoro-5-phenyl-6,7-dihydro-5H-pyrrolo[1,2-b][1,2,4]triazol-2-yl)-2-methyl-propan-1-one;

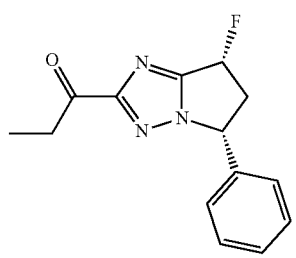 [SMILES: CCC(=O)c1nc2n(n1)[C@@H](c1ccccc1)C[C@H]2F]

1-[rac-(5R,7R)-7-fluoro-5-phenyl-6,7-dihydro-5H-pyrrolo[1,2-b][1,2,4]triazol-2-yl]propan-1-one;

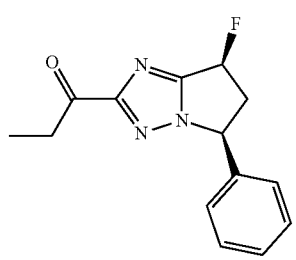 [SMILES: CCC(=O)c1nc2n(n1)[C@H](c1ccccc1)C[C@@H]2F]

1-[rac-(5S,7S)-7-fluoro-5-phenyl-6,7-dihydro-5H-pyrrolo[1,2-b][1,2,4]triazol-2-yl]propan-1-one;

422

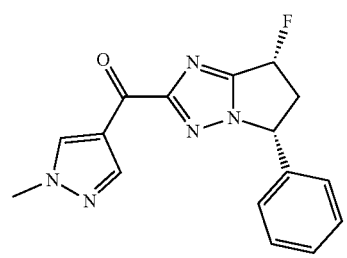 [SMILES: Cn1cc(C(=O)c2nc3n(n2)[C@@H](c2ccccc2)C[C@H]3F)cn1]

(1-methylpyrazol-4-yl)-[rac-(5R,7R)-7-fluoro-5-phenyl-6,7-dihydro-5H-pyrrolo[1,2-b][1,2,4]triazol-2-yl]methanone;

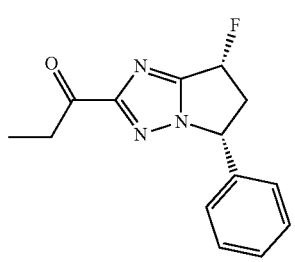 [SMILES: CCC(=O)c1nc2n(n1)[C@@H](c1ccccc1)C[C@H]2F]

1-[rac-(5R,7R)-7-fluoro-5-phenyl-6,7-dihydro-5H-pyrrolo[1,2-b][1,2,4]triazol-2-yl]propan-1-one;

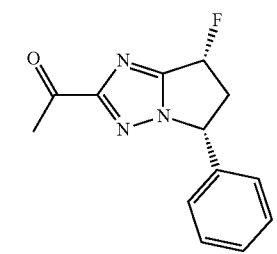 [SMILES: CC(=O)c1nc2n(n1)[C@@H](c1ccccc1)C[C@H]2F]

1-[rac-(5R,7R)-7-fluoro-5-phenyl-6,7-dihydro-5H-pyrrolo[1,2-b][1,2,4]triazol-2-yl]ethanone;

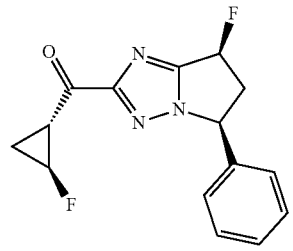 [SMILES: O=C(c1nc2n(n1)[C@H](c1ccccc1)C[C@@H]2F)[C@H]1C[C@@H]1F]

((5S,7S)-7-fluoro-5-phenyl-6,7-dihydro-5H-pyrrolo[1,2-b][1,2,4]triazol-2-yl)((1R,2S)-2-fluorocyclopropyl)methanone;

423

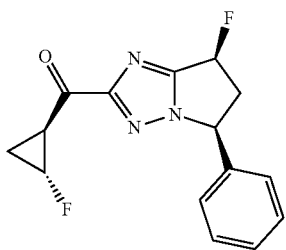 [SMILES: O=C(c1nc2n(n1)[C@H](c1ccccc1)C[C@@H]2F)[C@@H]1C[C@H]1F]

((5S,7S)-7-fluoro-5-phenyl-6,7-dihydro-5H-pyrrolo[1,2-b][1,2,4]triazol-2-yl)((1S,2R)-2-fluorocyclopropyl)methanone;

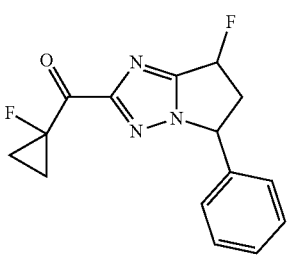 [SMILES: O=C(c1nc2n(n1)C(c1ccccc1)CC2F)C1(F)CC1]

(1-fluorocyclopropyl)-(rac-(5S,7S)-7-fluoro-5-phenyl-6,7-dihydro-5H-pyrrolo[1,2-b][1,2,4]triazol-2-yl)methanone;

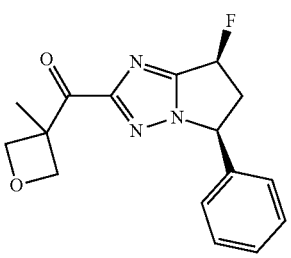 [SMILES: CC1(C(=O)c2nc3n(n2)[C@H](c2ccccc2)C[C@@H]3F)COC1]

(3-methyloxetan-3-yl)-5S,7S)-7-fluoro-5-phenyl-6,7-dihydro-5H-pyrrolo[1,2-b][1,2,4]triazol-2-yl]methanone;

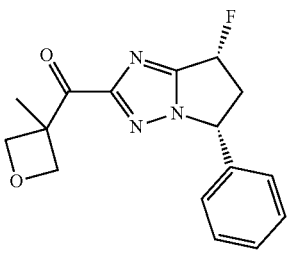 [SMILES: CC1(C(=O)c2nc3n(n2)[C@@H](c2ccccc2)C[C@H]3F)COC1]

(3-methyloxetan-3-yl)-[(5R,7R)-7-fluoro-5-phenyl-6,7-dihydro-5H-pyrrolo[1,2-b][1,2,4]triazol-2-yl]methanone;

424

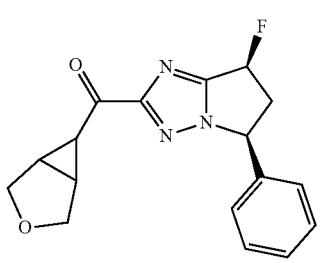 [SMILES: O=C(c1nc2n(n1)[C@H](c1ccccc1)C[C@@H]2F)C1C2COCC21]

3-oxabicyclo[3.1.0]hexan-6-yl-[rac-(5S,7S)-7-fluoro-5-phenyl-6,7-dihydro-5H-pyrrolo[1,2-b][1,2,4]triazol-2-yl]methanone;

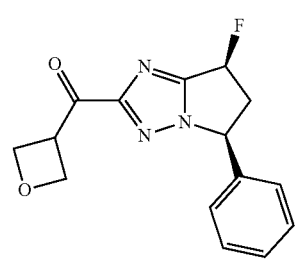 [SMILES: O=C(c1nc2n(n1)[C@H](c1ccccc1)C[C@@H]2F)C1COC1]

oxetan-3-yl-[rac-(5S,7S)-7-fluoro-5-phenyl-6,7-dihydro-5H-pyrrolo[1,2-b][1,2,4]triazol-2-yl]methanone;

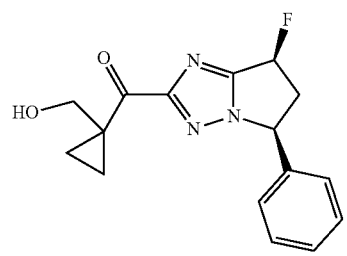 [SMILES: O=C(c1nc2n(n1)[C@H](c1ccccc1)C[C@@H]2F)C1(CO)CC1]

[1-(hydroxymethyl)cyclopropyl]-[rac-(5S,7S)-7-fluoro-5-phenyl-6,7-dihydro-5H-pyrrolo[1,2-b][1,2,4]triazol-2-yl]methanone;

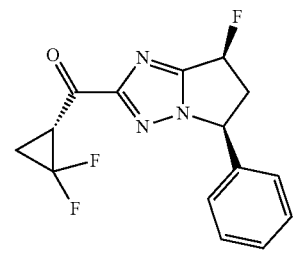 [SMILES: O=C(c1nc2n(n1)[C@H](c1ccccc1)C[C@@H]2F)[C@H]1CC1(F)F]

[(1R)-2,2-difluorocyclopropyl]-[(5S,7S)-7-fluoro-5-phenyl-6,7-dihydro-5H-pyrrolo[1,2-b] [1,2,4]triazol-2-yl]methanone;

425

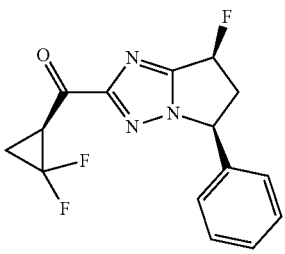 [SMILES: O=C(c1nc2n(n1)[C@H](c1ccccc1)C[C@@H]2F)[C@@H]1CC1(F)F]

[(1S)-2,2-difluorocyclopropyl]-[(5S,7S)-7-fluoro-5-phenyl-6,7-dihydro-5H-pyrrolo[1,2-b] [1,2,4]triazol-2-yl]methanone;

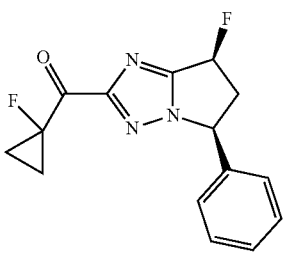 [SMILES: O=C(c1nc2n(n1)[C@H](c1ccccc1)C[C@@H]2F)C1(F)CC1]

(1-fluorocyclopropyl)-[(5S,7S)-7-fluoro-5-phenyl-6,7-dihydro-5H-pyrrolo[1,2-b] [1,2,4]triazol-2-yl]methanone;

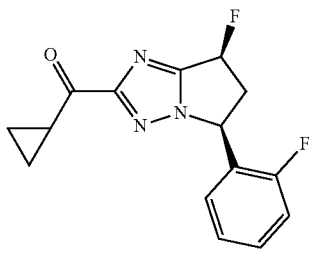 [SMILES: O=C(c1nc2n(n1)[C@H](c1ccccc1F)C[C@@H]2F)C1CC1]

cyclopropyl-[(5S,7S)-7-fluoro-5-(2-fluorophenyl)-6,7-dihydro-5H-pyrrolo[1,2-b][1,2,4]triazol-2-yl]methanone;

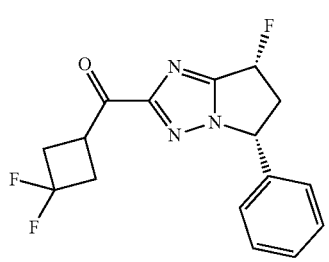 [SMILES: O=C(c1nc2n(n1)[C@@H](c1ccccc1)C[C@H]2F)C1CC(F)(F)C1]

(3,3-difluorocyclobutyl)-[(5R,7R)-7-fluoro-5-phenyl-6,7-dihydro-5H-pyrrolo[1,2-b][1,2,4]triazol-2-yl]methanone;

426

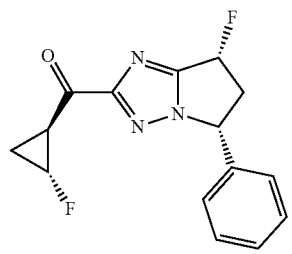 [SMILES: O=C(c1nc2n(n1)[C@@H](c1ccccc1)C[C@H]2F)[C@@H]1C[C@H]1F]

[(1S,2R)-2-fluorocyclopropyl]-[(5R,7R)-7-fluoro-5-phenyl-6,7-dihydro-5H-pyrrolo[1,2-b][1,2,4]triazol-2-yl]methanone;

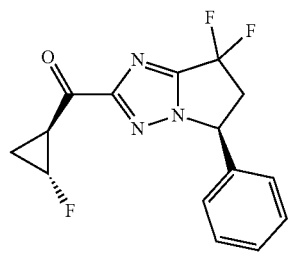 [SMILES: O=C(c1nc2n(n1)[C@H](c1ccccc1)CC2(F)F)[C@@H]1C[C@H]1F]

[(5S)-7,7-difluoro-5-phenyl-5,6-dihydropyrrolo[1,2-b][1,2,4]triazol-2-yl]-[(1S,2R)-2-fluorocyclopropyl]methanone;

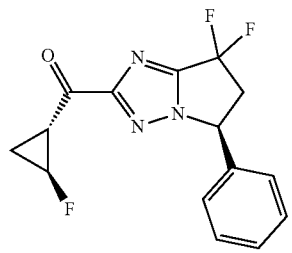 [SMILES: O=C(c1nc2n(n1)[C@H](c1ccccc1)CC2(F)F)[C@H]1C[C@@H]1F]

[(5S)-7,7-difluoro-5-phenyl-5,6-dihydropyrrolo[1,2-b][1,2,4]triazol-2-yl]-[(1R,2S)-2-fluorocyclopropyl]methanone;

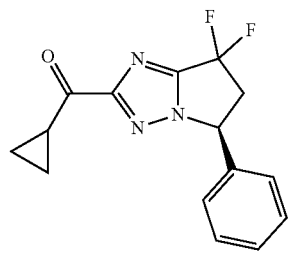 [SMILES: O=C(c1nc2n(n1)[C@H](c1ccccc1)CC2(F)F)C1CC1]

cyclopropyl-[(5S)-7,7-difluoro-5-phenyl-5,6-dihydropyrrolo[1,2-b][1,2,4]triazol-2-yl]methanone;

427

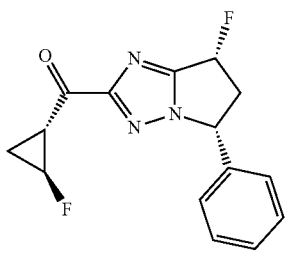 [SMILES: O=C(c1nc2n(n1)[C@@H](c1ccccc1)C[C@H]2F)[C@H]1C[C@@H]1F]

[(1R,2S)-2-fluorocyclopropyl]-[(5R,7R)-7-fluoro-5-phenyl-6,7-dihydro-5H-pyrrolo[1,2-b][1,2,4]triazol-2-yl]methanone;

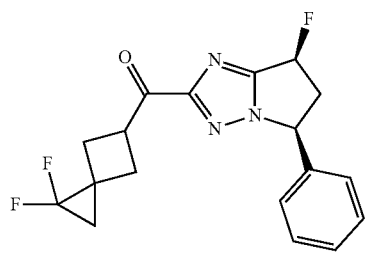 [SMILES: O=C(c1nc2n(n1)[C@H](c1ccccc1)C[C@@H]2F)C1CC2(C1)CC2(F)F]

(2,2-difluorospiro[2.3]hexan-5-yl)-[(5S,7S)-7-fluoro-5-phenyl-6,7-dihydro-5H-pyrrolo[1,2-b][1,2,4]triazol-2-yl]methanone;

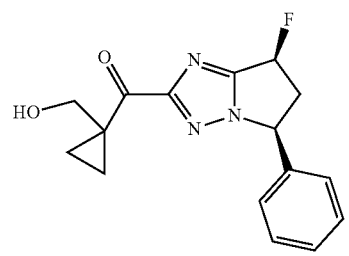 [SMILES: O=C(c1nc2n(n1)[C@H](c1ccccc1)C[C@@H]2F)C1(CO)CC1]

[1-(hydroxymethyl)cyclopropyl]-[(5S,7S)-7-fluoro-5-phenyl-6,7-dihydro-5H-pyrrolo[1,2-b][1,2,4]triazol-2-yl]methanone;

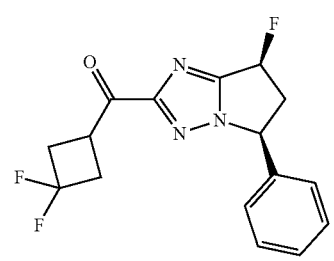 [SMILES: O=C(c1nc2n(n1)[C@H](c1ccccc1)C[C@@H]2F)C1CC(F)(F)C1]

(3,3-difluorocyclobutyl)-5S,7S)-7-fluoro-5-phenyl-6,7-dihydro-5H-pyrrolo[1,2-b][1,2,4]triazol-2-yl]methanone;

428

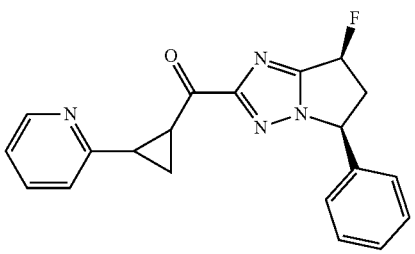 [SMILES: O=C(c1nc2n(n1)[C@H](c1ccccc1)C[C@@H]2F)C1CC1c1ccccn1]

[2-(2-pyridyl)cyclopropyl]-[(5S,7S)-7-fluoro-5-phenyl-6,7-dihydro-5H-pyrrolo[1,2-b][1,2,4]triazol-2-yl]methanone;

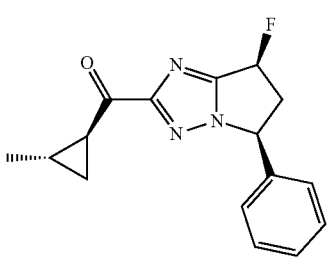 [SMILES: C[C@H]1C[C@@H]1C(=O)c1nc2n(n1)[C@H](c1ccccc1)C[C@@H]2F]

[(5S,7S)-7-fluoro-5-phenyl-6,7-dihydro-5H-pyrrolo[1,2-b][1,2,4]triazol-2-[rac-(1S,2S)-2-methylcyclopropyl]methanone;

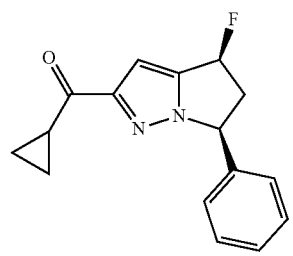 [SMILES: O=C(c1cc2n(n1)[C@H](c1ccccc1)C[C@@H]2F)C1CC1]

[(5S,7S)-7-fluoro-5-phenyl-6,7-dihydro-5H-pyrrolo[1,2-b][1,2,4]triazol-2-yl]-spiro[2.3]hexan-5-yl-methanone;

cyclopropyl-[rac-(4S,6S)-4-fluoro-6-phenyl-5,6-dihydro-4H-pyrrolo[1,2-b]pyrazol-2-yl]methanone;

429

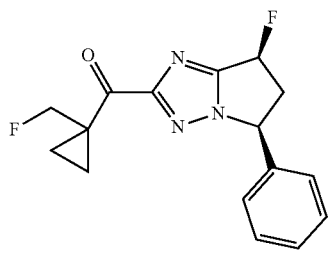 [SMILES: O=C(c1nc2n(n1)[C@H](c1ccccc1)C[C@@H]2F)C1(CF)CC1]

[1-(fluoromethyl)cyclopropyl]-[(5S,7S)-7-fluoro-5-phenyl-6,7-dihydro-5H-pyrrolo[1,2-b][1,2,4]triazol-2-yl]methanone;

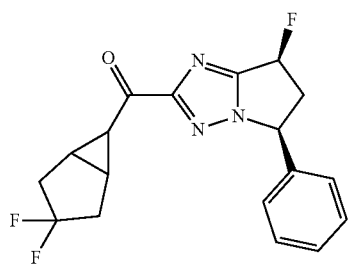 [SMILES: O=C(c1nc2n(n1)[C@H](c1ccccc1)C[C@@H]2F)C1C2CC(F)(F)CC21]

(3,3-difluoro-6-bicyclo[3.1.0]hexanyl)-5S,7S)-7-fluoro-5-phenyl-6,7-dihydro-5H-pyrrolo[1,2-b][1,2,4]triazol-2-yl]methanone;

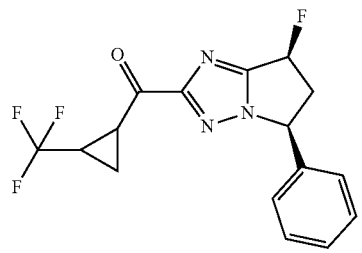 [SMILES: O=C(c1nc2n(n1)[C@H](c1ccccc1)C[C@@H]2F)C1CC1C(F)(F)F]

[(5S,7S)-7-fluoro-5-phenyl-6,7-dihydro-5H-pyrrolo[1,2-b][1,2,4]triazol-2-yl]-[2-(trifluoromethyl)cyclopropyl]methanone;

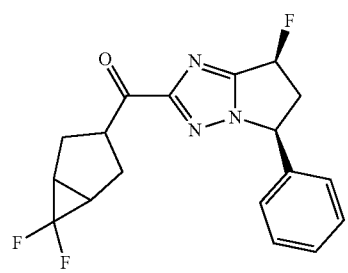 [SMILES: O=C(c1nc2n(n1)[C@H](c1ccccc1)C[C@@H]2F)C1CC2C(C1)C2(F)F]

(6,6-difluoro-3-bicyclo[3.1.0]hexanyl)-5S,7S)-7-fluoro-5-phenyl-6,7-dihydro-5H-pyrrolo[1,2-b][1,2,4]triazol-2-yl]methanone;

430

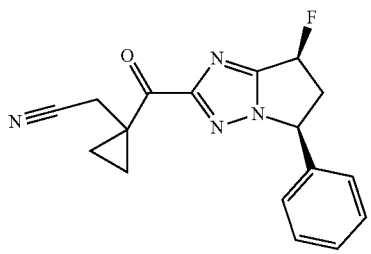 [SMILES: N#CCC1(C(=O)c2nc3n(n2)[C@H](c2ccccc2)C[C@@H]3F)CC1]

2-[1-[(5S,7S)-7-fluoro-5-phenyl-6,7-dihydro-5H-pyrrolo[1,2-b][1,2,4]triazole-2-carbonyl]cyclopropyl]acetonitrile;

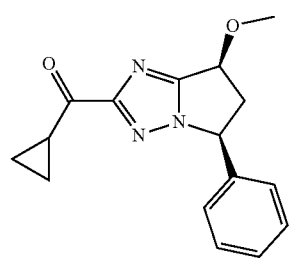 [SMILES: CO[C@H]1C[C@@H](c2ccccc2)n2nc(C(=O)C3CC3)nc21]

cyclopropyl-[(5S,7S)-7-methoxy-5-phenyl-6,7-dihydro-5H-pyrrolo[1,2-b][1,2,4]triazol-2-yl]methanone;

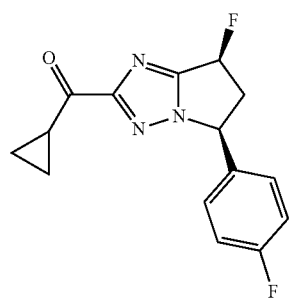 [SMILES: O=C(c1nc2n(n1)[C@H](c1ccc(F)cc1)C[C@@H]2F)C1CC1]

cyclopropyl-[(5S,7S)-7-fluoro-5-(4-fluorophenyl)-6,7-dihydro-5H-pyrrolo[1,2-b][1,2,4]triazol-2-yl]methanone;

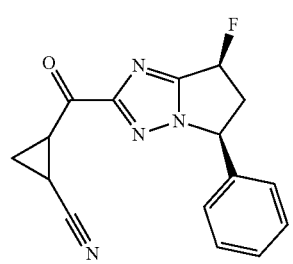 [SMILES: N#CC1CC1C(=O)c1nc2n(n1)[C@H](c1ccccc1)C[C@@H]2F]

2-[rac-(5S,7S)-7-fluoro-5-phenyl-6,7-dihydro-5H-pyrrolo[1,2-b][1,2,4]triazole-2-carbonyl]-cyclopropanecarbonitrile;

431

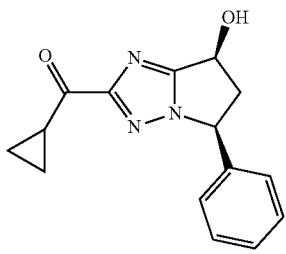 [SMILES: O=C(c1nc2n(n1)[C@H](c1ccccc1)C[C@@H]2O)C1CC1]

cyclopropyl-[(5S,7S)-7-hydroxy-5-phenyl-6,7-dihydro-5H-pyrrolo[1,2-b][1,2,4]triazol-2-yl]methanone;

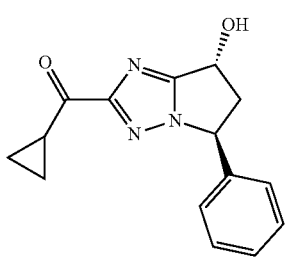

cyclopropyl-[(5S,7R)-7-hydroxy-5-phenyl-6,7-dihydro-5H-pyrrolo[1,2-b][1,2,4]triazol-2-yl]methanone;

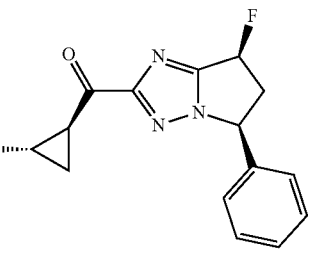

[(5S,7S)-7-fluoro-5-phenyl-6,7-dihydro-5H-pyrrolo[1,2-b][1,2,4]triazol-2-yl]-[(1S,2S)-2-methylcyclopropyl]methanone;

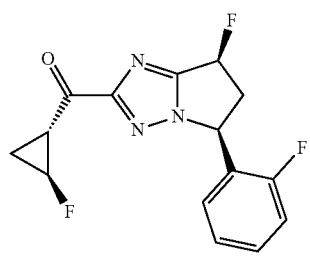 [SMILES: O=C(c1nc2n(n1)[C@H](c1ccccc1F)C[C@@H]2F)[C@H]1C[C@@H]1F]

[(1R,2S)-2-fluorocyclopropyl]-[(5S,7S)-7-fluoro-5-(2-fluorophenyl)-6,7-dihydro-5H-pyrrolo[1,2-b][1,2,4]triazol-2-yl]methanone;

432

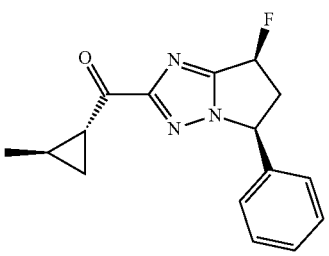 [SMILES: C[C@@H]1C[C@H]1C(=O)c1nc2n(n1)[C@H](c1ccccc1)C[C@@H]2F]

[(5S,7S)-7-fluoro-5-phenyl-6,7-dihydro-5H-pyrrolo[1,2-b][1,2,4]triazol-2-yl]-[(1R,2R)-2-methylcyclopropyl]methanone;

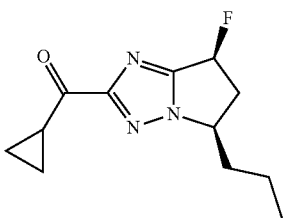 [SMILES: CCC[C@@H]1C[C@H](F)c2nc(C(=O)C3CC3)nn21]

cyclopropyl-[(5R,7S)-5-ethyl-7-fluoro-6,7-dihydro-5H-pyrrolo[1,2-b][1,2,4]triazol-2-yl]methanone;

cyclopropyl-[(5R,7S)-7-fluoro-5-propyl-6,7-dihydro-5H-pyrrolo[1,2-b][1,2,4]triazol-2-yl]methanone;

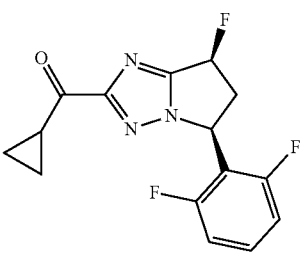 [SMILES: O=C(c1nc2n(n1)[C@H](c1c(F)cccc1F)C[C@@H]2F)C1CC1]

cyclopropyl-[(5S,7S)-5-(2,6-difluorophenyl)-7-fluoro-6,7-dihydro-5H-pyrrolo[1,2-b][1,2,4]triazol-2-yl]methanone;

433

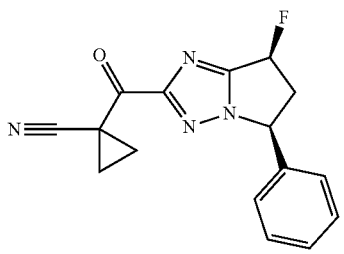 [SMILES: N#CC1(C(=O)c2nc3n(n2)[C@H](c2ccccc2)C[C@@H]3F)CC1]

1-[(5S,7S)-7-fluoro-5-phenyl-6,7-dihydro-5H-pyrrolo[1,2-b][1,2,4]triazole-2-carbonyl]cyclopropanecarbonitrile;

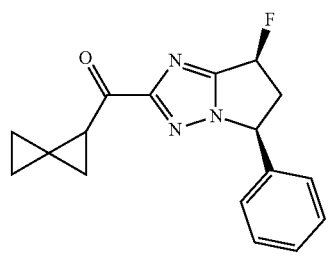 [SMILES: O=C(c1nc2n(n1)[C@H](c1ccccc1)C[C@@H]2F)C1CC12CC2]

[(5S,7S)-7-fluoro-5-phenyl-6,7-dihydro-5H-pyrrolo[1,2-b][1,2,4]triazol-2-yl]-spiro[2.2]pentan-2-yl-methanone;

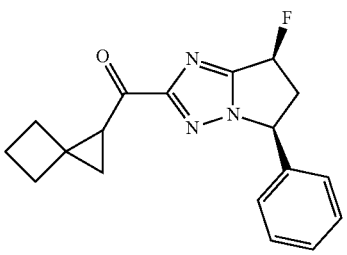 [SMILES: O=C(c1nc2n(n1)[C@H](c1ccccc1)C[C@@H]2F)C1CC12CCC2]

[(5S,7S)-7-fluoro-5-phenyl-6,7-dihydro-5H-pyrrolo[1,2-b][1,2,4]triazol-2-yl]-spiro[2.3]hexan-2-yl-methanone;

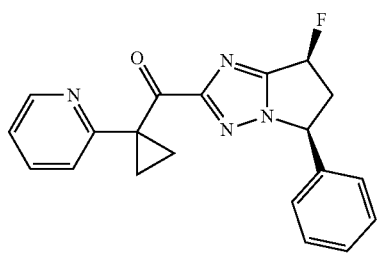 [SMILES: O=C(c1nc2n(n1)[C@H](c1ccccc1)C[C@@H]2F)C1(c2ccccn2)CC1]

[1-(2-pyridyl)cyclopropyl]-[(5S,7S)-7-fluoro-5-phenyl-6,7-dihydro-5H-pyrrolo[1,2-b][1,2,4]triazol-2-yl]methanone;

434

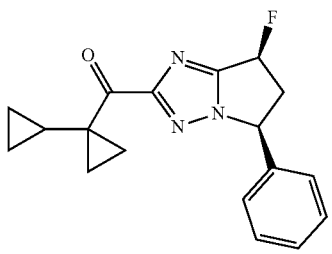 [SMILES: O=C(c1nc2n(n1)[C@H](c1ccccc1)C[C@@H]2F)C1(C2CC2)CC1]

(1-cyclopropylcyclopropyl)-[(5S,7S)-7-fluoro-5-phenyl-6,7-dihydro-5H-pyrrolo[1,2-b][1,2,4]triazol-2-yl]methanone;

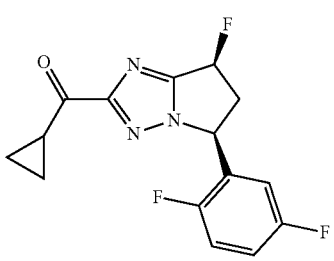 [SMILES: O=C(c1nc2n(n1)[C@H](c1cc(F)ccc1F)C[C@@H]2F)C1CC1]

cyclopropyl-[(5S,7S)-5-(2-chlorophenyl)-7-fluoro-6,7-dihydro-5H-pyrrolo[1,2-b][1,2,4]triazol-2-yl]methanone;

cyclopropyl-[(5S,7S)-5-(2,5-difluorophenyl)-7-fluoro-6,7-dihydro-5H-pyrrolo[1,2-b][1,2,4]triazol-2-yl]methanone;

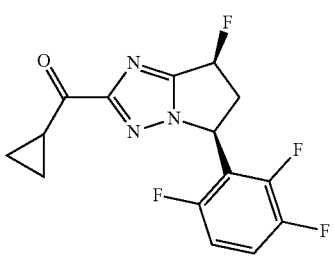 [SMILES: O=C(c1nc2n(n1)[C@H](c1c(F)ccc(F)c1F)C[C@@H]2F)C1CC1]

cyclopropyl-[(5S,7S)-7-fluoro-5-(2,3,6-trifluorophenyl)-6,7-dihydro-5H-pyrrolo[1,2-b][1,2,4]triazol-2-yl]methanone;

435

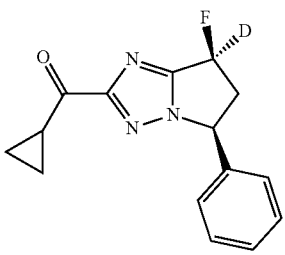 [SMILES: [2H][C@]1(F)C[C@@H](c2ccccc2)n2nc(C(=O)C3CC3)nc21]

cyclopropyl-[(5S,7S)-7-deuterio-7-fluoro-5-phenyl-5,6-dihydropyrrolo[1,2-b][1,2,4]triazol-2-yl]methanone;

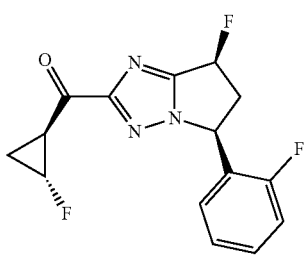 [SMILES: O=C(c1nc2n(n1)[C@H](c1ccccc1F)C[C@@H]2F)[C@@H]1C[C@H]1F]

[(1S,2R)-2-fluorocyclopropyl]-[(5S,7S)-7-fluoro-5-(2-fluorophenyl)-6,7-dihydro-5H-pyrrolo[1,2-b][1,2,4]triazol-2-yl]methanone;

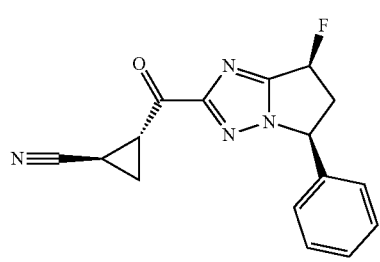 [SMILES: N#C[C@@H]1C[C@H]1C(=O)c1nc2n(n1)[C@H](c1ccccc1)C[C@@H]2F]

rac-(1R,2R)-2-[(5S,7S)-7-fluoro-5-phenyl-6,7-dihydro-5H-pyrrolo[1,2-b][1,2,4]triazole-2-carbonyl]cyclopropanecarbonitrile;

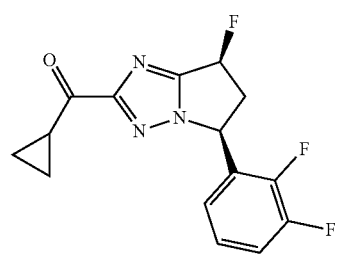 [SMILES: O=C(c1nc2n(n1)[C@H](c1cccc(F)c1F)C[C@@H]2F)C1CC1]

cyclopropyl-[(5S,7S)-5-(2,3-difluorophenyl)-7-fluoro-6,7-dihydro-5H-pyrrolo[1,2-b][1,2,4]triazol-2-yl]methanone;

436

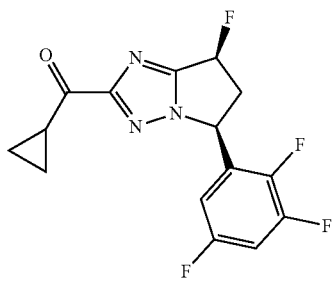 [SMILES: O=C(c1nc2n(n1)[C@H](c1cc(F)cc(F)c1F)C[C@@H]2F)C1CC1]

cyclopropyl-[(5S,7S)-7-fluoro-5-(2,3,5-trifluorophenyl)-6,7-dihydro-5H-pyrrolo[1,2-b][1,2,4]triazol-2-yl]methanone;

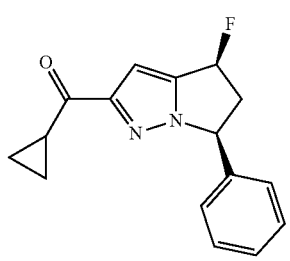 [SMILES: O=C(c1cc2n(n1)[C@H](c1ccccc1)C[C@@H]2F)C1CC1]

cyclopropyl-[(4S,6S)-4-fluoro-6-phenyl-5,6-dihydro-4H-pyrrolo[1,2-b]pyrazol-2-yl]methanone;

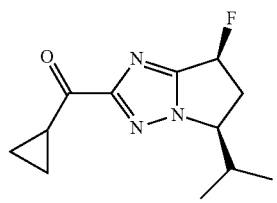 [SMILES: CC(C)[C@@H]1C[C@H](F)c2nc(C(=O)C3CC3)nn21]

cyclopropyl-[(5S,7S)-7-fluoro-5-isopropyl-6,7-dihydro-5H-pyrrolo[1,2-b][1,2,4]triazol-2-yl]methanone;

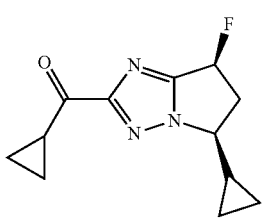 [SMILES: O=C(c1nc2n(n1)[C@H](C1CC1)C[C@@H]2F)C1CC1]

cyclopropyl-[(5S,7S)-5-cyclopropyl-7-fluoro-6,7-dihydro-5H-pyrrolo[1,2-b][1,2,4]triazol-2-yl]methanone;

| 437 | 438 |
|---|---|
| 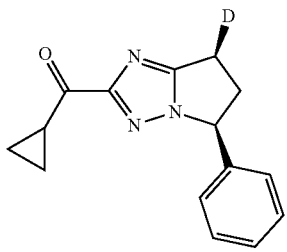 | 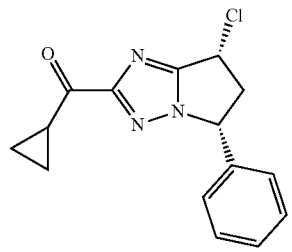 |
| cyclopropyl-[(5S,7S)-7-deuterio-5-phenyl-6,7-dihydro-5H-pyrrolo[1,2-b][1,2,4]triazol-2-yl]methanone; | cyclopropyl-[(5R,7R)-7-chloro-5-phenyl-6,7-dihydro-5H-pyrrolo[1,2-b][1,2,4]triazol-2-yl]methanone; |
| 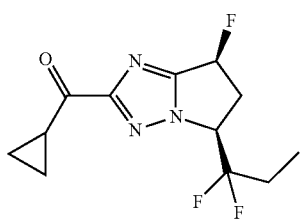 [SMILES: CCC(F)(F)[C@@H]1C[C@H](F)c2nc(C(=O)C3CC3)nn21] | 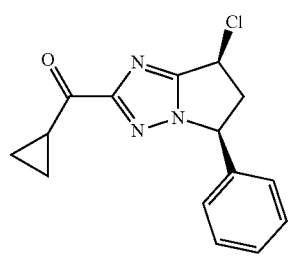 |
| cyclopropyl-[rac-(5S,7S)-5-(1,1-difluoropropyl)-7-fluoro-6,7-dihydro-5H-pyrrolo[1,2-b][1,2,4]triazol-2-yl]methanone; | cyclopropyl-[(5S,7S)-7-chloro-5-phenyl-6,7-dihydro-5H-pyrrolo[1,2-b][1,2,4]triazol-2-yl]methanone; |
| 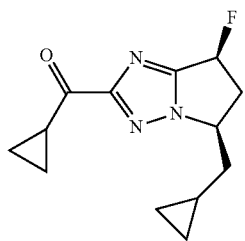 [SMILES: O=C(c1nc2n(n1)[C@H](CC1CC1)C[C@@H]2F)C1CC1] | 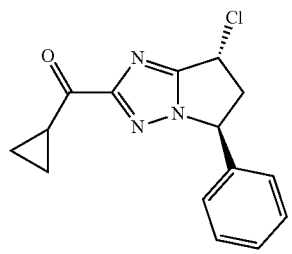 |
| cyclopropyl-[(5R,7S)-5-(cyclopropylmethyl)-7-fluoro-6,7-dihydro-5H-pyrrolo[1,2-b][1,2,4]triazol-2-yl]methanone; | cyclopropyl-[(5S,7R)-7-chloro-5-phenyl-6,7-dihydro-5H-pyrrolo[1,2-b][1,2,4]triazol-2-yl]methanone; |
| 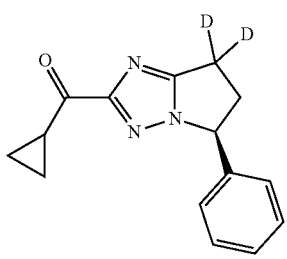 | 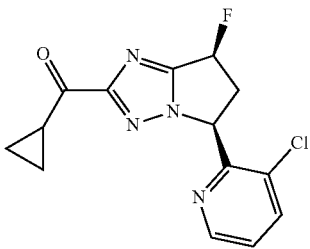 |
| cyclopropyl-[(5S)-7,7-dideuterio-5-phenyl-5,6-dihydropyrrolo[1,2-b][1,2,4]triazol-2-yl]methanone; | cyclopropyl-[rac-(5S,7S)-5-(3-chloro-2-pyridyl)-7-fluoro-6,7-dihydro-5H-pyrrolo[1,2-b][1,2,4]triazol-2-yl]methanone; |

439

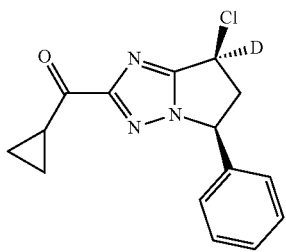 [SMILES: [2H][C@]1(Cl)C[C@@H](c2ccccc2)n2nc(C(=O)C3CC3)nc21]

cyclopropyl-[rac-(5S,7S)-7-chloro-7-deuterio-5-phenyl-5,6-dihydropyrrolo[1,2-b][1,2,4]triazol-2-yl]methanone;

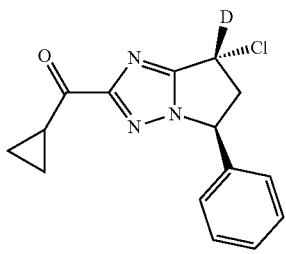 [SMILES: [2H][C@@]1(Cl)C[C@@H](c2ccccc2)n2nc(C(=O)C3CC3)nc21]

cyclopropyl-[rac-(5S,7R)-7-chloro-7-deuterio-5-phenyl-5,6-dihydropyrrolo[1,2-b][1,2,4]triazol-2-yl]methanone;

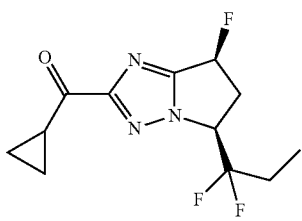 [SMILES: CCC(F)(F)[C@@H]1C[C@H](F)c2nc(C(=O)C3CC3)nn21]

cyclopropyl-[(5S,7S)-5-(1,1-difluoropropyl)-7-fluoro-6,7-dihydro-5H-pyrrolo[1,2-b][1,2,4]triazol-2-yl]methanone;

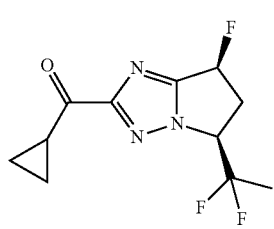 [SMILES: CC(F)(F)[C@@H]1C[C@H](F)c2nc(C(=O)C3CC3)nn21]

cyclopropyl-[rac-(5S,7S)-5-(1,1-difluoroethyl)-7-fluoro-6,7-dihydro-5H-pyrrolo[1,2-b][1,2,4]triazol-2-yl]methanone;

440

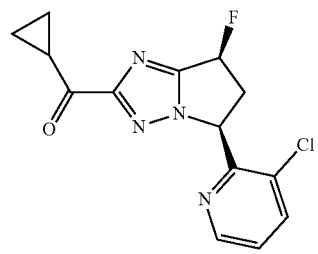 [SMILES: O=C(c1nc2n(n1)[C@H](c1ncccc1Cl)C[C@@H]2F)C1CC1]

cyclopropyl-[(5S,7S)-5-(3-chloro-2-pyridyl)-7-fluoro-6,7-dihydro-5H-pyrrolo[1,2-b][1,2,4]triazol-2-yl]methanone;

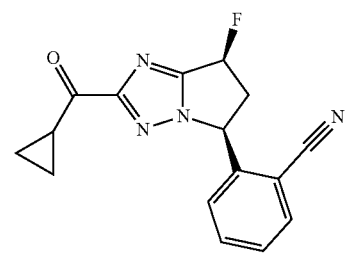 [SMILES: N#Cc1ccccc1[C@@H]1C[C@H](F)c2nc(C(=O)C3CC3)nn21]

2-[(5S,7S)-2-(cyclopropanecarbonyl)-7-fluoro-6,7-dihydro-5H-pyrrolo[1,2-b][1,2,4]triazol-5-yl]benzonitrile;

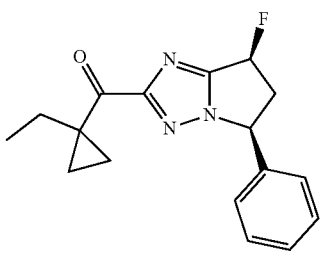 [SMILES: CCC1(C(=O)c2nc3n(n2)[C@H](c2ccccc2)C[C@@H]3F)CC1]

(1-ethylcyclopropyl)-[rac-(5S,7S)-7-fluoro-5-phenyl-6,7-dihydro-5H-pyrrolo[1,2-b][1,2,4]triazol-2-yl]methanone;

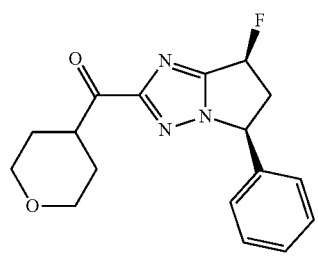 [SMILES: O=C(c1nc2n(n1)[C@H](c1ccccc1)C[C@@H]2F)C1CCOCC1]

[rac-(5S,7S)-7-fluoro-5-phenyl-6,7-dihydro-5H-pyrrolo[1,2-b][1,2,4]triazol-2-yl]-tetrahydropyran-4-yl-methanone;

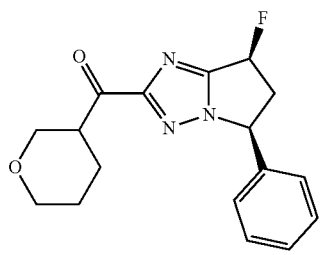 [SMILES: O=C(c1nc2n(n1)[C@H](c1ccccc1)C[C@@H]2F)C1CCCOC1]

[rac-(5S,7S)-7-fluoro-5-phenyl-6,7-dihydro-5H-pyrrolo[1,2-b][1,2,4]triazol-2-yl]-tetrahydropyran-3-yl-methanone;

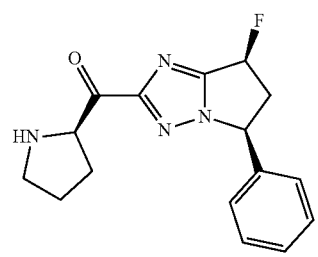 [SMILES: O=C(c1nc2n(n1)[C@H](c1ccccc1)C[C@@H]2F)[C@H]1CCCN1]

[rac-(5S,7S)-7-fluoro-5-phenyl-6,7-dihydro-5H-pyrrolo[1,2-b][1,2,4]triazol-2-yl]-[rac-(2R)-pyrrolidin-2-yl]methanone;

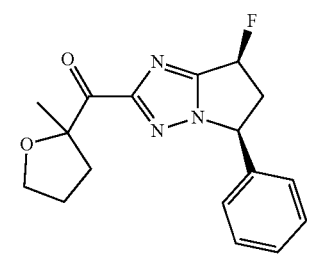 [SMILES: CC1(C(=O)c2nc3n(n2)[C@H](c2ccccc2)C[C@@H]3F)CCCO1]

(2-methyltetrahydrofuran-2-yl)-[rac-(5S,7S)-7-fluoro-5-phenyl-6,7-dihydro-5H-pyrrolo[1,2-b][1,2,4]triazol-2-yl]methanone;

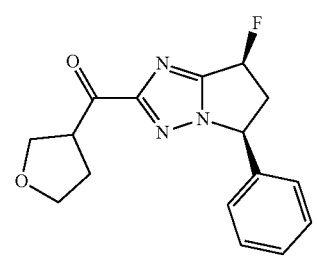

[rac-(5S,7S)-7-fluoro-5-phenyl-6,7-dihydro-5H-pyrrolo[1,2-b][1,2,4]triazol-2-yl]-tetrahydrofuran-3-yl-methanone;

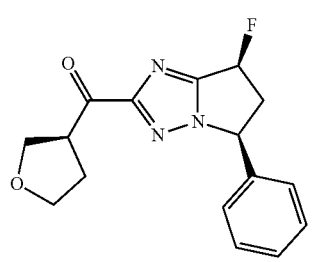 [SMILES: O=C(c1nc2n(n1)[C@H](c1ccccc1)C[C@@H]2F)[C@H]1CCOC1]

[rac-(5S,7S)-7-fluoro-5-phenyl-6,7-dihydro-5H-pyrrolo[1,2-b][1,2,4]triazol-2-yl]-[rac-(3S)-tetrahydrofuran-3-yl]methanone;

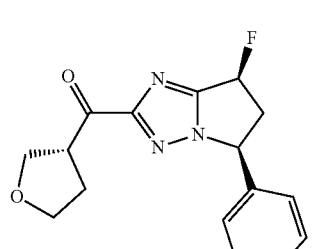

[rac-(5S,7S)-7-fluoro-5-phenyl-6,7-dihydro-5H-pyrrolo[1,2-b][1,2,4]triazol-2-yl]-[rac-(3R)-tetrahydrofuran-3-yl]methanone;

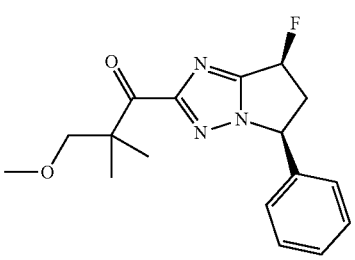 [SMILES: COCC(C)(C)C(=O)c1nc2n(n1)[C@H](c1ccccc1)C[C@@H]2F]

3-methoxy-2,2-dimethyl-1-[rac-(5S,7S)-7-fluoro-5-phenyl-6,7-dihydro-5H-pyrrolo[1,2-b][1,2,4]triazol-2-yl]propan-1-one;

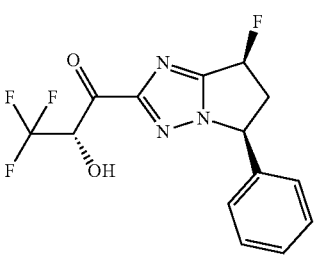 [SMILES: O=C(c1nc2n(n1)[C@H](c1ccccc1)C[C@@H]2F)[C@H](O)C(F)(F)F]

rac-(2S)-3,3,3-trifluoro-2-hydroxy-1-[rac-(5S,7S)-7-fluoro-5-phenyl-6,7-dihydro-5H-pyrrolo[1,2-b][1,2,4]triazol-2-yl]propan-1-one;

443

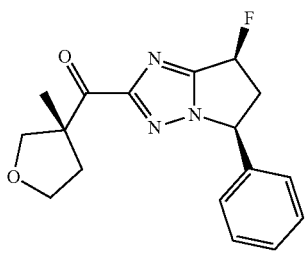 [SMILES: C[C@@]1(C(=O)c2nc3n(n2)[C@H](c2ccccc2)C[C@@H]3F)CCOC1]

[rac-(5S,7S)-7-fluoro-5-phenyl-6,7-dihydro-5H-pyrrolo[1,2-b][1,2,4]triazol-2-yl]-[rac-(3R)-3-methyltetrahydrofuran-3-yl]methanone;

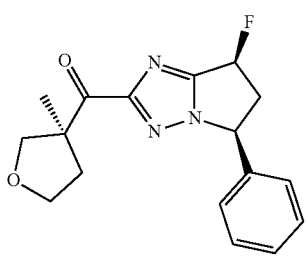 [SMILES: C[C@]1(C(=O)c2nc3n(n2)[C@H](c2ccccc2)C[C@@H]3F)CCOC1]

[rac-(5S,7S)-7-fluoro-5-phenyl-6,7-dihydro-5H-pyrrolo[1,2-b][1,2,4]triazol-2-yl]-[rac-(3 S)-3-methyltetrahydrofuran-3-yl]methanone;

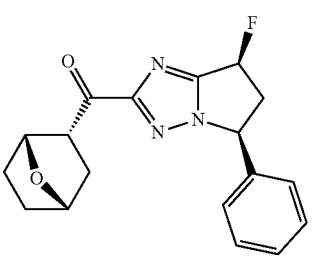 [SMILES: O=C(c1nc2n(n1)[C@H](c1ccccc1)C[C@@H]2F)[C@@H]1C[C@@H]2CC[C@H]1O2]

[rac-(5S,7S)-7-fluoro-5-phenyl-6,7-dihydro-5H-pyrrolo[1,2-b][1,2,4]triazol-2-yl]-[rac-(1R,2R,4S)-7-oxabicyclo[2.2.1]heptan-2-yl]methanone;

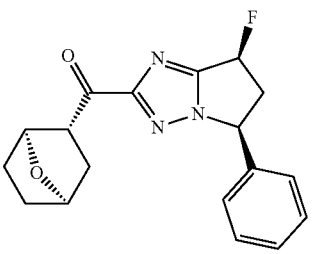 [SMILES: O=C(c1nc2n(n1)[C@H](c1ccccc1)C[C@@H]2F)[C@@H]1C[C@H]2CC[C@@H]1O2]

((1S,2R,4R)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone;

444

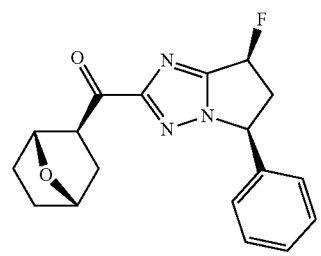 [SMILES: O=C(c1nc2n(n1)[C@H](c1ccccc1)C[C@@H]2F)[C@H]1C[C@@H]2CC[C@H]1O2]

((1R,2S,4S)-7-oxabicyclo[2.2.1]heptan-2-yl)((5S,7S)-7-fluoro-5-phenyl-6,7-dihydro-5H-pyrrolo[1,2-b][1,2,4]triazol-2-yl)methanone;

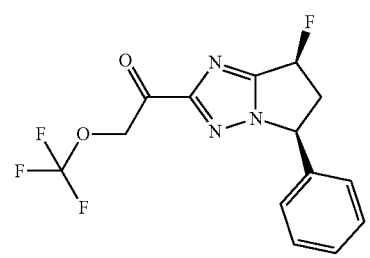 [SMILES: O=C(COC(F)(F)F)c1nc2n(n1)[C@H](c1ccccc1)C[C@@H]2F]

1-[rac-(5S,7S)-7-fluoro-5-phenyl-6,7-dihydro-5H-pyrrolo[1,2-b][1,2,4]triazol-2-yl]-2-(trifluoromethoxy)ethanone;

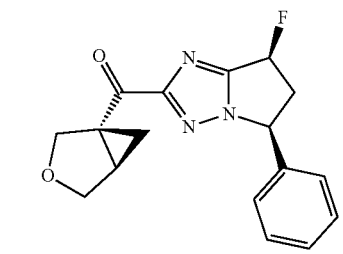 [SMILES: O=C(c1nc2n(n1)[C@H](c1ccccc1)C[C@@H]2F)[C@@]12COC[C@@H]1C2]

[rac-(5S,7S)-7-fluoro-5-phenyl-6,7-dihydro-5H-pyrrolo[1,2-b][1,2,4]triazol-2-yl]-[rac-(1R,5R)-3-oxabicyclo[3.1.0]hexan-1-yl]methanone;

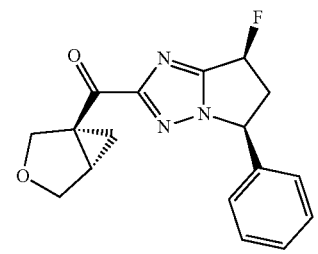 [SMILES: O=C(c1nc2n(n1)[C@H](c1ccccc1)C[C@@H]2F)[C@]12COC[C@H]1C2]

[rac-(5S,7S)-7-fluoro-5-phenyl-6,7-dihydro-5H-pyrrolo[1,2-b][1,2,4]triazol-2-yl]-[rac-(1S,5S)-3-oxabicyclo[3.1.0]hexan-1-yl]methanone;

445

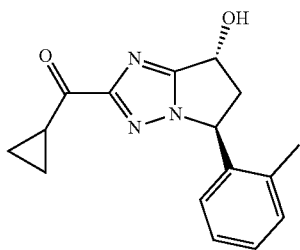 [SMILES: Cc1ccccc1[C@@H]1C[C@@H](O)c2nc(C(=O)C3CC3)nn21]

cyclopropyl((5S,7R)-7-hydroxy-5-(o-tolyl)-6,7-dihydro-5H-pyrrolo[1,2-b][1,2,4]triazol-2-yl]methanone;

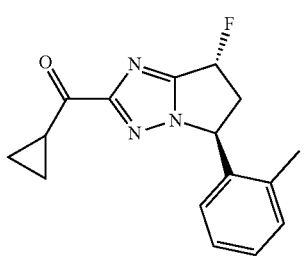 [SMILES: Cc1ccccc1[C@@H]1C[C@@H](F)c2nc(C(=O)C3CC3)nn21]

cyclopropyl-[rac-(5S,7R)-7-fluoro-5-(o-tolyl)-6,7-dihydro-5H-pyrrolo[1,2-b][1,2,4]triazol-2-yl]methanone;

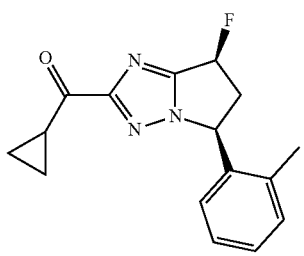 [SMILES: Cc1ccccc1[C@@H]1C[C@H](F)c2nc(C(=O)C3CC3)nn21]

cyclopropyl-[rac-(5S,7S)-7-fluoro-5-(o-tolyl)-6,7-dihydro-5H-pyrrolo[1,2-b][1,2,4]triazol-2-yl]methanone;

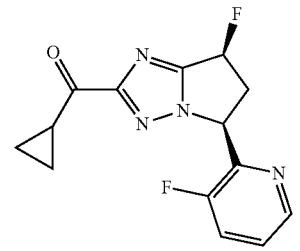 [SMILES: O=C(c1nc2n(n1)[C@H](c1ncccc1F)C[C@@H]2F)C1CC1]

cyclopropyl((5S,7S)-7-fluoro-5-(3-fluoropyridin-2-yl)-6,7-dihydro-5H-pyrrolo[1,2-b][1,2,4]triazol-2-yl]methanone;

446

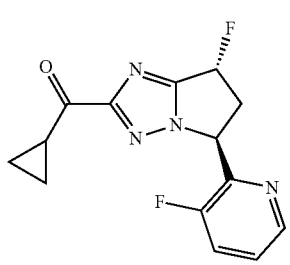 [SMILES: O=C(c1nc2n(n1)[C@H](c1ncccc1F)C[C@H]2F)C1CC1]

cyclopropyl((5S,7R)-7-fluoro-5-(3-fluoropyridin-2-yl)-6,7-dihydro-5H-pyrrolo[1,2-b][1,2,4]triazol-2-yl)methanone;

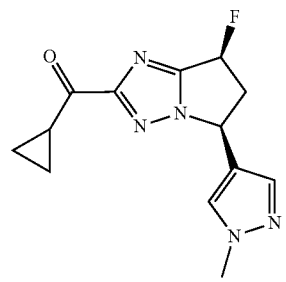 [SMILES: Cn1cc([C@@H]2C[C@H](F)c3nc(C(=O)C4CC4)nn32)cn1]

cyclopropyl((5S,7S)-7-fluoro-5-(1-methyl-1H-pyrazol-4-yl)-6,7-dihydro-5H-pyrrolo[1,2-b][1,2,4]triazol-2-yl)methanone;

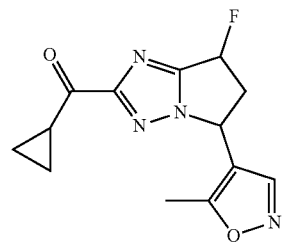

cyclopropyl(7-fluoro-5-(5-methylisoxazol-4-yl)-6,7-dihydro-5H-pyrrolo[1,2-b][1,2,4]triazol-2-yl)methanone;

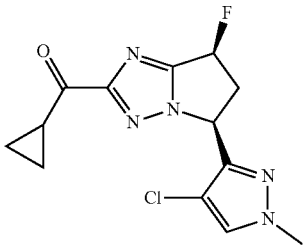 [SMILES: Cn1cc(Cl)c([C@@H]2C[C@H](F)c3nc(C(=O)C4CC4)nn32)n1]

((5S,7S)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone;

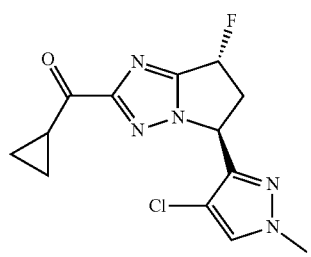 [SMILES: Cn1cc(Cl)c([C@@H]2C[C@@H](F)c3nc(C(=O)C4CC4)nn32)n1]

((5S,7R)-5-(4-chloro-1-methyl-1H-pyrazol-3-yl)-7-fluoro-6,7-dihydro-5H-pyrrolo[1,2-b][1,2,4]triazol-2-yl)(cyclopropyl)methanone;

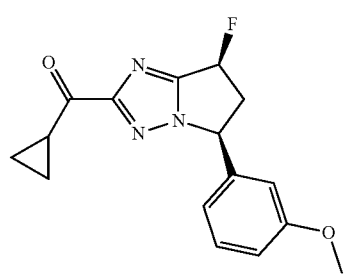 [SMILES: COc1cccc([C@@H]2C[C@H](F)c3nc(C(=O)C4CC4)nn32)c1]

cyclopropyl((5S,7S)-7-fluoro-5-(3-methoxyphenyl)-6,7-dihydro-5H-pyrrolo[1,2-b][1,2,4]triazol-2-yl)methanone;

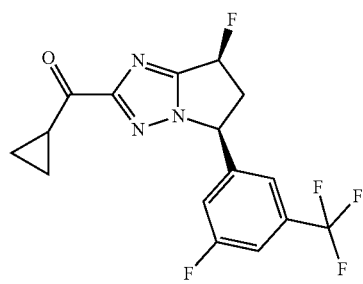 [SMILES: O=C(c1nc2n(n1)[C@H](c1cc(F)cc(C(F)(F)F)c1)C[C@@H]2F)C1CC1]

cyclopropyl((5S,7S)-7-fluoro-5-(3-fluoro-5-(trifluoromethyl)phenyl)-6,7-dihydro-5H-pyrrolo[1,2-b][1,2,4]triazol-2-yl)methanone;

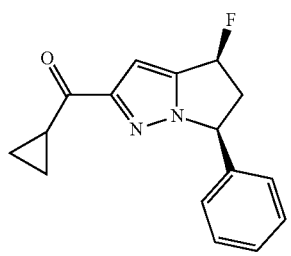 [SMILES: O=C(c1cc2n(n1)[C@H](c1ccccc1)C[C@@H]2F)C1CC1]

cyclopropyl((4S,6S)-4-fluoro-6-phenyl-5,6-dihydro-4H-pyrrolo[1,2-b]pyrazol-2-yl)methanone;

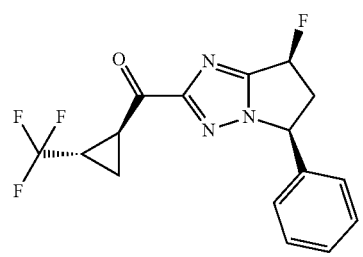 [SMILES: O=C(c1nc2n(n1)[C@H](c1ccccc1)C[C@@H]2F)[C@H]1C[C@@H]1C(F)(F)F]

[rac-(5S,7S)-7-fluoro-5-phenyl-6,7-dihydro-5H-pyrrolo[1,2-b][1,2,4]triazol-2-yl]-[rac-(1S,2S)-2-(trifluoromethyl)cyclopropyl]methanone;

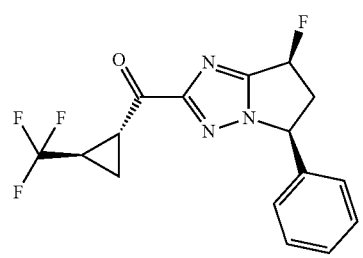 [SMILES: O=C(c1nc2n(n1)[C@H](c1ccccc1)C[C@@H]2F)[C@@H]1C[C@H]1C(F)(F)F]

[rac-(5S,7S)-7-fluoro-5-phenyl-6,7-dihydro-5H-pyrrolo[1,2-b][1,2,4]triazol-2-yl]-[rac-(1R,2R)-2-(trifluoromethyl)cyclopropyl]methanone;

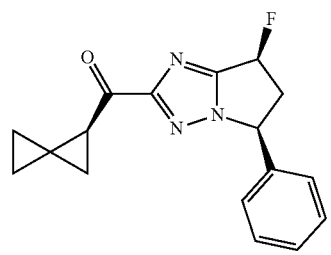 [SMILES: O=C(c1nc2n(n1)[C@H](c1ccccc1)C[C@@H]2F)[C@H]1CC12CC2]

[rac-(5S,7S)-7-fluoro-5-phenyl-6,7-dihydro-5H-pyrrolo[1,2-b][1,2,4]triazol-2-yl]-[rac-(2S)-spiro[2.2]pentan-2-yl]methanone; and

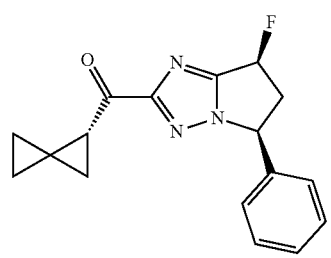 [SMILES: O=C(c1nc2n(n1)[C@H](c1ccccc1)C[C@@H]2F)[C@@H]1CC12CC2]

[rac-(5S,7S)-7-fluoro-5-phenyl-6,7-dihydro-5H-pyrrolo[1,2-b][1,2,4]triazol-2-yl]-[rac-(2R)-spiro[2.2]pentan-2-yl]methanone.

6. The method of claim 1, wherein $R^2$ is selected from the group consisting of phenyl, monofluorophenyl, difluorophenyl, monochlorophenyl and dichlorophenyl.

7. The method of claim 1, wherein the A ring and the B ring together are selected from the group consisting of:

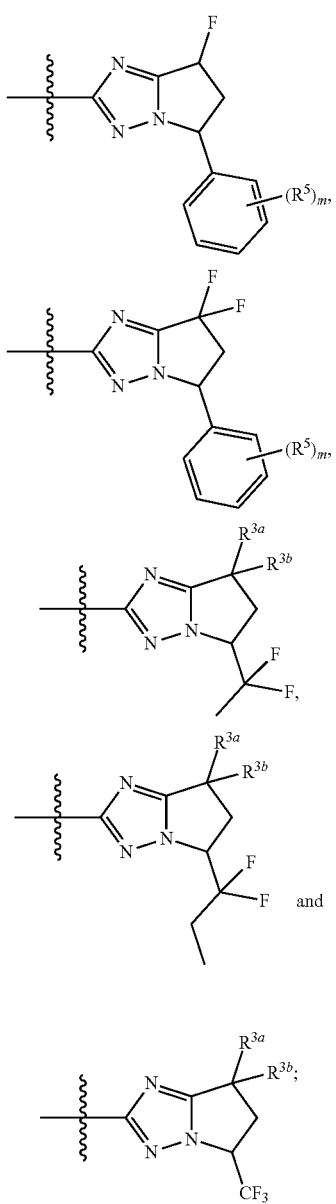

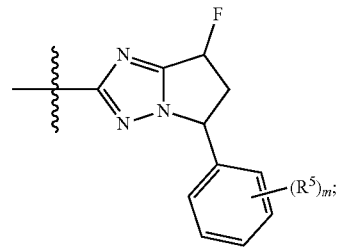

wherein:
each $R^5$ is selected from the group consisting of H, F, Cl, $C_1$-$C_4$ alkyl, $C_1$-$C_4$ haloalkyl, $C_1$-$C_4$ alkoxy and $C_1$-$C_4$ haloalkoxy; and
m is 1, 2 or 3.

9. The method of claim 1, wherein $R^2$ is selected from the group consisting of phenyl, monofluorophenyl, and difluorophenyl.

10. The method of claim 1, wherein $R^2$ is phenyl.

11. A method for the treatment of a disease or disorder in a human, the method comprising administration to the human of an effective treatment amount of a compound, or a pharmaceutically acceptable salt thereof, selected from:

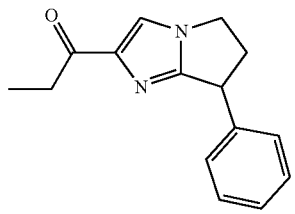 [SMILES: CCC(=O)c1cn2c(n1)C(c1ccccc1)CC2]

1-(7-phenyl-6,7-dihydro-5H-pyrrolo[1,2-a]imidazol-2-yl)propan-1-one;

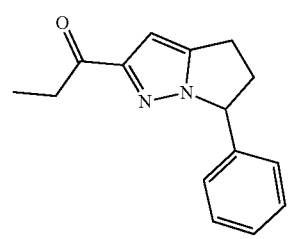 [SMILES: CCC(=O)c1cc2n(n1)C(c1ccccc1)CC2]

1-(6-phenyl-5,6-dihydro-4H-pyrrolo[1,2-b]pyrazol-2-yl)propan-1-one;

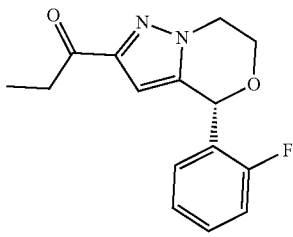 [SMILES: CCC(=O)c1cc2n(n1)CCO[C@@H]2c1ccccc1F]

1-[rac-(4R)-4-(2-fluorophenyl)-6,7-dihydro-4H-pyrazolo[5,1-c][1,4]oxazin-2-yl]propan-1-one;

wherein:
$R^{3a}$ and $R^{3b}$ are selected as follows:
(i) one of $R^{3a}$ and $R^{3b}$ is H, and the other is selected from the group consisting of D, F, Cl, OH, CN, $C_1$-$C_4$ alkyl, $C_1$-$C_4$ haloalkyl, cyclopropyl, $C_1$-$C_4$ alkoxy and $C_1$-$C_4$ haloalkoxy;
(ii) each of $R^{3a}$ and $R^{3b}$ is selected from the group consisting of D, F, Cl, OH, CN and methyl, provided that $R^{3a}$ and $R^{3b}$ cannot both be OH or CN; or
(iii) $R^{3a}$ and $R^{3b}$ together form cyclopropyl;
each $R^5$ is selected from the group consisting of H, F, Cl, $C_1$-$C_4$ alkyl, $C_1$-$C_4$ haloalkyl, $C_1$-$C_4$ alkoxy and $C_1$-$C_4$ haloalkoxy; and
m is 1, 2 or 3.

8. The method of claim 1, wherein the A ring and the B ring together are:

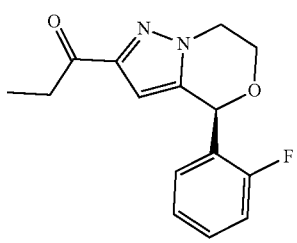 [SMILES: CCC(=O)c1cc2n(n1)CCO[C@H]2c1ccccc1F]

1-[rac-(4S)-4-(2-fluorophenyl)-6,7-dihydro-4H-pyrazolo[5,1-c][1,4]oxazin-2-yl]propan-1-one;

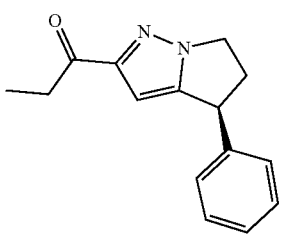 [SMILES: CCC(=O)c1cc2n(n1)CC[C@H]2c1ccccc1]

(S)-1-(4-phenyl-5,6-dihydro-4H-pyrrolo[1,2-b]pyrazol-2-yl)propan-1-one;

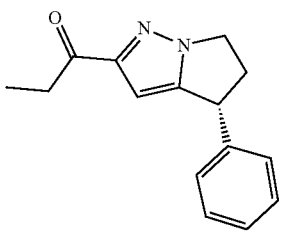 [SMILES: CCC(=O)c1cc2n(n1)CC[C@@H]2c1ccccc1]

(R)-1-(4-phenyl-5,6-dihydro-4H-pyrrolo[1,2-b]pyrazol-2-yl)propan-1-one;

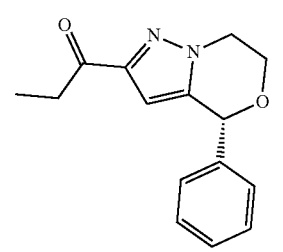 [SMILES: CCC(=O)c1cc2n(n1)CCO[C@@H]2c1ccccc1]

1-[rac-(4R)-4-phenyl-6,7-dihydro-4H-pyrazolo[5,1-c][1,4] oxazin-2-yl]propan-1-one;

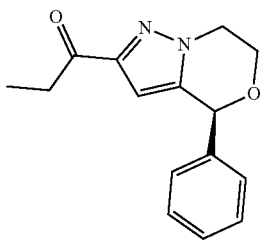 [SMILES: CCC(=O)c1cc2n(n1)CCO[C@H]2c1ccccc1]

1-[rac-(4S)-4-phenyl-6,7-dihydro-4H-pyrazolo[5,1-c][1,4] oxazin-2-yl]propan-1-one;

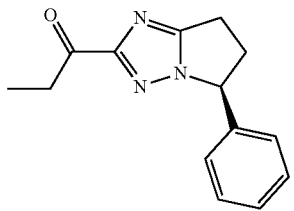 [SMILES: CCC(=O)c1nc2n(n1)[C@H](c1ccccc1)CC2]

1-[rac-(5S)-5-phenyl-6,7-dihydro-5H-pyrrolo[1,2-b][1,2,4]triazol-2-yl]propan-1-one;

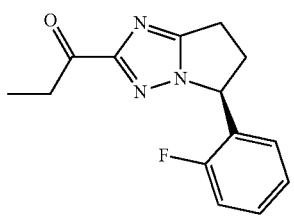 [SMILES: CCC(=O)c1nc2n(n1)[C@H](c1ccccc1F)CC2]

1-[rac-(5S)-5-(2-fluorophenyl)-6,7-dihydro-5H-pyrrolo[1,2-b][1,2,4]triazol-2-yl]propan-1-one;

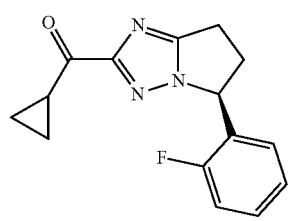 [SMILES: O=C(c1nc2n(n1)[C@H](c1ccccc1F)CC2)C1CC1]

cyclopropyl-[rac-(5S)-5-(2-fluorophenyl)-6,7-dihydro-5H-pyrrolo[1,2-b][1,2,4]triazol-2-yl]methanone;

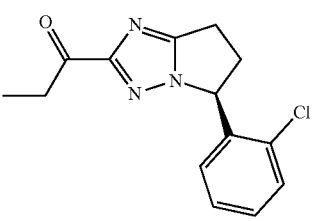 [SMILES: CCC(=O)c1nc2n(n1)[C@H](c1ccccc1Cl)CC2]

1-[(5S)-5-(2-chlorophenyl)-6,7-dihydro-5H-pyrrolo[1,2-b][1,2,4]triazol-2-yl]propan-1-one;

453

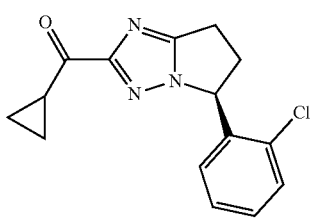 [SMILES: O=C(c1nc2n(n1)[C@H](c1ccccc1Cl)CC2)C1CC1]

cyclopropyl-[(5S)-5-(2-chlorophenyl)-6,7-dihydro-5H-pyrrolo[1,2-b][1,2,4]triazol-2-yl]methanone;

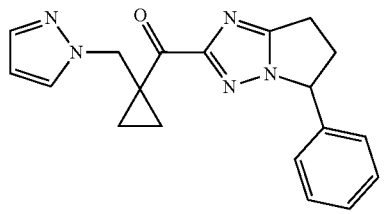 [SMILES: O=C(c1nc2n(n1)C(c1ccccc1)CC2)C1(Cn2cccn2)CC1]

454

(5-phenyl-6,7-dihydro-5H-pyrrolo[1,2-b][1,2,4]triazol-2-yl)$_{41}$-(pyrazol-1-ylmethyl)cyclopropyl]methanone;

wherein the disease or disorder is selected from the group consisting of Parkinson's Disease, Lewy body dementia, multiple system atrophy, Parkinson-plus syndrome, tauopathy, Alzheimer's Disease, frontotemporal dementia, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathy, progressive supranuclear palsy, corticobasal degeneration, multiple sclerosis, inflammatory bowel disease, Crohn's disease, ulcerative colitis, glaucoma, psoriasis, psoriatic arthritis, rheumatoid arthritis, spondyloarthritis, juvenile idiopathic arthritis, and osteoarthritis.

* * * * *